US012559462B2

(12) United States Patent
Semple et al.

(10) Patent No.: US 12,559,462 B2
(45) Date of Patent: Feb. 24, 2026

(54) PYRIMIDINE DERIVATIVES AS MODULATORS OF THE 5-HT$_{2A}$ SEROTONIN RECEPTOR USEFUL FOR THE TREATMENT OF DISORDERS RELATED THERETO

(71) Applicant: Arena Pharmaceuticals, Inc., New York, NY (US)

(72) Inventors: Graeme Semple, San Diego, CA (US); Thuy-Anh Tran, San Diego, CA (US)

(73) Assignee: Arena Pharmaceuticals, Inc., New York, NY (US)

( * ) Notice: Subject to any disclaimer, the term of this patent is extended or adjusted under 35 U.S.C. 154(b) by 477 days.

(21) Appl. No.: 18/249,762

(22) PCT Filed: Oct. 26, 2021

(86) PCT No.: PCT/US2021/056693
§ 371 (c)(1),
(2) Date: Apr. 20, 2023

(87) PCT Pub. No.: WO2022/093849
PCT Pub. Date: May 5, 2022

(65) Prior Publication Data

US 2025/0270172 A1 Aug. 28, 2025

Related U.S. Application Data

(60) Provisional application No. 63/133,096, filed on Dec. 31, 2020, provisional application No. 63/106,069, filed on Oct. 27, 2020.

(51) Int. Cl.

| | |
|---|---|
| *C07D 239/26* | (2006.01) |
| *A61K 31/505* | (2006.01) |
| *A61K 31/506* | (2006.01) |
| *A61K 31/5377* | (2006.01) |
| *A61K 31/5386* | (2006.01) |
| *C07D 401/12* | (2006.01) |
| *C07D 401/14* | (2006.01) |
| *C07D 403/12* | (2006.01) |
| *C07D 403/14* | (2006.01) |
| *C07D 405/14* | (2006.01) |
| *C07D 413/12* | (2006.01) |
| *C07D 413/14* | (2006.01) |
| *C07D 417/14* | (2006.01) |
| *C07D 471/10* | (2006.01) |
| *C07D 487/04* | (2006.01) |
| *C07D 491/107* | (2006.01) |
| *C07D 498/04* | (2006.01) |
| *C07D 498/08* | (2006.01) |

(52) U.S. Cl.
CPC .......... *C07D 239/26* (2013.01); *A61K 31/505* (2013.01); *A61K 31/506* (2013.01); *A61K 31/5377* (2013.01); *A61K 31/5386* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 417/14* (2013.01); *C07D 471/10* (2013.01); *C07D 487/04* (2013.01); *C07D 491/107* (2013.01); *C07D 498/04* (2013.01); *C07D 498/08* (2013.01)

(58) Field of Classification Search
CPC .. C07D 239/26; C07D 401/12; C07D 401/14; C07D 403/12; C07D 403/14; C07D 405/14; C07D 413/12; C07D 413/14; C07D 417/14; C07D 471/10; C07D 487/04; C07D 491/107; C07D 498/04; C07D 498/08; C07D 405/12; C07D 417/12; C07D 491/08; A61K 31/505; A61K 31/506; A61K 31/5377; A61K 31/5386; A61P 9/00
See application file for complete search history.

(56) References Cited

U.S. PATENT DOCUMENTS

| | | | |
|---|---|---|---|
| 2012/0028920 A1 | 2/2012 | Yamashita et al. | |
| 2012/0270861 A1 | 10/2012 | Teegarden et al. | |
| 2019/0307677 A1 | 10/2019 | Yang et al. | |

FOREIGN PATENT DOCUMENTS

| | | | |
|---|---|---|---|
| GB | 1199037 * | 7/1970 | ............ A61K 27/00 |
| WO | 2022/093849 A1 | 5/2022 | |

OTHER PUBLICATIONS

International Patent Application No. PCT/US2021/056693, filed Oct. 26, 2021, Search Report and Written Opinion mailed Jan. 5, 2022, (WO 2022/093849) published May 5, 2022, 12 pages.
International Preliminary Report on Patentability, mailed on May 11, 2023, for WO Application No. PCT/US2021/056693, 6 pages.

* cited by examiner

*Primary Examiner* — Joseph K McKane
*Assistant Examiner* — David M Shim
(74) *Attorney, Agent, or Firm* — Young-In J. Oh

(57) ABSTRACT

Provided is a compound of Formula (I) or a pharmaceutically acceptable salt thereof, that is a modulator of 5-HT$_{2A}$ and can be used in treating diseases and disorders associated with 5-HT$_{2A}$ serotonin receptor expression and/or activity. Thus, also provided are methods of treating 5HT$_{2A}$-related diseases and disorders.

17 Claims, No Drawings

PYRIMIDINE DERIVATIVES AS MODULATORS OF THE 5-$HT_{2A}$ SEROTONIN RECEPTOR USEFUL FOR THE TREATMENT OF DISORDERS RELATED THERETO

This application is a national stage application under 35 U.S.C. § 371 of PCT//US2021/056693, filed on Oct. 26, 2021, which claims the benefit of U.S. Provisional Patent Application No. 63/133,096, filed on Dec. 31, 2020, and U.S. Provisional Patent Application No. 63/106,069, filed on Oct. 27, 2020, the disclosures of which are hereby incorporated by reference in their entirety.

TECHNICAL FIELD

The present disclosure relates to compounds and pharmaceutical compositions thereof that modulate the activity of the 5-$HT_{2A}$ serotonin receptor. The compounds and pharmaceutical compositions thereof are useful in the treatment of diseases or disorders associated with the 5-$HT_{2A}$ serotonin receptor.

BACKGROUND

Receptors for serotonin (5-hydroxytryptamine, 5-HT) are an important class of G protein coupled receptors. Serotonin receptors are divided into seven subfamilies, referred to as 5-$HT_1$ through 5-$HT_7$, inclusive. These subfamilies are further divided into subtypes. For example, the 5-$HT_2$ subfamily is divided into three receptor subtypes: 5-$HT_{2A}$, 5-$HT_{2B}$, and 5-$HT_{2C}$. Certain modulators of 5-$HT_{2A}$ serotonin receptor activity are useful in the treatment of platelet aggregation, coronary artery disease, myocardial infarction, transient ischemic attack, angina, stroke, atrial fibrillation, blood clot formation, or symptoms thereof.

There is a need for compounds that can be used to treat disorders related to the 5-$HT_{2A}$ serotonin receptor, including disorders of the cardiovascular system. In particular, there is a need for compounds that possess physical and chemical stability and favorable pharmacokinetic properties.

SUMMARY

The present disclosure relates in some embodiments to a compound of Formula (I):

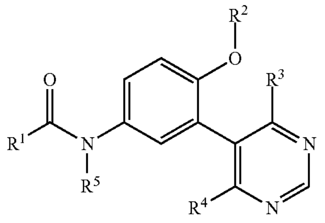

(I)

or a pharmaceutically acceptable salt thereof, wherein $R^1$, $R^2$, $R^3$, and $R^4$ are as defined herein.

In some embodiments, the present disclosure relates to a pharmaceutical composition comprising a compound of Formula (I) or a pharmaceutically acceptable salt thereof, and a pharmaceutically acceptable carrier.

In some embodiments, the present disclosure relates to a method of treating a $5HT_{2A}$-related disorder in an individual in need thereof, comprising prescribing and/or administering a therapeutically effective amount of a compound or pharmaceutical composition as disclosed herein.

In some embodiments, the $5HT_{2A}$-related disorder is selected from the group consisting of coronary artery disease, myocardial infarction, transient ischemic attack, angina, stroke, blood clot formation, atrial fibrillation, or symptoms thereof.

In some embodiments, the $5HT_{2A}$-related disorder is related to conditions associated with platelet aggregation.

In some embodiments, the $5HT_{2A}$-related disorder pertains to methods for reducing the risk of blood clot formation.

In some embodiments, the $5HT_{2A}$-related disorder pertains to methods for reducing the risk of blood clot formation in an angioplasty or coronary bypass surgery.

In some embodiments, the $5HT_{2A}$-related disorder pertains to methods for reducing the risk of blood clot formation in an individual suffering from atrial fibrillation.

In some embodiments, the $5HT_{2A}$-related disorder is related to the effects of percutaneous coronary intervention (PCI), such as microvascular obstruction (MVO), myocardial injury, reduced cardiac function (such as reduced left ventricular (LV) function), or a major adverse cardiac event (MACE) following PCI. In some embodiments, the $5HT_{2A}$-related disorder is related to MVO following PCI for acute coronary syndrome (ACS). In some embodiments, the ACS is ST-elevation myocardial infarction (STEMI), non-ST-elevation myocardial infarction (NSTEMI), or unstable angina. In some embodiments, the $5HT_{2A}$-related disorder is MVO or myocardial injury.

In some embodiments, the $5HT_{2A}$-related disorder is Raynaud's (also referred to as Raynaud/Raynaud's syndrome, Raynaud/Raynaud's disease, and/or Raynaud/Raynaud's phenomenon). In some embodiments, the $5HT_{2A}$-related disorder is secondary Raynaud's. In some embodiments, the $5HT_{2A}$-related disorder is Raynaud's secondary to systemic sclerosis (SSc-RP).

Also provided in the present disclosure is a method of modulating a 5-$HT_{2A}$ receptor in a cell, comprising contacting the receptor with a compound of Formula (I) or pharmaceutically acceptable salt thereof.

Other features and advantages of the processes, formulations, and uses provided herein will be apparent from the following detailed description and from the claims.

DETAILED DESCRIPTION

Definitions

For clarity and consistency, the following definitions will be used throughout this patent document.

The term "agonists" is intended to mean moieties that interact and activate the receptor, such as the 5-$HT_{2A}$ serotonin receptor, and initiate a physiological or pharmacological response characteristic of that receptor. For example, when moieties activate the intracellular response upon binding to the receptor, or enhance GTP binding to membranes.

The term "antagonists" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

The term "contact or contacting" is intended to mean bringing the indicated moieties together, whether in an in vitro system or an in vivo system. Thus, "contacting" a $5\text{-HT}_{2A}$ serotonin receptor with a compound of the invention includes the administration of a compound of the present invention to an individual, preferably a human, having a $5\text{-HT}_{2A}$ serotonin receptor, as well as, for example, introducing a compound of the invention into a sample containing a cellular or more purified preparation containing a $5\text{-HT}_{2A}$ serotonin receptor.

The term "inverse agonists" is intended to mean moieties that bind to the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The term "modulate or modulating" is intended to mean an increase or decrease in the amount, quality, response or effect of a particular activity, function or molecule.

As used herein, "administering" means to provide a compound or other therapy, remedy, or treatment such that an individual internalizes a compound.

The term "prescribing" refers to order, authorize, or recommend the use of a drug or other therapy, remedy, or treatment. In some embodiments, a health care provider orally advises, recommends, or authorizes the use of a compound, dosage regimen, or other treatment to an individual. The health care provider may or may not provide a written prescription for the compound, dosage regimen, or treatment. Further, the health care provider may or may not provide the compound or treatment to the individual. For example, the health care provider can advise the individual where to obtain the compound without providing the compound. In some embodiments, a health care provider can provide a written prescription for the compound, dosage regimen, or treatment to the individual. A prescription can be written on paper or recorded on electronic media. In addition, a prescription can be called in (oral) or faxed in (written) to a pharmacy or a dispensary. In some embodiments, a sample of the compound or treatment is given to the individual. As used herein, giving a sample of a compound constitutes an implicit prescription for the compound. Different health care systems around the world use different methods for prescribing and administering compounds or treatments, and these methods are encompassed by the disclosure herein.

A health care provider can include, for example, a physician, nurse, nurse practitioner, or other health care professional who can prescribe or administer compounds (drugs) for the disorders disclosed herein. In addition, a health care provider can include anyone who can recommend, prescribe, administer, or prevent an individual from receiving a compound or drug, including, for example, an insurance provider.

The terms "in need of treatment" and "in need thereof" when referring to treatment, are used interchangeably to mean a judgment made by a caregiver (e.g., physician, nurse, or nurse practitioner in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the disclosure. Accordingly, the compounds of the disclosure can be used in a protective or preventive manner; or compounds of the disclosure can be used to alleviate, inhibit, or ameliorate the disease, condition, or disorder.

The term "individual" refers to any animal, including mammals such as mice, rats, and other rodents, rabbits, dogs, cats, swine, cattle, sheep, horses, primates, and humans. In some embodiments, "individual" refers to humans.

The term "composition" refers to a compound or crystalline form thereof, including but not limited to, salts, solvates, and hydrates of a compound of the present invention, in combination with at least one additional component, such as, a composition obtained/prepared during synthesis, preformulation, in-process testing (i.e., TLC, HPLC, NMR samples), and the like.

The term "hydrate" as used herein means a compound of the invention or a salt thereof that further includes a stoichiometric or non-stoichiometric amount of water bound by non-covalent intermolecular forces.

The term "pharmaceutical composition" refers to a specific composition comprising at least one active ingredient, including but not limited to, salts, solvates, and hydrates of compounds of the present disclosure, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The phrase "pharmaceutically acceptable salts, solvates, and hydrates" when referring to a compound/compounds as described herein embraces pharmaceutically acceptable solvates and/or hydrates of the compound/compounds, pharmaceutically acceptable salts of the compound/compounds, as well as pharmaceutically acceptable solvates and/or hydrates of pharmaceutically acceptable salts of the compound/compounds. It is also understood that when the phrase "pharmaceutically acceptable solvates and hydrates" or the phrase "pharmaceutically acceptable solvate or hydrate" is used when referring to a compound/compounds as described herein that are salts, it embraces pharmaceutically acceptable solvates and/or hydrates of such salts. It is also understood by a person of ordinary skill in the art that hydrates are a subgenus of solvates.

The term "compound," as used herein, is meant to include all stereoisomers, geometric isomers, tautomers, and isotopes of the structures depicted, unless otherwise specified. All compounds, and pharmaceutically acceptable salts thereof, can be found together with other substances such as water and solvents (e.g., in the form of hydrates and solvates) or can be isolated. For example, the term "solvate," as used herein, means a compound or a salt thereof that further includes a stoichiometric or non-stoichiometric amount of a solvent bound by non-covalent intermolecular forces. Exemplary solvents are volatile, non-toxic, and/or acceptable for administration to humans in trace amounts. The term "hydrate" as used herein means a compound or a salt thereof that further includes a stoichiometric or non-stoichiometric amount of water bound by non-covalent intermolecular forces. The term "compound" is also meant to be agnostic as to how the compound is formed, be it synthetically or biologically. For example, a compound of the present disclosure can be produced in the body through metabolism.

The terms "prevent," "preventing," and "prevention" refer to the elimination or reduction of the occurrence or onset of one or more symptoms associated with a particular disorder. For example, the terms "prevent," "preventing," and "prevention" can refer to the administration of therapy on a prophylactic or preventative basis to an individual who may ultimately manifest at least one symptom of a disorder but who has not yet done so. Such individuals can be identified on the basis of risk factors that are known to correlate with the subsequent occurrence of the disease, such as the presence of a biomarker. Alternatively, prevention therapy can be administered as a prophylactic measure without prior identification of a risk factor. Delaying the onset of the at least one episode and/or symptom of a disorder can also be considered prevention or prophylaxis.

The terms "treat," "treating," and "treatment" refer to the administration of therapy to an individual who already manifests, or who has previously manifested, at least one symptom of a disease, disorder, condition, dependence, or behavior. For example, "treating" can include any of the following with respect to a disease, disorder, condition, dependence, or behavior: alleviating, abating, ameliorating, improving, inhibiting (e.g., arresting the development), relieving, or causing regression. "Treating" can also include treating the symptoms, preventing additional symptoms, preventing the underlying physiological causes of the symptoms, or stopping the symptoms (either prophylactically and/or therapeutically) of a disease, disorder, condition, dependence, or behavior. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder.

The term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which can include one or more of the following:

(1) preventing the disorder, for example, preventing a disease, condition, or disorder in an individual who may be predisposed to the disease, condition, or disorder but does not yet experience or display the relevant pathology or symptomatology;

(2) inhibiting the disorder, for example, inhibiting a disease, condition, or disorder in an individual who is experiencing or displaying the relevant pathology or symptomatology (i.e., arresting further development of the pathology and/or symptomatology); and (3) ameliorating the disorder, for example, ameliorating a disease, condition, or disorder in an individual who is experiencing or displaying the relevant pathology or symptomatology (i.e., reversing the pathology and/or symptomatology).

In some embodiments, the term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which includes preventing the disorder, for example, preventing a disease, condition, or disorder in an individual who may be predisposed to the disease, condition, or disorder but does not yet experience or display the relevant pathology or symptomatology.

In some embodiments, the term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which includes inhibiting the disorder, for example, inhibiting a disease, condition, or disorder in an individual who is experiencing or displaying the relevant pathology or symptomatology (i.e., arresting further development of the pathology and/or symptomatology).

In some embodiments, the term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which includes ameliorating the disorder, for example, ameliorating a disease, condition, or disorder in an individual who is experiencing or displaying the relevant pathology or symptomatology (i.e., reversing the pathology and/or symptomatology).

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "alkoxy" means an alkyl-O— group in which the alkyl group is as described herein. Exemplary alkoxy groups include methoxy, ethoxy, n-propoxy, i-propoxy, n-butoxy, s-butoxy, t-butoxy, pentoxy, hexoxy and heptoxy, and also the linear or branched positional isomers thereof.

As used herein, "cycloalkyl" means a non-aromatic cyclic ring system containing only carbon atoms in the ring system backbone, such as cyclopropyl, cyclobutyl, cyclopentyl, cyclohexyl, and cyclohexenyl. Cycloalkyl may include multiple fused rings. Cycloalkyl may have any degree of saturation provided that none of the rings in the ring system are aromatic. Cycloalkyl groups can either be unsubstituted or substituted with one or more substituents. In some embodiments, cycloalkyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, and 2,3-dihydro-1H-indenyl. In some embodiments, the aryl is phenyl.

As used herein, "halo," "halide," or "halogen" refers to a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched alkyl substituted with one or more chloro, bromo, fluoro, and/or iodo atom(s). In some embodiments, a haloalkyl is a fluoroalkyl, wherein one or more of the hydrogen atoms have been substituted by fluoro. In some embodiments, haloalkyls are of 1 to 3 carbons in length (e.g., 1 to 2 carbons in length or 1 carbon in length).

As used herein, "haloalkylene" means a bivalent branched, or straight chain alkylene substituted with one or more chloro, bromo, fluoro, and/or iodo atom(s), such as chloromethylene, dichloromethylene, 1,1-dichloroethylene, and 1,2-dichloroehtylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "oxo" means =O, wherein the double bond is to a carbon atom.

As used herein, the term "heteroaryl" means a mono- or bicyclic group having 5 to 10 ring atoms, such as 5, 6, 8, 9, or 10 ring atoms, such as 5, 6, 9, or 10 ring atoms; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrrolo[2,3-6]pyridinyl, quinazolinyl, quinolinyl, thieno[2,3-c]pyridinyl, pyrazolo[3,4-6]pyridinyl, pyrazolo[3,4-c]pyridinyl, pyrazolo[4,3-c]pyridine, pyrazolo[4,3-6]pyridinyl, tetrazolyl, chromane, 2,3-dihydrobenzofuran, tetrahydroquinoline, and isoindoline. In some embodiments, the heteroaryl is selected from thienyl, pyridinyl, furyl, pyrazolyl, imidazolyl, isoindolinyl, pyranyl, pyrazinyl, and pyrimidinyl.

As used herein, "heterocyclyl" means a 3-14 membered, such as 3-11 membered, such as 3-8 membered nonaromatic mono-, bi- or tricyclic group comprising at least one heteroatom in the ring system backbone. Bicyclic and tricyclic heterocyclyl groups may include fused ring systems, spirocyclic ring systems, and bridged ring systems and may include multiple fused rings. In some embodiments, heterocyclyls have one to four heteroatom(s) independently selected from N, O, and S. In some embodiments, heterocyclyls have one to three heteroatom(s) independently selected from N, O, and S. In some embodiments, heterocyclyls have one to two heteroatom(s) independently selected from N, O, and S. In some embodiments, monocyclic heterocyclyls are 3-membered rings. In some embodiments, monocyclic heterocyclyls are 4-membered rings. In some embodiments, monocyclic heterocyclyls are 5-membered rings. In some embodiments, monocyclic heterocyclyls are 6-membered rings. In some embodiments, monocyclic heterocyclyls are 7-membered rings. As used herein, "monocyclic heterocyclyl" means a single nonaromatic cyclic ring comprising at least one heteroatom in the ring system backbone. Examples of heterocyclyls include aziridinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, and thiomorpholinyl. In some embodiments, the heterocyclyl is selected from azetidinyl, morpholinyl, piperazinyl, pyrrolidinyl, and tetrahydropyridinyl. As used herein, "bicyclic heterocyclyl" means a nonaromatic bicyclic ring system comprising at least one heteroatom in the ring system backbone. Examples of bicyclic heterocyclyls include 2-azabicyclo[1.1.0] butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, 2-oxa-5-azabicyclo[2.2.1]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, and 2-azabicyclo[2.2.2]octane. As used herein, "spirocyclic heterocyclyl" means a nonaromatic bicyclic ring system comprising at least one heteroatom in the ring system backbone and with the rings connected through just one atom. Examples of spirocyclic heterocyclyls include 2-azaspiro[2.2]pentane, 2-oxa-6-azaspiro[3.3]heptane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[3.5]nonane, 2,7-diazaspiro[3.5]nonane, 1,7-diazaspiro[4.5]decane, 2,5-diazaspiro[3.6]decane, 1-oxa-8-azaspiro[4.5]decane, 2-oxa-8-azaspiro[4.5]decane.

Compound of Formula (I)

Provided herein is a compound of Formula (I)

(I)

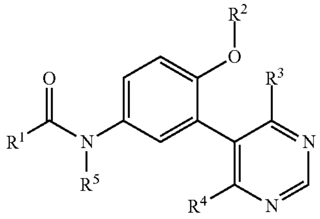

and pharmaceutically acceptable salts thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)

OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(=O)—($C_1$-$C_3$ alkyl), ($C_1$-$C_3$ alkylene)-$SO_2$—($C_1$-$C_3$ alkyl), and C(=NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S;

$R^3$ and $R^4$ are each independently selected from H, $C_1$-$C_6$ alkyl, and $C_1$-$C_6$ haloalkyl; and $R^5$ is selected from H and $C_1$-$C_6$ alkyl.

The Group $R^1$

In some embodiments, $R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl.

In some embodiments, $R^1$ is $C_1$-$C_6$ alkyl optionally substituted with one or more substituents independently selected from halogen and —O—($C_1$-$C_3$ alkyl).

In some embodiments, $R^1$ is $C_1$-$C_4$ alkyl optionally substituted with one or more substituents independently selected from fluorine, methoxy, and ethoxy.

In some embodiments, $R^1$ is methyl optionally substituted with one or more substituents independently selected from fluorine, methoxy, and ethoxy.

In some embodiments, $R^1$ is ethyl optionally substituted with one or more substituents independently selected from fluorine, methoxy, and ethoxy.

In some embodiments, $R^1$ is $C_3$-$C_6$ cycloalkyl optionally substituted with one or more substituents independently selected from halogen, —OH, $C_1$-$C_3$ haloalkyl, ($C_3$-$C_6$ cycloalkyl), —O—($C_1$-$C_3$ alkyl), ($C_1$-$C_3$ alkylene)-O—($C_1$-$C_3$ alkyl), and phenyl.

In some embodiments, $R^1$ is $C_3$-$C_6$ cycloalkyl optionally substituted with one or more substituents independently selected from fluorine, —OH, fluoromethyl, methoxy, ethoxy, and phenyl.

In some embodiments, $R^1$ is cyclobutyl optionally substituted with one or more substituents independently selected from fluorine and methoxy.

In some embodiments, $R^1$ is cyclopropyl optionally substituted with one or more substituents independently selected from fluorine, —OH, fluoromethyl, methoxy, ethoxy, and phenyl.

In some embodiments, $R^1$ is phenyl optionally substituted with one or more substituents independently selected from halogen, —CN, —$NH_2$, $C_1$-$C_3$ alkyl, ($C_1$-$C_3$ haloalkyl), and —O—($C_1$-$C_3$ alkyl).

In some embodiments, $R^1$ is phenyl optionally substituted with one or more substituents independently selected from fluorine, —CN, —$NH_2$, methyl, and methoxy.

In some embodiments, $R^1$ is ($C_1$-$C_3$ alkylene)-($C_3$-$C_6$ cycloalkyl), wherein the alkylene and cycloalkyl are each optionally substituted with one or more substituents independently selected from halogen, $C_1$-$C_3$ alkyl, and —O—($C_1$-$C_3$ alkyl).

In some embodiments, $R^1$ is ($C_1$-$C_3$ alkylene)-(cyclopropyl), wherein the alkylene and cyclopropyl are each optionally substituted with one or more substituents independently selected from halogen, $C_1$-$C_3$ alkyl, and —O—($C_1$-$C_3$ alkyl).

In some embodiments, $R^1$ is ($C_1$-$C_3$ alkylene)-(cyclopropyl), wherein the cyclopropyl is optionally substituted with methoxy.

In some embodiments, $R^1$ is ($C_1$-$C_3$ alkylene)-phenyl, wherein the alkylene and phenyl are each optionally substituted with one or more substituents independently selected from halogen, —$NH_2$, $C_1$-$C_3$ alkyl, ($C_1$-$C_3$ haloalkyl), and —O—($C_1$-$C_3$ alkyl).

In some embodiments, $R^1$ is ($C_1$-$C_3$ alkylene)-phenyl, wherein the alkylene and phenyl are each optionally substituted with one or more substituents independently selected from fluorine, —$NH_2$, methyl, and methoxy.

In some embodiments, $R^1$ is ($C_1$-$C_3$ haloalkylene)-phenyl, wherein the phenyl is optionally substituted with one or more substituents independently selected from halogen, —$NH_2$, $C_1$-$C_3$ alkyl, ($C_1$-$C_3$ haloalkyl), and —O—($C_1$-$C_3$ alkyl).

In some embodiments, $R^1$ is ($C_1$-$C_3$ haloalkylene)-phenyl, wherein the phenyl is optionally substituted with one or more substituents independently selected from fluorine, —$NH_2$, methyl, and methoxy.

In some embodiments, $R^1$ is 5-10 membered heteroaryl optionally substituted with one or more substituents independently selected from halogen, $C_1$-$C_3$ alkyl, and —O—($C_1$-$C_3$ alkyl).

In some embodiments, $R^1$ is 5-6 membered heteroaryl optionally substituted with one or more substituents independently selected from chlorine, fluorine, methyl, ethyl, isopropyl, and methoxy.

In some embodiments, $R^1$ is 5-6 membered heteroaryl selected from 1H-pyrrolyl, 1H-pyrazolyl, furanyl, isoxazolyl, oxazolyl, 1,2,4-oxadiazolyl, 1,2,5-oxadiazolyl, isothiazolyl, thiazolyl, 1,2,3-thiadiazolyl, 1H-1,2,4-triazolyl, pyridinyl, and pyrimidinyl, each of which is optionally substituted with one or more substituents independently selected from chlorine, fluorine, methyl, ethyl, isopropyl, and methoxy.

In some embodiments $R^1$ is selected from 1H-pyrrolyl, 1-methyl-1H-pyrrolyl, 3-fluoro-1-methyl-1H-pyrrolyl, 1H-pyrazolyl, 1-methyl-1H-pyrazolyl, 2-methyl-1H-pyrazolyl, 3-ethyl-1H-pyrazolyl, 3-isopropyl-1H-pyrazolyl, 1,4-dimethyl-1H-pyrazolyl, 1,5-dimethyl-1H-pyrazolyl, 4-fluoro-1-methyl-1H-pyrazolyl, 4-fluoro-2-methyl-1H-pyrazolyl, 3-ethyl-1-methyl-1H-pyrazolyl, furanyl, 2-methylfuranyl, 5-methylfuranyl, isoxazolyl, 3-methylisoxazolyl, 4-methylisoxazolyl, 5-methylisoxazolyl, oxazolyl, 2-methyloxazolyl, 4-methyloxazolyl, 5-methyloxazolyl, 2,4-dimethyloxazolyl, 2,5-dimethyloxazolyl, 1,2,4-oxadiazolyl, 3-methyl-1,2,4-oxadiazolyl, 5-methyl-1,2,4-oxadiazolyl, 3-methyl-1,2,5-oxadiazolyl, isothiazolyl, 3-methylisothiazolyl, 4-methylisothiazolyl, 5-methylisothiazolyl, thiazolyl, 2-methylthiazolyl, 4-methylthiazolyl, 5-methylthiazolyl, 2,4-dimethylthiazolyl, 2,5-dimethylthiazolyl, 4-methyl-1,2,3-thiadiazolyl, 2-isopropyl-4-methylthiazolyl, 1-methyl-1H-1,2,4-triazolyl, pyridinyl, 3-methoxypyridinyl, 4-methoxypyridinyl, 5-methoxypyridinyl, 4-chloropyridinyl, 3-fluoropyridinyl, 4-fluoropyridinyl, 5-fluoropyridinyl, pyrimidinyl, and 5-fluoropyrimidinyl.

In some embodiments, $R^1$ is ($C_1$-$C_3$ alkylene)-(5-10 membered heteroaryl) optionally substituted with one or more substituents independently selected from halogen, $C_1$-$C_3$ alkyl, and —O—($C_1$-$C_3$ alkyl).

In some embodiments, $R^1$ is ($C_1$-$C_3$ alkylene)-(5-10 membered heteroaryl) optionally substituted with one or more substituents independently selected from fluorine, methyl, ethyl, isopropyl, and methoxy.

In some embodiments, $R^1$ is ($C_1$-$C_3$ alkylene)-(5-10 membered heteroaryl), wherein the 5-10 membered heteroaryl is selected from 1,2,3,4-tetrahydropyrrolo[1,2-a]pyrazine, 4,5,6,7-tetrahydropyrazolo[1,5-a]pyrazine, 5,6,7,8-tetrahydroimidazo[1,2-a]pyrazine, 5,6,7,8-tetrahydro-[1,2,4]triazolo[4,3-a]pyrazine, 1H-pyrrolyl, 1H-pyrazolyl, furanyl, isoxazolyl, oxazolyl, 1,2,4-oxadiazolyl, 1,2,5-oxadiazolyl, isothiazolyl, thiazolyl, 1,2,3-thiadiazolyl, 1H-1,2,4-triazolyl, and pyridinyl, each of which is optionally substituted with one or more substituents independently selected from fluorine, methyl, ethyl, isopropyl, and methoxy.

In some embodiments, $R^1$ is ($C_1$-$C_3$ alkylene)-(5-10 membered heteroaryl), wherein the 5-10 membered heteroaryl is selected from 1H-pyrrolyl, 1-methyl-1H-pyrrolyl, 1H-pyrazolyl, 1-methyl-1H-pyrazolyl, 1,5-dimethyl-1H-pyrazolyl, isoxazolyl, 3-methylisoxazolyl, oxazolyl, 2-methyloxazolyl, 4-methyloxazolyl, thiazolyl, 2-methylthiazolyl, 4-methylthiazolyl, 5-methylthiazolyl, isothiazolyl, 1,2,4-oxadiazolyl, 3-methyl-1,2,4-oxadiazolyl, 5-methyl-1,2,4-oxadiazolyl, pyridinyl, 3-fluoropyridinyl, 1,2,3,4-tetrahydropyrrolo[1,2-a]pyrazinyl, 4,5,6,7-tetrahydropyrazolo[1,5-a]pyrazinyl, 5,6,7,8-tetrahydroimidazo[1,2-a]pyrazine, and 5,6,7,8-tetrahydro-[1,2,4]triazolo[4,3-a]pyrazine.

In some embodiments, $R^1$ is 5-9 membered heterocycloalkyl optionally substituted with one or more substituents independently selected from halogen and $C_1$-$C_3$ alkyl.

In some embodiments, $R^1$ is 5-9 membered heterocycloalkyl selected from tetrahydro-2H-pyranyl, tetrahydrofuranyl, 6-oxaspiro[2.5]octanyl, and 3-oxabicyclo[3.1.0]hexanyl, each of which is optionally substituted with one or more substituents independently selected from halogen and $C_1$-$C_3$ alkyl.

In some embodiments, $R^1$ is selected from 4-fluorotetrahydro-2H-pyranyl, tetrahydrofuranyl, and 3-oxabicyclo[3.1.0]hexanyl.

In some embodiments, $R^1$ is ($C_1$-$C_3$ alkylene)-(5-9 membered heterocycloalkyl), wherein the heterocycloalkyl is optionally substituted with one or more substituents independently selected from halogen and $C_1$-$C_3$ alkyl.

In some embodiments, $R^1$ is ($C_1$-$C_3$ alkylene)-(5-6 membered heterocycloalkyl), wherein the 5-6 membered heterocycloalkyl is selected from pyrrolidinyl and tetrahydrofuranyl, each of which is optionally substituted with one or more substituents independently selected from halogen and $C_1$-$C_3$ alkyl.

In some embodiments, $R^1$ is ($C_1$-$C_3$ alkylene)-O—($C_3$-$C_6$ cycloalkyl), wherein the cycloalkyl is optionally substituted with one or more substituents independently selected from halogen and $C_1$-$C_3$ alkyl.

In some embodiments, $R^1$ is selected from methylcyclopropoxy and methylcyclobutoxy.

In some embodiments, $R^1$ is ($C_1$-$C_3$ alkylene)-NH—($C_3$-$C_6$ cycloalkyl), wherein the cycloalkyl is optionally substituted with one or more substituents independently selected from halogen and $C_1$-$C_3$ alkyl.

In some embodiments, $R^1$ is selected from methylcyclopropanamine and methylcyclopentanamine.

The Group $R^2$

In some embodiments, $R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is 4-6 membered heterocycloalkyl optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is selected from azetidinyl, pyrrolidinyl, and piperidinyl, each of which is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is selected from azetidinyl, pyrrolidinyl, and piperidinyl, each of which is optionally substituted with one or more $C_1$-$C_3$ alkyl.

In some embodiments, $R^2$ is azetidinyl optionally substituted with methyl or ethyl.

In some embodiments, $R^2$ is ($C_1$-$C_3$ alkylene)-(4-10 membered heterocycloalkyl), wherein the heterocycloalkyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is ($C_1$-$C_3$ alkylene)-(4-10 membered heterocycloalkyl) and the 4-10 membered heterocycloalkyl is selected from azetidinyl, pyrrolidinyl, piperidinyl, piperazinyl, morpholinyl, 3-azabicyclo[3.1.0]hexanyl, 2-oxa-5-azabicyclo[2.2.1]heptanyl, 3-oxa-6-azabicyclo[3.1.1]heptanyl, octahydropyrrolo[1,2-hexahydro-3H-oxazolo[3,4-a]pyrazinyl, 1,4-oxazepanyl, 2-oxa-6-a]pyrazinyl, azaspiro[3.3]heptanyl, 6-oxa-1-azaspiro[3.3]heptanyl, 1,7-diazaspiro[3.5]nonanyl, 2,7-diazaspiro[3.5]nonanyl, 1-oxa-8-azaspiro[4.5]decanyl, and 2-oxa-8-azaspiro[4.5]decanyl, each of which is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is an optionally substituted ($C_1$-$C_3$ alkyl)-(4-10 membered heterocycloalkyl), where the 4-10 membered heterocycloalkyl is selected from azetidinyl, azetidinyl-3-ol, 3-fluoroazetidinyl, pyrrolidinyl, pyrrolidinyl-3-ol, 3-methoxypyrrolidinyl, 2-(pyrrolidin-3-yl)acetic acid, piperidinyl, piperidinyl-4-ol, 2-(piperidin-4-yl)acetic acid, 4-methoxypiperidinyl, piperazinyl, piperazinyl-1-carbaldehyde, 1-methylpiperazinyl-2-one, 1-(piperazin-1-yl)ethan-1-one, 1-(methylsulfonyl) piperazinyl, 2-hydroxy-1-(piperazin-1-yl)ethan-1-one, 2-oxo-2-(piperazin-1-yl)acetic acid, morpholinyl, 3-azabicyclo[3.1.0]hexanyl, 2-oxa-5-azabicyclo[2.2.1]heptanyl, 3-oxa-6-azabicyclo[3.1.1]heptanyl, octahydropyrrolo[1,2-a]pyrazinyl, hexahydropyrrolo[1,2-a]pyrazinyl-6 (2H)-one, hexahydro-3H-oxazolo[3,4-a]pyrazinyl, hexahydro-3H-oxazolo[3,4-a]pyrazinyl-3-one, 1,4-oxazepanyl-7-one, 2-oxa-6-azaspiro[3.3]heptanyl, 6-oxa-1-azaspiro[3.3]heptanyl, 1,7-diazaspiro[3.5]nonanyl, 1,7-diazaspiro[3.5]nonanyl-2-one, 2,7-diazaspiro[3.5]nonanyl, 2,7-diazaspiro[3.5]nonanyl-1-one, 1-oxa-8-azaspiro[4.5]decanyl, 1-oxa-8-azaspiro[4.5]decanyl-2-one, 2-oxa-8-azaspiro[4.5]decanyl, and 2-oxa-8-azaspiro[4.5]decanyl-1-one.

In some embodiments, $R^2$ is ($C_1$-$C_3$ alkylene)-(4-10 membered heterocycloalkyl) and the 4-10 membered heterocycloalkyl is azetidinyl optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is ($C_1$-$C_3$ alkylene)-(4-10 membered heterocycloalkyl) and the 4-10 membered heterocycloalkyl is pyrrolidinyl optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is ($C_1$-$C_3$ alkylene)-(4-10 membered heterocycloalkyl) and the 4-10 membered heterocycloalkyl is morpholinyl optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^2$ is ($C_1$-$C_3$ alkylene)-$NR^{2A}R^{2B}$.

In some embodiments, $R^2$ is $CH_2$—$NR^{2A}R^{2B}$.

In some embodiments, $R^2$ is $(CH_2)_2$—$NR^{2A}R^{2B}$.

In some embodiments, $R^2$ is $(CH_2)_3$—$NR^{2A}R^{2B}$.

The groups $R^{2A}$ and $R^{2B}$

In some embodiments, $R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S.

In some embodiments, $R^{2A}$ is selected from H and $C_1$-$C_3$ alkyl.

In some embodiments, $R^{2B}$ is selected from $C_1$-$C_3$ alkyl, $C_3$-$C_6$ cycloalkyl, $C_1$-$C_3$ haloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl).

In some embodiments, $R^{2A}$ is H and $R^{2B}$ is selected from ($C_1$-$C_3$ alkylene)-O—($C_1$-$C_3$ alkyl) and C(═NH)($C_1$-$C_3$ alkyl).

In some embodiments, $R^{2A}$ is H and $R^{2B}$ is selected from 2-methoxyethyl and ethan-1-imine.

In some embodiments, $R^{2A}$ is $C_1$-$C_3$ alkyl and $R^{2B}$ is selected from $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), and ($C_1$-$C_3$ alkylene)-$SO_2$—($C_1$-$C_3$ alkyl).

In some embodiments, $R^{2A}$ is $C_1$-$C_3$ alkyl and $R^{2B}$ is selected from methyl, ethyl, propyl, 2-fluoroethyl, 2-methoxyethyl, ethan-1-ol, cyclopropylmethyl, cyclobutyl, 2-(methylsulfinyl)ethyl, and 2-(methylsulfonyl)ethyl.

In some embodiments, $R^{2A}$ and $R^{2B}$, taken together with the nitrogen to which they are attached, form an aziridinyl ring optionally substituted with one or more $C_1$-$C_3$ alkyl.

In some embodiments, $R^{2A}$ and $R^{2B}$, taken together with the nitrogen to which they are attached, form an azetidinyl ring optionally substituted with one or more substituents independently selected from halogen, —OH, and $C_1$-$C_3$ alkyl.

In some embodiments, $R^{2A}$ and $R^{2B}$, taken together with the nitrogen to which they are attached, form an azetidinyl ring optionally substituted with fluorine.

In some embodiments, $R^{2A}$ and $R^{2B}$, taken together with the nitrogen to which they are attached, form an azetidinyl ring optionally substituted with —OH.

In some embodiments, $R^{2A}$ and $R^{2B}$, taken together with the nitrogen to which they are attached, form a pyrrolidinyl ring optionally substituted with one or more substituents independently selected from —OH, $C_1$-$C_3$ alkyl, —O—($C_1$-$C_3$ alkyl), and ($C_1$-$C_3$ alkylene)-C(O)OH.

In some embodiments, $R^{2A}$ and $R^{2B}$, taken together with the nitrogen to which they are attached, form a pyrrolidinyl ring optionally substituted with methoxy.

In some embodiments, $R^{2A}$ and $R^{2B}$, taken together with the nitrogen to which they are attached, form a pyrrolidinyl ring optionally substituted with ($C_2$ alkylene)-C(O)OH.

In some embodiments, $R^{2A}$ and $R^{2B}$, taken together with the nitrogen to which they are attached, form a piperidinyl ring optionally substituted with one or more substituents independently selected from —OH, $C_1$-$C_3$ alkyl, O—($C_1$-$C_3$ alkyl), and ($C_1$-$C_3$ alkylene)-C(O)OH.

In some embodiments, $R^{2A}$ and $R^{2B}$, taken together with the nitrogen to which they are attached, form a piperidinyl ring optionally substituted with methoxy.

In some embodiments, $R^{2A}$ and $R^{2B}$, taken together with the nitrogen to which they are attached, form a piperidinyl ring optionally substituted with ($C_2$ alkylene)-C(O)OH.

In some embodiments, $R^{2A}$ and $R^{2B}$, taken together with the nitrogen to which they are attached, form a morpholinyl ring optionally substituted with one or more $C_1$-$C_3$ alkyl.

In some embodiments, $R^{2A}$ and $R^{2B}$, taken together with the nitrogen to which they are attached, form a thiomorpholinyl ring optionally substituted with one or more $C_1$-$C_3$ alkyl.

In some embodiments, $R^{2A}$ and $R^{2B}$, taken together with the nitrogen to which they are attached, form a piperazinyl ring optionally substituted with one or more substituents independently selected from oxo, $C_1$-$C_3$ alkyl, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments, $R^{2A}$ and $R^{2B}$, taken together with the nitrogen to which they are attached, form a piperazinyl ring optionally substituted with —C(O)H.

In some embodiments, $R^{2A}$ and $R^{2B}$, taken together with the nitrogen to which they are attached, form a piperazinyl ring optionally substituted with —C(O)$CH_3$.

In some embodiments, $R^{2A}$ and $R^{2B}$, taken together with the nitrogen to which they are attached, form a piperazinyl ring optionally substituted with —C(O)$CH_2$—OH.

In some embodiments, $R^{2A}$ and $R^{2B}$, taken together with the nitrogen to which they are attached, form a piperazinyl ring optionally substituted with —C(O)C(O)OH.

In some embodiments, $R^{2A}$ and $R^{2B}$, taken together with the nitrogen to which they are attached, form a piperazinyl ring optionally substituted with —$SO_2CH_3$.

In some embodiments, $R^{2A}$ and $R^{2B}$, taken together with the nitrogen to which they are attached, form a 3-azabicyclo [3.1.0]hexanyl ring optionally substituted with one or more $C_1$-$C_3$ alkyl.

In some embodiments, $R^{2A}$ and $R^{2B}$, taken together with the nitrogen to which they are attached, form a 2-oxa-5-azabicyclo[2.2.1]heptanyl ring optionally substituted with one or more $C_1$-$C_3$ alkyl.

In some embodiments, $R^{2A}$ and $R^{2B}$, taken together with the nitrogen to which they are attached, form a 3-oxa-6-azabicyclo[3.1.1]heptanyl ring optionally substituted with one or more $C_1$-$C_3$ alkyl.

In some embodiments, $R^{2A}$ and $R^{2B}$, taken together with the nitrogen to which they are attached, form a 1,4-oxazepanyl ring optionally substituted with one or more substituents independently selected from oxo and $C_1$-$C_3$ alkyl.

In some embodiments, $R^{2A}$ and $R^{2B}$, taken together with the nitrogen to which they are attached, form a 2-oxa-6-azaspiro[3.3]heptanyl ring optionally substituted with one or more $C_1$-$C_3$ alkyl.

In some embodiments, $R^{2A}$ and $R^{2B}$, taken together with the nitrogen to which they are attached, form a 6-oxa-1-azaspiro[3.3]heptanyl ring optionally substituted with one or more $C_1$-$C_3$ alkyl.

In some embodiments, $R^{2A}$ and $R^{2B}$, taken together with the nitrogen to which they are attached, form a 1,7-diazaspiro[3.5]nonanyl ring optionally substituted with one or more substituents independently selected from oxo and $C_1$-$C_3$ alkyl.

In some embodiments, $R^{2A}$ and $R^{2B}$, taken together with the nitrogen to which they are attached, form a 1,7-diazaspiro[3.5]nonanyl ring optionally substituted with oxo.

In some embodiments, $R^{2A}$ and $R^{2B}$, taken together with the nitrogen to which they are attached, form a 2,7-diazaspiro[3.5]nonanyl ring optionally substituted with one or more substituents independently selected from oxo and $C_1$-$C_3$ alkyl.

In some embodiments, $R^{2A}$ and $R^{2B}$, taken together with the nitrogen to which they are attached, form a 2,7-diazaspiro[3.5]nonanyl ring optionally substituted with oxo.

In some embodiments, $R^{2A}$ and $R^{2B}$, taken together with the nitrogen to which they are attached, form a 1-oxa-8-azaspiro[4.5]decanyl ring optionally substituted with one or more substituents independently selected from oxo and $C_1$-$C_3$ alkyl.

In some embodiments, $R^{2A}$ and $R^{2B}$, taken together with the nitrogen to which they are attached, form a 1-oxa-8-azaspiro[4.5]decanyl ring optionally substituted with oxo.

In some embodiments, $R^{2A}$ and $R^{2B}$, taken together with the nitrogen to which they are attached, form a 2-oxa-8-azaspiro[4.5]decanyl ring optionally substituted with one or more substituents independently selected from oxo and $C_1$-$C_3$ alkyl.

In some embodiments, $R^{2A}$ and $R^{2B}$, taken together with the nitrogen to which they are attached, form a 2-oxa-8-azaspiro[4.5]decanyl ring optionally substituted with oxo.

In some embodiments, $R^{2A}$ and $R^{2B}$, taken together with the nitrogen to which they are attached, form an octahydropyrrolo[1,2-a]pyrazinyl ring optionally substituted with one or more substituents independently selected from oxo and $C_1$-$C_3$ alkyl.

In some embodiments, $R^{2A}$ and $R^{2B}$, taken together with the nitrogen to which they are attached, form an octahydropyrrolo[1,2-a]pyrazinyl ring optionally substituted with OXO.

In some embodiments, $R^{2A}$ and $R^{2B}$, taken together with the nitrogen to which they are attached, form a hexahydro-3H-oxazolo[3,4-a]pyrazinyl ring optionally substituted with one or more substituents independently selected from oxo and $C_1$-$C_3$ alkyl.

In some embodiments, $R^{2A}$ and $R^{2B}$, taken together with the nitrogen to which they are attached, form a hexahydro-3H-oxazolo[3,4-a]pyrazinyl ring optionally substituted with oxo.

The groups $R^3$ and $R^4$

In some embodiments, $R^3$ and $R^4$ are each independently selected from H, $C_1$-$C_6$ alkyl, and $C_1$-$C_6$ haloalkyl.

In some embodiments, one of $R^3$ and $R^4$ is H and the other is $C_1$-$C_6$ alkyl.

In some embodiments, one of $R^3$ and $R^4$ is H and the other is methyl.

In some embodiments, $R^3$ and $R^4$ are each $C_1$-$C_6$ alkyl.

In some embodiments, $R^3$ and $R^4$ are each $C_1$-$C_3$ alkyl.

In some embodiments, $R^3$ and $R^4$ are each methyl.

In some embodiments, $R^3$ and $R^4$ are each H.

In some embodiments, the compound of Formula (I) is a compound of Formula (Ia):

(Ia)

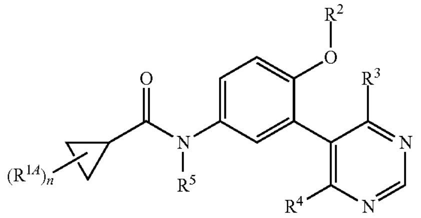

and pharmaceutically acceptable salts thereof, wherein:

each $R^{1A}$ is independently selected from halogen, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(=NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S;

$R^3$ and $R^4$ are each independently selected from H, $C_1$-$C_6$ alkyl, and $C_1$-$C_6$ haloalkyl;

$R^5$ is selected from H and $C_1$-$C_6$ alkyl; and n is 0, 1, 2, 3, 4, or 5.

In some embodiments of the compound of Formula (Ia):

$R^{1A}$ is selected from H, halogen, —OH, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(=NH)($C_1$-$C_3$ alkyl);

or $R^{2A}$ and $R^{2B}$, taken together with the nitrogen to which they are attached, form a 3-9 membered heterocycloalkyl ring optionally substituted with one or more $C_1$-$C_3$ alkyl, and optionally containing one additional heteroatom selected from the group of N, O, and S;

$R^3$ and $R^4$ are each independently selected from H and $C_1$-$C_6$ alkyl;

$R^5$ is selected from H and $C_1$-$C_6$ alkyl; and n is 0, 1, or 2.

In some embodiments of the compound of Formula (Ia), $R^{1A}$ is H.

In some embodiments of the compound of Formula (Ia), $R^{1A}$ is halogen. In some embodiments, $R^{1A}$ is fluorine.

In some embodiments of the compound of Formula (Ia), $R^{1A}$ is —OH.

In some embodiments of the compound of Formula (Ia), $R^{1A}$ is $C_1$-$C_3$ haloalkyl. In some embodiments, $R^{1A}$ is fluoromethyl.

In some embodiments of the compound of Formula (Ia), $R^{1A}$ is —O—($C_1$-$C_3$ alkyl).

In some embodiments, $R^{1A}$ is methoxy. In some embodiments, $R^{1A}$ is ethoxy.

In some embodiments of the compound of Formula (Ia), $R^{1A}$ is phenyl.

In some embodiments of the compound of Formula (Ia), $R^5$ is H.

In some embodiments of the compound of Formula (Ia), $R^5$ is methyl.

In some embodiments of the compound of Formula (Ia), n is 0.

In some embodiments of the compound of Formula (Ia), n is 1.

In some embodiments of the compound of Formula (Ia), n is 2.

In some embodiments, the compound of Formula (I) is a compound of Formula (Ia'):

(Ia')

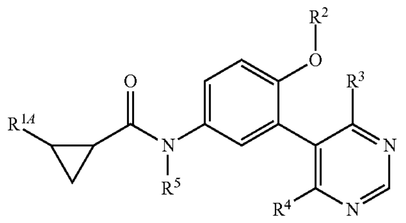

and pharmaceutically acceptable salts thereof, wherein:

$R^{1A}$ is selected from halogen, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(=NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S; and $R^3$ and $R^4$ are each independently selected from H, $C_1$-$C_6$ alkyl, and $C_1$-$C_6$ haloalkyl; and $R^5$ is selected from H and $C_1$-$C_6$ alkyl.

In some embodiments of the compound of Formula (Ia'):

$R^{1A}$ is selected from H, halogen, —OH, $C_1$-$C_3$ haloalkyl, ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, $C_1$-$C_3$ alkyl, —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(=NH)($C_1$-$C_3$ alkyl);

or $R^{2A}$ and $R^{2B}$, taken together with the nitrogen to which they are attached, form a 3-9 membered heterocycloalkyl ring optionally substituted with one or more $C_1$-$C_3$ alkyl, and optionally containing one additional heteroatom selected from the group of N, O, and S; and $R^3$ and $R^4$ are each independently selected from H and $C_1$-$C_6$ alkyl; and $R^5$ is selected from H and $C_1$-$C_6$ alkyl.

In some embodiments of the compound of Formula (Ia'), $R^{1A}$ is H.

In some embodiments of the compound of Formula (Ia'), $R^{1A}$ is halogen. In some embodiments, $R^{1A}$ is fluorine.

In some embodiments of the compound of Formula (Ia'), $R^{1A}$ is —O—($C_1$-$C_3$ alkyl). In some embodiments, $R^{1A}$ is ethoxy.

In some embodiments of the compound of Formula (Ia'), $R^5$ is H.

In some embodiments of the compound of Formula (Ia'), $R^5$ is methyl.

In some embodiments, the compound of Formula (I) is a compound of Formula (Ia"):

(Ia")

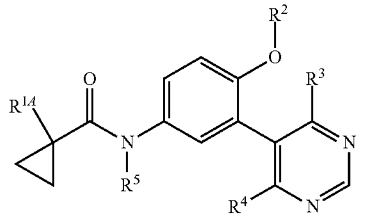

and pharmaceutically acceptable salts thereof, wherein:

$R^{1A}$ is selected from halogen, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S; and $R^3$ and $R^4$ are each independently selected from H, $C_1$-$C_6$ alkyl, and $C_1$-$C_6$ haloalkyl; and $R^5$ is selected from H and $C_1$-$C_6$ alkyl.

In some embodiments of the compound of Formula (Ia'):

$R^{1A}$ is selected from H, halogen, —OH, $C_1$-$C_3$ haloalkyl, ($C_3$-$C_6$ cycloalkyl), —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkyl)-C(O)OH, —C(O)H, —C(O)($C_1$-$C_3$ alkyl), —C(O)($C_1$-$C_3$ alkyl)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl);

or $R^{2A}$ and $R^{2B}$, taken together with the nitrogen to which they are attached, form a 3-9 membered heterocycloalkyl ring optionally substituted with one or more $C_1$-$C_3$ alkyl, and optionally containing one additional heteroatom selected from the group of N, O, and S; and $R^3$ and $R^4$ are each independently selected from H and $C_1$-$C_6$ alkyl; and $R^5$ is selected from H and $C_1$-$C_6$ alkyl.

In some embodiments of the compound of Formula (Ia"), $R^{1A}$ is H.

In some embodiments of the compound of Formula (Ia"), $R^{1A}$ is halogen. In some embodiments, $R^{1A}$ is fluorine.

In some embodiments of the compound of Formula (Ia"), $R^{1A}$ is —OH.

In some embodiments of the compound of Formula (Ia"), $R^{1A}$ is $C_1$-$C_3$ haloalkyl. In some embodiments, $R^{1A}$ is fluoromethyl.

In some embodiments of the compound of Formula (Ia"), $R^{1A}$ is —O—($C_1$-$C_3$ alkyl). In some embodiments, $R^{1A}$ is methoxy. In some embodiments, $R^{1A}$ is ethoxy.

In some embodiments of the compound of Formula (Ia"), $R^{1A}$ is phenyl.

In some embodiments of the compound of Formula (Ia"), $R^5$ is H.

In some embodiments of the compound of Formula (Ia"), $R^5$ is methyl.

In some embodiments of the compounds of Formulas (Ia), (Ia'), and (Ia"), $R^2$ is 4-6 membered heterocycloalkyl. In some embodiments, $R^2$ is selected from azetidinyl, pyrrolidinyl, and piperidinyl. In some embodiments, $R^2$ is azetidinyl. In some embodiments, $R^2$ is pyrrolidinyl. In some embodiments, $R^2$ is piperidinyl.

In some embodiments of the compounds of Formulas (Ia), (Ia'), and (Ia"), $R^2$ is ($C_1$-$C_3$ alkylene)-(4-10 membered heterocycloalkyl), wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments of the compounds of Formulas (Ia), (Ia'), and (Ia"), $R^2$ is ($C_1$ alkylene)-(4-6 membered heterocycloalkyl). In some embodiments, the 4-6 membered heterocycloalkyl is selected from azetidinyl, pyrrolidinyl, piperidinyl, and morpholinyl. In some embodiments, the 4-6 membered heterocycloalkyl is azetidinyl. In some embodiments, the 4-6 membered heterocycloalkyl is pyrrolidinyl. In some embodiments, the 4-6 membered heterocycloalkyl is piperidinyl. In some embodiments, the 4-6 membered heterocycloalkyl is morpholinyl.

In some embodiments of the compounds of Formulas (Ia), (Ia'), and (Ia"), $R^2$ is ($C_2$ alkylene)-(4-10 membered heterocycloalkyl), wherein the heterocycloalkyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl).

In some embodiments of the compounds of Formulas (Ia), (Ia'), and (Ia"), $R^2$ is ($C_2$ alkylene)-(4-10 membered heterocycloalkyl), wherein the heterocycloalkyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl), and wherein the heterocycloalkyl is connected to the ($C_2$ alkylene)- at a carbon atom of the heterocycloalkyl, wherein the carbon atom of the heterocycloalkyl has(S) stereochemistry.

In some embodiments of the compounds of Formulas (Ia), (Ia'), and (Ia"), $R^2$ is ($C_2$ alkylene)-(4-10 membered heterocycloalkyl), wherein the heterocycloalkyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl), and wherein the heterocycloalkyl is connected to the ($C_2$ alkylene)- at a carbon atom of the heterocycloalkyl, wherein the carbon atom of the heterocycloalkyl has (R) stereochemistry.

In some embodiments of the compounds of Formulas (Ia), (Ia'), and (Ia"), $R^2$ is ($C_2$ alkylene)-(azetidinyl), wherein the azetidinyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl). In some embodiments of the compounds of Formulas (Ia), (Ia'), and (Ia"), $R^2$ is ($C_2$ alkylene)-(azetidinyl), wherein the azetidinyl is optionally substituted with halogen or —OH. In some embodiments, $R^2$ is ($C_2$ alkylene)-(azetidinyl), wherein the azetidinyl is optionally substituted with fluorine. In some embodiments, $R^2$ is ($C_2$ alkylene)-(azetidinyl), wherein the azetidinyl is optionally substituted with —OH. In some embodiments, $R^2$ is ($C_2$ alkylene)-(azetidinyl).

In some embodiments of the compounds of Formulas (Ia), (Ia'), and (Ia"), $R^2$ is ($C_2$ alkylene)-(pyrrolidinyl), wherein the pyrrolidinyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl). In some embodiments of the compounds of Formulas (Ia), (Ia'), and (Ia"), $R^2$ is ($C_2$ alkylene)-(pyrrolidinyl), wherein the pyrrolidinyl is optionally substituted with —O—($C_1$-$C_3$ alkyl) or ($C_1$-$C_3$ alkylene)-C(O)OH. In some embodiments, $R^2$ is ($C_2$ alkylene)-(pyrrolidinyl), wherein the pyrrolidinyl is optionally substituted with methoxy. In some embodiments, $R^2$ is ($C_2$ alkylene)-(pyrrolidinyl), wherein the pyrrolidinyl is optionally substituted with —$CH_2$—C(O)OH. In some embodiments, $R^2$ is ($C_2$ alkylene)-(pyrrolidinyl).

In some embodiments of the compounds of Formulas (Ia), (Ia'), and (Ia"), $R^2$ is ($C_2$ alkylene)-(piperidinyl), wherein the piperidinyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl). In some embodiments of the compounds of Formulas (Ia), (Ia'), and (Ia"), $R^2$ is ($C_2$ alkylene)-(piperidinyl), wherein the piperidinyl is optionally substituted with —O—($C_1$-$C_3$ alkyl) or ($C_1$-$C_3$ alkylene)-C(O)OH. In some embodiments, $R^2$ is ($C_2$ alkylene)-(piperidinyl), wherein the piperidinyl is optionally substituted with methoxy. In some embodiments, $R^2$ is ($C_2$ alkylene)-(piperidinyl), wherein the piperidinyl is optionally substituted with —$CH_2$—C(O)OH. In some embodiments, $R^2$ is ($C_2$ alkylene)-(piperidinyl).

In some embodiments of the compounds of Formulas (Ia), (Ia'), and (Ia"), $R^2$ is ($C_2$ alkylene)-(piperazinyl), wherein the piperazinyl is optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl). In some embodiments of the compounds of Formulas (Ia), (Ia'), and (Ia"), $R^2$ is ($C_2$ alkylene)-(piperazinyl), wherein the piperazinyl is optionally substituted with —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl). In some embodiments, $R^2$ is ($C_2$ alkylene)-(piperazinyl), wherein the piperazinyl is optionally substituted with —C(O)H. In some embodiments, $R^2$ is ($C_2$ alkylene)-(piperazinyl), wherein the piperazinyl is optionally substituted with —C(O)OH. In some embodiments, $R^2$ is ($C_2$ alkylene)-(piperazinyl), wherein the piperazinyl is optionally substituted with —C(O)($C_1$-$C_3$ alkyl). In some embodiments, $R^2$ is ($C_2$ alkylene)-(piperazinyl), wherein the piperazinyl is optionally substituted with —C(O)$CH_3$. In some embodiments, $R^2$ is ($C_2$ alkylene)-(piperazinyl), wherein the piperazinyl is optionally substituted with —C(O)($C_1$-$C_3$ alkylene)-OH. In some embodiments, $R^2$ is ($C_2$ alkylene)-(piperazinyl), wherein the piperazinyl is optionally substituted with —C(O)$CH_2$—OH. In some embodiments, $R^2$ is ($C_2$ alkylene)-(piperazinyl), wherein the piperazinyl is optionally substituted with —C(O)C(O)OH. In some embodiments, $R^2$ is ($C_2$ alkylene)-(piperazinyl), wherein the piperazinyl is optionally substituted with —$SO_2$($C_1$-$C_3$ alkyl). In some embodiments, $R^2$ is ($C_2$ alkylene)-(piperazinyl), wherein the piperazinyl is optionally substituted with —$SO_2CH_3$. In some embodiments, $R^2$ is ($C_2$ alkylene)-(piperazinyl).

In some embodiments of the compounds of Formulas (Ia), (Ia'), and (Ia"), $R^2$ is ($C_2$ alkylene)-(morpholinyl).

In some embodiments of the compounds of Formulas (Ia), (Ia'), and (Ia"), $R^2$ is ($C_2$ alkylene)-(3-azabicyclo[3.1.0]hexanyl).

In some embodiments of the compounds of Formulas (Ia), (Ia'), and (Ia"), $R^2$ is ($C_2$ alkylene)-(2-oxa-5-azabicyclo[2.2.1]heptanyl).

In some embodiments of the compounds of Formulas (Ia), (Ia'), and (Ia"), $R^2$ is ($C_2$ alkylene)-(2-oxa-6-azaspiro[3.3]heptanyl).

In some embodiments of the compounds of Formulas (Ia), (Ia'), and (Ia"), $R^2$ is ($C_2$ alkylene)-(octahydropyrrolo[1,2-a]pyrazinyl) optionally substituted with oxo. In some embodiments, $R^2$ is ($C_2$ alkylene)-(hexahydropyrrolo[1,2-a]pyrazinyl-6 (2H)-one).

In some embodiments of the compounds of Formulas (Ia), (Ia'), and (Ia"), $R^2$ is ($C_2$ alkylene)-(hexahydro-3H-oxazolo[3,4-a]pyrazinyl) optionally substituted with oxo. In some embodiments, $R^2$ is ($C_2$ alkylene)-(hexahydro-3H-oxazolo[3,4-a]pyrazinyl-3-one).

In some embodiments of the compounds of Formulas (Ia), (Ia'), and (Ia"), $R^2$ is ($C_2$ alkylene)-(1,7-diazaspiro[3.5]nonanyl) optionally substituted with oxo. In some embodiments, $R^2$ is ($C_2$ alkylene)-(1,7-diazaspiro[3.5]nonanyl-2-one).

In some embodiments of the compounds of Formulas (Ia), (Ia'), and (Ia"), $R^2$ is ($C_2$ alkylene)-(2,7-diazaspiro[3.5]nonanyl) optionally substituted with oxo. In some embodiments, $R^2$ is ($C_2$ alkylene)-(2,7-diazaspiro[3.5]nonanyl-1-one).

In some embodiments of the compounds of Formulas (Ia), (Ia'), and (Ia"), $R^2$ is ($C_2$ alkylene)-(1-oxa-8-azaspiro[4.5]decanyl) optionally substituted with oxo. In some embodiments, $R^2$ is ($C_2$ alkylene)-(1-oxa-8-azaspiro[4.5]decanyl-2-one).

In some embodiments of the compounds of Formulas (Ia), (Ia'), and (Ia"), $R^2$ is ($C_2$ alkylene)-(2-oxa-8-azaspiro[4.5]decanyl) optionally substituted with oxo. In some embodiments, $R^2$ is ($C_2$ alkylene)-(2-oxa-8-azaspiro[4.5]decanyl-1-one).

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl).

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is H and $R^{2B}$ is selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl).

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is H and $R^{2B}$ is selected from ($C_1$-$C_3$ alkylene)-O—($C_1$-$C_3$ alkyl) and C(═NH)($C_1$-$C_3$ alkyl).

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is H and $R^{2B}$ is selected from ($C_1$-$C_3$ alkylene)-O-(2-methoxyethyl) and C(═NH)$CH_3$.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl).

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is selected from $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), and ($C_1$-$C_3$ alkylene)-$SO_2$—($C_1$-$C_3$ alkyl).

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is $C_1$-$C_3$ alkyl. In some embodiments, $R^{2A}$ is $C_1$-$C_3$ alkyl and $R^{2B}$ is selected from methyl, ethyl, and propyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is $C_1$-$C_3$ haloalkyl. In some embodiments, $R^{2A}$ is $C_1$-$C_3$ alkyl and $R^{2B}$ is 2-fluoroethyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is $C_3$-$C_6$ cycloalkyl. In some embodiments, $R^{2A}$ is $C_1$-$C_3$ alkyl and $R^{2B}$ is cyclopropyl or cyclobutyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-O—($C_1$-$C_3$ alkyl). In some embodiments, $R^{2A}$ is $C_1$-$C_3$ alkyl and $R^{2B}$ is 2-methoxyethyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-OH. In some embodiments, $R^{2A}$ is $C_1$-$C_3$ alkyl and $R^{2B}$ is ethan-1-ol.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-($C_3$-$C_6$ cycloalkyl). In some embodiments, $R^{2A}$ is $C_1$-$C_3$ alkyl and $R^{2B}$ is cyclopropylmethyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-$SO_2$—($C_1$-$C_3$ alkyl). In some embodiments, $R^{2A}$ is $C_1$-$C_3$ alkyl and $R^{2B}$ is 2-(methylsulfonyl)ethyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form a 3-9 membered heterocycloalkyl ring optionally substituted with one or more $C_1$-$C_3$ alkyl, and optionally containing one additional heteroatom selected from the group of N, O, and S.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form an aziridinyl ring optionally substituted with one or more $C_1$-$C_3$ alkyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form an azetidinyl ring optionally substituted with one or more $C_1$-$C_3$ alkyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form a pyrrolidinyl ring optionally substituted with one or more substituents independently selected from $C_1$-$C_3$ alkyl, —O—($C_1$-$C_3$ alkyl), and ($C_1$-$C_3$ alkylene)-C(O)OH.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form a piperidinyl ring optionally substituted with one or more $C_1$-$C_3$ alkyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form a morpholinyl ring optionally substituted with one or more $C_1$-$C_3$ alkyl.

In some embodiments of the compounds of Formulas (Ia), (Ia'), and (Ia"), $R^2$ is ($C_1$-$C_3$ alkylene)-$NR^{2A}R^{2B}$, wherein $R^{2A}$ and $R^{2B}$, taken together with the nitrogen to which they are attached, form a thiomorpholinyl ring optionally substituted with one or more $C_1$-$C_3$ alkyl.

In some embodiments of the compounds of Formulas (Ia), (Ia'), and (Ia"), $R^3$ and $R^4$ are each $C_1$-$C_6$ alkyl. In some embodiments of the compounds of Formulas (Ia), (Ia'), and (Ia"), $R^3$ and $R^4$ are each $C_1$-$C_3$ alkyl. In some embodiments of the compounds of Formulas (Ia), (Ia'), and (Ia"), $R^3$ and $R^4$ are each methyl.

In some embodiments, the compound of Formula (I) is a compound of Formula (Ib):

(Ib)

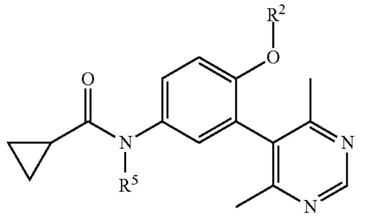

and pharmaceutically acceptable salts thereof, wherein:

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(=NH)($C_1$-$C_3$ alkyl);

or $R^{2A}$ and $R^{2B}$, taken together with the nitrogen to they are attached, form a 3-9 membered heterocycloalkyl ring optionally substituted with one or more $C_1$-$C_3$ alkyl, and optionally containing one additional heteroatom selected from the group of N, O, and S; and $R^5$ is selected from H and $C_1$-$C_6$ alkyl.

In some embodiments of the compound of Formula (Ib), $R^5$ is H.

In some embodiments of the compound of Formula (Ib), $R^5$ is methyl.

In some embodiments of the compound of Formula (Ib), $R^2$ is 4-6 membered heterocycloalkyl. In some embodiments, $R^2$ is selected from azetidinyl, pyrrolidinyl, and piperidinyl. In some embodiments, $R^2$ is azetidinyl. In some embodiments, $R^2$ is pyrrolidinyl. In some embodiments, $R^2$ is piperidinyl.

In some embodiments of the compound of Formula (Ib), $R^2$ is ($C_1$-$C_3$ alkylene)-(4-10 membered heterocycloalkyl), wherein the alkylene and heterocycloalkyl are each optionally substituted with one or more substituents independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

In some embodiments of the compound of Formula (Ib), $R^2$ is ($C_1$ alkylene)-(4-6 membered heterocycloalkyl). In some embodiments, the 4-6 membered heterocycloalkyl is selected from azetidinyl, pyrrolidinyl, and piperidinyl. In some embodiments, the 4-6 membered heterocycloalkyl is azetidinyl. In some embodiments, the 4-6 membered heterocycloalkyl is pyrrolidinyl. In some embodiments, the 4-6 membered heterocycloalkyl is piperidinyl.

In some embodiments of the compound of Formula (Ib), $R^2$ is ($C_2$ alkylene)-(4-10 membered heterocycloalkyl), wherein the heterocycloalkyl is optionally substituted with one or more substituents independently selected from halogen, oxo, —OH, —O—($C_1$-$C_3$ alkyl), ($C_1$-$C_3$ alkylene)-C(O)OH, —C(O)H, —C(O)($C_1$-$C_3$ alkyl), —C(O)C(O)OH, and —$SO_2$($C_1$-$C_3$ alkyl).

In some embodiments of the compound of Formula (Ib), $R^2$ is ($C_2$ alkylene)-(azetidinyl), wherein the azetidinyl is optionally substituted with halogen or —OH. In some embodiments, $R^2$ is ($C_2$ alkylene)-(azetidinyl), wherein the azetidinyl is optionally substituted with fluorine. In some embodiments, $R^2$ is ($C_2$ alkylene)-(azetidinyl), wherein the azetidinyl is optionally substituted with —OH. In some embodiments, $R^2$ is ($C_2$ alkylene)-(azetidinyl).

In some embodiments of the compound of Formula (Ib), $R^2$ is ($C_2$ alkylene)-(pyrrolidinyl), wherein the pyrrolidinyl is optionally substituted with —O—($C_1$-$C_3$ alkyl) or ($C_1$-$C_3$ alkylene)-C(O)OH. In some embodiments, $R^2$ is ($C_2$ alkylene)-(pyrrolidinyl), wherein the pyrrolidinyl is optionally substituted with methoxy. In some embodiments, $R^2$ is ($C_2$ alkylene)-(pyrrolidinyl), wherein the pyrrolidinyl is optionally substituted with —$CH_2$—C(O)OH. In some embodiments, $R^2$ is ($C_2$ alkylene)-(pyrrolidinyl).

In some embodiments of the compound of Formula (Ib), $R^2$ is ($C_2$ alkylene)-(piperidinyl), wherein the piperidinyl is optionally substituted with —O—($C_1$-$C_3$ alkyl) or ($C_1$-$C_3$ alkylene)-C(O)OH. In some embodiments, $R^2$ is ($C_2$ alkylene)-(piperidinyl), wherein the piperidinyl is optionally substituted with methoxy. In some embodiments, $R^2$ is ($C_2$ alkylene)-(piperidinyl), wherein the piperidinyl is optionally substituted with —$CH_2$—C(O)OH. In some embodiments, $R^2$ is ($C_2$ alkylene)-(piperidinyl).

In some embodiments of the compound of Formula (Ib), $R^2$ is ($C_2$ alkylene)-(piperazinyl), wherein the piperazinyl is optionally substituted with —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl). In some embodiments, $R^2$ is ($C_2$ alkylene)-(piperazinyl), wherein the piperazinyl is optionally substituted with —C(O)H. In some embodiments, $R^2$ is ($C_2$ alkylene)-(piperazinyl), wherein the piperazinyl is optionally substituted with —C(O)OH. In some embodiments, $R^2$ is ($C_2$ alkylene)-(piperazinyl), wherein the piperazinyl is optionally substituted with —C(O)($C_1$-$C_3$ alkyl). In some embodiments, $R^2$ is ($C_2$ alkylene)-(piperazinyl), wherein the piperazinyl is optionally substituted with —C(O)$CH_3$. In some embodiments, $R^2$ is ($C_2$ alkylene)-(piperazinyl), wherein the piperazinyl is optionally substituted with —C(O)($C_1$-$C_3$ alkylene)-OH. In some embodiments, $R^2$ is ($C_2$ alkylene)-(piperazinyl), wherein the piperazinyl is optionally substituted with —C(O)$CH_2$—OH. In some embodiments, $R^2$ is ($C_2$ alkylene)-(piperazinyl), wherein the piperazinyl is optionally substituted with —C(O)C(O)OH. In some embodiments, $R^2$ is ($C_2$ alkylene)-(piperazinyl), wherein the piperazinyl is optionally substituted with —$SO_2$($C_1$-$C_3$ alkyl). In some embodiments, $R^2$ is ($C_2$ alkylene)-(piperazinyl), wherein the piperazinyl is optionally substituted with —$SO_2CH_3$. In some embodiments, $R^2$ is ($C_2$ alkylene)-(piperazinyl).

In some embodiments of the compound of Formula (Ib), $R^2$ is ($C_2$ alkylene)-(morpholinyl).

In some embodiments of the compound of Formula (Ib), $R^2$ is ($C_2$ alkylene)-(3-azabicyclo[3.1.0]hexanyl).

In some embodiments of the compound of Formula (Ib), $R^2$ is ($C_2$ alkylene)-(2-oxa-5-azabicyclo[2.2.1]heptanyl).

In some embodiments of the compound of Formula (Ib), $R^2$ is ($C_2$ alkylene)-(2-oxa-6-azaspiro[3.3]heptanyl).

In some embodiments of the compound of Formula (Ib), $R^2$ is ($C_2$ alkylene)-(octahydropyrrolo[1,2-a]pyrazinyl) optionally substituted with oxo. In some embodiments, $R^2$ is ($C_2$ alkylene)-(hexahydropyrrolo[1,2-a]pyrazinyl-6 (2H)-one).

In some embodiments of the compound of Formula (Ib), $R^2$ is ($C_2$ alkylene)-(hexahydro-3H-oxazolo[3,4-a]pyrazinyl) optionally substituted with oxo. In some embodiments, $R^2$ is ($C_2$ alkylene)-(hexahydro-3H-oxazolo[3,4-a]pyrazinyl-3-one).

In some embodiments of the compound of Formula (Ib), $R^2$ is ($C_2$ alkylene)-(1,7-diazaspiro[3.5]nonanyl) optionally substituted with oxo. In some embodiments, $R^2$ is ($C_2$ alkylene)-(1,7-diazaspiro[3.5]nonanyl-2-one).

In some embodiments of the compound of Formula (Ib), $R^2$ is ($C_2$ alkylene)-(2,7-diazaspiro[3.5]nonane) optionally substituted with oxo. In some embodiments, $R^2$ is ($C_2$ alkylene)-(2,7-diazaspiro[3.5]nonan-1-one).

In some embodiments of the compound of Formula (Ib), $R^2$ is ($C_2$ alkylene)-(1-oxa-8-azaspiro[4.5]decanyl) optionally substituted with oxo. In some embodiments, $R^2$ is ($C_2$ alkylene)-(1-oxa-8-azaspiro[4.5]decanyl-2-one).

In some embodiments of the compound of Formula (Ib), $R^2$ is ($C_2$ alkylene)-(2-oxa-8-azaspiro[4.5]decanyl) optionally substituted with oxo. In some embodiments, $R^2$ is ($C_2$ alkylene)-(2-oxa-8-azaspiro[4.5]decanyl-1-one).

In some embodiments of the compound of Formula (Ib), $R^2$ is ($C_1$-$C_3$ alkylene)-$NR^{2A}R^{2B}$, wherein $R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl).

In some embodiments of the compound of Formula (Ib), $R^2$ is ($C_1$-$C_3$ alkylene)-$NR^{2A}R^{2B}$, wherein $R^{2A}$ is H and $R^{2B}$ is selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl).

In some embodiments of the compound of Formula (Ib), $R^2$ is ($C_1$-$C_3$ alkylene)-$NR^{2A}R^{2B}$, wherein $R^{2A}$ is H and $R^{2B}$ is selected from ($C_1$-$C_3$ alkylene)-O—($C_1$-$C_3$ alkyl) and C(═NH)($C_1$-$C_3$ alkyl).

In some embodiments of the compound of Formula (Ib), $R^2$ is ($C_1$-$C_3$ alkylene)-$NR^{2A}R^{2B}$, wherein $R^{2A}$ is H and $R^{2B}$ is selected from ($C_1$-$C_3$ alkyl) ene-O-(2-methoxyethyl) and C(═NH)$CH_3$.

In some embodiments of the compound of Formula (Ib), $R^2$ is ($C_1$-$C_3$ alkyl)-$NR^{2A}R^{2B}$, wherein $R^{2A}$ is $C_1$-$C_3$ alkyl and $R^{2B}$ is selected from H, $C_1$-$C_3$ alkyl, $C_1$-$C_3$ haloalkyl, $C_3$-$C_6$ cycloalkyl, ($C_1$-$C_3$ alkyl)-O—($C_1$-$C_3$ alkyl), ($C_1$-$C_3$ alkyl)-OH, ($C_1$-$C_3$ alkyl)-($C_3$-$C_6$ cycloalkyl), ($C_1$-$C_3$ alkyl)-$SO_2$—($C_1$-$C_3$ alkyl), and C(═NH)($C_1$-$C_3$ alkyl).

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is selected from $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), and ($C_1$-$C_3$ alkylene)-$SO_2$—($C_1$-$C_3$ alkyl).

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is $C_1$-$C_3$ alkyl. In some embodiments, $R^{2A}$ is $C_1$-$C_3$ alkyl and $R^{2B}$ is selected from methyl, ethyl, and propyl.

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is $C_1$-$C_3$ haloalkyl. In some embodiments, $R^{2A}$ is $C_1$-$C_3$ alkyl and $R^{2B}$ is 2-fluoroethyl.

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is $C_3$-$C_6$ cycloalkyl. In some embodiments, $R^{2A}$ is $C_1$-$C_3$ alkyl and $R^{2B}$ is cyclopropyl or cyclobutyl.

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-O—($C_1$-$C_3$ alkyl). In some embodiments, $R^{2A}$ is $C_1$-$C_3$ alkyl and $R^{2B}$ is 2-methoxyethyl.

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-OH. In some embodiments, $R^{2A}$ is $C_1$-$C_3$ alkyl and $R^{2B}$ is ethan-1-ol.

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-($C_3$-$C_6$ cycloalkyl). In some embodiments, $R^{2A}$ is $C_1$-$C_3$ alkyl and $R^{2B}$ is cyclopropylmethyl.

In some embodiments of the compound of Formula (Ib), $R^2$ is ($C_1$-$C_3$ alkylene)-$NR^{2A}R^{2B}$, wherein $R^{2A}$ is $C_1$-$C_3$ alkyl and $R^{2B}$ is ($C_1$-$C_3$ alkylene)-$SO_2$—($C_1$-$C_3$ alkyl). In some embodiments, $R^{2A}$ is $C_1$-$C_3$ alkyl and $R^{2B}$ is 2-(methylsulfonyl)ethyl.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form a 3-9 membered heterocycloalkyl ring optionally substituted with one or more $C_1$-$C_3$ alkyl, and optionally containing one additional heteroatom selected from the group of N, O, and S.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form an aziridinyl ring optionally substituted with one or more $C_1$-$C_3$ alkyl.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form an azetidinyl ring optionally substituted with one or more $C_1$-$C_3$ alkyl.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form a pyrrolidinyl ring optionally substituted with one or more $C_1$-$C_3$ alkyl.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form a piperidinyl ring optionally substituted with one or more $C_1$-$C_3$ alkyl.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form a morpholinyl ring optionally substituted with one or more $C_1$-$C_3$ alkyl.

In some embodiments of the compound of Formula (Ib), $R^2$ is ($C_1$-$C_3$ alkylene)-$NR^{2A}R^{2B}$, wherein $R^{2A}$ and $R^{2B}$, taken together with the nitrogen to which they are attached, form a thiomorpholinyl ring optionally substituted with one or more $C_1$-$C_3$ alkyl.

In some embodiments, the compound of Formula (I) is a compound of Formula (Ic):

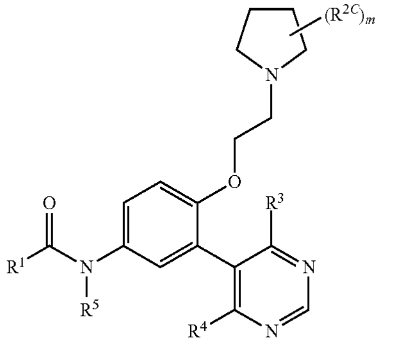

(Ic)

and pharmaceutically acceptable salts thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

each $R^{2C}$ is independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^3$ and $R^4$ are each independently selected from H, $C_1$-$C_6$ alkyl, and $C_1$-$C_6$ haloalkyl;

$R^5$ is selected from H and $C_1$-$C_6$ alkyl; and m is 0, 1, 2, 3, 4, 5, or 6.

In some embodiments of the compound of Formula (Ic):

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

each $R^{2C}$ is independently selected from halogen, ($C_1$-$C_3$ alkyl), —O—($C_1$-$C_3$ alkyl), ($C_1$-$C_3$ alkylene)-C(O)OH, —C(O)OH;

$R^3$ and $R^4$ are each independently selected from H, $C_1$-$C_6$ alkyl, and $C_1$-$C_6$ haloalkyl;

$R^5$ is selected from H and $C_1$-$C_6$ alkyl; and m is 0, 1, or 2.

In some embodiments of the compound of Formula (Ic), $R^1$ is $C_1$-$C_6$ alkyl optionally substituted with one or more substituents independently selected from halogen and —O—($C_1$-$C_3$ alkyl).

In some embodiments of the compound of Formula (Ic), $R^1$ is $C_1$-$C_6$ alkyl optionally substituted with one or more substituents independently selected from fluorine and methoxy.

In some embodiments of the compound of Formula (Ic), $R^1$ is $C_3$-$C_6$ cycloalkyl optionally substituted with one or more substituents independently selected from halogen, —OH, ($C_1$-$C_3$ haloalkyl), and —O—($C_1$-$C_3$ alkyl).

In some embodiments of the compound of Formula (Ic), $R^1$ is $C_3$-$C_6$ cycloalkyl optionally substituted with one or more substituents independently selected from fluorine, —OH, methoxy, ethoxy, and fluoromethyl.

In some embodiments of the compound of Formula (Ic), $R^1$ is cyclopropyl.

In some embodiments of the compound of Formula (Ic), $R^1$ is phenyl optionally substituted with one or more substituents independently selected from halogen, ($C_1$-$C_3$ alkyl), and —O—($C_1$-$C_3$ alkyl).

In some embodiments of the compound of Formula (Ic), $R^1$ is phenyl optionally substituted with one or more substituents independently selected from fluorine, methyl, and methoxy.

In some embodiments of the compound of Formula (Ic), $R^1$ is 5-10 membered heteroaryl optionally substituted with one or more substituents independently selected from halogen, ($C_1$-$C_3$ alkyl), and —O—($C_1$-$C_3$ alkyl).

In some embodiments of the compound of Formula (Ic), $R^1$ is 5-10 membered heteroaryl optionally substituted with one or more substituents independently selected from fluorine, methyl, and methoxy.

In some embodiments of the compound of Formula (Ic), $R^1$ is (5-9 membered heterocycloalkyl).

In some embodiments of the compound of Formula (Ic), $R^1$ is ($C_1$-$C_3$ alkylene)-($C_3$-$C_6$ cycloalkyl).

In some embodiments of the compound of Formula (Ic), $R^1$ is ($C_1$-$C_3$ alkylene)-phenyl, wherein the alkylene and phenyl and each optionally substituted with one or more substituents independently selected from halogen, —($C_1$-$C_3$ alkyl), and —($C_3$-$C_6$ cycloalkyl).

In some embodiments of the compound of Formula (Ic), $R^1$ is ($C_1$-$C_3$ alkylene)-phenyl, wherein the alkylene and phenyl and each optionally substituted with one or more substituents independently selected from fluorine, methyl, and cyclopropyl.

In some embodiments of the compound of Formula (Ic), $R^1$ is ($C_1$-$C_3$ haloalkylene)-phenyl.

In some embodiments of the compound of Formula (Ic), $R^1$ is ($C_1$-$C_3$ alkylene)-(5-10 membered heteroaryl), wherein the alkylene and heteroaryl are each optionally substituted with one or more substituents independently selected from halogen and ($C_1$-$C_3$ alkyl).

In some embodiments of the compound of Formula (Ic), $R^1$ is ($C_1$-$C_3$ alkylene)-(5-10 membered heteroaryl), wherein the alkylene and heteroaryl are each optionally substituted with one or more substituents independently selected from fluorine and methyl.

In some embodiments of the compound of Formula (Ic), $R^1$ is ($C_1$-$C_3$ alkylene)-(5-9 membered heterocycloalkyl).

In some embodiments of the compound of Formula (Ic), $R^1$ is ($C_1$-$C_3$ alkylene)-O—($C_3$-$C_6$ cycloalkyl).

In some embodiments of the compound of Formula (Ic), $R^1$ is ($C_1$-$C_3$ alkylene)-NH—($C_3$-$C_6$ cycloalkyl).

In some embodiments of the compound of Formula (Ic), $R^{2C}$ is —O—($C_1$-$C_3$ alkyl).

In some embodiments of the compound of Formula (Ic), $R^{2C}$ is methoxy.

In some embodiments of the compound of Formula (Ic), $R^{2C}$ is —C(O)OH.

In some embodiments of the compound of Formula (Ic), $R^{2C}$ is ($C_1$-$C_3$ alkylene)-C(O)OH.

In some embodiments of the compound of Formula (Ic), $R^{2C}$ is —$CH_2$—C(O)OH.

In some embodiments of the compound of Formula (Ic), $R^3$ and $R^4$ are each $C_1$-$C_6$ alkyl.

In some embodiments of the compound of Formula (Ic), $R^3$ and $R^4$ are each methyl.

In some embodiments of the compound of Formula (Ic), $R^5$ is H.

In some embodiments of the compound of Formula (Ic), $R^5$ is $C_1$-$C_6$ alkyl.

In some embodiments of the compound of Formula (Ic), $R^5$ is methyl.

In some embodiments of the compound of Formula (Ic), m is 0.

In some embodiments of the compound of Formula (Ic), m is 1.

In some embodiments, the compound of Formula (I) is a compound of Formula (Id):

(Id)

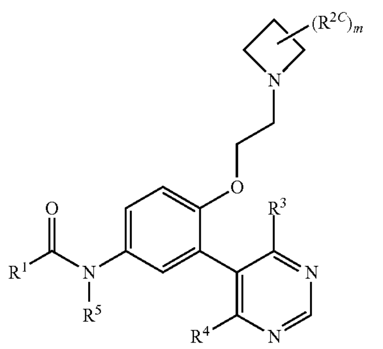

and pharmaceutically acceptable salts thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

each $R^{2C}$ is independently selected from halogen, oxo, —OH, ($C_1$-$C_3$ alkyl), —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^3$ and $R^4$ are each independently selected from H, $C_1$-$C_6$ alkyl, and $C_1$-$C_6$ haloalkyl;

$R^5$ is selected from H and $C_1$-$C_6$ alkyl; and m is 0, 1, 2, 3, 4, 5, or 6.

In some embodiments of the compound of Formula (Id):

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

each $R^{2C}$ is independently selected from halogen, —OH, and ($C_1$-$C_3$ alkyl);

$R^3$ and $R^4$ are each independently selected from H and $C_1$-$C_6$ alkyl;

$R^5$ is selected from H and $C_1$-$C_6$ alkyl; and m is 0, 1, or 2.

In some embodiments of the compound of Formula (Id), $R^1$ is $C_1$-$C_6$ alkyl, In some embodiments of the compound of Formula (Id), $R^1$ is $C_3$-$C_6$ cycloalkyl optionally substituted with one or more substituents independently selected from halogen, ($C_1$-$C_3$ haloalkyl), and —O—($C_1$-$C_3$ alkyl).

In some embodiments of the compound of Formula (Id), $R^1$ is $C_3$-$C_6$ cycloalkyl optionally substituted with one or more substituents independently selected from fluorine, fluoromethyl, and ethoxy.

In some embodiments of the compound of Formula (Id), $R^1$ is cyclopropyl.

In some embodiments of the compound of Formula (Id), $R^1$ is phenyl optionally substituted with one or more substituents independently selected from halogen, —CN, $C_1$-$C_3$ alkyl, and —O—($C_1$-$C_3$ alkyl).

In some embodiments of the compound of Formula (Id), $R^1$ is phenyl optionally substituted with one or more substituents independently selected from fluorine, —CN, methyl, methoxy.

In some embodiments of the compound of Formula (Id), $R^1$ is 5-10 membered heteroaryl optionally substituted with one or more substituents independently selected from halogen and $C_1$-$C_3$ alkyl.

In some embodiments of the compound of Formula (Id), $R^1$ is 5-10 membered heteroaryl optionally substituted with one or more substituents independently selected from fluorine and methyl.

In some embodiments of the compound of Formula (Id), $R^1$ is 5-9 membered heterocycloalkyl.

In some embodiments of the compound of Formula (Id), $R^1$ is ($C_1$-$C_3$ alkylene)-($C_3$-$C_6$ cycloalkyl).

In some embodiments of the compound of Formula (Id), $R^1$ is ($C_1$-$C_3$ alkylene)-phenyl, wherein the alkylene and phenyl are each optionally substituted with one or more substituents independently selected from halogen and —O—($C_1$-$C_3$ alkyl).

In some embodiments of the compound of Formula (Id), $R^1$ is ($C_1$-$C_3$ alkylene)-phenyl, wherein the alkylene and phenyl are each optionally substituted with one or more substituents independently selected from fluorine and methoxy.

In some embodiments of the compound of Formula (Id), $R^1$ is ($C_1$-$C_3$ haloalkylene)-phenyl.

In some embodiments of the compound of Formula (Id), $R^1$ is ($C_1$-$C_3$ alkylene)-(5-10 membered heteroaryl), wherein the alkylene and heteroaryl are each optionally substituted with one or more substituents independently selected from halogen.

In some embodiments of the compound of Formula (Id), $R^1$ is ($C_1$-$C_3$ alkylene)-(5-10 membered heteroaryl), wherein the alkylene and heteroaryl are each optionally substituted with one or more substituents independently selected from fluorine.

In some embodiments of the compound of Formula (Id), $R^1$ is ($C_1$-$C_3$ alkylene)-(5-9 membered heterocycloalkyl).

In some embodiments of the compound of Formula (Id), $R^1$ is ($C_1$-$C_3$ alkylene)-O—($C_3$-$C_6$ cycloalkyl).

In some embodiments of the compound of Formula (Id), $R^1$ is ($C_1$-$C_3$ alkylene)-NH—($C_3$-$C_6$ cycloalkyl).

In some embodiments of the compound of Formula (Id), $R^{2C}$ is halogen.

In some embodiments of the compound of Formula (Id), $R^{2C}$ is fluorine.

In some embodiments of the compound of Formula (Id), $R^{2C}$ is —OH.

In some embodiments of the compound of Formula (Id), $R^3$ and $R^4$ are each $C_1$-$C_6$ alkyl.

In some embodiments of the compound of Formula (Id), $R^3$ and $R^4$ are each methyl.

In some embodiments of the compound of Formula (Id), $R^5$ is H.

In some embodiments of the compound of Formula (Id), $R^5$ is $C_1$-$C_6$ alkyl.

In some embodiments of the compound of Formula (Id), $R^5$ is methyl.

In some embodiments of the compound of Formula (Id), m is 0.

In some embodiments of the compound of Formula (Id), m is 1.

In some embodiments, the compound of Formula (I) is a compound of Formula (Ie):

(Ie)

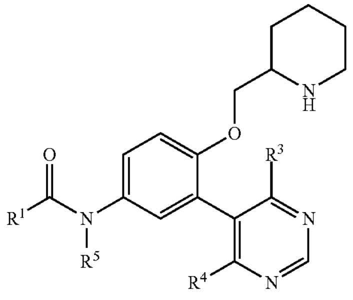

and pharmaceutically acceptable salts thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^3$ and $R^4$ are each independently selected from H, $C_1$-$C_6$ alkyl, and $C_1$-$C_6$ haloalkyl; and $R^5$ is selected from H and $C_1$-$C_6$ alkyl.

In some embodiments of the compound of Formula (Ie):

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^3$ and $R^4$ are each independently selected from H and $C_1$-$C_6$ alkyl; and $R^5$ is H.

In some embodiments of the compound of Formula (Ie), $R^1$ is $C_1$-$C_6$ alkyl optionally substituted with one or more substituents independently selected from halogen.

In some embodiments of the compound of Formula (Ie), $R^1$ is $C_1$-$C_6$ alkyl optionally substituted with one or more substituents independently selected from fluorine.

In some embodiments of the compound of Formula (Ie), $R^1$ is $C_3$-$C_6$ cycloalkyl optionally substituted with one or more substituents independently selected from halogen, —OH, and —O—($C_1$-$C_3$ alkyl).

In some embodiments of the compound of Formula (Ie), $R^1$ is $C_3$-$C_6$ cycloalkyl optionally substituted with one or more substituents independently selected from fluorine, —OH, methoxy, and ethoxy.

In some embodiments of the compound of Formula (Ie), $R^1$ is cyclopropyl.

In some embodiments of the compound of Formula (Ie), $R^1$ is phenyl optionally substituted with one or more substituents independently selected from halogen and —O—($C_1$-$C_3$ alkyl).

In some embodiments of the compound of Formula (Ie), $R^1$ is phenyl optionally substituted with one or more substituents independently selected from fluorine and methoxy.

In some embodiments of the compound of Formula (Ie), $R^1$ is 5-10 membered heteroaryl optionally substituted with one or more substituents independently selected from halogen and $C_1$-$C_3$ alkyl.

In some embodiments of the compound of Formula (Ie), $R^1$ is 5-10 membered heteroaryl optionally substituted with one or more substituents independently selected from fluorine and methyl.

In some embodiments of the compound of Formula (Ie), $R^1$ is 5-9 membered heterocycloalkyl optionally substituted with one or more substituents independently selected from halogen.

In some embodiments of the compound of Formula (Ie), $R^1$ is 5-9 membered heterocycloalkyl optionally substituted with one or more substituents independently selected from fluorine.

In some embodiments of the compound of Formula (Ie), $R^1$ is ($C_1$-$C_3$ alkylene)-($C_3$-$C_6$ cycloalkyl).

In some embodiments of the compound of Formula (Ie), $R^1$ is ($C_1$-$C_3$ alkylene)-phenyl.

In some embodiments of the compound of Formula (Ie), $R^1$ is ($C_1$-$C_3$ haloalkylene)-phenyl.

In some embodiments of the compound of Formula (Ie), $R^1$ is ($C_1$-$C_3$ alkylene)-(5-10 membered heteroaryl).

In some embodiments of the compound of Formula (Ie), $R^1$ is ($C_1$-$C_3$ alkylene)-(5-9 membered heterocycloalkyl).

In some embodiments of the compound of Formula (Ie), $R^1$ is ($C_1$-$C_3$ alkylene)-O—($C_3$-$C_6$ cycloalkyl).

In some embodiments of the compound of Formula (Ie), $R^1$ is ($C_1$-$C_3$ alkylene)-NH—($C_3$-$C_6$ cycloalkyl).

In some embodiments of the compound of Formula (Ie), $R^3$ and $R^4$ are each $C_1$-$C_6$ alkyl.

In some embodiments of the compound of Formula (Ie), $R^3$ and $R^4$ are each methyl.

In some embodiments of the compound of Formula (Ie), $R^5$ is H.

In some embodiments of the compound of Formula (Ie), $R^5$ is $C_1$-$C_6$ alkyl.

In some embodiments of the compound of Formula (Ie), $R^5$ is methyl.

In some embodiments, the compound of Formula (I) is a compound of Formula (If):

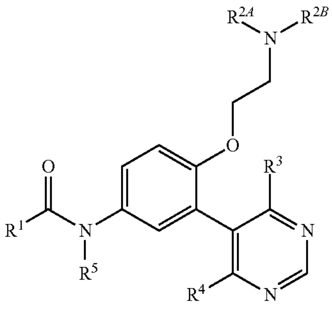

(If)

and pharmaceutically acceptable salts thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl);

$R^3$ and $R^4$ are each independently selected from H, $C_1$-$C_6$ alkyl, and $C_1$-$C_6$ haloalkyl; and $R^5$ is selected from H and $C_1$-$C_6$ alkyl.

In some embodiments of the compound of Formula (If):

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, ($C_1$-$C_3$ haloalkyl), ($C_3$-$C_6$ cycloalkyl), —O—($C_1$-$C_3$ alkyl), ($C_1$-$C_3$ alkylene)-O—($C_1$-$C_3$ alkyl), and phenyl;

$R^{2A}$ is selected from H and $C_1$-$C_3$ alkyl;

$R^{2B}$ is selected from $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl);

$R^3$ and $R^4$ are each independently selected from H and $C_1$-$C_6$ alkyl; and $R^5$ is H.

In some embodiments of the compound of Formula (If), $R^1$ is $C_1$-$C_6$ alkyl.

In some embodiments of the compound of Formula (If), $R^1$ is $C_3$-$C_6$ cycloalkyl optionally substituted with one or more substituents independently selected from halogen.

In some embodiments of the compound of Formula (If), $R^1$ is $C_3$-$C_6$ cycloalkyl optionally substituted with one or more substituents independently selected from fluorine.

In some embodiments of the compound of Formula (If), $R^1$ is cyclopropyl.

In some embodiments of the compound of Formula (If), $R^1$ is phenyl optionally substituted with one or more substituents independently selected from halogen and —O—($C_1$-$C_3$ alkyl).

In some embodiments of the compound of Formula (If), $R^1$ is phenyl optionally substituted with one or more substituents independently selected from fluorine and methoxy.

In some embodiments of the compound of Formula (If), $R^1$ is 5-10 membered heteroaryl optionally substituted with one or more substituents independently selected from halogen and $C_1$-$C_3$ alkyl In some embodiments of the compound of Formula (If), $R^1$ is 5-10 membered heteroaryl optionally substituted with one or more substituents independently selected from fluorine and methyl.

In some embodiments of the compound of Formula (If), $R^1$ is 5-9 membered heterocycloalkyl.

In some embodiments of the compound of Formula (If), $R^1$ is ($C_1$-$C_3$ alkylene)-($C_3$-$C_6$ cycloalkyl).

In some embodiments of the compound of Formula (If), $R^1$ is ($C_1$-$C_3$ alkylene)-phenyl.

In some embodiments of the compound of Formula (If), $R^1$ is ($C_1$-$C_3$ haloalkylene)-phenyl.

In some embodiments of the compound of Formula (If), $R^1$ is ($C_1$-$C_3$ alkylene)-(5-10 membered heteroaryl).

In some embodiments of the compound of Formula (If), $R^1$ is ($C_1$-$C_3$ alkylene)-(5-9 membered heterocycloalkyl).

In some embodiments of the compound of Formula (If), $R^1$ is ($C_1$-$C_3$ alkylene)-O—($C_3$-$C_6$ cycloalkyl).

In some embodiments of the compound of Formula (If), $R^1$ is ($C_1$-$C_3$ alkylene)-NH—($C_3$-$C_6$ cycloalkyl).

In some embodiments of the compound of Formula (If), $R^{2A}$ is H.

In some embodiments of the compound of Formula (If), $R^{2A}$ is $C_1$-$C_3$ alkyl.

In some embodiments of the compound of Formula (If), $R^{2A}$ is methyl.

In some embodiments of the compound of Formula (If), $R^{2A}$ is ethyl.

In some embodiments of the compound of Formula (If), $R^{2A}$ is propyl.

In some embodiments of the compound of Formula (If), $R^{2B}$ is $C_1$-$C_3$ alkyl.

In some embodiments of the compound of Formula (If), $R^{2B}$ is methyl.

In some embodiments of the compound of Formula (If), $R^{2B}$ is ethyl.

In some embodiments of the compound of Formula (If), $R^{2B}$ is propyl.

In some embodiments of the compound of Formula (If), $R^{2B}$ is $C_1$-$C_3$ haloalkyl.

In some embodiments of the compound of Formula (If), $R^{2B}$ is 2-fluoroethyl.

In some embodiments of the compound of Formula (If), $R^{2B}$ is $C_3$-$C_6$ cycloalkyl.

In some embodiments of the compound of Formula (If), $R^{2B}$ is cyclopropyl.

In some embodiments of the compound of Formula (If), $R^{2B}$ is cyclobutyl.

In some embodiments of the compound of Formula (If), $R^{2B}$ is ($C_1$-$C_3$ alkylene)-O—($C_1$-$C_3$ alkyl).

In some embodiments of the compound of Formula (If), $R^{2B}$ is $(CH_2)_2$—O—$CH_3$.

In some embodiments of the compound of Formula (If), $R^{2B}$ is ($C_1$-$C_3$ alkylene)-OH.

In some embodiments of the compound of Formula (If), $R^{2B}$ is $(CH_2)_2$—OH.

In some embodiments of the compound of Formula (If), $R^{2B}$ is ($C_1$-$C_3$ alkylene)-($C_3$-$C_6$ cycloalkyl).

In some embodiments of the compound of Formula (If), $R^{2B}$ is cyclopropylmethyl.

In some embodiments of the compound of Formula (If), $R^{2B}$ is ($C_1$-$C_3$ alkylene)-S(═O)—($C_1$-$C_3$ alkyl).

In some embodiments of the compound of Formula (If), $R^{2B}$ is $(CH_2)_2$—SO—$CH_3$.

In some embodiments of the compound of Formula (If), $R^{2B}$ is ($C_1$-$C_3$ alkylene)-$SO_2$—($C_1$-$C_3$ alkyl).

In some embodiments of the compound of Formula (If), $R^{2B}$ is $(CH_2)_2$—$SO_2$—$CH_3$.

In some embodiments of the compound of Formula (If), $R^{2B}$ is C(═NH)($C_1$-$C_3$ alkyl).

In some embodiments of the compound of Formula (If), $R^{2B}$ is C(═NH)($CH_3$).

In some embodiments, the compound of Formula (I), or a pharmaceutically acceptable salt thereof, is selected from a compound shown in Table 1.

TABLE 1

| Cmpd No. | Chemical Structure | Chemical Name |
|---|---|---|
| 200 | 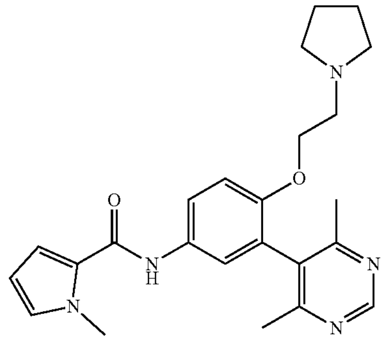 | N-[3-(4,6-dimethylpyrimidin-5-yl)-4-(2-(pyrrolidin-1-yl)ethoxy)phenyl]-1-methyl-1H-pyrrole-2-carboxamide |
| 201 | 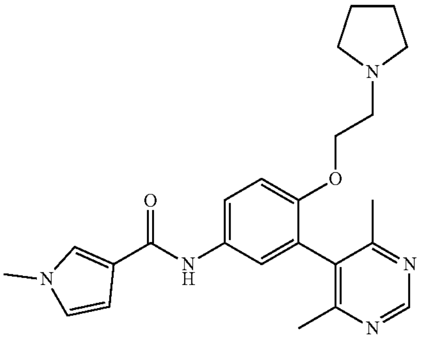 [SMILES: Cc1ncnc(C)c1-c1cc(NC(=O)c2ccn(C)c2)ccc1OCCN1CCCC1] | N-(3-(4,6-dimethylpyrimidin-5-yl)-4-(2-(pyrrolidin-1-yl)ethoxy)phenyl)-1-methyl-1H-pyrrole-3-carboxamide |
| 202 | 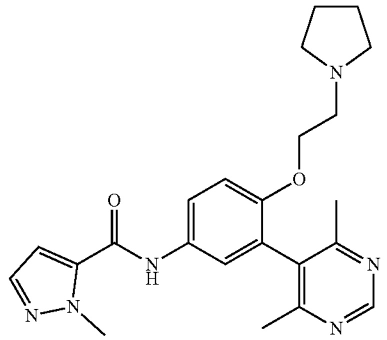 [SMILES: Cc1ncnc(C)c1-c1cc(NC(=O)c2ccnn2C)ccc1OCCN1CCCC1] | N-(3-(4,6-dimethylpyrimidin-5-yl)-4-(2-(pyrrolidin-1-yl)ethoxy)phenyl)-1-methyl-1H-pyrazole-5-carboxamide |

TABLE 1-continued

| Cmpd No. | Chemical Structure | Chemical Name |
| --- | --- | --- |
| 203 | 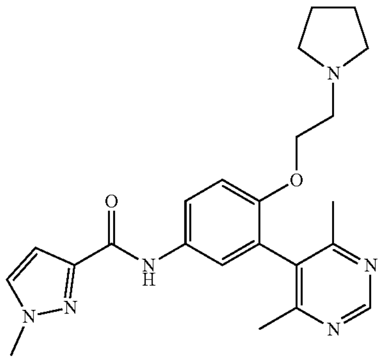 [SMILES: Cc1ncnc(C)c1-c1cc(NC(=O)c2ccn(C)n2)ccc1OCCN1CCCC1] | N-(3-(4,6-dimethylpyrimidin-5-yl)-4-(2-(pyrrolidin-1-yl)ethoxy)phenyl)-1-methyl-1H-pyrazole-3-carboxamide |
| 204 | 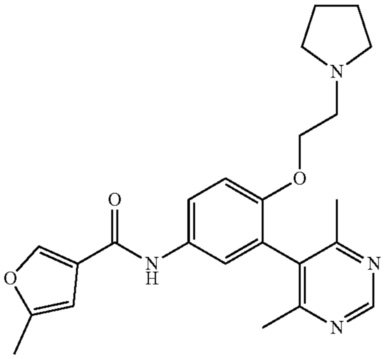 [SMILES: Cc1cc(C(=O)Nc2ccc(OCCN3CCCC3)c(-c3c(C)ncnc3C)c2)co1] | N-(3-(4,6-dimethylpyrimidin-5-yl)-4-(2-(pyrrolidin-1-yl)ethoxy)phenyl)-5-methylfuran-3-carboxamide |
| 205 | 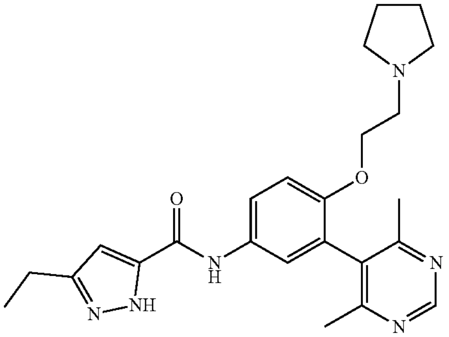 [SMILES: CCc1cc(C(=O)Nc2ccc(OCCN3CCCC3)c(-c3c(C)ncnc3C)c2)[nH]n1] | N-(3-(4,6-dimethylpyrimidin-5-yl)-4-(2-(pyrrolidin-1-yl)ethoxy)phenyl)-3-ethyl-1H-pyrazole-5-carboxamide |
| 206 | 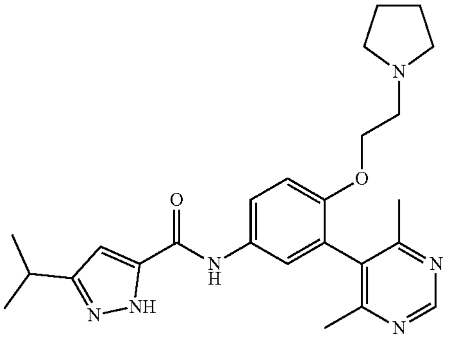 [SMILES: Cc1ncnc(C)c1-c1cc(NC(=O)c2cc(C(C)C)n[nH]2)ccc1OCCN1CCCC1] | N-(3-(4,6-dimethylpyrimidin-5-yl)-4-(2-(pyrrolidin-1-yl)ethoxy)phenyl)-3-isopropyl-1H-pyrazole-5-carboxamide |

TABLE 1-continued
| Cmpd No. | Chemical Structure | Chemical Name |
| --- | --- | --- |
| 207 | 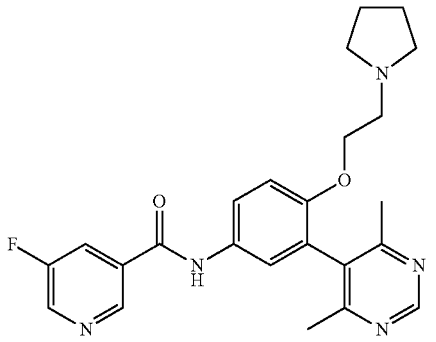 [SMILES: Cc1ncnc(C)c1-c1cc(NC(=O)c2cncc(F)c2)ccc1OCCN1CCCC1] | N-(3-(4,6-dimethylpyrimidin-5-yl)-4-(2-(pyrrolidin-1-yl)ethoxy)phenyl)-5-fluoronicotinamide |
| 208 | 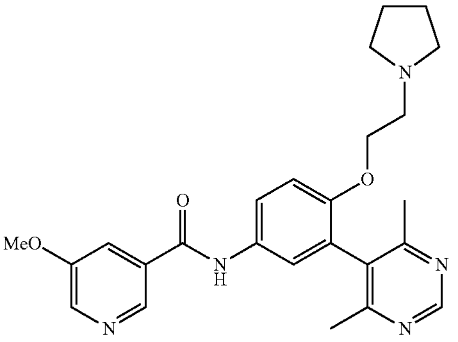 | N-(3-(4,6-dimethylpyrimidin-5-yl)-4-(2-(pyrrolidin-1-yl)ethoxy)phenyl)-5-methoxynicotinamide |
| 209 | 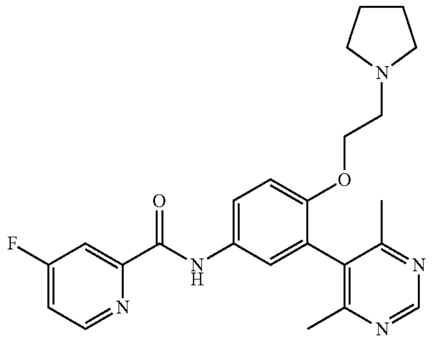 [SMILES: Cc1ncnc(C)c1-c1cc(NC(=O)c2cc(F)ccn2)ccc1OCCN1CCCC1] | N-(3-(4,6-dimethylpyrimidin-5-yl)-4-(2-(pyrrolidin-1-yl)ethoxy)phenyl)-4-fluoropicolinamide |
| 210 | 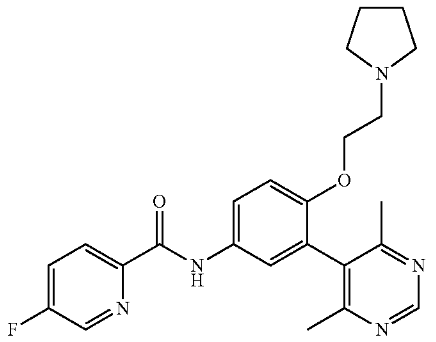 [SMILES: Cc1ncnc(C)c1-c1cc(NC(=O)c2ccc(F)cn2)ccc1OCCN1CCCC1] | N-(3-(4,6-dimethylpyrimidin-5-yl)-4-(2-(pyrrolidin-1-yl)ethoxy)phenyl)-5-fluoropicolinamide |

TABLE 1-continued

| Cmpd No. | Chemical Structure | Chemical Name |
|---|---|---|
| 211 | 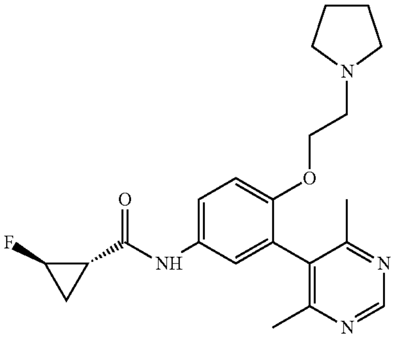 [SMILES: Cc1ncnc(C)c1-c1cc(NC(=O)[C@@H]2C[C@H]2F)ccc1OCCN1CCCC1] | (1S,2R)-N-(3-(4,6-dimethylpyrimidin-5-yl)-4-(2-(pyrrolidin-1-yl)ethoxy)phenyl)-2-fluorocyclopropane-1-carboxamide |
| 212 | 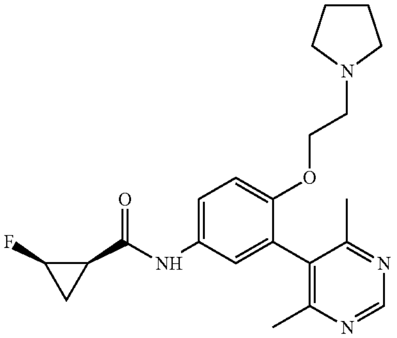 [SMILES: Cc1ncnc(C)c1-c1cc(NC(=O)[C@H]2C[C@H]2F)ccc1OCCN1CCCC1] | (1R,2R)-N-(3-(4,6-dimethylpyrimidin-5-yl)-4-(2-(pyrrolidin-1-yl)ethoxy)phenyl)-2-fluorocyclopropane-1-carboxamide |
| 213 | 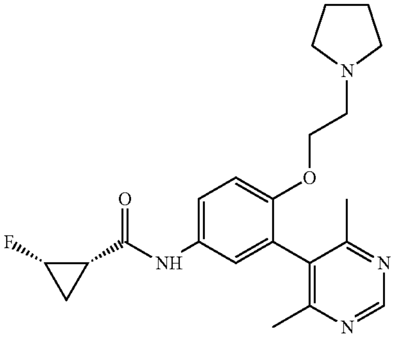 [SMILES: Cc1ncnc(C)c1-c1cc(NC(=O)[C@@H]2C[C@@H]2F)ccc1OCCN1CCCC1] | (1S,2S)-N-(3-(4,6-dimethylpyrimidin-5-yl)-4-(2-(pyrrolidin-1-yl)ethoxy)phenyl)-2-fluorocyclopropane-1-carboxamide |
| 214 | 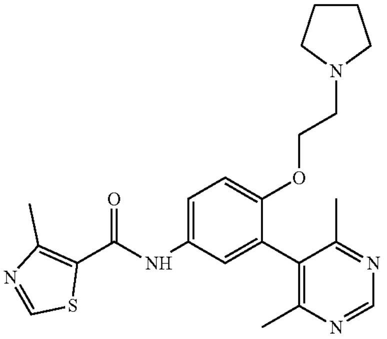 | N-(3-(4,6-dimethylpyrimidin-5-yl)-4-(2-(pyrrolidin-1-yl)ethoxy)phenyl)-4-methylthiazole-5-carboxamide |

TABLE 1-continued

| Cmpd No. | Chemical Structure | Chemical Name |
| --- | --- | --- |
| 215 | 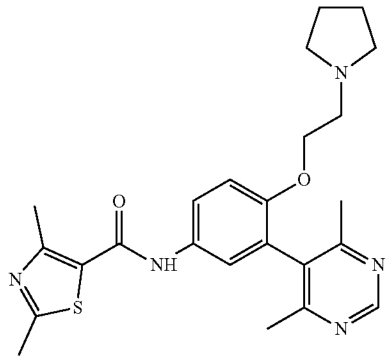 [SMILES: Cc1nc(C)c(C(=O)Nc2ccc(OCCN3CCCC3)c(-c3c(C)ncnc3C)c2)s1] | N-(3-(4,6-dimethylpyrimidin-5-yl)-4-(2-(pyrrolidin-1-yl)ethoxy)phenyl)-2,4-dimethylthiazole-5-carboxamide |
| 216 | 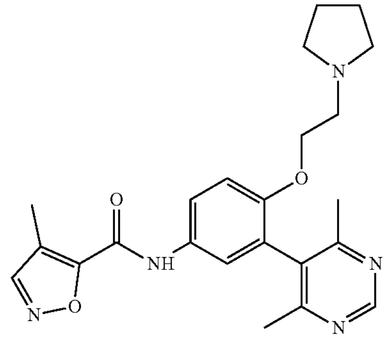 [SMILES: Cc1cnoc1C(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-4-methylisoxazole-5-carboxamide |
| 217 | 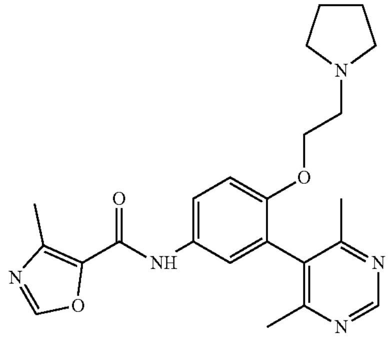 [SMILES: Cc1ncoc1C(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-4-methyloxazole-5-carboxamide |
| 218 | 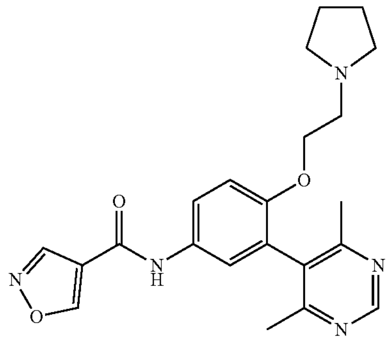 [SMILES: Cc1ncnc(C)c1-c1cc(NC(=O)c2cnoc2)ccc1OCCN1CCCC1] | N-(3-(4,6-dimethylpyrimidin-5-yl)-4-(2-(pyrrolidin-1-yl)ethoxy)phenyl)isoxazole-4-carboxamide |

TABLE 1-continued

| Cmpd No. | Chemical Structure | Chemical Name |
|---|---|---|
| 219 | 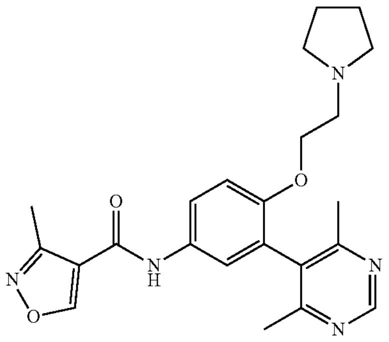 [SMILES: Cc1nocc1C(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-3-methylisoxazole-4-carboxamide |
| 220 | 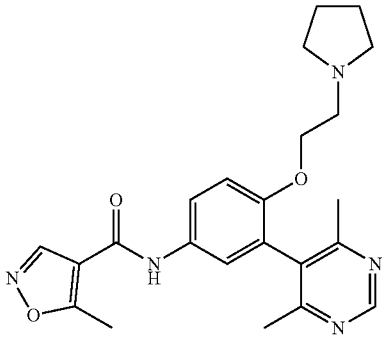 [SMILES: Cc1ncnc(C)c1-c1cc(NC(=O)c2cnoc2C)ccc1OCCN1CCCC1] | N-(3-(4,6-dimethylpyrimidin-5-yl)-4-(2-(pyrrolidin-1-yl)ethoxy)phenyl)-5-methylisoxazole-4-carboxamide |
| 221 | 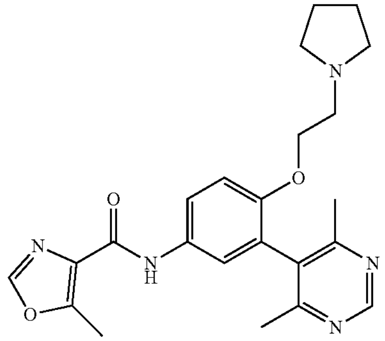 [SMILES: Cc1ncnc(C)c1-c1cc(NC(=O)c2ncoc2C)ccc1OCCN1CCCC1] | N-(3-(4,6-dimethylpyrimidin-5-yl)-4-(2-(pyrrolidin-1-yl)ethoxy)phenyl)-5-methyloxazole-4-carboxamide |
| 222 | 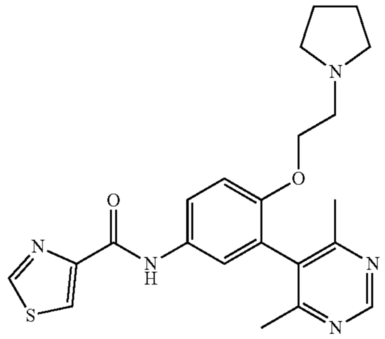 [SMILES: Cc1ncnc(C)c1-c1cc(NC(=O)c2cscn2)ccc1OCCN1CCCC1] | N-(3-(4,6-dimethylpyrimidin-5-yl)-4-(2-(pyrrolidin-1-yl)ethoxy)phenyl)isothiazole-4-carboxamide |

TABLE 1-continued

| Cmpd No. | Chemical Structure | Chemical Name |
| --- | --- | --- |
| 223 | 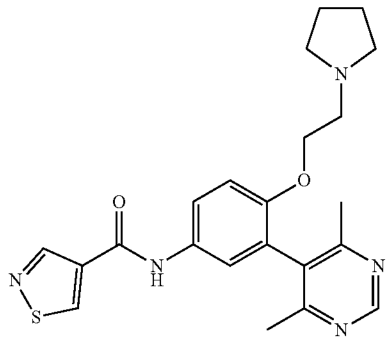 | N-(3-(4,6-dimethylpyrimidin-5-yl)-4-(2-(pyrrolidin-1-yl)ethoxy)phenyl)-3-methylisothiazole-4-carboxamide |
| 224 | 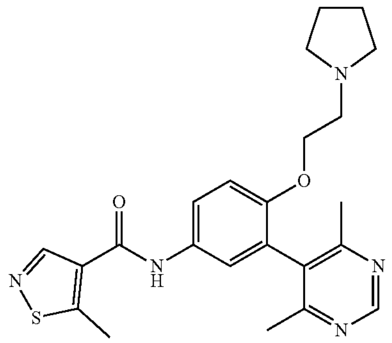 [SMILES: Cc1ncnc(C)c1-c1cc(NC(=O)c2cnsc2C)ccc1OCCN1CCCC1] | N-(3-(4,6-dimethylpyrimidin-5-yl)-4-(2-(pyrrolidin-1-yl)ethoxy)phenyl)-5-methylthiazole-4-carboxamide |
| 225 | 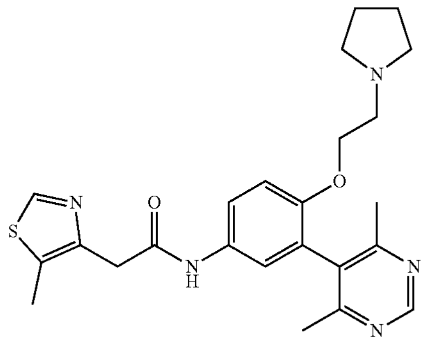 [SMILES: Cc1ncnc(C)c1-c1cc(NC(=O)Cc2ncsc2C)ccc1OCCN1CCCC1] | N-(3-(4,6-dimethylpyrimidin-5-yl)-4-(2-(pyrrolidin-1-yl)ethoxy)phenyl)-2-(5-methylthiazol-4-yl)acetamide |
| 226 | 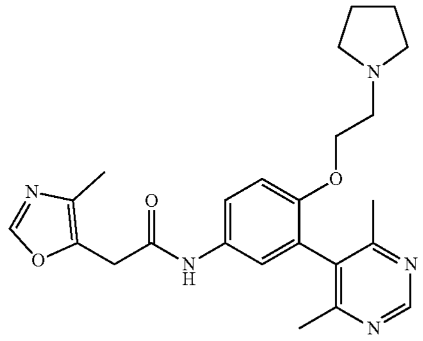 | N-(3-(4,6-dimethylpyrimidin-5-yl)-4-(2-(pyrrolidin-1-yl)ethoxy)phenyl)-2-(4-methyloxazol-5-yl)acetamide |

TABLE 1-continued

| Cmpd No. | Chemical Structure | Chemical Name |
| --- | --- | --- |
| 227 | 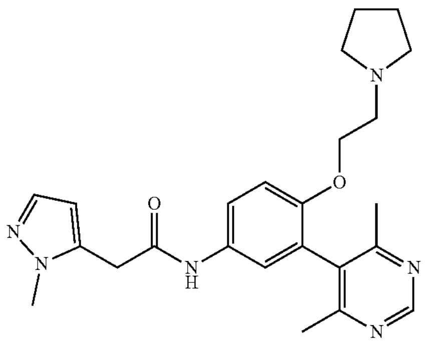 [SMILES: Cc1ncnc(C)c1-c1cc(NC(=O)Cc2ccnn2C)ccc1OCCN1CCCC1] | N-(3-(4,6-dimethylpyrimidin-5-yl)-4-(2-(pyrrolidin-1-yl)ethoxy)phenyl)-2-(1-methyl-1H-pyrazol-5-yl)acetamide |
| 228 | 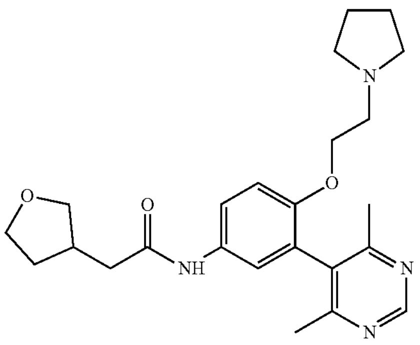 [SMILES: Cc1ncnc(C)c1-c1cc(NC(=O)CC2CCCO2)ccc1OCCN1CCCC1] | N-(3-(4,6-dimethylpyrimidin-5-yl)-4-(2-(pyrrolidin-1-yl)ethoxy)phenyl)-2-(tetrahydrofuran-3-yl)acetamide |
| 229 | 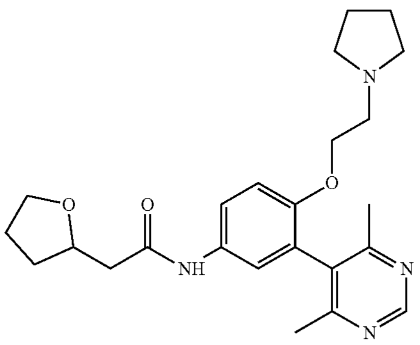 | N-(3-(4,6-dimethylpyrimidin-5-yl)-4-(2-(pyrrolidin-1-yl)ethoxy)phenyl)-2-(tetrahydrofuran-2-yl)acetamide |
| 230 | 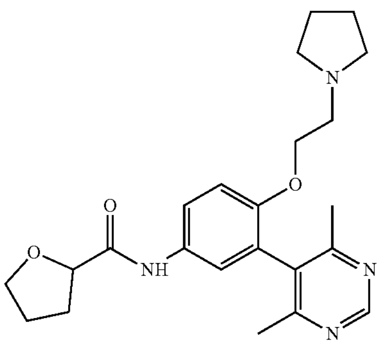 [SMILES: Cc1ncnc(C)c1-c1cc(NC(=O)C2CCCO2)ccc1OCCN1CCCC1] | N-(3-(4,6-dimethylpyrimidin-5-yl)-4-(2-(pyrrolidin-1-yl)ethoxy)phenyl)tetrahydrofuran-2-carboxamide |

TABLE 1-continued

| Cmpd No. | Chemical Structure | Chemical Name |
|---|---|---|
| 231 | 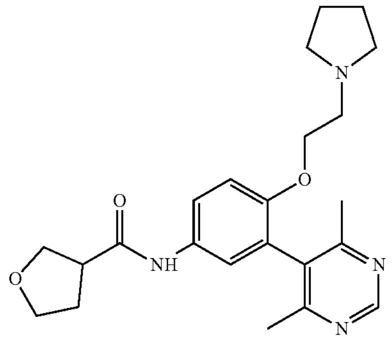 [SMILES: Cc1ncnc(C)c1-c1cc(NC(=O)C2CCOC2)ccc1OCCN1CCCC1] | N-(3-(4,6-dimethylpyrimidin-5-yl)-4-(2-(pyrrolidin-1-yl)ethoxy)phenyl)tetrahydrofuran-3-carboxamide |
| 232 | 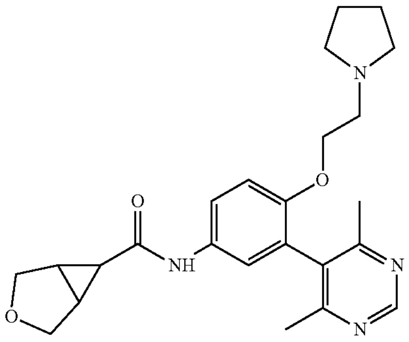 [SMILES: Cc1ncnc(C)c1-c1cc(NC(=O)C2C3COCC32)ccc1OCCN1CCCC1] | N-(3-(4,6-dimethylpyrimidin-5-yl)-4-(2-(pyrrolidin-1-yl)ethoxy)phenyl)-3-oxabicyclo[3.1.0]hexane-6-carboxamide |
| 233 | 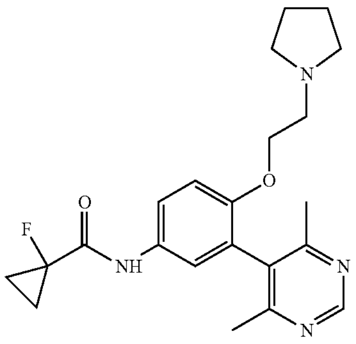 [SMILES: Cc1ncnc(C)c1-c1cc(NC(=O)C2(F)CC2)ccc1OCCN1CCCC1] | N-(3-(4,6-dimethylpyrimidin-5-yl)-4-(2-(pyrrolidin-1-yl)ethoxy)phenyl)-3-oxabicyclo[3.1.0]hexane-6-carboxamide |
| 234 | 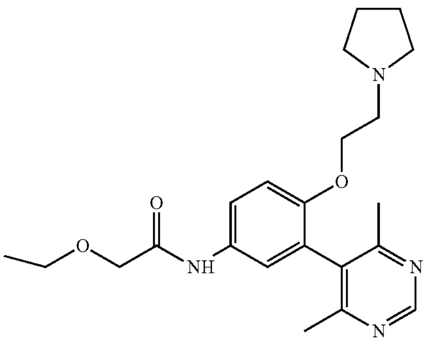 [SMILES: CCOCC(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-2-ethoxyacetamide |

TABLE 1-continued

| Cmpd No. | Chemical Structure | Chemical Name |
| --- | --- | --- |
| 235 | 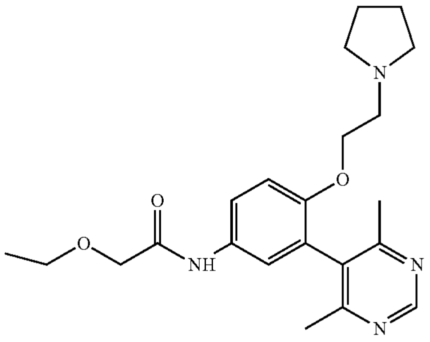 [SMILES: CCOCC(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-3-methoxypropanamide |
| 236 | 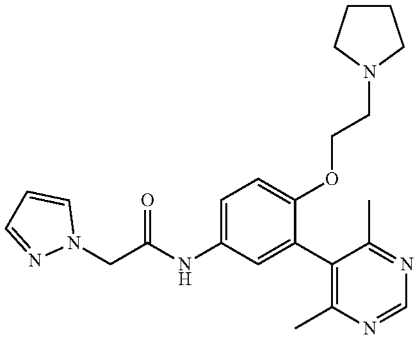 [SMILES: Cc1ncnc(C)c1-c1cc(NC(=O)Cn2cccn2)ccc1OCCN1CCCC1] | N-(3-(4,6-dimethylpyrimidin-5-yl)-4-(2-(pyrrolidin-1-yl)ethoxy)phenyl)-2-(1H-pyrazol-1-yl)acetamide |
| 237 | 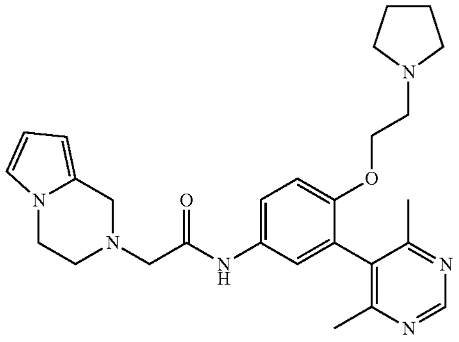 [SMILES: Cc1ncnc(C)c1-c1cc(NC(=O)CN2CCn3cccc3C2)ccc1OCCN1CCCC1] | 2-(3,4-dihydro-1H-pyrrolo[1,2-a]pyrazin-2-yl)-N-[3-(4,6-dimethylpyrimidin-5-yl)-4-(2-pyrrolidin-1-ylethoxy)phenyl]acetamide |
| 238 | 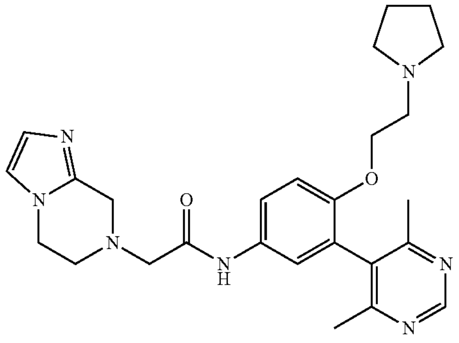 [SMILES: Cc1ncnc(C)c1-c1cc(NC(=O)CN2CCn3ccnc3C2)ccc1OCCN1CCCC1] | 2-(6,8-dihydro-5H-imidazo[1,2-a]pyrazin-7-yl)-N-[3-(4,6-dimethylpyrimidin-5-yl)-4-(2-pyrrolidin-1-ylethoxy)phenyl]acetamide |

TABLE 1-continued

| Cmpd No. | Chemical Structure | Chemical Name |
| --- | --- | --- |
| 239 | 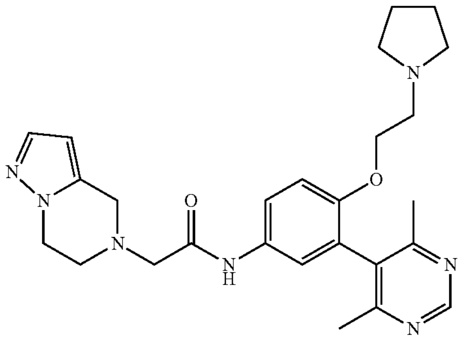 [SMILES: Cc1ncnc(C)c1-c1cc(NC(=O)CN2CCn3nccc3C2)ccc1OCCN1CCCC1] | 2-(6,7-dihydropyrazolo[1,5-a]pyrazin-5(4H)-yl)-N-(3-(4,6-dimethylpyrimidin-5-yl)-4-(2-(pyrrolidin-1-yl)ethoxy)phenyl)acetamide |
| 240 | 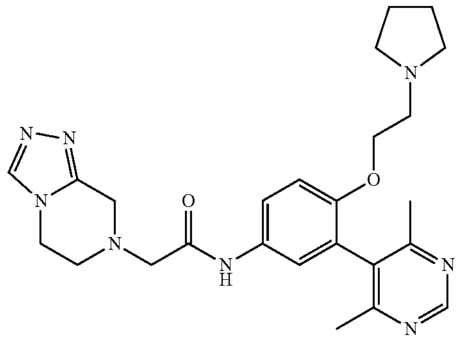 [SMILES: Cc1ncnc(C)c1-c1cc(NC(=O)CN2CCn3cnnc3C2)ccc1OCCN1CCCC1] | 2-(5,6-dihydro-[1,2,4]triazolo[4,3-a]pyrazin-7(8H)-yl)-N-(3-(4,6-dimethylpyrimidin-5-yl)-4-(2-(pyrrolidin-1-yl)ethoxy)phenyl)acetamide |
| 241 | 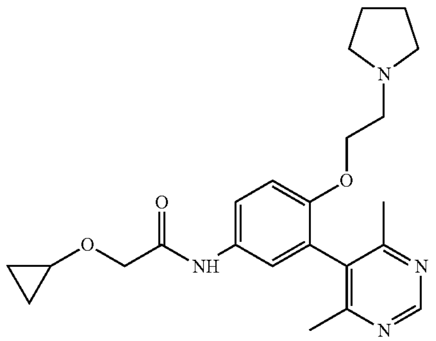 [SMILES: Cc1ncnc(C)c1-c1cc(NC(=O)COC2CC2)ccc1OCCN1CCCC1] | 2-(cyclopropoxy)-N-[3-(4,6-dimethylpyrimidin-5-yl)-4-(2-pyrrolidin-1-ylethoxy)phenyl]acetamide |
| 242 | 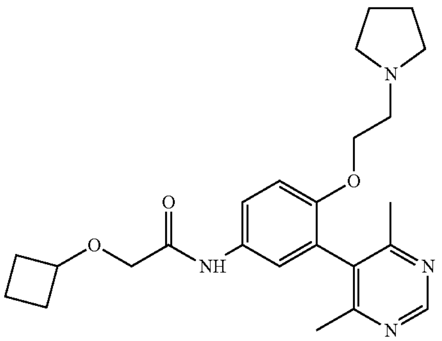 [SMILES: Cc1ncnc(C)c1-c1cc(NC(=O)COC2CCC2)ccc1OCCN1CCCC1] | 2-cyclobutoxy-N-(3-(4,6-dimethylpyrimidin-5-yl)-4-(2-(pyrrolidin-1-yl)ethoxy)phenyl)acetamide |

TABLE 1-continued

| Cmpd No. | Chemical Structure | Chemical Name |
| --- | --- | --- |
| 243 | 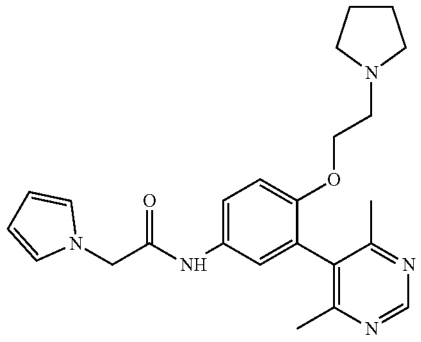 [SMILES: Cc1ncnc(C)c1-c1cc(NC(=O)Cn2cccc2)ccc1OCCN1CCCC1] | N-[3-(4,6-dimethylpyrimidin-5-yl)-4-(2-pyrrolidin-1-ylethoxy)phenyl]-2-pyrrol-1-yl-acetamide |
| 244 | 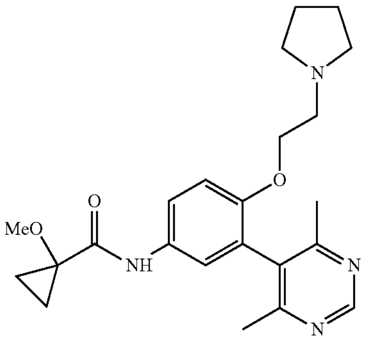 [SMILES: COC1(C(=O)Nc2ccc(OCCN3CCCC3)c(-c3c(C)ncnc3C)c2)CC1] | N-[3-(4,6-dimethylpyrimidin-5-yl)-4-(2-pyrrolidin-1-ylethoxy)phenyl]-1-methoxy-cyclopropanecarboxamide |
| 245 | 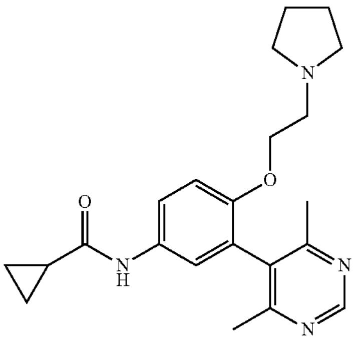 [SMILES: Cc1ncnc(C)c1-c1cc(NC(=O)C2CC2)ccc1OCCN1CCCC1] | N-(3-(4,6-dimethylpyrimidin-5-yl)-4-(2-(pyrrolidin-1-yl)ethoxy)phenyl)cyclopropanecarboxamide |
| 246 | 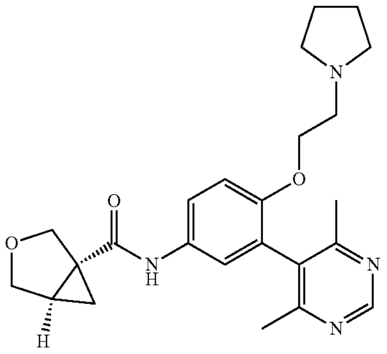 [SMILES: Cc1ncnc(C)c1-c1cc(NC(=O)[C@@]23COC[C@@H]2C3)ccc1OCCN1CCCC1] | (1R,5R)-N-[3-(4,6-dimethylpyrimidin-5-yl)-4-(2-pyrrolidin-1-ylethoxy)phenyl]-3-oxabicyclo[3.1.0]hexane-1-carboxamide |

TABLE 1-continued

| Cmpd No. | Chemical Structure | Chemical Name |
| --- | --- | --- |
| 247 | 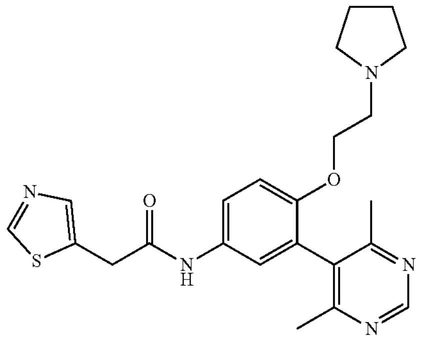 [SMILES: Cc1ncnc(C)c1-c1cc(NC(=O)Cc2cncs2)ccc1OCCN1CCCC1] | N-[3-(4,6-dimethylpyrimidin-5-yl)-4-(2-pyrrolidin-1-ylethoxy)phenyl]-2-thiazol-5-yl-acetamide |
| 248 | 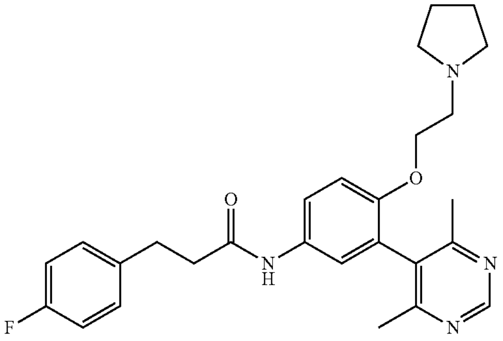 [SMILES: Cc1ncnc(C)c1-c1cc(NC(=O)CCc2ccc(F)cc2)ccc1OCCN1CCCC1] | N-[3-(4,6-dimethylpyrimidin-5-yl)-4-(2-pyrrolidin-1-ylethoxy)phenyl]-3-(4-fluorophenyl)propanamide |
| 249 | 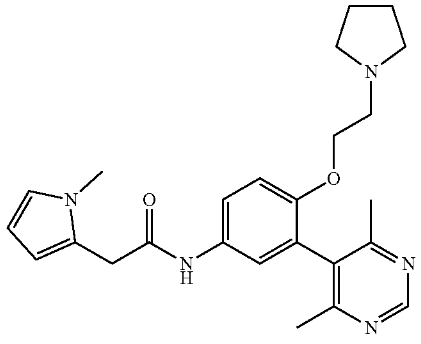 [SMILES: Cc1ncnc(C)c1-c1cc(NC(=O)Cc2cccn2C)ccc1OCCN1CCCC1] | N-(3-(4,6-dimethylpyrimidin-5-yl)-4-(2-(pyrrolidin-1-yl)ethoxy)phenyl)-2-(1-methyl-1H-pyrrol-2-yl)acetamide |
| 250 | 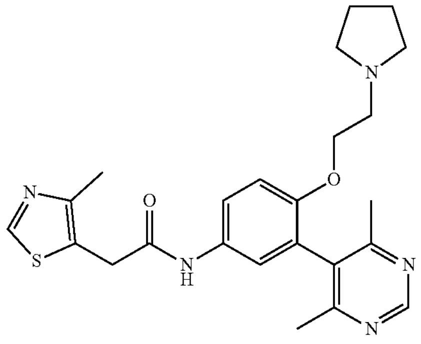 [SMILES: Cc1ncsc1CC(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-2-(4-methylthiazol-5-yl)acetamide |

TABLE 1-continued

| Cmpd No. | Chemical Structure | Chemical Name |
| --- | --- | --- |
| 251 | 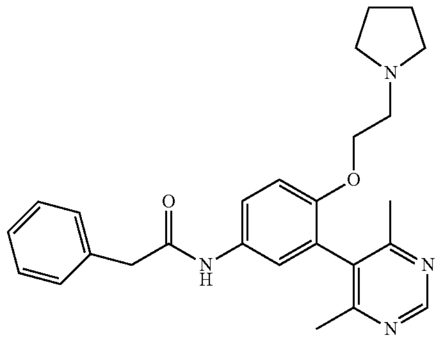 [SMILES: Cc1ncnc(C)c1-c1cc(NC(=O)Cc2ccccc2)ccc1OCCN1CCCC1] | N-(3-(4,6-dimethylpyrimidin-5-yl)-4-(2-(pyrrolidin-1-yl)ethoxy)phenyl)-2-phenylacetamide |
| 252 | 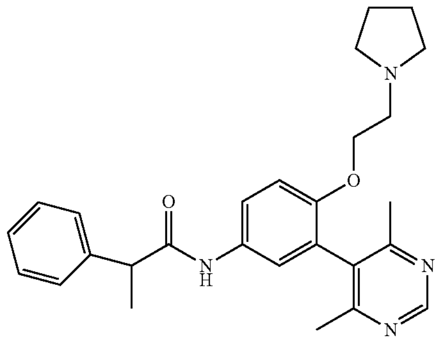 [SMILES: Cc1ncnc(C)c1-c1cc(NC(=O)C(C)c2ccccc2)ccc1OCCN1CCCC1] | N-(3-(4,6-dimethylpyrimidin-5-yl)-4-(2-(pyrrolidin-1-yl)ethoxy)phenyl)-2-phenylpropanamide |
| 253 | 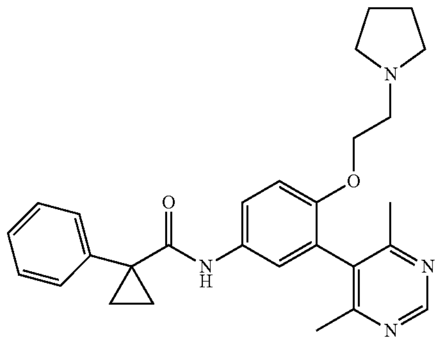 [SMILES: Cc1ncnc(C)c1-c1cc(NC(=O)C2(c3ccccc3)CC2)ccc1OCCN1CCCC1] | N-(3-(4,6-dimethylpyrimidin-5-yl)-4-(2-(pyrrolidin-1-yl)ethoxy)phenyl)-1-phenylcyclopropane-1-carboxamide |
| 254 | 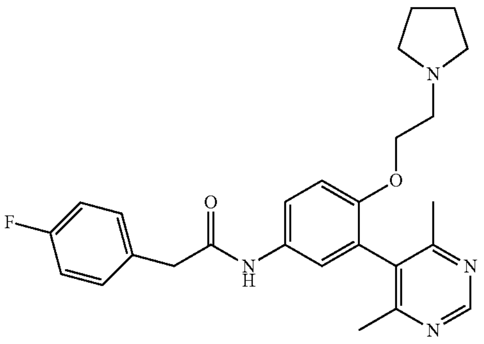 [SMILES: Cc1ncnc(C)c1-c1cc(NC(=O)Cc2ccc(F)cc2)ccc1OCCN1CCCC1] | N-(3-(4,6-dimethylpyrimidin-5-yl)-4-(2-(pyrrolidin-1-yl)ethoxy)phenyl)-2-(4-fluorophenyl)acetamide |

TABLE 1-continued

| Cmpd No. | Chemical Structure | Chemical Name |
|---|---|---|
| 255 | 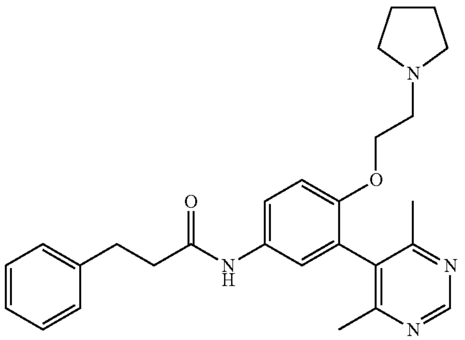 [SMILES: Cc1ncnc(C)c1-c1cc(NC(=O)CCc2ccccc2)ccc1OCCN1CCCC1] | N-(3-(4,6-dimethylpyrimidin-5-yl)-4-(2-(pyrrolidin-1-yl)ethoxy)phenyl)-3-phenylpropanamide |
| 256 | 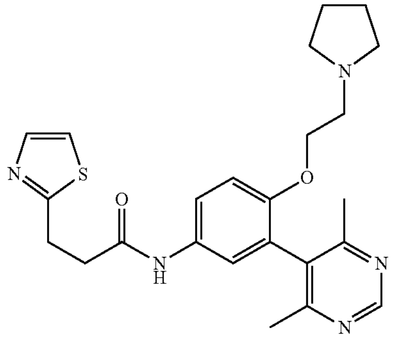 [SMILES: Cc1ncnc(C)c1-c1cc(NC(=O)CCc2nccs2)ccc1OCCN1CCCC1] | N-(3-(4,6-dimethylpyrimidin-5-yl)-4-(2-(pyrrolidin-1-yl)ethoxy)phenyl)-3-(thiazol-2-yl)propanamide |
| 257 | 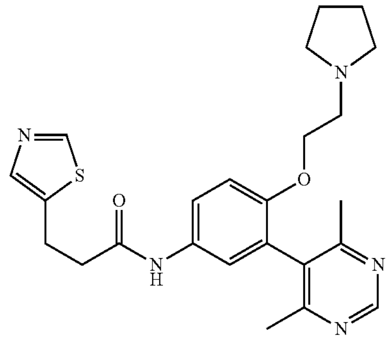 [SMILES: Cc1ncnc(C)c1-c1cc(NC(=O)CCc2cncs2)ccc1OCCN1CCCC1] | N-(3-(4,6-dimethylpyrimidin-5-yl)-4-(2-(pyrrolidin-1-yl)ethoxy)phenyl)-3-(thiazol-5-yl)propanamide |
| 258 | 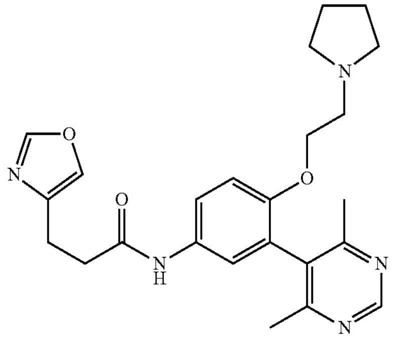 [SMILES: Cc1ncnc(C)c1-c1cc(NC(=O)CCc2cocn2)ccc1OCCN1CCCC1] | N-[3-(4,6-dimethylpyrimidin-5-yl)-4-(2-pyrrolidin-1-ylethoxy)phenyl]-3-oxazol-4-yl-propanamide |

TABLE 1-continued

| Cmpd No. | Chemical Structure | Chemical Name |
|---|---|---|
| 259 | 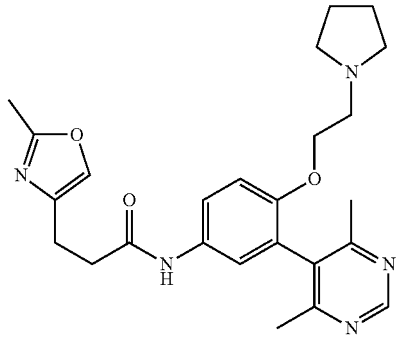 [SMILES: Cc1nc(CCC(=O)Nc2ccc(OCCN3CCCC3)c(-c3c(C)ncnc3C)c2)co1] | N-[3-(4,6-dimethylpyrimidin-5-yl)-4-(2-pyrrolidin-1-ylethoxy)phenyl]-3-(2-methyloxazol-4-yl)propanamide |
| 260 | 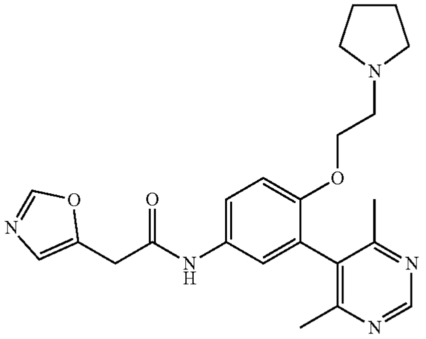 [SMILES: Cc1ncnc(C)c1-c1cc(NC(=O)Cc2cnco2)ccc1OCCN1CCCC1] | N-[3-(4,6-dimethylpyrimidin-5-yl)-4-(2-pyrrolidin-1-ylethoxy)phenyl]-2-oxazol-5-yl-acetamide |
| 261 | 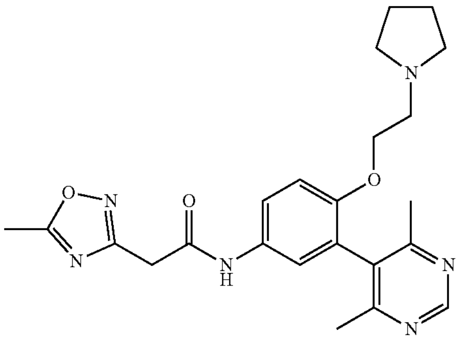 [SMILES: Cc1nc(CC(=O)Nc2ccc(OCCN3CCCC3)c(-c3c(C)ncnc3C)c2)no1] | N-(3-(4,6-dimethylpyrimidin-5-yl)-4-(2-(pyrrolidin-1-yl)ethoxy)phenyl)-2-(5-methyl-1,2,4-oxadiazol-3-yl)acetamide |
| 262 | 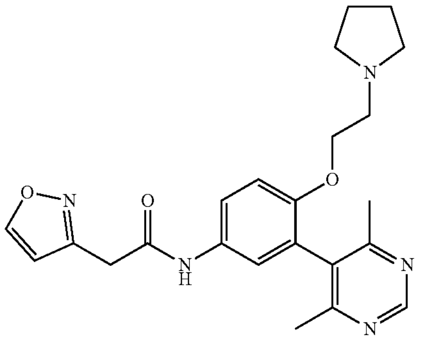 [SMILES: Cc1ncnc(C)c1-c1cc(NC(=O)Cc2ccon2)ccc1OCCN1CCCC1] | N-(3-(4,6-dimethylpyrimidin-5-yl)-4-(2-(pyrrolidin-1-yl)ethoxy)phenyl)-2-(isoxazol-3-yl)acetamide |

TABLE 1-continued

| Cmpd No. | Chemical Structure | Chemical Name |
| --- | --- | --- |
| 263 | 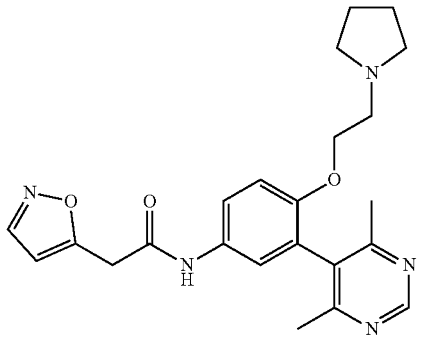 [SMILES: Cc1ncnc(C)c1-c1cc(NC(=O)Cc2ccno2)ccc1OCCN1CCCC1] | N-(3-(4,6-dimethylpyrimidin-5-yl)-4-(2-(pyrrolidin-1-yl)ethoxy)phenyl)-2-(isoxazol-5-yl)acetamide |
| 264 | 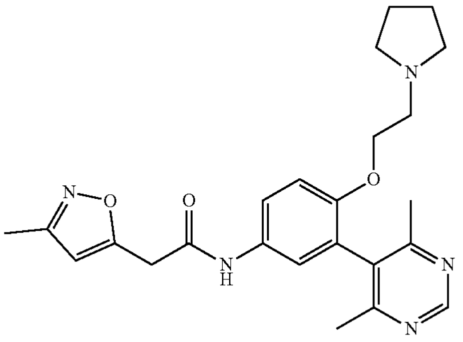 [SMILES: Cc1cc(CC(=O)Nc2ccc(OCCN3CCCC3)c(-c3c(C)ncnc3C)c2)on1] | N-(3-(4,6-dimethylpyrimidin-5-yl)-4-(2-(pyrrolidin-1-yl)ethoxy)phenyl)-2-(3-methylisoxazol-5-yl)acetamide |
| 265 | 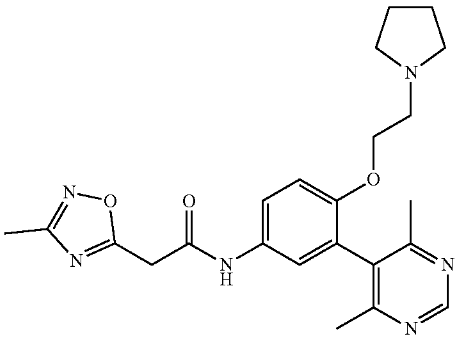 [SMILES: Cc1noc(CC(=O)Nc2ccc(OCCN3CCCC3)c(-c3c(C)ncnc3C)c2)n1] | N-(3-(4,6-dimethylpyrimidin-5-yl)-4-(2-(pyrrolidin-1-yl)ethoxy)phenyl)-2-(3-methyl-1,2,4-oxadiazol-5-yl)acetamide |
| 266 | 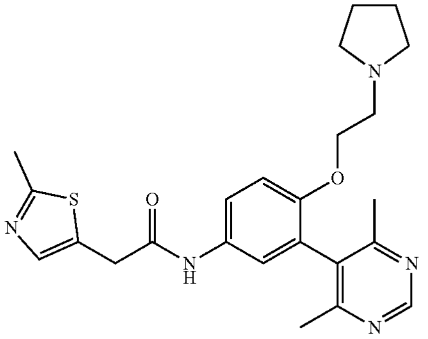 [SMILES: Cc1ncc(CC(=O)Nc2ccc(OCCN3CCCC3)c(-c3c(C)ncnc3C)c2)s1] | N-(3-(4,6-dimethylpyrimidin-5-yl)-4-(2-(pyrrolidin-1-yl)ethoxy)phenyl)-2-(2-methylthiazol-5-yl)acetamide |

TABLE 1-continued

| Cmpd No. | Chemical Structure | Chemical Name |
| --- | --- | --- |
| 267 | 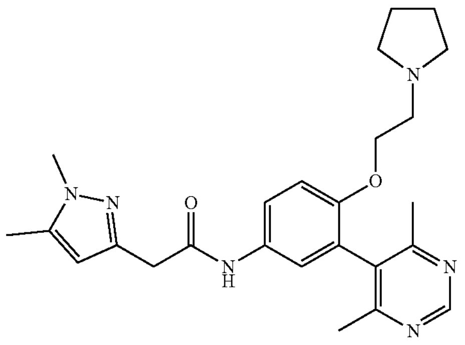 [SMILES: Cc1ncnc(C)c1-c1cc(NC(=O)Cc2cc(C)n(C)n2)ccc1OCCN1CCCC1] | 2-(1,5-dimethyl-1H-pyrazol-3-yl)-N-(3-(4,6-dimethylpyrimidin-5-yl)-4-(2-(pyrrolidin-1-yl)ethoxy)phenyl)acetamide |
| 268 | 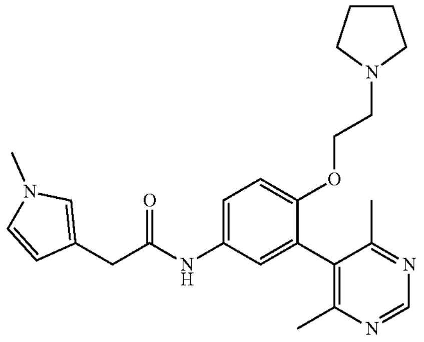 [SMILES: Cc1ncnc(C)c1-c1cc(NC(=O)Cc2ccn(C)c2)ccc1OCCN1CCCC1] | N-[3-(4,6-dimethylpyrimidin-5-yl)-4-(2-pyrrolidin-1-ylethoxy)phenyl]-2-(1-methylpyrrol-3-yl)acetamide |
| 269 | 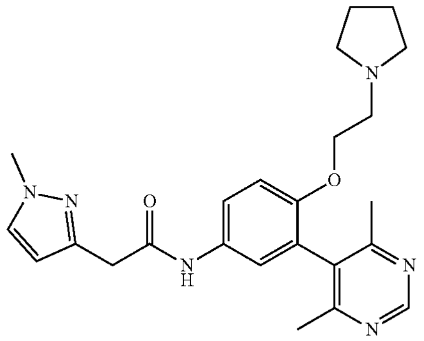 [SMILES: Cc1ncnc(C)c1-c1cc(NC(=O)Cc2ccn(C)n2)ccc1OCCN1CCCC1] | N-[3-(4,6-dimethylpyrimidin-5-yl)-4-(2-pyrrolidin-1-ylethoxy)phenyl]-2-(1-methylpyrazol-3-yl)acetamide |
| 270 | 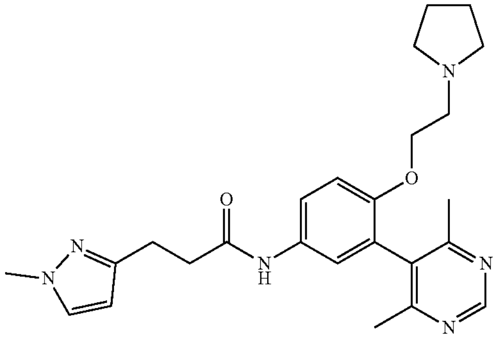 [SMILES: Cc1ncnc(C)c1-c1cc(NC(=O)CCc2ccn(C)n2)ccc1OCCN1CCCC1] | N-[3-(4,6-dimethylpyrimidin-5-yl)-4-(2-pyrrolidin-1-ylethoxy)phenyl]-3-(1-methylpyrazol-3-yl)propanamide |

TABLE 1-continued
| Cmpd No. | Chemical Structure | Chemical Name |
|---|---|---|
| 271 | 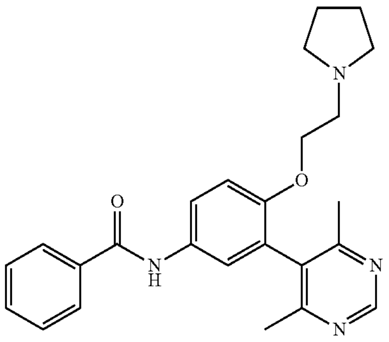 [SMILES: Cc1ncnc(C)c1-c1cc(NC(=O)c2ccccc2)ccc1OCCN1CCCC1] | N-[3-(4,6-dimethylpyrimidin-5-yl)-4-(2-pyrrolidin-1-ylethoxy)phenyl]benzamide |
| 272 | 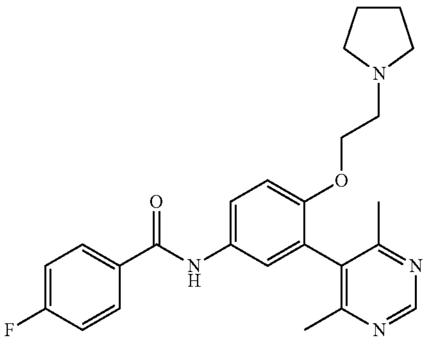 | N-(3-(4,6-dimethylpyrimidin-5-yl)-4-(2-(pyrrolidin-1-yl)ethoxy)phenyl)-4-fluorobenzamide |
| 273 | 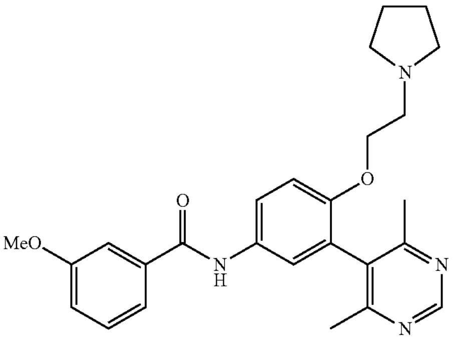 [SMILES: COc1cccc(C(=O)Nc2ccc(OCCN3CCCC3)c(-c3c(C)ncnc3C)c2)c1] | N-(3-(4,6-dimethylpyrimidin-5-yl)-4-(2-(pyrrolidin-1-yl)ethoxy)phenyl)-3-methoxybenzamide |
| 274 | 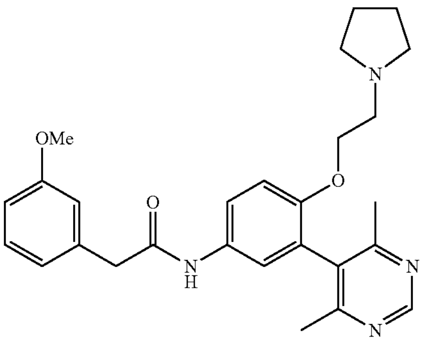 [SMILES: COc1cccc(CC(=O)Nc2ccc(OCCN3CCCC3)c(-c3c(C)ncnc3C)c2)c1] | N-(3-(4,6-dimethylpyrimidin-5-yl)-4-(2-(pyrrolidin-1-yl)ethoxy)phenyl)-2-(3-methoxyphenyl)acetamide |

TABLE 1-continued

| Cmpd No. | Chemical Structure | Chemical Name |
|---|---|---|
| 275 | 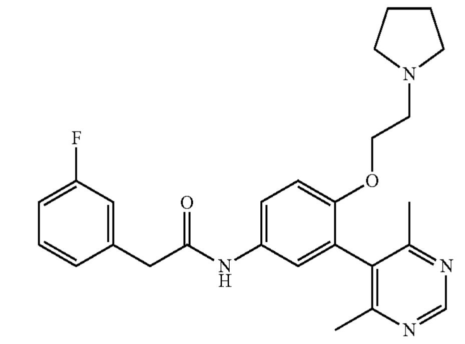 [SMILES: Cc1ncnc(C)c1-c1cc(NC(=O)Cc2cccc(F)c2)ccc1OCCN1CCCC1] | N-(3-(4,6-dimethylpyrimidin-5-yl)-4-(2-(pyrrolidin-1-yl)ethoxy)phenyl)-2-(3-fluorophenyl)acetamide |
| 276 | 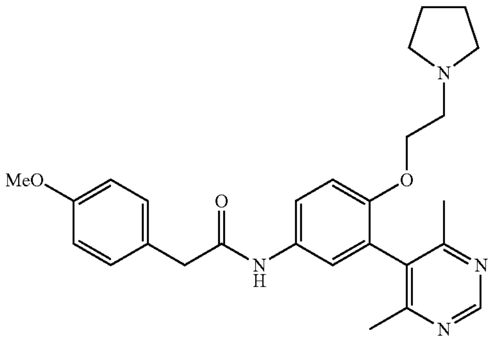 [SMILES: COc1ccc(CC(=O)Nc2ccc(OCCN3CCCC3)c(-c3c(C)ncnc3C)c2)cc1] | N-(3-(4,6-dimethylpyrimidin-5-yl)-4-(2-(pyrrolidin-1-yl)ethoxy)phenyl)-2-(4-methoxyphenyl)acetamide |
| 277 | 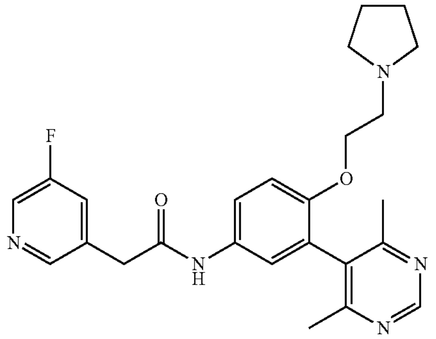 [SMILES: Cc1ncnc(C)c1-c1cc(NC(=O)Cc2cncc(F)c2)ccc1OCCN1CCCC1] | N-(3-(4,6-dimethylpyrimidin-5-yl)-4-(2-(pyrrolidin-1-yl)ethoxy)phenyl)-2-(5-fluoropyridin-3-yl)acetamide |
| 278 | 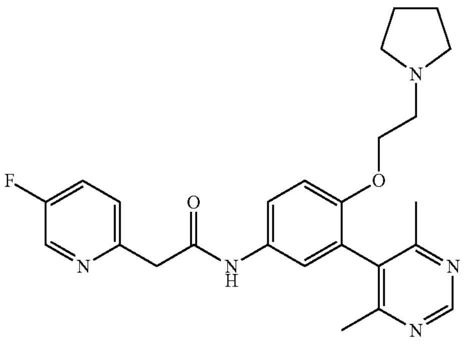 [SMILES: Cc1ncnc(C)c1-c1cc(NC(=O)Cc2ccc(F)cn2)ccc1OCCN1CCCC1] | N-(3-(4,6-dimethylpyrimidin-5-yl)-4-(2-(pyrrolidin-1-yl)ethoxy)phenyl)-2-(5-fluoropyridin-2-yl)acetamide |

TABLE 1-continued

| Cmpd No. | Chemical Structure | Chemical Name |
|---|---|---|
| 279 | 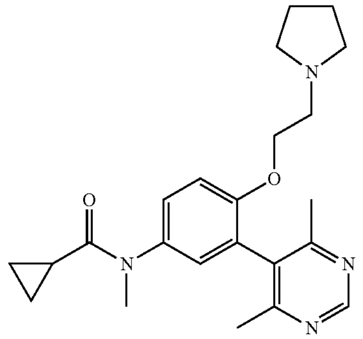 [SMILES: Cc1ncnc(C)c1-c1cc(N(C)C(=O)C2CC2)ccc1OCCN1CCCC1] | N-[3-(4,6-dimethylpyrimidin-5-yl)-4-(2-pyrrolidin-1-ylethoxy)phenyl]-N-methyl-cyclopropanecarboxamide |
| 280 | 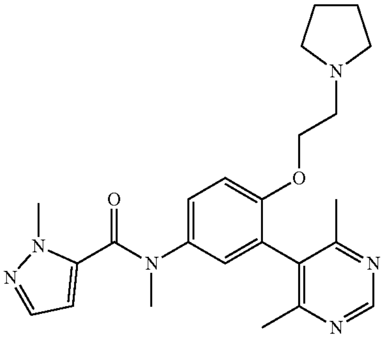 [SMILES: Cc1ncnc(C)c1-c1cc(N(C)C(=O)c2ccnn2C)ccc1OCCN1CCCC1] | N-[3-(4,6-dimethylpyrimidin-5-yl)-4-(2-pyrrolidin-1-ylethoxy)phenyl]-N,2-dimethyl-pyrazole-3-carboxamide |
| 281 | 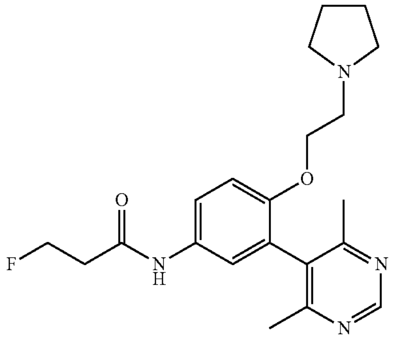 [SMILES: Cc1ncnc(C)c1-c1cc(NC(=O)CCF)ccc1OCCN1CCCC1] | N-[3-(4,6-dimethylpyrimidin-5-yl)-4-(2-pyrrolidin-1-ylethoxy)phenyl]-3-fluoro-propanamide |
| 282 | 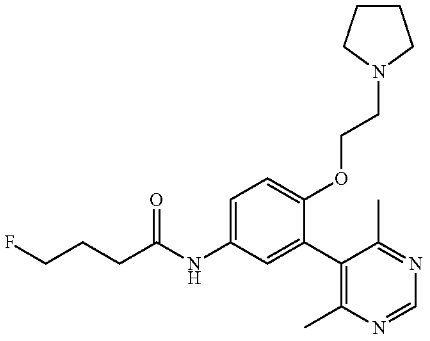 [SMILES: Cc1ncnc(C)c1-c1cc(NC(=O)CCCF)ccc1OCCN1CCCC1] | N-[3-(4,6-dimethylpyrimidin-5-yl)-4-(2-pyrrolidin-1-ylethoxy)phenyl]-4-fluoro-butanamide |

TABLE 1-continued

| Cmpd No. | Chemical Structure | Chemical Name |
| --- | --- | --- |
| 283 | 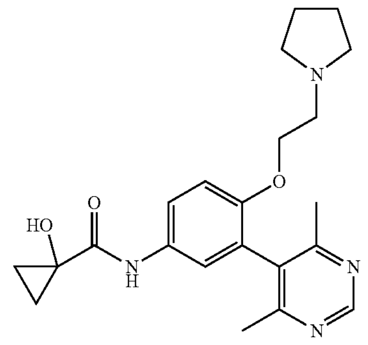 [SMILES: Cc1ncnc(C)c1-c1cc(NC(=O)C2(O)CC2)ccc1OCCN1CCCC1] | N-[3-(4,6-dimethylpyrimidin-5-yl)-4-(2-pyrrolidin-1-ylethoxy)phenyl]-1-hydroxy-cyclopropanecarboxamide |
| 284 | 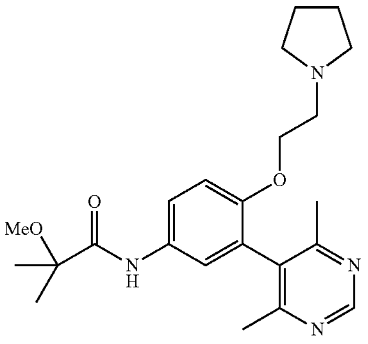 [SMILES: COC(C)(C)C(=O)Nc1ccc(OCCN2CCCC2)c(-c2c(C)ncnc2C)c1] | N-[3-(4,6-dimethylpyrimidin-5-yl)-4-(2-pyrrolidin-1-ylethoxy)phenyl]-2-methoxy-2-methyl-propanamide |
| 285 | 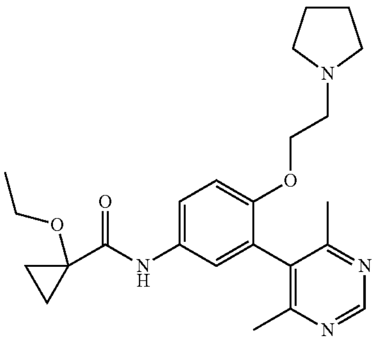 [SMILES: CCOC1(C(=O)Nc2ccc(OCCN3CCCC3)c(-c3c(C)ncnc3C)c2)CC1] | N-[3-(4,6-dimethylpyrimidin-5-yl)-4-(2-pyrrolidin-1-ylethoxy)phenyl]-1-ethoxy-cyclopropanecarboxamide |
| 286 | 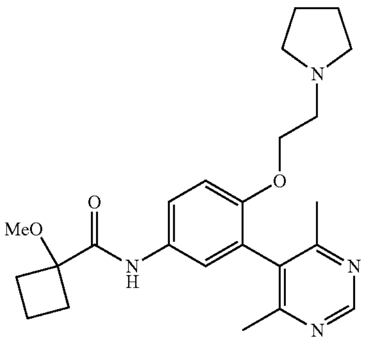 [SMILES: COC1(C(=O)Nc2ccc(OCCN3CCCC3)c(-c3c(C)ncnc3C)c2)CCC1] | N-[3-(4,6-dimethylpyrimidin-5-yl)-4-(2-pyrrolidin-1-ylethoxy)phenyl]-1-methoxy-cyclobutanecarboxamide |

TABLE 1-continued

| Cmpd No. | Chemical Structure | Chemical Name |
| --- | --- | --- |
| 287 | 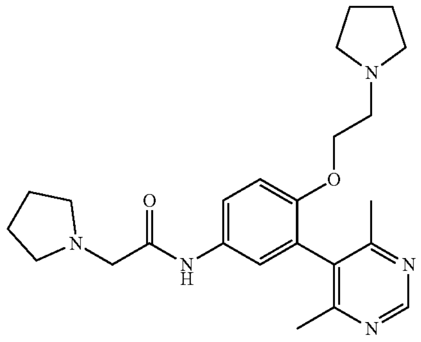 [SMILES: Cc1ncnc(C)c1-c1cc(NC(=O)CN2CCCC2)ccc1OCCN1CCCC1] | N-[3-(4,6-dimethylpyrimidin-5-yl)-4-(2-pyrrolidin-1-ylethoxy)phenyl]-2-pyrrolidin-1-yl-acetamide |
| 288 | 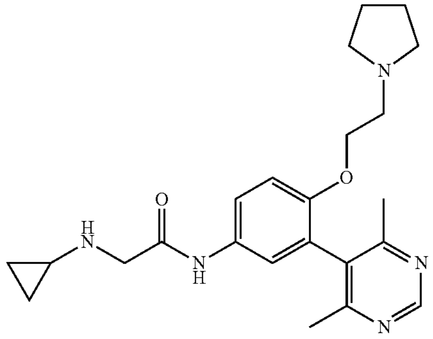 [SMILES: Cc1ncnc(C)c1-c1cc(NC(=O)CNC2CC2)ccc1OCCN1CCCC1] | 2-(cyclopropylamino)-N-[3-(4,6-dimethylpyrimidin-5-yl)-4-(2-pyrrolidin-1-ylethoxy)phenyl]acetamide |
| 289 | 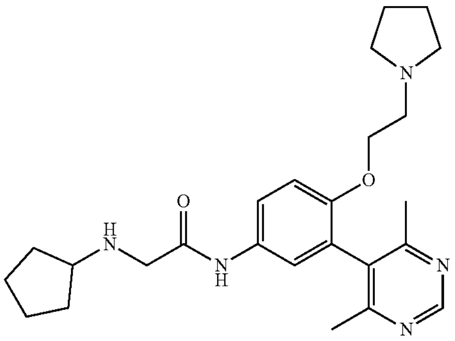 [SMILES: Cc1ncnc(C)c1-c1cc(NC(=O)CNC2CCCC2)ccc1OCCN1CCCC1] | 2-(cyclopentylamino)-N-(3-(4,6-dimethylpyrimidin-5-yl)-4-(2-(pyrrolidin-1-yl)ethoxy)phenyl)acetamide |
| 290 | 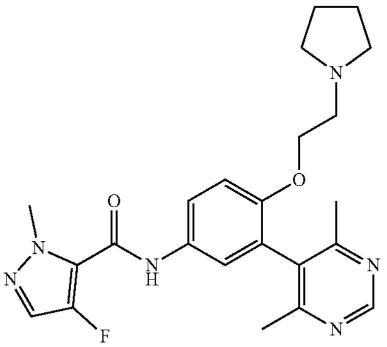 [SMILES: Cc1ncnc(C)c1-c1cc(NC(=O)c2c(F)cnn2C)ccc1OCCN1CCCC1] | N-[3-(4,6-dimethylpyrimidin-5-yl)-4-(2-pyrrolidin-1-ylethoxy)phenyl]-4-fluoro-2-methyl-pyrazole-3-carboxamide |

TABLE 1-continued

| Cmpd No. | Chemical Structure | Chemical Name |
| --- | --- | --- |
| 291 | 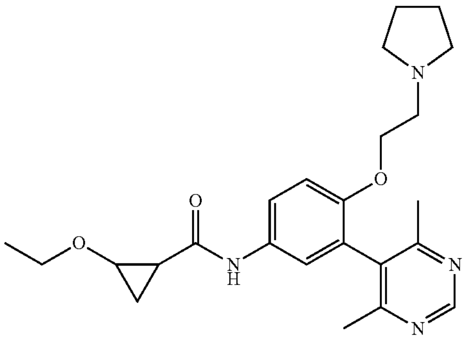 [SMILES: CCOC1CC1C(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-2-ethoxycyclopropane-1-carboxamide |
| 292 | 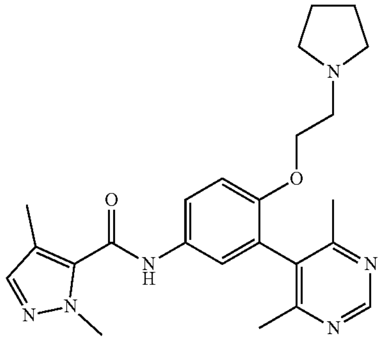 [SMILES: Cc1cnn(C)c1C(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-1,4-dimethyl-1H-pyrazole-5-carboxamide |
| 293 | 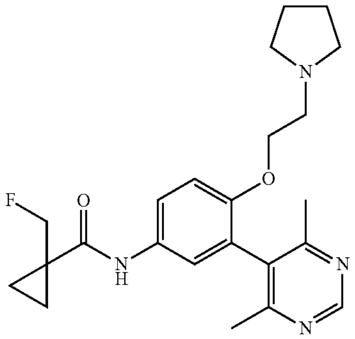 [SMILES: Cc1ncnc(C)c1-c1cc(NC(=O)C2(CF)CC2)ccc1OCCN1CCCC1] | N-(3-(4,6-dimethylpyrimidin-5-yl)-4-(2-(pyrrolidin-1-yl)ethoxy)phenyl)-1-(fluoromethyl)cyclopropane-1-carboxamide |
| 294 | 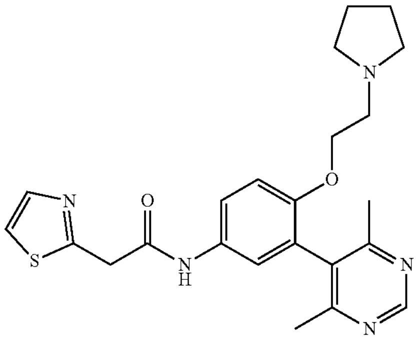 [SMILES: Cc1ncnc(C)c1-c1cc(NC(=O)Cc2nccs2)ccc1OCCN1CCCC1] | N-(3-(4,6-dimethylpyrimidin-5-yl)-4-(2-(pyrrolidin-1-yl)ethoxy)phenyl)-2-(thiazol-2-yl)acetamide |

TABLE 1-continued

| Cmpd No. | Chemical Structure | Chemical Name |
| --- | --- | --- |
| 295 | 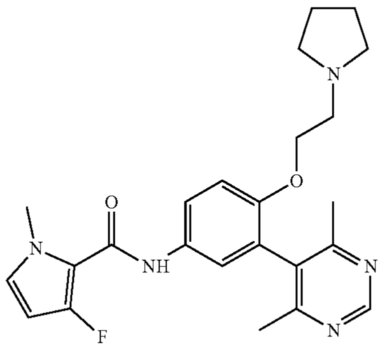 [SMILES: Cc1ncnc(C)c1-c1cc(NC(=O)c2c(F)ccn2C)ccc1OCCN1CCCC1] | N-[3-(4,6-dimethylpyrimidin-5-yl)-4-(2-pyrrolidin-1-ylethoxy)phenyl]-3-fluoro-1-methyl-pyrrole-2-carboxamide |
| 296 | 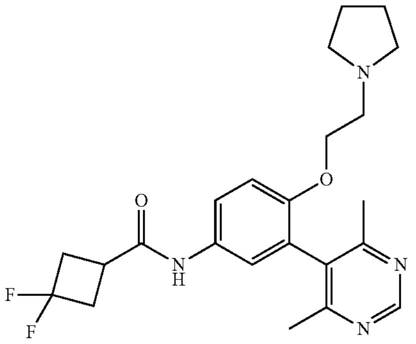 [SMILES: Cc1ncnc(C)c1-c1cc(NC(=O)C2CC(F)(F)C2)ccc1OCCN1CCCC1] | N-(3-(4,6-dimethylpyrimidin-5-yl)-4-(2-(pyrrolidin-1-yl)ethoxy)phenyl)-3,3-difluorocyclobutane-1-carboxamide |
| 297 | 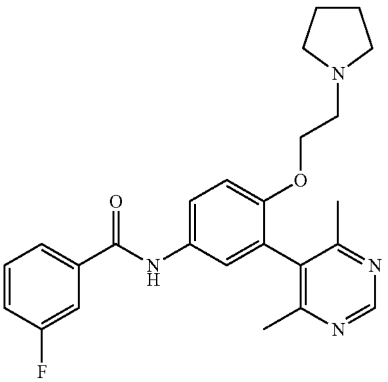 [SMILES: Cc1ncnc(C)c1-c1cc(NC(=O)c2cccc(F)c2)ccc1OCCN1CCCC1] | N-(3-(4,6-dimethylpyrimidin-5-yl)-4-(2-(pyrrolidin-1-yl)ethoxy)phenyl)-3-fluorobenzamide |
| 298 | 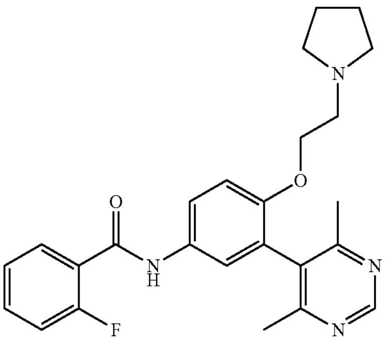 [SMILES: Cc1ncnc(C)c1-c1cc(NC(=O)c2ccccc2F)ccc1OCCN1CCCC1] | N-(3-(4,6-dimethylpyrimidin-5-yl)-4-(2-(pyrrolidin-1-yl)ethoxy)phenyl)-2-fluorobenzamide |

TABLE 1-continued

| Cmpd No. | Chemical Structure | Chemical Name |
| --- | --- | --- |
| 299 | 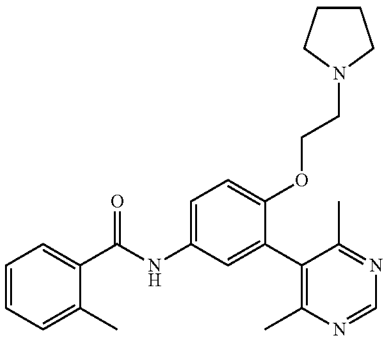 [SMILES: Cc1ccccc1C(=O)Nc1ccc(OCCN2CCCC2)c(-c2c(C)ncnc2C)c1] | N-(3-(4,6-dimethylpyrimidin-5-yl)-4-(2-(pyrrolidin-1-yl)ethoxy)phenyl)-2-methylbenzamide |
| 300 | 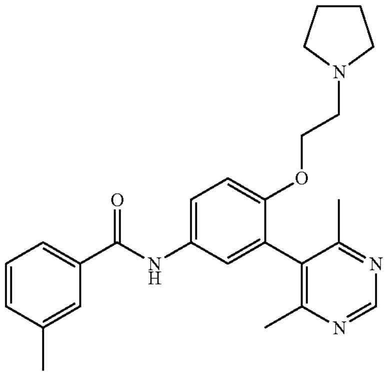 [SMILES: Cc1cccc(C(=O)Nc2ccc(OCCN3CCCC3)c(-c3c(C)ncnc3C)c2)c1] | N-(3-(4,6-dimethylpyrimidin-5-yl)-4-(2-(pyrrolidin-1-yl)ethoxy)phenyl)-3-methylbenzamide |
| 301 | 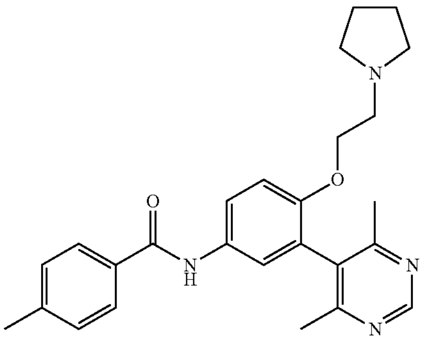 [SMILES: Cc1ccc(C(=O)Nc2ccc(OCCN3CCCC3)c(-c3c(C)ncnc3C)c2)cc1] | N-(3-(4,6-dimethylpyrimidin-5-yl)-4-(2-(pyrrolidin-1-yl)ethoxy)phenyl)-4-methylbenzamide |
| 302 | 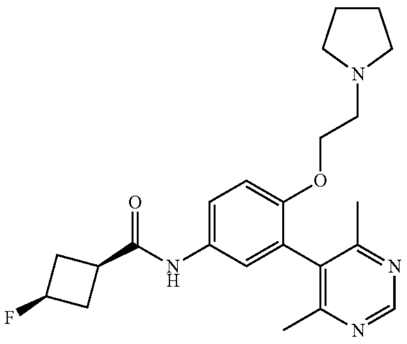 [SMILES: Cc1ncnc(C)c1-c1cc(NC(=O)[C@H]2C[C@@H](F)C2)ccc1OCCN1CCCC1] | (1s,3s)-N-(3-(4,6-dimethylpyrimidin-5-yl)-4-(2-(pyrrolidin-1-yl)ethoxy)phenyl)-3-fluorocyclobutane-1-carboxamide |

TABLE 1-continued

| Cmpd No. | Chemical Structure | Chemical Name |
| --- | --- | --- |
| 303 | 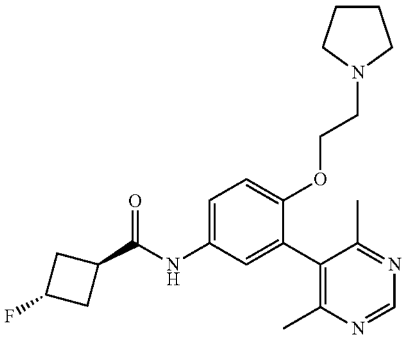 [SMILES: Cc1ncnc(C)c1-c1cc(NC(=O)[C@H]2C[C@H](F)C2)ccc1OCCN1CCCC1] | (1r,3r)-N-(3-(4,6-dimethylpyrimidin-5-yl)-4-(2-(pyrrolidin-1-yl)ethoxy)phenyl)-3-fluorocyclobutane-1-carboxamide |
| 304 | 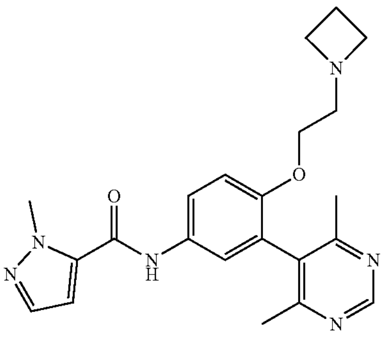 [SMILES: Cc1ncnc(C)c1-c1cc(NC(=O)c2ccnn2C)ccc1OCCN1CCC1] | N-[4-[2-(azetidin-1-yl)ethoxy]-3-(4,6-dimethylpyrimidin-5-yl)phenyl]-2-methyl-pyrazole-3-carboxamide |
| 305 | 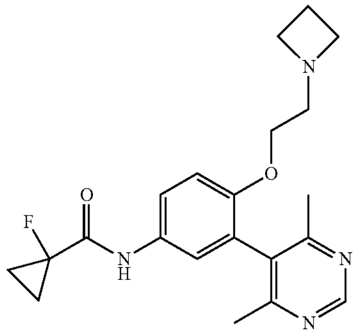 [SMILES: Cc1ncnc(C)c1-c1cc(NC(=O)C2(F)CC2)ccc1OCCN1CCC1] | N-(4-(2-(azetidin-1-yl)ethoxy)-3-(4,6-dimethylpyrimidin-5-yl)phenyl)-1-fluorocyclopropane-1-carboxamide |
| 306 | 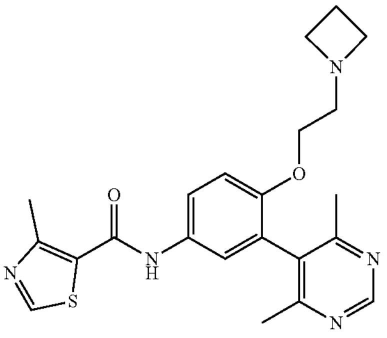 [SMILES: Cc1ncsc1C(=O)Nc1ccc(OCCN2CCC2)c(-c2c(C)ncnc2C)c1] | N-(4-(2-(azetidin-1-yl)ethoxy)-3-(4,6-dimethylpyrimidin-5-yl)phenyl)-4-methylthiazole-5-carboxamide |

TABLE 1-continued
| Cmpd No. | Chemical Structure | Chemical Name |
| --- | --- | --- |
| 307 | 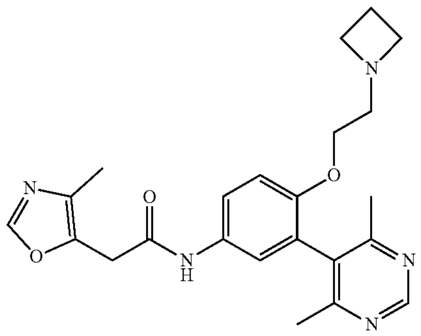 [SMILES: Cc1ncoc1CC(=O)Nc1ccc(OCCN2CCC2)c(-c2c(C)ncnc2C)c1] | N-(4-(2-(azetidin-1-yl)ethoxy)-3-(4,6-dimethylpyrimidin-5-yl)phenyl)-2-(4-methylthiazol-5-yl)acetamide |
| 308 | 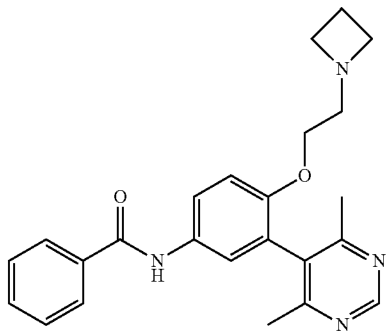 [SMILES: Cc1ncnc(C)c1-c1cc(NC(=O)c2ccccc2)ccc1OCCN1CCC1] | N-(4-(2-(azetidin-1-yl)ethoxy)-3-(4,6-dimethylpyrimidin-5-yl)phenyl)benzamide |
| 309 | 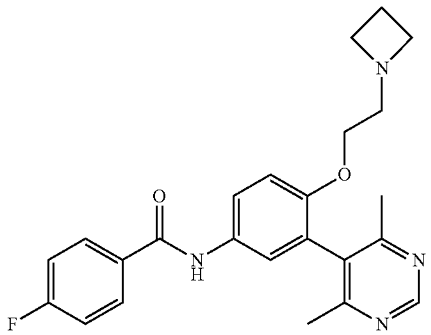 [SMILES: Cc1ncnc(C)c1-c1cc(NC(=O)c2ccc(F)cc2)ccc1OCCN1CCC1] | N-(4-(2-(azetidin-1-yl)ethoxy)-3-(4,6-dimethylpyrimidin-5-yl)phenyl)-4-fluorobenzamide |
| 310 | 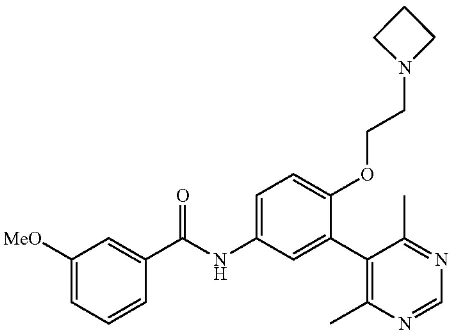 [SMILES: COc1cccc(C(=O)Nc2ccc(OCCN3CCC3)c(-c3c(C)ncnc3C)c2)c1] | N-(4-(2-(azetidin-1-yl)ethoxy)-3-(4,6-dimethylpyrimidin-5-yl)phenyl)-3-methoxybenzamide |

TABLE 1-continued

| Cmpd No. | Chemical Structure | Chemical Name |
|---|---|---|
| 311 | 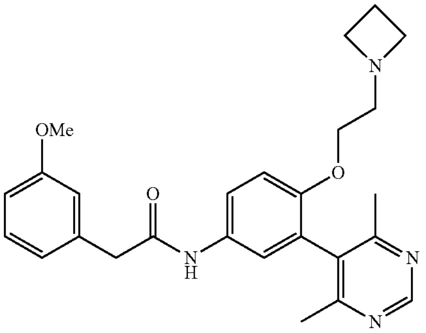 [SMILES: COc1cccc(CC(=O)Nc2ccc(OCCN3CCC3)c(-c3c(C)ncnc3C)c2)c1] | N-(4-(2-(azetidin-1-yl)ethoxy)-3-(4,6-dimethylpyrimidin-5-yl)phenyl)-2-(3-methoxyphenyl)acetamide |
| 312 | 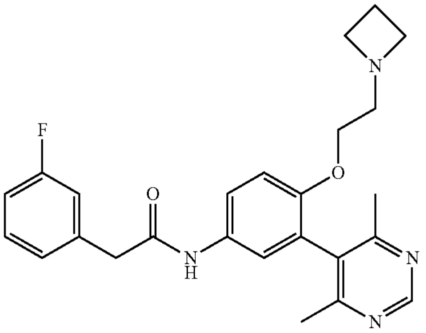 [SMILES: Cc1ncnc(C)c1-c1cc(NC(=O)Cc2cccc(F)c2)ccc1OCCN1CCC1] | N-(4-(2-(azetidin-1-yl)ethoxy)-3-(4,6-dimethylpyrimidin-5-yl)phenyl)-2-(3-fluorophenyl)acetamide |
| 313 | 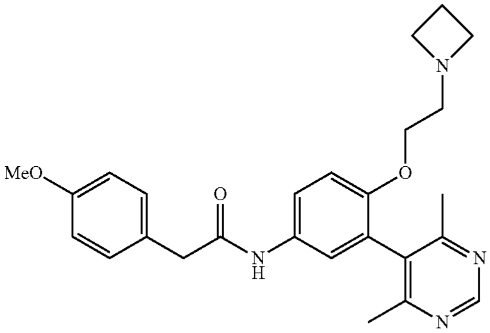 [SMILES: COc1ccc(CC(=O)Nc2ccc(OCCN3CCC3)c(-c3c(C)ncnc3C)c2)cc1] | N-(4-(2-(azetidin-1-yl)ethoxy)-3-(4,6-dimethylpyrimidin-5-yl)phenyl)-2-(4-methoxyphenyl)acetamide |
| 314 | 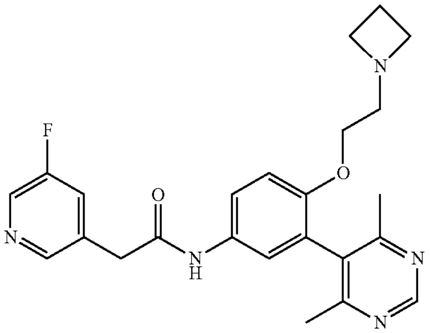 [SMILES: Cc1ncnc(C)c1-c1cc(NC(=O)Cc2cncc(F)c2)ccc1OCCN1CCC1] | N-(4-(2-(azetidin-1-yl)ethoxy)-3-(4,6-dimethylpyrimidin-5-yl)phenyl)-2-(5-fluoropyridin-3-yl)acetamide |

TABLE 1-continued

| Cmpd No. | Chemical Structure | Chemical Name |
|---|---|---|
| 315 | 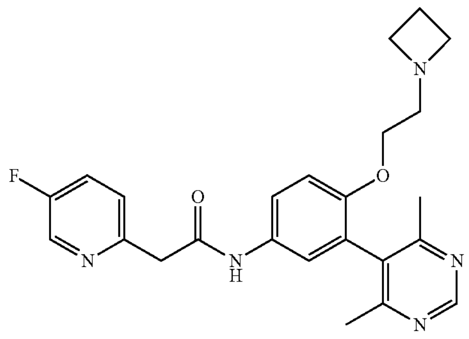 [SMILES: Cc1ncnc(C)c1-c1cc(NC(=O)Cc2ccc(F)cn2)ccc1OCCN1CCC1] | N-(4-(2-(azetidin-1-yl)ethoxy)-3-(4,6-dimethylpyrimidin-5-yl)phenyl)-2-(5-fluoropyridin-2-yl)acetamide |
| 316 | 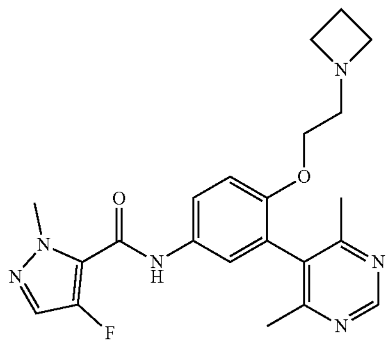 [SMILES: Cc1ncnc(C)c1-c1cc(NC(=O)c2c(F)cnn2C)ccc1OCCN1CCC1] | N-(4-(2-(azetidin-1-yl)ethoxy)-3-(4,6-dimethylpyrimidin-5-yl)phenyl)-4-fluoro-1-methyl-1H-pyrazole-5-carboxamide |
| 317 | 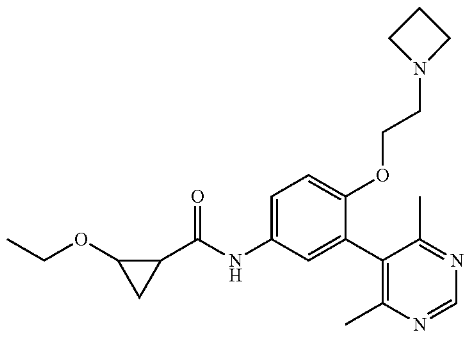 [SMILES: CCOC1CC1C(=O)Nc1ccc(OCCN2CCC2)c(-c2c(C)ncnc2C)c1] | N-(4-(2-(azetidin-1-yl)ethoxy)-3-(4,6-dimethylpyrimidin-5-yl)phenyl)-2-ethoxycyclopropane-1-carboxamide |
| 318 | 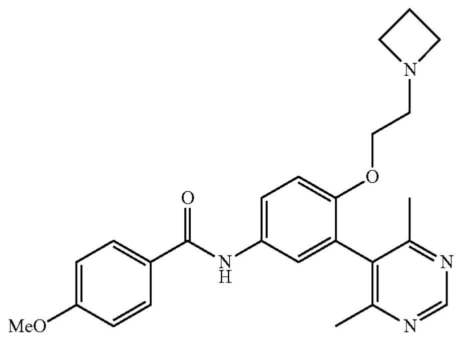 [SMILES: COc1ccc(C(=O)Nc2ccc(OCCN3CCC3)c(-c3c(C)ncnc3C)c2)cc1] | N-(4-(2-(azetidin-1-yl)ethoxy)-3-(4,6-dimethylpyrimidin-5-yl)phenyl)-4-methoxybenzamide |

TABLE 1-continued
| Cmpd No. | Chemical Structure | Chemical Name |
| --- | --- | --- |
| 319 | 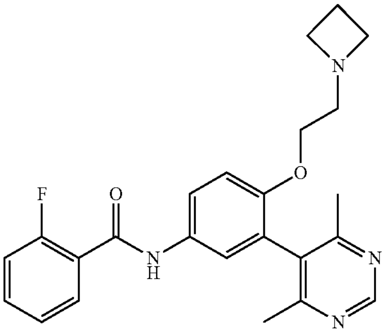 | N-(4-(2-(azetidin-1-yl)ethoxy)-3-(4,6-dimethylpyrimidin-5-yl)phenyl)-2-fluorobenzamide |
| 320 | 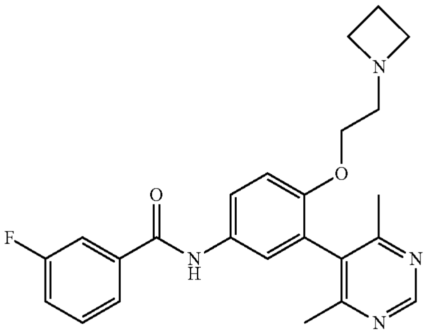 [SMILES: Cc1ncnc(C)c1-c1cc(NC(=O)c2cccc(F)c2)ccc1OCCN1CCC1] | N-(4-(2-(azetidin-1-yl)ethoxy)-3-(4,6-dimethylpyrimidin-5-yl)phenyl)-3-fluorobenzamide |
| 321 | 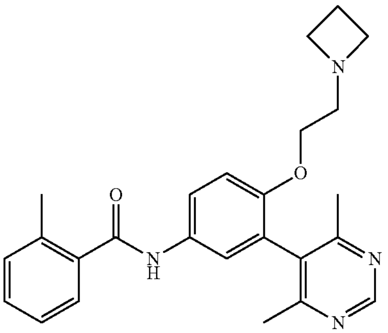 [SMILES: Cc1ccccc1C(=O)Nc1ccc(OCCN2CCC2)c(-c2c(C)ncnc2C)c1] | N-(4-(2-(azetidin-1-yl)ethoxy)-3-(4,6-dimethylpyrimidin-5-yl)phenyl)-2-methylbenzamide |
| 322 | 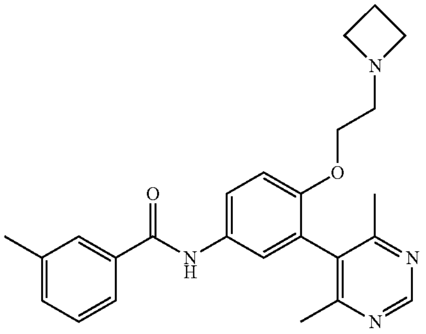 [SMILES: Cc1cccc(C(=O)Nc2ccc(OCCN3CCC3)c(-c3c(C)ncnc3C)c2)c1] | N-(4-(2-(azetidin-1-yl)ethoxy)-3-(4,6-dimethylpyrimidin-5-yl)phenyl)-3-methylbenzamide |

TABLE 1-continued
| Cmpd No. | Chemical Structure | Chemical Name |
| --- | --- | --- |
| 323 | 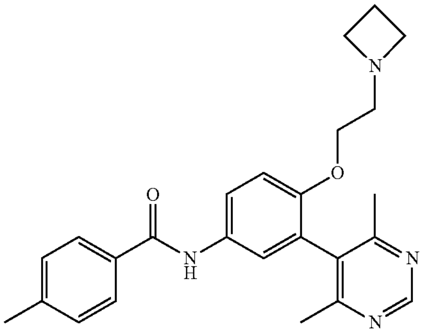 [SMILES: Cc1ccc(C(=O)Nc2ccc(OCCN3CCC3)c(-c3c(C)ncnc3C)c2)cc1] | N-(4-(2-(azetidin-1-yl)ethoxy)-3-(4,6-dimethylpyrimidin-5-yl)phenyl)-4-methylbenzamide |
| 324 | 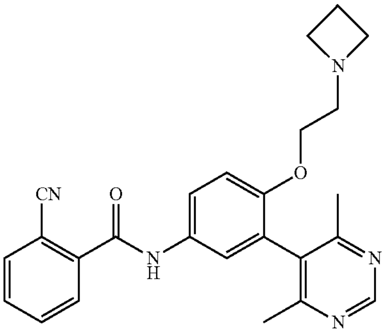 [SMILES: Cc1ncnc(C)c1-c1cc(NC(=O)c2ccccc2C#N)ccc1OCCN1CCC1] | N-(4-(2-(azetidin-1-yl)ethoxy)-3-(4,6-dimethylpyrimidin-5-yl)phenyl)-2-cyanobenzamide |
| 325 | 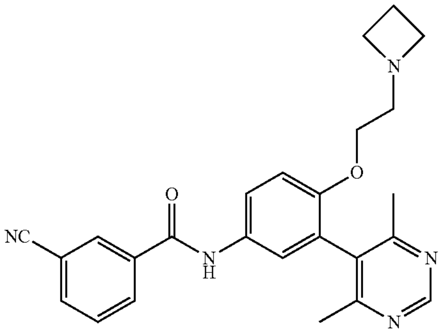 [SMILES: Cc1ncnc(C)c1-c1cc(NC(=O)c2cccc(C#N)c2)ccc1OCCN1CCC1] | N-(4-(2-(azetidin-1-yl)ethoxy)-3-(4,6-dimethylpyrimidin-5-yl)phenyl)-3-cyanobenzamide |
| 326 | 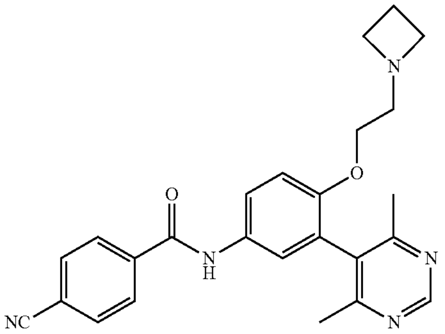 [SMILES: Cc1ncnc(C)c1-c1cc(NC(=O)c2ccc(C#N)cc2)ccc1OCCN1CCC1] | N-(4-(2-(azetidin-1-yl)ethoxy)-3-(4,6-dimethylpyrimidin-5-yl)phenyl)-4-cyanobenzamide |

TABLE 1-continued

| Cmpd No. | Chemical Structure | Chemical Name |
|---|---|---|
| 327 | 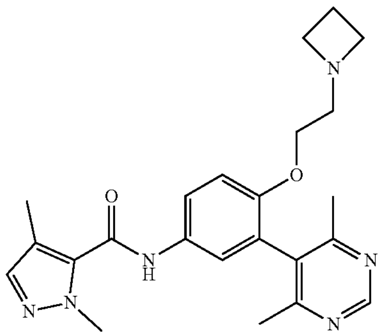 [SMILES: Cc1cnn(C)c1C(=O)Nc1ccc(OCCN2CCC2)c(-c2c(C)ncnc2C)c1] | N-(4-(2-(azetidin-1-yl)ethoxy)-3-(4,6-dimethylpyrimidin-5-yl)phenyl)-1,4-dimethyl-1H-pyrazole-5-carboxamide |
| 328 | 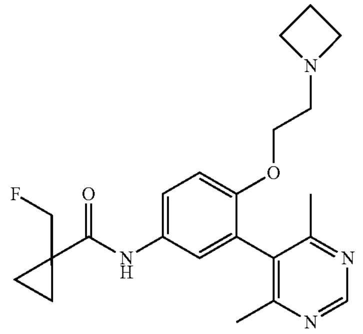 [SMILES: Cc1ncnc(C)c1-c1cc(NC(=O)C2(CF)CC2)ccc1OCCN1CCC1] | N-(4-(2-(azetidin-1-yl)ethoxy)-3-(4,6-dimethylpyrimidin-5-yl)phenyl)-1-(fluoromethyl)cyclopropane-1-carboxamide |
| 329 | 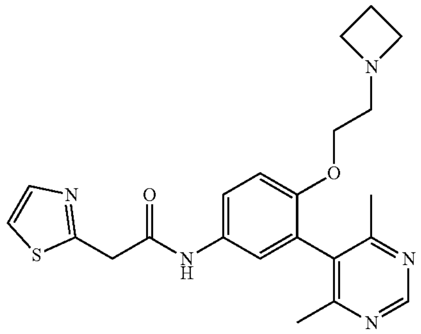 [SMILES: Cc1ncnc(C)c1-c1cc(NC(=O)Cc2nccs2)ccc1OCCN1CCC1] | N-(4-(2-(azetidin-1-yl)ethoxy)-3-(4,6-dimethylpyrimidin-5-yl)phenyl)-2-(thiazol-2-yl)acetamide |
| 330 | 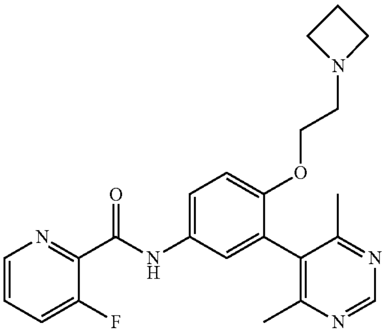 [SMILES: Cc1ncnc(C)c1-c1cc(NC(=O)c2ncccc2F)ccc1OCCN1CCC1] | N-(4-(2-(azetidin-1-yl)ethoxy)-3-(4,6-dimethylpyrimidin-5-yl)phenyl)-3-fluoropicolinamide |

TABLE 1-continued

| Cmpd No. | Chemical Structure | Chemical Name |
|---|---|---|
| 331 | 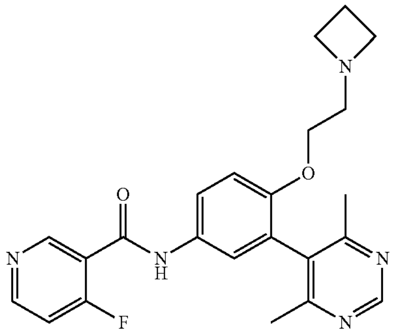 [SMILES: Cc1ncnc(C)c1-c1cc(NC(=O)c2cnccc2F)ccc1OCCN1CCC1] | N-(4-(2-(azetidin-1-yl)ethoxy)-3-(4,6-dimethylpyrimidin-5-yl)phenyl)-4-fluoronicotinamide |
| 332 | 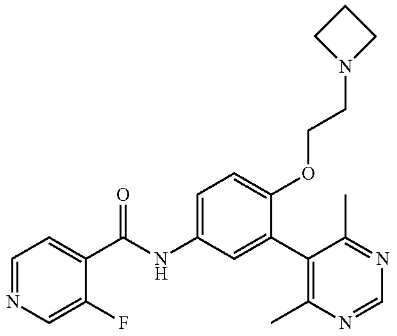 [SMILES: Cc1ncnc(C)c1-c1cc(NC(=O)c2ccncc2F)ccc1OCCN1CCC1] | N-(4-(2-(azetidin-1-yl)ethoxy)-3-(4,6-dimethylpyrimidin-5-yl)phenyl)-3-fluoroisonicotinamide |
| 333 | 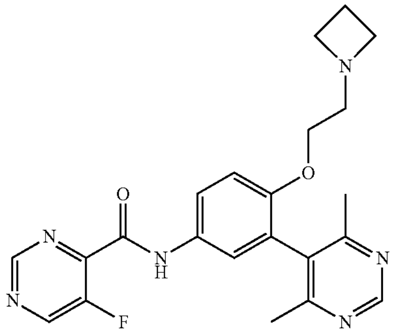 [SMILES: Cc1ncnc(C)c1-c1cc(NC(=O)c2ncncc2F)ccc1OCCN1CCC1] | N-(4-(2-(azetidin-1-yl)ethoxy)-3-(4,6-dimethylpyrimidin-5-yl)phenyl)-5-fluoropyrimidine-4-carboxamide |
| 334 | 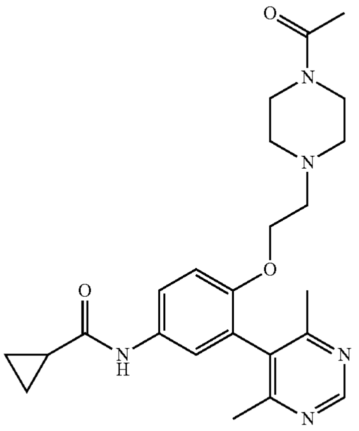 [SMILES: CC(=O)N1CCN(CCOc2ccc(NC(=O)C3CC3)cc2-c2c(C)ncnc2C)CC1] | N-[4-[2-(4-acetylpiperazin-1-yl)ethoxy]-3-(4,6-dimethylpyrimidin-5-yl)phenyl]cyclopropanecarboxamide |

TABLE 1-continued

| Cmpd No. | Chemical Structure | Chemical Name |
|---|---|---|
| 335 | 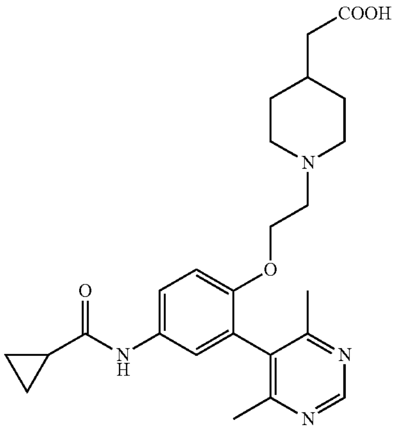 [SMILES: Cc1ncnc(C)c1-c1cc(NC(=O)C2CC2)ccc1OCCN1CCC(CC(=O)O)CC1] | 2-[1-[2-[4-(cyclopropanecarbonylamino)-2-(4,6-dimethylpyrimidin-5-yl)phenoxy]ethyl]-4-piperidyl]acetic acid |
| 336 | 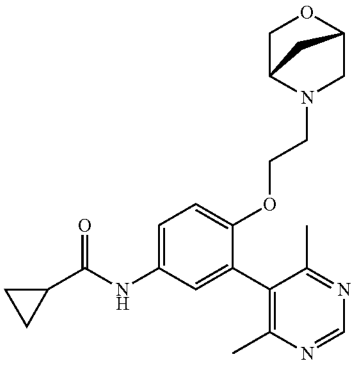 [SMILES: Cc1ncnc(C)c1-c1cc(NC(=O)C2CC2)ccc1OCCN1C[C@@H]2C[C@H]1CO2] | N-[3-(4,6-dimethylpyrimidin-5-yl)-4-[2-[(1S,4S)-2-oxa-5-azabicyclo[2.2.1]heptan-5-yl]ethoxy]phenyl]cyclopropanecarboxamide |
| 337 | 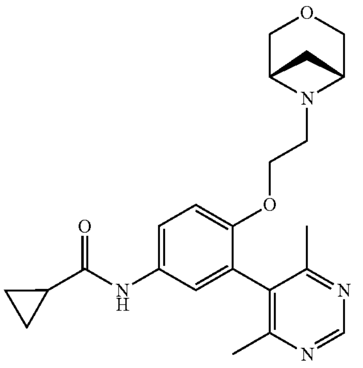 [SMILES: Cc1ncnc(C)c1-c1cc(NC(=O)C2CC2)ccc1OCCN1[C@@H]2COC[C@H]1C2] | N-[3-(4,6-dimethylpyrimidin-5-yl)-4-[2-[(1S,5R)-3-oxa-6-azabicyclo[3.1.1]heptan-6-yl]ethoxy phenyl]cyclopropanecarboxamide |
| 338 | 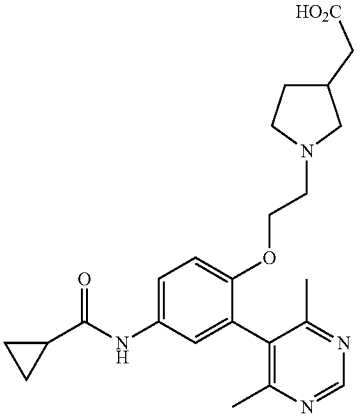 [SMILES: Cc1ncnc(C)c1-c1cc(NC(=O)C2CC2)ccc1OCCN1CCC(CC(=O)O)C1] | 2-[1-[2-[4-(cyclopropanecarbonylamino)-2-(4,6-dimethylpyrimidin-5-yl)phenoxy]ethyl]pyrrolidin-3-yl]acetic acid |

TABLE 1-continued
| Cmpd No. | Chemical Structure | Chemical Name |
| --- | --- | --- |
| 339 | 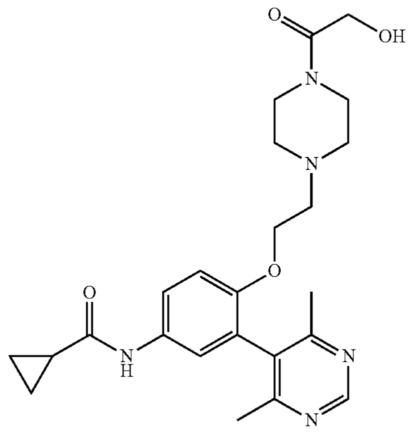 [SMILES: Cc1ncnc(C)c1-c1cc(NC(=O)C2CC2)ccc1OCCN1CCN(C(=O)CO)CC1] | N-[3-(4,6-dimethylpyrimidin-5-yl)-4-[2-[4-(2-hydroxyacetyl)piperazin-1-yl]ethoxy]phenyl]cyclopropanecarboxamide |
| 340 | 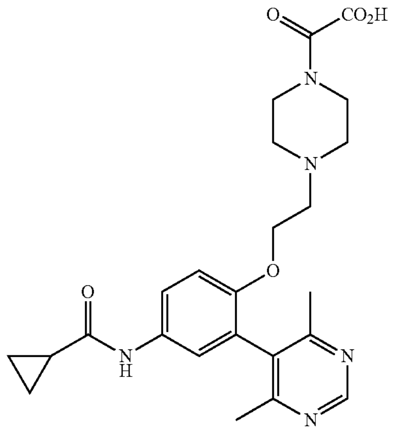 [SMILES: Cc1ncnc(C)c1-c1cc(NC(=O)C2CC2)ccc1OCCN1CCN(C(=O)C(=O)O)CC1] | 2-[4-[2-[4-(cyclopropanecarbonylamino)-2-(4,6-dimethylpyrimidin-5-yl)phenoxy]ethyl]piperazin-1-yl]-2-oxo-acetic acid |
| 341 | 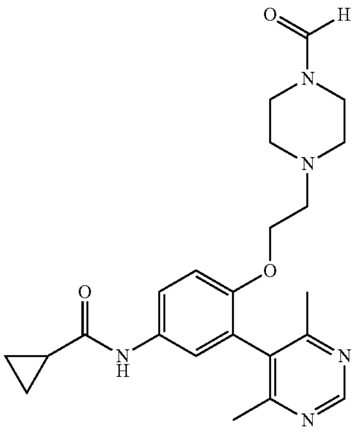 [SMILES: Cc1ncnc(C)c1-c1cc(NC(=O)C2CC2)ccc1OCCN1CCN(C=O)CC1] | N-[3-(4,6-dimethylpyrimidin-5-yl)-4-[2-(4-formylpiperazin-1-yl)ethoxy]phenyl]cyclopropanecarboxamide |

TABLE 1-continued

| Cmpd No. | Chemical Structure | Chemical Name |
| --- | --- | --- |
| 342 | 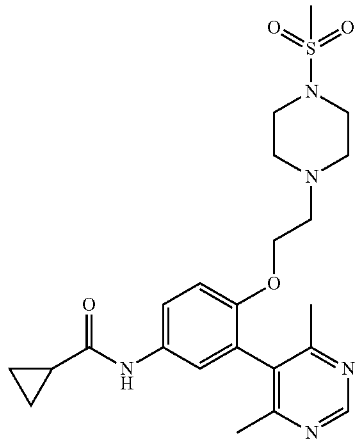 [SMILES: Cc1ncnc(C)c1-c1cc(NC(=O)C2CC2)ccc1OCCN1CCN(S(C)(=O)=O)CC1] | N-[3-(4,6-dimethylpyrimidin-5-yl)-4-[2-(4-methylsulfonylpiperazin-1-yl)ethoxy]phenyl]cyclopropanecarboxamide |
| 343 | 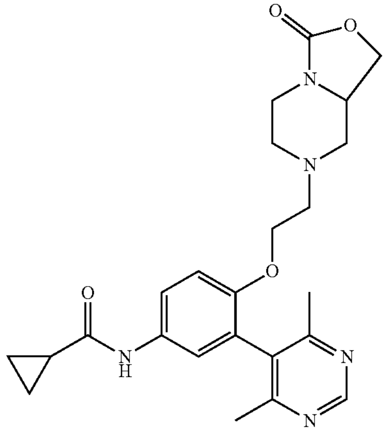 [SMILES: Cc1ncnc(C)c1-c1cc(NC(=O)C2CC2)ccc1OCCN1CCN2C(=O)OCC2C1] | N-[3-(4,6-dimethylpyrimidin-5-yl)-4-[2-(3-oxo-5,6,8,8a-tetrahydro-1H-oxazolo[3,4-a]pyrazin-7-yl)ethoxy]phenyl]cyclopropanecarboxamide |
| 344 | 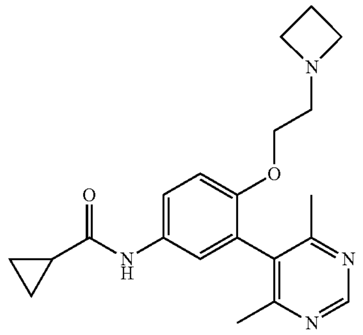 [SMILES: Cc1ncnc(C)c1-c1cc(NC(=O)C2CC2)ccc1OCCN1CCC1] | N-(4-(2-(azetidin-1-yl)ethoxy)-3-(4,6-dimethylpyrimidin-5-yl)phenyl)cyclopropanecarboxamide |
| 345 | 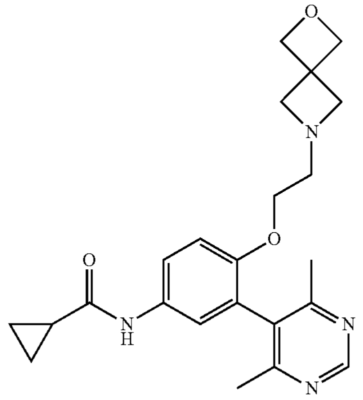 [SMILES: Cc1ncnc(C)c1-c1cc(NC(=O)C2CC2)ccc1OCCN1CC2(COC2)C1] | N-(4-(2-(2-oxa-6-azaspiro[3.3]heptan-6-yl)ethoxy)-3-(4,6-dimethylpyrimidin-5-yl)phenyl)cyclopropanecarboxamide |

TABLE 1-continued
| Cmpd No. | Chemical Structure | Chemical Name |
| --- | --- | --- |
| 346 | 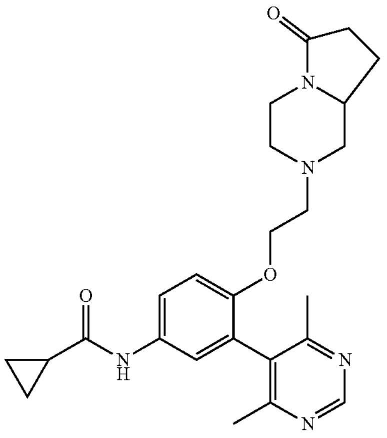 [SMILES: Cc1ncnc(C)c1-c1cc(NC(=O)C2CC2)ccc1OCCN1CCN2C(=O)CCC2C1] | N-(3-(4,6-dimethylpyrimidin-5-yl)-4-(2-(6-oxohexahydropyrrolo[1,2-a]pyrazin-2(1H)-yl)ethoxy)phenyl)cyclopropanecarboxamide |
| 347 | 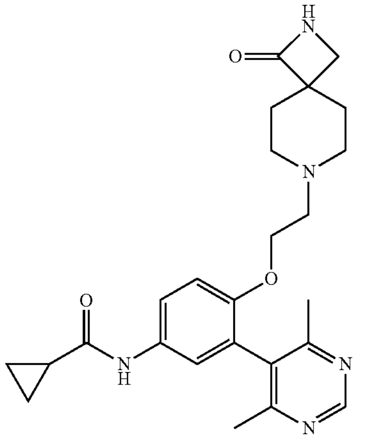 [SMILES: Cc1ncnc(C)c1-c1cc(NC(=O)C2CC2)ccc1OCCN1CCC2(CC1)CNC2=O] | N-(3-(4,6-dimethylpyrimidin-5-yl)-4-(2-(1-oxo-2,7-diazaspiro[3.5]nonan-7-yl)ethoxy)phenyl)cyclopropanecarboxamide |
| 348 | 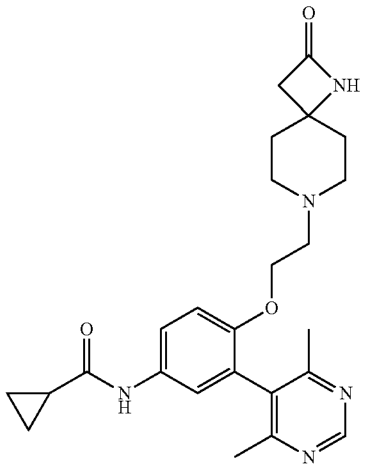 | N-(3-(4,6-dimethylpyrimidin-5-yl)-4-(2-(2-oxo-1,7-diazaspiro[3.5]nonan-7-yl)ethoxy)phenyl)cyclopropanecarboxamide |

TABLE 1-continued
| Cmpd No. | Chemical Structure | Chemical Name |
|---|---|---|
| 349 | 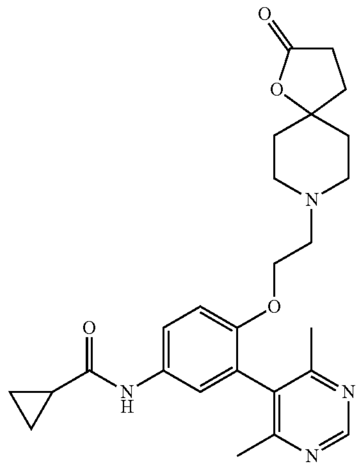 [SMILES: Cc1ncnc(C)c1-c1cc(NC(=O)C2CC2)ccc1OCCN1CCC2(CCC(=O)O2)CC1] | N-(3-(4,6-dimethylpyrimidin-5-yl)-4-(2-(2-oxo-1-oxa-8-azaspiro[4.5]decan-8-yl)ethoxy)phenyl)cyclopropanecarboxamide |
| 350 | 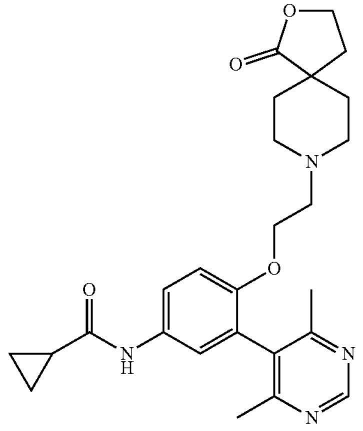 [SMILES: Cc1ncnc(C)c1-c1cc(NC(=O)C2CC2)ccc1OCCN1CCC2(CCOC2=O)CC1] | N-(3-(4,6-dimethylpyrimidin-5-yl)-4-(2-(1-oxo-2-oxa-8-azaspiro[4.5]decan-8-yl)ethoxy)phenyl)cyclopropanecarboxamide |
| 351 | 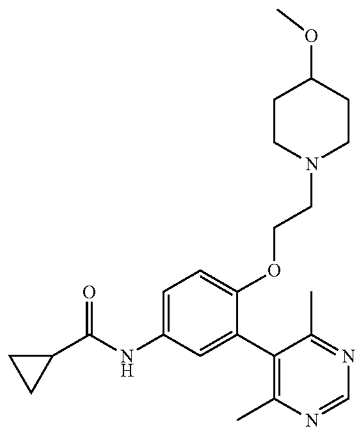 [SMILES: COC1CCN(CCOc2ccc(NC(=O)C3CC3)cc2-c2c(C)ncnc2C)CC1] | N-(3-(4,6-dimethylpyrimidin-5-yl)-4-(2-(4-methoxypiperidin-1-yl)ethoxy)phenyl)cyclopropanecarboxamide |

TABLE 1-continued

| Cmpd No. | Chemical Structure | Chemical Name |
|---|---|---|
| 352 | 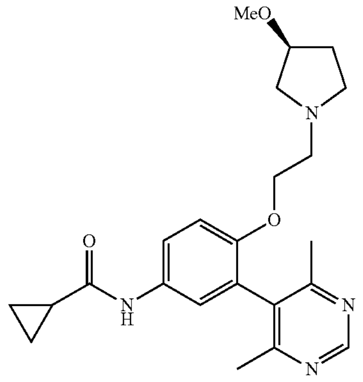 [SMILES: CO[C@H]1CCN(CCOc2ccc(NC(=O)C3CC3)cc2-c2c(C)ncnc2C)C1] | (S)-N-(3-(4,6-dimethylpyrimidin-5-yl)-4-(2-(3-methoxypyrrolidin-1-yl)ethoxy)phenyl)cyclopropanecarboxamide |
| 353 | 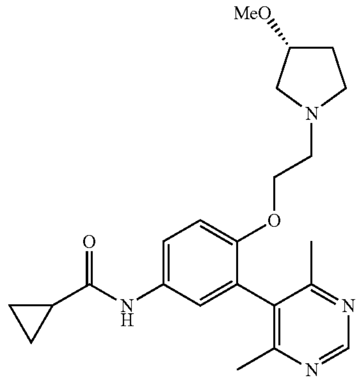 [SMILES: CO[C@@H]1CCN(CCOc2ccc(NC(=O)C3CC3)cc2-c2c(C)ncnc2C)C1] | (R)-N-(3-(4,6-dimethylpyrimidin-5-yl)-4-(2-(3-methoxypyrrolidin-1-yl)ethoxy)phenyl)cyclopropanecarboxamide |
| 354 | 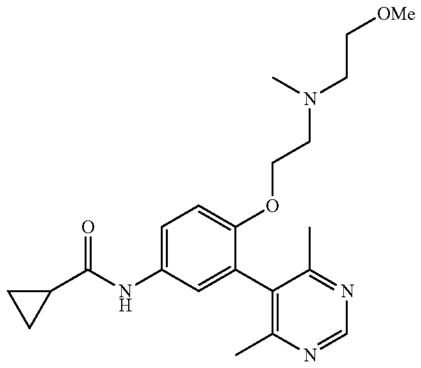 [SMILES: COCCN(C)CCOc1ccc(NC(=O)C2CC2)cc1-c1c(C)ncnc1C] | N-[3-(4,6-dimethylpyrimidin-5-yl)-4-[2-[2-methoxyethyl(methyl)amino]ethoxy]phenyl] cyclopropanecarboxamide |
| 355 | 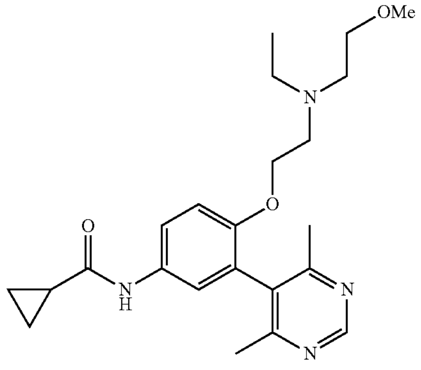 [SMILES: CCN(CCOC)CCOc1ccc(NC(=O)C2CC2)cc1-c1c(C)ncnc1C] | N-(3-(4,6-dimethylpyrimidin-5-yl)-4-(2-(ethyl(2-methoxyethyl)amino)ethoxy)phenyl)cyclopropanecarboxamide |

TABLE 1-continued

| Cmpd No. | Chemical Structure | Chemical Name |
|---|---|---|
| 356 | 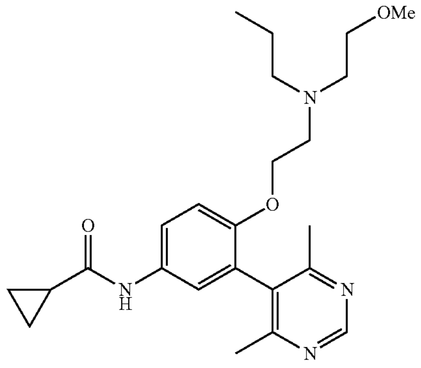 [SMILES: CCCN(CCOC)CCOc1ccc(NC(=O)C2CC2)cc1-c1c(C)ncnc1C] | N-(3-(4,6-dimethylpyrimidin-5-yl)-4-(2-((2-methoxyethyl)(propyl)amino)ethoxy)phenyl)cyclopropanecarboxamide |
| 357 | 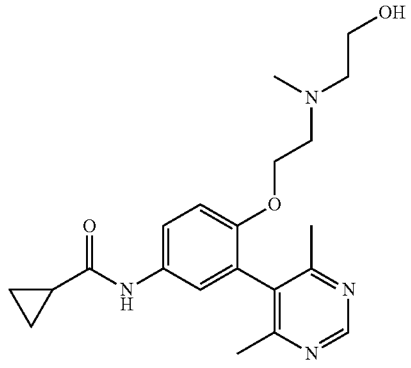 [SMILES: Cc1ncnc(C)c1-c1cc(NC(=O)C2CC2)ccc1OCCN(C)CCO] | N-(3-(4,6-dimethylpyrimidin-5-yl)-4-(2-((2-hydroxyethyl)(methyl)amino)ethoxy)phenyl)cyclopropanecarboxamide |
| 358 | 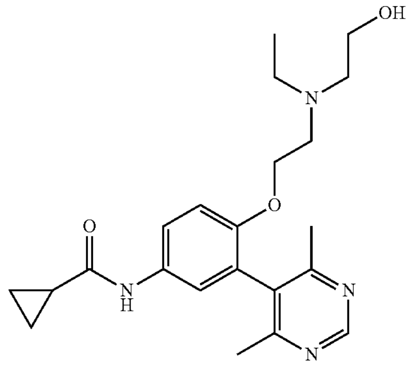 [SMILES: CCN(CCO)CCOc1ccc(NC(=O)C2CC2)cc1-c1c(C)ncnc1C] | N-(3-(4,6-dimethylpyrimidin-5-yl)-4-(2-(ethyl(2-hydroxyethyl)amino)ethoxy)phenyl)cyclopropanecarboxamide |
| 359 | 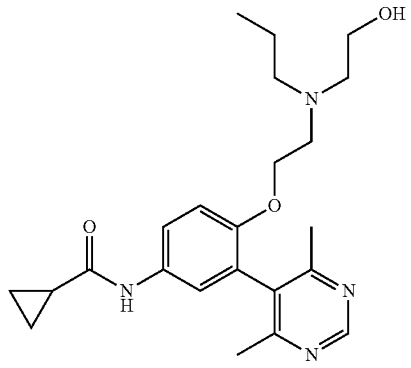 [SMILES: CCCN(CCO)CCOc1ccc(NC(=O)C2CC2)cc1-c1c(C)ncnc1C] | N-(3-(4,6-dimethylpyrimidin-5-yl)-4-(2-((2-hydroxyethyl)(propyl)amino)ethoxy)phenyl)cyclopropanecarboxamide |

TABLE 1-continued

| Cmpd No. | Chemical Structure | Chemical Name |
| --- | --- | --- |
| 360 | 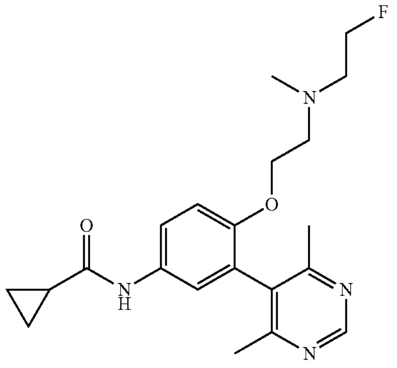 [SMILES: Cc1ncnc(C)c1-c1cc(NC(=O)C2CC2)ccc1OCCN(C)CCF] | N-(3-(4,6-dimethylpyrimidin-5-yl)-4-(2-((2-fluoroethyl)(methyl)amino)ethoxy)phenyl)cyclopropanecarboxamide |
| 361 | 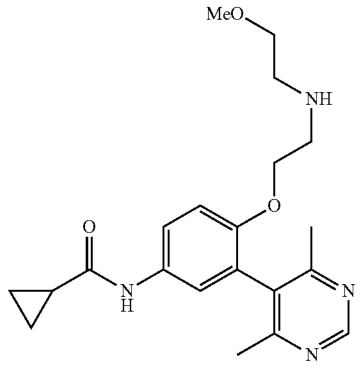 [SMILES: COCCNCCOc1ccc(NC(=O)C2CC2)cc1-c1c(C)ncnc1C] | N-(3-(4,6-dimethylpyrimidin-5-yl)-4-(2-((2-methoxyethyl)amino)ethoxy)phenyl)cyclopropanecarboxamide |
| 362 | 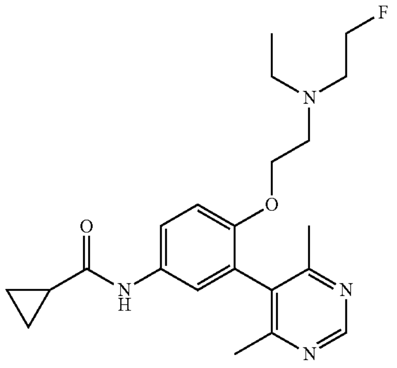 [SMILES: CCN(CCF)CCOc1ccc(NC(=O)C2CC2)cc1-c1c(C)ncnc1C] | N-[3-(4,6-dimethylpyrimidin-5-yl)-4-[2-[ethyl(2-fluoroethyl)amino]ethoxy]phenyl]cyclopropanecarboxamide |
| 363 | 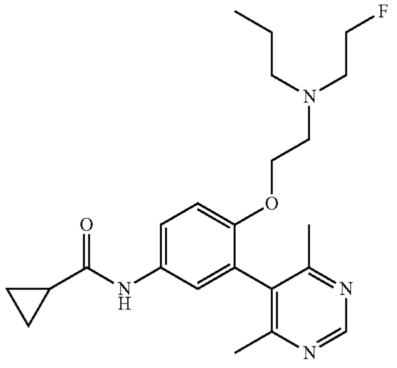 [SMILES: CCCN(CCF)CCOc1ccc(NC(=O)C2CC2)cc1-c1c(C)ncnc1C] | N-[3-(4,6-dimethylpyrimidin-5-yl)-4-[2-[2-fluoroethyl(propyl)amino]ethoxyphenyl]cyclopropanecarboxamide |

TABLE 1-continued

| Cmpd No. | Chemical Structure | Chemical Name |
|---|---|---|
| 364 | 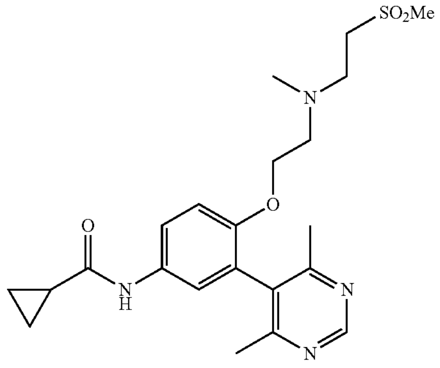 [SMILES: Cc1ncnc(C)c1-c1cc(NC(=O)C2CC2)ccc1OCCN(C)CCS(C)(=O)=O] | N-(3-(4,6-dimethylpyrimidin-5-yl)-4-(2-(methyl(2-(methylsulfonyl)ethyl)amino)ethoxy)phenyl)cyclopropanecarboxamide |
| 365 | 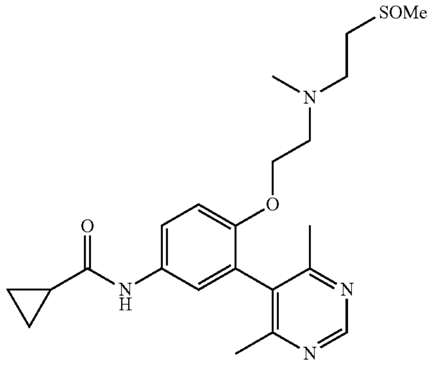 | N-[3-(4,6-dimethylpyrimidin-5-yl)-4-[2-[methyl(2-methylsulfinylethyl)amino]ethoxy]phenyl]cyclopropanecarboxamide |
| 366 | 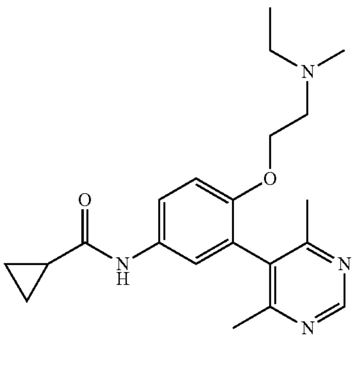 [SMILES: CCN(C)CCOc1ccc(NC(=O)C2CC2)cc1-c1c(C)ncnc1C] | N-[3-(4,6-dimethylpyrimidin-5-yl)-4-[2-[ethyl(methyl)amino]ethoxy]phenyl]cyclopropanecarboxamide |
| 367 | 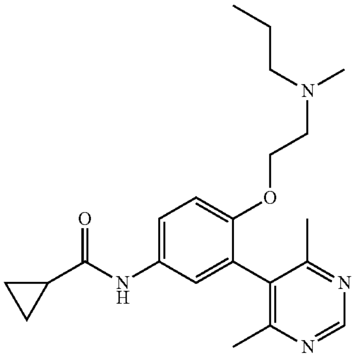 [SMILES: CCCN(C)CCOc1ccc(NC(=O)C2CC2)cc1-c1c(C)ncnc1C] | N-(3-(4,6-dimethylpyrimidin-5-yl)-4-(2-(methyl(propyl)amino)ethoxy)phenyl)cyclopropanecarboxamide |

TABLE 1-continued

| Cmpd No. | Chemical Structure | Chemical Name |
| --- | --- | --- |
| 368 | 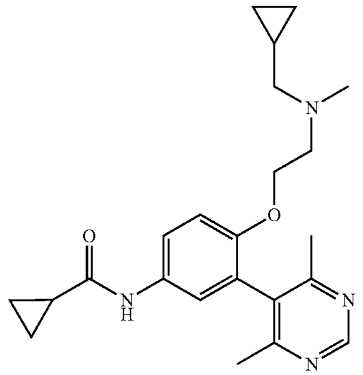 [SMILES: Cc1ncnc(C)c1-c1cc(NC(=O)C2CC2)ccc1OCCN(C)CC1CC1] | N-(4-(2-((cyclopropylmethyl)(methyl)amino)ethoxy)-3-(4,6-dimethylpyrimidin-5-yl)phenyl)cyclopropanecarboxamide |
| 369 | 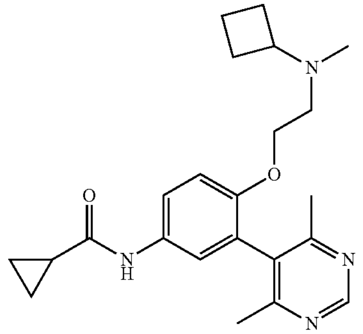 [SMILES: Cc1ncnc(C)c1-c1cc(NC(=O)C2CC2)ccc1OCCN(C)C1CCC1] | N-(4-(2-(cyclobutyl(methyl)amino)ethoxy)-3-(4,6-dimethylpyrimidin-5-yl)phenyl)cyclopropanecarboxamide |
| 370 | 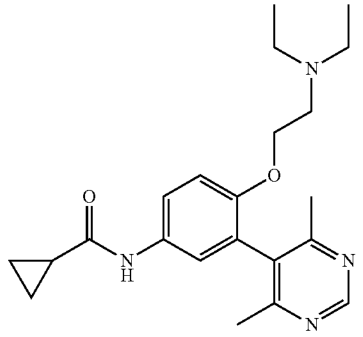 [SMILES: CCN(CC)CCOc1ccc(NC(=O)C2CC2)cc1-c1c(C)ncnc1C] | N-(4-(2-(diethylamino)ethoxy)-3-(4,6-dimethylpyrimidin-5-yl)phenyl)cyclopropanecarboxamide |
| 371 | 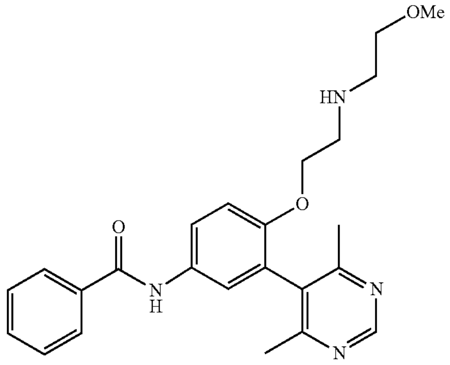 [SMILES: COCCNCCOc1ccc(NC(=O)c2ccccc2)cc1-c1c(C)ncnc1C] | N-(3-(4,6-dimethylpyrimidin-5-yl)-4-(2-((2-methoxyethyl)amino)ethoxy)phenyl)benzamide |

TABLE 1-continued

| Cmpd No. | Chemical Structure | Chemical Name |
| --- | --- | --- |
| 372 | 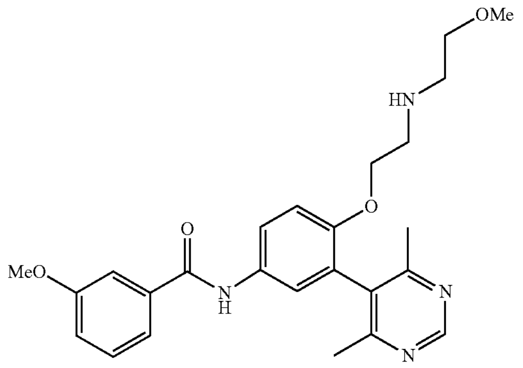 [SMILES: COCCNCCOc1ccc(NC(=O)c2cccc(OC)c2)cc1-c1c(C)ncnc1C] | N-(3-(4,6-dimethylpyrimidin-5-yl)-4-(2-((2-methoxyethyl)amino)ethoxy)phenyl)-3-methoxybenzamide |
| 373 | 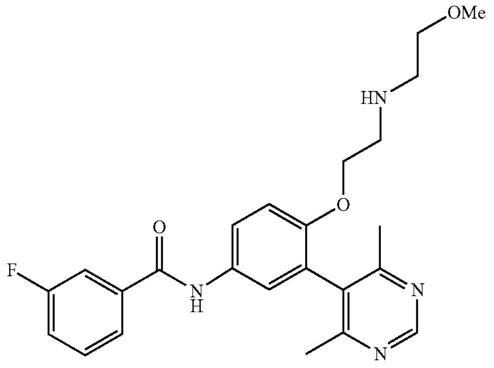 [SMILES: COCCNCCOc1ccc(NC(=O)c2cccc(F)c2)cc1-c1c(C)ncnc1C] | N-(3-(4,6-dimethylpyrimidin-5-yl)-4-(2-((2-methoxyethyl)amino)ethoxy)phenyl)-3-fluorobenzamide |
| 374 | 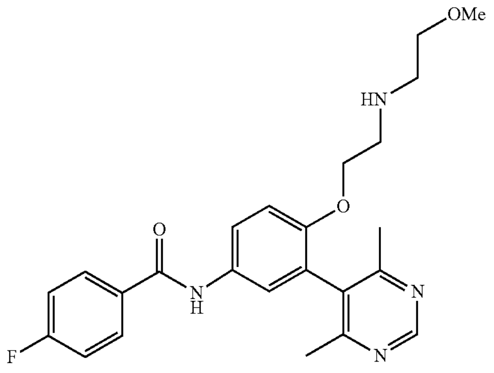 [SMILES: COCCNCCOc1ccc(NC(=O)c2ccc(F)cc2)cc1-c1c(C)ncnc1C] | N-(3-(4,6-dimethylpyrimidin-5-yl)-4-(2-((2-methoxyethyl)amino)ethoxy)phenyl)-4-fluorobenzamide |
| 375 | 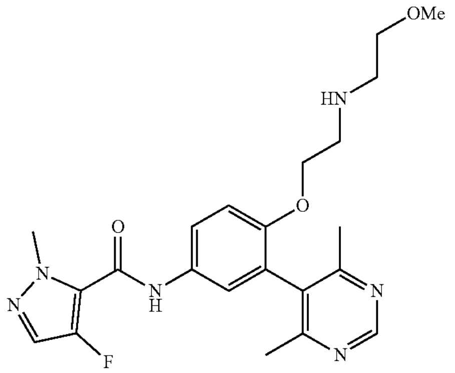 [SMILES: COCCNCCOc1ccc(NC(=O)c2c(F)cnn2C)cc1-c1c(C)ncnc1C] | N-(3-(4,6-dimethylpyrimidin-5-yl)-4-(2-((2-methoxyethyl)amino)ethoxy)phenyl)-4-fluoro-1-methyl-1H-pyrazole-5-carboxamide |

TABLE 1-continued

| Cmpd No. | Chemical Structure | Chemical Name |
|---|---|---|
| 376 | 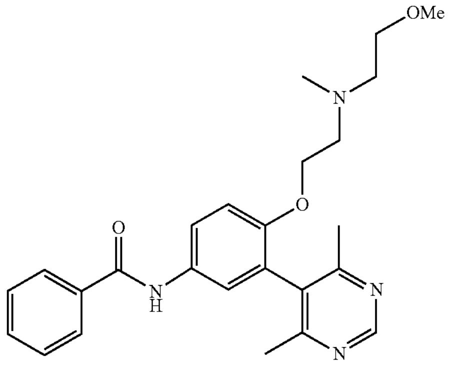 [SMILES: COCCN(C)CCOc1ccc(NC(=O)c2ccccc2)cc1-c1c(C)ncnc1C] | N-(3-(4,6-dimethylpyrimidin-5-yl)-4-(2-((2-methoxyethyl)(methyl)amino)ethoxy)phenyl)benzamide |
| 377 | 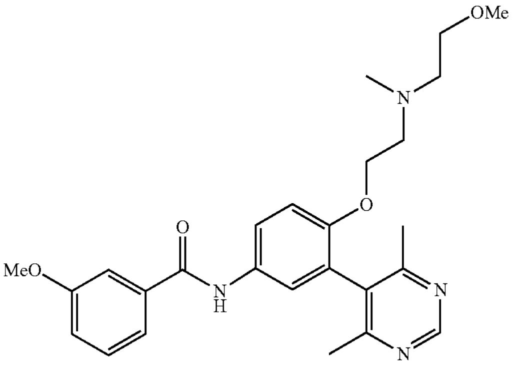 [SMILES: COCCN(C)CCOc1ccc(NC(=O)c2cccc(OC)c2)cc1-c1c(C)ncnc1C] | N-(3-(4,6-dimethylpyrimidin-5-yl)-4-(2-((2-methoxyethyl)(methyl)amino)ethoxy)phenyl)-3-methoxybenzamide |
| 378 | 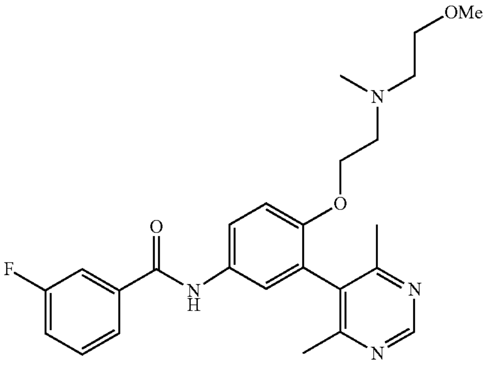 [SMILES: COCCN(C)CCOc1ccc(NC(=O)c2cccc(F)c2)cc1-c1c(C)ncnc1C] | N-(3-(4,6-dimethylpyrimidin-5-yl)-4-(2-((2-methoxyethyl)(methyl)amino)ethoxy)phenyl)-3-fluorobenzamide |
| 379 | 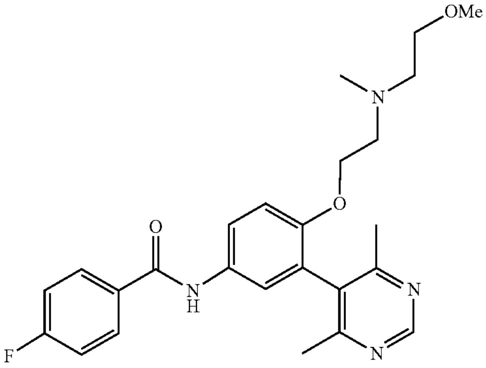 [SMILES: COCCN(C)CCOc1ccc(NC(=O)c2ccc(F)cc2)cc1-c1c(C)ncnc1C] | N-(3-(4,6-dimethylpyrimidin-5-yl)-4-(2-((2-methoxyethyl)(methyl)amino)ethoxy)phenyl)-4-fluorobenzamide |

TABLE 1-continued

| Cmpd No. | Chemical Structure | Chemical Name |
|---|---|---|
| 380 | 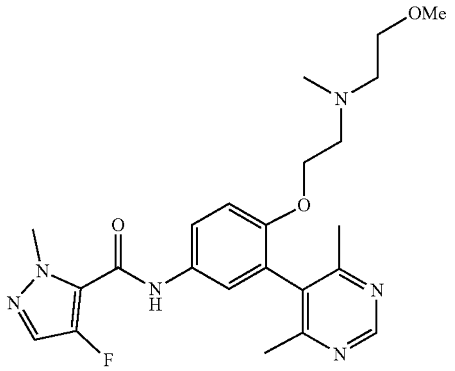 [SMILES: COCCN(C)CCOc1ccc(NC(=O)c2c(F)cnn2C)cc1-c1c(C)ncnc1C] | N-(3-(4,6-dimethylpyrimidin-5-yl)-4-(2-((2-methoxyethyl)(methyl)amino)ethoxy)phenyl)-4-fluoro-1-methyl-1H-pyrazole-5-carboxamide |
| 381 | 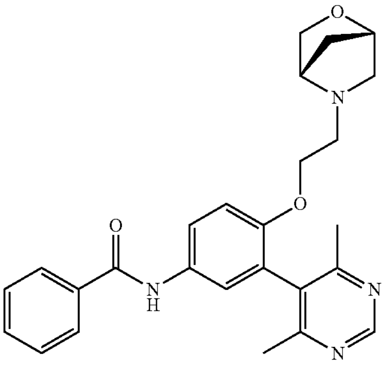 [SMILES: Cc1ncnc(C)c1-c1cc(NC(=O)c2ccccc2)ccc1OCCN1C[C@@H]2C[C@H]1CO2] | N-(4-(2-((1S,4S)-2-oxa-5-azabicyclo[2.2.1]heptan-5-yl)ethoxy)-3-(4,6-dimethylpyrimidin-5-yl)phenyl)benzamide |
| 382 | 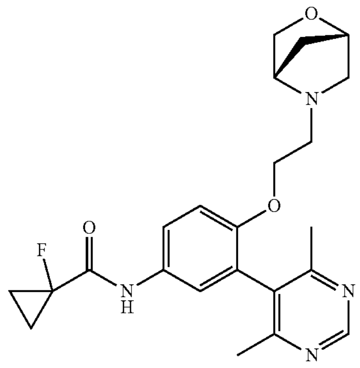 [SMILES: Cc1ncnc(C)c1-c1cc(NC(=O)C2(F)CC2)ccc1OCCN1C[C@@H]2C[C@H]1CO2] | N-(4-(2-((1S,4S)-2-oxa-5-azabicyclo[2.2.1]heptan-5-yl)ethoxy)-3-(4,6-dimethylpyrimidin-5-yl)phenyl)-1-fluorocyclopropane-1-carboxamide |
| 383 | 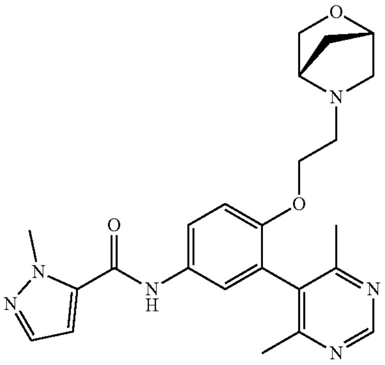 [SMILES: Cc1ncnc(C)c1-c1cc(NC(=O)c2ccnn2C)ccc1OCCN1C[C@@H]2C[C@H]1CO2] | N-(4-(2-((1S,4S)-2-oxa-5-azabicyclo[2.2.1]heptan-5-yl)ethoxy)-3-(4,6-dimethylpyrimidin-5-yl)phenyl)-1-methyl-1H-pyrazole-5-carboxamide |

TABLE 1-continued

| Cmpd No. | Chemical Structure | Chemical Name |
| --- | --- | --- |
| 384 | 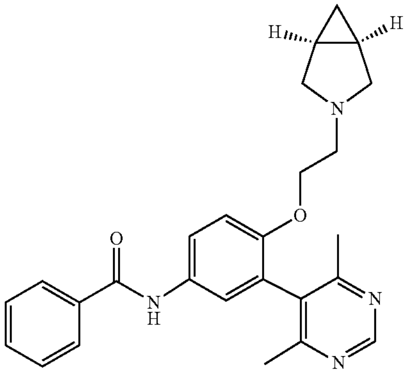 [SMILES: Cc1ncnc(C)c1-c1cc(NC(=O)c2ccccc2)ccc1OCCN1C[C@H]2C[C@H]2C1] | N-[4-[2-[(1R, 5S)-3-azabicyclo[3.1.0]hexan-3-yl]ethoxy]-3-(4,6-dimethylpyrimidin-5-yl)phenyl]benzamide |
| 385 | 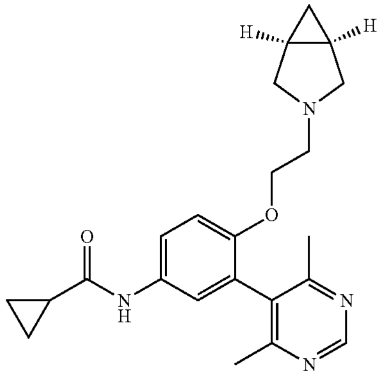 [SMILES: Cc1ncnc(C)c1-c1cc(NC(=O)C2CC2)ccc1OCCN1C[C@H]2C[C@H]2C1] | N-(4-(2-((1R,5S)-3-azabicyclo[3.1.0]hexan-3-yl)ethoxy)-3-(4,6-dimethylpyrimidin-5-yl)phenyl)cyclopropanecarboxamide |
| 386 | 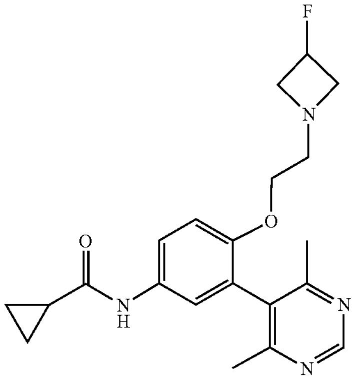 [SMILES: Cc1ncnc(C)c1-c1cc(NC(=O)C2CC2)ccc1OCCN1CC(F)C1] | N-[3-(4,6-dimethylpyrimidin-5-yl)-4-[2-(3-fluoroazetidin-1-yl)ethoxy]phenyl]cyclopropanecarboxamide |
| 387 | 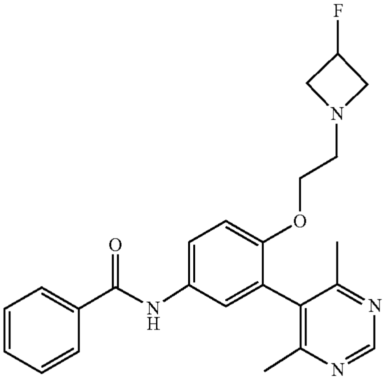 [SMILES: Cc1ncnc(C)c1-c1cc(NC(=O)c2ccccc2)ccc1OCCN1CC(F)C1] | N-[3-(4, 6-dimethylpyrimidin-5-yl)-4-[2-(3-fluoroazetidin-1-yl)ethoxy]phenyl]benzamide |

TABLE 1-continued

| Cmpd No. | Chemical Structure | Chemical Name |
| --- | --- | --- |
| 388 | 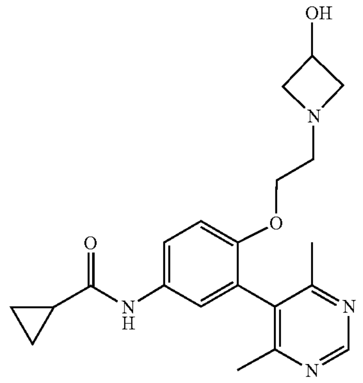 [SMILES: Cc1ncnc(C)c1-c1cc(NC(=O)C2CC2)ccc1OCCN1CC(O)C1] | N-[3-(4,6-dimethylpyrimidin-5-yl)-4-[2-(3-hydroxyazetidin-1-yl)ethoxy]phenyl]cyclopropanecarboxamide |
| 389 | 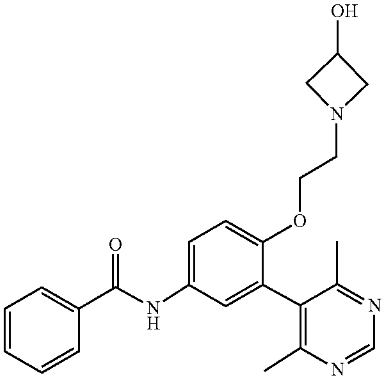 [SMILES: Cc1ncnc(C)c1-c1cc(NC(=O)c2ccccc2)ccc1OCCN1CC(O)C1] | N-[3-(4,6-dimethylpyrimidin-5-yl)-4-[2-(3-hydroxyazetidin-1-yl)ethoxy]phenyl]benzamide |
| 390 | 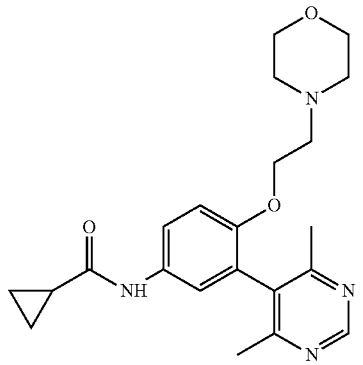 [SMILES: Cc1ncnc(C)c1-c1cc(NC(=O)C2CC2)ccc1OCCN1CCOCC1] | N-[3-(4,6-dimethylpyrimidin-5-yl)-4-(2-morpholinoethoxy)phenyl]cyclopropanecarboxamide |
| 391 | 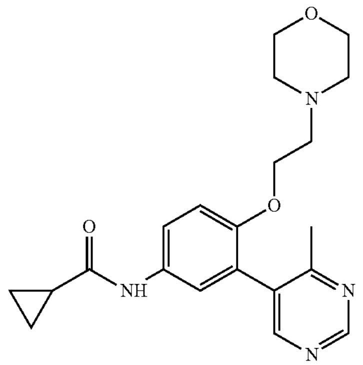 [SMILES: Cc1ncncc1-c1cc(NC(=O)C2CC2)ccc1OCCN1CCOCC1] | N-(3-(4-methylpyrimidin-5-yl)-4-(2-morpholinoethoxy)phenyl)cyclopropanecarboxamide |

TABLE 1-continued

| Cmpd No. | Chemical Structure | Chemical Name |
|---|---|---|
| 392 | 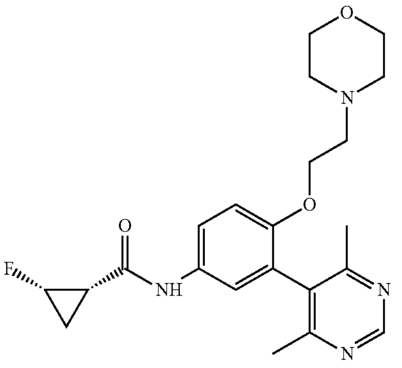 [SMILES: Cc1ncnc(C)c1-c1cc(NC(=O)[C@@H]2C[C@@H]2F)ccc1OCCN1CCOCC1] | (1S,2S)-N-[3-(4,6-dimethylpyrimidin-5-yl)-4-(2-morpholinoethoxy)phenyl]-2-fluoro-cyclopropanecarboxamide |
| 393 | 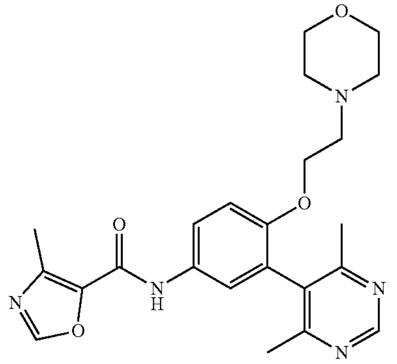 [SMILES: Cc1ncoc1C(=O)Nc1ccc(OCCN2CCOCC2)c(-c2c(C)ncnc2C)c1] | N-(3-(4,6-dimethylpyrimidin-5-yl)-4-(2-morpholinoethoxy)phenyl)-4-methyloxazole-5-carboxamide |
| 394 | 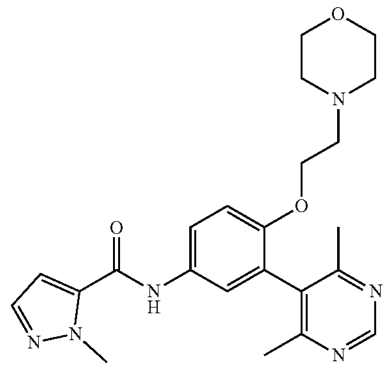 [SMILES: Cc1ncnc(C)c1-c1cc(NC(=O)c2ccnn2C)ccc1OCCN1CCOCC1] | N-(3-(4,6-dimethylpyrimidin-5-yl)-4-(2-morpholinoethoxy)phenyl)-1-methyl-1H-pyrazole-5-carboxamide |
| 395 | 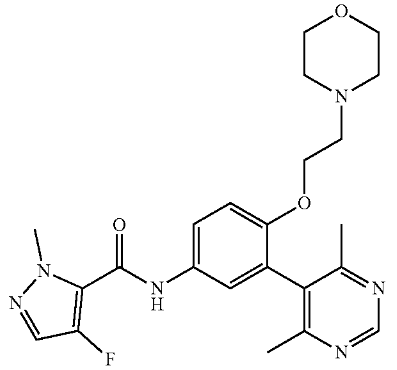 [SMILES: Cc1ncnc(C)c1-c1cc(NC(=O)c2c(F)cnn2C)ccc1OCCN1CCOCC1] | N-[3-(4,6-dimethylpyrimidin-5-yl)-4-(2-morpholinoethoxy)phenyl]-4-fluoro-2-methyl-pyrazole-3-carboxamide |

TABLE 1-continued

| Cmpd No. | Chemical Structure | Chemical Name |
| --- | --- | --- |
| 396 | 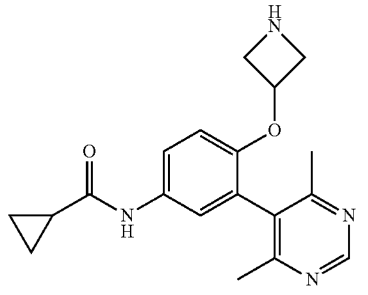 [SMILES: Cc1ncnc(C)c1-c1cc(NC(=O)C2CC2)ccc1OC1CNC1] | N-[4-(azetidin-3-yloxy)-3-(4,6-dimethylpyrimidin-5-yl)phenyl]cyclopropanecarboxamide |
| 397 | 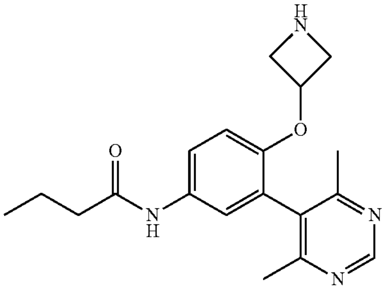 [SMILES: CCCC(=O)Nc1ccc(OC2CNC2)c(-c2c(C)ncnc2C)c1] | N-(4-(azetidin-3-yloxy)-3-(4,6-dimethylpyrimidin-5-yl)phenyl)butyramide |
| 398 | 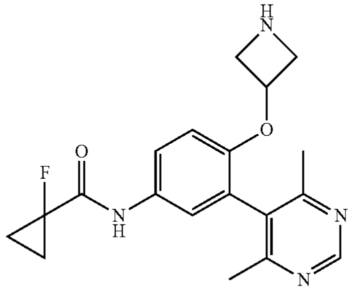 [SMILES: Cc1ncnc(C)c1-c1cc(NC(=O)C2(F)CC2)ccc1OC1CNC1] | N-(4-(azetidin-3-yloxy)-3-(4,6-dimethylpyrimidin-5-yl)phenyl)-1-fluorocyclopropane-1-carboxamide |
| 399 | 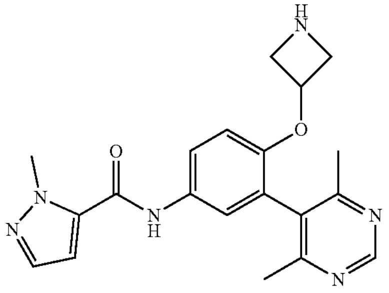 [SMILES: Cc1ncnc(C)c1-c1cc(NC(=O)c2ccnn2C)ccc1OC1CNC1] | N-(4-(azetidin-3-yloxy)-3-(4,6-dimethylpyrimidin-5-yl)phenyl)-1-methyl-1H-pyrazole-5-carboxamide |
| 400 | 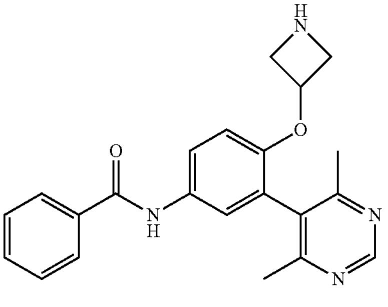 [SMILES: Cc1ncnc(C)c1-c1cc(NC(=O)c2ccccc2)ccc1OC1CNC1] | N-(4-(azetidin-3-yloxy)-3-(4,6-dimethylpyrimidin-5-yl)phenyl)benzamide |

TABLE 1-continued

| Cmpd No. | Chemical Structure | Chemical Name |
| --- | --- | --- |
| 401 | 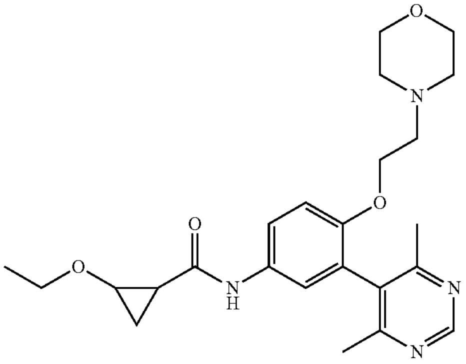 [SMILES: CCOC1CC1C(=O)Nc1ccc(OCCN2CCOCC2)c(-c2c(C)ncnc2C)c1] | N-(3-(4,6-dimethylpyrimidin-5-yl)-4-(2-morpholinoethoxy)phenyl)-2-ethoxycyclopropane-1-carboxamide |
| 402 | 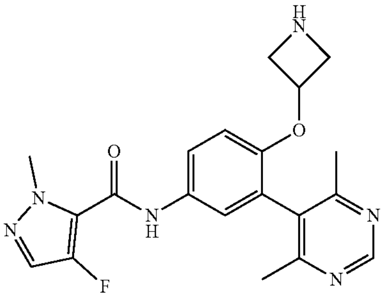 [SMILES: Cc1ncnc(C)c1-c1cc(NC(=O)c2c(F)cnn2C)ccc1OC1CNC1] | N-(4-(azetidin-3-yloxy)-3-(4,6-dimethylpyrimidin-5-yl)phenyl)-4-fluoro-1-methyl-1H-pyrazole-5-carboxamide |
| 403 | 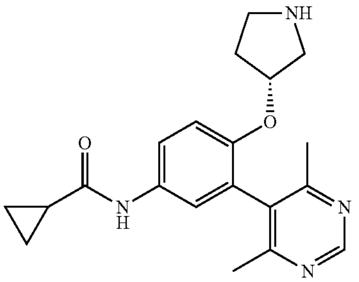 [SMILES: Cc1ncnc(C)c1-c1cc(NC(=O)C2CC2)ccc1O[C@@H]1CCNC1] | N-[3-(4,6-dimethylpyrimidin-5-yl)-4-[(3R)-pyrrolidin-3-yl]oxy-phenyl]cyclopropanecarboxamide |
| 404 | 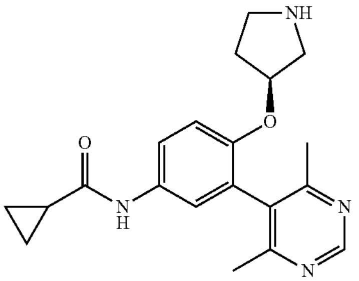 [SMILES: Cc1ncnc(C)c1-c1cc(NC(=O)C2CC2)ccc1O[C@H]1CCNC1] | (S)-N-(3-(4,6-dimethylpyrimidin-5-yl)-4-(pyrrolidin-3-yloxy)phenyl)cyclopropanecarboxamide |
| 405 | 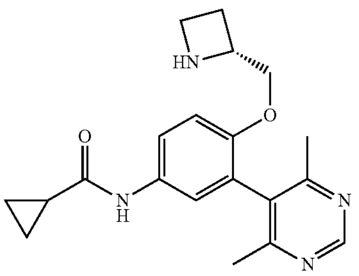 [SMILES: Cc1ncnc(C)c1-c1cc(NC(=O)C2CC2)ccc1OC[C@H]1CCN1] | N-[4-[[(2R)-azetidin-2-yl]methoxy]-3-(4,6-dimethylpyrimidin-5-yl)phenyl]cyclopropanecarboxamide |

TABLE 1-continued

| Cmpd No. | Chemical Structure | Chemical Name |
| --- | --- | --- |
| 406 | 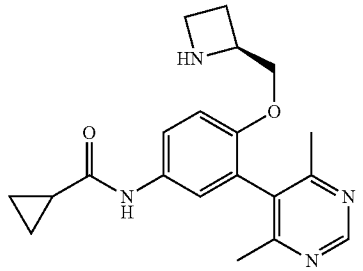 [SMILES: Cc1ncnc(C)c1-c1cc(NC(=O)C2CC2)ccc1OC[C@@H]1CCN1] | (S)-N-(4-(azetidin-2-ylmethoxy)-3-(4,6-dimethylpyrimidin-5-yl)phenyl)cyclopropanecarboxamide |
| 407 | 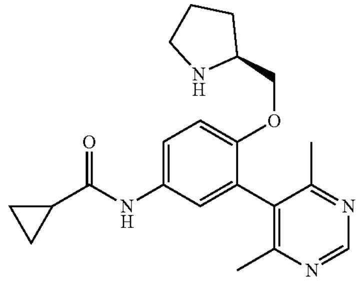 [SMILES: Cc1ncnc(C)c1-c1cc(NC(=O)C2CC2)ccc1OC[C@@H]1CCCN1] | N-[3-(4,6-dimethylpyrimidin-5-yl)-4-[[(2S)-pyrrolidin-2-yl]methoxy phenyl]cyclopropanecarboxamide |
| 408 | 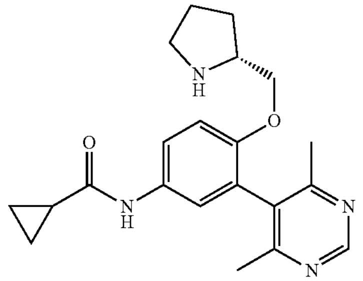 [SMILES: Cc1ncnc(C)c1-c1cc(NC(=O)C2CC2)ccc1OC[C@H]1CCCN1] | (R)-N-(3-(4,6-dimethylpyrimidin-5-yl)-4-(pyrrolidin-2-ylmethoxy)phenyl)cyclopropanecarboxamide |
| 409 | 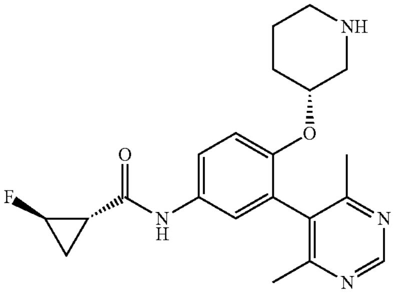 [SMILES: Cc1ncnc(C)c1-c1cc(NC(=O)[C@@H]2C[C@H]2F)ccc1O[C@@H]1CCCNC1] | (1S,2R)-N-(3-(4,6-dimethylpyrimidin-5-yl)-4-(((R)-piperidin-3-yl)oxy)phenyl)-2-fluorocyclopropane-1-carboxamide |
| 410 | 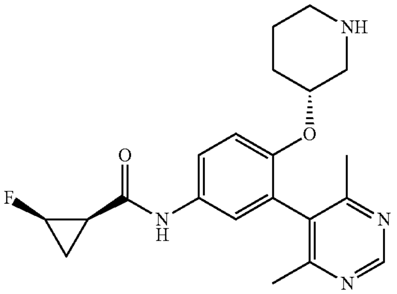 [SMILES: Cc1ncnc(C)c1-c1cc(NC(=O)[C@H]2C[C@H]2F)ccc1O[C@@H]1CCCNC1] | (1R,2R)-N-(3-(4,6-dimethylpyrimidin-5-yl)-4-(((R)-piperidin-3-yl)oxy)phenyl)-2-fluorocyclopropane-1-carboxamide |

TABLE 1-continued

| Cmpd No. | Chemical Structure | Chemical Name |
| --- | --- | --- |
| 411 | 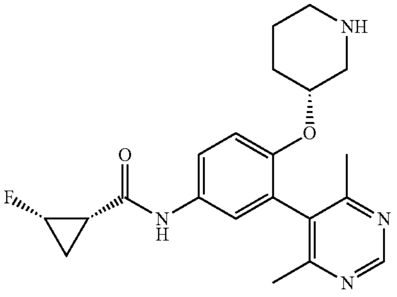 [SMILES: Cc1ncnc(C)c1-c1cc(NC(=O)[C@@H]2C[C@@H]2F)ccc1O[C@@H]1CCCNC1] | (1S,2S)-N-(3-(4,6-dimethylpyrimidin-5-yl)-4-(((R)-piperidin-3-yl)oxy)phenyl)-2-fluorocyclopropane-1-carboxamide |
| 412 | 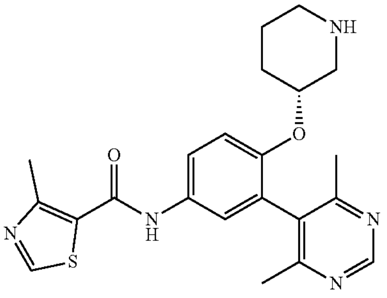 [SMILES: Cc1ncsc1C(=O)Nc1ccc(O[C@@H]2CCCNC2)c(-c2c(C)ncnc2C)c1] | (R)-N-(3-(4,6-dimethylpyrimidin-5-yl)-4-(piperidin-3-yloxy)phenyl)-4-methylthiazole-5-carboxamide |
| 413 | 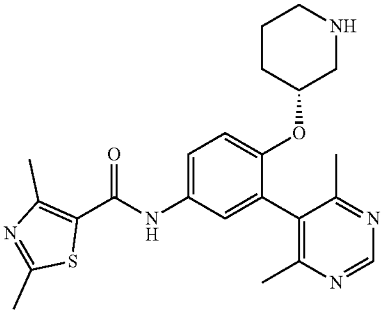 [SMILES: Cc1nc(C)c(C(=O)Nc2ccc(O[C@@H]3CCCNC3)c(-c3c(C)ncnc3C)c2)s1] | (R)-N-(3-(4,6-dimethylpyrimidin-5-yl)-4-(piperidin-3-yloxy)phenyl)-2,4-dimethylthiazole-5-carboxamide |
| 414 | 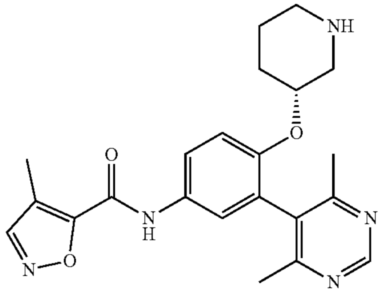 [SMILES: Cc1cnoc1C(=O)Nc1ccc(O[C@@H]2CCCNC2)c(-c2c(C)ncnc2C)c1] | (R)-N-(3-(4,6-dimethylpyrimidin-5-yl)-4-(piperidin-3-yloxy)phenyl)-4-methylisoxazole-5-carboxamide |
| 415 | 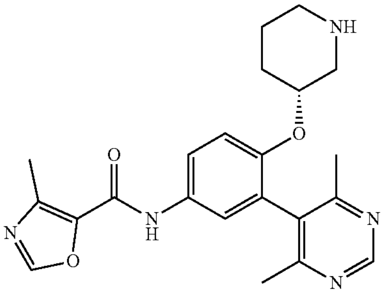 | (R)-N-(3-(4,6-dimethylpyrimidin-5-yl)-4-(piperidin-3-yloxy)phenyl)-4-methyloxazole-5-carboxamide |

TABLE 1-continued

| Cmpd No. | Chemical Structure | Chemical Name |
| --- | --- | --- |
| 416 | 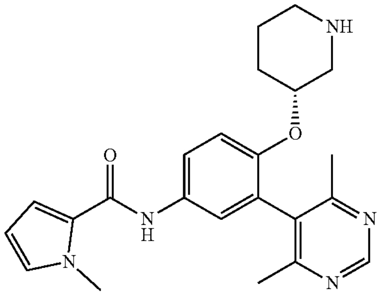 [SMILES: Cc1ncnc(C)c1-c1cc(NC(=O)c2cccn2C)ccc1O[C@@H]1CCCNC1] | (R)-N-(3-(4,6-dimethylpyrimidin-5-yl)-4-(piperidin-3-yloxy)phenyl)-1-methyl-1H-pyrrole-2-carboxamide |
| 417 | 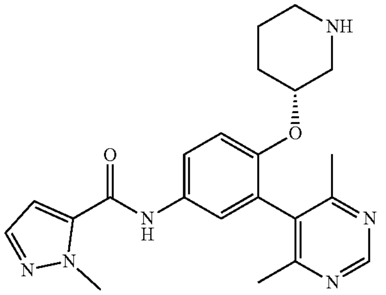 [SMILES: Cc1ncnc(C)c1-c1cc(NC(=O)c2ccnn2C)ccc1O[C@@H]1CCCNC1] | (R)-N-(3-(4,6-dimethylpyrimidin-5-yl)-4-(piperidin-3-yloxy)phenyl)-1-methyl-1H-pyrazole-5-carboxamide |
| 418 | 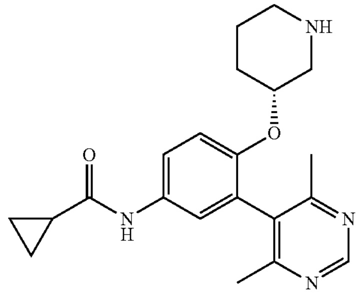 [SMILES: Cc1ncnc(C)c1-c1cc(NC(=O)C2CC2)ccc1O[C@@H]1CCCNC1] | (R)-N-(3-(4,6-dimethylpyrimidin-5-yl)-4-(piperidin-3-yloxy)phenyl)cyclopropanecarboxamide |
| 419 | 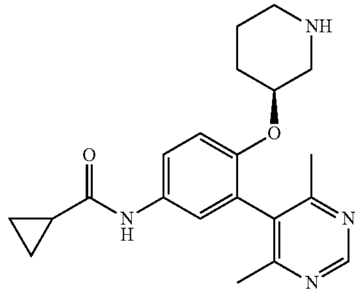 [SMILES: Cc1ncnc(C)c1-c1cc(NC(=O)C2CC2)ccc1O[C@H]1CCCNC1] | (S)-N-(3-(4,6-dimethylpyrimidin-5-yl)-4-(piperidin-3-yloxy)phenyl)cyclopropanecarboxamide |
| 420 | 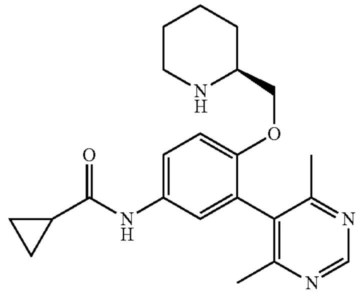 [SMILES: Cc1ncnc(C)c1-c1cc(NC(=O)C2CC2)ccc1OC[C@@H]1CCCCN1] | N-[3-(4,6-dimethylpyrimidin-5-yl)-4-[(2S)-2-piperidyl]methoxy]phenyl]cyclopropanecarboxamide |

TABLE 1-continued

| Cmpd No. | Chemical Structure | Chemical Name |
| --- | --- | --- |
| 421 | 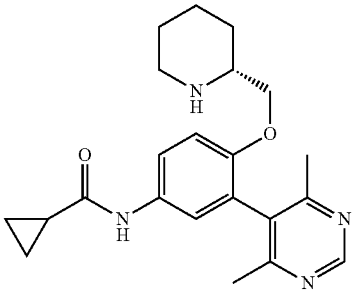 [SMILES: Cc1ncnc(C)c1-c1cc(NC(=O)C2CC2)ccc1OC[C@H]1CCCCN1] | N-[3-(4,6-dimethylpyrimidin-5-yl)-4-[(2R)-2-piperidyl]methoxy]phenyl]cyclopropanecarboxamide |
| 422 | 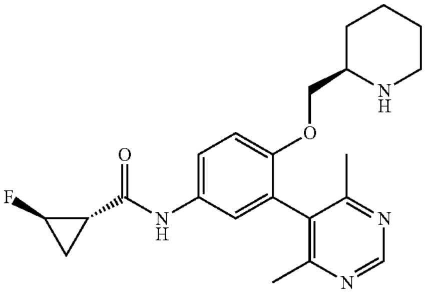 [SMILES: Cc1ncnc(C)c1-c1cc(NC(=O)[C@@H]2C[C@H]2F)ccc1OC[C@H]1CCCCN1] | (1S,2R)-N-[3-(4,6-dimethylpyrimidin-5-yl)-4-[[(2R)-2-piperidyl]methoxy]phenyl]-2-fluoro-cyclopropanecarboxamide |
| 423 | 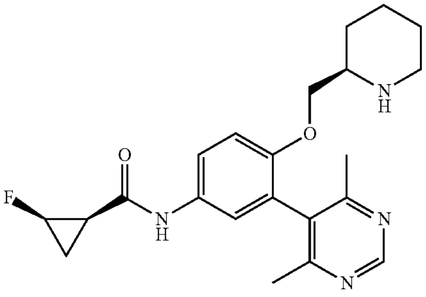 [SMILES: Cc1ncnc(C)c1-c1cc(NC(=O)[C@H]2C[C@H]2F)ccc1OC[C@H]1CCCCN1] | (1R,2R)-N-(3-(4,6-dimethylpyrimidin-5-yl)-4-(((R)-piperidin-2-yl)methoxy)phenyl)-2-fluorocyclopropane-1-carboxamide |
| 424 | 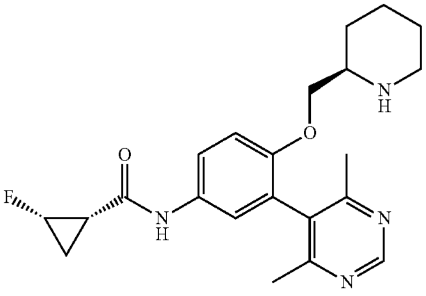 [SMILES: Cc1ncnc(C)c1-c1cc(NC(=O)[C@@H]2C[C@@H]2F)ccc1OC[C@H]1CCCCN1] | (1S,2S)-N-(3-(4,6-dimethylpyrimidin-5-yl)-4-(((R)-piperidin-2-yl)methoxy)phenyl)-2-fluorocyclopropane-1-carboxamide |
| 425 | 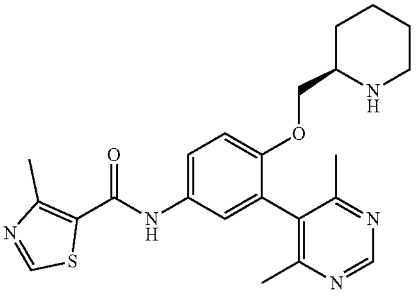 [SMILES: Cc1ncsc1C(=O)Nc1ccc(OC[C@H]2CCCCN2)c(-c2c(C)ncnc2C)c1] | (R)-N-(3-(4,6-dimethylpyrimidin-5-yl)-4-(piperidin-2-ylmethoxy)phenyl)-4-methylthiazole-5-carboxamide |

TABLE 1-continued

| Cmpd No. | Chemical Structure | Chemical Name |
|---|---|---|
| 426 | 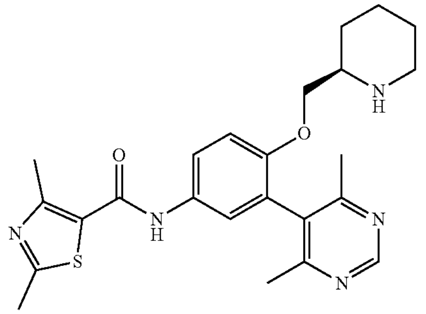 [SMILES: Cc1nc(C)c(C(=O)Nc2ccc(OC[C@H]3CCCCN3)c(-c3c(C)ncnc3C)c2)s1] | (R)-N-(3-(4,6-dimethylpyrimidin-5-yl)-4-(piperidin-2-ylmethoxy)phenyl)-2,4-dimethylthiazole-5-carboxamide |
| 427 | 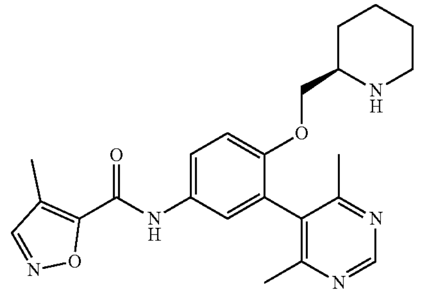 [SMILES: Cc1cnoc1C(=O)Nc1ccc(OC[C@H]2CCCCN2)c(-c2c(C)ncnc2C)c1] | (R)-N-(3-(4,6-dimethylpyrimidin-5-yl)-4-(piperidin-2-ylmethoxy)phenyl)-4-methylisoxazole-5-carboxamide |
| 428 | 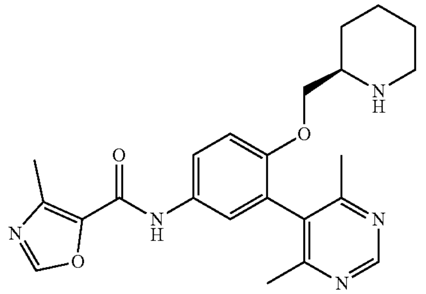 [SMILES: Cc1ncoc1C(=O)Nc1ccc(OC[C@H]2CCCCN2)c(-c2c(C)ncnc2C)c1] | (R)-N-(3-(4,6-dimethylpyrimidin-5-yl)-4-(piperidin-2-ylmethoxy)phenyl)-4-methyloxazole-5-carboxamide |
| 429 | 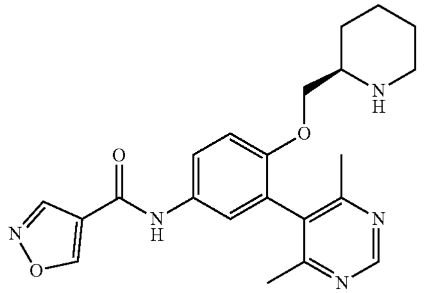 [SMILES: Cc1ncnc(C)c1-c1cc(NC(=O)c2cnoc2)ccc1OC[C@H]1CCCCN1] | (R)-N-(3-(4,6-dimethylpyrimidin-5-yl)-4-(piperidin-2-ylmethoxy)phenyl)isoxazole-4-carboxamide |
| 430 | 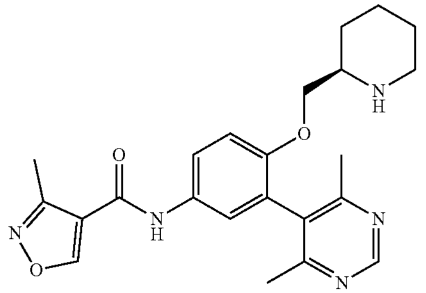 [SMILES: Cc1nocc1C(=O)Nc1ccc(OC[C@H]2CCCCN2)c(-c2c(C)ncnc2C)c1] | (R)-N-(3-(4,6-dimethylpyrimidin-5-yl)-4-(piperidin-2-ylmethoxy)phenyl)-3-methylisoxazole-4-carboxamide |

TABLE 1-continued

| Cmpd No. | Chemical Structure | Chemical Name |
|---|---|---|
| 431 | 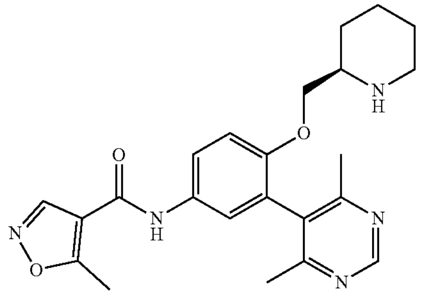 [SMILES: Cc1ncnc(C)c1-c1cc(NC(=O)c2cnoc2C)ccc1OC[C@H]1CCCCN1] | (R)-N-(3-(4,6-dimethylpyrimidin-5-yl)-4-(piperidin-2-ylmethoxy)phenyl)-5-methylisoxazole-4-carboxamide |
| 432 | 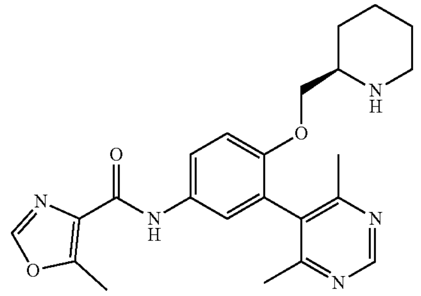 | (R)-N-(3-(4,6-dimethylpyrimidin-5-yl)-4-(piperidin-2-ylmethoxy)phenyl)-5-methyloxazole-4-carboxamide |
| 433 | 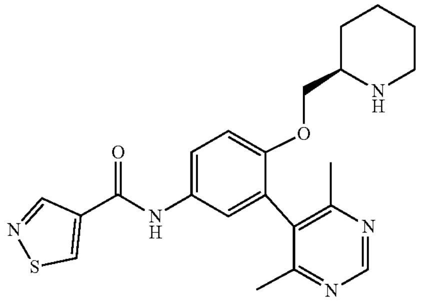 [SMILES: Cc1ncnc(C)c1-c1cc(NC(=O)c2cnsc2)ccc1OC[C@H]1CCCCN1] | (R)-N-(3-(4,6-dimethylpyrimidin-5-yl)-4-(piperidin-2-ylmethoxy)phenyl)isothiazole-4-carboxamide |
| 434 | 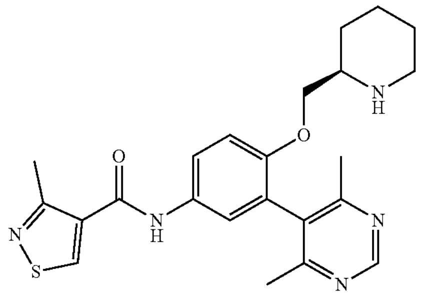 [SMILES: Cc1nscc1C(=O)Nc1ccc(OC[C@H]2CCCCN2)c(-c2c(C)ncnc2C)c1] | (R)-N-(3-(4,6-dimethylpyrimidin-5-yl)-4-(piperidin-2-ylmethoxy)phenyl)-3-methylisothiazole-4-carboxamide |
| 435 | 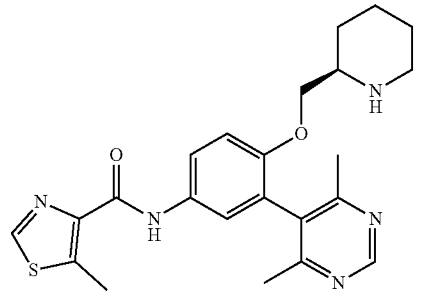 [SMILES: Cc1ncnc(C)c1-c1cc(NC(=O)c2ncsc2C)ccc1OC[C@H]1CCCCN1] | (R)-N-(3-(4,6-dimethylpyrimidin-5-yl)-4-(piperidin-2-ylmethoxy)phenyl)-5-methylthiazole-4-carboxamide |

TABLE 1-continued

| Cmpd No. | Chemical Structure | Chemical Name |
| --- | --- | --- |
| 436 | 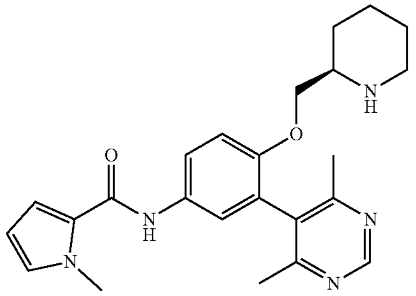 [SMILES: Cc1ncnc(C)c1-c1cc(NC(=O)c2cccn2C)ccc1OC[C@H]1CCCCN1] | (R)-N-(3-(4,6-dimethylpyrimidin-5-yl)-4-(piperidin-2-ylmethoxy)phenyl)-1-methyl-1H-pyrrole-2-carboxamide |
| 437 | 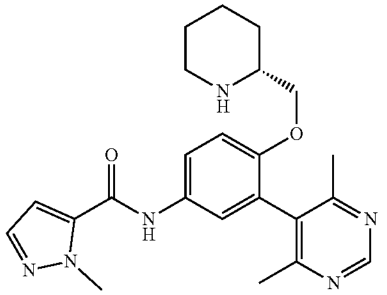 [SMILES: Cc1ncnc(C)c1-c1cc(NC(=O)c2ccnn2C)ccc1OC[C@H]1CCCCN1] | N-[3-(4,6-dimethylpyrimidin-5-yl)-4-[(2R)-2-piperidyl]methoxy]phenyl]-2-methyl-pyrazole-3-carboxamide |
| 438 | 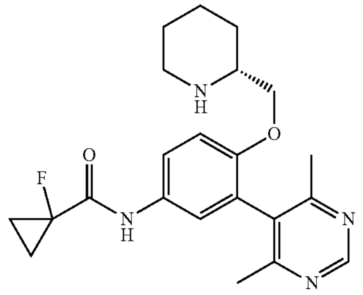 [SMILES: Cc1ncnc(C)c1-c1cc(NC(=O)C2(F)CC2)ccc1OC[C@H]1CCCCN1] | N-[3-(4,6-dimethylpyrimidin-5-yl)-4-[[(2R)-2-piperidyl]methoxy]phenyl]-1-fluoro-cyclopropanecarboxamide |
| 439 | 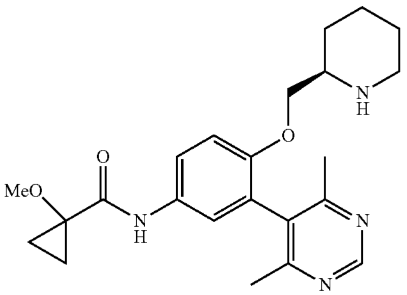 [SMILES: COC1(C(=O)Nc2ccc(OC[C@H]3CCCCN3)c(-c3c(C)ncnc3C)c2)CC1] | (R)-N-(3-(4,6-dimethylpyrimidin-5-yl)-4-(piperidin-2-ylmethoxy)phenyl)-1-methoxycyclopropane-1-carboxamide |
| 440 | 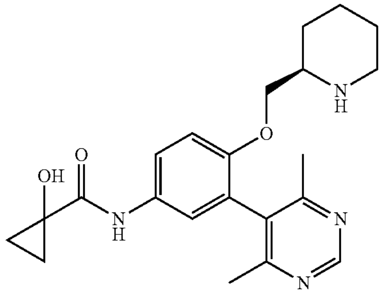 [SMILES: Cc1ncnc(C)c1-c1cc(NC(=O)C2(O)CC2)ccc1OC[C@H]1CCCCN1] | (R)-N-(3-(4,6-dimethylpyrimidin-5-yl)-4-(piperidin-2-ylmethoxy)phenyl)-1-hydroxycyclopropane-1-carboxamide |

TABLE 1-continued

| Cmpd No. | Chemical Structure | Chemical Name |
| --- | --- | --- |
| 441 | 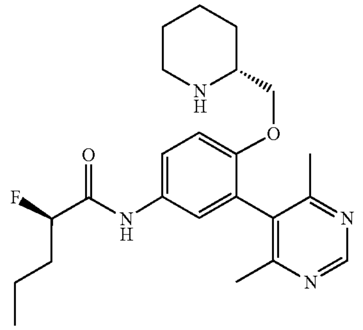 [SMILES: CCC[C@@H](F)C(=O)Nc1ccc(OC[C@H]2CCCCN2)c(-c2c(C)ncnc2C)c1] | (R)-N-[3-(4,6-dimethylpyrimidin-5-yl)-4-[[(2R)-2-piperidyl]methoxy]phenyl]-2-fluoro-pentanamide |
| 442 | 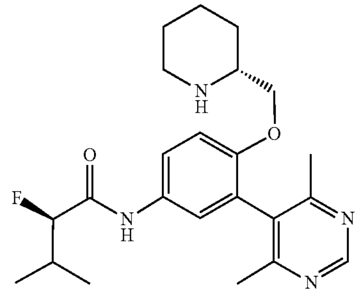 [SMILES: Cc1ncnc(C)c1-c1cc(NC(=O)[C@H](F)C(C)C)ccc1OC[C@H]1CCCCN1] | (R)-N-(3-(4,6-dimethylpyrimidin-5-yl)-4-(((R)-piperidin-2-yl)methoxy)phenyl)-2-fluoro-3-methylbutanamide |
| 443 | 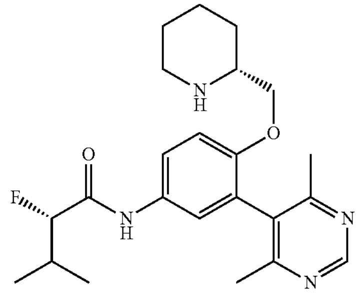 [SMILES: Cc1ncnc(C)c1-c1cc(NC(=O)[C@@H](F)C(C)C)ccc1OC[C@H]1CCCCN1] | (S)-N-(3-(4,6-dimethylpyrimidin-5-yl)-4-(((R)-piperidin-2-yl)methoxy)phenyl)-2-fluoro-3-methylbutanamide |
| 444 | 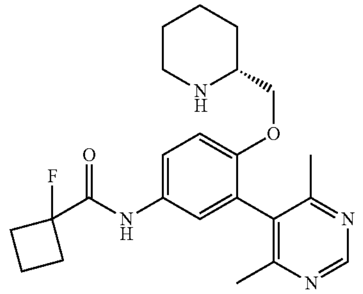 [SMILES: Cc1ncnc(C)c1-c1cc(NC(=O)C2(F)CCC2)ccc1OC[C@H]1CCCCN1] | (R)-N-(3-(4,6-dimethylpyrimidin-5-yl)-4-(piperidin-2-ylmethoxy)phenyl)-1-fluorocyclobutane-1-carboxamide |
| 445 | 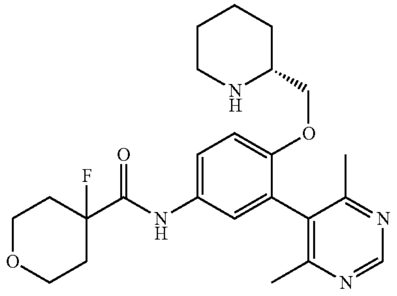 [SMILES: Cc1ncnc(C)c1-c1cc(NC(=O)C2(F)CCOCC2)ccc1OC[C@H]1CCCCN1] | (R)-N-(3-(4,6-dimethylpyrimidin-5-yl)-4-(piperidin-2-ylmethoxy)phenyl)-4-fluorotetrahydro-2H-pyran-4-carboxamide |

TABLE 1-continued

| Cmpd No. | Chemical Structure | Chemical Name |
| --- | --- | --- |
| 446 | 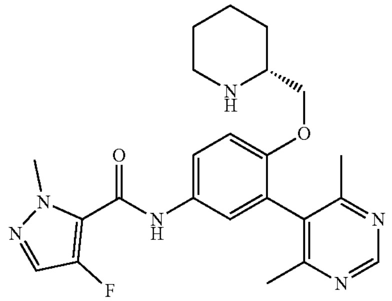 [SMILES: Cc1ncnc(C)c1-c1cc(NC(=O)c2c(F)cnn2C)ccc1OC[C@H]1CCCCN1] | (R)-N-(3-(4,6-dimethylpyrimidin-5-yl)-4-(piperidin-2-ylmethoxy)phenyl)-4-fluoro-1-methyl-1H-pyrazole-5-carboxamide |
| 447 | 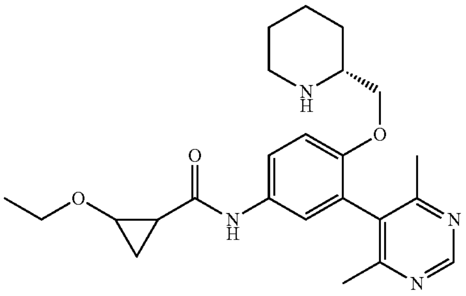 [SMILES: CCOC1CC1C(=O)Nc1ccc(OC[C@H]2CCCCN2)c(-c2c(C)ncnc2C)c1] | N-(3-(4,6-dimethylpyrimidin-5-yl)-4-(((R)-piperidin-2-yl)methoxy)phenyl)-2-ethoxycyclopropane-1-carboxamide |
| 448 | 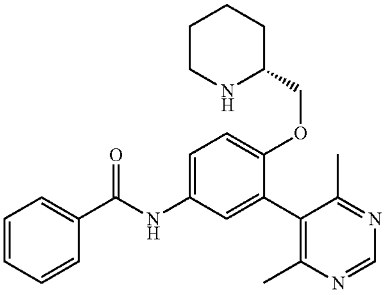 [SMILES: Cc1ncnc(C)c1-c1cc(NC(=O)c2ccccc2)ccc1OC[C@H]1CCCCN1] | (R)-N-(3-(4,6-dimethylpyrimidin-5-yl)-4-(piperidin-2-ylmethoxy)phenyl)benzamide |
| 449 | 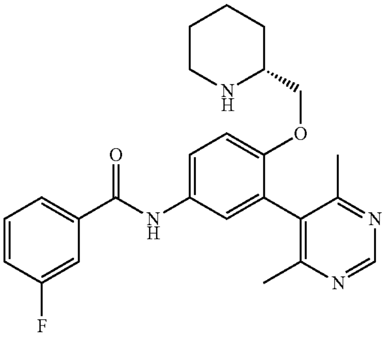 [SMILES: Cc1ncnc(C)c1-c1cc(NC(=O)c2cccc(F)c2)ccc1OC[C@H]1CCCCN1] | (R)-N-(3-(4,6-dimethylpyrimidin-5-yl)-4-(piperidin-2-ylmethoxy)phenyl)-3-fluorobenzamide |
| 450 | 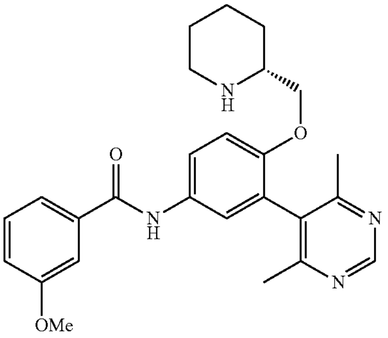 [SMILES: COc1cccc(C(=O)Nc2ccc(OC[C@H]3CCCCN3)c(-c3c(C)ncnc3C)c2)c1] | (R)-N-(3-(4,6-dimethylpyrimidin-5-yl)-4-(piperidin-2-ylmethoxy)phenyl)-3-methoxybenzamide |

TABLE 1-continued

| Cmpd No. | Chemical Structure | Chemical Name |
| --- | --- | --- |
| 451 | 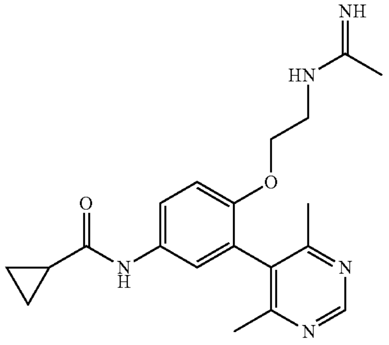 [SMILES: CC(=N)NCCOc1ccc(NC(=O)C2CC2)cc1-c1c(C)ncnc1C] | N-(4-(2-acetimidamidoethoxy)-3-(4,6-dimethylpyrimidin-5-yl)phenyl)cyclopropanecarboxamide |
| 452 | 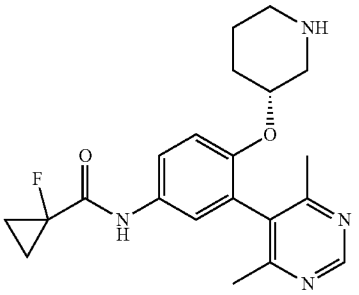 [SMILES: Cc1ncnc(C)c1-c1cc(NC(=O)C2(F)CC2)ccc1O[C@@H]1CCCNC1] | (R)-N-(3-(4,6-dimethylpyrimidin-5-yl)-4-(piperidin-3-yloxy)phenyl)-1-fluorocyclopropane-1-carboxamide |
| 453 | 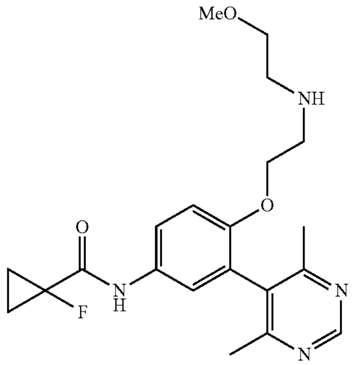 [SMILES: COCCNCCOc1ccc(NC(=O)C2(F)CC2)cc1-c1c(C)ncnc1C] | N-(3-(4,6-dimethylpyrimidin-5-yl)-4-(2-((2-methoxyethyl)amino)ethoxy)phenyl)-1-fluorocyclopropane-1-carboxamide |

In some embodiments, the compound having the structure selected from the group consisting of a compound of Table 1 herein, or a pharmaceutically acceptable salt thereof, wherein the salt is selected from the group consisting of salts of acetic acid, benzenesulfonic acid, benzoic acid, citric acid, ethanesulfonic acid, fumaric acid, hydrochloric acid, maleic acid, malic acid, methanesulfonic acid, nitric acid, oxalic acid, phosphoric acid, succinic acid, sulfuric acid, tartaric acid, and p-toluenesulfonic acid.

In some embodiments, the compound having the structure selected from the group consisting of a compound of Table 1 herein, or a pharmaceutically acceptable salt thereof, wherein the salt is selected from the group consisting of salts of acetic acid, benzenesulfonic acid, benzoic acid, citric acid, ethanesulfonic acid, fumaric acid, hydrochloric acid, maleic acid, malic acid, methanesulfonic acid, nitric acid, oxalic acid, phosphoric acid, succinic acid, sulfuric acid, tartaric acid, and p-toluenesulfonic acid.

In some embodiments, the compound having the structure selected from the group consisting of a compound of Table 1 herein, or a pharmaceutically acceptable salt thereof, wherein the salt is selected from the group consisting of salts of benzenesulfonic acid, citric acid, fumaric acid, hydrochloric acid, methanesulfonic acid, phosphoric acid, succinic acid, sulfuric acid and p-toluenesulfonic acid.

In some embodiments, the compound having the structure selected from the group consisting of a compound of Table 1 herein, or a pharmaceutically acceptable salt thereof, wherein the salt is selected from the group consisting of salts of benzenesulfonic acid, citric acid, phosphoric acid, succinic acid, and p-toluenesulfonic acid.

In some embodiments, the compound having the structure selected from the group consisting of a compound of Table 1 herein, or a pharmaceutically acceptable salt thereof, wherein the salt is selected from the group consisting of salts of benzenesulfonic acid, citric acid, and succinic acid.

In one embodiment, the compound having the structure selected from the group consisting of a compound of Table 1 herein, or a pharmaceutically acceptable salt of acetic acid.

In one embodiment, the compound having the structure selected from the group consisting of a compound of Table 1 herein, or a pharmaceutically acceptable salt of benzenesulfonic acid.

In one embodiment, the compound having the structure selected from the group consisting of a compound of Table 1 herein, or a pharmaceutically acceptable salt of benzoic acid.

In one embodiment, the compound having the structure selected from the group consisting of a compound of Table 1 herein, or a pharmaceutically acceptable salt of citric acid.

In one embodiment, the compound having the structure selected from the group consisting of a compound of Table 1 herein, or a pharmaceutically acceptable salt of fumaric acid.

In one embodiment, the compound having the structure selected from the group consisting of a compound of Table 1 herein, or a pharmaceutically acceptable salt of hydrochloric acid.

In one embodiment, the compound having the structure selected from the group consisting of a compound of Table 1 herein, or a pharmaceutically acceptable salt of maleic acid.

In one embodiment, the compound having the structure selected from the group consisting of a compound of Table 1 herein, or a pharmaceutically acceptable salt of methanesulfonic acid.

In one embodiment, the compound having the structure selected from the group consisting of a compound of Table 1 herein, or a pharmaceutically acceptable salt of oxalic acid.

In one embodiment, the compound having the structure selected from the group consisting of a compound of Table 1 herein, or a pharmaceutically acceptable salt of phosphoric acid.

In one embodiment, the compound having the structure selected from the group consisting of a compound of Table 1 herein, or a pharmaceutically acceptable salt of succinic acid.

In one embodiment, the compound having the structure selected from the group consisting of a compound of Table 1 herein, or a pharmaceutically acceptable salt of sulfuric acid.

In one embodiment, the compound having the structure selected from the group consisting of a compound of Table 1 herein, or a pharmaceutically acceptable salt of p-toluenesulfonic acid.

Additionally, individual compounds and chemical genera of the present invention, for example those compounds found in TABLE 1 including diastereomers and enantiomers thereof, encompass all pharmaceutically acceptable salts, solvates, and particularly hydrates, thereof.

The compounds of the Formula (I) of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis,* 3rd Edition, 1999 [Wiley]; incorporated herein by reference in its entirety).

It is understood that the present invention embraces each diastereomer, each enantiomer and mixtures thereof of each compound and generic formulae disclosed herein just as if they were each individually disclosed with the specific stereochemical designation for each chiral carbon. Separation of the individual isomers (such as chiral HPLC, recrystallization of diastereomeric mixtures, and the like) or selective synthesis (such as enantiomeric selective syntheses, and the like) of the individual isomers is accomplished by application of various methods which are well known to practitioners in the art.

Indications and Methods of Prophylaxis and/or Treatment

The compounds of Formula (I), and pharmaceutically acceptable salts thereof, are useful as $5\text{-HT}_{2A}$ serotonin receptor modulators for the treatment of disorders associated with $5\text{-HT}_{2A}$ serotonin receptor expression and/or activity, such as cardiovascular disorders (for example, coronary artery disease, myocardial infarction, transient ischemic attack, angina, stroke, atrial fibrillation, platelet aggregation, and blood clot formation or symptoms thereof.

The modulators of $5\text{-HT}_{2A}$ receptor activity disclosed herein are believed to be useful in the treatment of several diseases and disorders, and in the amelioration of symptoms thereof. Without limitation, some of them include the following: Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood as a result of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation blood clots that cause first or second strokes.

Angioplasty is a catheter-based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

$5\text{-HT}_{2A}$ receptors are expressed on smooth muscle of blood vessels and 5-HT secreted by activated platelets causes vasoconstriction as well as activation of additional platelets during clotting. There is evidence that a $5\text{-HT}_{2A}$ inverse agonist will inhibit platelet aggregation and thus be a potential treatment as an antiplatelet therapy (see Satimura, K, et al., Clin Cardiol 2002 Jan. 25 (1): 28-32; and Wilson, H. C et al., Thromb Haemost 1991 Sep. 2; 66 (3):355-60).

The 5-$HT_{2A}$ inverse agonists disclosed herein provide beneficial improvement in microcirculation to patients in need of antiplatelet therapy by antagonizing the vasoconstrictive products of the aggregating platelets in, for example and not limitation, the indications described above. Accordingly, in some embodiments, the present invention provides methods for reducing platelet aggregation in a patient in need thereof comprising administering to said patient a composition comprising a 5-$HT_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of said treatment, comprising administering to said patient a composition comprising a 5-$HT_{2A}$ inverse agonist disclosed herein.

In further embodiments, the present invention provides methods for reducing risk of blood clot formation in an angioplasty or coronary bypass surgery patient, or a patient suffering from atrial fibrillation, comprising administering to a said patient a composition comprising a 5-$HT_{2A}$ inverse agonist disclosed herein at a time where such risk exists.

In further embodiments, the present invention provides methods for reducing risk of, or treating the effects of, PCI, comprising administering to a patient a composition comprising a 5-$HT_{2A}$ inverse agonist disclosed herein at a time where such risk exists.

In further embodiments, the present invention provides methods for the prevention or treatment of Raynaud's, comprising administering to a patient a composition comprising a 5-$HT_{2A}$ inverse agonist disclosed herein.

Synthetic Methods:

Example processes and intermediates of the present disclosure are provided below in Scheme 1. As will be appreciated by those skilled in the art, the compounds provided herein, including salts thereof, can be prepared using known organic synthesis techniques and can be synthesized according to any of numerous possible synthetic routes, such as that provided in Scheme 1.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Scheme 1 provides general guidance in connection with preparing the compounds of the invention. For instance, the compound of Formula (I) can be prepared as shown in Scheme 1.

Scheme 1

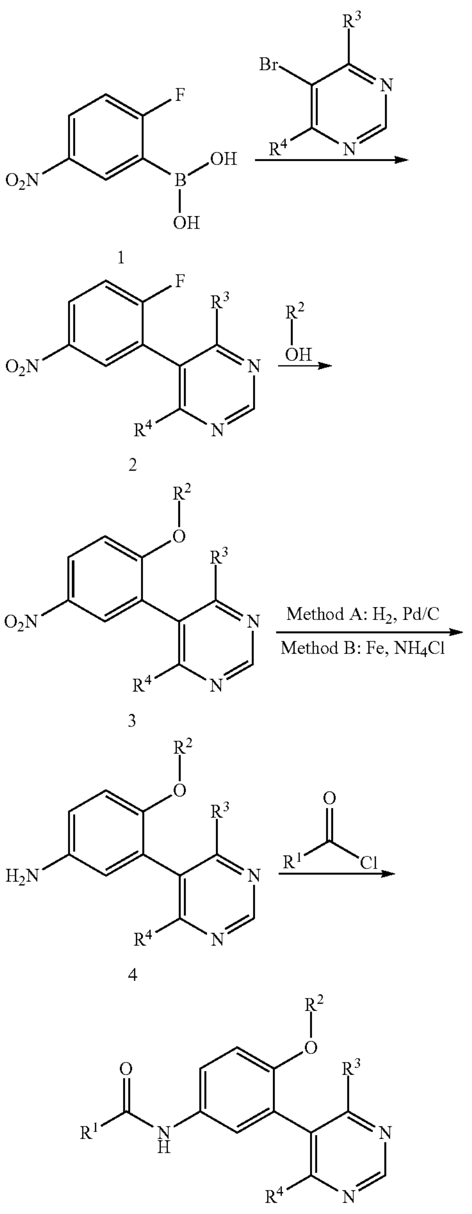

1

2

3

4

Polymorphs and Pseudopolymorphs

The present disclosure includes polymorphs and pseudopolymorphs of the compound of Formula (I) of the present disclosure. Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, crystalline phases can contain an API host and either solvent or water molecules, respectively, as guests.

Crystalline phases that share the same API host, but differ with respect to the guests, can be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly published a polymorph screen of 245 compounds consisting of a "wide variety of structural types" that revealed about 90% of them exhibited multiple solid forms. Overall, approximately half of the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7 (6), 1007-1026).

Isotopes

The present disclosure includes all isotopes of atoms occurring in the compounds provided herein. Isotopes include those atoms having the same atomic number but different mass numbers. It is appreciated that certain features of the disclosure include every combination of one or more atoms in the compounds provided herein that is replaced with an atom having the same atomic number but a different mass number. One such example is the replacement of an atom that is the most naturally abundant isotope, such as $^{1}H$ or $^{12}C$, found in one of the compounds provided herein with a different atom that is not the most naturally abundant isotope, such as $^{2}H$ or $^{3}H$ (replacing $^{1}H$), or $^{11}C$, $^{13}C$, or $^{14}C$ (replacing $^{12}C$). A compound where such a replacement has taken place is commonly referred to as being isotopically-labeled. Isotopic-labeling of the present compounds can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^{2}H$ (deuterium) and $^{3}H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Also provided are compositions, such as those prepared during synthesis or preformulation, and pharmaceutical compositions, such as those prepared with the intent of using in a mammal for the treatment of one or more of the disorders described herein, comprising one or more of the present compounds, where the naturally occurring distribution of the isotopes in the composition is perturbed. Also provided herein are compositions and pharmaceutical compositions comprising compounds of the present disclosure where the salt is enriched at one or more positions with an isotope other than the most naturally abundant isotope. Methods are readily available to measure such isotope perturbations or enrichments, such as mass spectrometry, and for isotopes that are radio-isotopes additional methods are available, such as radio-detectors used in connection with HPLC or GC.

One challenge in drug development is improving absorption, distribution, metabolism, excretion, and toxicity (ADMET) properties while maintaining a desired pharmacological profile. Structural changes to improve ADMET properties often alter the pharmacology of a lead compound. While the effects of deuterium substitution on ADMET properties are unpredictable, in select cases deuterium can improve a compound's ADMET properties with minimal perturbation of its pharmacology.

Another object of the present disclosure relates to radio-labeled compounds of the present disclosure that would be useful not only in radio-imaging but also in assays, both in vitro and in vivo, for localizing and quantitating 5-$HT_{2A}$ receptors in tissue samples, including human, and for identifying 5-$HT_{2A}$ receptor ligands by inhibition binding of a radio-labeled compound. It is a further object of this disclosure to develop novel 5-$HT_{2A}$ receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro 5-$HT_{2A}$ serotonin receptor labeling and competition assays, compounds that incorporate $^{3}H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (I) that has incorporated at least one radionuclide; in some embodiments the radionuclide is selected from the group consisting of $^{3}H$, $^{14}C$, $^{125}I$, $^{35}S$ and $^{82}Br$.

Certain isotopically-labeled compounds of the present disclosure are useful in compound and/or substrate tissue distribution assays. In some embodiments, the radionuclide $^{3}H$ and/or $^{14}C$ isotopes are useful in these studies. Further, substitution with heavier isotopes such as deuterium (i.e., $^{2}H$) can afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed in the present disclosure, by substituting an isotopically labeled reagent for a non-isotopically labeled reagent. Moreover, it should be understood that all of the atoms represented in the compounds of the present disclosure can be either the most commonly occurring isotope of such atoms or the scarcer radio-isotope or nonradioactive isotope. Synthetic methods for incorporating radio-isotopes into organic compounds are applicable to compounds of the invention and are well known in the art.

Methods

The compound of Formula (I) or any other Formula herein, such as Formulae (Ia), (Ia'), (Ia"), (Ib), (Ic), (Id), (Ie), or (If), and pharmaceutically acceptable salts thereof, have activity as 5-$HT_{2A}$ receptor modulators. Accordingly, the compound of Formula (I) or any other Formula herein, such as Formulae (Ia), (Ia'), (Ia"), (Ib), (Ic), (Id), (Ie), or (If), and pharmaceutically acceptable salts thereof, can be used in methods of modulating the 5-$HT_{2A}$ receptor by contacting the receptor with a compound of Formula (I) or any other Formula herein, such as Formulae (Ia), (Ia'), (Ia"), (Ib), (Ic), (Id), (Ie), or (If), or pharmaceutically acceptable salt thereof, or compositions thereof, as described herein. In further embodiments, a compound of Formula (I) or any other Formula herein, such as Formulae (Ia), (Ia'), (Ia"), (Ib), (Ic), (Id), (Ie), or (If), or pharmaceutically acceptable salt thereof can be used to modulate 5-$HT_{2A}$ receptors in an individual in need of such modulation by administering a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

The present disclosure further provides methods of treating diseases associated with the 5-$HT_{2A}$ receptor in an individual (e.g., patient) by administering to the individual in need of such treatment a therapeutically effective amount or dose of a compound of Formula (I) or any other Formula herein, such as Formulae (Ia), (Ia'), (Ia"), (Ib), (Ic), (Id), (Ie), or (If), or pharmaceutically acceptable salt thereof or a pharmaceutical composition thereof. A disease or disorder associated with or directly or indirectly linked to the expression or activity of the 5-$HT_{2A}$ receptor is a disorder or disease in an individual which can be prevented, inhibited, ameliorated, treated or cured by modulation (e.g., agonism, antagonism, or inverse agonism) of the 5-$HT_{2A}$ receptor, for example, by administering to the individual in need thereof a therapeutically effective amount of a compound of the present disclosure or pharmaceutically acceptable salt thereof or composition containing a compound of the present disclosure or pharmaceutically acceptable salt thereof. The disease can be any disease, disorder or condition that is directly or indirectly linked to expression or activity of the 5-$HT_{2A}$ receptor.

Examples of diseases directly or indirectly linked to expression or activity of the 5-$HT_{2A}$ receptor include, but are not limited to, platelet aggregation, coronary artery disease, myocardial infarction, transient ischemic attack, angina, stroke, atrial fibrillation, and blood clot formation or symptoms thereof.

The present disclosure provides methods of treating coronary artery disease, myocardial infarction, transient ischemic attack, angina, stroke, and atrial fibrillation, comprising administering to a patient in need thereof a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

The present disclosure further provides methods for treating conditions related to platelet aggregation comprising prescribing and/or administering to a patient in need thereof a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof. It is understood that treatment of platelet aggregation refers to any reduction of platelet aggregation that results in an amelioration of a pathophysiological condition associated with platelet aggregation.

The present disclosure further provides methods of treating one or more conditions associated with platelet aggregation comprising prescribing and/or administering to a patient in need thereof a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

The present disclosure further provides methods of reducing the risk of blood clot formation in an angioplasty or coronary bypass surgery in an individual comprising prescribing and/or administering to a patient in need thereof a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

The present disclosure further provides methods of reducing the risk of blood clot formation in an individual suffering from atrial fibrillation comprising prescribing and/or administering to a patient a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

The present disclosure further provides methods of reducing the risk of, or treating the effects of, PCI in an individual comprising prescribing and/or administering to a patient a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

The present disclosure further provides methods of treating or preventing Raynaud's in an individual comprising prescribing and/or administering to a patient a therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

In some embodiments, the method further includes the step of identifying a patient, where the patient is in need of treatment for the particular disease being treated. In some embodiments, the identifying step is performed prior to administration to the patient the therapeutically effective amount of a compound of Formula (I) or any other Formula herein, such as Formulae (Ia), (Ia'), (Ia"), (Ib), (Ic), (Id), (Ie), or (If), or pharmaceutically acceptable salt thereof.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method of treatment of the human or animal body by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method of treatment of a $5HT_{2A}$-related disorder of the human or animal body by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method of treatment of platelet aggregation, coronary artery disease, myocardial infarction, transient ischemic attack, angina, stroke, atrial fibrillation, blood clot formation, or symptoms thereof, in the human or animal body by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method of treatment of coronary artery disease, myocardial infarction, transient ischemic attack, angina, stroke or atrial fibrillation in the human or animal body by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method for treating platelet aggregation in the human or animal body by therapy. It is understood that treatment of platelet aggregation refers to any reduction of platelet aggregation that results in an amelioration of a pathophysiological condition associated with platelet aggregation.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method for treating one or more conditions associated with platelet aggregation in the human or animal body by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method for reducing the risk of blood clot formation in an angioplasty or coronary bypass surgery individual by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method for reducing the risk of blood clot formation in an individual suffering from atrial fibrillation by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method for reducing the risk of, or treating the effects of, PCI in an individual by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof in a method for treating or preventing Raynaud's in an individual by therapy.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for treating a $5HT_{2A}$-related disorder.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for treating disease or disorder selected from platelet aggregation, coronary artery disease, myocardial infarction, transient ischemic attack, angina, stroke, atrial fibrillation, blood clot formation, or symptoms thereof.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for treating coronary artery disease, myocardial infarction, transient ischemic attack, angina, stroke, or atrial fibrillation.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for treating platelet aggregation. It is understood that treatment of platelet aggregation refers to any reduction of platelet aggregation that results in an amelioration of a pathophysiological condition associated with platelet aggregation.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for treating one or more conditions associated with platelet aggregation.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for reducing the risk of blood clot formation in an angioplasty or coronary bypass surgery individual.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for reducing the risk of blood clot formation in an individual suffering from atrial fibrillation.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for reducing the risk of, or treating the effects of, PCI in an individual.

One aspect of the present disclosure pertains to use of a compound of Formula (I) or any other Formula herein, such as Formulae (Ia), (Ia'), (Ia"), (Ib), (Ic), (Id), (Ie), or (If), or pharmaceutically acceptable salt thereof for the manufacture of a medicament for treating or preventing Raynaud's in an individual.

Pharmaceutical Compositions

A further aspect of the present disclosure pertains to pharmaceutical compositions comprising the compound of Formula (I) or any other Formula herein, such as Formulae (Ia), (Ia'), (Ia"), (Ib), (Ic), (Id), (Ie), or (If), or pharmaceutically acceptable salt thereof as described herein and one or more pharmaceutically acceptable carriers. In some embodiments, the pharmaceutical composition comprises a compound of Formula (I) or any other Formula herein, such as Formulae (Ia), (Ia'), (Ia"), (Ib), (Ic), (Id), (Ie), or (If), and a pharmaceutically acceptable carrier. In some embodiments, the pharmaceutical composition comprises a salt of the compound of Formula (I) or any other Formula herein, such as Formulae (Ia), (Ia'), (Ia"), (Ib), (Ic), (Id), (Ie), or (If), and a pharmaceutically acceptable carrier.

Some embodiments of the present disclosure include a method of producing a pharmaceutical composition comprising admixing the compound of Formula (I) or any other Formula herein, such as Formulae (Ia), (Ia'), (Ia"), (Ib), (Ic), (Id), (Ie), or (If), or pharmaceutically acceptable salt thereof and a pharmaceutically acceptable carrier.

Some embodiments of the present disclosure include a method of producing a pharmaceutical composition comprising admixing a salt of the compound of Formula (I) or any other Formula herein, such as Formulae (Ia), (Ia'), (Ia"), (Ib), (Ic), (Id), (Ie), or (If), as disclosed herein and a pharmaceutically acceptable carrier.

Formulations can be prepared by any suitable method known to those skilled in the art. In some embodiments, the formulation is prepared by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tableting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives, such as suspending or emulsifying agents, non-aqueous vehicles (including edible oils), preservatives, and flavorings and colorants can be added to the liquid preparations. Parenteral dosage forms can be prepared by dissolving the compound of Formula (I) or any other Formula herein, such as Formulae (Ia), (Ia'), (Ia"), (Ib), (Ic), (Id), (Ie), or (If), or a pharmaceutically acceptable salt thereof in a suitable liquid vehicle and filter sterilizing the solution before filling and sealing an appropriate vial or ampoule. These are just a few examples of the many appropriate methods well known in the art for preparing dosage forms.

A compound of Formula (I) or any other Formula herein, such as Formulae (Ia), (Ia'), (Ia"), (Ib), (Ic), (Id), (Ie), or (If), or pharmaceutically acceptable salt thereof can be formulated into pharmaceutical compositions using techniques well known to those in the art. Suitable pharmaceutically acceptable carriers, outside those mentioned herein, are known in the art; for example, see Remington, *The Science and Practice of Pharmacy,* $20^{th}$ Ed., 2000, Lippincott Williams & Wilkins, (Editors: Gennaro, A. R., et al.).

While it is possible that, for use in treatment, the compound of Formula (I) or any other Formula herein, such as Formulae (Ia), (Ia'), (Ia"), (Ib), (Ic), (Id), (Ie), or (If), or pharmaceutically acceptable salt thereof can, in an alternative use, be administered as a raw or pure chemical, it is preferable however to present the compound or active ingredient as a pharmaceutical formulation or composition further comprising a pharmaceutically acceptable carrier.

The disclosure thus further provides pharmaceutical formulations comprising a compound of Formula (I) or any other Formula herein, such as Formulae (Ia), (Ia'), (Ia"), (Ib), (Ic), (Id), (Ie), or (If), or pharmaceutically acceptable salt thereof together with one or more pharmaceutically acceptable carriers and/or prophylactic ingredients. The carrier(s) is "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compound of Formula (I) or any other Formula herein, such as Formulae (Ia), (Ia'), (Ia"), (Ib), (Ic), (Id), (Ie), or (If), or pharmaceutically acceptable salt thereof, together with a conventional adjuvant, carrier, or diluent, can thus be placed into the form of a pharmaceutical formulation and unit dosage thereof, and in such form can be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms can comprise conventional ingredients in conventional proportions, with or without additional active compounds or principles, and such unit dosage forms can contain any suitable effective amount of the active ingredient commensurate with the intended daily dosage range to be employed.

For oral administration, the pharmaceutical composition can be in the form of, for example, a tablet, capsule, suspension or liquid. In some embodiments, the pharmaceutical composition is made in the form of a dosage unit containing a particular amount of the active ingredient. Examples of such dosage units include, but are not limited to, capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient can also be administered by injection as a composition where, for example, saline, dextrose or water can be used as a suitable pharmaceutically acceptable carrier.

The compound of Formula (I) or any other Formula herein, such as Formulae (Ia), (Ia'), (Ia"), (Ib), (Ic), (Id), (Ie), or (If), or pharmaceutically acceptable salt thereof can be used as an active ingredient in pharmaceutical compositions, specifically as a 5-$HT_{2A}$ receptor modulator. The term "active ingredient" is defined in the context of a "pharmaceutical composition" and means a component of a pharmaceutical composition that provides the primary pharmacological effect, as opposed to an "inactive ingredient" which would generally be recognized as providing no pharmaceutical benefit.

The dose, when using the compound of Formula (I) or any other Formula herein, such as Formulae (Ia), (Ia'), (Ia"), (Ib), (Ic), (Id), (Ie), or (If), or pharmaceutically acceptable salt thereof, can vary within wide limits, as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compound of Formula (I) or any other Formula herein, such as Formulae (Ia), (Ia'), (Ia"), (Ib), (Ic), (Id), (Ie), or (If), or pharmaceutically acceptable salt thereof. Representative doses of the present disclosure include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses can be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations can merely be based on the weight of the animal model in comparison to another, such as a mammal, preferably a human, however, more often, these extrapolations are not simply based on weights, but rather incorporate a variety of factors. Representative factors include, but are not limited to, the type, age, weight, sex, diet, and medical condition of the patient, the severity of the disease, the route of administration, pharmacological considerations such as the activity, efficacy, pharmacokinetic and toxicology profiles of the particular compound employed, whether a drug delivery system is utilized, or whether an acute or chronic disease state is being treated or prophylaxis is conducted or on whether further active compounds are administered in addition to the compound of Formula (I) or any other Formula herein, such as Formulae (Ia), (Ia'), (Ia"), (Ib), (Ic), (Id), (Ie), or (If), or pharmaceutically acceptable salt thereof or as part of a drug combination. The dosage regimen for treating a disease or condition with the compound of Formula (I) or any other Formula herein, such as Formulae (Ia), (Ia'), (Ia"), (Ib), (Ic), (Id), (Ie), or (If), or pharmaceutically acceptable salt thereof and/or compositions of this disclosure is selected in accordance with a variety factors as described in the present disclosure. Thus, the actual dosage regimen employed can vary widely and therefore can deviate from a preferred dosage regimen. One skilled in the art will recognize that dosages and dosage regimens outside these typical ranges can be tested and, where appropriate, can be used in the methods of the present disclosure.

The desired dose can be presented in a single dose or as divided doses administered at appropriate intervals, for example, as two, three, four or more sub-doses per day. The sub-dose itself can be further divided, e.g., into a number of discrete loosely spaced administrations. The daily dose can be divided, for example, when relatively large amounts are administered as deemed appropriate, into several, for example 2, 3 or 4, partial administrations. If appropriate, depending on individual behavior, it may be necessary to deviate upward or downward from the daily dose indicated.

The compound of Formula (I) or any other Formula herein, such as Formulae (Ia), (Ia'), (Ia"), (Ib), (Ic), (Id), (Ie), or (If), or pharmaceutically acceptable salt thereof can be administrated in a wide variety of oral and parenteral dosage forms. It will be obvious to those skilled in the art that the following dosage forms can contain, as the active component, either the compound of Formula (I) or any other Formula herein, such as Formulae (Ia), (Ia'), (Ia"), (Ib), (Ic), (Id), (Ie), or (If), or a pharmaceutically acceptable salt thereof.

For preparing pharmaceutical compositions from the compound of Formula (I) or any other Formula herein, such as Formulae (Ia), (Ia'), (Ia"), (Ib), (Ic), (Id), (Ie), or (If), or pharmaceutically acceptable salt thereof, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets can contain varying percentage amounts of the active compound. A representative amount in a powder or tablet can contain from about 0.5% to about 90% of the active compound. A skilled artisan would know when amounts outside of this range are necessary. Suitable carriers for powders and tablets include, but are not limited to, magnesium carbonate, magnesium stearate, talc, sugar, lactose, pectin, dextrin, starch, gelatin, tragacanth, methylcellulose, sodium carboxymethylcellulose, a low melting wax, and cocoa butter. The term "preparation" is intended to include the formulation of the active compound with an encapsulating material as carrier, providing a capsule in which the active component, with or without carriers, is surrounded by a carrier, which is thus in association with it. Similarly, cachets and lozenges are included in some embodiments. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration can be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. In addition, fatty acids, such as oleic acid, can find use in the preparation of injectables.

The compound of Formula (I) or any other Formula herein, such as Formulae (Ia), (Ia'), (Ia"), (Ib), (Ic), (Id), (Ie), or (If), or pharmaceutically acceptable salt thereof can thus be formulated for parenteral administration (e.g., by injection, for example, bolus injection or continuous infusion) and can be presented in unit dose form in ampoules, prefilled syringes, small volume infusion or in multi-dose containers with an added preservative. The pharmaceutical compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included, in some embodiments, are solid form preparations which are intended to be converted, shortly before use, to liquid form preparations for oral administration. Such liquid forms can include solutions, suspensions, and emulsions. These preparations can contain, in addition to the active component, for example, colorants, flavors, stabilizers, buffers, artificial and natural sweeteners, dispersants, thickeners, and solubilizing agents.

For topical administration to the epidermis, the compound of Formula (I) or any other Formula herein, such as Formulae (Ia), (Ia'), (Ia"), (Ib), (Ic), (Id), (Ie), or (If), or pharmaceutically acceptable salt thereof can be formulated as ointments, creams or lotions, or as a transdermal patch.

Ointments and creams can, for example, be formulated with an aqueous or oily base with the addition of suitable thickening and/or gelling agents. Lotions can be formulated with an aqueous or oily base and can also contain one or more emulsifying agents, stabilizing agents, dispersing agents, suspending agents, thickening agents, or coloring agents.

Formulations suitable for topical administration in the mouth include, but are not limited to, lozenges comprising active agent in a flavored base, for example, sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations can be provided in single or multi-dose form. In the case of a dropper or pipette, administration can be achieved by the patient administering an appropriate, predetermined volume of the solution or suspension. In the case of a spray, this may be achieved, for example, by means of a metering atomizing spray pump.

Administration to the respiratory tract can also be achieved by means of an aerosol formulation in which the active ingredient is provided in a pressurized pack with a suitable propellant. If the compound of Formula (I) or any other Formula herein, such as Formulae (Ia), (Ia'), (Ia"), (Ib), (Ic), (Id), (Ie), or (If), or pharmaceutically acceptable salt thereof or pharmaceutical compositions comprising the compound of Formula (I) or any other Formula herein, such as Formulae (Ia), (Ia'), (Ia"), (Ib), (Ic), (Id), (Ie), or (If), or pharmaceutically acceptable salt thereof are administered as aerosols, for example, as nasal aerosols or by inhalation, this can be carried out, for example, using a spray, a nebulizer, a pump nebulizer, an inhalation apparatus, a metered inhaler, or a dry powder inhaler. Pharmaceutical forms for administration of the compound of Formula (I) or any other Formula herein, such as Formulae (Ia), (Ia'), (Ia"), (Ib), (Ic), (Id), (Ie), or (If), or pharmaceutically acceptable salt thereof as an aerosol can be prepared by processes well-known to the person skilled in the art. For their preparation, for example, solutions or dispersions of the compound of Formula (I) or any other Formula herein, such as Formulae (Ia), (Ia'), (Ia"), (Ib), (Ic), (Id), (Ie), or (If), or pharmaceutically acceptable salt thereof in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, including, but not limited to, carbon dioxide and CFCs, such as dichlorodifluoromethane, trichlorofluoromethane, and dichlorotetrafluoroethane. The aerosol can also contain a surfactant. In some embodiments, the surfactant is lecithin. The dose of drug can be controlled by provision of a metered valve.

In formulations intended for administration to the respiratory tract, including intranasal formulations, the compound will generally have a small particle size, for example, on the order of 10 microns or less. Such a particle size can be obtained by means known in the art, for example by micronization. When desired, formulations adapted to give sustained release of the active ingredient can be employed.

Alternatively, the active ingredients can be provided in the form of a dry powder, for example, a powder mix of the compound in a suitable powder base such as lactose, starch, or starch derivatives such as hydroxypropylmethylcellulose (HPMC) and polyvinylpyrrolidone (PVP). In some embodiments, the powder carrier will form a gel in the nasal cavity. The powder composition can be presented in unit dose form, for example in capsules or cartridges of, e.g., gelatin, or blister packs from which the powder can be administered by means of an inhaler.

In some embodiments, the pharmaceutical preparations are in unit dosage forms. In such form, the preparation is subdivided into unit doses containing appropriate quantities of the active component. The unit dosage form can be a packaged preparation, where the package contains discrete quantities of preparation, such as packeted tablets, capsules, and powders in vials or ampoules. In some embodiments, the unit dosage form is a capsule, tablet, cachet, or lozenge itself, or it is the appropriate number of any of these in packaged form.

Tablets or capsules for oral administration and liquids for intravenous administration are preferred compositions.

The compounds provided herein may optionally exist as pharmaceutically acceptable salts including pharmaceutically acceptable acid addition salts prepared from pharmaceutically acceptable non-toxic acids including inorganic and organic acids. Representative acids include, but are not limited to acetic, benzenesulfonic, benzoic, camphorsulfonic, citric, dichloroacetic, ethanesulfonic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain compounds provided herein which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1$,$N^2$-dibenzylethane-1,2-diamine), chloroprocaine (2-(diethylamino)ethyl 4-(chloroamino)benzoate), choline, diethanolamine, ethylenediamine, meglumine ((2R, 3R,4R,5S)-6-(methylamino) hexane-1,2,3,4,5-pentaol), procaine (2-(diethylamino)ethyl 4-aminobenzoate), and the like. Certain pharmaceutically acceptable salts are listed in Berge, et. al., Journal of Pharmaceutical Sciences, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds provided herein may form solvates with standard low molecular weight solvents using methods known to the skilled artisan.

Compounds provided herein can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds provided herein containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in Bioreversible Carriers in Drug Design, ed. Edward B. Roche, American Pharmaceutical Association and Pergamon Press, 1987.

Some embodiments of the present disclosure include a method of producing a pharmaceutical composition for "combination therapy" comprising admixing the compound of Formula (I) or any other Formula herein, such as Formulae (Ia), (Ia'), (Ia"), (Ib), (Ic), (Id), (Ie), or (If), or pharmaceutically acceptable salt thereof together with at least one known pharmaceutical agent as described herein and a pharmaceutically acceptable carrier.

It is noted that when the 5-$HT_{2A}$ receptor modulators are utilized as active ingredients in a pharmaceutical composition, these are not intended for use only in humans, but in other non-human mammals as well. Indeed, advances in the area of animal health-care mandate that consideration be given for the use of active agents, such as 5-$HT_{2A}$ receptor modulators, for the treatment of a 5-$HT_{2A}$ mediated diseases or disorders in domestic animals (e.g., cats and dogs) and in other domestic animals (e.g., such as cows, chickens, and fish). Those of ordinary skill in the art will understand the utility of such compounds in such settings.

EXAMPLES

Example 1—Preparation of Compounds of Formula (I)

Experimental procedures for the preparation of compounds of Formula (I) are provided below.

N-(3-(4,6-dimethylpyrimidin-5-yl)-4-(2-(pyrrolidin-1-yl)ethoxy)phenyl)-1-methyl-1H-pyrrole-2-carboxamide (200)

Preparation of 5-(2-fluoro-5-nitro-phenyl)-4,6-dimethyl-pyrimidine (1)

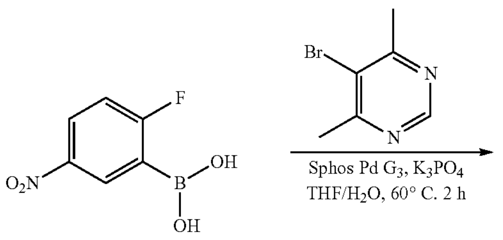

-continued

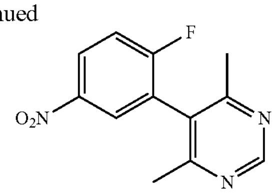

1

A mixture of 5-bromo-4,6-dimethyl-pyrimidine (1 g, 5.35 mmol, 1 eq.), (2-fluoro-5-nitro-phenyl) boronic acid (1.19 g, 6.42 mmol, 1.2 eq.), SPhos Pd G3 (125.23 mg, 160.50 μmol, 0.03 eq.), and $K_3PO_4$ (3.40 g, 16.05 mmol, 3 eq.) in THF (50 mL) and $H_2O$ (10 mL) was degassed and purged with $N_2$ three times, and then the mixture was stirred at 60° C. for 2 hrs under an $N_2$ atmosphere (monitored by LCMS). The reaction mixture was concentrated in vacuum to give a residue. The residue was purified by column chromatography ($SiO_2$, petroleum ether/ethyl acetate=9/1 to 1/1). 5-(2-Fluoro-5-nitro-phenyl)-4,6-dimethyl-pyrimidine ((1), 1.28 g, 5.18 mmol, 96.78% yield) was obtained as a white solid.

LCMS (ESI): m/z [M+H] calcd for $C_{12}H_{11}FN_3O_2$: 248.08; found: 248.1.

Scaled-Up Synthesis:

A mixture of 5-bromo-4,6-dimethyl-pyrimidine (20 g, 106.93 mmol, 1 eq.), (2-fluoro-5-nitro-phenyl) boronic acid (23.73 g, 128.32 mmol, 1.2 eq.), SPhos Pd $G_3$ (2.50 g, 3.21 mmol, 0.03 eq.), and $K_3PO_4$ (68.09 g, 320.79 mmol, 3 eq.) in THF (500 mL) and $H_2O$ (100 mL) was degassed and purged with $N_2$ three times, and then the mixture was stirred at 60° C. for 12 hrs under an $N_2$ atmosphere. The reaction mixture was concentrated under reduced pressure at 40° C. to remove THE to give a turbid liquid. The residue was then extracted with ethyl acetate (3×150 mL). The combined organic layer was washed with saturated NaCl aqueous solution, dried with anhydrous $Na_2SO_4$, filtered, and concentrated under reduced pressure to obtain a solid. 500 mL methyl tert-butyl ether was added to the claybank solid, stirred for 30 min and solids were separated out. The precipitate was collected by filtering and dried under vacuum. 5-(2-Fluoro-5-nitro-phenyl)-4,6-dimethyl-pyrimidine ((1), 17 g, 68.76 mmol, 64.31% yield) was obtained as a brown solid.

LCMS (ESI): m/z [M+H] calcd for $C_{12}H_{11}FN_3O_2$: 248.08; found: 248.1.

$^1H$ NMR (400 MHZ, methanol-$d_4$) δ=8.96 (s, 1H), 8.50-8.44 (m, 1H), 8.36 (dd, J=2.9, 6.1 Hz, 1H), 7.58 (t, J=8.8 Hz, 1H), 2.32 (s, 6H).

Preparation of 4,6-dimethyl-5-[5-nitro-2-(2-pyrrolidin-1-ylethoxy)phenyl]pyrimidine (2)

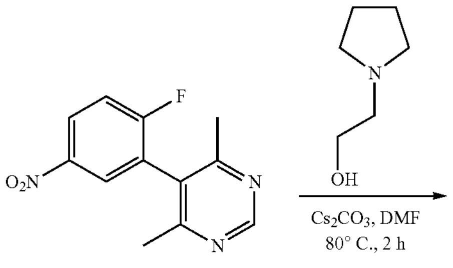

1

-continued

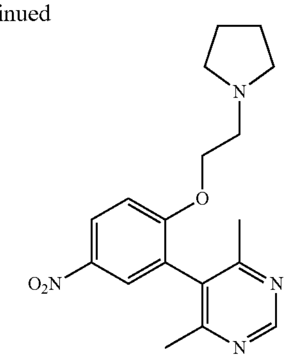

2

A mixture of 5-(2-fluoro-5-nitro-phenyl)-4,6-dimethyl-pyrimidine ((1), 1.28 g, 5.18 mmol, 1 eq.), 2-(pyrrolidin-1-yl)ethanol (596.31 mg, 5.18 mmol, 605.39 μL, 1 eq.) and $Cs_2CO_3$ (3.37 g, 10.35 mmol, 2 eq.) in DMF (10 mL) was stirred at 80° C. for 2 hrs (monitored by LCMS). The reaction mixture was filtered and concentrated in vacuum to give a residue. 4,6-Dimethyl-5-[5-nitro-2-(2-pyrrolidin-1-ylethoxy)phenyl]pyrimidine ((2), 1.7 g, 4.97 mmol, crude) was obtained as a black oil.

LCMS (ESI): m/z [M+H] calcd for $C_{18}H_{23}N_4O_3$: 343.17; found: 343.2.

Scaled-Up Synthesis:

To a solution of 5-(2-fluoro-5-nitro-phenyl)-4,6-dimethyl-pyrimidine ((1), 10 g, 40.45 mmol, 1 eq.) in DMF (20 mL) was added 2-pyrrolidin-1-ylethanol (5.12 g, 44.49 mmol, 5.20 mL, 1.1 eq.) and $Cs_2CO_3$ (13.18 g, 40.45 mmol, 1 eq.). The mixture was stirred at 120° C. for 12 hrs. The reaction mixture was partitioned between $H_2O$ (50 mL) and ethyl acetate (200 mL). The organic phase was separated, dried over $Na_2SO_4$, filtered and concentrated under reduced pressure to give a residue. The residue was purified by prep-HPLC (neutral condition) to afford 4,6-Dimethyl-5-[5-nitro-2-(2-pyrrolidin-1-ylethoxy)phenyl]pyrimidine ((2), 7 g, 20.44 mmol, 50.54% yield) as a brown oil.

LCMS (ESI): m/z [M+H] calcd for $C_{18}H_{23}N_4O_3$: 343.17; found: 343.2.

Preparation of 3-(4,6-dimethylpyrimidin-5-yl)-4-(2-pyrrolidin-1-ylethoxy)aniline (3)

Method A

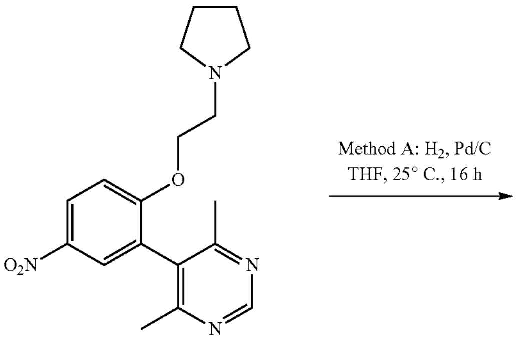

2

-continued

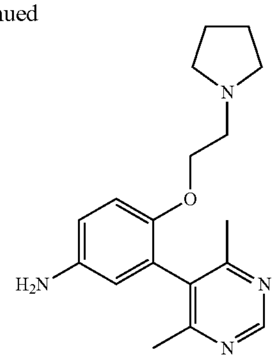

3

To a solution of 4,6-dimethyl-5-[5-nitro-2-(2-pyrrolidin-1-ylethoxy)phenyl]pyrimidine ((2), 1.6 g, 4.67 mmol, 1 eq.) in THF (20 mL) was added Pd/C (553.43 mg, 467.30 μmol, 10% purity, 0.1 eq.) under an $N_2$ atmosphere. The suspension was degassed and purged with $H_2$ three times. The mixture was stirred under $H_2$ (15 psi) at 25° C. for 16 hrs (monitored by LCMS). The reaction mixture was filtered and concentrated in vacuum to give a residue. The crude product was purified by reversed-phase HPLC (0.1% $NH_3 \cdot H_2O$). 3-(4,6-Dimethylpyrimidin-5-yl)-4-(2-pyrrolidin-1-ylethoxy)aniline ((3), 660 mg, 2.01 mmol, 42.95% yield, 95% purity) was obtained as a white solid.

LCMS (ESI): m/z [M+H] calcd for $C_{18}H_{25}N_4O$: 313.20; found: 313.2.

Method B

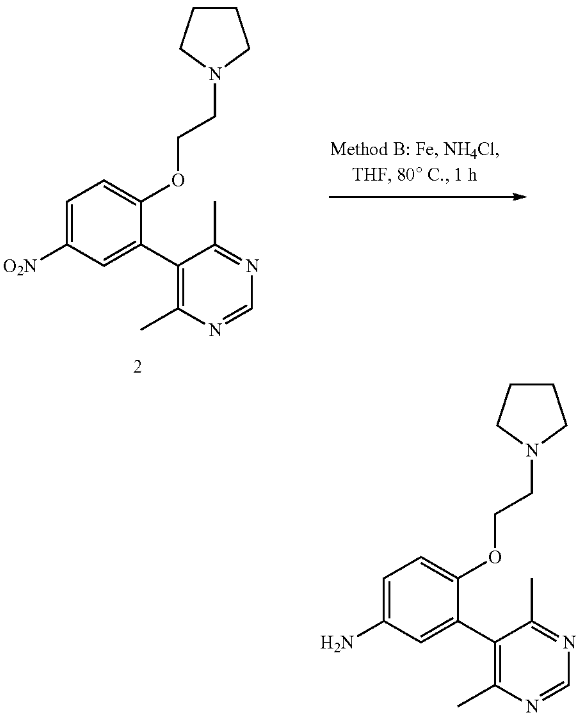

2

3

A mixture of 4,6-dimethyl-5-[5-nitro-2-(2-pyrrolidin-1-ylethoxy)phenyl]pyrimidine ((2), 400 mg, 1.17 mmol, 1 eq.), Fe (260.96 mg, 4.67 mmol, 4 eq.), and $NH_4Cl$ (499.93 mg, 9.35 mmol, 8 eq.) in EtOH (5 mL) and $H_2O$ (5 mL) was stirred at 80° C. for 1 hr (monitored by LCMS). The reaction mixture was filtered and the filtrate was concentrated in vacuum to give a residue. The residue was washed with a mixture of EtOAc:MeOH=10:1 (20 mL×2), and the filtrate was concentrated in vacuum to give the crude product. The crude product was purified by reversed-phase HPLC (0.1% $NH_3 \cdot H_2O$). 3-(4,6-Dimethylpyrimidin-5-yl)-4-(2-pyrrolidin-1-ylethoxy)aniline ((3), 360 mg, 1.12 mmol, 95.68% yield, 97% purity) was obtained as a white solid.

LCMS (ESI): m/z [M+H] calcd for $C_{18}H_{25}N_4O$: 313.20; found: 313.3.

Scaled-Up Synthesis:

To a solution of 4,6-dimethyl-5-[5-nitro-2-(2-pyrrolidin-1-ylethoxy)phenyl]pyrimidine ((2), 3 g, 8.76 mmol, 1 eq.) in THF (10 mL) was added Pd/C under an $N_2$ atmosphere. The suspension was degassed and purged with $H_2$ three times. The mixture was stirred under $H_2$ (15 psi) at 25° C. for 3 hrs. The mixture was filtered and then concentrated under vacuum to afford 3-(4,6-dimethylpyrimidin-5-yl)-4-(2-pyrrolidin-1-ylethoxy)aniline ((3), 2.6 g, 8.32 mmol, 94.98% yield) as a brown oil, which was used in the next step directly without further purification.

LCMS (ESI): m/z [M+H] calcd for $C_{18}H_{24}N_4O$: 312.20; found: 313.2.

$^1H$ NMR (400 MHZ, DMSO-$d_6$) δ=8.81 (s, 1H), 6.88 (d, J=8.3 Hz, 1H), 6.62 (dd, J=2.9, 8.8 Hz, 1H), 6.35 (d, J=2.9 Hz, 1H), 4.78 (br s, 2H), 3.86 (t, J=5.9 Hz, 2H), 2.51 (d, J=2.0 Hz, 2H), 2.26-2.20 (m, 4H), 2.17 (s, 6H), 1.54 (td, J=3.1, 6.6 Hz, 4H).

Preparation of N-(3-(4,6-dimethylpyrimidin-5-yl)-4-(2-(pyrrolidin-1-yl)ethoxy)phenyl)-1-methyl-1H-pyrrole-2-carboxamide (200)

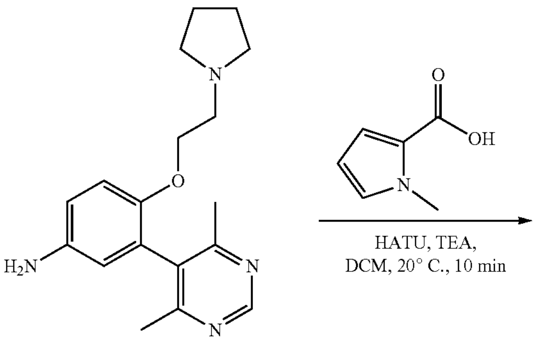

3

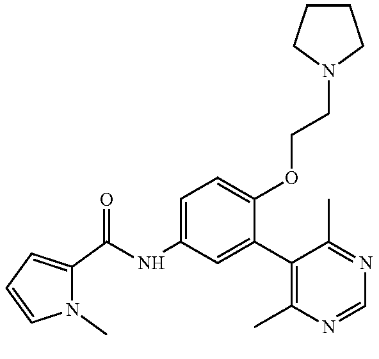

200

To a solution of 1-methylpyrrole-2-carboxylic acid (30.84 mg, 246.47, 1.1 eq.), HATU (93.72 mg, 246.47 μmol, 1.1 eq.) and TEA (45.35 mg, 448.13 μmol, 62.37 μL, 2 eq.) in DMF (1 mL) was added 3-(4,6-dimethylpyrimidin-5-yl)-4-(2-pyrrolidin-1-ylethoxy)aniline ((3), 70 mg, 224.07 μmol, 1 eq.). The mixture was stirred at 25° C. for 10 min (monitored by LC-MS). The reaction mixture was concentrated under reduced pressure to give a residue. The residue was purified by prep-HPLC (column: Phenomenex Gemini-NX C18 75*30 mm*3 μm; mobile phase: [water (0.1% TFA)-ACN]; B %: 20%-30%, 7 min). N-[3-(4,6-dimethylpyrimidin-5-yl)-4-(2-pyrrolidin-1-ylethoxy)phenyl]-1-methyl-pyrrole-2-carboxamide (48.64 mg, 91.16 μmol, 40.69% yield, 100% purity, TFA) was obtained as a yellow gum.

LCMS (ESI): m/z [M+H] calcd for $C_{24}H_{30}N_5O_2$: 420.24; found: 420.7.

$^1H$ NMR (400 MHZ, methanol-$d_4$) δ=8.96 (s, 1H), 7.77 (dd, J=2.6, 8.9 Hz, 1H), 7.52 (d, J=2.4 Hz, 1H), 7.24 (d, J=8.9 Hz, 1H), 6.98 (dd, J=1.3, 3.9 Hz, 1H), 6.91 (s, 1H), 6.13 (dd, J=2.8, 3.7 Hz, 1H), 4.41-4.31 (m, 2H), 3.94 (s, 3H), 3.59-3.51 (m, 2H), 3.42 (br s, 2H), 2.90 (br s, 2H), 2.37 (s, 6H), 2.08-1.86 (m, 4H).

N-(3-(4,6-dimethylpyrimidin-5-yl)-4-(2-(pyrrolidin-1-yl)ethoxy)phenyl)-1-methyl-1H-pyrrole-3-carboxamide (201)

201

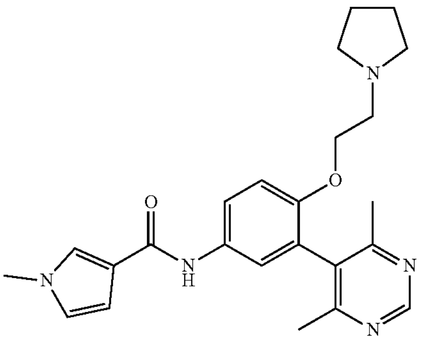

Compound 201 was prepared according to the synthesis described for compound 200, substituting 1-methyl-1H-pyrrole-3-carboxylic acid for 1-methylpyrrole-2-carboxylic acid.

LCMS (ESI): m/z [M+H] calcd for $C_{24}H_{30}N_5O_2$: 420.24; found: 420.7.

$^1H$ NMR (400 MHz, methanol-$d_4$) δ=8.84 (s, 1H), 7.71 (dd, J=2.6, 8.8 Hz, 1H), 7.45 (d, J=2.4 Hz, 1H), 7.37 (s, 1H), 7.14 (d, J=8.9 Hz, 1H), 6.71 (t, J=2.4 Hz, 1H), 6.66-6.61 (m, 1H), 4.13 (t, J=5.4 Hz, 2H), 3.71 (s, 3H), 2.76 (t, J=5.3 Hz, 2H), 2.42-2.34 (m, 4H), 2.29 (s, 6H), 1.70 (td, J=3.2, 6.5 Hz, 4H).

N-(3-(4,6-dimethylpyrimidin-5-yl)-4-(2-(pyrrolidin-1-yl)ethoxy)phenyl)-1-methyl-1H-pyrazole-5-carboxamide (202)

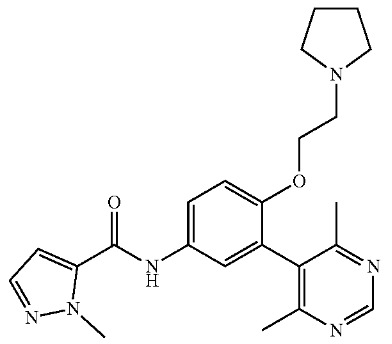

202

Compound 202 was prepared according to the synthesis described for compound 200, substituting 1-methyl-1H-pyrazole-5-carboxylic acid for 1-methylpyrrole-2-carboxylic acid.

LCMS (ESI): m/z [M+H] calcd for $C_{23}H_{29}N_6O_2$: 421.23; found: 421.7.

$^1$H NMR (400 MHZ, methanol-d$_4$) δ=8.85 (s, 1H), 7.74 (dd, J=2.6, 8.9 Hz, 1H), 7.50 (dd, J=2.3, 4.6 Hz, 2H), 7.18 (d, J=8.9 Hz, 1H), 6.95 (d, J=1.8 Hz, 1H), 4.17-4.12 (m, 5H), 2.75 (t, J=5.3 Hz, 2H), 2.37 (br s, 4H), 2.29 (s, 6H), 1.75-1.64 (m, 4H).

N-(3-(4,6-dimethylpyrimidin-5-yl)-4-(2-(pyrrolidin-1-yl)ethoxy)phenyl)-1-methyl-1H-pyrazole-3-carboxamide (203)

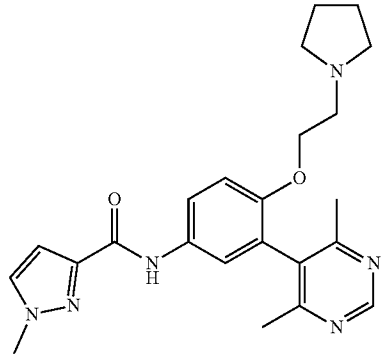

203

Compound 203 was prepared according to the synthesis described for compound 200, substituting 1-methyl-1H-pyrazole-3-carboxylic acid for 1-methylpyrrole-2-carboxylic acid.

LCMS (ESI): m/z [M+H] calcd for $C_{23}H_{29}N_6O_2$: 421.23; found: 421.8.

$^1$H NMR (400 MHZ, methanol-d$_4$) δ=8.85 (s, 1H), 7.78 (dd, J=2.6, 8.9 Hz, 1H), 7.67 (d, J=2.2 Hz, 1H), 7.54 (d, J=2.6 Hz, 1H), 7.17 (d, J=9.0 Hz, 1H), 6.80 (d, J=2.2 Hz, 1H), 4.14 (t, J=5.4 Hz, 2H), 3.98 (s, 3H), 2.75 (t, J=5.3 Hz, 2H), 2.43-2.33 (m, 4H), 2.29 (s, 6H), 1.69 (td, J=3.2, 6.5 Hz, 4H).

N-(3-(4,6-dimethylpyrimidin-5-yl)-4-(2-(pyrrolidin-1-yl)ethoxy)phenyl)-5-methylfuran-3-carboxamide (204)

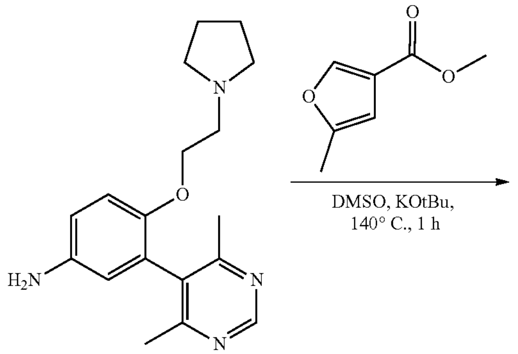

3

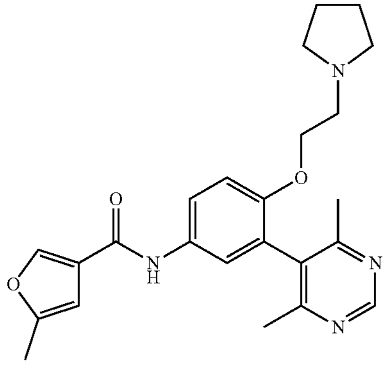

204

To a solution of methyl 5-methylfuran-3-carboxylate (31.40 mg, 224.07 μmol, 1 eq.) and KOtBu (50.29 mg, 448.14 μmol, 2 eq.) in DMSO (1 mL) was added 3-(4,6-dimethylpyrimidin-5-yl)-4-(2-pyrrolidin-1-ylethoxy)aniline ((3), 70 mg, 224.07 μmol, 1 eq.). The mixture was stirred at 140° C. for 1 hr (monitored by LC-MS). The reaction mixture was concentrated under reduced pressure to give a residue. The residue was purified by prep-HPLC (column: Xtimate C18 150*40 mm*10 um; mobile phase: [water (0.05% ammonia hydroxide v/v)-ACN]; B %: 23%-53%, 10 min). N-[3-(4,6-dimethylpyrimidin-5-yl)-4-(2-pyrrolidin-1-ylethoxy)phenyl]-5-methyl-furan-3-carboxamide (7.87 mg, 18.34 μmol, 8.19% yield, 98% purity) was obtained as a yellow gum.

LCMS (ESI): m/z [M+H] calcd for $C_{24}H_{29}N_4O_3$: 421.22; found: 421.3.

$^1$H NMR (400 MHZ, methanol-d$_4$) δ=8.87 (s, 1H), 8.04 (s, 1H), 7.74 (dd, J=2.6, 8.9 Hz, 1H), 7.48 (d, J=2.4 Hz, 1H), 7.18 (d, J=8.9 Hz, 1H), 6.52 (s, 1H), 4.17 (t, J=5.3 Hz, 2H), 2.83 (t, J=5.2 Hz, 2H), 2.45 (br s, 4H), 2.34 (s, 3H), 2.31 (s, 6H), 1.73 (br s, 4H).

N-(3-(4,6-dimethylpyrimidin-5-yl)-4-(2-(pyrrolidin-1-yl)ethoxy)phenyl)-3-ethyl-1H-pyrazole-5-carboxamide (205)

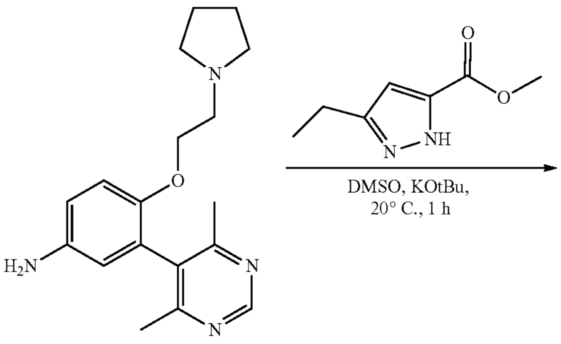

3

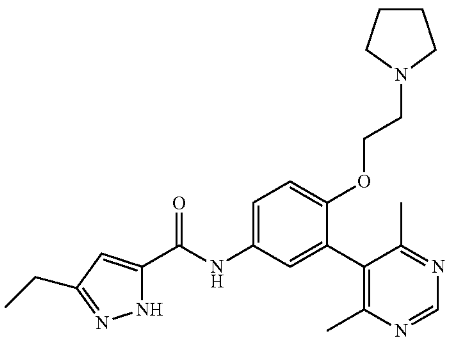

205

A mixture of 3-(4,6-dimethylpyrimidin-5-yl)-4-(2-pyrrolidin-1-ylethoxy)aniline ((3), 70 mg, 224.07 μmol, 1 eq.), methyl 3-ethyl-1H-pyrazole-5-carboxylate (51.81 mg, 336.10 μmol, 1.5 eq.), and KOtBu (50.29 mg, 448.13 μmol, 2 eq.) in DMSO (1 mL) was stirred at 140° C. for 1 hr. The reaction mixture was concentrated under reduced pressure to give a residue. The residue was purified by prep-HPLC (column: Waters Xbridge 150*25 mm*5 um; mobile phase: [water (0.05% ammonia hydroxide v/v)-ACN]; B %: 25%-55%, 10 min). N-[3-(4,6-dimethylpyrimidin-5-yl)-4-(2-pyrrolidin-1-ylethoxy)phenyl]-3-ethyl-1H-pyrazole-5-carboxamide (13.12 mg, 29.89 μmol, 13.34% yield, 99% purity) was obtained as a yellow solid.

LCMS (ESI): m/z [M+H] calcd for $C_{24}H_{31}N_6O_2$: 435.25; found: 435.5.

$^1$H NMR (400 MHZ, methanol-d$_4$) δ=8.84 (s, 1H), 7.78 (dd, J=2.6, 8.9 Hz, 1H), 7.54 (d, J=2.4 Hz, 1H), 7.16 (d, J=9.0 Hz, 1H), 6.62 (s, 1H), 4.13 (t, J=5.3 Hz, 2H), 2.80-2.66 (m, 4H), 2.40-2.33 (m, 4H), 2.29 (s, 6H), 1.69 (td, J=3.0, 6.4 Hz, 4H), 1.29 (t, J=7.6 Hz, 3H).

N-(3-(4,6-dimethylpyrimidin-5-yl)-4-(2-(pyrrolidin-1-yl)ethoxy)phenyl)-3-isopropyl-1H-pyrazole-5-carboxamide (206)

206

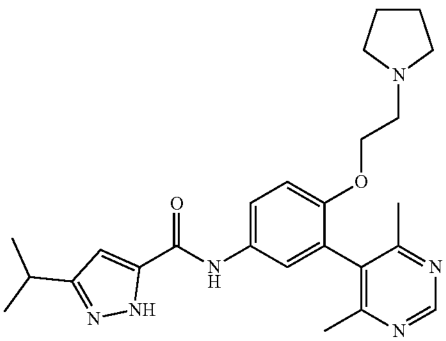

Compound 206 was prepared according to the synthesis described for compound 200, substituting 3-isopropyl-1H-pyrazole-5-carboxylic acid for 1-methylpyrrole-2-carboxylic acid.

LCMS (ESI): m/z [M+H] calcd for $C_{25}H_{33}N_6O_2$: 449.26; found: 449.8.

$^1$H NMR (400 MHZ, methanol-d$_4$) δ=8.87 (s, 1H), 7.80 (dd, J=2.6, 8.9 Hz, 1H), 7.56 (d, J=2.4 Hz, 1H), 7.19 (d, J=8.9 Hz, 1H), 6.63 (br s, 1H), 4.16 (t, J=5.3 Hz, 2H), 3.08 (td, J=6.9, 13.7 Hz, 1H), 2.77 (br t, J=5.0 Hz, 2H), 2.40 (br s, 4H), 2.32 (s, 6H), 1.71 (br s, 4H), 1.34 (d, J=7.0 Hz, 6H).

N-(3-(4,6-dimethylpyrimidin-5-yl)-4-(2-(pyrrolidin-1-yl)ethoxy)phenyl)-5-fluoronicotinamide (207)

207

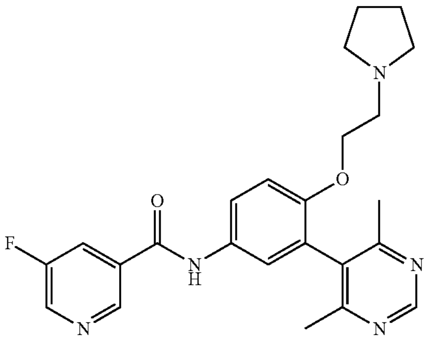

Compound 207 was prepared according to the synthesis described for compound 200, substituting 5-fluoronicotinic acid for 1-methylpyrrole-2-carboxylic acid.

LCMS (ESI): m/z [M+H] calcd for $C_{24}H_{27}FN_5O_2$: 436.21; found: 436.3.

$^1$H NMR (400 MHZ, methanol-d$_4$) δ=8.98 (s, 1H), 8.87 (s, 1H), 8.69 (d, J=2.7 Hz, 1H), 8.16 (td, J=2.1, 9.1 Hz, 1H), 7.81 (dd, J=2.6, 8.9 Hz, 1H), 7.57 (d, J=2.6 Hz, 1H), 7.22 (d, J=8.9 Hz, 1H), 4.18 (t, J=5.3 Hz, 2H), 2.79 (t, J=5.3 Hz, 2H), 2.44-2.38 (m, 4H), 2.32 (s, 6H), 1.72 (td, J=3.2, 6.5 Hz, 4H).

N-(3-(4,6-dimethylpyrimidin-5-yl)-4-(2-(pyrrolidin-1-yl)ethoxy)phenyl)-5-methoxynicotinamide (208)

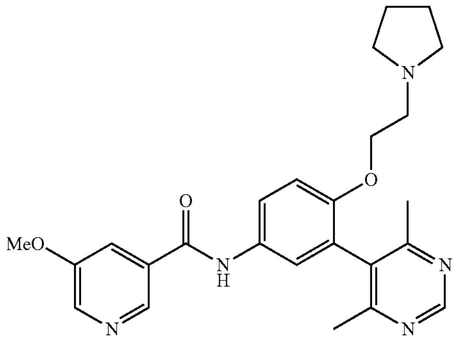

208

Compound 208 was prepared according to the synthesis described for compound 200, substituting 5-methoxynicotinic acid for 1-methylpyrrole-2-carboxylic acid.

LCMS (ESI): m/z [M+H] calcd for $C_{25}H_{30}N_5O_3$: 448.23; found: 448.7.

$^1$H NMR (400 MHZ, methanol-$d_4$) δ=8.87 (s, 1H), 8.72-8.67 (m, 1H), 8.42 (d, J=2.7 Hz, 1H), 7.95-7.88 (m, 1H), 7.81 (dd, J=2.6, 8.9 Hz, 1H), 7.56 (d, J=2.6 Hz, 1H), 7.21 (d, J=9.0 Hz, 1H), 4.17 (t, J=5.3 Hz, 2H), 3.97 (s, 3H), 2.78 (t, J=5.3 Hz, 2H), 2.42-2.36 (m, 4H), 2.31 (s, 6H), 1.74-1.68 (m, 4H).

N-(3-(4,6-dimethylpyrimidin-5-yl)-4-(2-(pyrrolidin-1-yl)ethoxy)phenyl)-4-fluoropicolinamide (209)

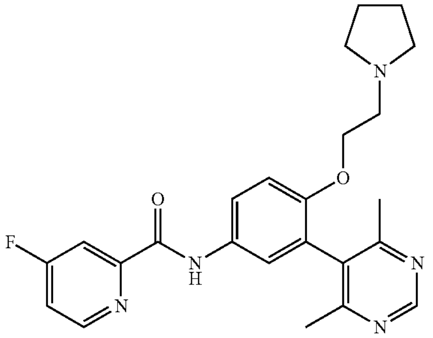

209

Compound 209 was prepared according to the synthesis described for compound 200, substituting 4-fluoropicolinic acid for 1-methylpyrrole-2-carboxylic acid.

LCMS (ESI): m/z [M+H] calcd for $C_{24}H_{27}FN_5O_2$: 436.21; found: 436.3.

$^1$H NMR (400 MHZ, methanol-$d_4$) δ=8.85 (s, 1H), 8.71 (dd, J=5.6, 8.0 Hz, 1H), 7.93 (dd, J=2.5, 9.5 Hz, 1H), 7.89 (dd, J=2.6, 8.9 Hz, 1H), 7.65 (d, J=2.7 Hz, 1H), 7.41 (ddd, J=2.6, 5.6, 8.3 Hz, 1H), 7.20 (d, J=9.0 Hz, 1H), 4.16 (t, J=5.4 Hz, 2H), 2.78 (t, J=5.4 Hz, 2H), 2.40 (br t, J=5.4 Hz, 4H), 2.30 (s, 6H), 1.70 (td, J=3.3, 6.8 Hz, 4H).

N-(3-(4,6-dimethylpyrimidin-5-yl)-4-(2-(pyrrolidin-1-yl)ethoxy)phenyl)-5-fluoropicolinamide (210)

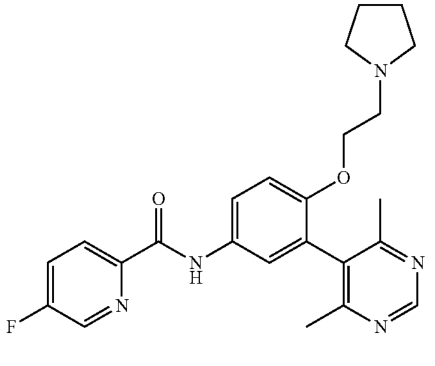

210

Compound 210 was prepared according to the synthesis described for compound 200, substituting 5-fluoropicolinic acid for 1-methylpyrrole-2-carboxylic acid.

LCMS (ESI): m/z [M+H] calcd for $C_{24}H_{27}FN_5O_2$: 436.21; found: 436.8.

$^1$H NMR (400 MHZ, methanol-$d_4$) δ=8.85 (s, 1H), 8.59 (d, J=2.7 Hz, 1H), 8.26 (dd, J=4.6, 8.7 Hz, 1H), 7.86 (dd, J=2.6, 8.9 Hz, 1H), 7.80 (dt, J=2.8, 8.5 Hz, 1H), 7.63 (d, J=2.6 Hz, 1H), 7.20 (d, J=9.0 Hz, 1H), 4.15 (t, J=5.3 Hz, 2H), 2.75 (t, J=5.3 Hz, 2H), 2.40-2.33 (m, 4H), 2.30 (s, 6H), 1.75-1.64 (m, 4H).

(1S,2R)—N-(3-(4,6-dimethylpyrimidin-5-yl)-4-(2-(pyrrolidin-1-yl)ethoxy)phenyl)-2-fluorocyclopropane-1-carboxamide (211)

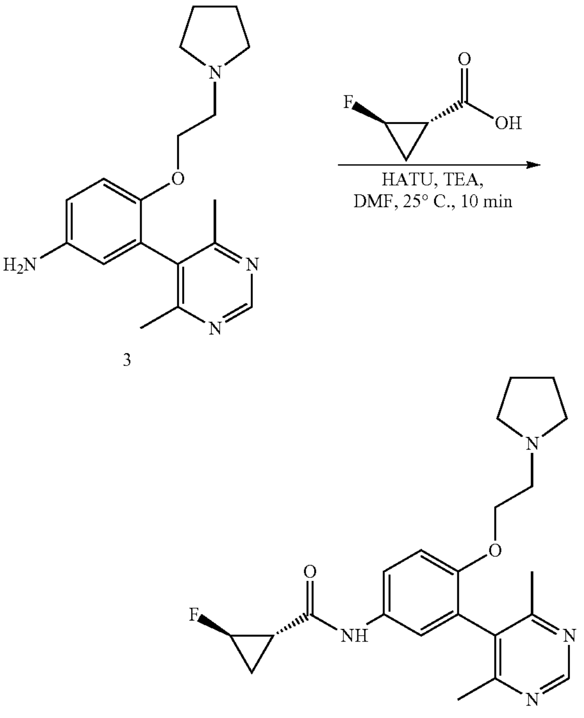

3

211

To a solution of (1S,2R)-2-fluorocyclopropanecarboxylic acid (31.98 mg, 307.29 μmol, 1.2 eq.), HATU (146.05 mg, 384.11 μmol, 1.5 eq.) and TEA (51.82 mg, 512.15 μmol, 71.29 μL, 2 eq.) in DMF (1 mL) was added 3-(4,6-dimethylpyrimidin-5-yl)-4-(2-pyrrolidin-1-ylethoxy)aniline ((3), 80 mg, 256.08 μmol, 1 eq.). The mixture was stirred at 25° C. for 10 min (monitored by LC-MS). The reaction mixture was concentrated under reduced pressure to give a residue. The residue was purified by prep-HPLC (column: Xtimate C18 150*40 mm*10 um; mobile phase: [water (0.05% ammonia hydroxide v/v)-ACN]; B %: 20%-50%, 10 min). (1S,2R)—N-[3-(4,6-dimethylpyrimidin-5-yl)-4-(2-pyrrolidin-1-ylethoxy)phenyl]-2-fluoro-cyclopropanecarboxamide (30.36 mg, 76.19 μmol, 29.75% yield, 100% purity) was obtained as a brown solid.

LCMS (ESI): m/z [M+H] calcd for $C_{22}H_{28}FN_4O_2$: 399.21; found: 399.3.

$^1$H NMR (400 MHz, methanol-d$_4$) δ=8.84 (s, 1H), 7.59 (dd, J=2.8, 8.9 Hz, 1H), 7.38 (d, J=2.4 Hz, 1H), 7.13 (d, J=8.8 Hz, 1H), 4.73-4.72 (m, 1H), 4.11 (t, J=5.4 Hz, 2H), 2.73 (t, J=5.4 Hz, 2H), 2.39-2.31 (m, 4H), 2.27 (s, 6H), 2.26-2.23 (m, 1H), 1.69-1.66 (m, 4H), 1.-35-1.28 (m, 2H).

(1R,2R)—N-(3-(4,6-dimethylpyrimidin-5-yl)-4-(2-(pyrrolidin-1-yl)ethoxy)phenyl)-2-fluorocyclopropane-1-carboxamide (212)

212

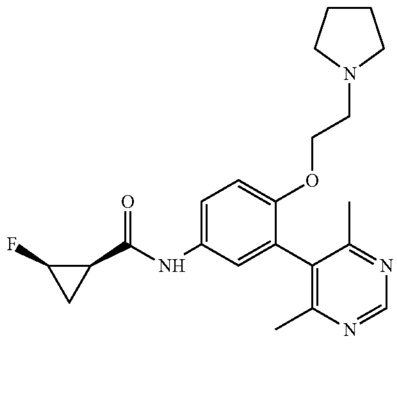

Compound 212 was prepared according to the synthesis described for compound 211, substituting (1R,2R)-2-fluorocyclopropane-1-carboxylic acid for (1S,2R)-2-fluorocyclopropanecarboxylic acid.

LCMS (ESI): m/z [M+H] calcd for $C_{22}H_{28}FN_4O_2$: 399.21; found: 399.3.

$^1$H NMR (400 MHZ, methanol-d$_4$) δ=8.84 (s, 1H), 7.61 (dd, J=2.7, 8.9 Hz, 1H), 7.41 (d, J=2.7 Hz, 1H), 7.13 (d, J=9.0 Hz, 1H), 4.93-4.91 (m, 1H), 4.11 (t, J=5.4 Hz, 2H), 2.73 (t, J=5.4 Hz, 2H), 2.39-2.31 (m, 4H), 2.27 (s, 6H), 1.96 (dtd, J=5.0, 6.9, 9.2 Hz, 1H), 1.79-1.63 (m, 5H), 1.15 (tdd, J=6.4, 9.1, 12.4 Hz, 1H).

(1S,2S)—N-(3-(4,6-dimethylpyrimidin-5-yl)-4-(2-(pyrrolidin-1-yl)ethoxy)phenyl)-2-fluorocyclopropane-1-carboxamide (213)

213

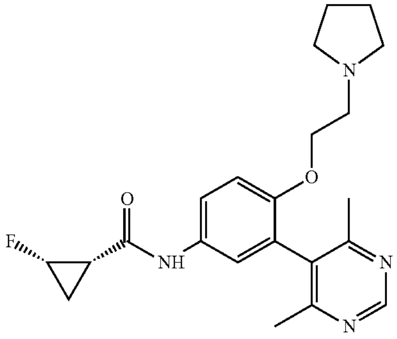

Compound 213 was prepared according to the synthesis described for compound 211, substituting (1S,2S)-2-fluorocyclopropane-1-carboxylic acid for (1S,2R)-2-fluorocyclopropanecarboxylic acid.

LCMS (ESI): m/z [M+H] calcd for $C_{22}H_{28}FN_4O_2$: 399.21; found: 399.3.

$^1$H NMR (400 MHZ, methanol-d$_4$) δ=8.86 (s, 1H), 7.63 (dd, J=2.7, 8.9 Hz, 1H), 7.43 (d, J=2.7 Hz, 1H), 7.15 (d, J=9.0 Hz, 1H), 4.95-4.93 (m, 1H), 4.13 (t, J=5.4 Hz, 2H), 2.75 (t, J=5.4 Hz, 2H), 2.41-2.33 (m, 4H), 2.29 (s, 6H), 1.98 (dtd, J=4.9, 6.9, 9.1 Hz, 1H), 1.81-1.64 (m, 5H), 1.24-1.09 (m, 1H)

N-(3-(4,6-dimethylpyrimidin-5-yl)-4-(2-(pyrrolidin-1-yl)ethoxy)phenyl)-4-methylthiazole-5-carboxamide (214)

214

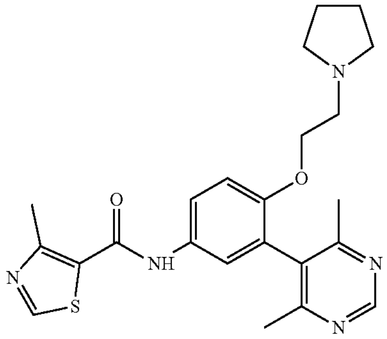

Compound 214 was prepared according to the synthesis described for compound 211, substituting 4-methylthiazole-5-carboxylic for (1S,2R)-2-acid fluorocyclopropanecarboxylic acid.

LCMS (ESI): m/z [M+H] calcd for $C_{23}H_{28}N_5O_2S$: 438.19; found: 438.2.

$^1$H NMR (400 MHZ, methanol-d$_4$) δ=9.01 (s, 1H), 8.85 (s, 1H), 7.71 (dd, J=2.6, 8.9 Hz, 1H), 7.46 (d, J=2.4 Hz, 1H), 7.19 (d, J=9.0 Hz, 1H), 4.18 (t, J=5.3 Hz, 2H), 2.87 (t, J=5.3 Hz, 2H), 2.69 (s, 3H), 2.53-2.44 (m, 4H), 2.31-2.28 (m, 6H), 1.73 (td, J=3.4, 6.8 Hz, 4H).

N-(3-(4,6-dimethylpyrimidin-5-yl)-4-(2-(pyrrolidin-1-yl)ethoxy)phenyl)-2,4-dimethylthiazole-5-carboxamide (215)

215

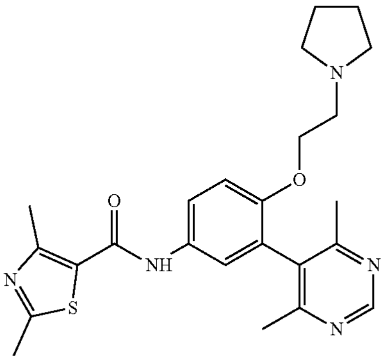

Compound 215 was prepared according to the synthesis described for compound 211, substituting 2,4-dimethylthiazole-5-carboxylic acid for (1S,2R)-2-fluorocyclopropanecarboxylic acid.

LCMS (ESI): m/z [M+H] calcd for $C_{24}H_{30}N_5O_2S$: 452.21; found: 452.3.

$^{1}$H NMR (400 MHZ, methanol-$d_4$) δ=8.84 (s, 1H), 7.67 (dd, J=2.6, 8.9 Hz, 1H), 7.43 (d, J=2.4 Hz, 1H), 7.17 (d, J=9.0 Hz, 1H), 4.14 (t, J=5.4 Hz, 2H), 2.74 (t, J=5.4 Hz, 2H), 2.69 (s, 3H), 2.60 (s, 3H), 2.41-2.32 (m, 4H), 2.29 (s, 6H), 1.69 (td, J=3.3, 6.8 Hz, 4H).

N-(3-(4,6-dimethylpyrimidin-5-yl)-4-(2-(pyrrolidin-1-yl)ethoxy)phenyl)-4-methylisoxazole-5-carboxamide (216)

216

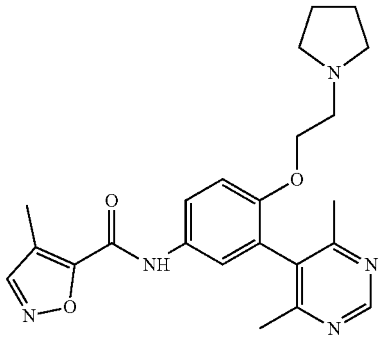

Compound 216 was prepared according to the synthesis described for compound 211, substituting 4-methylisoxazole-5-carboxylic acid for (1S,2R)-2-fluorocyclopropanecarboxylic acid.

LCMS (ESI): m/z [M+H] calcd for $C_{23}H_{28}N_5O_3$: 422.21; found: 422.2.

$^{1}$H NMR (400 MHZ, DMSO-$d_6$) δ=10.71 (s, 1H), 8.90 (s, 1H), 8.71 (s, 1H), 7.84 (dd, J=2.6, 8.7 Hz, 1H), 7.62 (d, J=2.6 Hz, 1H), 7.25 (d, J=8.9 Hz, 1H), 4.27 (br s, 2H), 3.45 (br s, 2H), 3.27-3.15 (m, 2H), 2.81-2.69 (m, 2H), 2.27 (s, 3H), 2.20 (s, 6H), 1.91-1.78 (m, 2H), 1.77-1.62 (m, 2H).

N-(3-(4,6-dimethylpyrimidin-5-yl)-4-(2-(pyrrolidin-1-yl)ethoxy)phenyl)-4-methyloxazole-5-carboxamide (217)

217

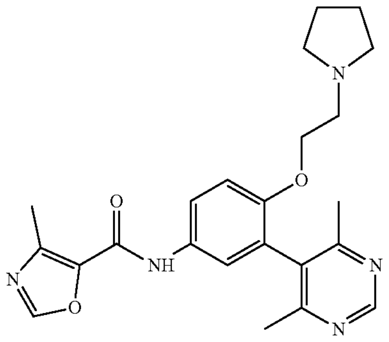

Compound 217 was prepared according to the synthesis described for compound substituting acid for (1S,2R)-2-211, 4-methyloxazole-5-carboxylic fluorocyclopropanecarboxylic acid.

LCMS (ESI): m/z [M+H] calcd for $C_{23}H_{28}N_5O_3$: 422.21; found: 422.3.

$^{1}$H NMR (400 MHZ, methanol-$d_4$) δ=8.85 (s, 1H), 8.24 (s, 1H), 7.75 (dd, J=2.7, 8.9 Hz, 1H), 7.50 (d, J=2.7 Hz, 1H), 7.18 (d, J=8.9 Hz, 1H), 4.14 (t, J=5.4 Hz, 2H), 2.75 (t, J=5.4 Hz, 2H), 2.50 (s, 3H), 2.40-2.33 (m, 4H), 2.29 (s, 6H), 1.69 (td, J=3.3, 6.8 Hz, 4H).

N-(3-(4,6-dimethylpyrimidin-5-yl)-4-(2-(pyrrolidin-1-yl)ethoxy)phenyl)isoxazole-4-carboxamide (218)

218

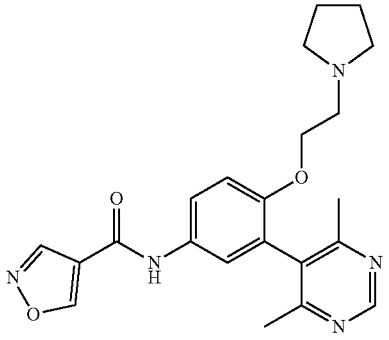

Compound 218 was prepared according to the synthesis described for compound 211, substituting isoxazole-4-carboxylic acid for (1S,2R)-2-fluorocyclopropanecarboxylic acid.

LCMS (ESI): m/z [M+H] calcd for $C_{22}H_{26}N_5O_3$: 408.20; found: 408.2.

$^{1}$H NMR (400 MHZ, DMSO-$d_6$) δ=10.33 (s, 1H), 9.94-9.74 (m, 1H), 9.56 (s, 1H), 9.07 (s, 1H), 8.90 (s, 1H), 7.77 (dd, J=2.6, 9.0 Hz, 1H), 7.49 (d, J=2.6 Hz, 1H), 7.26 (d, J=9.0 Hz, 1H), 4.27 (t, J=5.0 Hz, 2H), 3.48-3.40 (m, 2H), 3.21 (br d, J=5.1 Hz, 2H), 2.80-2.68 (m, 2H), 2.20 (s, 6H), 1.93-1.78 (m, 2H), 1.78-1.63 (m, 2H).

N-(3-(4,6-dimethylpyrimidin-5-yl)-4-)(2-(pyrrolidin-1-yl)ethoxy)phenyl)-3-methylisoxazole-4-carboxamide (219)

219

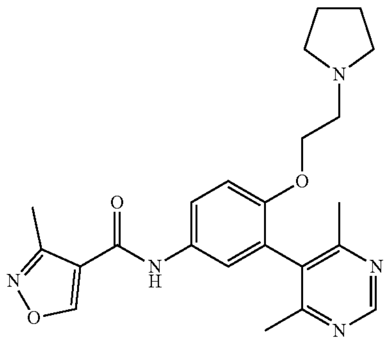

Compound 219 was prepared according to the synthesis described for compound 211, substituting 3-methylisoxazole-4-carboxylic acid for (1S,2R)-2-fluorocyclopropanecarboxylic acid.

LCMS (ESI): m/z [M+H] calcd for $C_{23}H_{28}N_5O_3$: 422.21; found: 422.0.

$^1$H NMR (400 MHZ, methanol-$d_4$) δ=9.15 (s, 1H), 8.86 (s, 1H), 7.71 (dd, J=2.7, 8.9 Hz, 1H), 7.47 (d, J=2.6 Hz, 1H), 7.19 (d, J=8.9 Hz, 1H), 4.18 (t, J=5.3 Hz, 2H), 2.91 (br t, J=5.1 Hz, 2H), 2.53 (br s, 4H), 2.48 (s, 3H), 2.29 (s, 6H), 1.75 (td, J=3.4, 6.8 Hz, 4H).

N-(3-(4,6-dimethylpyrimidin-5-yl)-4-(2-(pyrrolidin-1-yl)ethoxy)phenyl)-5-methylisoxazole-4-carboxamide (220)

220

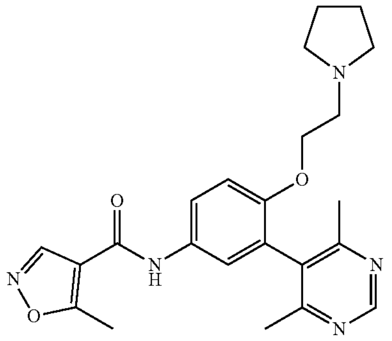

Compound 220 was prepared according to the synthesis described for compound 211, substituting 5-methylisoxazole-4-carboxylic acid for (1S,2R)-2-fluorocyclopropanecarboxylic acid.

LCMS (ESI): m/z [M+H] calcd for $C_{23}H_{28}N_5O_3$: 422.21; found: 422.3.

$^1$H NMR (400 MHZ, DMSO-$d_6$) δ=10.09 (br s, 1H), 9.98-9.38 (m, 1H), 9.05 (s, 1H), 8.90 (s, 1H), 7.75 (dd, J=2.6, 8.9 Hz, 1H), 7.51 (d, J=2.1 Hz, 1H), 7.25 (d, J=8.9 Hz, 1H), 4.33-4.20 (m, 2H), 3.46-3.45 (m, 2H), 3.26-3.17 (m, 2H), 2.79-2.69 (m, 2H), 2.67 (s, 3H), 2.20 (s, 6H), 1.91-1.78 (m, 2H), 1.77-1.62 (m, 2H).

N-(3-(4,6-dimethylpyrimidin-5-yl)-4-(2-(pyrrolidin-1-yl)ethoxy)phenyl)-5-methyloxazole-4-carboxamide (221)

221

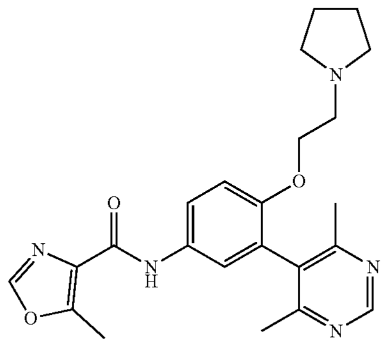

Compound 221 was prepared according to the synthesis described for compound 211, substituting 5-methyloxazole-4-carboxylic acid for (1S,2R)-2-fluorocyclopropanecarboxylic acid.

LCMS (ESI): m/z [M+H] calcd for $C_{23}H_{28}N_5O_3$: 422.21; found: 422.8.

$^1$H NMR (400 MHZ, methanol-$d_4$) δ=8.84 (s, 1H), 8.06 (s, 1H), 7.76 (dd, J=2.6, 8.9 Hz, 1H), 7.56-7.52 (m, 1H), 7.17 (d, J=8.9 Hz, 1H), 4.14 (t, J=5.3 Hz, 2H), 2.75 (t, J=5.3 Hz, 2H), 2.67-2.63 (m, 3H), 2.37 (br s, 4H), 2.29 (s, 6H), 1.69 (br s, 4H).

N-(3-(4,6-dimethylpyrimidin-5-yl)-4-(2-(pyrrolidin-1-yl)ethoxy)phenyl)isothiazole-4-carboxamide (222)

222

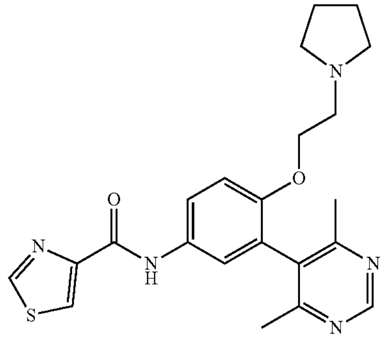

Compound 222 was prepared according to the synthesis described for compound 211, substituting isothiazole-4-carboxylic acid for (1S,2R)-2-fluorocyclopropanecarboxylic acid.

LCMS (ESI): m/z [M+H] calcd for $C_{22}H_{26}N_5O_2S$: 424.18; found: 424.7.

$^1$H NMR (400 MHZ, methanol-$d_4$) δ=9.55 (s, 1H), 8.97 (s, 1H), 8.86 (s, 1H), 7.79 (dd, J=2.6, 8.9 Hz, 1H), 7.53 (d, J=2.7 Hz, 1H), 7.20 (d, J=9.0 Hz, 1H), 4.19 (t, J=5.3 Hz, 2H), 2.91 (t, J=5.2 Hz, 2H), 2.53 (br s, 4H), 2.30 (s, 6H), 1.75 (td, J=3.4, 6.8 Hz, 4H).

N-(3-(4,6-dimethylpyrimidin-5-yl)-4-(2-(pyrrolidin-1-yl)ethoxy)phenyl)-3-methylisothiazole-4-carboxamide (223)

223

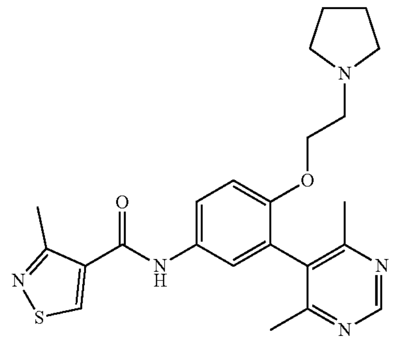

Compound 223 was prepared according to the synthesis described for compound 211, substituting 3-methylisothiazole-4-carboxylic acid for (1S,2R)-2-fluorocyclopropanecarboxylic acid.

LCMS (ESI): m/z [M+H] calcd for $C_{23}H_{28}N_5O_2S$: 438.19; found: 438.8.

$^1$H NMR (400 MHz, methanol-$d_4$) δ=9.36 (s, 1H), 8.86 (s, 1H), 7.76 (dd, J=2.5, 8.9 Hz, 1H), 7.50 (d, J=2.4 Hz, 1H), 7.20 (d, J=9.0 Hz, 1H), 4.20 (t, J=5.3 Hz, 2H), 2.95 (br t, J=5.1 Hz, 2H), 2.65 (s, 3H), 2.56 (br s, 4H), 2.30 (s, 6H), 1.76 (td, J=3.4, 6.7 Hz, 4H).

N-(3-(4,6-dimethylpyrimidin-5-yl)-4-(2-(pyrrolidin-1-yl)ethoxy)phenyl)-5-methylthiazole-4-carboxamide (224)

224

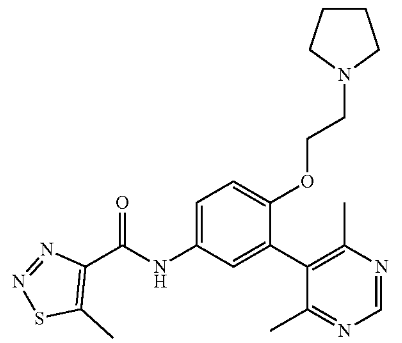

Compound 224 was prepared according to the synthesis described for compound 211, substituting 5-methylthiazole-4-carboxylic acid for (1S,2R)-2-fluorocyclopropanecarboxylic acid.

LCMS (ESI): m/z [M+H] calcd for $C_{23}H_{28}N_5O_2S$: 438.19; found: 438.8.

$^1$H NMR (400 MHZ, methanol-$d_4$) δ=8.85 (s, 1H), 8.77 (s, 1H), 7.78 (dd, J=2.7, 8.9 Hz, 1H), 7.56 (d, J=2.7 Hz, 1H), 7.18 (d, J=8.9 Hz, 1H), 4.15 (t, J=5.4 Hz, 2H), 2.84 (s, 3H), 2.79-2.73 (m, 2H), 2.39 (br s, 4H), 2.30 (s, 6H), 1.70 (td, J=3.3, 6.7 Hz, 4H).

N-(3-(4,6-dimethylpyrimidin-5-yl)-4-(2-(pyrrolidin-1-yl)ethoxy)phenyl)-2-(5-methylthiazol-4-yl)acetamide (225)

Preparation of 5-methylthiazole-4-carbonyl chloride (4)

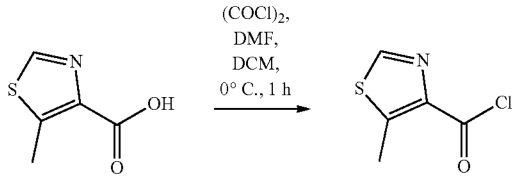

4

To a mixture of 5-methylthiazole-4-carboxylic acid (1 g, 6.98 mmol, 1 eq.) in DCM (10 mL) was added $(COCl)_2$ (975.24 mg, 7.68 mmol, 672.58 μL, 1.1 eq.) and DMF (0.05 mL) at 0° C. under $N_2$. The mixture was stirred at 0° C. for 1 h. The mixture was concentrated under reduced pressure. 5-methylthiazole-4-carbonyl chloride ((4), 1.13 g, crude) was obtained as a yellow oil.

Preparation of 2-(5-methylthiazol-4-yl)acetic acid (5)

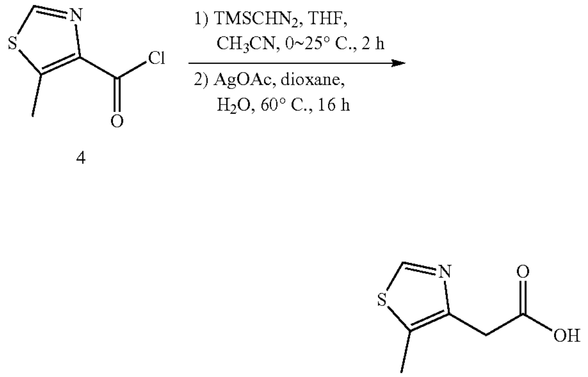

4

5

To a mixture of 5-methylthiazole-4-carbonyl chloride ((4), 1.13 g, 6.99 mmol, 1 eq.) in THF (8 mL) and $CH_3CN$ (8 mL) was added $TMSCHN_2$ (2 M, 6.99 mL, 2 eq.) at 0° C. under $N_2$. The mixture was stirred at 25° C. for 2 h. Then the reaction mixture was concentrated under reduced pressure. The residue was diluted with dioxane (8 mL) and $H_2O$ (8 mL), AgOAc (350.12 mg, 2.10 mmol, 107.40 μL, 0.3 eq.) was added and the mixture was stirred at 60° C. for 16 h. The mixture was filtered and concentrated in vacuum. The crude product was purified by reversed-phase HPLC (0.1% TFA condition). 2-(5-methylthiazol-4-yl)acetic acid ((5), 320 mg, 1.63 mmol, 23.29% yield, 80% purity) was obtained as a yellow solid.

$^1$H NMR (400 MHZ, methanol-$d_4$) δ=8.72 (s, 1H), 3.77 (s, 2H), 2.44 (s, 3H).

Preparation of N-(3-(4,6-dimethylpyrimidin-5-yl)-4-(2-(pyrrolidin-1-yl)ethoxy)phenyl)-2-(5-methylthiazol-4-yl)acetamide (225)

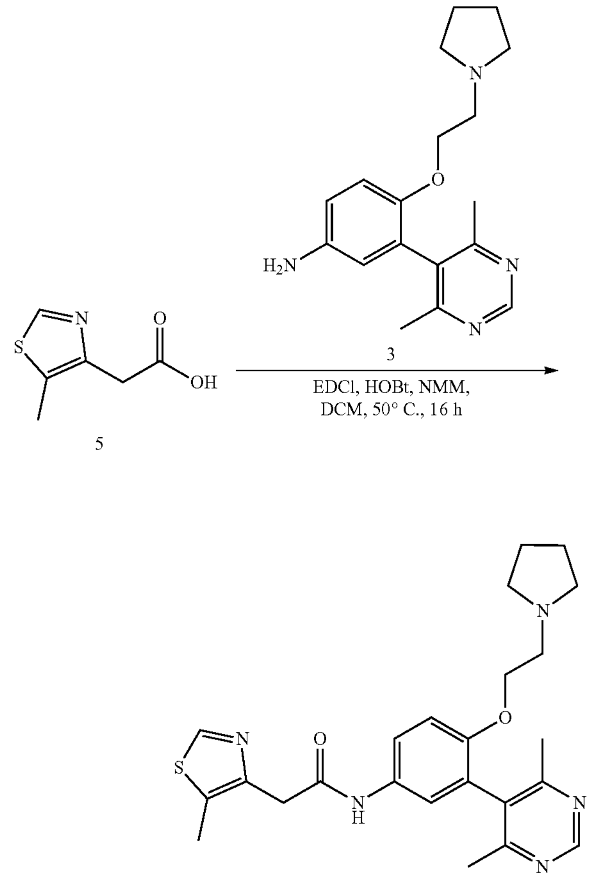

225

To a mixture of 2-(5-methylthiazol-4-yl)acetic acid ((5), 75.47 mg, 480.14 μmol, 1.5 eq.) and HATU (182.56 mg, 480.14 μmol, 1.5 eq.) in DMF (2 mL) was added TEA (64.78 mg, 640.19 μmol, 89.11 μL, 2 eq.). The mixture was stirred at 25° C. for 30 min, then 3-(4,6-dimethylpyrimidin-5-yl)-4-(2-pyrrolidin-1-ylethoxy)aniline ((3), 100 mg, 320.09 μmol, 1 eq.) was added and the mixture was stirred at 50° C. for 16 hours. The mixture was concentrated under reduced pressure. The residue was purified by prep-HPLC (column: Phenomenex Gemini-NX C18 75*30 mm*3 um; mobile phase: [water (0.1% TFA)-ACN]; B %: 15%-25%, 7 min). N-[3-(4,6-dimethylpyrimidin-5-yl)-4-(2-pyrrolidin-1-ylethoxy)phenyl]-2-(5-methylthiazol-4-yl)acetamide (17.41 mg, 30.17 μmol, 9.42% yield, 98% purity, TFA) was obtained as a yellow gum.

LCMS (ESI): m/z [M+H] calcd for $C_{24}H_{30}N_5O_2S$: 452.20; found: 452.2.

$^1$H NMR (400 MHZ, methanol-$d_4$) δ=8.90 (s, 1H), 8.82 (s, 1H), 7.68 (dd, J=2.6, 8.9 Hz, 1H), 7.47 (d, J=2.5 Hz, 1H), 7.20 (d, J=9.0 Hz, 1H), 4.36-4.29 (m, 2H), 3.87 (s, 2H), 3.53-3.48 (m, 2H), 3.43-3.33 (m, 2H), 2.91-2.81 (m, 2H), 2.50 (s, 3H), 2.29 (s, 6H), 2.02 (br d, J=10.0 Hz, 2H), 1.88 (br s, 2H).

N-(3-(4,6-dimethylpyrimidin-5-yl)-4-(2-(pyrrolidin-1-yl)ethoxy)phenyl)-2-(4-methyloxazol-5-yl)acetamide (226)

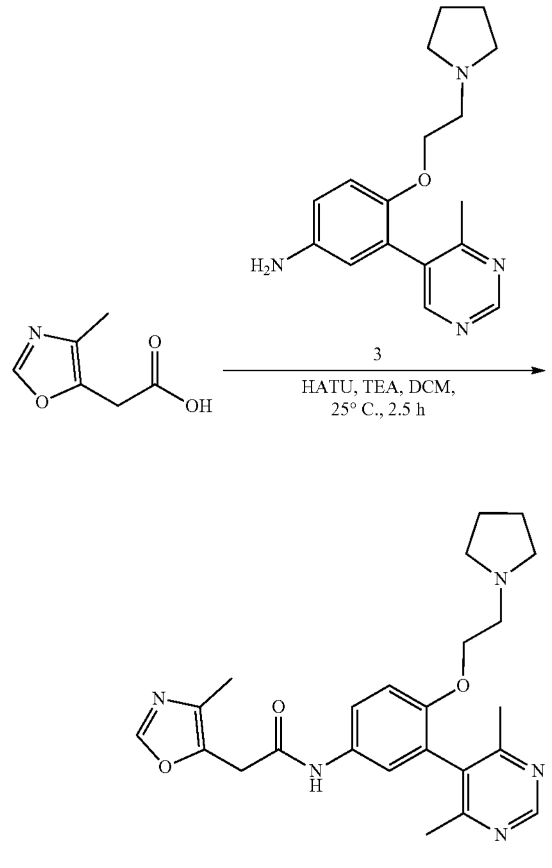

226

To a solution of 2-(4-methyloxazol-5-yl)acetic acid (49.69 mg, 352.10 μmol, 1.1 eq.) in DCM (2 mL) was added HATU (146.05 mg, 384.11 μmol, 1.2 eq.) and TEA (97.17 mg, 960.28 μmol, 133.66 μL, 3 eq.) stirred at 25° C. for 0.5 h, then 3-(4,6-dimethylpyrimidin-5-yl)-4-(2-pyrrolidin-1-ylethoxy)aniline ((3), 100 mg, 320.09 μmol, 1 eq.) was added. The mixture was stirred at 25° C. for 2 h. The reaction mixture was adjusted by trifluoroacetic acid to pH 5, concentrated under reduced pressure to give a residue. The residue was purified by prep-HPLC (column: Phenomenex Luna C18 150*25 mm*10 um; mobile phase: [water (0.1% TFA)-ACN]; B %: 8%-28%, 10 min). N-[3-(4,6-dimethylpyrimidin-5-yl)-4-(2-pyrrolidin-1-ylethoxy)phenyl]-2-(4-methyloxazol-5-yl)acetamide (15.18 mg, 26.31 μmol, 8.22% yield, 95.263% purity, TFA) was obtained as a brown gum.

LCMS (ESI): m/z [M+H] calcd for $C_{24}H_{30}N_5O_3$: 436.23; found: 436.3.

$^1$H NMR (400 MHZ, methanol-$d_4$) δ=8.93 (s, 1H), 8.07 (s, 1H), 7.68 (dd, J=2.6, 9.0 Hz, 1H), 7.46 (d, J=2.5 Hz, 1H), 7.21 (d, J=9.0 Hz, 1H), 4.38-4.28 (m, 2H), 3.81 (s, 2H), 3.54-3.48 (m, 2H), 3.37 (br d, J=5.5 Hz, 2H), 2.87 (br d, J=4.5 Hz, 2H), 2.31 (s, 6H), 2.17 (s, 3H), 2.02 (br dd, J=3.7, 5.1 Hz, 2H), 1.94-1.83 (m, 2H).

N-(3-(4,6-dimethylpyrimidin-5-yl)-4-(2-(pyrrolidin-1-yl)ethoxy)phenyl)-2-(1-methyl-1H-pyrazol-5-yl) acetamide (227)

227

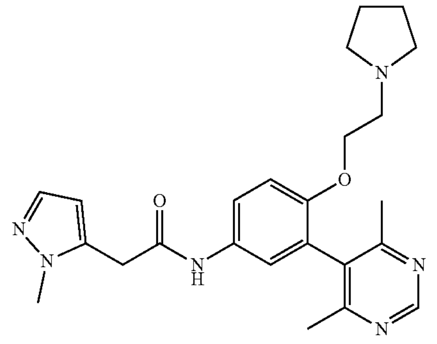

Compound 227 was prepared according to the synthesis described for compound 225, substituting 2-(1-methyl-1H-pyrazol-5-yl)acetic acid for 2-(5-methylthiazol-4-yl)acetic acid.

LCMS (ESI): m/z [M+H] calcd for $C_{24}H_{30}N_6O_2$: 435.24; found: 435.3.

$^1$H NMR (400 MHZ, methanol-$d_4$) δ=8.89 (s, 1H), 7.69 (dd, J=2.6, 8.8 Hz, 1H), 7.42 (dd, J=2.3, 12.4 Hz, 2H), 7.20 (d, J=8.9 Hz, 1H), 6.24 (d, J=2.0 Hz, 1H), 4.36-4.28 (m, 2H), 3.87 (s, 3H), 3.84 (s, 2H), 3.54-3.48 (m, 2H), 3.40-3.33 (m, 2H), 2.91-2.81 (m, 2H), 2.29 (s, 6H), 2.03 (br d, J=6.4 Hz, 2H), 1.87 (br d, J=6.4 Hz, 2H).

N-(3-(4,6-dimethylpyrimidin-5-yl)-4-(2-(pyrrolidin-1-yl)ethoxy)phenyl)-2-(tetrahydrofuran-3-yl)acetamide (228)

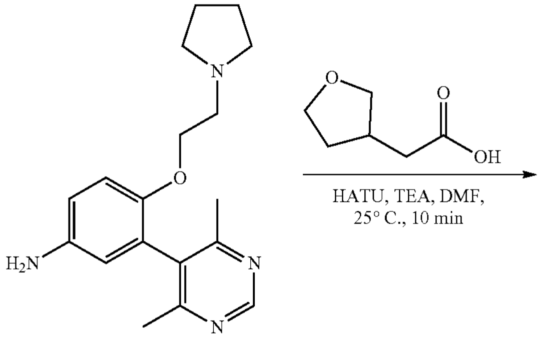

3

-continued

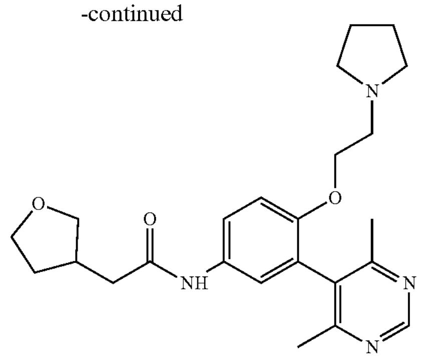

228

To a mixture of 2-tetrahydrofuran-3-ylacetic acid (87.06 mg, 669.00 μmol, 1.1 eq.), HATU (277.50 mg, 729.81 μmol, 1.2 eq.) and TEA (123.08 mg, 1.22 mmol, 169.30 μL, 2 eq.) in DMF (2 mL) was added 3-(4,6-dimethylpyrimidin-5-yl)-4-(2-pyrrolidin-1-ylethoxy)aniline ((3), 200 mg, 608.18 μmol, 1 eq.). The mixture was stirred at 25° C. for 10 min (monitored by LC-MS). The reaction mixture was concentrated under reduced pressure to give a residue. The residue was purified by prep-HPLC (column: Waters Xbridge C18 150*50 mm*10 μm; mobile phase: [water (10 mM $NH_4HCO_3$)-ACN]; B %: 10%-40%, 11.5 min). N-[3-(4,6-dimethylpyrimidin-5-yl)-4-(2-pyrrolidin-1-ylethoxy)phenyl]-2-tetrahydrofuran-3-yl-acetamide (145.98 mg, 336.98 μmol, 55.41% yield, 98% purity) was obtained as a yellow gum.

LCMS (ESI): m/z [M+H] calcd for $C_{24}H_{33}N_4O_3$: 425.25; found: 425.1.

$^1$H NMR (400 MHZ, methanol-$d_4$) δ=8.84 (s, 1H), 7.61 (dd, J=2.7, 8.9 Hz, 1H), 7.39 (d, J=2.6 Hz, 1H), 7.13 (d, J=8.9 Hz, 1H), 4.14 (t, J=5.3 Hz, 2H), 3.94 (dd, J=7.1, 8.4 Hz, 1H), 3.88 (dt, J=5.3, 8.2 Hz, 1H), 3.77 (q, J=7.7 Hz, 1H), 3.47 (dd, J=6.5, 8.4 Hz, 1H), 2.82 (t, J=5.3 Hz, 2H), 2.78-2.60 (m, 1H), 2.51-2.40 (m, 6H), 2.27 (s, 6H), 2.22-2.08 (m, 1H), 1.75-1.69 (m, 4H), 1.69-1.62 (m, 1H).

N-(3-(4,6-dimethylpyrimidin-5-yl)-4-(2-(pyrrolidin-1-yl)ethoxy)phenyl)-2-(tetrahydrofuran-2-yl)acetamide (229)

229

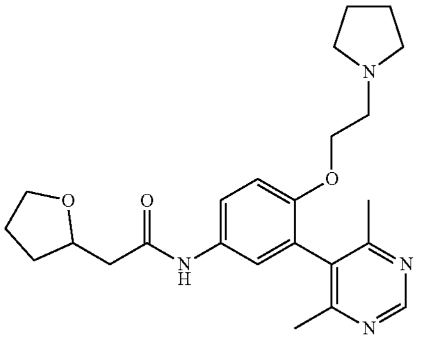

Compound 229 was prepared according to the synthesis described for compound 228, substituting 2-tetrahydrofuran-2-ylacetic acid for 2-tetrahydrofuran-3-ylacetic acid.

LCMS (ESI): m/z [M+H] calcd for $C_{24}H_{33}N_4O_3$: 425.25; found: 425.3.

$^1$H NMR (400 MHZ, methanol-$d_4$) δ=8.84 (s, 1H), 7.61 (dd, J=2.5, 8.7 Hz, 1H), 7.41 (d, J=2.6 Hz, 1H), 7.12 (d, J=8.8 Hz, 1H), 4.36-4.24 (m, 1H), 4.11 (t, J=5.3 Hz, 2H), 3.90 (q, J=7.3 Hz, 1H), 3.75 (q, J=7.3 Hz, 1H), 2.74 (t, J=5.2 Hz, 2H), 2.61-2.46 (m, 2H), 2.36 (br s, 4H), 2.27 (s, 6H), 2.18-2.07 (m, 1H), 2.03-1.87 (m, 2H), 1.73-1.58 (m, 5H).

N-(3-(4,6-dimethylpyrimidin-5-yl)-4-(2-(pyrrolidin-1-yl)ethoxy)phenyl)tetrahydrofuran-2-carboxamide (230)

230

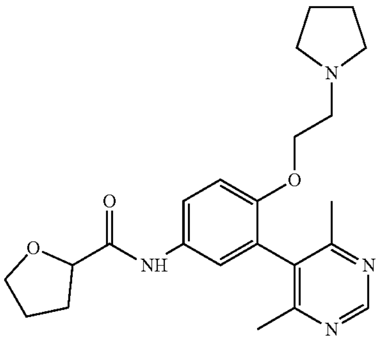

Compound 230 was prepared according to the synthesis described for compound 228, substituting tetrahydrofuran-2-carboxylic acid for 2-tetrahydrofuran-3-ylacetic acid.

LCMS (ESI): m/z [M+H] calcd for $C_{23}H_{31}N_4O_3$: 411.24; found: 411.0.

$^1$H NMR (400 MHZ, methanol-$d_4$) δ=8.84 (s, 1H), 7.72-7.66 (m, 1H), 7.43 (d, J=2.6 Hz, 1H), 7.15 (d, J=7.8 Hz, 1H), 4.42 (dd, J=5.9, 8.3 Hz, 1H), 4.15 (q, J=5.1 Hz, 2H), 4.12-4.06 (m, 1H), 3.96-3.89 (m, 1H), 2.88-2.78 (m, 2H), 2.53-2.40 (m, 4H), 2.39-2.29 (m, 1H), 2.29-2.24 (m, 6H), 2.13-2.02 (m, 1H), 2.00-1.90 (m, 2H), 1.76-1.66 (m, 4H).

N-(3-(4,6-dimethylpyrimidin-5-yl)-4-(2-(pyrrolidin-1-yl)ethoxy)phenyl)tetrahydrofuran-3-carboxamide (231)

231

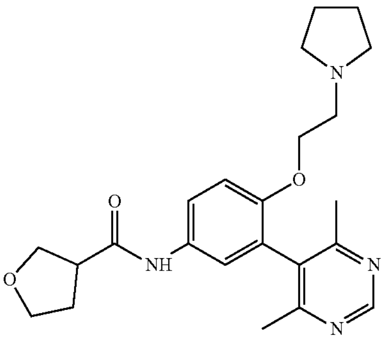

Compound 231 was prepared according to the synthesis described for compound 228, substituting tetrahydrofuran-3-carboxylic acid for 2-tetrahydrofuran-3-ylacetic acid.

LCMS (ESI): m/z [M+H] calcd for $C_{23}H_{31}N_4O_3$: 411.24; found: 411.0.

$^1$H NMR (400 MHZ, methanol-$d_4$) δ=8.84 (s, 1H), 7.61 (dd, J=2.7, 8.9 Hz, 1H), 7.41 (d, J=2.7 Hz, 1H), 7.13 (d, J=9.0 Hz, 1H), 4.12 (t, J=5.4 Hz, 2H), 4.05-3.99 (m, 1H), 3.96-3.86 (m, 2H), 3.85-3.78 (m, 1H), 3.23-3.11 (m, 1H), 2.74 (t, J=5.4 Hz, 2H), 2.40-2.33 (m, 4H), 2.27 (s, 6H), 2.20 (q, J=7.1 Hz, 2H), 1.69 (td, J=3.3, 6.8 Hz, 4H).

N-(3-(4,6-dimethylpyrimidin-5-yl)-4-(2-(pyrrolidin-1-yl)ethoxy)phenyl)-3-oxabicyclo[3.1.0]hexane-6-carboxamide (232)

232

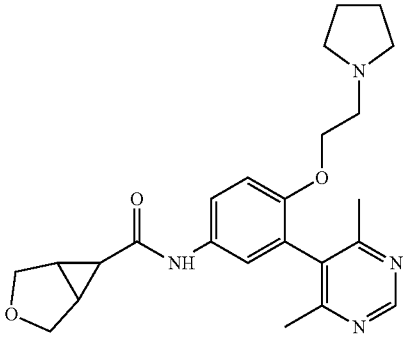

Compound 232 was prepared according to the synthesis described for compound 228, substituting 3-oxabicyclo[3.1.0]hexane-6-carboxylic acid for 2-tetrahydrofuran-3-ylacetic acid.

LCMS (ESI): m/z [M+H] calcd for $C_{24}H_{31}N_4O_3$: 423.24; found: 423.0.

$^1$H NMR (400 MHZ, methanol-$d_4$) δ=8.86 (s, 1H), 7.61 (dd, J=2.3, 8.8 Hz, 1H), 7.39 (d, J=2.4 Hz, 1H), 7.15 (d, J=8.9 Hz, 1H), 4.20 (t, J=5.1 Hz, 2H), 3.93 (d, J=8.7 Hz, 2H), 3.77 (d, J=8.4 Hz, 2H), 3.08 (br s, 2H), 2.70 (br s, 4H), 2.27 (s, 6H), 2.17 (br s, 2H), 1.84-1.77 (m, 4H), 1.67 (t, J=3.1 Hz, 1H).

N-(3-(4,6-dimethylpyrimidin-5-yl)-4-(2-(pyrrolidin-1-yl)ethoxy)phenyl)-3-oxabicyclo[3.1.0]hexane-6-carboxamide (233)

233

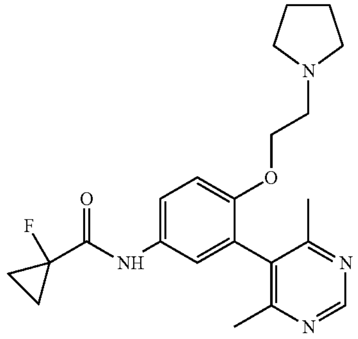

Compound 233 was prepared according to the synthesis described for compound 228, substituting 1-fluorocyclopropane-1-carboxylic acid for 2-tetrahydrofuran-3-ylacetic acid.

LCMS (ESI): m/z [M+H] calcd for $C_{22}H_{28}FN_4O_2$: 399.22; found: 399.0.

$^1$H NMR (400 MHZ, methanol-$d_4$) δ=8.84 (s, 1H), 7.69 (dd, J=2.6, 8.9 Hz, 1H), 7.43 (d, J=2.6 Hz, 1H), 7.15 (d, J=9.0 Hz, 1H), 4.13 (t, J=5.4 Hz, 2H), 2.75 (t, J=5.4 Hz, 2H), 2.41-2.33 (m, 4H), 2.28 (s, 6H), 1.69 (td, J=3.3, 6.8 Hz, 4H), 1.42-1.37 (m, 2H), 1.36 (s, 2H).

N-(3-(4,6-dimethylpyrimidin-5-yl)-4-(2-(pyrrolidin-1-yl)ethoxy)phenyl)-2-ethoxyacetamide (234)

234

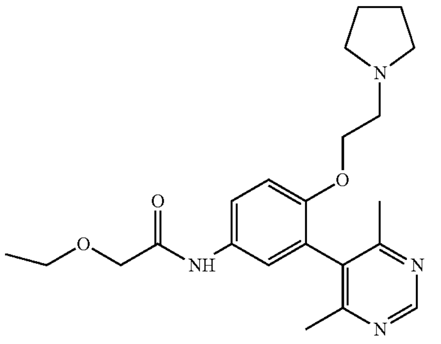

Compound 234 was prepared according to the synthesis described for compound 228, substituting 2-ethoxyacetic acid for 2-tetrahydrofuran-3-ylacetic acid.

LCMS (ESI): m/z [M+H] calcd for $C_{22}H_{31}N_4O_3$: 399.24; found: 399.3.

$^1$H NMR (400 MHZ, methanol-$d_4$) δ-8.85 (s, 1H), 7.68 (dd, J=2.4, 8.9 Hz, 1H), 7.45 (d, J=2.4 Hz, 1H), 7.15 (d, J=8.9 Hz, 1H), 4.16 (t, J=5.2 Hz, 2H), 4.07 (s, 2H), 3.65 (q, J=7.0 Hz, 2H), 2.85 (t, J=5.3 Hz, 2H), 2.47 (br s, 4H), 2.27 (s, 6H), 1.72 (br s, 4H), 1.28 (t, J=7.0 Hz, 3H).

N-(3-(4,6-dimethylpyrimidin-5-yl)-4-(2-(pyrrolidin-1-yl)ethoxy)phenyl)-3-methoxypropanamide (235)

235

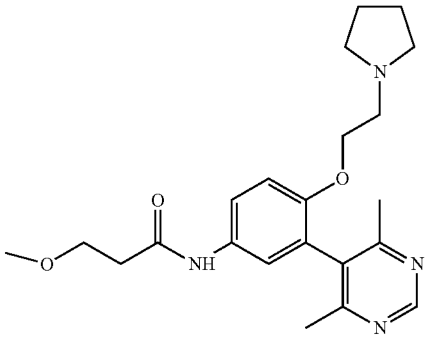

Compound 235 was prepared according to the synthesis described for compound 228, substituting 3-methoxypropanoic acid for 2-tetrahydrofuran-3-ylacetic acid.

LCMS (ESI): m/z [M+H] calcd for $C_{22}H_{31}N_4O_3$: 399.24; found: 399.3.

$^1$H NMR (400 MHZ, methanol-$d_4$) δ=8.84 (s, 1H), 7.61 (dd, J=2.3, 8.9 Hz, 1H), 7.44-7.39 (m, 1H), 7.12 (d, J=8.9 Hz, 1H), 4.12 (t, J=5.3 Hz, 2H), 3.71 (t, J=6.1 Hz, 2H), 3.38-3.33 (m, 3H), 2.73 (t, J=5.3 Hz, 2H), 2.60 (t, J=6.1 Hz, 2H), 2.36 (br s, 4H), 2.27 (s, 6H), 1.68 (br s, 4H).

N-(3-(4,6-dimethylpyrimidin-5-yl)-4-(2-(pyrrolidin-1-yl)ethoxy)phenyl)-2-(1H-pyrazol-1-yl)acetamide (236)

236

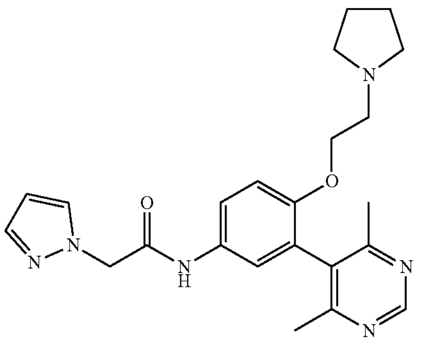

Compound 236 was prepared according to the synthesis described for compound 228, substituting 2-(1H-pyrazol-1-yl)acetic acid for 2-tetrahydrofuran-3-ylacetic acid.

LCMS (ESI): m/z [M+H] calcd for $C_{22}H_{29}N_6O_2$: 421.23; found: 421.0.

$^1$H NMR (400 MHZ, methanol-$d_4$) δ=8.84 (s, 1H), 7.72 (d, J=2.2 Hz, 1H), 7.62 (dd, J=2.6, 8.9 Hz, 1H), 7.55 (d, J=1.7 Hz, 1H), 7.42 (d, J=2.6 Hz, 1H), 7.14 (d, J=9.0 Hz, 1H), 6.35 (t, J=2.1 Hz, 1H), 5.03 (s, 2H), 4.13 (t, J=5.3 Hz, 2H), 2.79 (t, J=5.3 Hz, 2H), 2.42 (br s, 4H), 2.26 (s, 6H), 1.70 (td, J=3.3, 6.8 Hz, 4H).

2-(3,4-dihydro-1H-pyrrolo[1,2-a]pyrazin-2-yl)-N-[3-(4,6-dimethylpyrimidin-5-yl)-4-(2-pyrrolidin-1-ylethoxy)phenyl]acetamide (237)

Preparation of 2-chloro-N-[3-(4,6-dimethylpyrimidin-5-yl)-4-(2-pyrrolidin-1-ylethoxy)phenyl]acetamide (6)

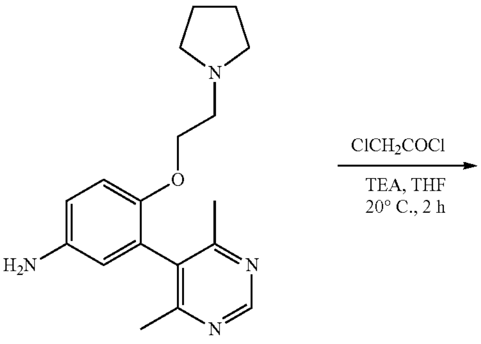

3

-continued

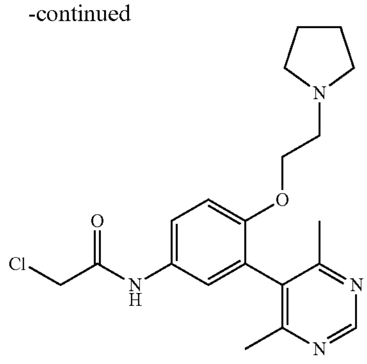

6

To a solution of 3-(4,6-dimethylpyrimidin-5-yl)-4-(2-pyrrolidin-1-ylethoxy)aniline ((3), 200 mg, 640.19 μmol, 1 eq.) in THF (4 mL) was added TEA (194.34 mg, 1.92 mmol, 267.32 μL, 3 eq.) and 2-chloroacetyl chloride (86.77 mg, 768.23 μmol, 61.10 μL, 1.2 eq.). The mixture was stirred at 20° C. for 2 hrs (monitored by TLC). The reaction mixture was concentrated under reduced pressure to give a residue. The residue was purified by column chromatography ($SiO_2$, petroleum ether:ethyl acetate=1:1 to ethyl acetate:methanol=1:1). 2-Chloro-N-[3-(4,6-dimethylpyrimidin-5-yl)-4-(2-pyrrolidin-1-ylethoxy)phenyl]acetamide ((6), 180 mg, 462.86 μmol, 72.30% yield) was obtained as a yellow oil.

Preparation of 2-(3,4-dihydro-1H-pyrrolo[1,2-a]pyrazin-2-yl)-N-[3-(4,6-dimethylpyrimidin-5-yl)-4-(2-pyrrolidin-1-ylethoxy)phenyl]acetamide (237)

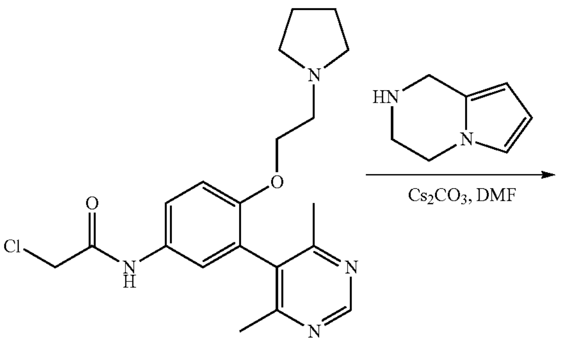

6

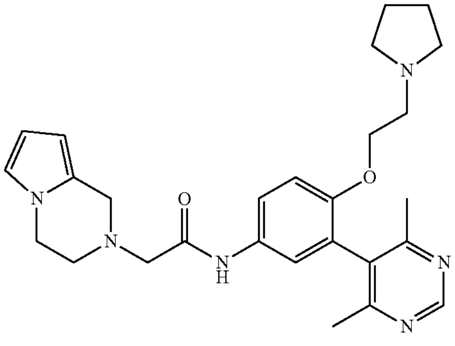

237

To a solution of 2-chloro-N-[3-(4,6-dimethylpyrimidin-5-yl)-4-(2-pyrrolidin-1-ylethoxy)phenyl]acetamide ((6), 90 mg, 231.43 μmol, 1 eq.) in DMF (1 mL) was added $Cs_2CO_3$ (226.21 mg, 694.28 μmol, 3 eq.), fumaric acid, and 1,2,3,4-tetrahydropyrrolo[1,2-a]pyrazine (66.16 mg, 277.71 μmol, 1.2 eq.). The mixture was stirred at 80° C. for 16 hrs. The reaction mixture was filtered and concentrated under reduced pressure to give a residue. The residue was purified by prep-HPLC (column: Phenomenex Gemini-NX C18 75*30 mm*3 μm; mobile phase: [water (0.05% ammonia hydroxide v/v)-ACN]; B %: 32%-72%, 10 min). 2-(3,4-dihydro-1H-pyrrolo[1,2-a]pyrazin-2-yl)-N-[3-(4,6-dimethylpyrimidin-5-yl)-4-(2-pyrrolidin-1-ylethoxy)phenyl]acetamide (7.3 mg, 15.04 μmol, 6.50% yield, 97.754% purity) was obtained as a yellow oil.

LCMS (ESI): m/z [M+H] calcd for $C_{27}H_{36}N_6O_2$: 475.27; found: 475.2.

$^1H$ NMR (400 MHZ, methanol-$d_4$) δ=8.83 (s, 1H), 7.65 (dd, J=2.7, 8.9 Hz, 1H), 7.45 (d, J=2.7 Hz, 1H), 7.13 (d, J=8.9 Hz, 1H), 6.62-6.50 (m, 1H), 6.03 (t, J=3.1 Hz, 1H), 5.86-5.68 (m, 1H), 4.12 (t, J=5.4 Hz, 2H), 4.06 (t, J=5.6 Hz, 2H), 3.78 (s, 2H), 3.37 (s, 2H), 3.01 (t, J=5.6 Hz, 2H), 2.74 (t, J=5.3 Hz, 2H), 2.38-2.33 (m, 4H), 2.28-2.24 (m, 6H), 1.69 (td, J=3.3, 6.6 Hz, 4H).

2-(6,8-dihydro-5H-imidazo[1,2-a]pyrazin-7-yl)-N-[3-(4,6-dimethylpyrimidin-5-yl)-4-(2-pyrrolidin-1-ylethoxy)phenyl]acetamide (238)

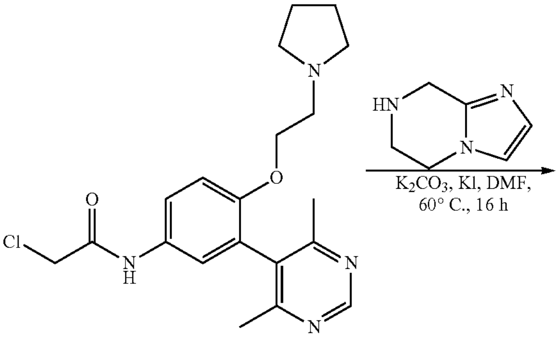

6

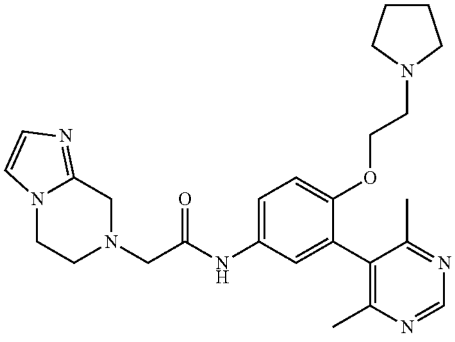

238

A mixture of 2-chloro-N-[3-(4,6-dimethylpyrimidin-5-yl)-4-(2-pyrrolidin-1-ylethoxy)phenyl]acetamide ((6), 50 mg, 104.14 μmol, 81% purity, 1 eq.), 5,6,7,8-tetrahydroimidazo[1,2-a]pyrazine (19.95 mg, 124.97 μmol, 1.2 eq., HCl), KI (3.46 mg, 20.83 μmol, 0.2 eq.) and $K_2CO_3$ (43.18 mg, 312.43 μmol, 3 eq.) in DMF (1 mL) was stirred at 60° C. for 16 hr (monitored by LC-MS). The reaction mixture was concentrated under reduced pressure to give a residue. The product was purified by prep-HPLC (column: Waters Xbridge 150*25 mm*5 μm; mobile phase: [water (0.05% ammonia hydroxide v/v)-ACN]; B %: 15%-45%, 10 min). 2-(6,8-dihydro-5H-imidazo[1,2-a]pyrazin-7-yl)-N-[3-(4,6-dimethylpyrimidin-5-yl)-4-(2-pyrrolidin-1-ylethoxy)phenyl]acetamide (14.57 mg, 29.72 μmol, 28.53% yield, 97% purity) was obtained as a yellow solid.

LCMS (ESI): m/z [M+H] calcd for $C_{26}H_{34}N_7O_2$: 476.27; found: 476.2.

$^1$H NMR (400 MHZ, methanol-$d_4$) δ=8.96 (s, 1H), 7.77 (dd, J=2.6, 9.0 Hz, 1H), 7.54 (dt, J=2.3, 4.0 Hz, 3H), 7.24 (d, J=9.0 Hz, 1H), 4.41-4.36 (m, 2H), 4.33 (t, J=5.4 Hz, 2H), 4.21 (s, 2H), 3.60 (s, 2H), 3.57-3.51 (m, 2H), 3.41 (br d, J=5.3 Hz, 2H), 3.28 (br t, J=5.3 Hz, 2H), 2.94-2.82 (m, 2H), 2.34 (s, 6H), 2.04-1.86 (m, 4H).

2-(6,7-dihydropyrazolo[1,5-a]pyrazin-5 (4H)-yl)-N-(3-(4,6-dimethylpyrimidin-5-yl)-4-(2-(pyrrolidin-1-yl)ethoxy)phenyl)acetamide (239)

239

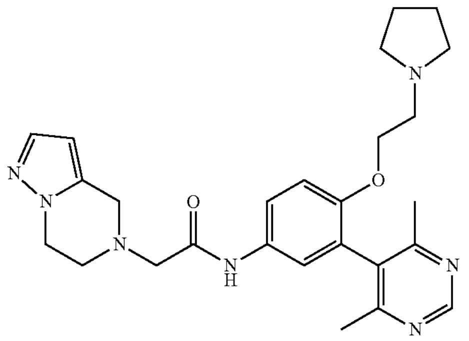

Compound 239 was prepared according to the synthesis described for compound substituting 4,5,6,7-tetrahydropyrazolo[1,5-a]pyrazine for 1,2,3,4-237, tetrahydropyrrolo[1,2-a]pyrazine.

LCMS (ESI): m/z [M+H] calcd for $C_{26}H_{34}N_7O_2$: 476.27; found: 476.3.

$^1$H NMR (400 MHZ, methanol-$d_4$) δ=8.83 (s, 1H), 7.66 (dd, J=2.6, 8.9 Hz, 1H), 7.45 (t, J=2.1 Hz, 2H), 7.13 (d, J=9.0 Hz, 1H), 6.08 (s, 1H), 4.24 (t, J=5.6 Hz, 2H), 4.16-4.08 (m, 2H), 3.91 (s, 2H), 3.44 (s, 2H), 3.15 (t, J=5.6 Hz, 2H), 2.73 (t, J=5.4 Hz, 2H), 2.38-2.33 (m, 4H), 2.26 (s, 6H), 1.73-1.64 (m, 4H).

2-(5,6-dihydro-[1,2,4]triazolo[4,3-a]pyrazin-7 (8H)-yl)-N-(3-(4,6-dimethylpyrimidin-5-yl)-4-(2-(pyrrolidin-1-yl)ethoxy)phenyl)acetamide (240)

240

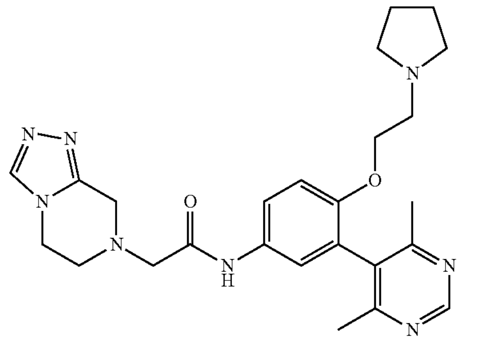

Compound 240 was prepared according to the synthesis described for compound 237, substituting 5,6,7,8-tetrahydro-[1,2,4]triazolo[4,3-a]pyrazine for 1,2,3,4-tetrahydropyrrolo[1,2-a]pyrazine.

LCMS (ESI): m/z [M+H] calcd for $C_{26}H_{34}N_7O_2$: 477.27; found: 477.3.

$^1$H NMR (400 MHZ, methanol-$d_4$) δ=8.84 (s, 1H), 8.46 (s, 1H), 7.67 (dd, J=2.6, 8.9 Hz, 1H), 7.44 (d, J=2.6 Hz, 1H), 7.14 (d, J=8.9 Hz, 1H), 4.23 (t, J=5.5 Hz, 2H), 4.14-4.10 (m, 2H), 4.03 (s, 2H), 3.51 (s, 2H), 3.13 (t, J=5.5 Hz, 2H), 2.73 (t, J=5.4 Hz, 2H), 2.40-2.32 (m, 4H), 2.27 (s, 6H), 1.68 (td, J=3.3, 6.8 Hz, 4H).

2-(cyclopropoxy)-N-[3-(4,6-dimethylpyrimidin-5-yl)-4-(2-pyrrolidin-1-ylethoxy)phenyl]acetamide (241)

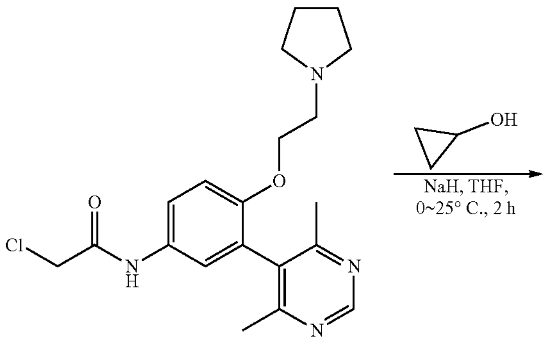

6

-continued

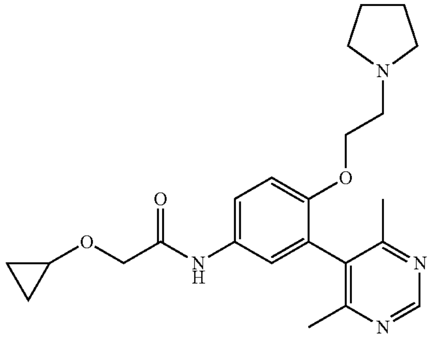

241

To a solution of cyclopropanol (89.61 mg, 1.54 mmol, 3 eq.) in THF (1 mL) was added NaH (61.71 mg, 1.54 mmol, 60% purity, 3 eq.), the mixture was stirred at 0° C. for 1 h and then 2-chloro-N-[3-(4,6-dimethylpyrimidin-5-yl)-4-(2-pyrrolidin-1-ylethoxy)phenyl]acetamide ((6), 200 mg, 514.28 μmol, 1 eq.). The mixture was stirred at 25° C. for 2 h. $NH_4Cl$ aqueous solution was added to the mixture to pH-6, and then diluted with water (10 mL) and extracted with 30 mL ethyl acetate (10 mL×3). The combined organic phase was concentrated under reduced pressure to give a residue. The residue was purified by prep-HPLC (column: Phenomenex Gemini-NX C18 75*30 mm*3 μm; mobile phase: [water (0.1% TFA)-ACN]; B %: 18%-28%, 7 min). 2-(cyclopropoxy)-N-[3-(4,6-dimethylpyrimidin-5-yl)-4-(2-pyrrolidin-1-ylethoxy)phenyl]acetamide (16.12 mg, 30.31 μmol, 5.89% yield, 98.614% purity, TFA) was obtained as a yellow gum.

LCMS (ESI): m/z [M+H] calcd for $C_{23}H_{31}N_4O_3$: 411.23; found: 411.2.

$^1$H NMR (400 MHZ, methanol-$d_4$) δ=8.90 (d, J=2.4 Hz, 1H), 7.78-7.69 (m, 1H), 7.46 (t, J=2.2 Hz, 1H), 7.21 (d, J=9.0 Hz, 1H), 4.38-4.29 (m, 2H), 4.14 (s, 2H), 3.55-3.49 (m, 3H), 3.40-3.33 (m, 2H), 2.93-2.77 (m, 2H), 2.30 (d, J=1.5 Hz, 6H), 2.05-1.97 (m, 2H), 1.94-1.83 (m, 2H), 0.77-0.63 (m, 2H), 0.60-0.48 (m, 2H).

2-cyclobutoxy-N-(3-(4,6-dimethylpyrimidin-5-yl)-4-(2-(pyrrolidin-1-yl)ethoxy)phenyl)acetamide (242)

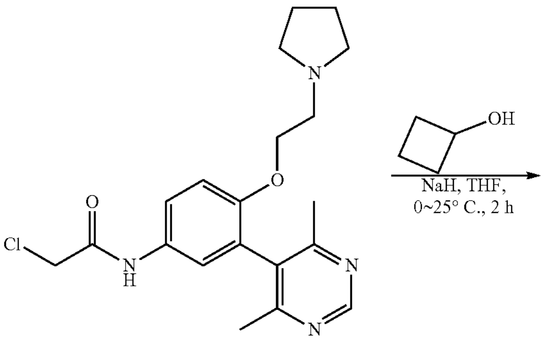

6

-continued

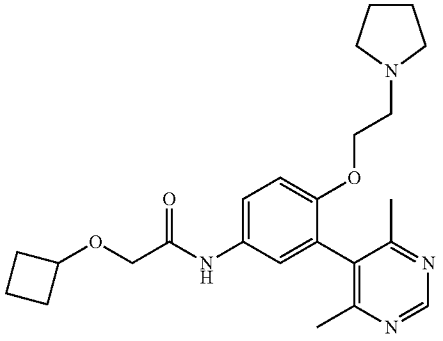

242

To a solution of cyclobutanol (111.25 mg, 1.54 mmol, 3 eq.) in THF (2 mL) was added NaH (61.71 mg, 1.54 mmol, 60% purity, 3 eq.), then was stirred at 0° C. for 1 h. 2-Chloro-N-[3-(4,6-dimethylpyrimidin-5-yl)-4-(2-pyrrolidin-1-ylethoxy)phenyl]acetamide ((6), 200 mg, 514.28 μmol, 1 eq.) was then added. The mixture was stirred at 25° C. for 2 hrs. $NH_4Cl$ aqueous solution was added to the reaction mixture to pH=6. The reaction mixture was diluted with water (10 mL) and extracted with 30 mL ethyl acetate (10 mL×3). The combined organic phases were concentrated under reduced pressure to give a residue. The residue was purified by prep-HPLC (column: Waters Xbridge 150*25 mm*5 μm; mobile phase: [water (0.05% ammonia hydroxide v/v)-ACN]; B %: 25%-55%, 9.5 min). 2-(cyclobutoxy)-N-[3-(4,6-dimethylpyrimidin-5-yl)-4-(2-pyrrolidin-1-ylethoxy)phenyl]acetamide (4.27 mg, 9.81 μmol, 1.91% yield, 97.511% purity) was obtained as a yellow gum.

LCMS (ESI): m/z [M+H] calcd for $C_{24}H_{33}N_4O$: 425.25; found: 426.3 (deuterated product was detected).

$^1$H NMR (400 MHZ, methanol-$d_4$) δ=8.85 (s, 1H), 7.69 (dd, J=2.6, 8.9 Hz, 1H), 7.44 (d, J=2.7 Hz, 1H), 7.16 (d, J=8.9 Hz, 1H), 4.18 (t, J=5.4 Hz, 2H), 4.13-4.04 (m, 1H), 3.99 (s, 2H), 3.02-2.88 (m, 2H), 2.68-2.46 (m, 4H), 2.28 (s, 8H), 2.10-1.99 (m, 2H), 1.80-1.71 (m, 5H), 1.56 (br d, J=10.8 Hz, 1H).

N-[3-(4,6-dimethylpyrimidin-5-yl)-4-(2-pyrrolidin-1-ylethoxy)phenyl]-2-pyrrol-1-yl-acetamide (243)

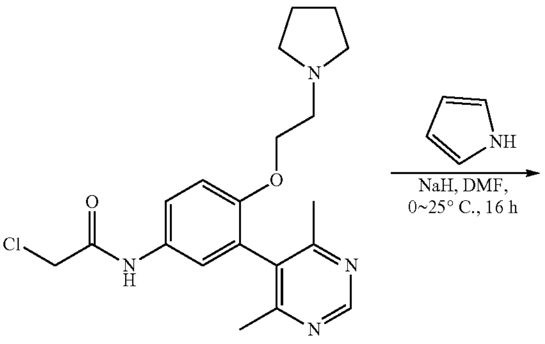

6

-continued

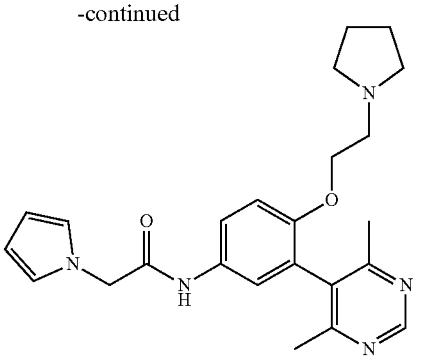

243

To a solution of pyrrole (103.51 mg, 1.54 mmol, 107.04 μL, 3 eq.) in DMF (2 mL) was added NaH (61.71 mg, 1.54 mmol, 60% purity, 3 eq.). The mixture was stirred at 0° C. for 1 h, then 2-chloro-N-[3-(4,6-dimethylpyrimidin-5-yl)-4-(2-pyrrolidin-1-ylethoxy)phenyl]acetamide ((6), 200 mg, 514.28 μmol, 1 eq.) was added. The mixture was stirred at 25° C. for 16 hrs. $NH_4Cl$ aqueous solution was added to the reaction mixture to pH=6, diluted with water (10 mL) and extracted with 30 mL ethyl acetate (10 mL×3). The combined organic phase was concentrated under reduced pressure to give a residue. The residue was purified by prep-HPLC (column: Phenomenex Gemini-NX C18 75*30 mm*3 μm; mobile phase: [water (0.1% TFA)-ACN]; B %: 20%-30%, 7 min). N-[3-(4,6-dimethylpyrimidin-5-yl)-4-(2-pyrrolidin-1-ylethoxy)phenyl]-2-pyrrol-1-yl-acetamide (12.77 mg, 23.93 μmol, 4.65% yield, 100% purity, TFA) was obtained as a yellow gum.

LCMS (ESI): m/z [M+H] calcd for $C_{24}H_{30}N_5O_2$: 420.23; found: 420.3.

$^1H$ NMR (400 MHZ, methanol-$d_4$) δ=8.89 (s, 1H), 7.66 (dd, J=2.6, 9.0 Hz, 1H), 7.44 (d, J=2.7 Hz, 1H), 7.20 (d, J=9.0 Hz, 1H), 6.75 (t, J=2.1 Hz, 2H), 6.12 (t, J=2.1 Hz, 2H), 4.75 (s, 2H), 4.34-4.30 (m, 2H), 3.52-3.48 (m, 2H), 3.40-3.33 (m, 2H), 2.90-2.80 (m, 2H), 2.28 (s, 6H), 2.02 (br d, J=8.6 Hz, 2H), 1.93-1.82 (m, 2H).

N-[3-(4,6-dimethylpyrimidin-5-yl)-4-(2-pyrrolidin-1-ylethoxy)phenyl]-1-methoxy-cyclopropanecarboxamide (244)

Preparation of methyl 1-methoxycyclopropanecarboxylate (7)

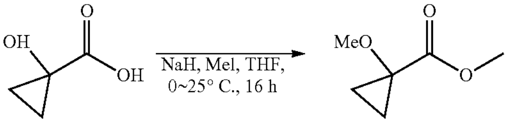

7

To a solution of 1-hydroxycyclopropanecarboxylic acid (200 mg, 1.96 mmol, 1 eq.) in DMF (1 mL) was added NaH (196.06 mg, 4.90 mmol, 60% purity, 2.50 eq.) and MeI (695.77 mg, 4.90 mmol, 305.16 μL, 2.50 eq.). The mixture was stirred at 25° C. for 16 hrs. The reaction mixture was diluted with water (30 mL) and extracted with ethyl acetate 60 mL (20 mL×3). The combined organic layers were dried over $Na_2SO_4$, filtered and concentrated under reduced pressure to give a residue. Methyl 1-methoxycyclopropanecarboxylate ((7), 250 mg, crude) was obtained as a yellow oil.

$^1H$ NMR (400 MHZ, DMSO-$d_6$) δ=3.65 (s, 3H), 3.29 (s, 3H), 1.17-1.12 (m, 4H)

Preparation of 1-methoxycyclopropanecarboxylic acid (8)

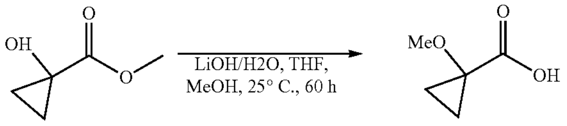

7

8

To a solution of methyl 1-methoxycyclopropanecarboxylate ((7), 250 mg, 1.92 mmol, 1 eq.) in THF (6 mL) and MeOH (6 mL) was added LiOH (2 M, 2.88 mL, 3.00 eq.). The mixture was stirred at 25° C. for 60 hrs. The resulting mixture was diluted with 2 mL 1.0 M NaOH (aq.), and extracted with 60 mL EtOAc (60 mL×3). The combined aqueous extracts were acidified to pH 2 with the addition of 4.0 M HCl (aq), then extracted with 60 mL EtOAc (20 mL×3). The combined EtOAc extracts were dried over anhydrous $Na_2SO_4$, filtered and concentrated under vacuum. 1-Methoxycyclopropanecarboxylic acid ((8), 50 mg, crude) was obtained as a yellow oil.

$^1H$ NMR (400 MHZ, DMSO-$d_6$) δ=3.29 (s, 3H), 1.12-1.06 (m, 2H), 1.02-0.97 (m, 2H).

N-[3-(4,6-dimethylpyrimidin-5-yl)-4-(2-pyrrolidin-1-ylethoxy)phenyl]-1-methoxy-cyclopropanecarboxamide (244)

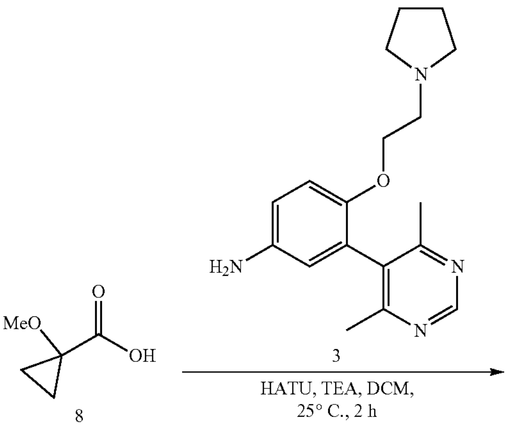

8

3

-continued

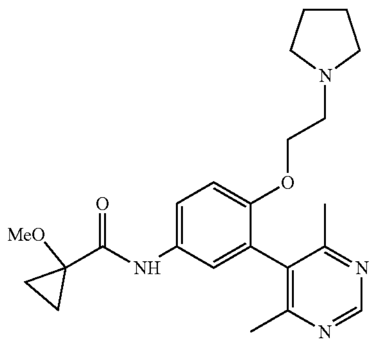

244

To a solution of 1-methoxycyclopropanecarboxylic acid ((8), 24.53 mg, 211.27 μmol, 1.1 eq.) in DCM (1 mL) was added HATU (87.63 mg, 230.47 μmol, 1.2 eq.) and TEA (58.30 mg, 576.18 μmol, 80.20 μL, 3 eq.). The reaction mixture was stirred at 25° C. for 0.5 hrs, then 3-(4,6-dimethylpyrimidin-5-yl)-4-(2-pyrrolidin-1-ylethoxy)aniline ((3), 60 mg, 192.06 μmol, 1 eq.) was added. The mixture was stirred at 25° C. for 2 hrs. The reaction mixture was filtered and concentrated under reduced pressure to give a residue. The residue was purified by prep-HPLC (column: Phenomenex Gemini-NX C18 75*30 mm*3 μm; mobile phase: [water (0.1% TFA)-ACN]; B %: 15%-25%, 7 min). N-[3-(4,6-dimethylpyrimidin-5-yl)-4-(2-pyrrolidin-1-ylethoxy)phenyl]-1-methoxy-cyclopropanecarboxamide (11.27 mg, 21.23 μmol, 11.05% yield, 98.808% purity, TFA) was obtained as a yellow gum.

LCMS (ESI): m/z [M+H] calcd for $C_{23}H_{31}N_4O_3$: 411.23; found: 411.2.

$^1$H NMR (400 MHZ, methanol-$d_4$) δ=8.89 (s, 1H), 7.75 (dd, J=2.7, 8.9 Hz, 1H), 7.51-7.42 (m, 1H), 7.21 (d, J=9.0 Hz, 1H), 4.37-4.28 (m, 2H), 3.54-3.49 (m, 2H), 3.42 (s, 3H), 3.40-3.34 (m, 2H), 2.93-2.78 (m, 2H), 2.31 (s, 6H), 2.09-1.95 (m, 2H), 1.89 (br dd, J=5.1, 7.0 Hz, 2H), 1.30-1.22 (m, 2H), 1.22-1.15 (m, 2H).

N-[3-(4,6-dimethylpyrimidin-5-yl)-4-(2-pyrrolidin-1-ylethoxy)phenyl]cyclopropanecarboxamide (245)

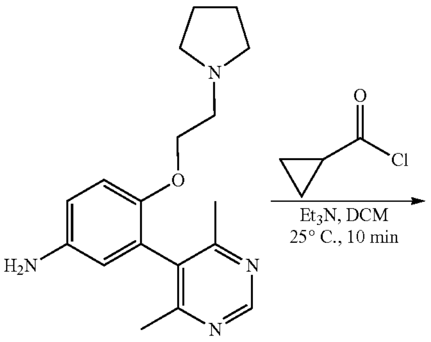

3

-continued

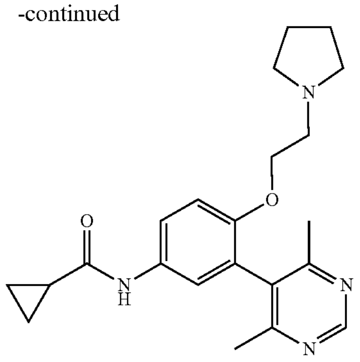

245

To a mixture of 3-(4,6-dimethylpyrimidin-5-yl)-4-(2-pyrrolidin-1-ylethoxy)aniline ((3), 300 mg, 912.27 μmol, 1 eq.) and triethylamine (184.62 mg, 1.82 mmol, 253.95 L, 2 eq.) in DCM (10 mL) was added cyclopropanecarbonyl chloride (104.90 mg, 1.00 mmol, 91.22 μL, 1.1 eq.), and then the mixture was stirred at 25° C. for 10 min (monitored by LCMS). The reaction mixture was quenched by addition of MeOH (1 mL), filtered and concentrated in vacuum to give a residue. The residue was purified by prep-HPLC (column: Waters Xbridge C18 150*50 mm*10 μm; mobile phase: [water (0.05% ammonia hydroxide v/v)-ACN]; B %: 20%-50%, 11.5 min). N-[3-(4,6-dimethylpyrimidin-5-yl)-4-(2-pyrrolidin-1-ylethoxy)phenyl]cyclopropanecarboxamide (138.63 mg, 364.35 μmol, 39.94% yield, 100% purity) was obtained as a brown solid.

LCMS (ESI): m/z [M+H] calcd for $C_{22}H_{29}N_4O_2$: 381.22; found: 381.2.

$^1$H NMR (400 MHZ, methanol-$d_4$) δ=8.83 (s, 1H), 7.58 (dd, J=2.6, 8.9 Hz, 1H), 7.39 (d, J=2.6 Hz, 1H), 7.12 (d, J=8.9 Hz, 1H), 4.11 (t, J=5.4 Hz, 2H), 2.73 (t, J=5.4 Hz, 2H), 2.41-2.33 (m, 4H), 2.27 (s, 6H), 1.78-1.72 (m, 1H), 1.69 (td, J=3.3, 6.9 Hz, 4H), 0.97-0.90 (m, 2H), 0.88-0.80 (m, 2H).

(1R,5R)—N-[3-(4,6-dimethylpyrimidin-5-yl)-4-(2-pyrrolidin-1-ylethoxy)phenyl]-3-oxabicyclo[3.1.0]hexane-1-carboxamide (246)

Preparation of ethyl (1S,5R)-2-oxo-3-oxabicyclo[3.1.0]hexane-1-carboxylate (9)

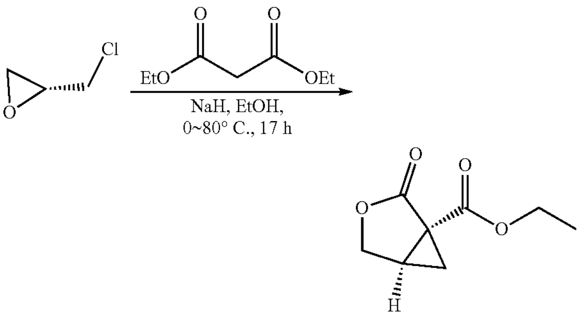

9

NaH (1.43 g, 35.67 mmol, 60% purity, 1.1 eq.) was dissolved in EtOH (10 mL) at 0° C. and stirred for 15 mins. The resulting sodium ethoxide was added to diethyl propanedioate (6.23 g, 38.91 mmol, 5.88 mL, 1.2 eq.) in EtOH (25 mL) at 0° C. for 15 mins, then was added a solution of (2R)-2-(chloromethyl) oxirane (3 g, 32.42 mmol, 2.54 mL, 1 eq.) in EtOH (5 mL) at 25° C., the mixture was stirred at 80° C. for 16 hrs. The reaction mixture was concentrated in vacuum to give a residue. The residue was quenched by the addition of saturated $NH_4Cl$ (50 mL), diluted with $H_2O$ (30 mL), and extracted with EtOAc (40 mL×3). The combined organic layers were washed with brine (40 mL), dried over anhydrous $Na_2SO_4$, filtered and concentrated under reduced pressure to give a residue. The residue was purified by column chromatography ($SiO_2$, petroleum ether/ethyl acetate=1:0/3:1). Ethyl (1S,5R)-2-oxo-3-oxabicyclo[3.1.0]hexane-1-carboxylate ((9), 3.1 g, 18.22 mmol, 56.19% yield) was obtained as a light yellow oil.

$^1H$ NMR (400 MHZ, chloroform-d) δ=4.37 (dd, J=4.8, 9.4 Hz, 1H), 4.26 (dq, J=2.3, 7.1 Hz, 2H), 4.21-4.17 (m, 1H), 2.73 (td, J=5.1, 8.2 Hz, 1H), 2.08 (dd, J=4.8, 8.1 Hz, 1H), 1.38 (t, J=5.1 Hz, 1H), 1.35-1.29 (m, 3H).

Preparation of ethyl (1R,2R)-1,2-bis(hydroxymethyl)cyclopropanecarboxylate (10)

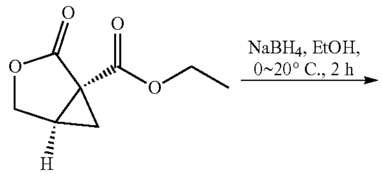

9

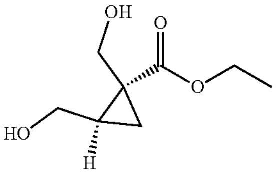

10

To a solution of ethyl (1S,5R)-2-oxo-3-oxabicyclo[3.1.0]hexane-1-carboxylate ((9), 1 g, 5.88 mmol, 1 eq.) in EtOH (10 mL) was added $NaBH_4$ (444.66 mg, 11.75 mmol, 2 eq.) at 0° C. The mixture was stirred at 20° C. for 2 hrs. The reaction mixture was quenched by addition HCl (1 M, 10 mL) at 0° C., concentrated under reduced pressure to give a residue, and then diluted with $H_2O$ (20 mL) and extracted with EtOAc (20 mL×3). The combined organic layers were washed with brine (20 mL), dried over anhydrous $Na_2SO_4$, filtered and concentrated under reduced pressure to give a colorless oil. Ethyl (1R,2R)-1,2-bis(hydroxymethyl)cyclopropanecarboxylate ((10), 420 mg, crude) was obtained as a colorless oil.

$^1H$ NMR (400 MHZ, chloroform-d) δ=4.53 (br d, J=12.6 Hz, 1H), 4.24-4.05 (m, 3H), 3.32 (br t, J=11.8 Hz, 1H), 3.22 (br d, J=12.8 Hz, 1H), 2.12-1.99 (m, 1H), 1.53-1.44 (m, 1H), 1.30-1.23 (t, 3H), 0.80-0.72 (m, 1H).

Preparation of ethyl (1R,5R)-3-oxabicyclo[3.1.0]hexane-1-carboxylate (11)

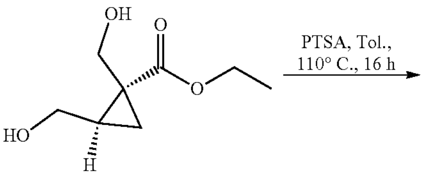

10

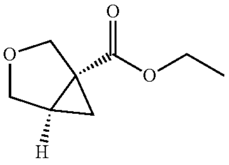

11

To a solution of ethyl (1R,2R)-1,2-bis(hydroxymethyl)cyclopropanecarboxylate ((10), 420 mg, 2.41 mmol, 1 eq.) in toluene (6 mL) was added TsOH (41.52 mg, 241.11 μmol, 0.1 eq.). The mixture was stirred at 110° C. for 16 hrs. The reaction mixture was concentrated in vacuum to give a residue. The residue was purified by column chromatography ($SiO_2$, petroleum ether/ethyl acetate=1:0 to 3:1). Ethyl (1R,5R)-3-oxabicyclo[3.1.0]hexane-1-carboxylate ((11), 60 mg, 384.18 μmol, 15.93% yield) was obtained as yellow oil.

$^1H$ NMR (400 MHZ, chloroform-d) δ=4.17 (q, J=7.1 Hz, 2H), 4.05 (d, J=8.6 Hz, 1H), 3.91 (d, J=8.6 Hz, 1H), 3.85-3.81 (m, 1H), 3.80-3.75 (m, 1H), 2.10 (ddd, J=2.8, 5.4, 8.3 Hz, 1H), 1.49 (dd, J=4.3, 8.3 Hz, 1H), 1.27 (t, J=7.1 Hz, 3H), 1.01 (t, J=4.9 Hz, 1H).

Preparation of (1R,5R)-3-oxabicyclo[3.1.0]hexane-1-carboxylic acid (12)

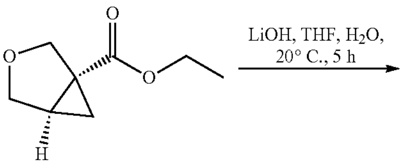

11

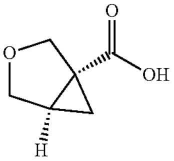

12

To a solution of ethyl (1R,5R)-3-oxabicyclo[3.1.0]hexane-1-carboxylate ((11), 60 mg, 384.18 μmol, 1 eq.) in THF (1 mL) and $H_2O$ (0.2 mL) was added $LiOH{\cdot}H_2O$ (32.24 mg, 768.35 μmol, 2 eq.). The mixture was stirred at 30° C. for 4 hrs. The reaction mixture was diluted with water (1 mL) and extracted with EtOAc (1 mL×2). To the aqueous layers was added HCl (1 M, 0.3 mL) to adjust to pH=5~6, extracted with EtOAc (1 mL×2). The combined organic layers were dried over anhydrous $Na_2SO_4$, filtered and concentrated under reduced pressure to give a residue.

(1R,5R)-3-oxabicyclo[3.1.0]hexane-1-carboxylic acid ((12), 32 mg, crude) was obtained as a yellow oil.

$^1$H NMR (400 MHZ, chloroform-d) δ=10.45 (bs, 1H), 4.05-4.05 (m, 1H) 3.91 (d, J=8.7 Hz, 1H), 3.87-3.83 (m, 1H), 3.81-3.76 (m, 1H), 2.19 (ddd, J=2.9, 5.6, 8.3 Hz, 1H), 1.57 (dd, J=4.4, 8.3 Hz, 1H), 1.10 (t, J=5.0 Hz, 1H).

(1R,5R)—N-[3-(4,6-dimethylpyrimidin-5-yl)-4-(2-pyrrolidin-1-ylethoxy)phenyl]-3-oxabicyclo[3.1.0]hexane-1-carboxamide (246)

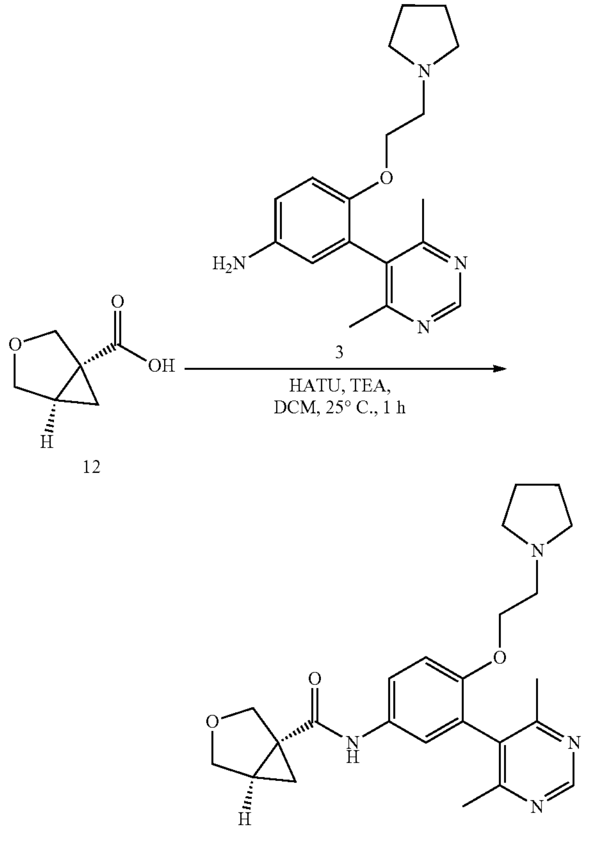

3

12

246

To a solution of (1R,5R)-3-oxabicyclo[3.1.0]hexane-1-carboxylic acid ((12), 32 mg, 249.75 μmol, 1 eq.) and $Et_3N$ (50.54 mg, 499.51 μmol, 69.53 μL, 2 eq.) in DMF (1 mL) was added HATU (113.96 mg, 299.70 μmol, 1.2 eq.), and stirred for 15 mins. Then was added 3-(4,6-dimethylpyrimidin-5-yl)-4-(2-pyrrolidin-1-ylethoxy)aniline ((3), 78.03 mg, 249.75 μmol, 1 eq.) and the mixture was stirred at 20° C. for 2 hrs. The reaction mixture was concentrated in vacuum to give a residue. The residue was purified by prep-HPLC (column: Phenomenex Gemini-NX C18 75*30 mm*3 μm; mobile phase: [water (0.1% TFA)-ACN]; B %: 15%-25%, 7 min). (1R,5R)—N-[3-(4,6-dimethylpyrimidin-5-yl)-4-(2-pyrrolidin-1-ylethoxy)phenyl]-3-oxabicyclo[3.1.0]hexane-1-carboxamide (43.11 mg, 79.54 μmol, 31.85% yield, 99% purity, TFA) was obtained as a yellow solid.

LCMS (ESI): m/z [M+H] calcd for $C_{24}H_{31}N_4O_3$: 423.2; found: 423.4.

$^1$H NMR (400 MHZ, methanol-d$_4$) δ=8.93 (s, 1H), 7.66 (dd, J=2.6, 9.0 Hz, 1H), 7.41 (d, J=2.6 Hz, 1H), 7.21 (d, J=9.0 Hz, 1H), 4.36-4.30 (m, 2H), 4.09-4.04 (m, 1H), 4.02-3.98 (m, 1H), 3.85-3.79 (m, 2H), 3.55-3.50 (m, 2H), 3.38 (br s, 2H), 2.94-2.81 (m, 2H), 2.32 (s, 6H), 2.23-2.17 (m, 1H), 2.03 (br s, 2H), 1.96-1.82 (m, 2H), 1.48-1.42 (m, 1H), 0.98 (t, J=4.9 Hz, 1H).

Preparation of N-[3-(4,6-dimethylpyrimidin-5-yl)-4-(2-pyrrolidin-1-ylethoxy)phenyl]-2-thiazol-5-yl-acetamide (247)

Preparation of thiazole-5-carbonyl chloride (13)

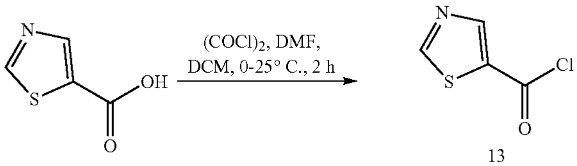 [SMILES: O=C(O)c1cncs1 ; O=C(Cl)c1cncs1]

13

To a solution of thiazole-5-carboxylic acid (500 mg, 3.87 mmol, 1 eq.) in DCM (5 mL) was added oxalyl dichloride (540.58 mg, 4.26 mmol, 372.82 μL, 1.1 eq.) and DMF (0.05 mL) at 0° C. The reaction mixture was stirred at 25° C. for 2 hrs. The reaction mixture was then concentrated in vacuum to give a residue. Thiazole-5-carbonyl chloride ((13), 570 mg, crude) was obtained as a brown solid.

Preparation of 2-thiazol-5-ylacetic acid (14)

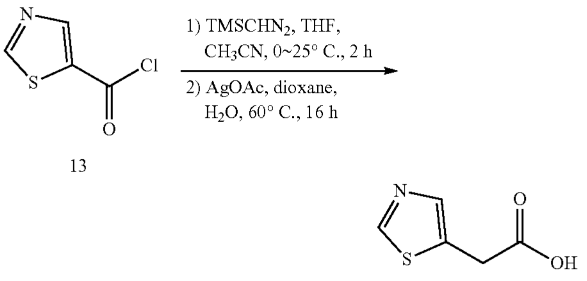

13

14

To a solution of thiazole-5-carbonyl chloride ((13), 570 mg, 3.86 mmol, 1 eq.) in THF (4 mL) and $CH_3CN$ (4 mL) was added $TMSCHN_2$ (2 M, 3.86 mL, 2 eq.) dropwise at 0° C. The mixture was stirred at 25° C. for 2 hrs. The mixture was concentrated in vacuum and diluted with dioxane (4 mL) and $H_2O$ (4 mL). Then AgOAc (193.40 mg, 1.16 mmol, 59.32 μL, 0.3 eq.) was added. The reaction mixture was stirred at 60° C. for 16 hrs. The reaction mixture was filtered and the filtrate was concentrated in vacuum to give a residue. The residue was purified by reversed-phase HPLC (0.1% TFA), followed by lyophilization. 2-Thiazol-5-ylacetic acid ((14), 140 mg, 977.90 μmol, 25.32% yield) was obtained as a yellow solid.

LCMS (ESI): m/z [M+H] calcd for $C_5H_6NO_2S$: 144.00; found: 144.1.

$^1$H NMR (400 MHZ, methanol-d$_4$) δ=8.92 (s, 1H), 7.74 (s, 1H), 3.95 (s, 2H).

Preparation of N-[3-(4,6-dimethylpyrimidin-5-yl)-4-(2-pyrrolidin-1-ylethoxy)phenyl]-2-thiazol-5-yl-acetamide (247)

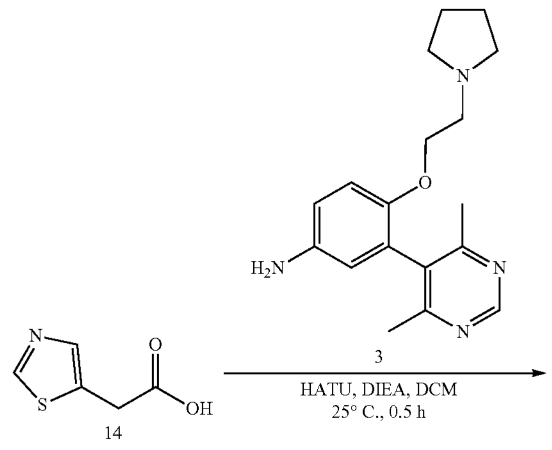

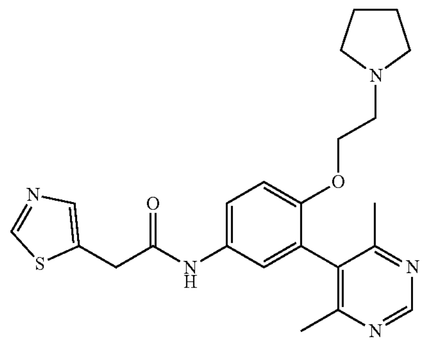

247

To a solution of 2-thiazol-5-ylacetic acid ((14), 50.41 mg, 352.10 μmol, 1.1 eq.) in DCM (2 mL) was added HATU (146.05 mg, 384.11 μmol, 1.2 eq.) and DIEA (124.11 mg, 960.28 μmol, 167.26 μL, 3 eq.). After 10 min, 3-(4,6-dimethylpyrimidin-5-yl)-4-(2-pyrrolidin-1-ylethoxy)aniline ((3), 100 mg, 320.09 μmol, 1 eq.) was added. The reaction mixture was stirred at 25° C. for 0.5 hrs. The reaction mixture was then concentrated in vacuum to give a residue. The residue was purified by prep-HPLC (column: Phenomenex Gemini-NX C18 75*30 mm*3 μm; mobile phase: [water (0.1% TFA)-ACN]; B %: 10%-20%, 7 min) followed by lyophilization. N-[3-(4,6-dimethylpyrimidin-5-yl)-4-(2-pyrrolidin-1-ylethoxy)phenyl]-2-thiazol-5-yl-acetamide (11.29 mg, 19.45 μmol, 6.07% yield, 95% purity, TFA) was obtained as a yellow gum.

LCMS (ESI): m/z [M+H] calcd for $C_{23}H_{27}N_5O_2S$: 438.19; found: 438.3.

$^1$H NMR (400 MHZ, methanol-$d_4$) δ=9.07 (s, 1H), 8.97-8.89 (m, 1H), 7.85 (s, 1H), 7.68 (dd, J=2.7, 8.9 Hz, 1H), 7.47 (d, J=2.6 Hz, 1H), 7.21 (d, J=8.9 Hz, 1H), 4.38-4.29 (m, 2H), 4.04 (d, J=0.7 Hz, 2H), 3.55-3.47 (m, 2H), 3.38 (br d, J=2.8 Hz, 2H), 2.96-2.76 (m, 2H), 2.31 (s, 6H), 2.02 (br d, J=9.0 Hz, 2H), 1.89 (br s, 2H).

N-[3-(4,6-dimethylpyrimidin-5-yl)-4-(2-pyrrolidin-1-ylethoxy)phenyl]-3-(4-fluorophenyl)propanamide (248)

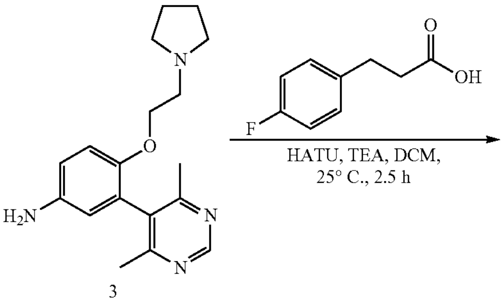

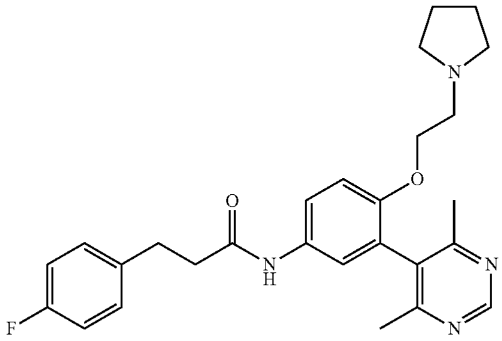

248

To a solution of 3-(4-fluorophenyl)propanoic acid (51.68 mg, 307.29 μmol, 1.2 eq.) in DCM (1 mL) was added HATU (116.84 mg, 307.29 μmol, 1.2 eq.) and TEA (77.74 mg, 768.23 μmol, 106.93 μL, 3 eq.). The reaction was stirred at 25° C. for 0.5 hrs, then 3-(4,6-dimethylpyrimidin-5-yl)-4-(2-pyrrolidin-1-ylethoxy)aniline ((3), 80 mg, 256.08 μmol, 1 eq.) was added. The mixture was stirred at 25° C. for 2 hrs. The reaction mixture was concentrated under reduced pressure to give a residue. The residue was purified by prep-HPLC (column: Waters Xbridge 150*25 mm*5 μm; mobile phase: [water (10 mM $NH_4HCO_3$)-ACN]; B %: 19%-49%, 9 min). N-[3-(4,6-dimethylpyrimidin-5-yl)-4-(2-pyrrolidin-1-ylethoxy)phenyl]-3-(4-fluorophenyl)propanamide (56.56 mg, 118.67 μmol, 46.34% yield, 97.052% purity) was obtained as a brown gum.

LCMS (ESI): m/z [M+H] calcd for $C_{27}H_{32}FN_4O_2$: 463.24; found: 463.3.

$^1$H NMR (400 MHZ, methanol-$d_4$) δ=8.84 (s, 1H), 7.56 (dd, J=2.6, 8.9 Hz, 1H), 7.32 (d, J=2.6 Hz, 1H), 7.29-7.21 (m, 2H), 7.11 (d, J=9.0 Hz, 1H), 7.04-6.93 (m, 2H), 4.11 (t, J=5.4 Hz, 2H), 2.98 (t, J=7.6 Hz, 2H), 2.75 (t, J=5.4 Hz, 2H), 2.64 (t, J=7.6 Hz, 2H), 2.42-2.34 (m, 4H), 2.26 (s, 6H), 1.69 (br t, J=3.4 Hz, 4H).

N-(3-(4,6-dimethylpyrimidin-5-yl)-4-(2-(pyrrolidin-1-yl)ethoxy)phenyl)-2-(1-methyl-1H-pyrrol-2-yl) acetamide (249)

249

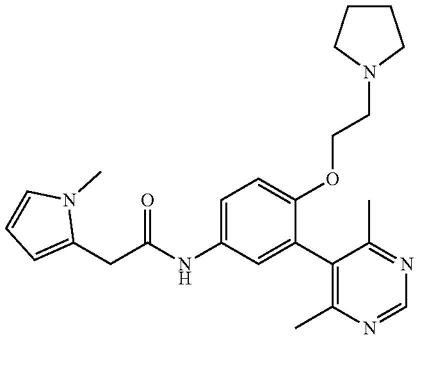

Compound 249 was prepared according to the synthesis described for compound 248, substituting 2-(1-methyl-1H-pyrrol-2-yl)acetic acid for 3-(4-fluorophenyl)propanoic acid.

LCMS (ESI): m/z [M+H] calcd for $C_{25}H_{32}N_5O_2$: 434.25; found: 434.3.

$^1$H NMR (400 MHZ, acetonitrile-d$_3$) δ=9.60-9.27 (m, 1H), 8.93 (s, 1H), 8.35 (br s, 1H), 7.64-7.58 (m, 1H), 7.35 (d, J=2.6 Hz, 1H), 7.07 (d, J=8.9 Hz, 1H), 6.61 (t, J=2.3 Hz, 1H), 6.01-5.94 (m, 2H), 4.27-4.21 (m, 2H), 3.63 (s, 2H), 3.57 (s, 3H), 3.34 (br d, J=4.0 Hz, 4H), 2.81 (br s, 2H), 2.25 (s, 6H), 1.91-1.78 (m, 4H).

N-(3-(4,6-dimethylpyrimidin-5-yl)-4-(2-(pyrrolidin-1-yl)ethoxy)phenyl)-2-(4-methylthiazol-5-yl)acetamide (250)

250

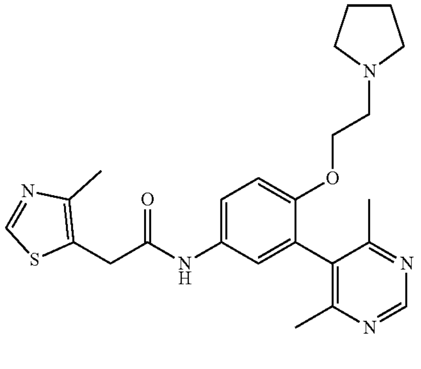

Compound 250 was prepared according to the synthesis described for compound 248, substituting 2-(4-methylthiazol-5-yl)acetic acid for 3-(4-fluorophenyl)propanoic acid.

LCMS (ESI): m/z [M+H] calcd for $C_{24}H_{30}N_5O_2S$: 452.20; found: 452.3.

$^1$H NMR (400 MHZ, methanol-d$_4$) δ-9.04 (s, 1H), 8.90 (s, 1H), 7.68 (dd, J=2.6, 9.0 Hz, 1H), 7.46 (d, J=2.5 Hz, 1H), 7.21 (d, J=9.0 Hz, 1H), 4.35-4.30 (m, 2H), 3.96 (s, 2H), 3.54-3.48 (m, 2H), 3.37 (br s, 2H), 2.95-2.76 (m, 2H), 2.46 (s, 3H), 2.29 (s, 6H), 2.07-1.95 (m, 2H), 1.95-1.82 (m, 2H).

N-(3-(4,6-dimethylpyrimidin-5-yl)-4-(2-(pyrrolidin-1-yl)ethoxy)phenyl)-2-phenylacetamide (251)

251

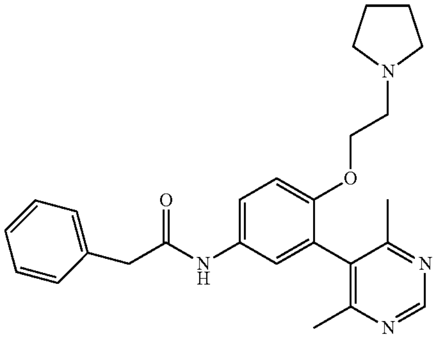

Compound 251 was prepared according to the synthesis described for compound 248, substituting 2-phenylacetic acid for 3-(4-fluorophenyl)propanoic acid.

LCMS (ESI): m/z [M+H] calcd for $C_{26}H_{31}N_4O_2$: 431.24; found: 431.3.

$^1$H NMR (400 MHZ, methanol-d$_4$) δ=8.83 (s, 1H), 7.61 (dd, J=2.6, 8.9 Hz, 1H), 7.39 (d, J=2.6 Hz, 1H), 7.38-7.28 (m, 4H), 7.28-7.21 (m, 1H), 7.12 (d, J=8.9 Hz, 1H), 4.12 (t, J=5.4 Hz, 2H), 3.67 (s, 2H), 2.76 (t, J=5.3 Hz, 2H), 2.42-2.36 (m, 4H), 2.26 (s, 6H), 1.69 (td, J=3.3, 6.8 Hz, 4H).

N-(3-(4,6-dimethylpyrimidin-5-yl)-4-(2-(pyrrolidin-1-yl)ethoxy)phenyl)-2-phenylpropanamide (252)

252

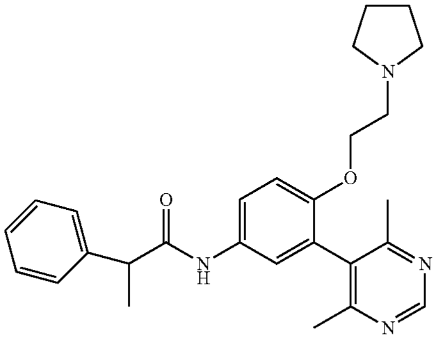

Compound 252 was prepared according to the synthesis described for compound 248, substituting 2-phenylpropanoic acid for 3-(4-fluorophenyl)propanoic acid.

LCMS (ESI): m/z [M+H] calcd for: $C_{27}H_{33}N_4O_2$: 445.25; found: 445.3.

$^1$H NMR (400 MHz, methanol-d$_4$) δ=8.83 (s, 1H), 7.58 (dd, J=2.7, 8.9 Hz, 1H), 7.43-7.37 (m, 2H), 7.36 (d, J=2.7 Hz, 1H), 7.34-7.28 (m, 2H), 7.27-7.20 (m, 1H), 7.10 (d, J=8.9 Hz, 1H), 4.10 (t, J=5.4 Hz, 2H), 3.79 (q, J=7.0 Hz, 1H), 2.74 (t, J=5.4 Hz, 2H), 2.42-2.33 (m, 4H), 2.25 (d, J=1.5 Hz, 6H), 1.69 (td, J=3.3, 6.8 Hz, 4H), 1.50 (d, J=7.1 Hz, 3H).

N-(3-(4,6-dimethylpyrimidin-5-yl)-4-(2-(pyrrolidin-1-yl)ethoxy)phenyl)-1-phenylcyclopropane-1-carboxamide (253)

253

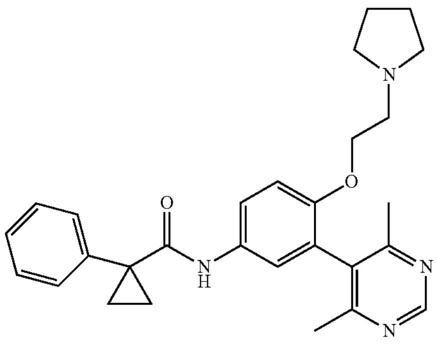

Compound 253 was prepared according to the synthesis described for compound 248, substituting 1-phenylcyclopropane-1-carboxylic acid for 3-(4-fluorophenyl)propanoic acid.

LCMS (ESI): m/z [M+H] calcd for: $C_{28}H_{33}N_4O_2$: 457.25; found: 457.4.

$^1$H NMR (400 MHZ, methanol-$d_4$) δ=8.82 (s, 1H), 7.53-7.46 (m, 2H), 7.45-7.38 (m, 3H), 7.38-7.30 (m, 1H), 7.22 (d, J=2.6 Hz, 1H), 7.08 (d, J=8.9 Hz, 1H), 4.11 (t, J=5.3 Hz, 2H), 2.80 (t, J=5.2 Hz, 2H), 2.43 (br s, 4H), 2.23 (s, 6H), 1.70 (td, J=3.3, 6.8 Hz, 4H), 1.61-1.54 (m, 2H), 1.20-1.14 (m, 2H).

N-(3-(4,6-dimethylpyrimidin-5-yl)-4-(2-(pyrrolidin-1-yl)ethoxy)phenyl)-2-(4-fluorophenyl)acetamide (254)

254

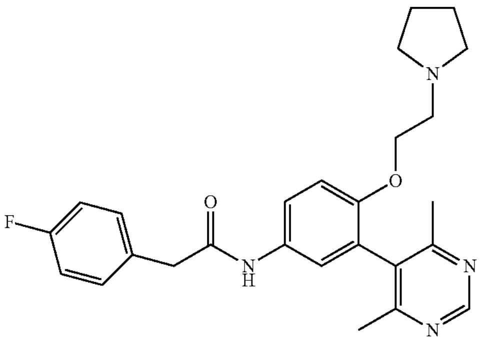

Compound 254 was prepared according to the synthesis described for compound 248, substituting 2-(4-fluorophenyl)acetic acid for 3-(4-fluorophenyl)propanoic acid.

LCMS (ESI): m/z [M+H] calcd for: $C_{26}H_{30}FN_4O_2$: 449.23; found: 449.3.

$^1$H NMR (400 MHZ, methanol-$d_4$) δ=8.83 (s, 1H), 7.61 (dd, J=2.6, 8.9 Hz, 1H), 7.47-7.27 (m, 3H), 7.12 (d, J=9.0 Hz, 1H), 7.09-6.99 (m, 2H), 4.12 (t, J=5.4 Hz, 2H), 3.65 (s, 2H), 2.78 (t, J=5.3 Hz, 2H), 2.45-2.36 (m, 4H), 2.25 (s, 6H), 1.76-1.64 (m, 4H).

N-(3-(4,6-dimethylpyrimidin-5-yl)-4-(2-(pyrrolidin-1-yl)ethoxy)phenyl)-3-phenylpropanamide (255)

255

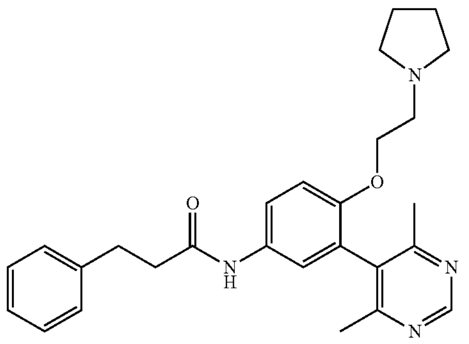

Compound 255 was prepared according to the synthesis described for compound 248, substituting 3-phenylpropanoic acid for 3-(4-fluorophenyl)propanoic acid.

LCMS (ESI): m/z [M+H] calcd for: $C_{27}H_{33}N_4O_2$: 445.25; found: 445.3.

$^1$H NMR (400 MHZ, methanol-$d_4$) δ=8.84 (s, 1H), 7.55 (dd, J=2.6, 9.0 Hz, 1H), 7.32 (d, J=2.6 Hz, 1H), 7.30-7.21 (m, 4H), 7.17 (td, J=2.8, 6.1 Hz, 1H), 7.10 (d, J=8.9 Hz, 1H), 4.11-4.11 (m, 1H), 4.11 (t, J=5.4 Hz, 1H), 2.99 (t, J=7.7 Hz, 2H), 2.73 (t, J=5.4 Hz, 2H), 2.65 (t, J=7.7 Hz, 2H), 2.39-2.33 (m, 4H), 2.26 (s, 6H), 1.68 (td, J=3.3, 6.8 Hz, 4H).

N-(3-(4,6-dimethylpyrimidin-5-yl)-4-(2-(pyrrolidin-1-yl)ethoxy)phenyl)-3-(thiazol-2-yl)propanamide (256)

256

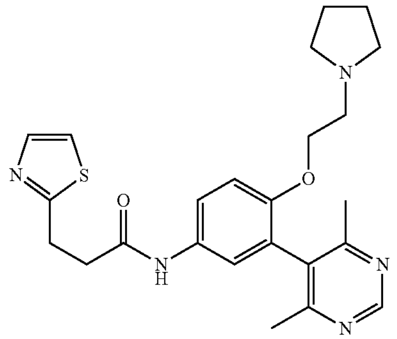

Compound 256 was prepared according to the synthesis described for compound 248, substituting 3-(thiazol-2-yl)propanoic acid for 3-(4-fluorophenyl)propanoic acid.

LCMS (ESI): m/z [M+H] calcd for: $C_{24}H_{30}N_5O_2S$: 452.20; found: 452.3.

$^1$H NMR (400 MHZ, methanol-$d_4$) δ=8.84 (s, 1H), 7.68 (d, J=3.4 Hz, 1H), 7.59 (dd, J=2.6, 8.9 Hz, 1H), 7.45 (d, J=3.4 Hz, 1H), 7.38 (d, J=2.5 Hz, 1H), 7.12 (d, J=9.0 Hz, 1H), 4.13 (t, J=5.3 Hz, 2H), 3.41 (t, J=7.3 Hz, 2H), 2.87 (t, J=7.3 Hz, 2H), 2.81 (t, J=5.3 Hz, 2H), 2.43 (br s, 4H), 2.26 (s, 6H), 1.71 (td, J=3.3, 6.7 Hz, 4H).

N-(3-(4,6-dimethylpyrimidin-5-yl)-4-(2-(pyrrolidin-1-yl)ethoxy)phenyl)-3-(thiazol-5-yl)propanamide (257)

257

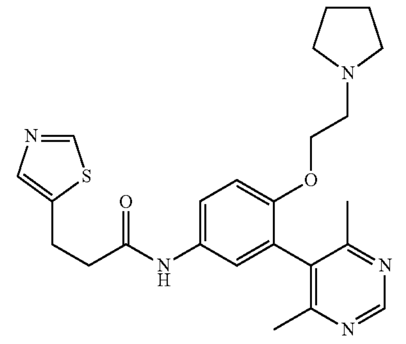

Compound 257 was prepared according to the synthesis described for compound 248, substituting 3-(thiazol-5-yl) propanoic acid for 3-(4-fluorophenyl)propanoic acid.

LCMS (ESI): m/z [M+H] calcd for $C_{24}H_{30}N_5O_2S$: 452.20; found: 452.2.

$^1$H NMR (400 MHZ, methanol-d$_4$) δ=8.84 (s, 2H), 7.69 (s, 1H), 7.58 (dd, J=2.6, 8.9 Hz, 1H), 7.36 (d, J=2.6 Hz, 1H), 7.12 (d, J=8.9 Hz, 1H), 4.11 (t, J=5.4 Hz, 2H), 3.29-3.26 (m, 2H), 2.74 (s, 4H), 2.40-2.33 (m, 4H), 2.26 (s, 6H), 1.73-1.65 (m, 4H).

N-[3-(4,6-dimethylpyrimidin-5-yl)-4-(2-pyrrolidin-1-ylethoxy)phenyl]-3-oxazol-4-yl-propanamide (258)

Preparation of ethyl 3-oxazol-4-ylprop-2-enoate (15)

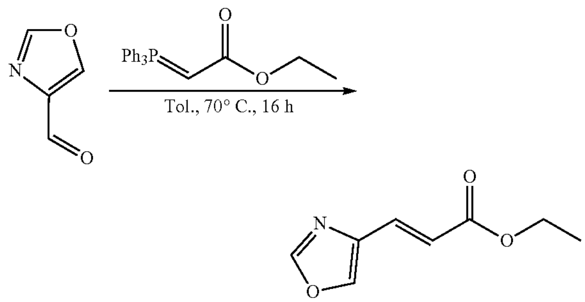

15

Ethyl 2-(triphenyl-phosphanylidene)acetate (789.54 mg, 2.27 mmol, 1.1 eq.) was added to a solution of oxazole-4-carbaldehyde (200 mg, 2.06 mmol, 1 eq.) in toluene (4 mL). The reaction mixture was stirred at 70° C. for 16 hrs. The reaction mixture was concentrated in vacuum to give a residue. The residue was purified by flash silica gel chromatography (ISCO®; 12 g SepaFlash® Silica Flash Column, eluent of 0~30% ethyl acetate/petroleum ether gradient). Ethyl 3-oxazol-4-ylprop-2-enoate ((15), 226 mg, 1.34 mmol, 64.96% yield, 99% purity) was obtained as a colorless oil.

LCMS (ESI): m/z [M+H] calcd for $C_8H_{10}NO_3$: 168.06; found: 168.2.

$^1$H NMR (400 MHZ, methanol-d$_4$) δ=8.21 (d, J=15.5 Hz, 2H), 7.57 (d, J=15.8 Hz, 1H), 6.57 (d, J=15.6 Hz, 1H), 4.23 (q, J=7.1 Hz, 2H), 1.31 (t, J=7.1 Hz, 3H).

Preparation of ethyl 3-oxazol-4-ylpropanoate (16)

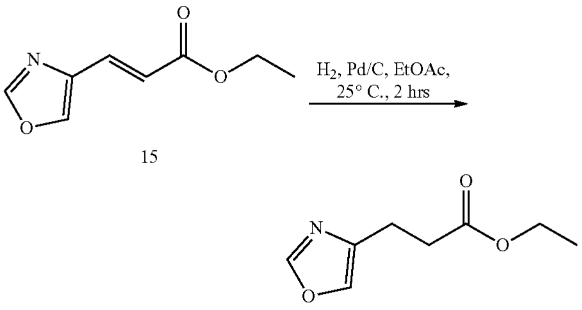

15

16

To a solution of ethyl 3-oxazol-4-ylprop-2-enoate ((15), 220 mg, 1.30 mmol, 1 eq.) in EtOAc (4 mL) was added Pd/C (20 mg, 10% purity). The suspension was degassed under vacuum and purged with $H_2$ several times. The mixture was stirred under $H_2$ (15 psi) at 25° C. for 2 hr. The reaction mixture was filtered and the filtrate was concentrated in vacuum to give a residue. Ethyl 3-oxazol-4-ylpropanoate ((16), 200 mg, crude) was obtained as a colorless oil.

LCMS (ESI): m/z [M+H] calcd for $C_8H_{12}NO_3$: 170.07; found: 170.2.

Preparation of 3-oxazol-4-ylpropanoic acid (17)

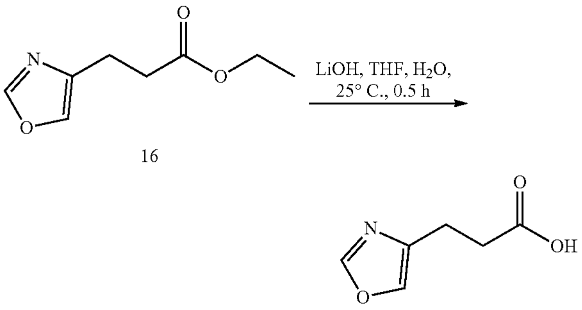

16

17

To a solution of ethyl 3-oxazol-4-ylpropanoate ((16), 200 mg, 1.18 mmol, 1 eq.) in THF (2 mL) was added LiOH (84.94 mg, 3.55 mmol, 3 eq.) in $H_2O$ (2 mL). The reaction mixture was stirred at 25° C. for 0.5 hrs. The reaction mixture was concentrated in vacuum and diluted with water (10 mL). To the aqueous phase was added HCl (1M) to adjust the mixture to pH=3 and extracted with EtOAC (10 mL×3). The combined organic phase was dried with anhydrous $Na_2SO_4$, and filtered, and the filtrate was concentrated in vacuum to give a residue. 3-Oxazol-4-ylpropanoic acid ((17), 120 mg, crude) was obtained as a white solid.

$^1$H NMR (400 MHZ, DMSO-d$_6$) δ=8.26 (s, 1H), 7.83 (d, J=1.1 Hz, 1H), 2.74-2.67 (m, 2H), 2.54 (d, J=7.6 Hz, 2H)

Preparation of N-[3-(4,6-dimethylpyrimidin-5-yl)-4-(2-pyrrolidin-1-ylethoxy)phenyl]-3-oxazol-4-yl-propanamide (258)

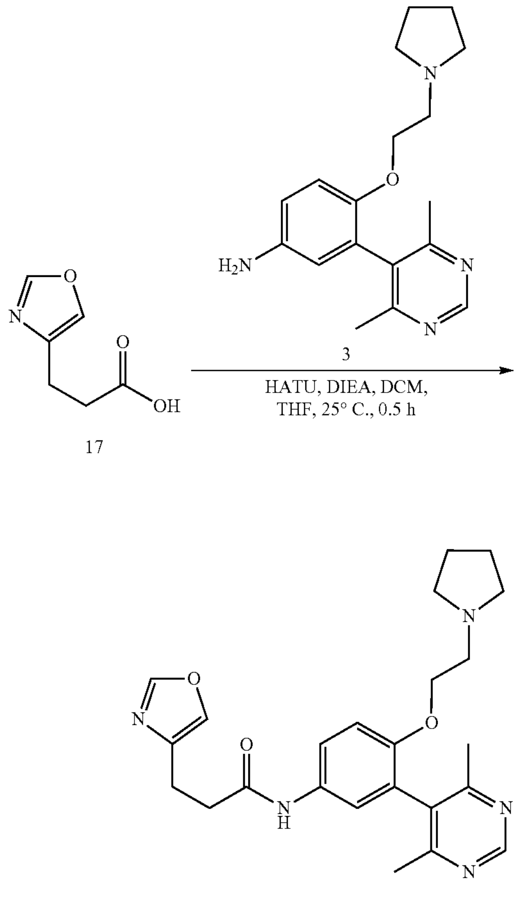

17

258

To a solution of 3-oxazol-4-ylpropanoic acid ((17), 49.69 mg, 352.10 μmol, 1.1 eq.) in DCM (3 mL) was added HATU (146.05 mg, 384.11 μmol, 1.2 eq.) and DIEA (124.11 mg, 960.27 μmol, 167.26 μL, 3 eq.). The mixture was stirred at 25° C. for 10 min and then 3-(4,6-dimethylpyrimidin-5-yl)-4-(2-pyrrolidin-1-ylethoxy)aniline ((3), 100 mg, 320.09 μmol, 1 eq.) in THF (1 mL) was added. The reaction mixture was stirred at 25° C. for 0.5 hrs. The reaction mixture was then concentrated in vacuum to give a residue. The residue was purified by prep-HPLC (column: Waters Xbridge 150*25 mm*5 μm; mobile phase: [water (0.05% ammonia hydroxide v/v)-ACN]; B %: 9%-38%, 10 min) followed by lyophilization. N-[3-(4,6-dimethylpyrimidin-5-yl)-4-(2-pyrrolidin-1-ylethoxy)phenyl]-3-oxazol-4-yl-propanamide (70.38 mg, 159.98 μmol, 49.98% yield, 99% purity) was obtained as an off-white solid.

LCMS (ESI): m/z [M+H] calcd for $C_{24}H_{29}N_5O_3$: 436.23; found: 436.3.

$^1$H NMR (400 MHZ, methanol-$d_4$) δ=8.84 (s, 1H), 8.13 (s, 1H), 7.71 (d, J=0.9 Hz, 1H), 7.58 (dd, J=2.6, 8.9 Hz, 1H), 7.37 (d, J=2.6 Hz, 1H), 7.12 (d, J=8.9 Hz, 1H), 5.49 (s, 1H), 4.11 (t, J=5.4 Hz, 2H), 2.97-2.88 (m, 2H), 2.77-2.66 (m, 4H), 2.40-2.31 (m, 4H), 2.26 (s, 6H), 1.68 (td, J=3.3, 6.8 Hz, 4H).

N-[3-(4,6-dimethylpyrimidin-5-yl)-4-(2-pyrrolidin-1-ylethoxy)phenyl]-3-(2-methyloxazol-4-yl)propanamide (259)

Preparation of ethyl 3-(2-methyloxazol-4-yl) prop-2-enoate (18)

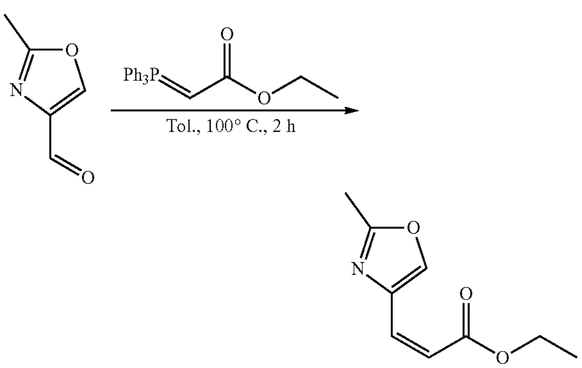

18

Ethyl 2-(triphenyl-phosphanylidene)acetate (689.86 mg, 1.98 mmol, 1.1 eq.) was added to a solution of 2-methyloxazole-4-carbaldehyde (200 mg, 1.80 mmol, 1 eq.) in toluene (2 mL). The reaction mixture was stirred at 100° C. for 2 hrs. The reaction mixture was then concentrated in vacuum to give a residue. The residue was purified by flash silica gel chromatography (ISCO®; 12 g SepaFlash® Silica Flash Column, eluent of 0~40% ethyl acetate/petroleum ether gradient). Ethyl 3-(2-methyloxazol-4-yl) prop-2-enoate ((18), 300 mg, 1.62 mmol, 90.14% yield, 98% purity) was obtained as a yellow oil.

LCMS (ESI): m/z [M+H] calcd for $C_9H_{12}NO_3$: 182.07; found: 182.2.

Preparation of ethyl 3-(2-methyloxazol-4-yl)propanoate (19)

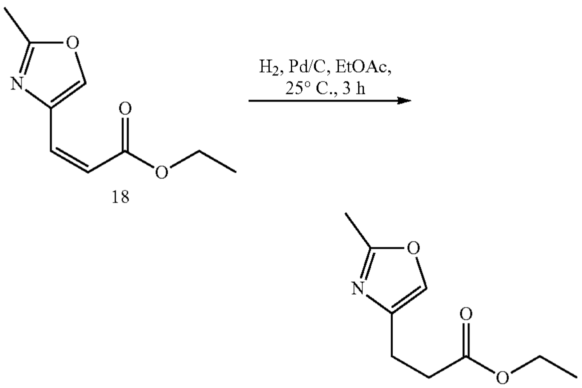

18

19

To a solution of ethyl 3-(2-methyloxazol-4-yl) prop-2-enoate ((18), 300 mg, 1.62 mmol, 1 eq.) in EtOAc (4 mL) was added Pd/C (20 mg, 10% purity). The suspension was degassed under vacuum and purged with $H_2$ several times. The mixture was stirred under $H_2$ (15 psi) at 25° C. for 3 hrs. The reaction mixture was filtered and the filtrate was concentrated in vacuum to give a residue. Ethyl 3-(2-methyloxazol-4-yl)propanoate ((19), 294 mg, crude) was obtained as a colorless oil.

LCMS (ESI): m/z [M+H] calcd for $C_9H_{14}NO_3$: 184.09; found: 184.1.

Preparation of 3-(2-methyloxazol-4-yl)propanoic acid (20)

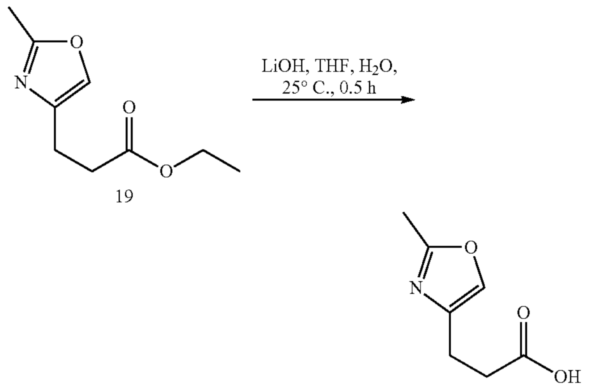

19

20

To a solution of ethyl 3-(2-methyloxazol-4-yl)propanoate ((19), 294 mg, 1.60 mmol, 1 eq.) in THF (2 mL) was added LiOH (115.29 mg, 4.81 mmol, 3 eq.) in $H_2O$ (2 mL). The reaction mixture was stirred at 25° C. for 0.5 hrs. The reaction mixture was concentrated in vacuum and diluted with water (10 mL). To the aqueous phase was added HCl (1M) to adjust to pH=3 and then was extracted with EtOAC (10 mL×3). The combined organic phase was dried with anhydrous $Na_2SO_4$, and filtered. The filtrate was concentrated to give a residue. 3-(2-Methyloxazol-4-yl)propanoic acid ((20), 160 mg, crude) was obtained as a white solid.

$^1$H NMR (400 MHZ, DMSO-$d_6$) δ=13.41-10.63 (m, 1H), 7.65 (s, 1H), 2.67-2.58 (m, 2H), 2.48 (s, 2H), 2.35 (s, 3H)

Preparation of N-[3-(4,6-dimethylpyrimidin-5-yl)-4-(2-pyrrolidin-1-ylethoxy)phenyl]-3-(2-methyloxazol-4-yl)propanamide (259)

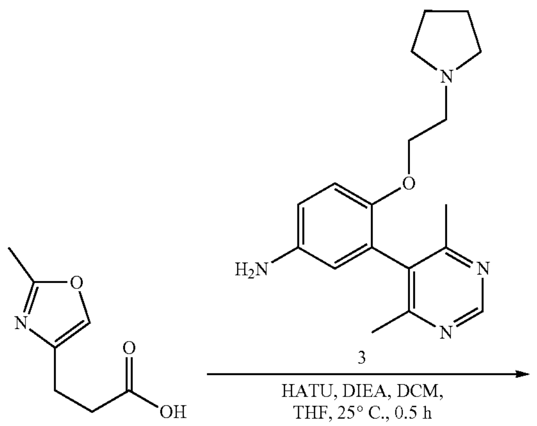

20

-continued

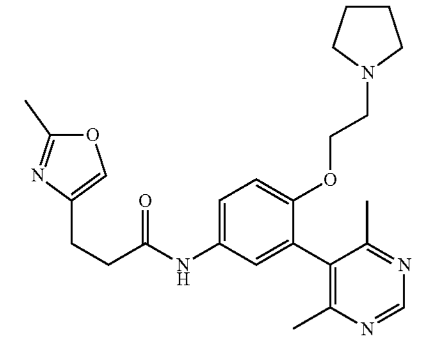

259

To a solution of 3-(2-methyloxazol-4-yl)propanoic acid ((20), 54.63 mg, 352.10 μmol, 1.1 eq.) in DCM (3 mL) was added HATU (146.05 mg, 384.11 μmol, 1.2 eq.) and DIEA (124.11 mg, 960.28 μmol, 167.26 μL, 3 eq.). The mixture was stirred at 25° C. for 10 min and then 3-(4,6-dimethylpyrimidin-5-yl)-4-(2-pyrrolidin-1-ylethoxy)aniline ((3), 100 mg, 320.09 μmol, 1 eq.) in THF (1 mL) was added. The reaction mixture was stirred at 25° C. for 0.5 hrs. The reaction mixture was concentrated in vacuum to give a residue. The residue was purified by prep-HPLC (column: Waters Xbridge 150*25 mm*5 μm; mobile phase: [water (0.05% ammonia hydroxide v/v)-ACN]; B %: 8%-38%, 10 min) followed by lyophilization. N-[3-(4,6-dimethylpyrimidin-5-yl)-4-(2-pyrrolidin-1-ylethoxy)phenyl]-3-(2-methyloxazol-4-yl)propanamide (73.60 mg, 162.08 μmol, 50.64% yield, 99% purity) was obtained as a yellow solid.

LCMS (ESI): m/z [M+H] calcd for $C_{25}H_{31}NO_3$: 450.24; found: 450.3.

$^1$H NMR (400 MHZ, methanol-$d_4$) δ=8.84 (s, 1H), 7.58 (dd, J=2.6, 8.9 Hz, 1H), 7.54 (s, 1H), 7.38 (d, J=2.6 Hz, 1H), 7.12 (d, J=8.9 Hz, 1H), 4.11 (t, J=5.4 Hz, 2H), 2.88-2.80 (m, 2H), 2.78-2.62 (m, 4H), 2.46-2.32 (m, 7H), 2.26 (s, 6H), 1.69 (td, J=3.3, 6.8 Hz, 4H).

N-[3-(4,6-dimethylpyrimidin-5-yl)-4-(2-pyrrolidin-1-ylethoxy)phenyl]-2-oxazol-5-yl-acetamide (260)

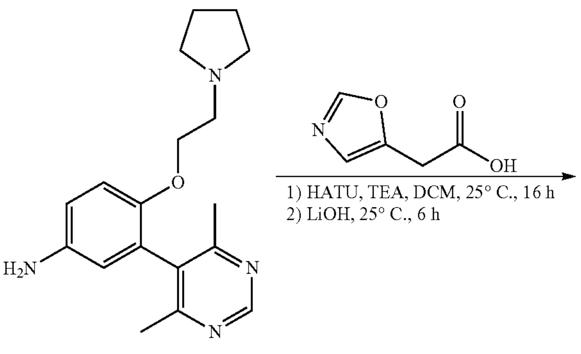

3

-continued

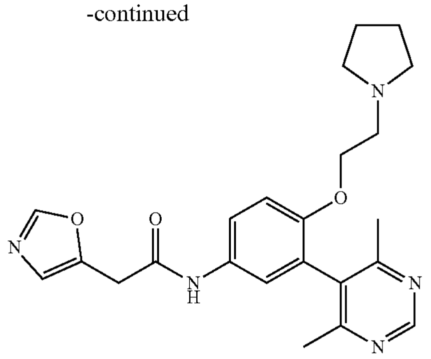

260

To a solution of 2-oxazol-5-ylacetic acid (24.41 mg, 192.06 μmol, 1.2 eq.) in DCM (1 mL) was added HATU (73.03 mg, 192.06 μmol, 1.2 eq.) and TEA (48.59 mg, 480.15 μmol, 66.83 μL, 3 eq.), then was stirred at 25° C. for 0.5 hrs. 3-(4,6-Dimethylpyrimidin-5-yl)-4-(2-pyrrolidin-1-ylethoxy)aniline ((3), 50 mg, 160.05 μmol, 1 eq.) was then added. The mixture was stirred at 25° C. for 16 hrs. LiOH (2 M, 1 mL, 12.50 eq.) was added to the mixture and the mixture was stirred at 25° C. for 6 hrs. The reaction mixture was then concentrated under reduced pressure to give a residue. The residue was purified by prep-HPLC (column: Phenomenex Gemini-NX C18 75*30 mm*3 μm; mobile phase: [water (0.1% TFA)-ACN]; B %: 10%-20%, 7 min). N-[3-(4,6-dimethylpyrimidin-5-yl)-4-(2-pyrrolidin-1-ylethoxy)phenyl]-2-oxazol-5-yl-acetamide (24.18 mg, 43.76 μmol, 27.34% yield, 96.906% purity, TFA) was obtained as a brown gum.

LCMS (ESI): m/z [M+H] calcd for $C_{23}H_{28}N_5O_3$: 422.21; found: 422.2.

$^1$H NMR (400 MHZ, methanol-$d_4$) δ=8.90 (s, 1H), 8.16 (s, 1H), 7.68 (d, J=2.7 Hz, 1H), 7.45 (d, J=2.7 Hz, 1H), 7.21 (d, J=8.9 Hz, 1H), 7.07 (s, 1H), 4.35-4.30 (m, 2H), 3.89-3.85 (m, 2H), 3.54-3.49 (m, 2H), 3.41-3.33 (m, 2H), 2.91-2.80 (m, 2H), 2.30 (s, 6H), 2.06-1.96 (m, 2H), 1.88 (br dd, J=5.3, 7.3 Hz, 2H).

N-(3-(4,6-dimethylpyrimidin-5-yl)-4-(2-(pyrrolidin-1-yl)ethoxy)phenyl)-2-(5-methyl-1,2,4-oxadiazol-3-yl)acetamide (261)

261

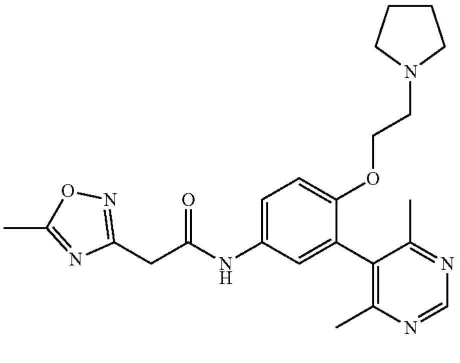

Compound 261 was prepared according to the synthesis described for compound 260, substituting 2-(5-methyl-1,2,4-oxadiazol-3-yl)acetic acid for 2-oxazol-5-ylacetic acid.

LCMS (ESI): m/z [M+H] calcd for $C_{23}H_{29}N_6O_3$: 437.22; found: 437.2.

$^1$H NMR (400 MHZ, methanol-$d_4$) δ=8.89 (s, 1H), 7.70 (dd, J=2.6, 9.0 Hz, 1H), 7.46 (d, J=2.5 Hz, 1H), 7.21 (d, J=9.0 Hz, 1H), 4.37-4.29 (m, 2H), 3.86 (s, 2H), 3.55-3.46 (m, 2H), 3.37 (br s, 2H), 2.86 (br d, J=5.0 Hz, 2H), 2.59 (s, 3H), 2.29 (s, 6H), 2.03 (br d, J=7.6 Hz, 2H), 1.94-1.82 (m, 2H).

N-(3-(4,6-dimethylpyrimidin-5-yl)-4-(2-(pyrrolidin-1-yl)ethoxy)phenyl)-2-(isoxazol-3-yl)acetamide (262)

262

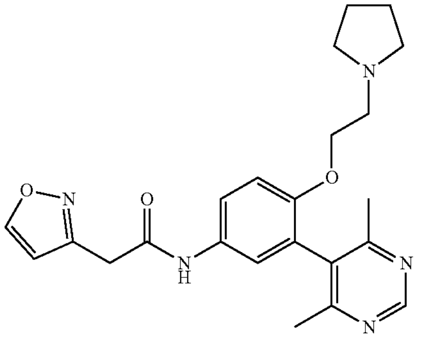

Compound 262 was prepared according to the synthesis described for compound 260, substituting 2-(isoxazol-3-yl)acetic acid for 2-oxazol-5-ylacetic acid.

LCMS (ESI): m/z [M+H] calcd for $C_{23}H_{28}N_5O$: 422.21; found: 422.2.

$^1$H NMR (400 MHZ, methanol-$d_4$) δ=8.89 (s, 1H), 8.62 (d, J=1.6 Hz, 1H), 7.67 (s, 1H), 7.46 (d, J=2.6 Hz, 1H), 7.20 (d, J=8.9 Hz, 1H), 6.55 (d, J=1.7 Hz, 1H), 4.36-4.29 (m, 2H), 3.84 (s, 2H), 3.54-3.47 (m, 2H), 3.36 (br d, J=8.1 Hz, 2H), 2.93-2.76 (m, 2H), 2.29 (s, 6H), 2.06-1.95 (m, 2H), 1.88 (br d, J=4.8 Hz, 2H).

N-(3-(4,6-dimethylpyrimidin-5-yl)-4-(2-(pyrrolidin-1-yl)ethoxy)phenyl)-2-(isoxazol-5-yl)acetamide (263)

263

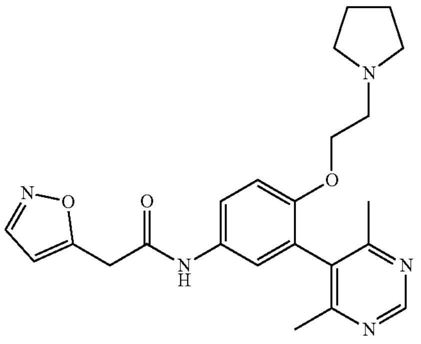

Compound 263 was prepared according to the synthesis described for compound 260, substituting 2-(isoxazol-5-yl)acetic acid for 2-oxazol-5-ylacetic acid.

LCMS (ESI): m/z [M+H] calcd for $C_{23}H_{28}N_5O_3$: 422.21; found: 422.3.

$^1$H NMR (400 MHZ, methanol-$d_4$) δ=8.90 (s, 1H), 8.35 (d, J=1.8 Hz, 1H), 7.74-7.65 (m, 1H), 7.45 (d, J=2.6 Hz, 1H), 7.21 (d, J=9.0 Hz, 1H), 6.39 (d, J=1.8 Hz, 1H), 4.36-4.29 (m, 2H), 3.97 (s, 2H), 3.55-3.47 (m, 2H), 3.40-3.34 (m, 2H), 2.86 (br d, J=6.1 Hz, 2H), 2.29 (s, 6H), 2.03 (br d, J=5.5 Hz, 2H), 1.93-1.82 (m, 2H).

N-(3-(4,6-dimethylpyrimidin-5-yl)-4-(2-(pyrrolidin-1-yl)ethoxy)phenyl)-2-(3-methylisoxazol-5-yl)acetamide (264)

264

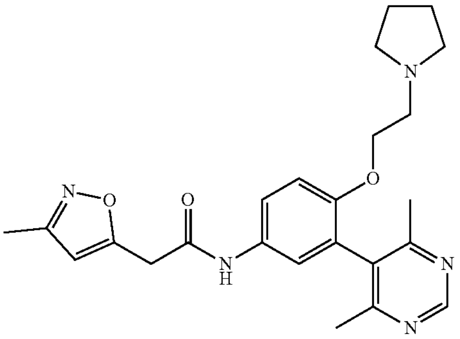

Compound 264 was prepared according to the synthesis described for compound 260, substituting 2-(3-methylisoxazol-5-yl)acetic acid for 2-oxazol-5-ylacetic acid.

LCMS (ESI): m/z [M+H] calcd for $C_{24}H_{30}N_5O_3$: 436.23; found: 436.2.

$^1$H NMR (400 MHZ, methanol-$d_4$) δ=8.89 (s, 1H), 7.69 (dd, J=2.6, 8.9 Hz, 1H), 7.45 (d, J=2.6 Hz, 1H), 7.21 (d, J=9.0 Hz, 1H), 6.25 (s, 1H), 4.36-4.29 (m, 2H), 3.89 (s, 2H), 3.54-3.49 (m, 2H), 3.41-3.34 (m, 2H), 2.86 (br s, 2H), 2.32-2.24 (m, 9H), 2.01 (br s, 2H), 1.88 (br d, J=6.3 Hz, 2H).

N-(3-(4,6-dimethylpyrimidin-5-yl)-4-(2-(pyrrolidin-1-yl)ethoxy)phenyl)-2-(3-methyl-1,2,4-oxadiazol-5-yl)acetamide (265)

265

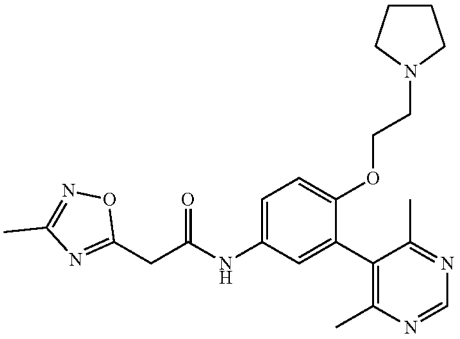

Compound 265 was prepared according to the synthesis described for compound 260, substituting 2-(3-methyl-1,2,4-oxadiazol-5-yl)acetic acid for 2-oxazol-5-ylacetic acid.

LCMS (ESI): m/z [M+H] calcd for $C_{23}H_{29}N_6O_3$: 437.22; found: 437.2.

$^1$H NMR (400 MHZ, methanol-$d_4$) δ=8.89 (s, 1H), 7.68 (s, 1H), 7.46 (t, J=2.8 Hz, 1H), 7.22 (d, J=9.0 Hz, 1H), 4.33 (t, J=4.3 Hz, 2H), 4.11-4.06 (m, 2H), (3.55-3.47 (m, 2H), 3.42-3.33 (m, 2H), 2.92-2.77 (m, 2H), 2.37 (s, 3H), 2.29 (s, 6H), 2.08-1.96 (m, 2H), 1.95-1.80 (m, 2H).

N-(3-(4,6-dimethylpyrimidin-5-yl)-4-(2-(pyrrolidin-1-yl)ethoxy)phenyl)-2-(2-methylthiazol-5-yl)acetamide (266)

266

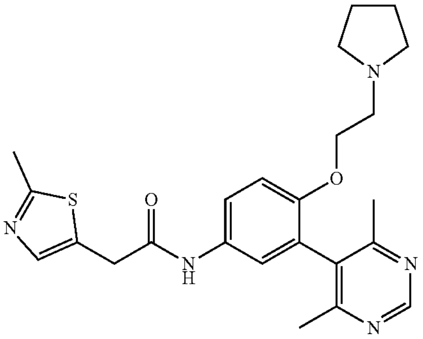

Compound 266 was prepared according to the synthesis described for compound 260, substituting 2-(2-methylthiazol-5-yl)acetic acid for 2-oxazol-5-ylacetic acid.

LCMS (ESI): m/z [M+H] calcd for $C_{24}H_{30}N_5O_2S$: 452.20; found: 452.3.

$^1$H NMR (400 MHZ, methanol-$d_4$) δ=8.88 (s, 1H), 7.67 (dd, J=2.6, 8.9 Hz, 1H), 7.47 (s, 1H), 7.43 (d, J=2.6 Hz, 1H), 7.19 (d, J=9.0 Hz, 1H), 4.29 (t, J=5.0 Hz, 2H), 3.90 (s, 2H), 3.39 (br s, 2H), 2.99 (br d, J=4.4 Hz, 4H), 2.66 (s, 3H), 2.28 (s, 6H), 1.91 (br s, 4H).

2-(1,5-dimethyl-1H-pyrazol-3-yl)-N-(3-(4,6-dimethylpyrimidin-5-yl)-4-(2-(pyrrolidin-1-yl)ethoxy)phenyl)acetamide (267)

267

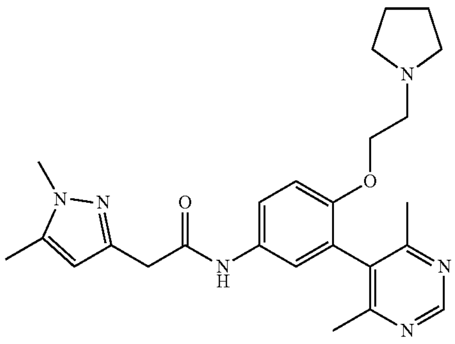

Compound 267 was prepared according to the synthesis described for compound 260, substituting 2-(1,5-dimethyl-1H-pyrazol-3-yl)acetic acid for 2-oxazol-5-ylacetic acid.

LCMS (ESI): m/z [M+H] calcd for $C_{25}H_{33}N_6O_2$: 449.26; found: 449.4.

$^1$H NMR (400 MHZ, methanol-$d_4$) δ=8.83 (s, 1H), 7.60 (dd, J=2.6, 8.9 Hz, 1H), 7.41 (d, J=2.6 Hz, 1H), 7.12 (d, J=9.0 Hz, 1H), 6.03 (s, 1H), 4.12 (t, J=5.4 Hz, 2H), 3.72 (s, 3H), 3.64-3.58 (m, 2H), 2.76 (t, J=5.3 Hz, 2H), 2.42-2.35 (m, 4H), 2.26 (s, 9H), 1.69 (td, J=3.3, 6.9 Hz, 4H).

N-[3-(4,6-dimethylpyrimidin-5-yl)-4-(2-pyrrolidin-1-ylethoxy)phenyl]-2-(1-methylpyrrol-3-yl)acetamide (268)

Preparation of ethyl 2-(1-methylpyrrol-3-yl)acetate (21)

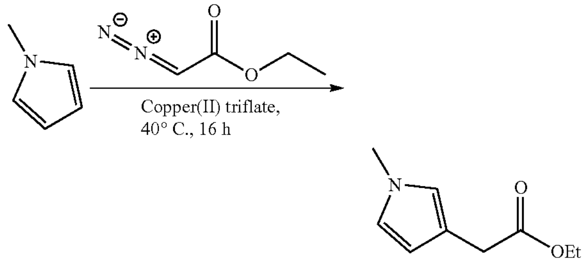

21

To a mixture of 1-methylpyrrole (1 g, 12.33 mmol, 1.10 mL, 1 eq.) and copper (II) triflate (222.94 mg, 616.40 μmol, 0.05 eq.) in DCM (3 mL) was added ethyl 2-diazoacetate (422.00 mg, 3.70 mmol, 387.15 μL, 0.3 eq.). The mixture was stirred at 40° C. for 16 hrs. LCMS showed the 1-methylpyrrole was consumed and the desired mass was detected. The mixture was filtered and concentrated in vacuum. The residue was purified by silica gel chromatography (column height: 250 mm, diameter: 100 mm, 100-200 mesh silica gel, petroleum ether/ethyl acetate=10/1, 8/1). 210 mg (mixture) of ethyl 2-(1-methylpyrrol-3-yl)acetate ((21), 210 mg, 1.22 mmol, 9.88% yield, 97% purity) was obtained as colorless oil.

LCMS (ESI): m/z [M+H] calcd for $C_9H_{14}NO_2$: 168.09; found: 168.2.

Preparation of 2-(1-methylpyrrol-3-yl)acetic acid (22)

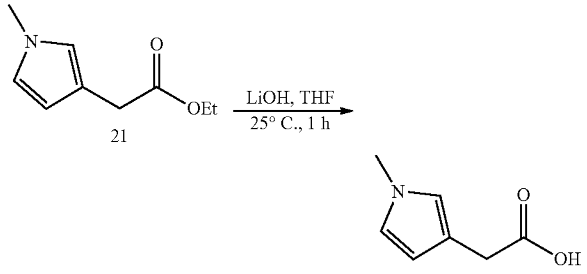

22

To a mixture (210 mg) of ethyl 2-(1-methylpyrrol-3-yl) acetate ((21), 210 mg, 1.26 mmol, 1 eq.), EtOH (3 mL) and $H_2O$ (1 mL) was added LiOH $H_2O$ (105.41 mg, 2.51 mmol, 2 eq.). The mixture was stirred at 25° C. for 1 hr. LCMS showed the ethyl 2-(1-methylpyrrol-3-yl)acetate and ethyl 2-(1-methylpyrrol-2-yl)acetate was consumed and the desired mass was detected. The mixture was concentrated to remove excess EtOH. The residue was acidified with 1M HCl (aq.) and, the pH was adjusted to 6-7. Then the mixture was concentrated. The residue was purified by prep-HPLC (column: Phenomenex Luna C18 150*25 mm*10 μm; mobile phase: [water (0.1% TFA)-ACN]; B %: 1%-25%, 10 min). 2-(1-methylpyrrol-3-yl)acetic acid ((22), 50 mg, 359.32 μmol, 28.61% yield) was obtained as a yellow oil.

$^1H$ NMR (400 MHZ, methanol-$d_4$) δ=6.58 (d, J=2.5 Hz, 1H), 6.55-6.51 (m, 1H), 5.95 (d, J=2.9 Hz, 1H), 5.94-5.90 (m, 1H), 3.59 (s, 3H), 3.56 (s, 2H), 3.38 (s, 2H), 3.35 (s, 1H).

Preparation of N-[3-(4,6-dimethylpyrimidin-5-yl)-4-(2-pyrrolidin-1-ylethoxy)phenyl]-2-(1-methylpyrrol-3-yl)acetamide (268)

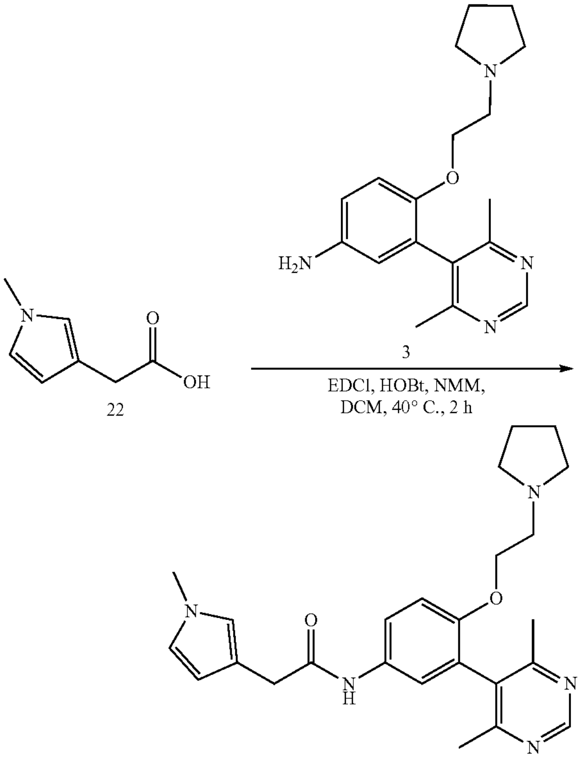

268

To a mixture of 3-(4,6-dimethylpyrimidin-5-yl)-4-(2-pyrrolidin-1-ylethoxy)aniline ((3), 80 mg, 256.08 μmol, 1 eq.) and 2-(1-methylpyrrol-3-yl)acetic acid ((22), 42.76 mg, 307.29 μmol, 1.2 eq.) in DCM (2 mL) was added EDCI (58.91 mg, 307.29 μmol, 1.2 eq.), HOBt (41.52 mg, 307.29 μmol, 1.2 eq.), and NMM (51.80 mg, 512.15 μmol, 56.31 μL, 2 eq.). The mixture was stirred at 40° C. for 2 h. The mixture was then concentrated under reduced pressure. The residue was purified by prep-HPLC (column: Phenomenex Gemini NX-C18 (75*30 mm*3 μm); mobile phase: [water (10 mM $NH_4HCO_3$)-ACN]; B %: 15%-45%, 8 min). N-[3-(4,6-dimethylpyrimidin-5-yl)-4-(2-pyrrolidin-1-ylethoxy) phenyl]-2-(1-methylpyrrol-3-yl)acetamide (9.97 mg, 22.31 μmol, 8.71% yield, 97% purity) was obtained as a brown gum.

LCMS (ESI): m/z [M+H] calcd for $C_{25}H_{32}NO_2$: 434.25; found: 434.2.

$^1H$ NMR (400 MHZ, methanol-$d_4$) δ=8.83 (s, 1H), 7.58 (dd, J=2.6, 8.9 Hz, 1H), 7.37 (d, J=2.6 Hz, 1H), 7.11 (d, J=9.0 Hz, 1H), 6.60 (s, 1H), 6.57 (t, J=2.4 Hz, 1H), 6.05-6.00 (m, 1H), 4.11 (t, J=5.4 Hz, 2H), 3.62-3.59 (m, 3H), 3.45

(s, 2H), 2.74 (t, J=5.4 Hz, 2H), 2.40-2.34 (m, 4H), 2.26 (s, 6H), 1.69 (td, J=3.3, 6.8 Hz, 4H).

N-[3-(4,6-dimethylpyrimidin-5-yl)-4-(2-pyrrolidin-1-ylethoxy)phenyl]-2-(1-methylpyrazol-3-yl)acetamide (269)

Preparation of 1-methylpyrazole-3-carbonyl chloride (23)

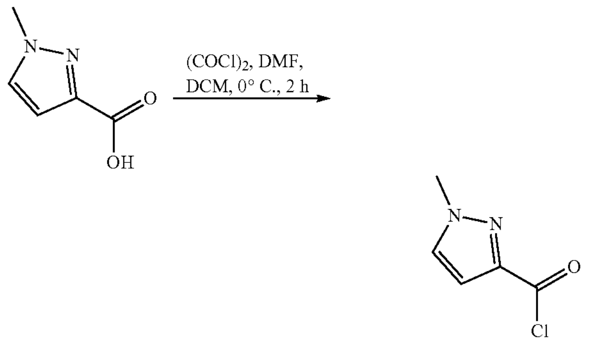

23

To a solution of 1-methylpyrazole-3-carboxylic acid (200 mg, 1.59 mmol, 1 eq.) in DCM (2 mL) was added $(COCl)_2$ (241.55 mg, 1.90 mmol, 166.58 μL, 1.2 eq.) and DMF (19.00 mg, 259.94 μmol, 20 μL, 1.64e-1 eq.) at 0° C. The mixture was stirred at 0° C. for 2 hrs (monitored by TLC). The reaction mixture was then concentrated under reduced pressure to give a residue. 1-Methylpyrazole-3-carbonyl chloride ((23), 220 mg, 1.52 mmol, 95.96% yield) was obtained as a yellow oil.

Preparation of 2-(1-methylpyrazol-3-yl)acetic acid (24)

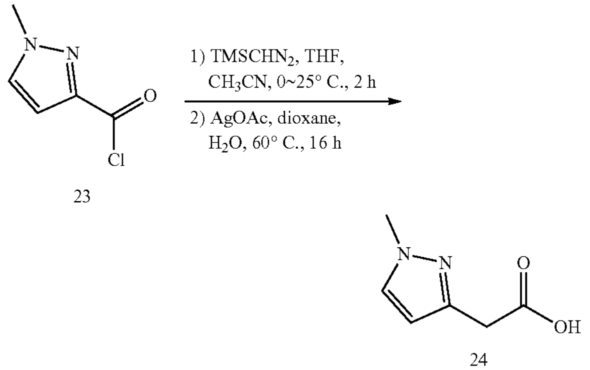

23

24

To a solution of 1-methylpyrazole-3-carbonyl chloride ((23), 220 mg, 1.52 mmol, 1 eq.) in THF (1 mL) and MeCN (1 mL) was added $TMSCHN_2$ (347.66 mg, 3.04 mmol, 2 eq.) at 0° C. The mixture was stirred at 25° C. for 2 hrs. The reaction mixture was concentrated under reduced pressure to give a residue, then the residue was dissolved in dioxane (1 mL) and $H_2O$ (1 mL). To the mixture was added AgOAc (50.80 mg, 304.37 μmol, 15.58 μL, 0.2 eq.). The mixture was stirred at 60° C. for 16 hrs (monitored by LC-MS). The reaction mixture was filtered and concentrated under reduced pressure to give a residue. The residue was purified by prep-HPLC (column: Waters Xbridge 150*25 mm*5 μm; mobile phase: [water (0.05% ammonia hydroxide v/v)-ACN]; B %: 1%-21%, 10 min). 2-(1-Methylpyrazol-3-yl) acetic acid ((24), 150 mg, 1.07 mmol, 70.33% yield) was obtained as a yellow oil.

LCMS (ESI): m/z [M−H] calcd for $C_7H_7N_2O_2$: 139.06; found: 139.1.

Preparation of N-[3-(4,6-dimethylpyrimidin-5-yl)-4-(2-pyrrolidin-1-ylethoxy)phenyl]-2-(1-methylpyrazol-3-yl)acetamide (269)

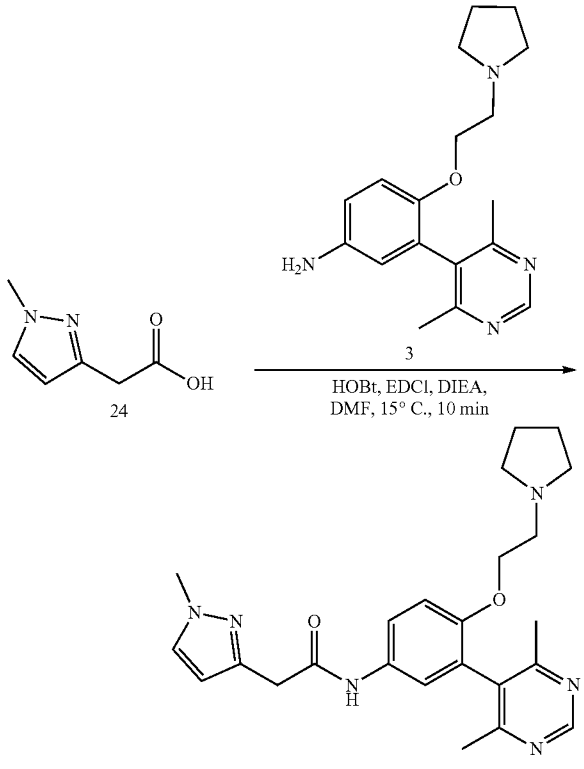

269

A mixture of 2-(1-methylpyrazol-3-yl)acetic acid ((24), 40 mg, 285.43 μmol, 1 eq.), 3-(4,6-dimethylpyrimidin-5-yl)-4-(2-pyrrolidin-1-ylethoxy)aniline ((3), 80.25 mg, 256.89 μmol, 0.9 eq.), HOBt (42.42 mg, 313.97 μmol, 1.1 eq.), EDCI (60.19 mg, 313.97 μmol, 1.1 eq.) and DIEA (73.78 mg, 570.86 μmol, 99.43 μL, 2 eq.) in DMF (2 mL) was stirred at 15° C. for 10 min. The mixture was stirred at 15° C. for 10 min (monitored by LC-MS). The reaction mixture was concentrated under reduced pressure to give a residue. The residue was purified by prep-HPLC (column: Waters Xbridge 150*25 mm*5 μm; mobile phase: [water (0.05% ammonia hydroxide v/v)-ACN]; B %: 15%-45%, 10 min). N-[3-(4,6-dimethylpyrimidin-5-yl)-4-(2-pyrrolidin-1-ylethoxy)phenyl]-2-(1-methylpyrazol-3-yl)acetamide (6.86 mg, 15.79 μmol, 5.53% yield, 100% purity) was obtained as a yellow gum.

LCMS (ESI): m/z [M+H] calcd for $C_{24}H_{31}N_6O_2$: 435.24; found: 435.3.

$^1H$ NMR (400 MHZ, methanol-$d_4$) δ=8.8 (s, 1H), 7.6 (d, J=8.8 Hz, 1H), 7.50 (s, 1H), 7.41 (s, 1H), 7.13 (d, J=8.8 Hz, 1H), 6.24 (s, 1H), 4.12-4.11 (m, 2H), 3.85 (s, 3H), 3.67 (s, 2H), 2.74-2.72 (m, 2H), 2.35 (br s, 4H), 2.59 (s, 6H), 1.68 (br s, 4H).

N-[3-(4,6-dimethylpyrimidin-5-yl)-4-(2-pyrrolidin-1-ylethoxy)phenyl]-3-(1-methylpyrazol-3-yl)propanamide (270)

Preparation of ethyl (E)-3-(1-methylpyrazol-3-yl) prop-2-enoate (25)

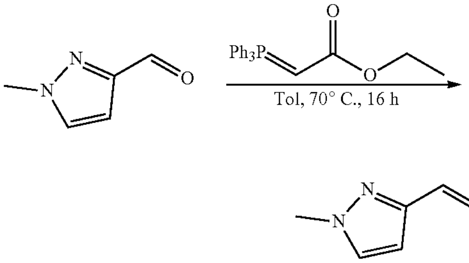

25

A mixture of 1-methylpyrazole-3-carbaldehyde (500 mg, 4.54 mmol, 1 eq.) and ethyl 2-(triphenyl-phosphanylidene) acetate (1.74 g, 4.99 mmol, 1.1 eq.) in toluene (10 mL) was stirred at 70° C. for 16 hrs. LCMS showed the 1-methylpyrazole-3-carbaldehyde was consumed and the desired mass was detected. The mixture was concentrated under reduced pressure. The residue was purified by silica gel chromatography (100-200 mesh silica gel, petroleum ether/ethyl acetate=5/1, 2/1). Ethyl (E)-3-(1-methylpyrazol-3-yl) prop-2-enoate ((25), 780 mg, 4.33 mmol, 95.32% yield) was obtained as a colorless oil.

$^1H$ NMR (400 MHZ, methanol-$d_4$) δ 7.68 (d, J=16.0 Hz, 1H), 7.34 (d, J=2.4 Hz, 1H), 6.48 (d, J=2.4 Hz, 1H), 6.41 (d, J=16.0 Hz, 1H), 4.27 (q, J=7.2 Hz, 2H), 3.93 (s, 3H), 1.34 (t, J=6.8 Hz, 3H).

Preparation of ethyl 3-(1-methylpyrazol-3-yl)propanoate (26)

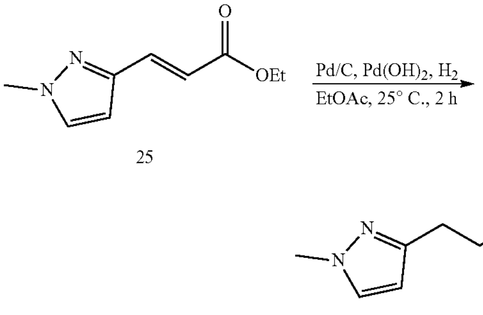

25

26

To a solution of ethyl (E)-3-(1-methylpyrazol-3-yl) prop-2-enoate ((25), 200 mg, 1.11 mmol, 1 eq.) in EtOAc (5 mL) was added Pd/C (10 mg, 10% purity) and $Pd(OH)_2$ (10 mg, 7.12 μmol, 10% purity) under $N_2$. The suspension was degassed under vacuum and purged with $H_2$ several times. The mixture was stirred under $H_2$ (15 psi) at 25° C. for 2 hrs. LCMS showed the ethyl (E)-3-(1-methylpyrazol-3-yl) prop-2-enoate was consumed and the desired mass was detected. The reaction mixture was filtered and the filtrate was concentrated. Ethyl 3-(1-methylpyrazol-3-yl)propanoate ((26), 190 mg, crude) was obtained as a colorless oil.

Preparation of 3-(1-methylpyrazol-3-yl)propanoic acid (27)

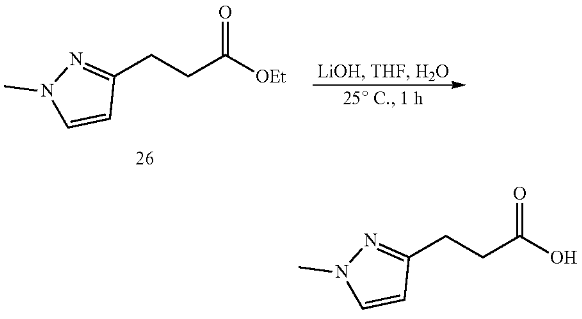

26

27

To a mixture of ethyl 3-(1-methylpyrazol-3-yl)propanoate ((26), 190 mg, 1.04 mmol, 1 eq.) in EtOH (3 mL) and $H_2O$ (1 mL) was added $LiOH·H_2O$ (87.51 mg, 2.09 mmol, 2 eq.). The mixture was stirred at 25° C. for 1 hr. LCMS showed the ethyl 3-(1-methylpyrazol-3-yl)propanoate was consumed. The mixture was concentrated to remove excess EtOH. The residue was acidified with 1M HCl (aq.), the pH was adjusted to 4-5, and then the mixture was concentrated. 3-(1-Methylpyrazol-3-yl)propanoic acid ((27), 150 mg, crude) was obtained as a colorless oil.

Preparation of N-[3-(4,6-dimethylpyrimidin-5-yl)-4-(2-pyrrolidin-1-ylethoxy)phenyl]-3-(1-methylpyrazol-3-yl)propanamide (270)

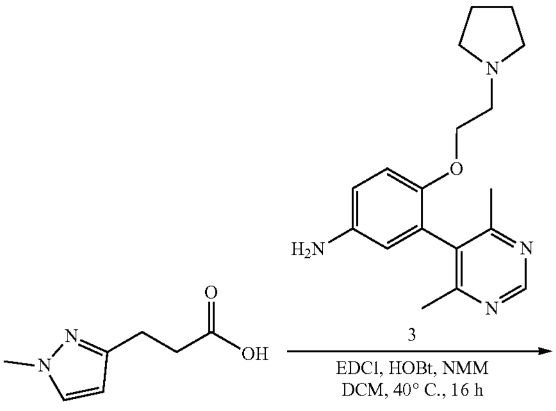

3

27

-continued

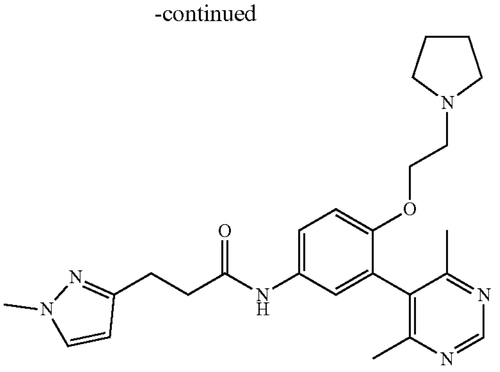

270

To a mixture of 3-(4,6-dimethylpyrimidin-5-yl)-4-(2-pyrrolidin-1-ylethoxy)aniline ((3), 60 mg, 192.06 μmol, 1 eq.) and 3-(1-methylpyrazol-3-yl)propanoic acid ((27), 44.41 mg, 288.08 μmol, 1.5 eq.) in DCM (2 mL) was added EDCI (55.23 mg, 288.08 μmol, 1.5 eq.), HOBt (38.93 mg, 288.08 μmol, 1.5 eq.), and NMM (58.28 mg, 576.17 μmol, 63.35 μL, 3 eq.). The mixture was stirred at 40° C. for 16 hrs. LCMS showed 3-(4,6-dimethylpyrimidin-5-yl)-4-(2-pyrrolidin-1-ylethoxy)aniline was consumed and the desired mass was detected. The mixture was concentrated under reduced pressure. The residue was purified by prep-HPLC (column: Phenomenex Gemini-NX C18 75*30 mm*3 μm; mobile phase: [water (0.1% TFA)-ACN]; B %: 22%-32%, 7 min). N-[3-(4,6-dimethylpyrimidin-5-yl)-4-(2-pyrrolidin-1-ylethoxy)phenyl]-3-(1-methylpyrazol-3-yl)propanamide (56.24 mg, 98.97 μmol, 51.53% yield, 99% purity, TFA) was obtained as a brown gum.

LCMS (ESI): m/z [M+H] calcd for $C_{25}H_{33}N_6O_2$: 449.26; found: 449.3.

$^1$H NMR (400 MHZ, methanol-d$_4$) δ=8.90 (s, 1H), 7.67 (dd, J=2.6, 8.9 Hz, 1H), 7.50-7.39 (m, 2H), 7.19 (d, J=9.0 Hz, 1H), 6.12 (d, J=2.3 Hz, 1H), 4.35-4.28 (m, 2H), 3.82 (s, 3H), 3.56-3.47 (m, 2H), 3.36 (br s, 2H), 2.98 (t, J=7.7 Hz, 2H), 2.92-2.81 (m, 2H), 2.69 (t, J=7.6 Hz, 2H), 2.29 (s, 6H), 2.02 (br s, 2H), 1.95-1.81 (m, 2H).

N-[3-(4,6-dimethylpyrimidin-5-yl)-4-(2-pyrrolidin-1-ylethoxy)phenyl]benzamide (271)

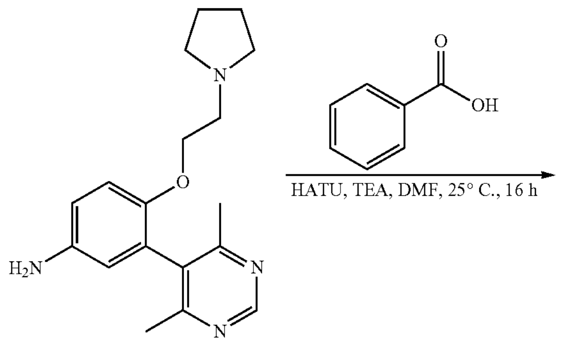

3

-continued

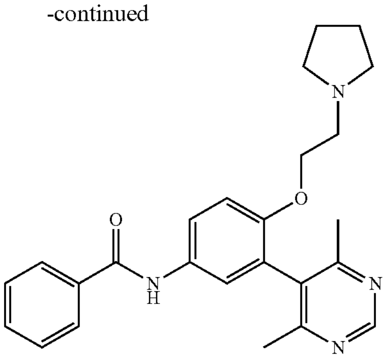

271

To a solution of benzoic acid (23.45 mg, 192.06 μmol, 29.32 μL, 1.2 eq.) in DMF (1 mL) was added HATU (73.03 mg, 192.06 μmol, 1.2 eq.) and TEA (48.59 mg, 480.14 μmol, 66.83 μL, 3 eq.), and was stirred at 25° C. for 0.5 hrs. 3-(4,6-Dimethylpyrimidin-5-yl)-4-(2-pyrrolidin-1-ylethoxy)aniline ((3), 50 mg, 160.05 μmol, 1 eq.) was then added. The mixture was stirred at 25° C. for 2 hrs. The reaction mixture was concentrated under reduced pressure to give a residue. The residue was purified by prep-HPLC (column: Phenomenex Gemini-NX C18 75*30 mm*3 μm; mobile phase: [water (0.1% TFA)-ACN]; B %: 20%-30%, 7 min). N-[3-(4,6-dimethylpyrimidin-5-yl)-4-(2-pyrrolidin-1-ylethoxy)phenyl]benzamide (34.93 mg, 65.84 μmol, 41.14% yield, 100% purity, TFA) was obtained as a brown solid.

LCMS (ESI): m/z [M+H] calcd for $C_{25}H_{29}N_4O_2$: 417.22; found: 417.2.

$^1$H NMR (400 MHZ, methanol-d$_4$) δ=8.91 (s, 1H), 7.97-7.91 (m, 2H), 7.85 (dd, J=2.4, 8.9 Hz, 1H), 7.62-7.49 (m, 4H), 7.25 (d, J=8.9 Hz, 1H), 4.38-4.33 (m, 2H), 3.57-3.49 (m, 2H), 3.39 (br s, 2H), 2.95-2.79 (m, 2H), 2.33 (s, 6H), 2.03 (br s, 2H), 1.96-1.84 (m, 2H).

N-(3-(4,6-dimethylpyrimidin-5-yl)-4-(2-(pyrrolidin-1-yl)ethoxy)phenyl)-4-fluorobenzamide (272)

272

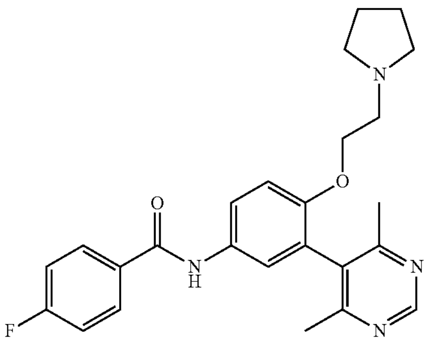

Compound 272 was prepared according to the synthesis described for compound 271, substituting 4-fluorobenzoic acid for benzoic acid.

LCMS (ESI): m/z [M+H] calcd for $C_{25}H_{28}FN_4O_2$: 435.21; found: 435.2.

$^1$H NMR (400 MHZ, methanol-d$_4$) δ=8.90 (s, 1H), 8.04-7.95 (m, 2H), 7.84 (dd, J=2.4, 8.8 Hz, 1H), 7.54 (d, J=2.6 Hz, 1H), 7.29-7.20 (m, 3H), 4.39-4.31 (m, 2H), 3.56-3.50

(m, 2H), 3.41-3.34 (m, 2H), 2.93-2.80 (m, 2H), 2.33 (s, 6H), 2.07-1.96 (m, 2H), 1.89 (br dd, J=5.3, 7.2 Hz, 2H).

N-(3-(4,6-dimethylpyrimidin-5-yl)-4-(2-(pyrrolidin-1-yl)ethoxy)phenyl)-3-methoxybenzamide (273)

273

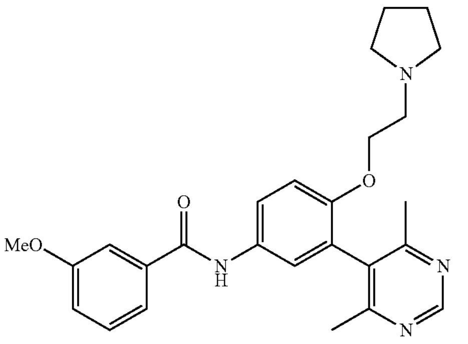

Compound 273 was prepared according to the synthesis described for compound 271, substituting 3-methoxybenzoic acid for benzoic acid.

LCMS (ESI): m/z [M+H] calcd for $C_{26}H_{31}N_4O_3$: 447.23; found: 447.2.

$^1$H NMR (400 MHZ, methanol-d$_4$) δ=8.90 (s, 1H), 7.86 (dd, J=2.7, 8.9 Hz, 1H), 7.57-7.46 (m, 3H), 7.46-7.39 (m, 1H), 7.25 (d, J=9.0 Hz, 1H), 7.15 (ddd, J=1.0, 2.6, 8.2 Hz, 1H), 4.35 (m, 2H), 3.87 (s, 3H), 3.53 (m, 2H), 3.38 (br d, J=5.6 Hz, 2H), 2.92-2.82 (m, 2H), 2.33 (s, 6H), 2.02 (br d, J=8.7 Hz, 2H), 1.96-1.84 (m, 2H).

N-(3-(4,6-dimethylpyrimidin-5-yl)-4-(2-(pyrrolidin-1-yl)ethoxy)phenyl)-2-(3-methoxyphenyl)acetamide (274)

274

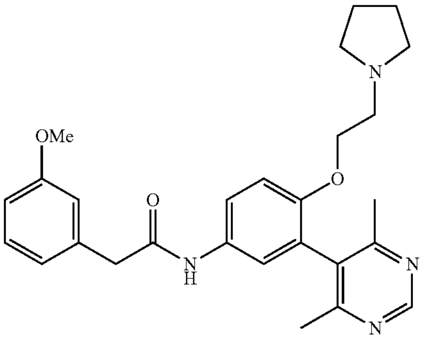

Compound 274 was prepared according to the synthesis described for compound 271, substituting 2-(3-methoxyphenyl)acetic acid for benzoic acid.

LCMS (ESI): m/z [M+H] calcd for $C_{27}H_{33}N_4O_3$: 461.25; found: 461.3.

$^1$H NMR (400 MHZ, methanol-d$_4$) δ=8.91 (s, 1H), 7.67 (td, J=2.0, 8.9 Hz, 1H), 7.45 (t, J=2.3 Hz, 1H), 7.30-7.12 (m, 2H), 6.98-6.87 (m, 2H), 6.87-6.76 (m, 1H), 4.32 (t, J=4.8 Hz, 2H), 3.79 (s, 3H), 3.65 (s, 2H), 3.54-3.47 (m, 2H), 3.43-3.33 (m, 2H), 2.91-2.78 (m, 2H), 2.30 (s, 6H), 2.02 (br d, J=9.8 Hz, 2H), 1.94-1.81 (m, 2H).

N-(3-(4,6-dimethylpyrimidin-5-yl)-4-(2-(pyrrolidin-1-yl)ethoxy)phenyl)-2-(3-fluorophenyl)acetamide (275)

275

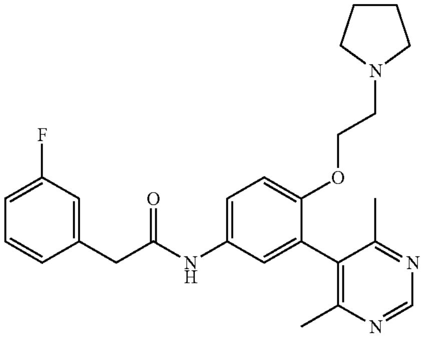

Compound 275 was prepared according to the synthesis described for compound 271, substituting 2-(3-fluorophenyl)acetic acid for benzoic acid.

LCMS (ESI): m/z [M+H] calcd for $C_{26}H_{30}FN_4O_2$: 449.23; found: 449.2.

$^1$H NMR (400 MHZ, methanol-d$_4$) δ=8.91 (s, 1H), 7.68 (dd, J=2.6, 8.9 Hz, 1H), 7.45 (d, J=2.6 Hz, 1H), 7.34 (dt, J=6.1, 7.9 Hz, 1H), 7.23-7.08 (m, 3H), 7.00 (dt, J=2.3, 8.4 Hz, 1H), 4.36-4.28 (m, 2H), 3.70 (s, 2H), 3.53-3.48 (m, 2H), 3.41-3.33 (m, 2H), 2.89-2.81 (m, 2H), 2.30 (s, 6H), 2.04-1.96 (m, 2H), 1.94-1.83 (m, 2H).

N-(3-(4,6-dimethylpyrimidin-5-yl)-4-(2-(pyrrolidin-1-yl)ethoxy)phenyl)-2-(4-methoxyphenyl)acetamide (276)

276

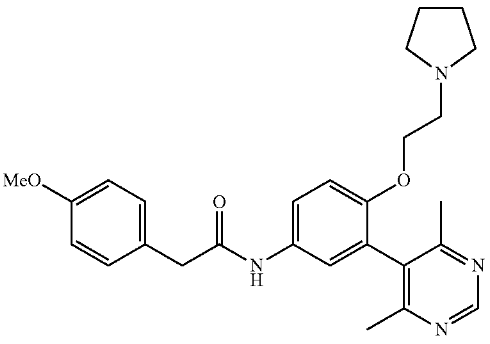

Compound 276 was prepared according to the synthesis described for compound 271, substituting 2-(4-methoxyphenyl)acetic acid for benzoic acid.

LCMS (ESI): m/z [M+H] calcd for $C_{27}H_{33}N_4O_3$: 461.25; found: 437.2.

$^1$H NMR (400 MHZ, methanol-d$_4$) δ=8.88 (s, 1H), 7.72-7.62 (m, 1H), 7.42 (d, J=2.5 Hz, 1H), 7.26 (d, J=8.8 Hz, 2H), 7.18 (d, J=9.0 Hz, 1H), 6.88 (d, J=8.8 Hz, 2H), 4.35-4.25 (m, 2H), 3.77 (s, 3H), 3.60 (s, 2H), 3.52-3.47 (m, 2H), 3.35 (br d, J=2.6 Hz, 2H), 2.84 (br dd, J=1.9, 3.8 Hz, 2H), 2.28 (s, 6H), 2.02 (br d, J=3.3 Hz, 2H), 1.88 (br dd, J=4.9, 6.3 Hz, 2H).

N-(3-(4,6-dimethylpyrimidin-5-yl)-4-(2-(pyrrolidin-1-yl)ethoxy)phenyl)-2-(5-fluoropyridin-3-yl)acetamide (277)

277

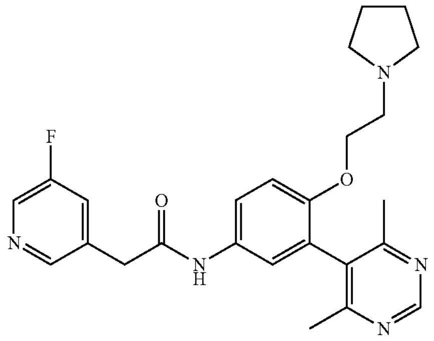

Compound 277 was prepared according to the synthesis described for compound 271, substituting 2-(5-fluoropyridin-3-yl)acetic acid for benzoic acid.

LCMS (ESI): m/z [M+H] calcd for $C_{25}H_{29}FN_5O_2$: 450.22; found: 450.8.

$^1$H NMR (400 MHZ, methanol-$d_4$) δ=8.90 (s, 1H), 8.48-8.36 (m, 2H), 7.74 (dd, J=1.9, 9.4 Hz, 1H), 7.69 (br dd, J=2.6, 9.0 Hz, 1H), 7.46 (d, J=2.6 Hz, 1H), 7.20 (d, J=9.0 Hz, 1H), 4.36-4.28 (m, 2H), 3.83 (s, 2H), 3.54-3.48 (m, 2H), 3.42-3.33 (m, 2H), 2.90-2.79 (m, 2H), 2.29 (s, 6H), 2.03 (br d, J=7.4 Hz, 2H), 1.95-1.82 (m, 2H).

N-(3-(4,6-dimethylpyrimidin-5-yl)-4-(2-(pyrrolidin-1-yl)ethoxy)phenyl)-2-(5-fluoropyridin-2-yl)acetamide (278)

278

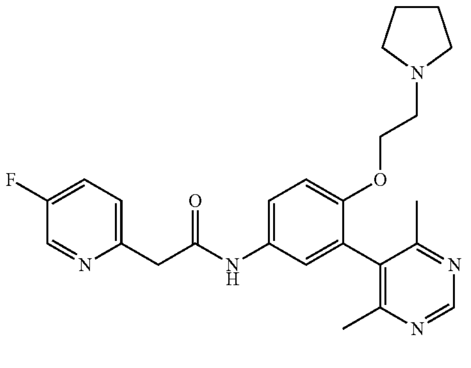

Compound 278 was prepared according to the synthesis described for compound 271, substituting 2-(5-fluoropyridin-2-yl)acetic acid for benzoic acid.

LCMS (ESI): m/z [M+H] calcd for $C_{25}H_{29}FN_5O_2$: 450.22; found: 450.8.

$^1$H NMR (400 MHZ, methanol-$d_4$) δ=8.85 (s, 1H), 8.41 (d, J=2.9 Hz, 1H), 7.69-7.55 (m, 2H), 7.49 (dd, J=4.5, 8.6 Hz, 1H), 7.44 (d, J=2.7 Hz, 1H), 7.15 (d, J=9.0 Hz, 1H), 4.19 (t, J=5.1 Hz, 2H), 3.90 (s, 2H), 3.01 (br d, J=4.6 Hz, 2H), 2.63 (br s, 4H), 2.27 (s, 6H), 1.83-1.72 (m, 4H).

N-[3-(4,6-dimethylpyrimidin-5-yl)-4-(2-pyrrolidin-1-ylethoxy)phenyl]-N-methyl-cyclopropanecarboxamide (279)

Preparation of 3-(4,6-dimethylpyrimidin-5-yl)-N-methyl-4-(2-pyrrolidin-1-ylethoxy)aniline (28)

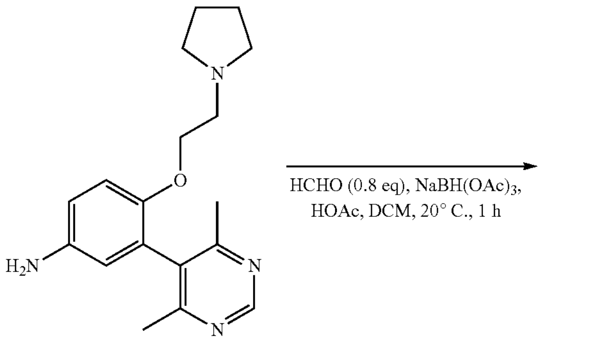

3

28

To a solution of 3-(4,6-dimethylpyrimidin-5-yl)-4-(2-pyrrolidin-1-ylethoxy)aniline ((3), 500 mg, 1.60 mmol, 1 eq.), HOAc (19.22 mg, 320.09 μmol, 18.31 μL, 0.2 eq.) and $NaBH(OAc)_3$ (678.41 mg, 3.20 mmol, 2 eq.) in DCM (10 mL) was added HCHO (103.90 mg, 1.28 mmol, 95.32 μL, 0.8 eq.) in DCM (5 mL) slowly. The reaction mixture was stirred at 25° C. for 1 hr. The reaction mixture was then quenched with $H_2O$ (6 mL). The reaction mixture was concentrated in vacuum. The crude product was purified by reversed-phase HPLC (0.1% $NH_3{\cdot}H_2O$ condition) followed by lyophilization. The residue was purified by prep-HPLC (column: Waters Xbridge 150*25 mm*5 μm; mobile phase: [water (10 mM $NH_4HCO_3$)-ACN]; B %: 8%-38%, 10 min) followed by lyophilization. 3-(4,6-Dimethylpyrimidin-5-yl)-N-methyl-4-(2-pyrrolidin-1-ylethoxy)aniline ((28), 180 mg, 551.41 μmol, 34.45% yield) was obtained as a yellow oil.

LCMS (ESI): m/z [M+H] calcd for $C_{19}H_{27}N_4O$: 327.21; found: 327.2.

Preparation of N-[3-(4,6-dimethylpyrimidin-5-yl)-4-(2-pyrrolidin-1-ylethoxy)phenyl]-N-methyl-cyclopropanecarboxamide (279)

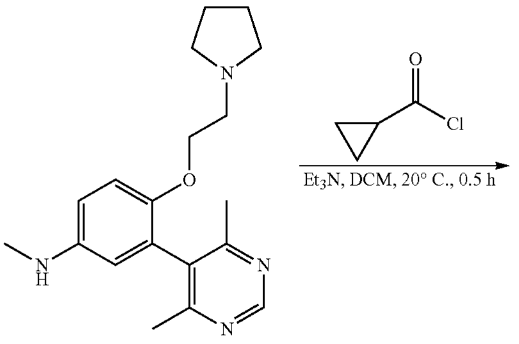

28

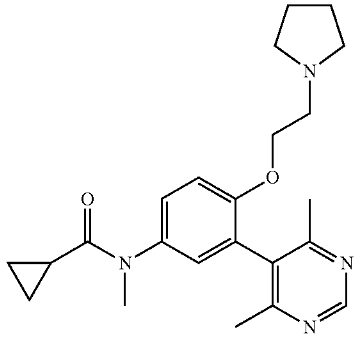

279

To a solution of 3-(4,6-dimethylpyrimidin-5-yl)-N-methyl-4-(2-pyrrolidin-1-ylethoxy)aniline ((28), 40 mg, 122.54 μmol, 1 eq.) and $Et_3N$ (24.80 mg, 245.07 μmol, 34.11 μL, 2 eq.) in DCM (1 mL) was added cyclopropanecarbonyl chloride (15.37 mg, 147.04 μmol, 13.37 μL, 1.2 eq.). The reaction mixture was stirred at 15° C. for 1 hr. The reaction mixture was concentrated in vacuum. The residue was purified by prep-HPLC (column: Waters Xbridge 150*25 mm*5 μm; mobile phase: [water (10 mM $NH_4HCO_3$)-ACN]; B %: 15%-45%, 9 min) followed by lyophilization. N-[3-(4,6-dimethylpyrimidin-5-yl)-4-(2-pyrrolidin-1-ylethoxy)phenyl]-N-methyl-cyclopropanecarboxamide (7.81 mg, 19.80 μmol, 16.16% yield, 100% purity) was obtained as an off-white solid.

LCMS (ESI): m/z [M+H] calcd for $C_{23}H_{31}N_4O_2$: 395.24; found: 395.2.

$^1$H NMR (400 MHZ, methanol-$d_4$) δ=8.86 (s, 1H), 7.53-7.40 (m, 1H), 7.34-7.16 (m, 2H), 4.19 (t, J=5.3 Hz, 2H), 3.28 (s, 2H), 2.79 (t, J=5.3 Hz, 2H), 2.45-2.34 (m, 4H), 2.28 (s, 6H), 1.75-1.64 (m, 4H), 1.54-1.43 (m, 1H), 0.97-0.88 (m, 2H), 0.74-0.63 (m, 1H), 0.75-0.63 (m, 1H)).

N-[3-(4,6-dimethylpyrimidin-5-yl)-4-(2-pyrrolidin-1-ylethoxy)phenyl]-N,2-dimethyl-pyrazole-3-carboxamide (280)

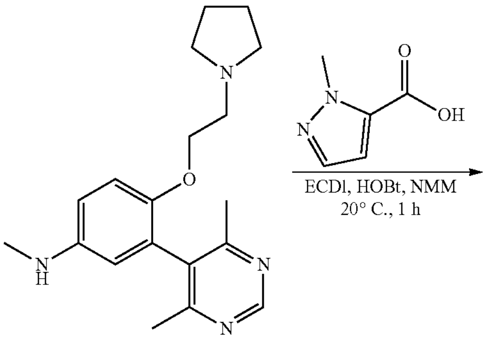

28

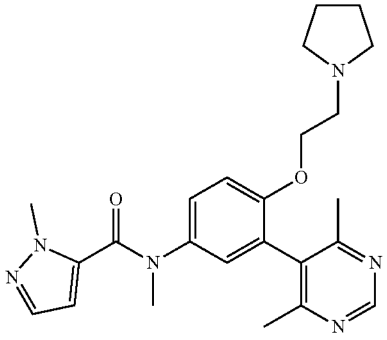

280

To a solution of 3-(4,6-dimethylpyrimidin-5-yl)-N-methyl-4-(2-pyrrolidin-1-ylethoxy)aniline ((28), 50 mg, 153.17 μmol, 1 eq.), 2-methylpyrazole-3-carboxylic acid (23.18 mg, 183.80 μmol, 1.2 eq.), EDCI (35.24 mg, 183.80 μmol, 1.2 eq.) and HOBt (24.84 mg, 183.80 μmol, 1.2 eq.) in DCM (1 mL) was added NMM (30.99 mg, 306.34 μmol, 33.68 μL, 2 eq.). The reaction mixture was stirred at 15° C. for 1 hr. The reaction mixture was concentrated in vacuum. The residue was purified by prep-HPLC (column: Phenomenex Gemini NX-C18 (75*30 mm*3 μm); mobile phase: [water (10 mM $NH_4HCO_3$)-ACN]; B %: 12%-42%, 8 min) followed by lyophilization. N-[3-(4,6-Dimethylpyrimidin-5-yl)-4-(2-pyrrolidin-1-ylethoxy)phenyl]-N,2-dimethyl-pyrazole-3-carboxamide (20.25 mg, 46.60 μmol, 30.42% yield, 100% purity) was obtained as an off-white gum.

LCMS (ESI): m/z [M+H] calcd for $C_{24}H_{31}N_6O_2$: 435.24; found: 435.3.

$^1$H NMR (400 MHZ, methanol-$d_4$) δ=8.81 (s, 1H), 7.44 (dd, J=2.8, 8.8 Hz, 1H), 7.26-7.14 (m, 2H), 7.01 (br d, J=1.8 Hz, 1H), 5.77 (br s, 1H), 4.14 (t, J=5.3 Hz, 2H), 3.97 (s, 3H), 3.47 (s, 3H), 2.75 (t, J=5.3 Hz, 2H), 2.40-2.32 (m, 4H), 2.11 (s, 6H), 1.76-1.61 (m, 4H).

N-[3-(4,6-dimethylpyrimidin-5-yl)-4-(2-pyrrolidin-1-ylethoxy)phenyl]-3-fluoro-propanamide (281)

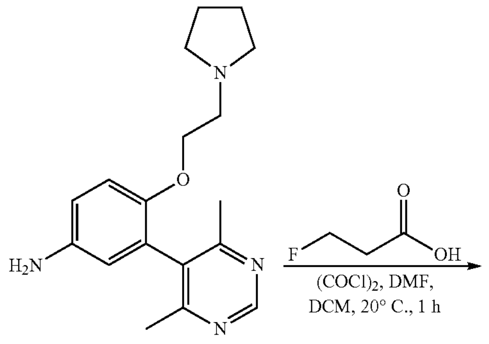

3

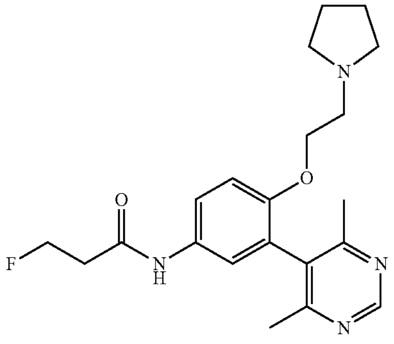

281

To a mixture of 3-fluoropropanoic acid (17.68 mg, 192.06 μmol, 1 eq.) and $(COCl)_2$ (24.38 mg, 192.06 μmol, 16.81 μL, 1 eq.) in DCM (1 mL) was added DMF (1.40 mg, 19.21 μmol, 1.48 μL, 0.1 eq.). The mixture was stirred at 15° C. for 10 min. To the mixture was added 3-(4,6-dimethylpyrimidin-5-yl)-4-(2-pyrrolidin-1-ylethoxy)aniline ((3), 60 mg, 192.06 μmol, 1 eq.). The mixture was stirred at 15° C. for 10 min (monitored by LC-MS). The reaction mixture was concentrated under reduced pressure to give a residue. The residue was purified by prep-HPLC (column: Phenomenex Synergi C18 150*25 mm*10 μm; mobile phase: [water (0.225% TFA)-ACN]; B %: 0%-25%, 10 min). N-[3-(4,6-dimethylpyrimidin-5-yl)-4-(2-pyrrolidin-1-ylethoxy)phenyl]-3-fluoro-propanamide (10 mg, 24.32 μmol, 12.66% yield, 94% purity) was obtained as a white solid.

LCMS (ESI): m/z [M+H] calcd for $C_{21}H_{27}FN_4O_3$: 387.22; found: 387.3.

$^1$H NMR (400 MHZ, methanol-$d_4$) δ=8.87 (s, 1H), 8.48 (br s, 1H), 7.67 (dd, J=2.5, 8.9 Hz, 1H), 7.45 (d, J=2.5 Hz, 1H), 7.18 (d, J=8.9 Hz, 1H), 4.81 (t, J=5.7 Hz, 1H), 4.70 (t, J=5.6 Hz, 1H), 4.32-4.26 (m, 2H), 3.35 (s, 2H), 2.97 (br s, 4H), 2.79 (t, J=5.7 Hz, 1H), 2.73 (t, J=5.6 Hz, 1H), 2.29 (s, 6H), 1.89 (br s, 4H).

N-[3-(4,6-dimethylpyrimidin-5-yl)-4-(2-pyrrolidin-1-ylethoxy)phenyl]-4-fluoro-butanamide (282)

Preparation of 4-fluorobutanoic acid (29)

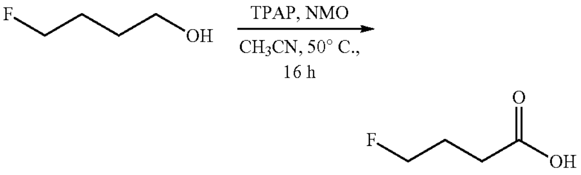

29

To a mixture of 4-fluorobutan-1-ol (1 g, 10.86 mmol, 1 eq.) and 4-methyl-4-oxido-morpholin-4-ium hydrate (7.34 g, 54.28 mmol, 5 eq.) in ACN (20 mL) was added TPAP (381.52 mg, 1.09 mmol, 0.1 eq.). The mixture was stirred at 50° C. for 16 hrs. LCMS showed the 4-fluorobutan-1-ol was consumed and the desired mass was detected. The mixture was concentrated under reduced pressure. The residue was poured into HCl (20 mL, 1M). The aqueous phase was extracted with ethyl acetate (30 mL). The combined organic phase was washed with HCl (20 mL×3), dried with anhydrous $Na_2SO_4$, filtered and concentrated in vacuum. 4-fluorobutanoic acid ((29), 600 mg, crude) was obtained as a yellow oil.

Preparation of N-[3-(4,6-dimethylpyrimidin-5-yl)-4-(2-pyrrolidin-1-ylethoxy)phenyl]-4-fluoro-butanamide (282)

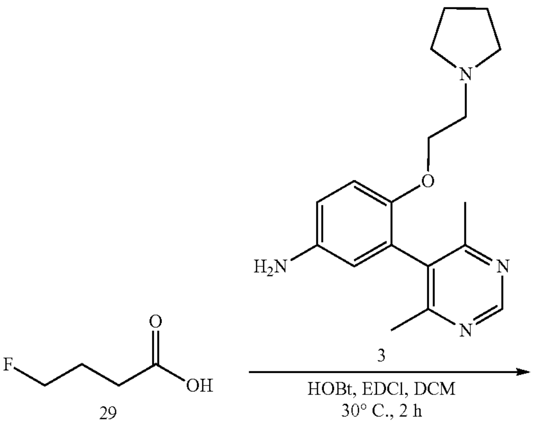

3

29

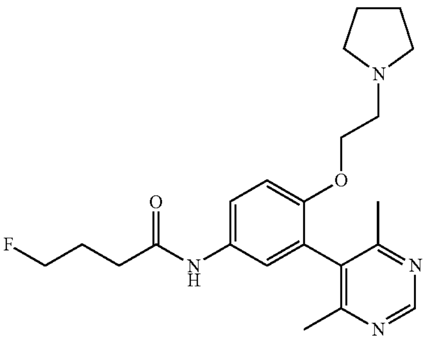

282

To a mixture of 3-(4,6-dimethylpyrimidin-5-yl)-4-(2-pyrrolidin-1-ylethoxy)aniline ((3), 50 mg, 160.05 μmol, 1 eq.), HOBt (32.44 mg, 240.07 μmol, 1.5 eq.) and 4-fluorobutanoic acid ((29), 25.47 mg, 240.07 μmol, 1.5 eq.) in DCM (1 mL) was added EDCI (46.02 mg, 240.07 μmol, 1.5 eq.). The mixture was stirred at 30° C. for 2 hrs. LCMS showed the 3-(4,6-dimethylpyrimidin-5-yl)-4-(2-pyrrolidin-1-ylethoxy)aniline was consumed and the desired mass was detected. The mixture was concentrated under reduced pressure. The residue was purified by prep-HPLC (column: Phenomenex Gemini NX-C18 (75*30 mm*3 μm); mobile phase: [water (10 mM $NH_4HCO_3$)-ACN]; B %: 8%-38%, 8 min). N-[3-(4,6-dimethylpyrimidin-5-yl)-4-(2-pyrrolidin-1-ylethoxy)phenyl]-4-fluoro-butanamide (35.26 mg, 85.40 μmol, 53.36% yield, 97% purity) was obtained as a brown gum.

LCMS (ESI): m/z [M+H] calcd for $C_{22}H_{30}FN_4O_2$: 401.23; found: 401.3.

$^1$H NMR (400 MHZ, methanol-$d_4$) δ=8.84 (s, 1H), 7.60 (dd, J=2.6, 8.9 Hz, 1H), 7.39 (d, J=2.7 Hz, 1H), 7.12 (d, J=8.9 Hz, 1H), 4.56 (t, J=5.9 Hz, 1H), 4.44 (t, J=5.9 Hz, 1H), 4.11 (t, J=5.4 Hz, 2H), 2.74 (t, J=5.4 Hz, 2H), 2.50 (t, J=7.5 Hz, 2H), 2.42-2.33 (m, 4H), 2.27 (s, 6H), 2.13-1.97 (m, 2H), 1.74-1.64 (m, 4H).

N-[3-(4,6-dimethylpyrimidin-5-yl)-4-(2-pyrrolidin-1-ylethoxy)phenyl]-1-hydroxy-cyclopropanecarboxamide (283)

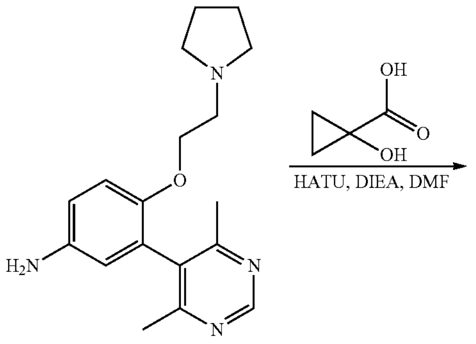

3

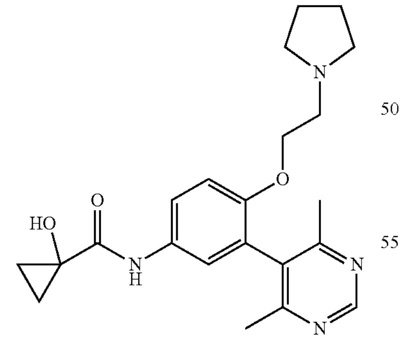

283

To a solution of 1-hydroxycyclopropanecarboxylic acid (39.21 mg, 384.11 μmol, 2 eq.) in DMF (1 mL) was added HATU (87.63 mg, 230.47 μmol, 1.2 eq.) and DIEA (74.46 mg, 576.17 μmol, 100.36 μL, 3 eq.). The reaction mixture was stirred at 15° C. for 30 min. 3-(4,6-dimethylpyrimidin-5-yl)-4-(2-pyrrolidin-1-ylethoxy)aniline ((3), 60 mg, 192.06 μmol, 1 eq.) was added to the reaction mixture. The reaction mixture was stirred at 40° C. for 17 hrs. The reaction mixture was then filtered. The filtrate was purified by prep-HPLC (column: Waters Xbridge 150*25 mm*5 μm; mobile phase: [water (10 mM $NH_4HCO_3$)-ACN]; B %: 7%-40%, 10 min) followed by lyophilization. N-[3-(4,6-dimethylpyrimidin-5-yl)-4-(2-pyrrolidin-1-ylethoxy)phenyl]-1-hydroxy-cyclopropanecarboxamide (30.93 mg, 75.67 μmol, 39.40% yield, 97% purity) was obtained as a yellow solid.

LCMS (ESI): m/z [M+H] calcd for $C_{22}H_{29}N_4O_3$: 397.22; found: 397.2.

$^1$H NMR (400 MHZ, methanol-$d_4$) δ=8.84 (s, 1H), 7.66 (dd, J=2.7, 8.9 Hz, 1H), 7.43 (d, J=2.7 Hz, 1H), 7.14 (d, J=9.0 Hz, 1H), 4.13 (t, J=5.4 Hz, 2H), 2.75 (t, J=5.4 Hz, 2H), 2.42-2.33 (m, 4H), 2.28 (s, 6H), 1.73-1.64 (m, 4H), 1.32-1.25 (m, 2H), 1.09-1.02 (m, 2H).

N-[3-(4,6-dimethylpyrimidin-5-yl)-4-(2-pyrrolidin-1-ylethoxy)phenyl]-2-methoxy-2-methyl-propanamide (284)

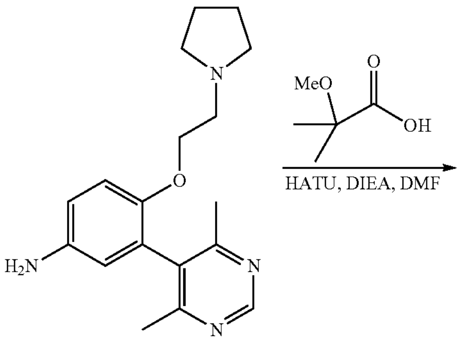

3

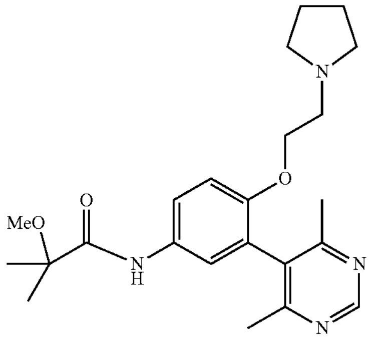

284

To a solution of 2-methoxy-2-methyl-propanoic acid (27.23 mg, 230.47 μmol, 1.2 eq.) in DMF (1 mL) was added HATU (87.63 mg, 230.47 μmol, 1.2 eq.) and DIEA (74.46 mg, 576.17 μmol, 100.36 μL, 3 eq.). The reaction mixture was stirred at 15° C. for 30 min. 3-(4,6-dimethylpyrimidin-5-yl)-4-(2-pyrrolidin-1-ylethoxy)aniline ((3), 60 mg, 192.06 μmol, 1 eq.) was added to the reaction mixture. The reaction mixture was stirred at 40° C. for 1 hr. The reaction mixture was filtered. The filtrate was purified by prep-HPLC (column: Waters Xbridge 150*25 mm*5 μm; mobile phase: [water (10 mM $NH_4HCO_3$)-ACN]; B %: 17%-47%, 10 min) followed by lyophilization. N-[3-(4,6-dimethylpyrimidin-5-yl)-4-(2-pyrrolidin-1-ylethoxy)phenyl]-2-methoxy-2-methyl-propanamide (44.94 mg, 103.49 μmol, 53.89% yield, 95% purity) was obtained as an orange gum.

LCMS (ESI): m/z [M+H] calcd for $C_{23}H_{33}N_4O_3$: 413.25; found: 413.4.

$^1$H NMR (400 MHZ, methanol-$d_4$) δ=8.84 (s, 1H), 7.67 (dd, J=2.7, 8.9 Hz, 1H), 7.42 (d, J=2.6 Hz, 1H), 7.14 (d, J=8.9 Hz, 1H), 4.12 (t, J=5.4 Hz, 2H), 3.35 (s, 3H), 2.74 (t, J=5.4 Hz, 2H), 2.41-2.33 (m, 4H), 2.27 (s, 6H), 1.73-1.65 (m, 4H), 1.44 (s, 6H).

N-[3-(4,6-dimethylpyrimidin-5-yl)-4-(2-pyrrolidin-1-ylethoxy)phenyl]-1-ethoxy-cyclopropanecarboxamide (285)

Preparation of ethyl 1-ethoxycyclopropanecarboxylate (30)

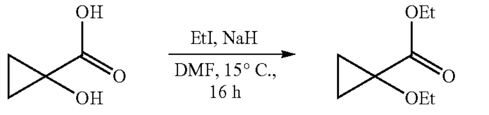

30

To a solution of 1-hydroxycyclopropanecarboxylic acid (500 mg, 4.90 mmol, 1 eq.) in DMF (10 mL) was added NaH (489.72 mg, 12.24 mmol, 60% purity, 2.5 eq.). The reaction mixture was stirred at 15° C. for 0.5 hrs. Iodoethane (1.91 g, 12.24 mmol, 979.32 μL, 2.5 eq.) was added to the reaction mixture. The reaction mixture was stirred at 15° C. for 16 hrs. The residue was poured into 50 mL saturated $NH_4Cl$ (aq). The aqueous phase was extracted with ethyl acetate (50 mL×3). The combined organic phase was washed with brine (30 mL), dried with anhydrous $Na_2SO_4$, filtered and concentrated in vacuum. Ethyl 1-ethoxycyclopropanecarboxylate ((30), 510 mg, crude) was obtained as a yellow oil.

Preparation of 1-ethoxycyclopropanecarboxylic acid (31)

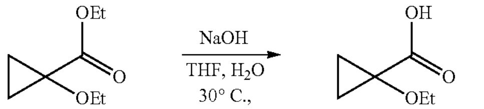

30 31

To a solution of ethyl 1-ethoxycyclopropanecarboxylate ((30), 510 mg, 3.22 mmol, 1 eq.) in THF (5 mL) was added NaOH (2 M, 3 mL, 1.86 eq.). The reaction mixture was stirred at 40° C. for 16 hrs. The aqueous phase was extracted with ethyl acetate (20 mL×2). The pH of the reaction mixture was adjusted to 5 with 1 M HCl (aq.). The aqueous phase was extracted with ethyl acetate (50 mL×4). The combined organic phase was washed with brine (40 mL), dried with anhydrous $Na_2SO_4$, filtered and concentrated in vacuum. 1-Ethoxycyclopropanecarboxylic acid ((31), 230 mg, 1.77 mmol, 54.82% yield) was obtained as a yellow oil.

Preparation of N-[3-(4,6-dimethylpyrimidin-5-yl)-4-(2-pyrrolidin-1-ylethoxy)phenyl]-1-ethoxy-cyclopropanecarboxamide (285)

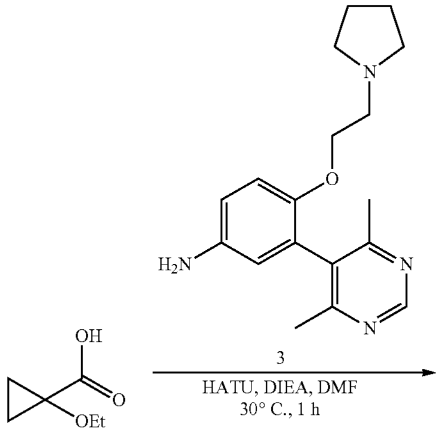

31

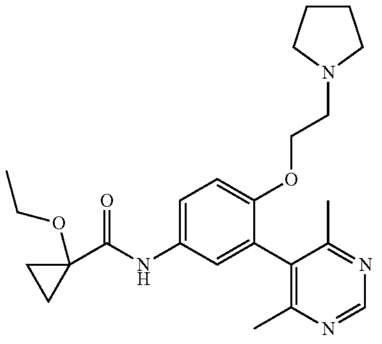

285

To a solution of 1-ethoxycyclopropanecarboxylic acid ((31), 29.99 mg, 230.47 μmol, 1.2 eq.) in DMF (1 mL) was added HATU (87.63 mg, 230.47 μmol, 1.2 eq.) and DIEA (74.46 mg, 576.18 μmol, 100.36 μL, 3 eq.). The reaction mixture was stirred at 15° C. for 30 min. 3-(4,6-Dimethylpyrimidin-5-yl)-4-(2-pyrrolidin-1-ylethoxy)aniline ((3), 60 mg, 192.06 μmol, 1 eq.) was added to the reaction mixture and the reaction mixture was stirred at 30° C. for 1 hr, then filtered. The filtrate was purified by prep-HPLC (column: Waters Xbridge 150*25 mm*5 μm; mobile phase: [water (10 mM $NH_4HCO_3$)-ACN]; B %: 20%-50%, 10 min) followed by lyophilization. N-[3-(4,6-dimethylpyrimidin-5-yl)-4-(2-pyrrolidin-1-ylethoxy)phenyl]-1-ethoxy-cyclopropanecarboxamide (34.46 mg, 77.92 μmol, 40.57% yield, 96% purity) was obtained as a brown gum.

LCMS (ESI): m/z [M+H] calcd for $C_{24}H_{33}N_4O_3$: 425.25; found: 425.3.

$^1$H NMR (400 MHZ, methanol-$d_4$) δ=8.84 (s, 1H), 7.65 (dd, J=2.7, 8.9 Hz, 1H), 7.41 (d, J=2.6 Hz, 1H), 7.15 (d, J=8.9 Hz, 1H), 4.13 (t, J=5.4 Hz, 2H), 3.65 (q, J=7.1 Hz, 2H), 2.74 (t, J=5.4 Hz, 2H), 2.41-2.33 (m, 4H), 2.28 (s, 6H), 1.73-1.65 (m, 4H), 1.30-1.23 (m, 5H), 1.20-1.13 (m, 2H).

N-[3-(4,6-dimethylpyrimidin-5-yl)-4-(2-pyrrolidin-1-ylethoxy)phenyl]-1-methoxy-cyclobutanecarboxamide (286)

Preparation of methyl 1-methoxycyclobutanecarboxylate (32)

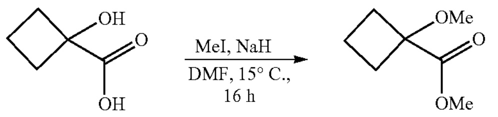

32

To a solution of 1-hydroxycyclobutanecarboxylic acid (300 mg, 2.58 mmol, 1 eq.) in DMF (5 mL) was added NaH (258.36 mg, 6.46 mmol, 60% purity, 2.5 eq.). The reaction mixture was stirred at 15° C. for 0.5 hrs. Iodomethane (916.79 mg, 6.46 mmol, 402.10 μL, 2.5 eq.) was added to the reaction mixture. The reaction mixture was stirred at 15° C. for 16 hrs. The residue was poured into 20 mL saturated $NH_4Cl$ (aq.). The pH of the mixture was adjusted to 8 with $NaHCO_3$. The aqueous phase was extracted with ethyl acetate (40 mL×3). The combined organic phase was washed with brine (20 mL), dried with anhydrous $Na_2SO_4$, filtered and concentrated in vacuum. Methyl 1-methoxycyclobutanecarboxylate ((32), 370 mg, crude) was obtained as a yellow oil.

Preparation of 1-methoxycyclobutanecarboxylic acid (33)

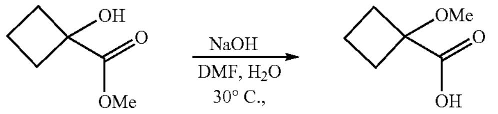

32 33

To a solution of methyl 1-methoxycyclobutanecarboxylate ((32), 370 mg, 2.57 mmol, 1 eq.) in THF (4 mL) was added NaOH (2 M, 2 mL, 1.56 eq.). The reaction mixture was stirred at 40° C. for 4 hrs. The aqueous phase was extracted with ethyl acetate (20 ml×2). The pH of the reaction mixture was adjusted to 5 with 1 M HCl (aq.). The aqueous phase was extracted with ethyl acetate (50 mL×4). The combined organic phase was washed with brine (40 mL), dried with anhydrous $Na_2SO_4$, filtered and concentrated in vacuum. 1-Methoxycyclobutanecarboxylic acid ((33), 100 mg, 768.39 μmol, 29.94% yield) was obtained as a yellow oil.

Preparation of N-[3-(4,6-dimethylpyrimidin-5-yl)-4-(2-pyrrolidin-1-ylethoxy)phenyl]-1-methoxy-cyclobutanecarboxamide (286)

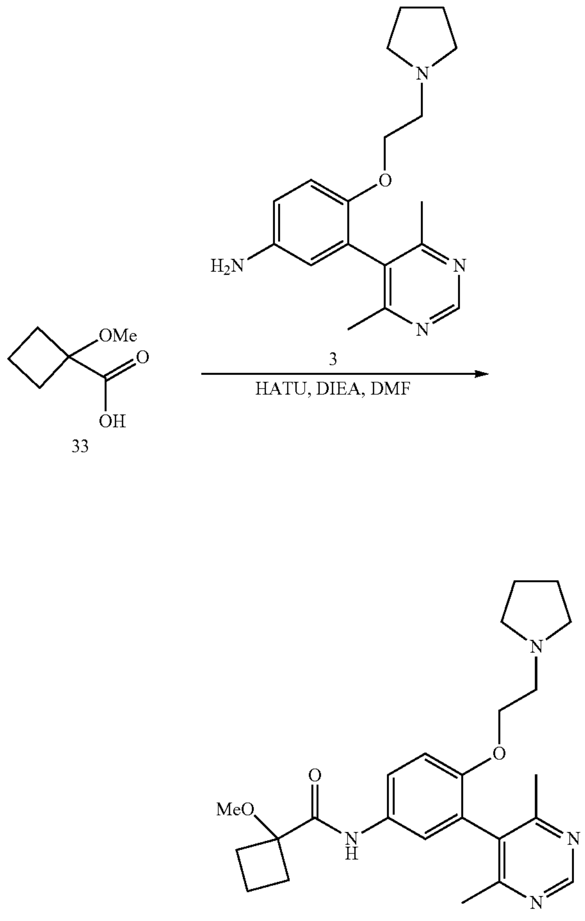

33 3 286

To a solution of 1-methoxycyclobutanecarboxylic acid ((33), 37.49 mg, 288.09 μmol, 1.5 eq.) in DMF (1 mL) was added HATU (87.63 mg, 230.47 μmol, 1.2 eq.) and DIEA (74.46 mg, 576.18 μmol, 100.36 μL, 3 eq.). The reaction mixture was stirred at 15° C. for 30 min. 3-(4,6-dimethylpyrimidin-5-yl)-4-(2-pyrrolidin-1-ylethoxy)aniline ((3), 60 mg, 192.06 μmol, 1 eq.) was added to the reaction mixture. The reaction mixture was stirred at 30° C. for 1 hr and then filtered. The filtrate was purified by prep-HPLC (column: Waters Xbridge 150*25 mm*5 μm; mobile phase: [water (10 mM $NH_4HCO_3$)-ACN]; B %: 24%-54%, 10 min) followed by lyophilization. N-[3-(4,6-dimethylpyrimidin-5-yl)-4-(2-pyrrolidin-1-ylethoxy)phenyl]-1-methoxy-cyclobutanecarboxamide (46.65 mg, 103.29 μmol, 53.78% yield, 94% purity) was obtained as a yellow gum.

LCMS (ESI): m/z [M+H] calcd for $C_{24}H_{33}N_4O_3$: 425.25; found: 425.4.

$^1H$ NMR (400 MHZ, methanol-$d_4$) δ=8.84 (s, 1H), 7.68 (dd, J=2.7, 8.9 Hz, 1H), 7.43 (d, J=2.7 Hz, 1H), 7.14 (d, J=8.9 Hz, 1H), 4.13 (t, J=5.4 Hz, 2H), 3.26 (s, 3H), 2.75 (t, J=5.4 Hz, 2H), 2.54-2.42 (m, 2H), 2.42-2.34 (m, 4H), 2.33-2.22 (m, 8H), 1.94-1.80 (m, 2H), 1.74-1.64 (m, 4H).

N-[3-(4,6-dimethylpyrimidin-5-yl)-4-(2-pyrrolidin-1-ylethoxy)phenyl]-2-pyrrolidin-1-yl-acetamide (287)

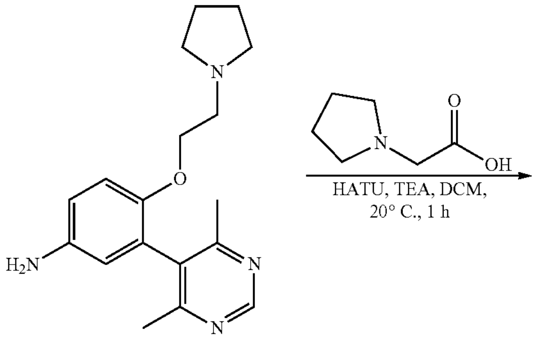

3

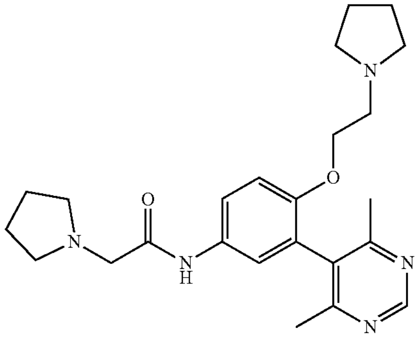

287

To a solution of 2-pyrrolidin-1-ylacetic acid (29.77 mg, 230.47 μmol, 1.2 eq.) in DCM (2 mL) was added HATU (80.33 mg, 211.26 μmol, 1.1 eq.) and TEA (58.30 mg, 576.17 μmol, 80.20 μL, 3 eq.) and 3-(4,6-dimethylpyrimidin-5-yl)-4-(2-pyrrolidin-1-ylethoxy)aniline ((3), 60 mg, 192.06 μmol, 1 eq.). The mixture was stirred at 20° C. for 1 hr. The reaction mixture was then concentrated under reduced pressure to give a residue. The residue was purified by prep-HPLC (column: Phenomenex Gemini NX-C18 (75*30 mm*3 μm); mobile phase: [water (10 mM $NH_4HCO_3$)-ACN]; B %: 8%-38%, 8 min). N-[3-(4,6-dimethylpyrimidin-5-yl)-4-(2-pyrrolidin-1-ylethoxy)phenyl]-2-pyrrolidin-1-yl-acetamide (37.01 mg, 86.51 μmol, 45.04% yield, 99% purity) was obtained as a brown gum.

LCMS (ESI): m/z [M+H] calcd for $C_{24}H_{34}N_5O_2$: 424.26; found: 424.3.

$^1$H NMR (400 MHZ, methanol-$d_4$) δ=8.84 (s, 1H), 7.65 (dd, J=2.6, 8.9 Hz, 1H), 7.45 (d, J=2.5 Hz, 1H), 7.14 (d, J=8.9 Hz, 1H), 4.13 (t, J=5.4 Hz, 2H), 3.34-3.32 (m, 2H), 2.75 (t, J=5.4 Hz, 2H), 2.73-2.65 (m, 4H), 2.43-2.32 (m, 4H), 2.27 (s, 6H), 1.86 (td, J=3.2, 6.7 Hz, 4H), 1.69 (td, J=3.3, 6.9 Hz, 4H).

2-(cyclopropylamino)-N-[3-(4,6-dimethylpyrimidin-5-yl)-4-(2-pyrrolidin-1-ylethoxy)phenyl]acetamide (288)

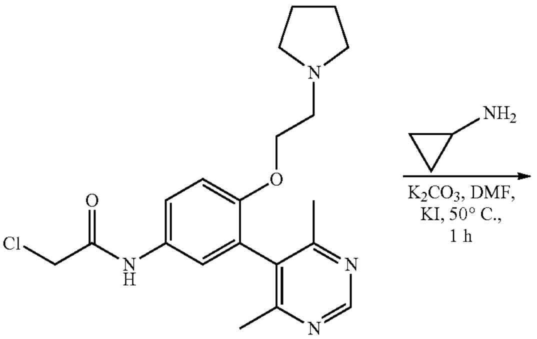

6

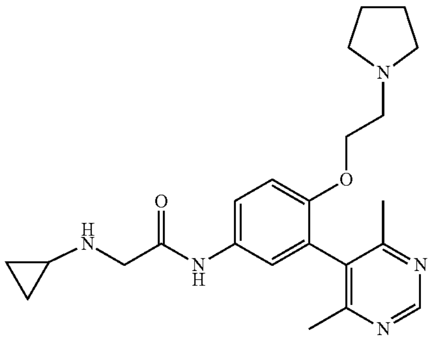

288

A mixture of cyclopropanamine (14.68 mg, 257.14 μmol, 17.82 μL, 2 eq.), 2-chloro-N-[3-(4,6-dimethylpyrimidin-5-yl)-4-(2-pyrrolidin-1-ylethoxy)phenyl]acetamide ((6), 50 mg, 128.57 μmol, 1 eq.), $K_2CO_3$ (35.54 mg, 257.14 μmol, 2 eq.), and KI (10.67 mg, 64.29 μmol, 0.5 eq.) in DMF (1 mL) was stirred at 50° C. for 1 hr. The reaction mixture was filtered and concentrated under reduced pressure to give a residue. The residue was purified by prep-HPLC (column: Waters Xbridge 150*25 mm*5 μm; mobile phase: [water (10 mM $NH_4HCO_3$)-ACN]; B %: 13%-43%, 9 min). 2-(Cyclopropylamino)-N-[3-(4,6-dimethylpyrimidin-5-yl)-4-(2-pyrrolidin-1-ylethoxy)phenyl]acetamide (28.11 mg, 67.27 μmol, 52.32% yield, 98% purity) was obtained as a yellow gum.

LCMS (ESI): m/z [M+H] calcd for $C_{23}H_{32}N_5O_2$: 410.25; found: 410.3.

$^1$H NMR (400 MHZ, methanol-$d_4$) δ=8.84 (s, 1H), 7.63 (dd, J=2.6, 8.9 Hz, 1H), 7.43 (d, J=2.6 Hz, 1H), 7.14 (d, J=8.9 Hz, 1H), 4.12 (t, J=5.4 Hz, 2H), 3.49-3.42 (m, 2H), 2.74 (t, J=5.4 Hz, 2H), 2.37 (br s, 4H), 2.32-2.22 (m, 7H), 1.73-1.65 (m, 4H), 0.52-0.38 (m, 4H).

2-(cyclopentylamino)-N-(3-(4,6-dimethylpyrimidin-5-yl)-4-(2-(pyrrolidin-1-yl)ethoxy)phenyl)acetamide (289)

289

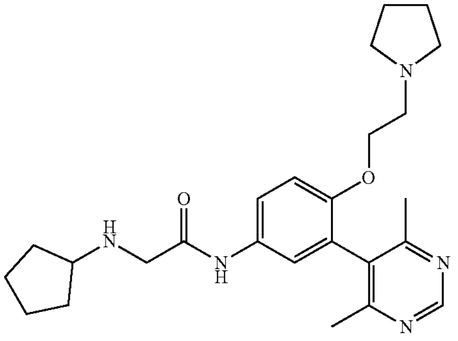

Compound 289 was prepared according to the synthesis described for compound 288, substituting cyclopentanamine for cyclopropanamine.

LCMS (ESI): m/z [M+H] calcd for $C_{25}H_{36}NO_2$: 438.28; found: 438.3.

$^1$H NMR (400 MHZ, methanol-d$_4$) δ=8.84 (s, 1H), 7.63 (dd, J=2.6, 8.9 Hz, 1H), 7.46 (d, J=2.5 Hz, 1H), 7.14 (d, J=9.0 Hz, 1H), 4.13 (t, J=5.4 Hz, 2H), 3.40 (s, 2H), 3.12 (quin, J=6.7 Hz, 1H), 2.75 (t, J=5.3 Hz, 2H), 2.38 (br s, 4H), 2.27 (s, 6H), 1.94-1.81 (m, 2H), 1.81-1.63 (m, 6H), 1.63-1.49 (m, 2H), 1.49-1.37 (m, 2H).

N-[3-(4,6-dimethylpyrimidin-5-yl)-4-(2-pyrrolidin-1-ylethoxy)phenyl]-4-fluoro-2-methyl-pyrazole-3-carboxamide (290)

Preparation of methyl 4-fluoro-2-methyl-pyrazole-3-carboxylate (34)

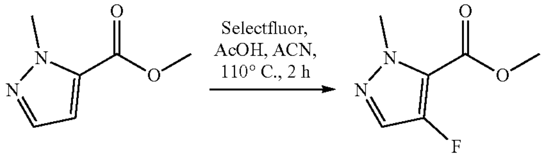

34

To a solution of methyl 2-methylpyrazole-3-carboxylate (5 g, 35.68 mmol, 1 eq.) in $CH_3CN$ (50 mL) was added Select F (25.28 g, 71.36 mmol, 2 eq.) and HOAc (10 mL). The mixture was stirred at 100° C. for 16 hrs. (monitored by LCMS). The mixture was diluted with water (200 mL) and then extracted with ethyl acetate (200 mL×2). The combined organic phase was washed with brine (100 mL), dried over anhydrous $Na_2SO_4$, filtered and concentrated in vacuo (water bath was kept at room temperature to avoid loss of product under vacuum as product is very volatile). The residue was purified by flash silica gel chromatography (ISCO®; 20 g SepaFlash® Silica Flash Column, eluent of 0~10% ethyl acetate/petroleum ether, gradient=35 mL/min). Methyl 4-fluoro-2-methyl-pyrazole-3-carboxylate ((34), 1.4 g, 8.85 mmol, 24.81% yield) was obtained as a white solid.

LCMS (ESI): m/z [M+H] calcd for $C_6H_8FN_2O_2$: 159.03, found: 159.1.

$^1$H NMR (400 MHZ, chloroform-d) δ=7.34 (d, J=4.4 Hz, 1H), 4.12 (d, J=0.8 Hz, 3H), 3.94 (s, 3H).

Preparation of 4-fluoro-2-methyl-pyrazole-3-carboxylic acid (35)

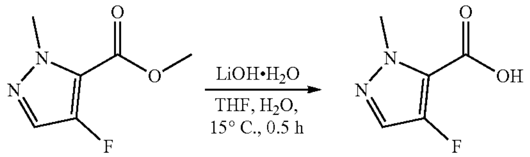

34 34

To a mixture of methyl 4-fluoro-2-methyl-pyrazole-3-carboxylate ((34), 180 mg, 1.14 mmol, 1 eq.) in MeOH (3 mL) and $H_2O$ (1 mL) was added $LiOH{\cdot}H_2O$ (95.53 mg, 2.28 mmol, 2 eq.). The mixture was stirred at 15° C. for 30 min (monitored by LCMS). The mixture was concentrated to remove excess EtOH. The residue was acidified with 1M HCl (aq.), and the pH was adjusted to 6-7. The mixture was concentrated. 4-fluoro-2-methyl-pyrazole-3-carboxylic acid ((35), 140 mg, crude) was obtained as a white solid.

Preparation of N-[3-(4,6-dimethylpyrimidin-5-yl)-4-(2-pyrrolidin-1-ylethoxy)phenyl]-4-fluoro-2-methyl-pyrazole-3-carboxamide (290)

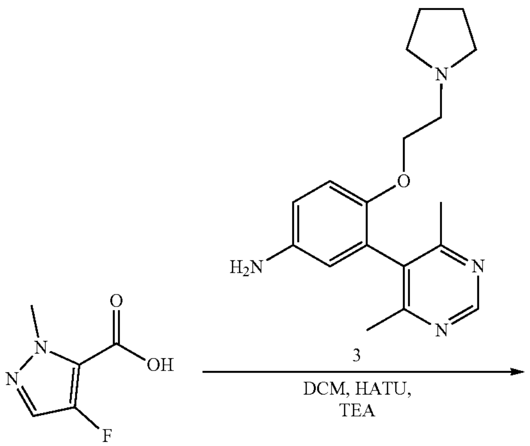

35

-continued

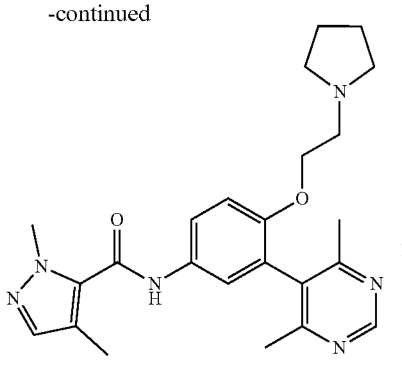

290

To a solution of 3-(4,6-dimethylpyrimidin-5-yl)-4-(2-pyrrolidin-1-ylethoxy)aniline ((3), 1.5 g, 4.80 mmol, 1 eq.) in DCM (15 mL) was added HATU (2.74 g, 7.20 mmol, 1.5 eq.), TEA (485.85 mg, 4.80 mmol, 668.29 μL, 1 eq.), and 4-fluoro-2-methyl-pyrazole-3-carboxylic acid ((35), 830.28 mg, 5.76 mmol, 1.2 eq.). The mixture was stirred at 30° C. for 16 hrs. The mixture was then concentrated in vacuo. The residue was purified by prep-HPLC (TFA condition, column: Phenomenex Synergi Max-RP 250*50 mm*10 μm; mobile phase: [water (0.1% TFA)-ACN]; B %: 5%-25%, 20 min). N-[3-(4,6-dimethylpyrimidin-5-yl)-4-(2-pyrrolidin-1-ylethoxy)phenyl]-4-fluoro-2-methyl-pyrazole-3-carboxamide (1.1 g, 1.97 mmol, 41.05% yield, 99. % purity, TFA) was obtained as a pink solid.

LCMS (ESI): m/z [M+H] calcd for $C_{23}H_{28}FN_6O_2$: 439.0, found: 439.2.

$^1$H NMR (400 MHZ, methanol-$d_4$) δ=8.92 (s, 1H), 7.80 (dd, J=2.4, 8.9 Hz, 1H), 7.55 (d, J=2.5 Hz, 1H), 7.47 (d, J=4.3 Hz, 1H), 7.25 (d, J=9.0 Hz, 1H), 4.40-4.31 (m, 2H), 4.05 (d, J=0.6 Hz, 3H), 3.57-3.50 (m, 2H), 3.38 (br s, 2H), 2.87 (br d, J=5.4 Hz, 2H), 2.33 (s, 6H), 2.03 (br d, J=4.9 Hz, 2H), 1.96-1.81 (m, 2H).

N-(3-(4,6-dimethylpyrimidin-5-yl)-4-(2-(pyrrolidin-1-yl)ethoxy)phenyl)-2-ethoxycyclopropane-1-carboxamide (291)

Preparation of ethyl 2-ethoxycyclopropanecarboxylate (36)

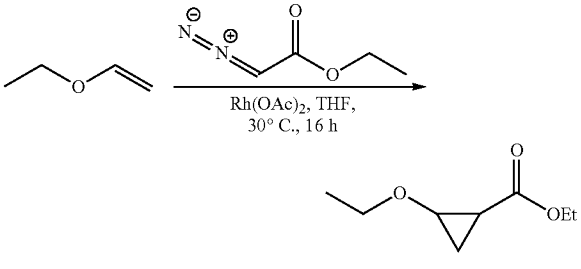

36

To a mixture of vinyloxyethane (1 g, 13.87 mmol, 1.33 mL, 1 eq.) and diacetoxyrhodium (306.49 mg, 693.43 μmol, 0.05 eq.) in THF (10 mL) was added ethyl 2-diazoacetate (1.58 g, 13.87 mmol, 1.45 mL, 1 eq.) in THF (10 mL) in portions under $N_2$. The mixture was stirred at 30° C. for 16 hrs under $N_2$ (monitored by LCMS). The mixture was filtered and concentrated in vacuum. The residue was purified by silica gel chromatography (100-200 mesh silica gel, petroleum ether/ethyl acetate=100/1, 50/1). Ethyl 2-ethoxycyclopropanecarboxylate ((36), 0.52 g, 3.29 mmol, 23.70% yield) was obtained as a colorless oil.

$^1$H NMR (400 MHZ, chloroform-d) δ=4.05 (q, J=7.1 Hz, 2H), 3.59-3.48 (m, 3H), 1.68 (ddd, J=2.0, 6.1, 9.5 Hz, 1H), 1.22-1.16 (m, 5H), 1.13 (t, J=7.0 Hz, 3H).

Preparation of 2-ethoxycyclopropanecarboxylic acid (37)

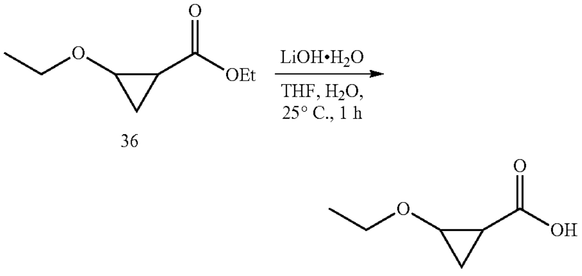

36

37

To a mixture of ethyl 2-ethoxycyclopropanecarboxylate ((36), 150 mg, 948.20 μmol, 1 eq.) in EtOH (3 mL) and $H_2O$ (1 mL) was added LiOH·$H_2O$ (79.58 mg, 1.90 mmol, 2 eq.). The mixture was stirred at 25° C. for 1 hr (monitored by LCMS). The mixture was concentrated to remove excess EtOH. The residue was acidified with 1M HCl (aq.), the pH was adjusted to 6-7, and then the mixture was concentrated. 2-Ethoxycyclopropanecarboxylic acid ((37), 90 mg, crude) was obtained as a colorless oil.

Preparation of N-(3-(4,6-dimethylpyrimidin-5-yl)-4-(2-(pyrrolidin-1-yl)ethoxy)phenyl)-2-ethoxycyclopropane-1-carboxamide (291)

291

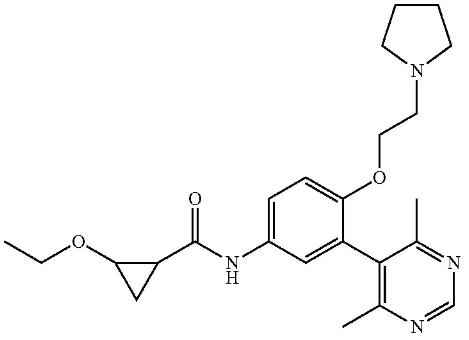

LCMS (ESI): m/z [M+H] calcd for $C_{24}H_{33}N_4O_3$: 425.0, found: 425.3.

$^1$H NMR (400 MHZ, methanol-$d_4$) δ 8.83 (s, 1H), 7.58 (dd, J=8.9, 2.6 Hz, 1H), 7.39 (d, J=2.6 Hz, 1H), 7.12 (d, J=8.9 Hz, 1H), 4.11 (t, J=5.4 Hz, 2H), 3.67-3.55 (m, 3H), 2.74 (t, J=5.3 Hz, 2H), 2.37 (br s, 4H), 1.89 (ddd, J=9.5, 5.9, 2.0 Hz, 1H), 1.73-1.64 (m, 4H), 1.28-1.16 (m, 5H).

N-(3-(4,6-dimethylpyrimidin-5-yl)-4-(2-(pyrrolidin-1-yl)ethoxy)phenyl)-1,4-dimethyl-1H-pyrazole-5-carboxamide (292)

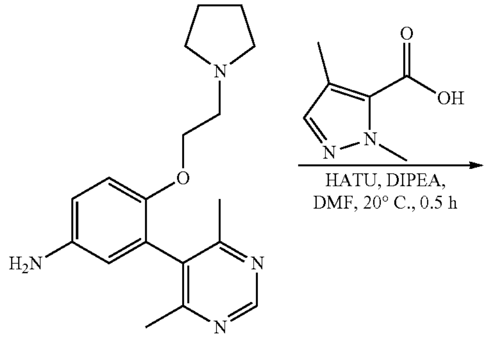

3

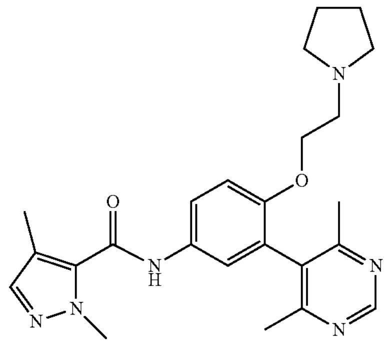

292

To a solution of 1,4-dimethyl-1H-pyrazole-5-carboxylic acid (39.5 mg, 281.68 μmol, 1.1 eq.) in DMF (2 mL) was added HATU (146.05 mg, 384.11 μmol, 1.5 eq.) and DIPEA (89.21 μL, 2 eq.). The mixture was stirred at 20° C. for 0.5 hrs. Then 3-(4,6-dimethylpyrimidin-5-yl)-4-(2-(pyrrolidin-1-yl)ethoxy)aniline ((3), 80 mg, 256.08 μmol, 1 eq.) was added to the solution, and the mixture was stirred at 20° C. for 12 hrs. The mixture was then filtered. The mixture was purified by prep-HPLC: column: Phenomenex Gemini-NX C18 75*30 mm*3 μm; mobile phase: [water (10 mM $NH_4HCO_3$)-ACN]; B %: 12%-42%, 8 min. N-(3-(4,6-dimethylpyrimidin-5-yl)-4-(2-(pyrrolidin-1-yl)ethoxy)phenyl)-1,4-dimethyl-1H-pyrazole-5-carboxamide (61.4 mg, 99% purity) was obtained as a yellow solid.

LCMS (ESI): m/z [M+H] calcd for: $C_{24}H_{31}N_6O_2$: 435.25; found: 435.30.

$^1$H NMR (400 MHZ, methanol-$d_4$) δ=8.88 (s, 1H), 7.88-7.65 (m, 1H), 7.56 (br s, 1H), 7.33 (s, 1H), 7.24 (d, J=9.0 Hz, 1H), 4.36 (t, J=5.0 Hz, 2H), 3.96 (s, 3H), 3.40 (t, J=4.9 Hz, 2H), 3.01 (br t, J=6.5 Hz, 4H), 2.31 (s, 6H), 2.24 (s, 3H), 1.94-1.86 (m, 4H).

N-(3-(4,6-dimethylpyrimidin-5-yl)-4-(2-(pyrrolidin-1-yl)ethoxy)phenyl)-1-(fluoromethyl)cyclopropane-1-carboxamide (293)

293

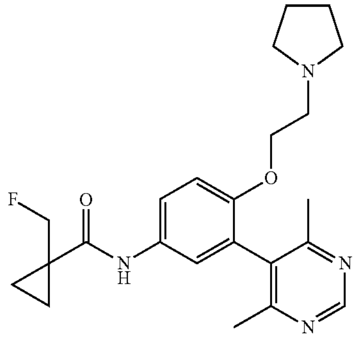

Compound 293 was prepared according to the synthesis described for compound 292, substituting 1-(fluoromethyl)cyclopropane-1-carboxylic acid for 1,4-dimethyl-1H-pyrazole-5-carboxylic acid.

LCMS (ESI): m/z [M+H] calcd for $C_{23}H_{30}FN_4O_2$: 413.24; found: 413.30.

$^1$H NMR (400 MHZ, methanol-$d_4$) δ=8.83 (s, 1H), 7.68-7.52 (m, 1H), 7.35 (d, J=2.6 Hz, 1H), 7.22-7.07 (m, 1H), 4.70 (s, 1H), 4.58 (s, 1H), 4.19-4.06 (m, 2H), 2.83-2.68 (m, 2H), 2.38 (br s, 4H), 2.31-2.20 (m, 6H), 1.75-1.64 (m, 4H), 1.37-1.28 (m, 2H), 1.03-0.93 (m, 2H).

N-(3-(4,6-dimethylpyrimidin-5-yl)-4-(2-(pyrrolidin-1-yl)ethoxy)phenyl)-2-(thiazol-2-yl)acetamide (294)

294

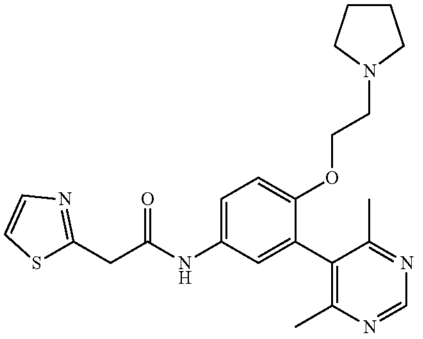

Compound 294 was prepared according to the synthesis described for compound 292, substituting 2-(thiazol-2-yl)acetic acid for 1,4-dimethyl-1H-pyrazole-5-carboxylic acid.

LCMS (ESI): m/z [M+H] calcd for $C_{23}H_{28}N_5O_2S$: 438.20; found: 438.30.

$^1$H NMR (400 MHZ, DMSO-$d_6$) δ=10.46-10.31 (m, 1H), 8.92-8.79 (m, 1H), 7.78-7.72 (m, 1H), 7.66-7.64 (m, 1H), 7.63-7.58 (m, 1H), 7.45-7.39 (m, 1H), 7.20-7.12 (m, 1H), 4.17-4.10 (m, 2H), 4.08-4.00 (m, 2H), 2.62-2.55 (m, 2H), 2.30-2.23 (m, 4H), 2.20-2.14 (m, 6H), 1.60-1.52 (m, 4H).

N-[3-(4,6-dimethylpyrimidin-5-yl)-4-(2-pyrrolidin-1-ylethoxy)phenyl]-3-fluoro-1-methyl-pyrrole-2-carboxamide (295)

Preparation of ethyl 3-fluoro-1-methyl-pyrrole-2-carboxylate (38)

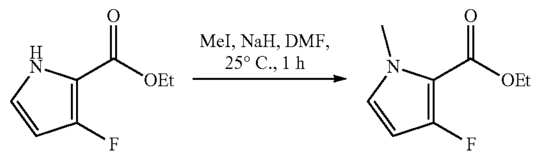

38

To a solution of ethyl 3-fluoro-1H-pyrrole-2-carboxylate (200 mg, 1.27 mmol, 1 eq.) and MeI (216.78 mg, 1.53 mmol, 95.08 μL, 1.2 eq.) in DMF (5 mL) was added NaH (61.09 mg, 1.53 mmol, 60% purity, 1.2 eq.). The reaction mixture was stirred at 25° C. for 1 hr. The residue was poured into 20 mL saturated $NH_4Cl$ (aq.). The aqueous phase was extracted with ethyl acetate (20 mL×3). The combined organic phase was washed with brine (30 mL×2), dried with anhydrous $Na_2SO_4$, filtered and concentrated in vacuum. Ethyl 3-fluoro-1-methyl-pyrrole-2-carboxylate ((38), 215 mg, 1.26 mmol, 98.69% yield) was obtained as a yellow oil.

$^1$H NMR (400 MHZ, DMSO-$d_6$) δ=6.99 (dd, J=3.0, 5.4 Hz, 1H), 5.99 (d, J=3.1 Hz, 1H), 4.22 (q, J=7.1 Hz, 2H), 3.77 (d, J=0.8 Hz, 3H), 1.26 (t, J=7.1 Hz, 3H).

Preparation of 3-fluoro-1-methyl-pyrrole-2-carboxylic acid (39)

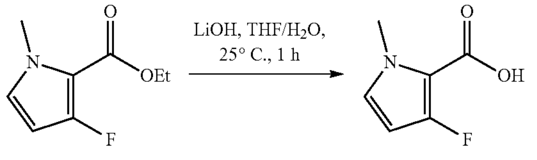

38 39

To a solution of ethyl 3-fluoro-1-methyl-pyrrole-2-carboxylate ((38), 215 mg, 1.26 mmol, 1 eq.) in THF (2 mL) was added LiOH (60.16 mg, 2.51 mmol, 2 eq.) in $H_2O$ (2 mL). The reaction mixture was stirred at 25° C. for 2 hrs. The residue was poured into water (20 mL). The aqueous phase was extracted with petroleum ether (20 mL×2). The pH of the aqueous phase was adjusted to 5 with 1 M HCl. The aqueous phase was extracted with ethyl acetate (20 mL×2). The combined organic phase was washed with brine (20 mL), dried with anhydrous $Na_2SO_4$, filtered and concentrated in vacuum. 3-Fluoro-1-methyl-pyrrole-2-carboxylic acid ((39), 90 mg, 628.86 μmol, 50.07% yield) was obtained as a white solid.

$^1$H NMR (400 MHZ, DMSO-$d_6$) δ=6.94 (dd, J=3.1, 5.4 Hz, 1H), 5.95 (d, J=3.1 Hz, 1H), 3.76 (s, 3H).

Preparation of N-[3-(4,6-dimethylpyrimidin-5-yl)-4-(2-pyrrolidin-1-ylethoxy)phenyl]-3-fluoro-1-methyl-pyrrole-2-carboxamide (295)

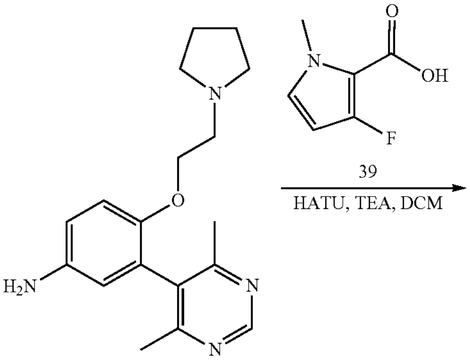

39

3

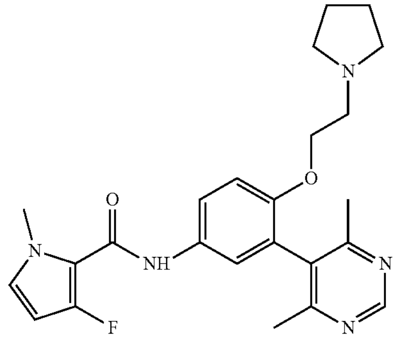

295

To a solution of 3-fluoro-1-methyl-pyrrole-2-carboxylic acid ((39), 43.98 mg, 307.29 μmol, 1.2 eq.) in DCM (2 mL) was added HATU (146.05 mg, 384.11 μmol, 1.5 eq.) and DIEA (66.19 mg, 512.15 μmol, 89.21 μL, 2 eq.). The reaction mixture was stirred at 25° C. for 0.5 hrs. 3-(4,6-dimethylpyrimidin-5-yl)-4-(2-pyrrolidin-1-ylethoxy)aniline ((3), 80 mg, 256.08 μmol, 1 eq.) was then added to the reaction mixture. The reaction mixture was stirred at 25° C. for 16 hrs. LCMS showed one main peak with the desired mass. The reaction mixture was concentrated in vacuum. The residue was purified by prep-HPLC (column: 3_Phenomenex Luna C18 75*30 mm*3 μm; mobile phase: [water (0.1% TFA)-ACN]; B %: 8%-38%, 8 min) followed by lyophilization. N-[3-(4,6-Dimethylpyrimidin-5-yl)-4-(2-pyrrolidin-1-ylethoxy)phenyl]-3-fluoro-1-methyl-pyrrole-2-carboxamide (50.61 mg, 113.36 μmol, 44.27% yield, 98% purity) was obtained as a yellow solid.

LCMS (ESI): m/z [M+H] calcd for $C_{24}H_{29}FN_5O_2$: 438.22; found: 438.2.

$^1$H NMR (400 MHZ, methanol-$d_4$) δ=8.90 (s, 1H), 7.73 (dd, J=2.6, 8.9 Hz, 1H), 7.49 (d, J=2.6 Hz, 1H), 7.22 (d, J=8.9 Hz, 1H), 6.77 (dd, J=3.1, 5.3 Hz, 1H), 5.95 (d, J=3.1 Hz, 1H), 4.41-4.25 (m, 2H), 3.85 (d, J=0.8 Hz, 3H), 3.56-3.49 (m, 2H), 3.38 (br s, 2H), 2.88 (br s, 2H), 2.33 (s, 6H), 2.11-1.80 (m, 4H).

N-(3-(4,6-dimethylpyrimidin-5-yl)-4-(2-(pyrrolidin-1-yl)ethoxy)phenyl)-3,3-difluorocyclobutane-1-carboxamide (296)

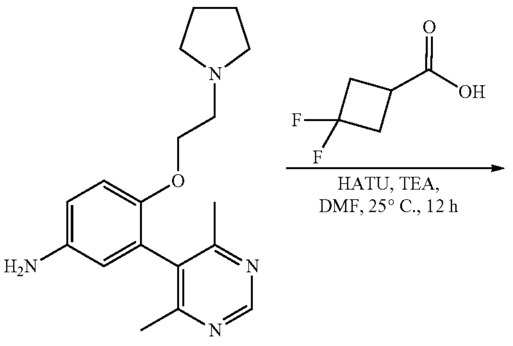

3

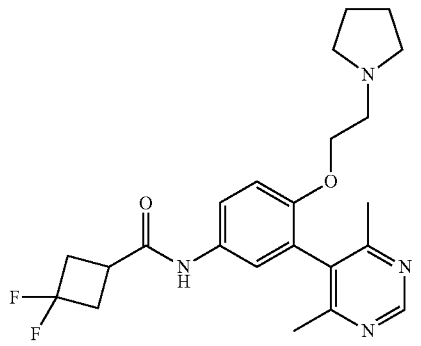

296

To a solution of 3-(4,6-dimethylpyrimidin-5-yl)-4-(2-pyrrolidin-1-ylethoxy)aniline ((3), 100 mg, 320.09 μmol, 1 eq.) in DMF (2 mL) was added 3,3-difluorocyclobutanecarboxylic acid (47.92 mg, 352.10 μmol, 1.1 eq.), HATU (182.56 mg, 480.14 μmol, 1.5 eq.) and TEA (97.17 mg, 960.28 μmol, 133.66 μL, 3 eq.). The mixture was stirred at 25° C. for 12 hrs. LCMS showed 3-(4,6-dimethylpyrimidin-5-yl)-4-(2-pyrrolidin-1-ylethoxy)aniline was consumed completely and one main peak with desired m/z. The residue was purified by prep-HPLC (TFA condition) to afford N-(3-(4,6-dimethylpyrimidin-5-yl)-4-(2-(pyrrolidin-1-yl)ethoxy) phenyl)-3,3-difluorocyclobutane-1-carboxamide (60.3 mg, 138.67 μmol, 43.32% yield, 99% purity) as a white gum.

LCMS (ESI): m/z [M+H] calcd for $C_{23}H_{29}N_4O_2F_2$: 431.3; found: 431.1.

$^1$H NMR (400 MHz, methanol-$d_4$) δ ppm 1.81-1.94 (m, 2H) 2.02 (br s, 2H) 2.30 (s, 6H) 2.70-2.95 (m, 6H) 3.01-3.14 (m, 1H) 3.36 (br d, J=9.38 Hz, 2H) 3.47-3.56 (m, 2H) 4.28-4.36 (m, 2H) 7.20 (d, J=9.01 Hz, 1H) 7.47 (d, J=2.63 Hz, 1H) 7.68 (dd, J=8.94, 2.56 Hz, 1H) 8.91 (s, 1H).

N-(3-(4,6-dimethylpyrimidin-5-yl)-4-(2-(pyrrolidin-1-yl)ethoxy)phenyl)-3-fluorobenzamide (297)

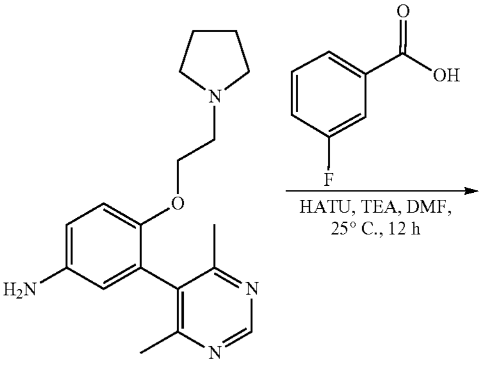

3

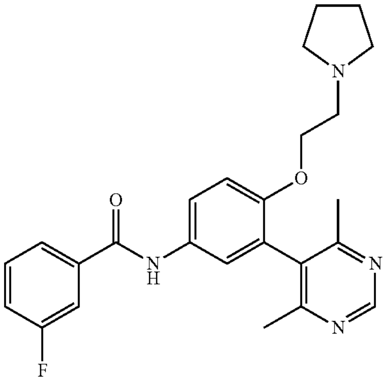

297

Compound 297 was prepared according to the synthesis described for compound 295, substituting 3-fluorobenzoic acid for 3,3-difluorocyclobutanecarboxylic acid.

LCMS (ESI): m/z [M+H] calcd for $C_{25}H_{28}N_4O_2F$: 435.2; found: 435.2.

$^1$H NMR (400 MHZ, methanol-$d_4$) δ=8.91 (s, 1H), 7.85 (dd, J=2.6, 8.9 Hz, 1H), 7.77 (br d, J=7.9 Hz, 1H), 7.68 (br d, J=9.6 Hz, 1H), 7.58-7.51 (m, 2H), 7.34 (dt, J=2.3, 8.3 Hz, 1H), 7.26 (d, J=9.0 Hz, 1H), 4.39-4.32 (m, 2H), 3.56-3.50 (m, 2H), 3.37 (br d, J=14.8 Hz, 2H), 2.86 (br s, 2H), 2.33 (s, 6H), 2.10-1.82 (m, 4H).

N-(3-(4,6-dimethylpyrimidin-5-yl)-4-(2-(pyrrolidin-1-yl)ethoxy)phenyl)-2-fluorobenzamide (298)

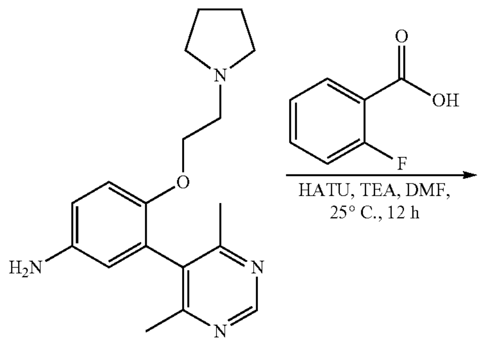

3

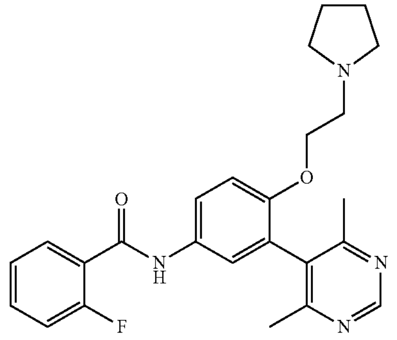

298

Compound 298 was prepared according to the synthesis described for compound 295, substituting 2-fluorobenzoic acid for 3,3-difluorocyclobutanecarboxylic acid.

LCMS (ESI): m/z [M+H] calcd for $C_{25}H_{28}N_4O_2F$: 435.2; found: 435.2.

$^1$H NMR (400 MHZ, methanol-$d_4$) δ=8.92 (s, 1H), 7.83 (dd, J=2.6, 8.9 Hz, 1H), 7.74 (dt, J=1.4, 7.4 Hz, 1H), 7.60-7.53 (m, 2H), 7.35-7.22 (m, 3H), 4.40-4.32 (m, 2H), 3.57-3.50 (m, 2H), 3.44-3.35 (m, 2H), 2.87 (br s, 2H), 2.34 (s, 6H), 2.07-1.83 (m, 4H).

N-(3-(4,6-dimethylpyrimidin-5-yl)-4-(2-(pyrrolidin-1-yl)ethoxy)phenyl)-2-methylbenzamide (299)

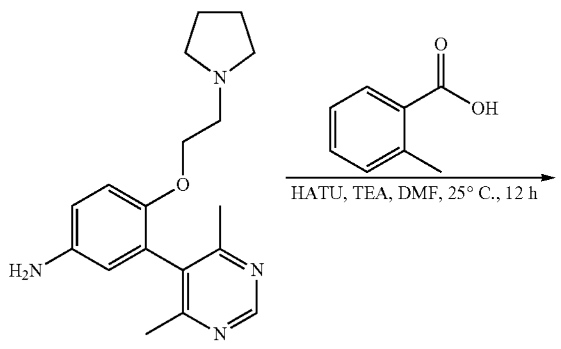

3

-continued

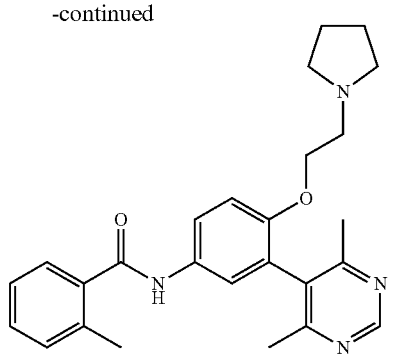

299

Compound 299 was prepared according to the synthesis described for compound 295, substituting 2-methylbenzoic acid for 3,3-difluorocyclobutanecarboxylic acid.

LCMS (ESI): m/z [M+H] calcd for $C_{26}H_{31}N_4O_2$: 431.2; found: 431.2.

$^1$H NMR (400 MHZ, methanol-$d_4$) δ=8.91 (s, 1H), 7.84 (dd, J=2.4, 8.9 Hz, 1H), 7.53 (d, J=2.5 Hz, 1H), 7.47 (d, J=7.5 Hz, 1H), 7.42-7.35 (m, 1H), 7.33-7.22 (m, 3H), 4.35 (t, J=4.8 Hz, 2H), 3.53 (t, J=4.8 Hz, 2H), 3.43-3.35 (m, 2H), 2.87 (br d, J=5.5 Hz, 2H), 2.46 (s, 3H), 2.33 (s, 6H), 2.08-1.85 (m, 4H).

N-(3-(4,6-dimethylpyrimidin-5-yl)-4-(2-(pyrrolidin-1-yl)ethoxy)phenyl)-3-methylbenzamide (300)

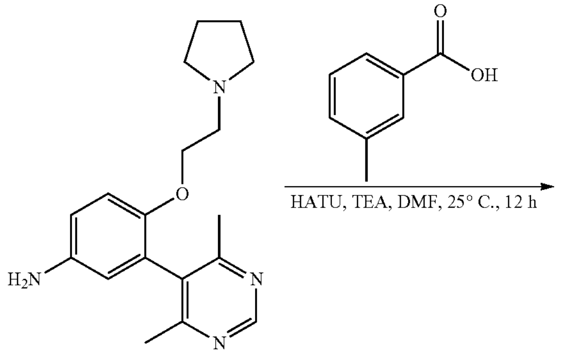

3

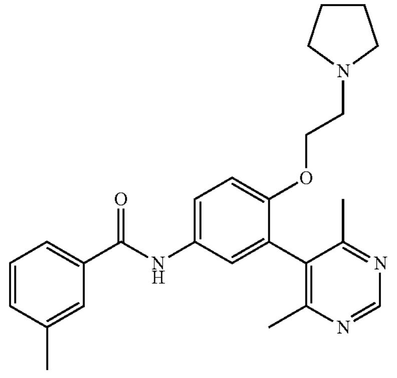

300

Compound 300 was prepared according to the synthesis described for compound 295, substituting 3-methylbenzoic acid for 3,3-difluorocyclobutanecarboxylic acid.

LCMS (ESI): m/z [M+H] calcd for $C_{26}H_{31}N_4O_2$: 431.2; found: 431.2.

$^1$H NMR (400 MHZ, methanol-$d_4$) δ=8.91 (s, 1H), 7.85 (dd, J=2.4, 9.0 Hz, 1H), 7.76 (s, 1H), 7.72 (br d, J=6.5 Hz, 1H), 7.56 (d, J=2.4 Hz, 1H), 7.44-7.37 (m, 2H), 7.25 (d, J=8.9 Hz, 1H), 4.38-4.32 (m, 2H), 3.57-3.51 (m, 2H), 3.38 (br s, 2H), 2.88 (br d, J=10.6 Hz, 2H), 2.44 (s, 3H), 2.34 (s, 6H), 2.07-1.84 (m, 4H).

N-(3-(4,6-dimethylpyrimidin-5-yl)-4-(2-(pyrrolidin-1-yl)ethoxy)phenyl)-4-methylbenzamide (301)

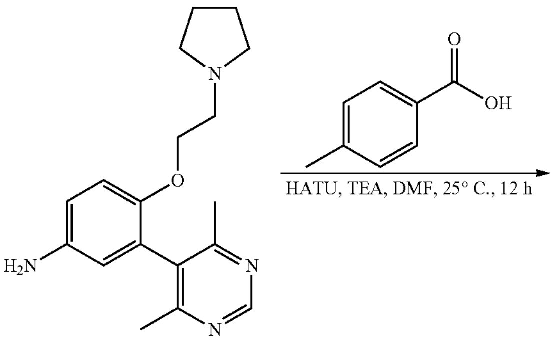

3

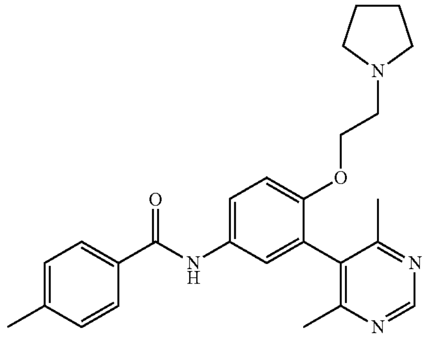

301

Compound 301 was prepared according to the synthesis described for compound 295, substituting 4-methylbenzoic acid for 3,3-difluorocyclobutanecarboxylic acid.

LCMS (ESI): m/z [M+H] calcd for $C_{26}H_{31}N_4O_2$: 431.2; found: 431.2.

$^1$H NMR (400 MHz, methanol-$d_4$) δ=8.91 (s, 1H), 7.84 (br d, J=8.3 Hz, 3H), 7.55 (d, J=2.4 Hz, 1H), 7.33 (d, J=8.1 Hz, 2H), 7.25 (d, J=9.0 Hz, 1H), 4.38-4.31 (m, 2H), 3.53 (t, J=4.7 Hz, 2H), 3.38 (br s, 2H), 2.93-2.83 (m, 2H), 2.42 (s, 3H), 2.34 (s, 6H), 2.08-1.83 (m, 4H).

(1s,3s)-N-(3-(4,6-dimethylpyrimidin-5-yl)-4-(2-(pyrrolidin-1-yl)ethoxy)phenyl)-3-fluorocyclobutane-1-carboxamide (302)

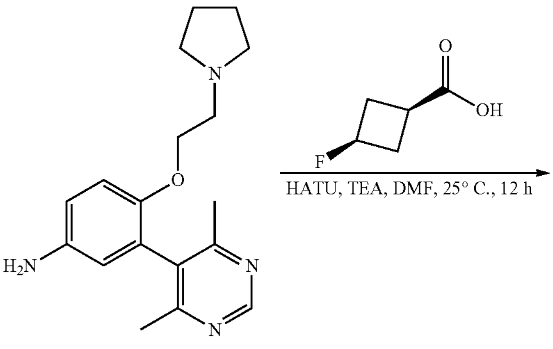

3

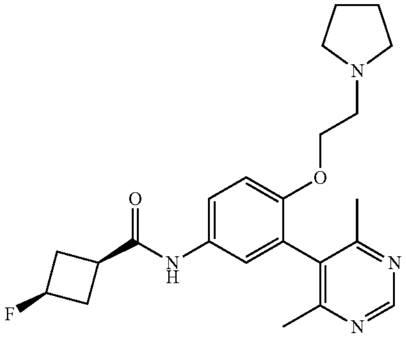

302

Compound 302 was prepared according to the synthesis described for compound 295, substituting (1s,3s)-3-fluorocyclobutane-1-carboxylic acid for 3,3-difluorocyclobutanecarboxylic acid.

LCMS (ESI): m/z [M+H] calcd for $C_{23}H_{30}FN_4O_2$: 413.2; found: 413.1.

$^1$H NMR (400 MHz, methanol-$d_4$) δ=8.92 (s, 1H), 7.67 (dd, J=2.5, 8.9 Hz, 1H), 7.47 (d, J=2.5 Hz, 1H), 7.20 (d, J=9.0 Hz, 1H), 5.09-4.89 (m, 1H), 4.33 (br t, J=4.7 Hz, 2H), 3.54-3.47 (m, 2H), 3.38 (br s, 2H), 2.85 (br s, 2H), 2.75-2.65 (m, 1H), 2.64-2.53 (m, 2H), 2.51-2.36 (m, 2H), 2.31 (s, 6H), 2.06-1.84 (m, 4H).

(1r,3r)-N-(3-(4,6-dimethylpyrimidin-5-yl)-4-(2-(pyrrolidin-1-yl)ethoxy)phenyl)-3-fluorocyclobutane-1-carboxamide (303)

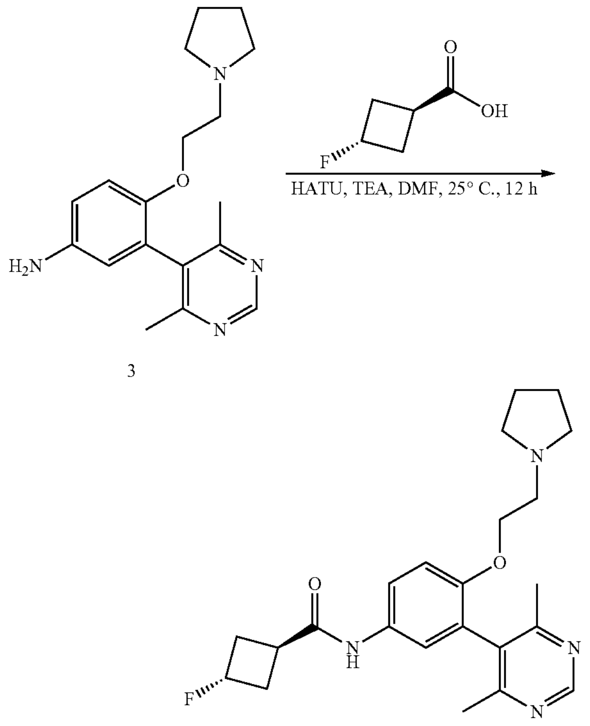

3

303

Compound 303 was prepared according to the synthesis described for compound (1r,3r)-3-fluorocyclobutane-1-carboxylic acid for 3,3-295, substituting difluorocyclobutanecarboxylic acid.

LCMS (ESI): m/z [M+H] calcd for $C_{23}H_{30}FN_4O_2$: 413.2; found: 413.1.

$^1$H NMR (400 MHz, methanol-$d_4$) δ=8.92 (s, 1H), 7.66 (dd, J=2.6, 9.0 Hz, 1H), 7.46 (d, J=2.5 Hz, 1H), 7.19 (d, J=9.0 Hz, 1H), 5.35-5.10 (m, 1H), 4.36-4.29 (m, 2H), 3.55-3.47 (m, 2H), 3.38 (br s, 2H), 3.28-3.19 (m, 1H), 2.86 (br d, J=2.6 Hz, 2H), 2.68-2.40 (m, 4H), 2.31 (s, 6H), 2.08-1.83 (m, 4H).

N-[4-[2-(azetidin-1-yl)ethoxy]-3-(4,6-dimethylpyrimidin-5-yl)phenyl]-2-methyl-pyrazole-3-carboxamide (304)

Preparation of 2-(azetidin-1-yl)-2-oxoethyl acetate (40)

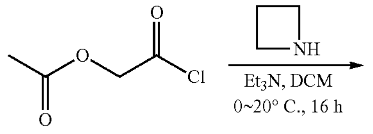

-continued

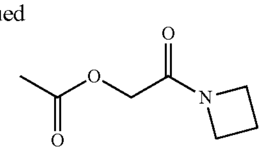

40

A mixture of azetidine as the hydrochloride salt (17.99 g, 192.26 mmol, 1.05 eq.) and TEA (40.76 g, 402.83 mmol, 56.07 mL, 2.2 eq.) in DCM (350 mL) was stirred at 20° C. for 1 h. Then (2-chloro-2-oxo-ethyl)acetate (25 g, 183.11 mmol, 19.69 mL, 1 eq.) was added dropwise to the reaction solution at 0° C. After the addition, the reaction mixture was stirred at 20° C. for 12 hrs. The reaction mixture was filtered to remove triethylamine as the hydrochloride salt, then water (150 mL) was added to the reaction mixture, extracted with DCM (100 mL×3), the combined organic layer was washed with brine (50 mL×3), dried over anhydrous $Na_2SO_4$, and concentrated to obtain 2-(azetidin-1-yl)-2-oxoethyl acetate ((40), 40 g crude with residual DCM), which was used in the next step without purification.

$^1$H NMR (400 MHZ, $CDCl_3$) 4.48 (s, 2H), 4.22 (t, J=7.7 Hz, 2H), 4.07 (t, J=7.8 Hz, 2H), 2.38-2.29 (m, 2H), 2.14 (s, 3H).

Preparation of 2-(azetidine-1-yl)ethanol (41)

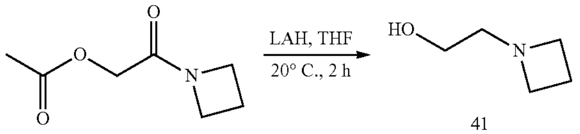

41

40

A solution of 2-(azetidin-1-yl)-2-oxoethyl acetate ((40), 40.00 g, 127.25 mmol, 1 eq.) in THF (100 mL) was added dropwise to LAH (12.07 g, 318.13 mmol, 2.5 eq.) in THF (200 mL) at 0° C. under $N_2$. The mixture was heated to 40° C. for 4 hrs. Then the reaction mixture was quenched by addition of $H_2O$ (12 mL) and 15% aq. NaOH (12 mL) at 0° C., then stirred at 20° C. for 30 min. Then $Na_2SO_4$ (150 g) was added to the reaction mixture. The mixture was filtered and the filtrate was concentrated under reduced pressure to give compound 2-(azetidine-1-yl)ethanol ((41), 7 g, 34.60 mmol, 27.19% yield, 50% purity) as a yellow oil, which was used in the next step directly without purification.

$^1$H NMR (400 MHZ, $CDCl_3$) 3.49-3.41 (m, 2H), 3.17 (t, J=7.1 Hz, 4H), 2.57-2.44 (m, 2H), 2.08-1.94 (m, 2H).

Preparation of 5-[2-[2-(azetidin-1-yl)ethoxy]-5-nitro-phenyl]-4,6-dimethyl-pyrimidine (42)

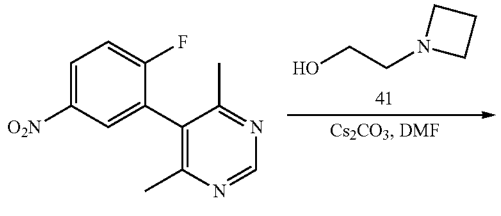

1

-continued

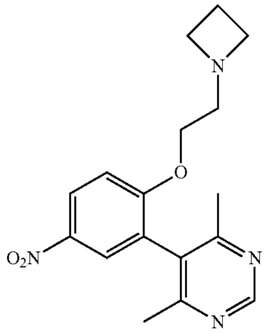

42

A mixture of 5-(2-fluoro-5-nitro-phenyl)-4,6-dimethyl-pyrimidine ((1), 3.2 g, 12.94 mmol, 1 eq.), 2-(azetidine-1-yl)ethanol ((41), 1.31 g, 12.94 mmol, 1 eq.) and $Cs_2CO_3$ (8.43 g, 25.89 mmol, 2 eq.) in DMF (35 mL) was stirred at 80° C. for 12 hrs. Water (30 mL) was added to the reaction mixture, and the reaction mixture was extracted with ethyl acetate (50 mL×3). The combined organic layer was washed with water (15 mL×3), brine (10 mL×3), then dried over $Na_2SO_4$, and concentrated to obtain crude product, which was purified by column chromatography ($SiO_2$, petroleum ether/ethyl acetate=10/1 to 0/1) then ($SiO_2$, DCM: MeOH=50:1~0:1). The eluent was concentrated to obtain 5-[2-[2-(azetidin-1-yl)ethoxy]-5-nitro-phenyl]-4,6-dimethyl-pyrimidine ((42), 2 g, 6.09 mmol, 47.06% yield) as a brownish red oil.

$^1H$ NMR (400 MHZ, $CDCl_3$) 8.95 (s, 1H), 8.34-8.25 (m, 1H), 8.02 (d, J=2.6 Hz, 1H), 7.05 (d, J=9.1 Hz, 1H), 4.06 (t, J=5.3 Hz, 2H), 2.95 (t, J=7.0 Hz, 4H), 2.64 (t, J=5.3 Hz, 2H), 2.24 (s, 6H), 2.00-1.88 (m, 2H).

Preparation of 4-[2-(azetidin-1-yl)ethoxy]-3-(4,6-dimethylpyrimidin-5-yl) aniline (43)

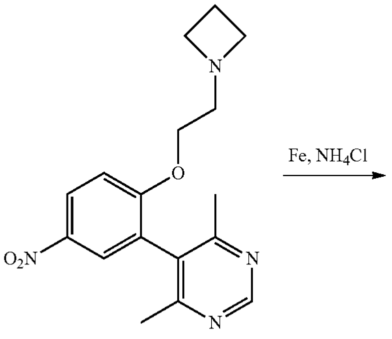

42

-continued

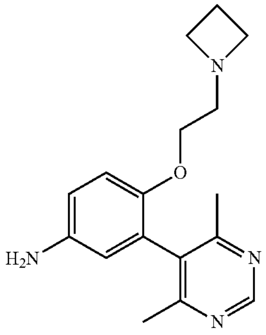

43

A mixture of 5-[2-[2-(azetidin-1-yl)ethoxy]-5-nitro-phenyl]-4,6-dimethyl-pyrimidine ((42), 2.5 g, 7.61 mmol, 1 eq.), Fe (2.13 g, 38.07 mmol, 5 eq.) and $NH_4Cl$ (3.26 g, 60.91 mmol, 8 eq.) in EtOH (25 mL) and $H_2O$ (12.5 mL) was stirred at 80° C. for 2 hrs. LCMS showed 5-[2-[2-(azetidin-1-yl)ethoxy]-5-nitro-phenyl]-4,6-dimethyl-pyrimidine was consumed completely and one new peak with the desired mass appeared. The reaction mixture was filtered, the filtrate was concentrated to obtain crude product, then MeOH (30 mL) was added, stirred at 20° C. for 0.5 hrs, and filtered. The filtrate was concentrated to obtain compound 4-[2-(azetidin-1-yl)ethoxy]-3-(4,6-dimethylpyrimidin-5-yl) aniline ((43), 1.7 g, 5.70 mmol, 74.83% yield) as a claybank solid, which was used in the next step directly without purification.

$^1H$ NMR (400 MHZ, methanol-$d_4$) 8.86 (s, 1H), 7.05 (br d, J=8.8 Hz, 1H), 6.93 (br d, J=7.4 Hz, 1H), 6.64 (br s, 1H), 4.15 (br s, 2H), 3.90 (t, J=7.9 Hz, 4H), 3.48 (br s, 2H), 3.33 (br s, 2H), 2.32 (s, 6H)

Preparation of N-[4-[2-(azetidin-1-yl)ethoxy]-3-(4,6-dimethylpyrimidin-5-yl)phenyl]-2-methyl-pyrazole-3-carboxamide (304)

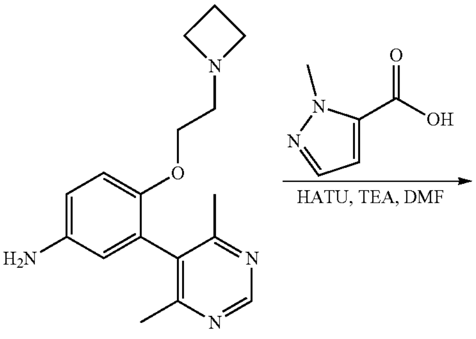

43

-continued

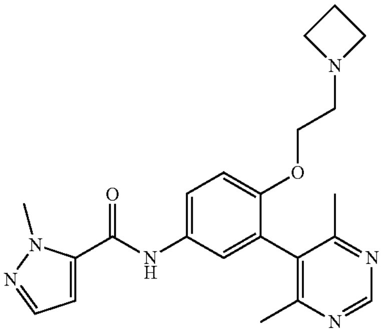

304

A mixture of 4-[2-(azetidin-1-yl)ethoxy]-3-(4,6-dimethylpyrimidin-5-yl) aniline ((43), 100 mg, 335.14 μmol, 1 eq.), 2-methylpyrazole-3-carboxylic acid (44.38 mg, 351.90 μmol, 1.05 eq.), HATU (152.92 mg, 402.17 μmol, 1.2 eq.) and DIEA (129.94 mg, 1.01 mmol, 175.12 μL, 3 eq.) in DCM (4 mL) was stirred at 20° C. for 12 hrs. The reaction mixture was concentrated to obtain crude product, which was purified by prep-HPLC (basic conditions: $NH_3 \cdot H_2O$ and acetonitrile) to obtain N-[4-[2-(azetidin-1-yl)ethoxy]-3-(4,6-dimethylpyrimidin-5-yl)phenyl]-2-methyl-pyrazole-3-carboxamide (23.80 mg, 56.50 μmol, 16.86% yield, 96.5% purity) as a brown solid.

LCMS (ESI): m/z [M+H] calcd for $C_{22}H_{27}N_6O_2$: 407.2; found: 407.2.

$^1H$ NMR (400 MHZ, methanol-$d_4$) δ=8.85 (s, 1H), 7.73 (dd, J=2.3, 8.9 Hz, 1H), 7.50 (dd, J=2.0, 6.4 Hz, 2H), 7.14 (d, J=9.0 Hz, 1H), 6.95 (s, 1H), 4.14 (s, 3H), 4.02 (t, J=5.0 Hz, 2H), 3.02 (t, J=7.2 Hz, 4H), 2.70 (t, J=5.0 Hz, 2H), 2.30 (s, 6H), 1.98 (quin, J=7.2 Hz, 2H).

N-(4-(2-(azetidin-1-yl)ethoxy)-3-(4,6-dimethylpyrimidin-5-yl)phenyl)-1-fluorocyclopropane-1-carboxamide (305)

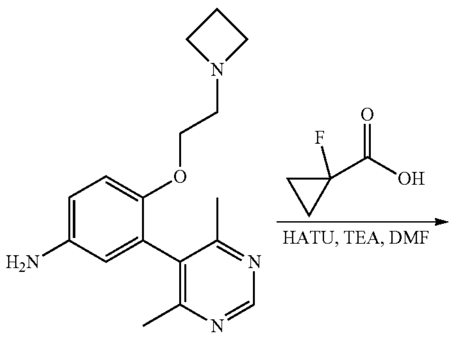

43

-continued

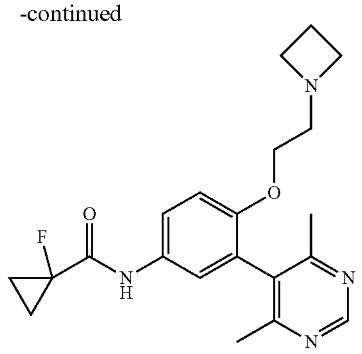

305

Compound 305 was prepared according to the synthesis described for compound 304, substituting 1-fluorocyclopropane-1-carboxylic acid for 2-methylpyrazole-3-carboxylic acid.

LCMS (ESI): m/z [M+H] calcd for $C_{21}H_{26}FN_4O_2$: 385.2; found: 385.2.

$^1H$ NMR (400 MHZ, methanol-$d_4$) δ=8.83 (s, 1H), 7.67 (dd, J=2.6, 8.9 Hz, 1H), 7.41 (d, J=2.6 Hz, 1H), 7.11 (d, J=8.9 Hz, 1H), 4.00 (t, J=5.1 Hz, 2H), 3.00 (br t, J=7.1 Hz, 4H), 2.69 (br t, J=4.9 Hz, 2H), 2.31 (s, 6H), 1.97 (quin, J=7.2 Hz, 2H), 1.43-1.34 (m, 4H).

N-(4-(2-(azetidin-1-yl)ethoxy)-3-(4,6-dimethylpyrimidin-5-yl)phenyl)-4-methylthiazole-5-carboxamide (306)

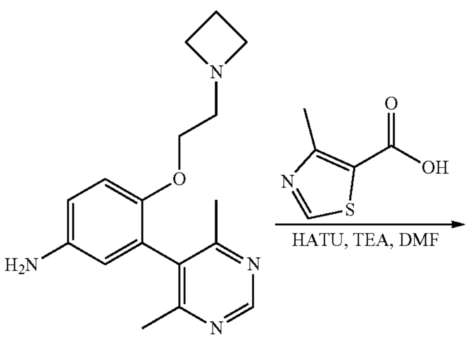

43

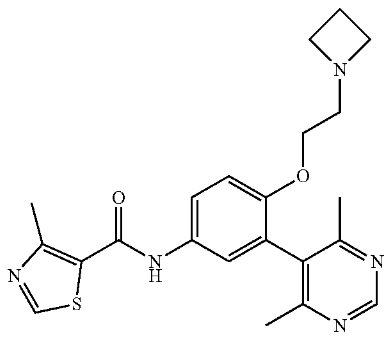

306

Compound 306 was prepared according to the synthesis described for compound 304, substituting 4-methylthiazole-5-carboxylic acid for 2-methylpyrazole-3-carboxylic acid.

LCMS (ESI): m/z [M+H] calcd for $C_{22}H_{26}N_5O_2S$: 424.2; found: 424.2.

$^1$H NMR (400 MHZ, methanol-$d_4$) δ-9.02 (s, 1H), 8.89 (s, 1H), 7.76 (dd, J=2.7, 8.9 Hz, 1H), 7.48 (d, J=2.6 Hz, 1H), 7.21 (d, J=9.0 Hz, 1H), 4.29-4.22 (m, 2H), 3.95-3.80 (m, 4H), 3.55-3.33 (m, 2H), 2.69 (s, 3H), 2.55-2.40 (m, 1H), 2.36-2.26 (m, 7H).

N-(4-(2-(azetidin-1-yl)ethoxy)-3-(4,6-dimethylpyrimidin-5-yl)phenyl)-2-(4-methylthiazol-5-yl)acetamide (307)

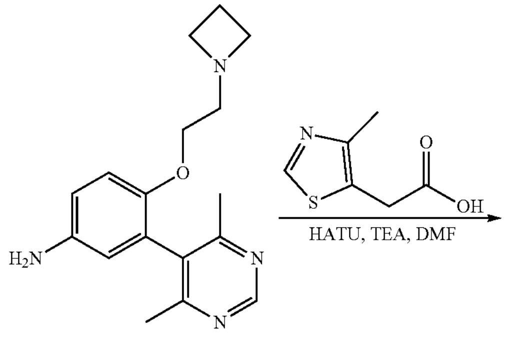

43

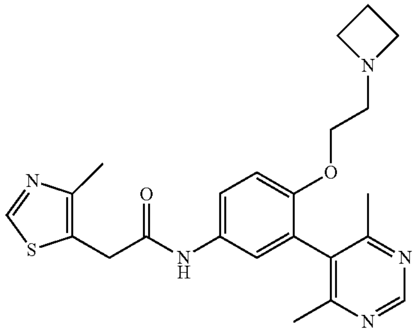

307

Compound 307 was prepared according to the synthesis described for compound 304, substituting 2-(4-methylthiazol-5-yl)acetic acid for 2-methylpyrazole-3-carboxylic acid.

LCMS (ESI): m/z [M+H] calcd for $C_{23}H_{28}N_5O_2S$: 438.2; found: 438.2.

$^1$H NMR (400 MHZ, methanol-$d_4$) δ=8.83 (s, 1H), 8.80 (s, 1H), 7.60 (dd, J=2.6, 8.9 Hz, 1H), 7.39 (d, J=2.7 Hz, 1H), 7.09 (d, J=9.0 Hz, 1H), 3.99 (t, J=5.1 Hz, 2H), 3.90 (s, 2H), 2.99 (br t, J=6.7 Hz, 4H), 2.67 (br s, 2H), 2.43 (s, 3H), 2.26 (s, 6H), 1.96 (t, J=7.2 Hz, 2H).

N-(4-(2-(azetidin-1-yl)ethoxy)-3-(4,6-dimethylpyrimidin-5-yl)phenyl)benzamide (308)

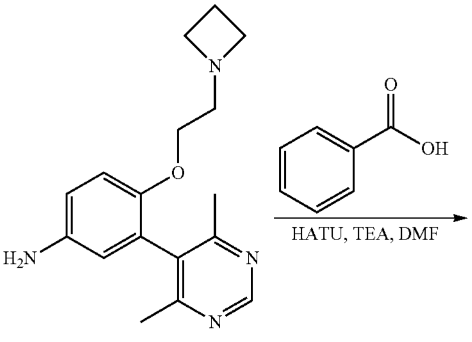

43

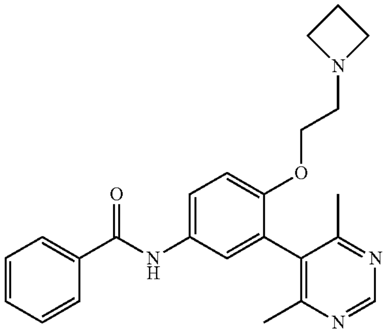

308

Compound 308 was prepared according to the synthesis described for compound 304, substituting benzoic acid for 2-methylpyrazole-3-carboxylic acid.

LCMS (ESI): m/z [M+H] calcd for $C_{24}H_{27}N_4O_2$: 403.2; found: 403.2.

$^1$H NMR (400 MHZ, methanol-$d_4$) δ=8.99 (s, 1H), 7.97-7.90 (m, 2H), 7.83 (dd, J=2.6, 8.9 Hz, 1H), 7.63-7.56 (m, 2H), 7.55-7.48 (m, 2H), 7.24 (d, J=9.0 Hz, 1H), 4.30-4.22 (m, 2H), 4.02-3.85 (m, 4H), 3.57-3.51 (m, 2H), 2.57-2.42 (m, 1H), 2.39 (s, 6H), 2.36-2.25 (m, 1H).

N-(4-(2-(azetidin-1-yl)ethoxy)-3-(4,6-dimethylpyrimidin-5-yl)phenyl)-4-fluorobenzamide (309)

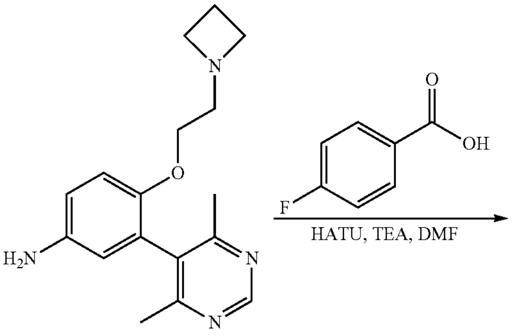

43

-continued

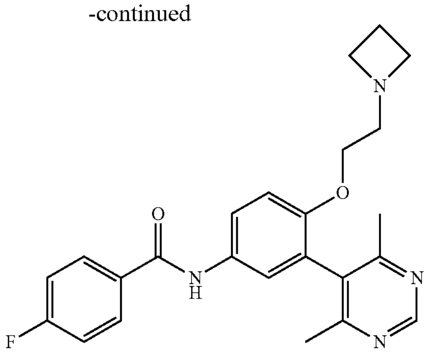

309

Compound 309 was prepared according to the synthesis described for compound 304, substituting 4-fluorobenzoic acid for 2-methylpyrazole-3-carboxylic acid.

LCMS (ESI): m/z [M+H] calcd for $C_{24}H_{26}FN_4O_2$: 421.2; found: 421.2.

$^1H$ NMR (400 MHZ, methanol-$d_4$) δ=8.84 (s, 1H), 7.99 (dd, J=5.4, 8.6 Hz, 2H), 7.74 (dd, J=2.4, 8.9 Hz, 1H), 7.49 (d, J=2.4 Hz, 1H), 7.24 (t, J=8.7 Hz, 2H), 7.14 (d, J=8.9 Hz, 1H), 4.02 (t, J=5.1 Hz, 2H), 3.00 (t, J=7.2 Hz, 4H), 2.69 (t, J=5.1 Hz, 2H), 2.30 (s, 6H), 1.97 (quin, J=7.2 Hz, 2H).

N-(4-(2-(azetidin-1-yl)ethoxy)-3-(4,6-dimethylpyrimidin-5-yl)phenyl)-3-methoxybenzamide (310)

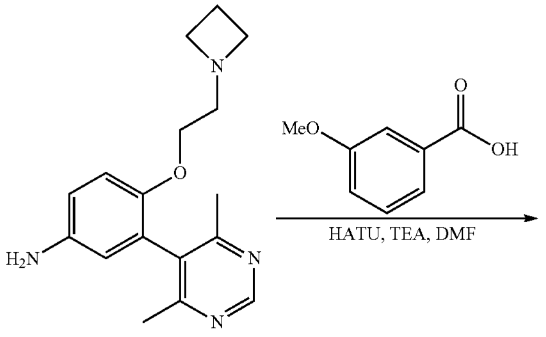

43

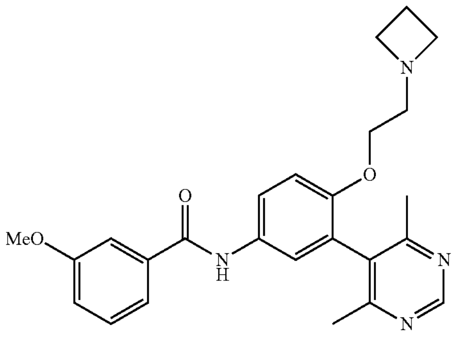

310

Compound 310 was prepared according to the synthesis described for compound 304, substituting 3-methoxybenzoic acid for 2-methylpyrazole-3-carboxylic acid.

LCMS (ESI): m/z [M+H] calcd for $C_{25}H_{29}N_4O_3$: 433.3; found: 433.3.

$^1H$ NMR (400M Hz, methanol-$d_4$) δ=8.84 (s, 1H), 7.76 (dd, J=2.4, 8.9 Hz, 1H), 7.49 (br dd, J=2.3, 7.0 Hz, 3H), 7.41 (t, J=7.9 Hz, 1H), 7.17-7.10 (m, 2H), 4.02 (t, J=5.0 Hz, 2H), 3.86 (s, 3H), 3.00 (t, J=7.2 Hz, 4H), 2.69 (t, J=5.1 Hz, 2H), 2.30 (s, 6H), 1.97 (quin, J=7.2 Hz, 2H).

N-(4-(2-(azetidin-1-yl)ethoxy)-3-(4,6-dimethylpyrimidin-5-yl)phenyl)-2-(3-methoxyphenyl)acetamide (311)

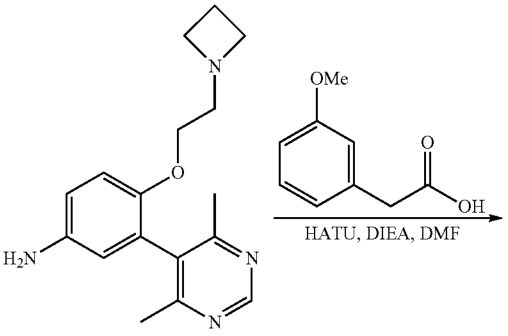

43

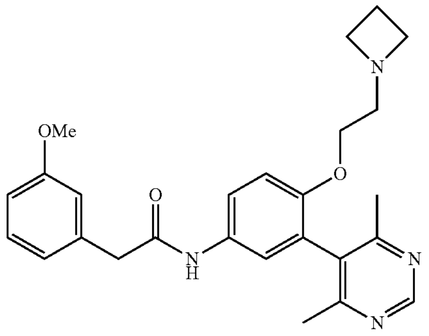

311

Compound 311 was prepared according to the synthesis described for compound 304, substituting 2-(3-methoxyphenyl)acetic acid for 2-methylpyrazole-3-carboxylic acid.

LCMS (ESI): m/z [M+H] calcd for $C_{26}H_{31}N_4O_3$: 447.2; found: 447.2.

$^1H$ NMR (400 MHZ, methanol-$d_4$) δ=8.82 (s, 1H), 7.59 (dd, J=2.4, 8.9 Hz, 1H), 7.38 (d, J=2.6 Hz, 1H), 7.27-7.19 (m, 1H), 7.08 (d, J=8.9 Hz, 1H), 6.96-6.89 (m, 2H), 6.86-6.76 (m, 1H), 3.98 (t, J=5.0 Hz, 2H), 3.78 (s, 3H), 3.63 (s, 2H), 2.99 (t, J=7.2 Hz, 4H), 2.67 (t, J=5.0 Hz, 2H), 2.25 (s, 6H), 1.96 (quin, J=7.2 Hz, 2H).

N-(4-(2-(azetidin-1-yl)ethoxy)-3-(4,6-dimethylpyrimidin-5-yl)phenyl)-2-(3-fluorophenyl)acetamide (312)

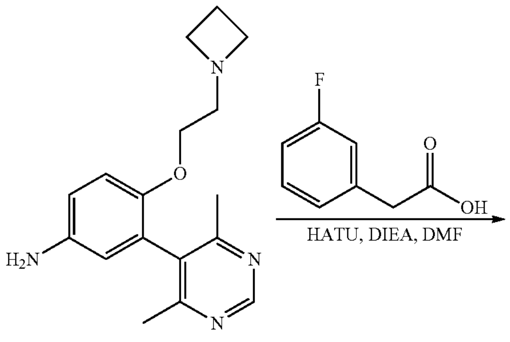

43

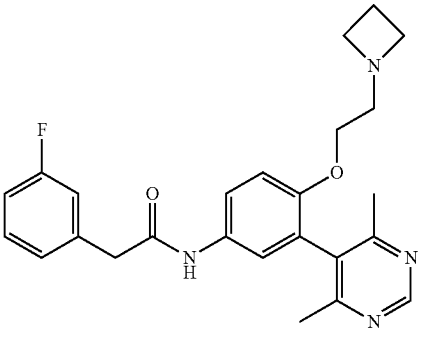

312

Compound 312 was prepared according to the synthesis described for compound 304, substituting 2-(3-fluorophenyl)acetic acid for 2-methylpyrazole-3-carboxylic acid.

LCMS (ESI): m/z [M+H] calcd for $C_{25}H_{28}FN_4O_2$: 435.2; found: 435.2.

$^1$H NMR (400 MHZ, methanol-$d_4$) δ=8.83 (s, 1H), 7.60 (dd, J=2.3, 8.9 Hz, 1H), 7.42-7.29 (m, 2H), 7.19-7.05 (m, 3H), 6.99 (br t, J=8.4 Hz, 1H), 3.98 (br t, J=4.9 Hz, 2H), 3.68 (s, 2H), 2.98 (t, J=7.1 Hz, 4H), 2.67 (br t, J=4.9 Hz, 2H), 2.25 (s, 6H), 1.95 (quin, J=7.1 Hz, 2H).

N-(4-(2-(azetidin-1-yl)ethoxy)-3-(4,6-dimethylpyrimidin-5-yl)phenyl)-2-(4-methoxyphenyl)acetamide (313)

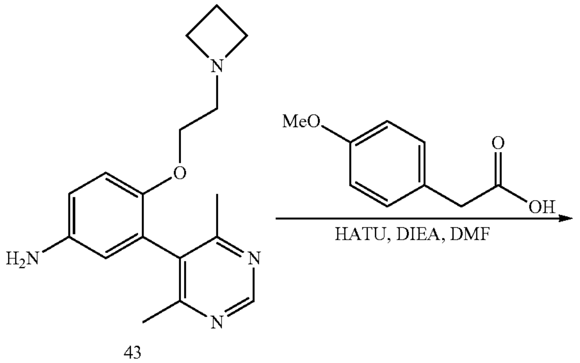

43

-continued

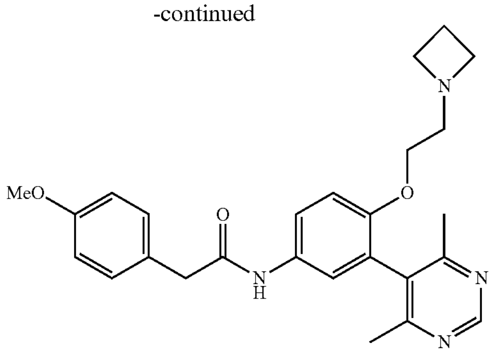

313

Compound 313 was prepared according to the synthesis described for compound 304, substituting 2-(4-methoxyphenyl)acetic acid for 2-methylpyrazole-3-carboxylic acid.

LCMS (ESI): m/z [M+H] calcd for $C_{26}H_{31}N_4O_3$: 447.3; found: 447.3.

$^1$H NMR (400 MHZ, methanol-$d_4$) δ=8.82 (s, 1H), 7.58 (dd, J=2.5, 8.9 Hz, 1H), 7.38 (d, J=2.6 Hz, 1H), 7.28-7.23 (m, J=8.4 Hz, 2H), 7.07 (d, J=9.0 Hz, 1H), 6.91-6.84 (m, J=8.6 Hz, 2H), 3.98 (t, J=5.1 Hz, 2H), 3.76 (s, 3H), 3.59 (s, 2H), 2.99 (t, J=7.2 Hz, 4H), 2.67 (t, J=5.0 Hz, 2H), 2.25 (s, 6H), 1.96 (quin, J=7.2 Hz, 2H).

N-(4-(2-(azetidin-1-yl)ethoxy)-3-(4,6-dimethylpyrimidin-5-yl)phenyl)-2-(5-fluoropyridin-3-yl)acetamide (314)

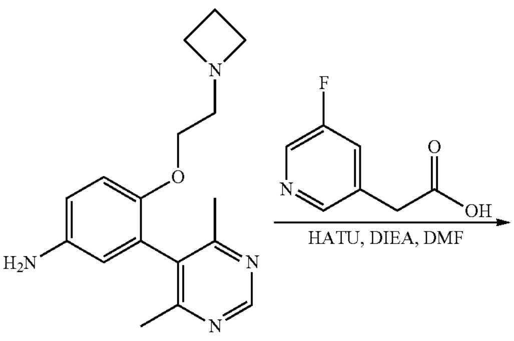

43

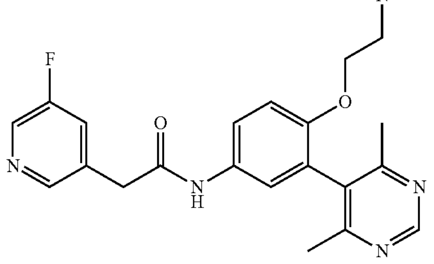

314

Compound 314 was prepared according to the synthesis described for compound 304, substituting 2-(5-fluoropyridin-3-yl)acetic acid for 2-methylpyrazole-3-carboxylic acid.

LCMS (ESI): m/z [M+H] calcd for $C_{24}H_{27}FN_5O_2$: 436.2; found: 436.2.

$^1$H NMR (400 MHZ, methanol-$d_4$) δ=8.83 (s, 1H), 8.44-8.32 (m, 2H), 7.72-7.55 (m, 2H), 7.40 (d, J=2.6 Hz, 1H), 7.09 (d, J=8.9 Hz, 1H), 3.99 (t, J=5.1 Hz, 2H), 3.79 (s, 2H), 3.00 (t, J=7.1 Hz, 4H), 2.68 (t, J=5.1 Hz, 2H), 2.29-2.20 (m, 6H), 1.96 (quin, J=7.2 Hz, 2H).

N-(4-(2-(azetidin-1-yl)ethoxy)-3-(4,6-dimethylpyrimidin-5-yl)phenyl)-2-(5-fluoropyridin-2-yl)acetamide (315)

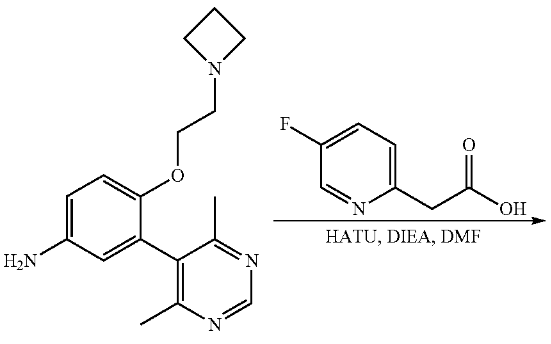

43

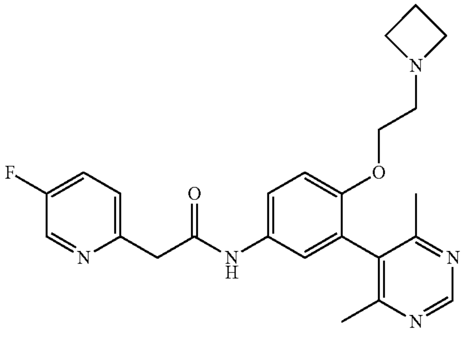

315

Compound 315 was prepared according to the synthesis described for compound 304, substituting 2-(5-fluoropyridin-2-yl)acetic acid for 2-methylpyrazole-3-carboxylic acid.

LCMS (ESI): m/z [M+H] calcd for $C_{24}H_{27}FN_5O_2$: 436.2; found: 436.2.

$^1$H NMR (400 MHZ, methanol-$d_4$) δ=8.83 (s, 1H), 8.40 (d, J=2.9 Hz, 1H), 7.64-7.57 (m, 2H), 7.48 (dd, J=4.4, 8.7 Hz, 1H), 7.41 (d, J=2.6 Hz, 1H), 7.09 (d, J=9.0 Hz, 1H), 3.99 (t, J=5.1 Hz, 2H), 3.89 (s, 2H), 2.99 (t, J=7.2 Hz, 4H), 2.67 (t, J=5.1 Hz, 2H), 2.26 (s, 6H), 2.03-1.89 (m, 2H).

N-(4-(2-(azetidin-1-yl)ethoxy)-3-(4,6-dimethylpyrimidin-5-yl)phenyl)-4-fluoro-1-methyl-1H-pyrazole-5-carboxamide (316)

316

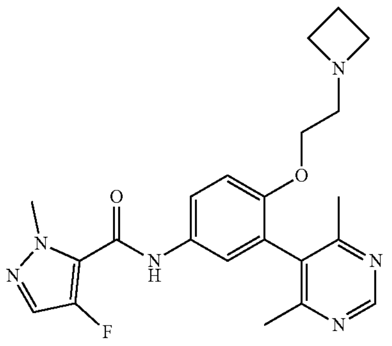

Compound 316 was prepared according to the synthesis described for compound 304, substituting 4-fluoro-1-methyl-1H-pyrazole-5-carboxylic acid for 2-methylpyrazole-3-carboxylic acid.

LCMS (ESI): m/z [M+H] calcd for $C_{22}H_{26}FN_6O_2$: 425.0, found: 425.3.

$^1$H NMR (400 MHZ, methanol-$d_4$) δ=8.90 (s, 1H), 7.78 (dd, J=2.3, 8.9 Hz, 1H), 7.53 (d, J=2.4 Hz, 1H), 7.47 (d, J=4.3 Hz, 1H), 7.22 (d, J=9.0 Hz, 1H), 4.30-4.21 (m, 2H), 4.05 (s, 3H), 3.98-3.77 (m, 4H), 3.58-3.47 (m, 2H), 2.56-2.42 (m, 1H), 2.32 (s, 6H), 2.30-2.20 (m, 1H).

N-(4-(2-(azetidin-1-yl)ethoxy)-3-(4,6-dimethylpyrimidin-5-yl)phenyl)-2-ethoxycyclopropane-1-carboxamide (317)

317

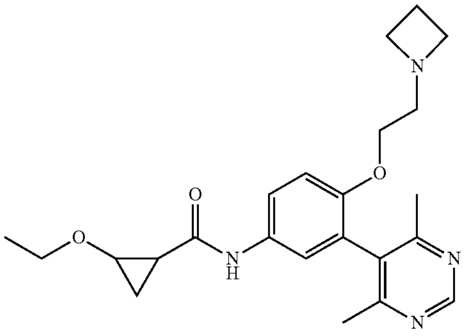

Compound 317 was prepared according to the synthesis described for compound 304, substituting 2-ethoxycyclopropane-1-carboxylic acid for 2-methylpyrazole-3-carboxylic acid.

LCMS (ESI): m/z [M+H] calcd for $C_{23}H_{31}N_4O_3$: 411.0, found: 411.3.

$^1$H NMR (400 MHZ, methanol-$d_4$) δ=8.83 (s, 1H), 7.56 (dd, J=2.7, 8.9 Hz, 1H), 7.38 (d, J=2.6 Hz, 1H), 7.08 (d, J=9.0 Hz, 1H), 3.99 (t, J=5.1 Hz, 2H), 3.66-3.55 (m, 3H), 3.00 (br t, J=7.2 Hz, 4H), 2.73-2.65 (m, 2H), 2.01-1.92 (m, 2H), 1.88 (ddd, J=2.0, 5.9, 9.4 Hz, 1H), 1.27-1.15 (m, 5H).

N-(4-(2-(azetidin-1-yl)ethoxy)-3-(4,6-dimethylpyrimidin-5-yl)phenyl)-4-methoxybenzamide (318)

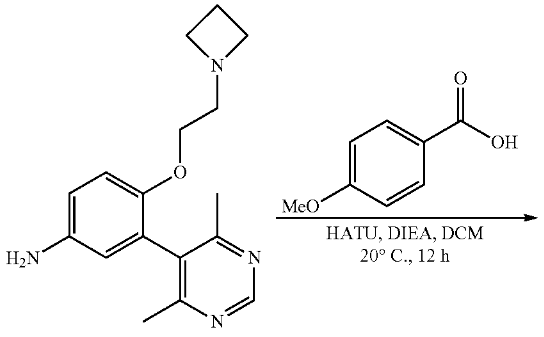

43

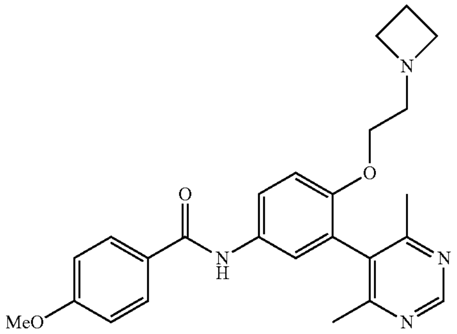

318

To a solution of 4-[2-(azetidin-1-yl)ethoxy]-3-(4,6-dimethylpyrimidin-5-yl) aniline ((43), 100 mg, 335.14 μmol, 1 eq.) in DCM (3 mL) was added HATU (191.15 mg, 502.71 μmol, 1.5 eq.), $Et_3N$ (101.74 mg, 1.01 mmol, 139.94 μL, 3 eq.), and 4-methoxybenzoic acid (61.19 mg, 402.17 μmol, 1.2 eq.). The mixture was stirred at 20° C. for 12 hrs. The reaction was complete as detected by LCMS. The solution was concentrated to afford the crude product. The residue was purified by prep-HPLC (TFA conditions) to afford N-(4-(2-(azetidin-1-yl)ethoxy)-3-(4,6-dimethylpyrimidin-5-yl)phenyl)-4-methoxybenzamide (27.9 mg, 64.51 μmol, 19.25% yield) as a white solid.

LCMS (ESI): m/z [M+H] calcd for $C_{25}H_{28}N_4O_3$: 433.2; found: 433.3.

$^1$H NMR (400 MHZ, methanol-$d_4$) δ=9.19 (s, 1H), 7.92 (d, J=8.7 Hz, 2H), 7.79 (d, J=8.9 Hz, 1H), 7.64-7.61 (m, 1H), 7.27 (d, J=9.0 Hz, 1H), 7.04 (d, J=8.6 Hz, 2H), 4.27 (t, J=4.6 Hz, 2H), 4.11-3.94 (m, 4H), 3.87 (s, 3H), 3.56 (br t, J=4.5 Hz, 2H), 2.60-2.46 (m, 7H), 2.35 (br dd, J=5.3, 10.5 Hz, 1H).

N-(4-(2-(azetidin-1-yl)ethoxy)-3-(4,6-dimethylpyrimidin-5-yl)phenyl)-2-fluorobenzamide (319)

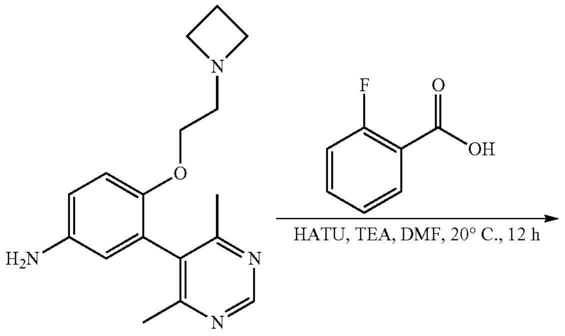

43

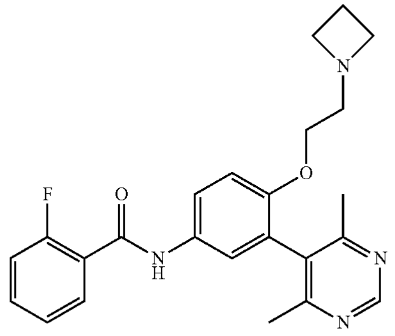

319

Compound 319 was prepared according to the synthesis described for compound 318, substituting 2-fluorobenzoic acid for 4-methoxybenzoic acid.

LCMS (ESI): m/z [M+H] calcd for $C_{24}H_{28}FN_4O_2$: 421.20; found: 421.3.

$^1$H NMR (400 MHZ, methanol-$d_4$) δ=8.87 (s, 1H), 8.45 (s, 1H), 7.81 (dd, J=2.7, 8.9 Hz, 1H), 7.74 (dt, J=1.8, 7.5 Hz, 1H), 7.60-7.51 (m, 2H), 7.35-7.17 (m, 3H), 4.23-4.17 (m, 2H), 3.69 (t, J=7.9 Hz, 4H), 3.34 (br d, J=4.9 Hz, 2H), 2.34-2.25 (m, 8H).

N-(4-(2-(azetidin-1-yl)ethoxy)-3-(4,6-dimethylpyrimidin-5-yl)phenyl)-3-fluorobenzamide (320)

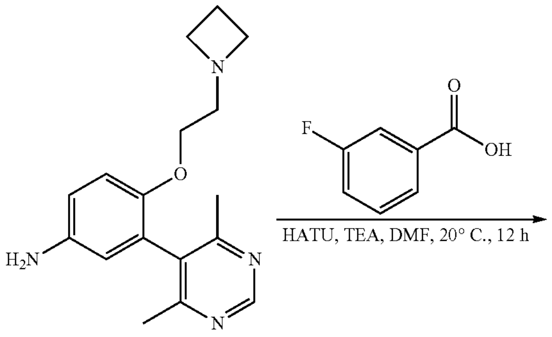

43

-continued

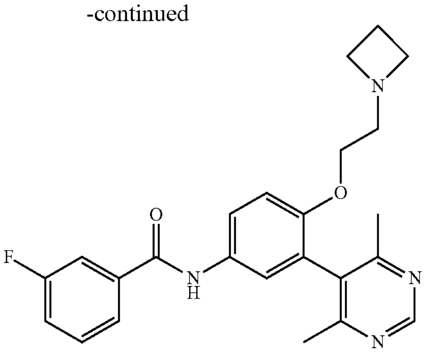

320

Compound 320 was prepared according to the synthesis described for compound 318, substituting 3-fluorobenzoic acid for 4-methoxybenzoic acid.

LCMS (ESI): m/z [M+H] calcd for $C_{24}H_{26}FN_4O_2$: 421.2; found: 421.2.

$^1$H NMR (400 MHZ, methanol-$d_4$) δ=8.89 (s, 1H), 7.87-7.82 (m, 1H), 7.79-7.75 (m, 1H), 7.71-7.65 (m, 1H), 7.57-7.50 (m, 2H), 7.37-7.30 (m, 1H), 7.22 (d, J=8.8 Hz, 1H), 4.28-4.21 (m, 2H), 3.97-3.79 (m, 4H), 3.55-3.50 (m, 2H), 2.55-2.41 (m, 1H), 2.33 (s, 6H), 2.31-2.29 (m, 1H).

N-(4-(2-(azetidin-1-yl)ethoxy)-3-(4,6-dimethylpyrimidin-5-yl)phenyl)-2-methylbenzamide (321)

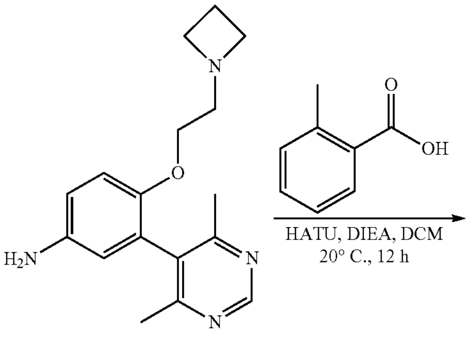

43

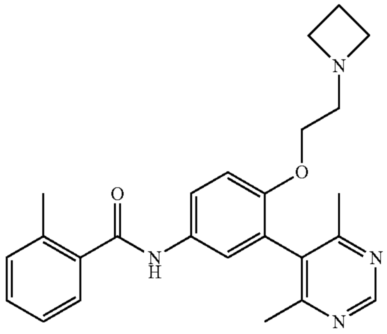

321

Compound 321 was prepared according to the synthesis described for compound 318, substituting 2-methylbenzoic acid for 4-methoxybenzoic acid.

LCMS (ESI): m/z [M+H] calcd for $C_{25}H_{28}N_4O_2$: 417.2; found: 417.2.

$^1$H NMR (400 MHz, methanol-$d_4$) δ=8.93 (s, 1H), 7.82 (dd, J=2.6, 9.0 Hz, 1H), 7.53 (d, J=2.5 Hz, 1H), 7.47 (d, J=7.6 Hz, 1H), 7.41-7.35 (m, 1H), 7.32-7.26 (m, 2H), 7.22 (d, J=9.0 Hz, 1H), 4.29-4.21 (m, 2H), 3.98-3.82 (m, 4H), 3.57-3.49 (m, 2H), 2.54-2.47 (m, 1H), 2.45 (s, 3H), 2.35 (s, 6H), 2.32-2.23 (m, 1H).

N-(4-(2-(azetidin-1-yl)ethoxy)-3-(4,6-dimethylpyrimidin-5-yl)phenyl)-3-methylbenzamide (322)

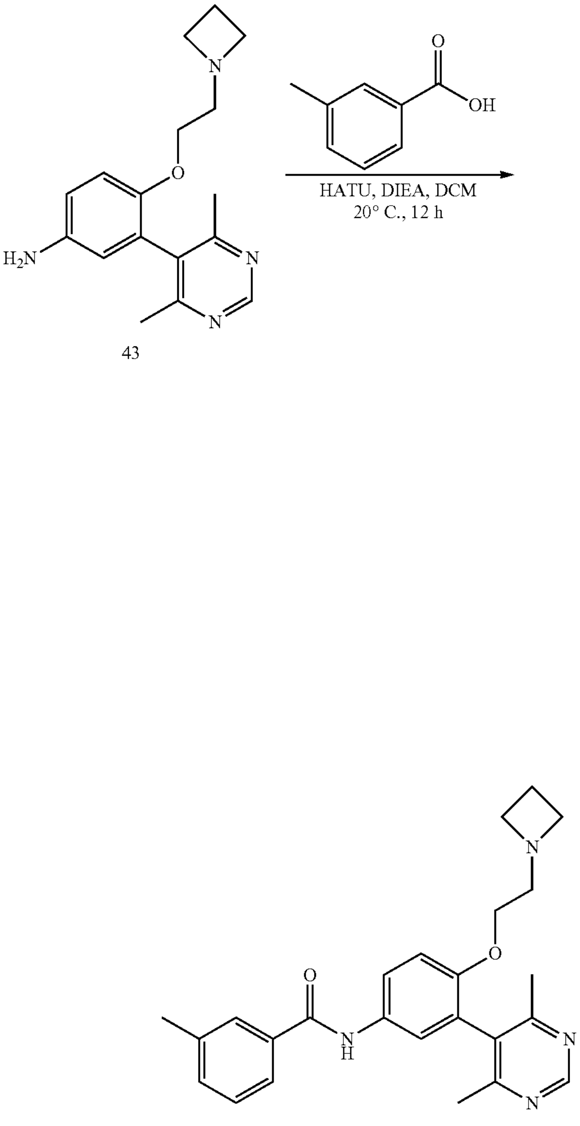

43

322

Compound 322 was prepared according to the synthesis described for compound 318, substituting 3-methylbenzoic acid for 4-methoxybenzoic acid.

LCMS (ESI): m/z [M+H] calcd for $C_{24}H_{29}N_4O_2$: 417.22; found: 417.4.

$^1$H NMR (400 MHZ, methanol-$d_4$) δ=8.88 (s, 1H), 8.45 (br s, 1H), 7.82 (dd, J=2.6, 9.0 Hz, 1H), 7.75 (s, 1H), 7.71 (br d, J=6.5 Hz, 1H), 7.53 (d, J=2.6 Hz, 1H), 7.43-7.37 (m, 2H), 7.20 (d, J=8.9 Hz, 1H), 4.21 (br s, 2H), 3.73 (br s, 4H), 3.38 (br s, 2H), 2.43 (s, 3H), 2.32 (m, 8H).

N-(4-(2-(azetidin-1-yl)ethoxy)-3-(4,6-dimethylpyrimidin-5-yl)phenyl)-4-methylbenzamide (323)

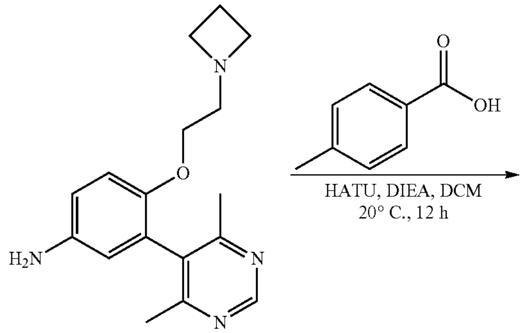

43

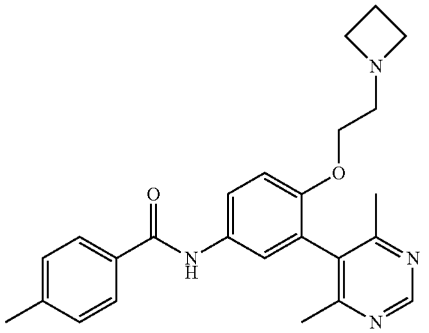

323

Compound 323 was prepared according to the synthesis described for compound 318, substituting 4-methylbenzoic acid for 4-methoxybenzoic acid.

LCMS (ESI): m/z [M+H] calcd for $C_{25}H_{28}N_4O_2$: 417.2; found: 417.2.

$^1$H NMR (400 MHZ, methanol-$d_4$) δ=8.93 (s, 1H), 7.86-7.79 (m, 3H), 7.54 (d, J=2.6 Hz, 1H), 7.33 (d, J=8.1 Hz, 2H), 7.22 (d, J=9.0 Hz, 1H), 4.28-4.23 (m, 2H), 3.96-3.82 (m, 4H), 3.55-3.50 (m, 2H), 2.55-2.44 (m, 1H), 2.42 (s, 3H), 2.35 (s, 6H), 2.32-2.23 (m, 1H).

N-(4-(2-(azetidin-1-yl)ethoxy)-3-(4,6-dimethylpyrimidin-5-yl)phenyl)-2-cyanobenzamide (324)

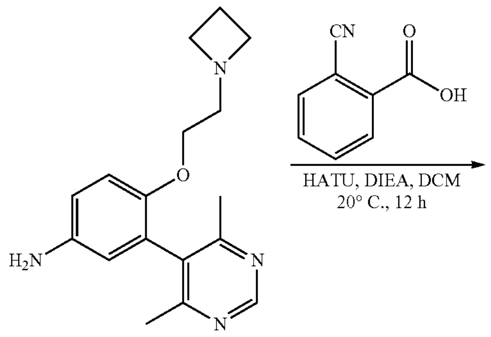

43

-continued

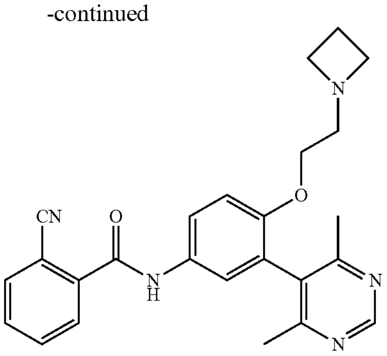

324

Compound 324 was prepared according to the synthesis described for compound 318, substituting 2-cyanobenzoic acid for 4-methoxybenzoic acid.

LCMS (ESI): m/z [M+H] calcd for $C_{25}H_{26}N_5O_2$: 428.2; found: 428.2.

$^1$H NMR (400 MHZ, methanol-$d_4$) δ-8.84 (s, 1H), 8.11 (br d, J=6.4 Hz, 1H), 7.92 (br d, J=6.9 Hz, 1H), 7.88-7.77 (m, 2H), 7.53 (br s, 1H), 7.27 (br s, 2H), 4.10 (br s, 2H), 3.03 (br t, J=7.1 Hz, 4H), 2.74 (br s, 2H), 2.35 (s, 6H), 2.03-1.95 (m, 2H).

N-(4-(2-(azetidin-1-yl)ethoxy)-3-(4,6-dimethylpyrimidin-5-yl)phenyl)-3-cyanobenzamide (325)

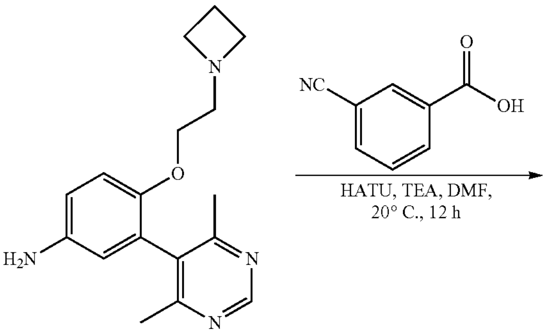

43

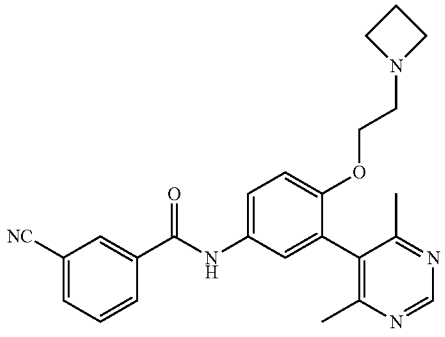

325

Compound 325 was prepared according to the synthesis described for compound 318, substituting 3-cyanobenzoic acid for 4-methoxybenzoic acid.

LCMS (ESI): m/z [M+H] calcd for $C_{25}H_{26}N_5O_2$: 428.2; found: 428.1.

$^1$H NMR (400 MHZ, methanol-$d_4$) δ=8.85 (s, 1H), 8.30 (t, J=1.4 Hz, 1H), 8.23 (td, J=1.4, 7.9 Hz, 1H), 7.94 (td, J=1.3, 7.9 Hz, 1H), 7.77 (dd, J=2.6, 9.0 Hz, 1H), 7.71 (t, J=7.9 Hz, 1H), 7.53 (d, J=2.6 Hz, 1H), 7.15 (d, J=9.0 Hz, 1H), 4.03 (t, J=5.0 Hz, 2H), 3.01 (t, J=7.1 Hz, 4H), 2.70 (t, J=5.2 Hz, 2H), 2.30 (s, 6H), 1.97 (quin, J=7.2 Hz, 2H).

N-(4-(2-(azetidin-1-yl)ethoxy)-3-(4,6-dimethylpyrimidin-5-yl)phenyl)-4-cyanobenzamide (326)

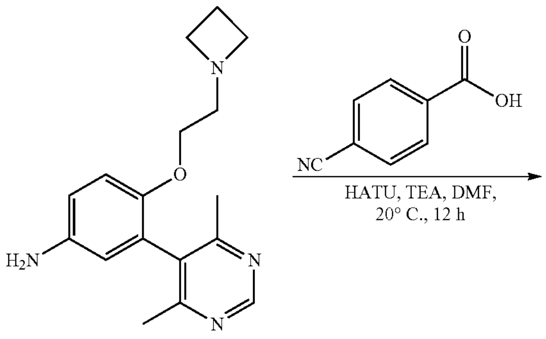

43

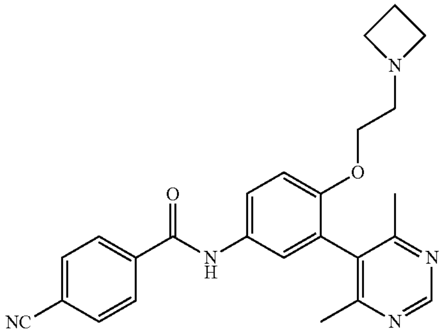

326

Compound 326 was prepared according to the synthesis described for compound 318, substituting 4-cyanobenzoic acid for 4-methoxybenzoic acid.

LCMS (ESI): m/z [M+H] calcd for $C_{25}H_{26}N_5O_2$: 428.2; found: 428.2.

$^1$H NMR (400 MHZ, methanol-$d_4$) δ=8.85 (s, 1H), 8.10-8.05 (m, 2H), 7.91-7.86 (m, 2H), 7.77 (dd, J=2.6, 9.0 Hz, 1H), 7.52 (d, J=2.6 Hz, 1H), 7.15 (d, J=9.2 Hz, 1H), 4.02 (t, J=5.2 Hz, 2H), 3.01 (t, J=7.2 Hz, 4H), 2.70 (t, J=5.2 Hz, 2H), 2.30 (s, 6H), 1.97 (quin, J=7.2 Hz, 2H).

N-(4-(2-(azetidin-1-yl)ethoxy)-3-(4,6-dimethylpyrimidin-5-yl)phenyl)-1,4-dimethyl-1H-pyrazole-5-carboxamide (327)

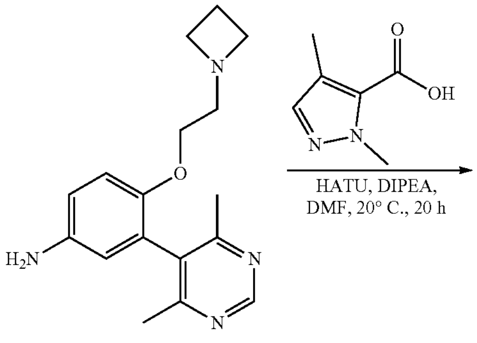

43

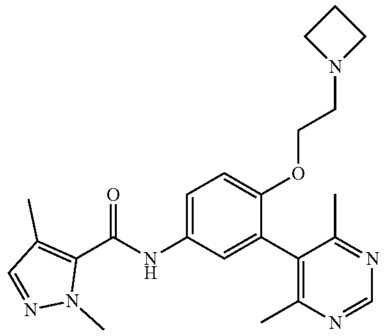

327

To a solution of 4-[2-(azetidin-1-yl)ethoxy]-3-(4,6-dimethylpyrimidin-5-yl) aniline ((43), 80 mg, 268.08 μmol, 1 eq.), 1,4-dimethyl-1H-pyrazole-5-carboxylic acid (41.33 mg, 294.92 μmol, 1.1 eq.) in DMF (2 mL) was added HATU (152.92 mg, 402.17 μmol, 1.5 eq.) and DIPEA (93.40 μL, 2 eq). The mixture was stirred at 20° C. for 12 hrs. The mixture was filtered, then purified by prep-HPLC: column: Phenomenex Gemini-NX C18 75*30 mm*3 μm; mobile phase: [water (10 mM $NH_4HCO_3$)-ACN]; B %: 8%-38%, 8 min. N-(4-(2-(azetidin-1-yl)ethoxy)-3-(4,6-dimethylpyrimidin-5-yl)phenyl)-1,4-dimethyl-1H-pyrazole-5-carboxamide (58.1 mg, 99% purity) was obtained as yellow solid.

LCMS (ESI): m/z [M+H] calcd for $C_{23}H_{29}N_6O_2$: 421.24; found: 421.30.

$^1$H NMR (400 MHz, methanol-$d_4$) δ=8.85 (s, 1H), 7.72 (dd, J=2.1, 8.8 Hz, 1H), 7.51 (d, J=2.1 Hz, 1H), 7.33 (s, 1H), 7.15 (d, J=8.9 Hz, 1H), 4.03 (t, J=5.1 Hz, 2H), 3.95 (s, 3H), 3.02 (t, J=7.2 Hz, 4H), 2.71 (t, J=5.1 Hz, 2H), 2.30 (s, 6H), 2.24 (s, 3H), 1.98 (quin, J=7.2 Hz, 2H).

N-(4-(2-(azetidin-1-yl)ethoxy)-3-(4,6-dimethylpyrimidin-5-yl)phenyl)-1-(fluoromethyl)cyclopropane-1-carboxamide (328)

328

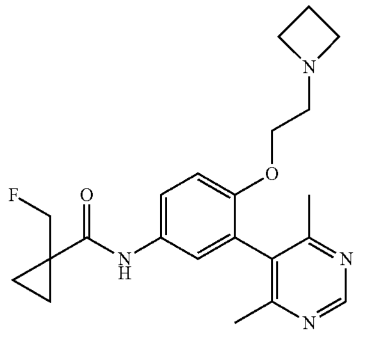

Compound 328 was prepared according to the synthesis described for compound 318, substituting 1-(fluoromethyl) cyclopropane-1-carboxylic acid for 1,4-dimethyl-1H-pyrazole-5-carboxylic acid.

LCMS (ESI): m/z [M+H] calcd for $C_{22}H_{28}FN_4O_2$: 399.21; found: 399.30.

$^1$H NMR (400 MHZ, METHANOL-$d_4$) δ=8.85 (s, 1H), 7.60 (dd, J=2.6, 8.9 Hz, 1H), 7.36 (d, J=2.6 Hz, 1H), 7.11 (d, J=9.0 Hz, 1H), 4.72 (s, 1H), 4.60 (s, 1H), 4.02 (t, J=5.1 Hz, 2H), 3.03 (t, J=7.2 Hz, 4H), 2.72 (t, J=5.1 Hz, 2H), 2.29 (s, 6H), 1.99 (t, J=7.2 Hz, 2H), 1.42-1.29 (m, 2H), 1.03-0.97 (m, 2H).

N-(4-(2-(azetidin-1-yl)ethoxy)-3-(4,6-dimethylpyrimidin-5-yl)phenyl)-2-(thiazol-2-yl)acetamide (329)

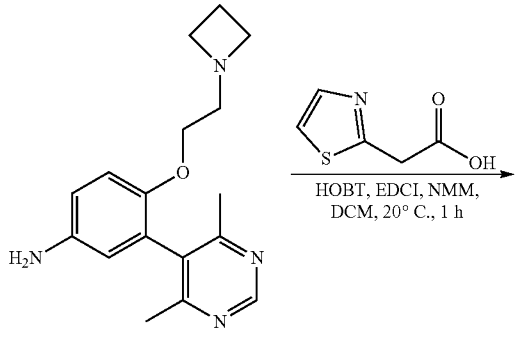

43

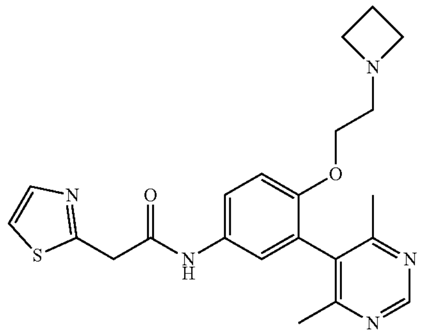

329

To a solution of 4-[2-(azetidin-1-yl)ethoxy]-3-(4,6-dimethylpyrimidin-5-yl) aniline ((57), 60 mg, 201.08 μmol, 1 eq.), 2-thiazol-2-ylacetic acid (37.42 mg, 261.41 μmol, 1.3 eq.) in DCM (3 mL) was added EDCI (50.11 mg, 261.41 μmol, 1.3 eq.), HOBt (35.32 mg, 261.41 μmol, 1.3 eq.), NMM (30.51 mg, 301.63 μmol, 33.16 μL, 1.5 eq.). The mixture was stirred at 20° C. for 1 hr and then concentrated. The mixture was purified by prep-HPLC: column: Waters Xbridge 150*25 mm*5 μm; mobile phase: [water (10 mM $NH_4HCO_3$)-ACN]; B %: 8%-43%, 9 min. N-[4-[2-(azetidin-1-yl)ethoxy]-3-(4,6-dimethylpyrimidin-5-yl)phenyl]-2-thiazol-2-yl-acetamide (60 mg, 140.25 μmol, 69.75% yield, 99% purity) was obtained as a white solid.

LCMS (ESI): m/z [M+H] calcd for $C_{22}H_{25}N_5O_2S$: 424.17; found: 424.10.

$^1$H NMR (400 MHZ, DMSO-$d_6$) δ=10.36 (s, 1H), 8.85 (s, 1H), 7.74 (d, J=3.4 Hz, 1H), 7.65 (d, J=3.3 Hz, 1H), 7.59 (dd, J=2.6, 8.9 Hz, 1H), 7.41 (d, J=2.7 Hz, 1H), 7.10 (d, J=9.0 Hz, 1H), 4.13 (s, 2H), 3.88 (t, J=5.3 Hz, 2H), 2.84 (t, J=6.9 Hz, 4H), 2.50-2.47 (m, 2H), 2.17 (s, 6H), 1.80 (quin, J=6.9 Hz, 2H).

N-(4-(2-(azetidin-1-yl)ethoxy)-3-(4,6-dimethylpyrimidin-5-yl)phenyl)-3-fluoropicolinamide (330)

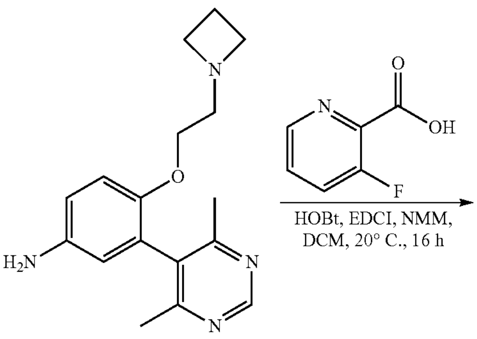

43

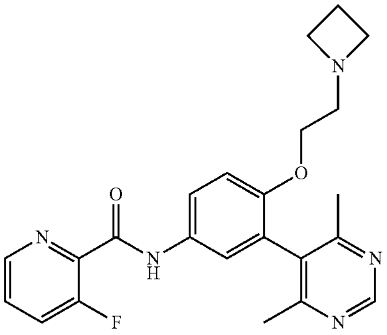

330

To a solution of 4-(2-(azetidin-1-yl)ethoxy)-3-(4,6-dimethylpyrimidin-5-yl) aniline ((57), 60 mg, 201.08 μmol, 1 eq.), 3-fluoropicolinic acid (28.37 mg, 201.08 μmol, 1 eq.) in DCM (0.5 mL) was added HOBt (32.60 mg, 241.3 μmol, 1.2 eq.), EDCI (46.26 mg, 241.3 μmol, 1.2 eq.) and NMM (30.51 mg, 301.63 μmol, 1.5 eq.). The mixture was stirred at 20° C. for 16 hrs (monitored by LCMS). The reaction mixture was concentrated under reduced pressure to give a residue. The residue was purified by prep-HPLC (column: Phenomenex Gemini-NX C18 75*30 mm*3 μm; mobile phase: [water (10 mM $NH_4HCO_3$)-ACN]; B %: 10%-40%, 8 min) and lyophilized. N-(4-(2-(azetidin-1-yl)ethoxy)-3-(4,6-dimethylpyrimidin-5-yl)phenyl)-3-fluoropicolinamide (42.81 mg, 100% purity) was obtained as a brown gum (42.81 mg, 100% purity).

LCMS (ESI): m/z [M+H] calcd for $C_{23}H_{25}FN_5O_2$: 422.19; found: 422.2.

$^1$H NMR (400 MHZ, methanol-d$_4$) δ=8.85 (s, 1H), 8.52 (d, J=4.5 Hz, 1H), 7.84 (dd, J=2.7, 8.9 Hz, 1H), 7.81-7.75 (m, 1H), 7.67 (td, J=4.1, 8.5 Hz, 1H), 7.60 (d, J=2.7 Hz, 1H), 7.16 (d, J=8.9 Hz, 1H), 4.03 (t, J=5.1 Hz, 2H), 3.02 (t, J=7.2 Hz, 4H), 2.71 (t, J=5.0 Hz, 2H), 2.30 (s, 6H), 1.98 (quin, J=7.2 Hz, 2H).

N-(4-(2-(azetidin-1-yl)ethoxy)-3-(4,6-dimethylpyrimidin-5-yl)phenyl)-4-fluoronicotinamide (331)

331

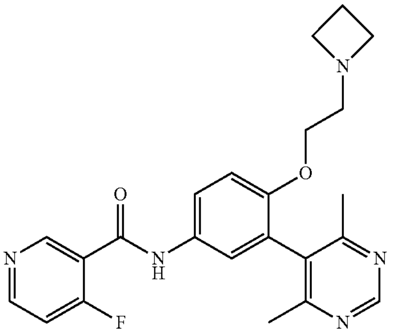

Compound 331 was prepared according to the synthesis described for compound 330, substituting 4-fluoronicotinic acid for 3-fluoropicolinic acid.

LCMS (ESI): m/z [M+H] calcd for $C_{23}H_{25}FN_5O_2$: 422.19; found: 422.2.

$^1$H NMR (400 MHZ, methanol-d$_4$) δ=8.85 (s, 1H), 8.64 (d, J=1.7 Hz, 1H), 8.54 (d, J=4.9 Hz, 1H), 7.75 (dd, J=2.6, 9.0 Hz, 1H), 7.72 (t, J=5.4 Hz, 1H), 7.53 (d, J=2.6 Hz, 1H), 7.16 (d, J=8.9 Hz, 1H), 4.03 (t, J=5.1 Hz, 2H), 3.02 (t, J=7.2 Hz, 4H), 2.71 (t, J=5.1 Hz, 2H), 2.30 (s, 6H), 1.98 (quin, J=7.2 Hz, 2H).

N-(4-(2-(azetidin-1-yl)ethoxy)-3-(4,6-dimethylpyrimidin-5-yl)phenyl)-3-fluoroisonicotinamide (332)

332

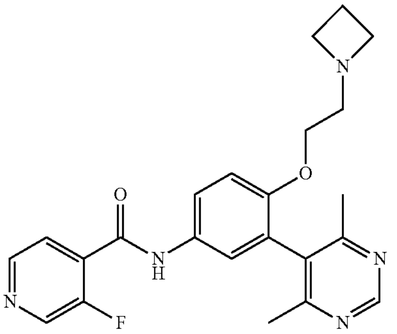

Compound 332 was prepared according to the synthesis described for compound 330, substituting 3-fluoroisonicotinic acid for 3-fluoropicolinic acid.

LCMS (ESI): m/z [M+H] calcd for $C_{23}H_{25}FN_5O_2$: 422.19; found: 422.2.

$^1$H NMR (400 MHZ, methanol-d$_4$) δ=8.85 (s, 1H), 8.63 (d, J=1.7 Hz, 1H), 8.54 (d, J=4.9 Hz, 1H), 7.75 (dd, J=2.7, 8.9 Hz, 1H), 7.72 (t, J=5.4 Hz, 1H), 7.54 (d, J=2.6 Hz, 1H), 7.16 (d, J=9.0 Hz, 1H), 4.03 (t, J=5.1 Hz, 2H), 3.02 (t, J=7.2 Hz, 4H), 2.71 (t, J=5.1 Hz, 2H), 2.30 (s, 6H), 1.98 (t, J=7.3 Hz, 2H).

N-(4-(2-(azetidin-1-yl)ethoxy)-3-(4,6-dimethylpyrimidin-5-yl)phenyl)-5-fluoropyrimidine-4-carboxamide (333)

333

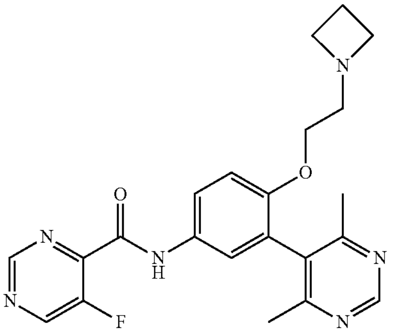

Compound 333 was prepared according to the synthesis described for compound 330, substituting 5-fluoropyrimidine-4-carboxylic acid for 3-fluoropicolinic acid.

LCMS (ESI): m/z [M+H] calcd for $C_{22}H_{24}FN_6O_2$: 423.19; found: 423.2.

$^1$H NMR (400 MHZ, methanol-d$_4$) δ=9.13 (d, J=2.4 Hz, 1H), 8.96 (d, J=2.9 Hz, 1H), 8.85 (s, 1H), 7.85 (dd, J=2.7, 8.9 Hz, 1H), 7.60 (d, J=2.6 Hz, 1H), 7.17 (d, J=8.9 Hz, 1H), 4.03 (t, J=5.1 Hz, 2H), 3.01 (t, J=7.2 Hz, 4H), 2.71 (t, J=5.1 Hz, 2H), 2.30 (s, 6H), 1.97 (t, J=7.3 Hz, 2H).

N-[4-[2-(4-acetylpiperazin-1-yl)ethoxy]-3-(4,6-dimethylpyrimidin-5-yl)phenyl]cyclopropanecarboxamide (334)

Preparation of N-[4-[2-(4-acetylpiperazin-1-yl)ethoxy]-3-bromo-phenyl]cyclopropanecarboxamide (44)

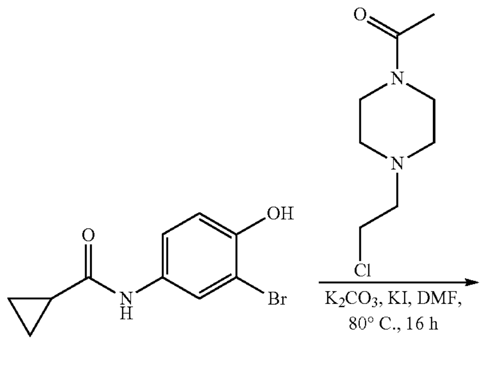

-continued

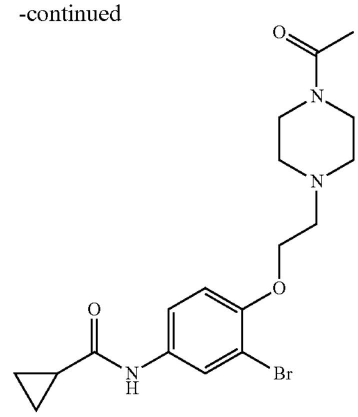

44

A mixture of N-(3-bromo-4-hydroxy-phenyl)cyclopropanecarboxamide (500 mg, 1.95 mmol, 1 eq.), 1-[4-(2-chloroethyl) piperazin-1-yl]ethanone (532.14 mg, 2.34 mmol, 1.2 eq., HCl), $K_2CO_3$ (728.55 mg, 5.27 mmol, 2.7 eq.) and KI (32.41 mg, 195.24 μmol, 0.1 eq.) in DMF (5 mL) was stirred at 80° C. for 16 hrs. The reaction mixture was concentrated in vacuo to give a residue. The residue was purified by flash silica gel chromatography (20 g SepaFlash® Silica Flash Column, eluent of 0~100% B/A at 35 mL/min, B: 15% MeOH in ethyl acetate, A: petroleum ether). N-[4-[2-(4-acetylpiperazin-1-yl)ethoxy]-3-bromophenyl]cyclopropanecarboxamide ((44), 240 mg, 567.38 μmol, 29.06% yield, 97% purity) was obtained as a yellow gum.

LCMS (ESI): m/z [M+H] calcd for $C_{18}H_{25}Br^{79/81}N_3O_3$: 410.1, 412.1; found: 410.0, 412.0.

Preparation of 4,6-dimethyl-5-(4,4,5,5-tetramethyl-1,3,2-dioxaborolan-2-yl)pyrimidine (45)

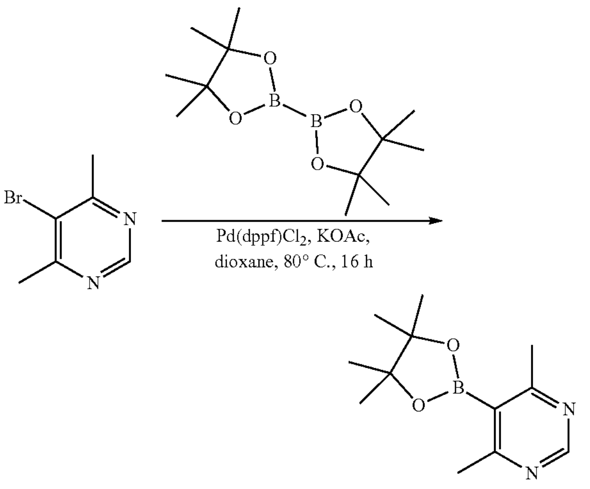

45

A mixture of 5-bromo-4,6-dimethyl-pyrimidine (1 g, 5.35 mmol, 1 eq.), 4,4,5,5-tetramethyl-2-(4,4,5,5-tetramethyl-1,3,2-dioxaborolan-2-yl)-1,3,2-dioxaborolane (4.07 g, 16.04 mmol, 3 eq.), $Pd(dppf)Cl_2$ (195.61 mg, 267.33 μmol, 0.05 eq.), and KOAc (787.06 mg, 8.02 mmol, 1.5 eq.) in dioxane (20 mL) was stirred at 80° C. for 16 hrs. The reaction mixture was concentrated in vacuo to give a residue. The residue was purified by flash silica gel chromatography (20 g SepaFlash® Silica Flash Column, eluent of 0~50% ethyl acetate/petroleum ether gradient at 30 mL/min). 4,6-Dimethyl-5-(4,4,5,5-tetramethyl-1,3,2-dioxaborolan-2-yl)pyrimidine ((45), 1.07 g, 4.57 mmol, 85.49% yield, 100% purity) was obtained as a colorless oil.

$^1$H NMR (400 MHZ, chloroform-d) δ=8.92 (s, 1H), 2.59 (s, 6H), 1.40 (s, 12H).

Preparation of N-[4-[2-(4-acetylpiperazin-1-yl)ethoxy]-3-(4,6-dimethylpyrimidin-5-yl)phenyl]cyclopropanecarboxamide (334)

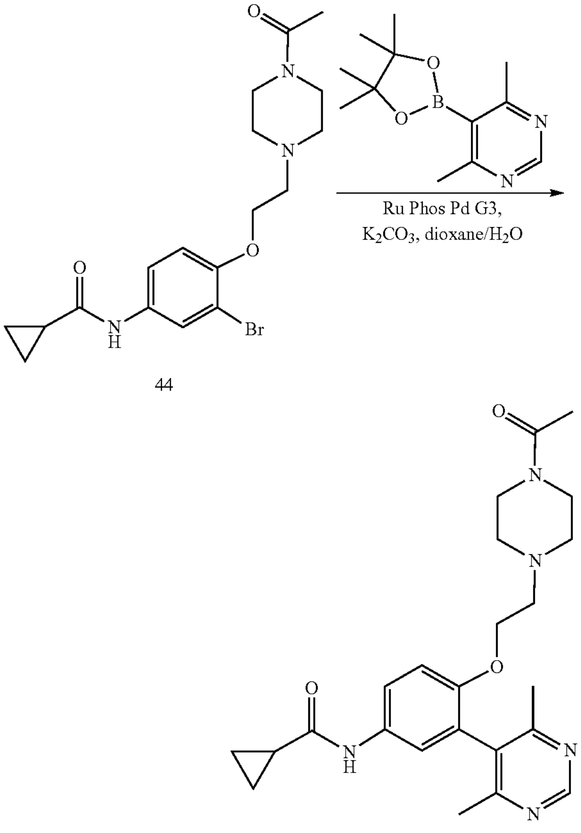

44

334

A of N-[4-[2-(4-acetylpiperazin-1-yl)ethoxy]-3-bromo-mixture phenyl]cyclopropanecarboxamide ((44), 200 mg, 472.82 μmol, 1 eq.), 4,6-dimethyl-5-(4,4,5,5-tetramethyl-1,3,2-dioxaborolan-2-yl)pyrimidine ((45), 553.44 mg, 2.36 mmol, 5 eq.), (2-dicyclohexylphosphino-2',6'-diisopropoxy-1,1'-biphenyl)[2-(2'-amino-1,1'-biphenyl)]palladium (II) methanesulfonate (39.54 mg, 47.28 μmol, 0.1 eq.), and $K_2CO_3$ (130.70 mg, 945.64 μmol, 2.0 eq.) in a mixed solvent of dioxane (1 mL) and $H_2O$ (0.1 mL) was stirred at 80° C. for 16 hrs. The reaction mixture was concentrated in vacuo to give a residue. The residue was purified by prep-HPLC (column: Xtimate C18 150*40 mm*10 μm; mobile phase: [water (0.05% ammonia hydroxide v/v)-ACN]; B %: 13%-43%, 10 min). N-[4-[2-(4-acetylpiperazin-1-yl)ethoxy]-3-(4,6-dimethylpyrimidin-5-yl)phenyl]cyclopropanecarboxamide (54.15 mg, 122.52 μmol, 25.91% yield, 99% purity) was obtained as a brown solid.

LCMS (ESI): m/z [M+H] calcd for $C_{24}H_{32}N_5O_3$: 438.24; found: 438.3.

$^1$H NMR (400 MHZ, methanol-$d_4$) δ ppm 0.81-0.96 (m, 4H) 1.70-1.77 (m, 1H) 2.07 (s, 3H) 2.24-2.35 (m, 10H) 2.65 (t, J=5.14 Hz, 2H) 3.38-3.49 (m, 4H) 4.12 (t, J=5.14 Hz, 2H) 7.12 (d, J=8.93 Hz, 1H) 7.37 (d, J=2.57 Hz, 1H) 7.59 (dd, J=8.93, 2.69 Hz, 1H) 8.85 (s, 1H).

2-[1-[2-[4-(cyclopropanecarbonylamino)-2-(4,6-dimethylpyrimidin-5-yl)phenoxy]ethyl]-4-piperidyl]acetic acid (335)

Preparation of methyl 2-[1-(2-hydroxyethyl)-4-piperidyl]acetate (46)

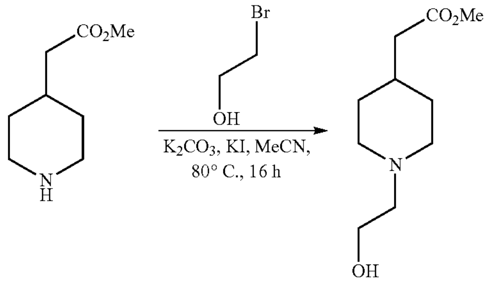

46

To a mixture of methyl 2-(4-piperidyl)acetate (500 mg, 2.58 mmol, 1 eq., HCl) and 2-bromoethanol (322.62 mg, 2.58 mmol, 183.31 μL, 1 eq.) in THF (10 mL) was added $K_2CO_3$ (1.43 g, 10.33 mmol, 4 eq.) and KI (85.71 mg, 516.34 μmol, 0.2 eq.). The mixture was stirred at 80° C. for 16 hrs. The reaction mixture was concentrated under vacuum. Methyl 2-[1-(2-hydroxyethyl)-4-piperidyl]acetate ((46), 519.60 mg, 2.58 mmol, 100.00% yield) was obtained as a white solid.

LCMS (ESI): m/z [M+H] calcd for $C_{10}H_{20}NO_3$: 202.14; found: 202.1.

Preparation of methyl 2-[1-[2-[2-(4,6-dimethylpyrimidin-5-yl)-4-nitro-phenoxy]ethyl]-4-piperidyl]acetate (47)

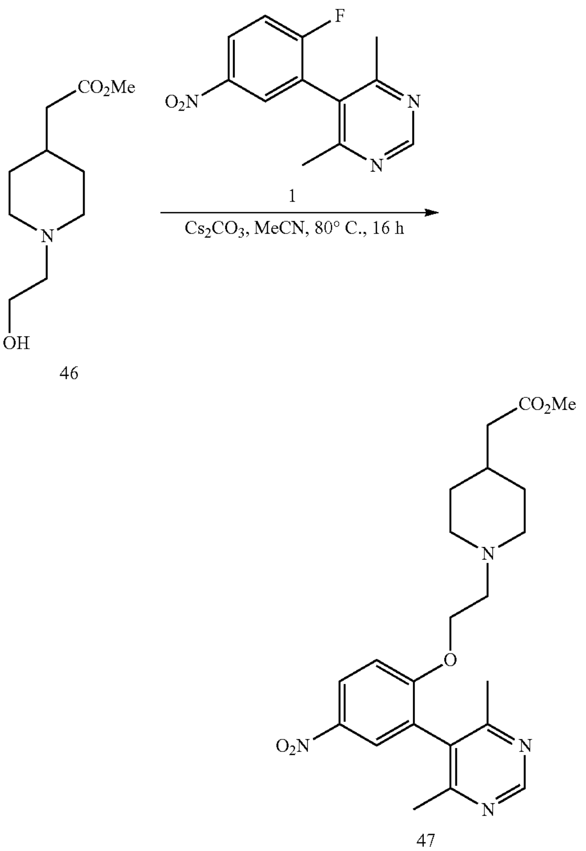

46

47

To the mixture of 5-(2-fluoro-5-nitro-phenyl)-4,6-dimethyl-pyrimidine ((1), 200 mg, 808.98 μmol, 1 eq.) and methyl 2-[1-(2-hydroxyethyl)-4-piperidyl]acetate ((46), 195.38 mg, 970.78 μmol, 1.2 eq.) in MeCN (3 mL) was added $Cs_2CO_3$ (527.16 mg, 1.62 mmol, 2 eq.). The mixture was stirred at 80° C. for 16 hrs. The reaction mixture was concentrated under vacuum, then the residue was poured into water (100 mL). The aqueous phase was extracted with ethyl acetate (100 mL×3). The combined organic phase was dried with anhydrous $Na_2SO_4$, filtered and concentrated in vacuum. The residue was purified by prep-HPLC (column: Shim-pack C18 150*25*10 μm; mobile phase: [water (0.1% TFA)-ACN]; B %: 10%-40%, 10 min) followed by vacuum. Methyl 2-[1-[2-[2-(4,6-dimethylpyrimidin-5-yl)-4-nitro-phenoxy]ethyl]-4-piperidyl]acetate ((47), 189 mg, 341.42 μmol, 42.20% yield, 98% purity, TFA) was obtained as a yellow gum.

LCMS (ESI): m/z [M+H] calcd for $C_{22}H_{29}N_4O_5$:429.21; found: 429.2.

$^1$H NMR (400 MHZ, methanol-$d_4$) δ=8.97-8.93 (m, 1H), 8.48-8.43 (m, 1H), 8.22 (d, J=2.9 Hz, 1H), 7.44-7.39 (m, 1H), 4.59-4.54 (m, 2H), 3.68 (s, 3H), 3.52-3.43 (m, 2H), 3.27 (br s, 1H), 3.16-2.97 (m, 1H), 2.83 (br t, J=12.4 Hz, 2H), 2.32 (br d, J=6.6 Hz, 2H), 2.30-2.26 (m, 6H), 2.02-1.93 (m, 1H), 1.88 (br d, J=14.9 Hz, 2H), 1.50-1.34 (m, 2H).

Preparation of methyl 2-[1-[2-[4-amino-2-(4,6-dimethylpyrimidin-5-yl)phenoxy]ethyl]-4-piperidyl]acetate (48)

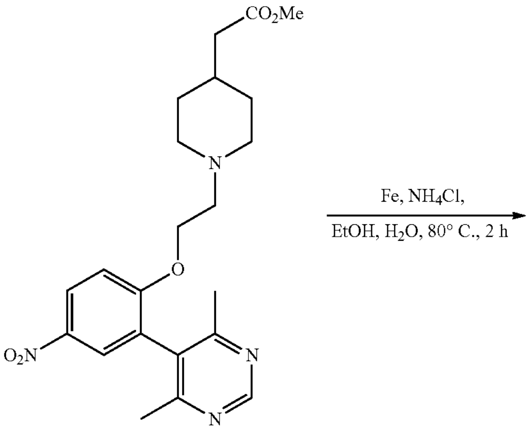

47

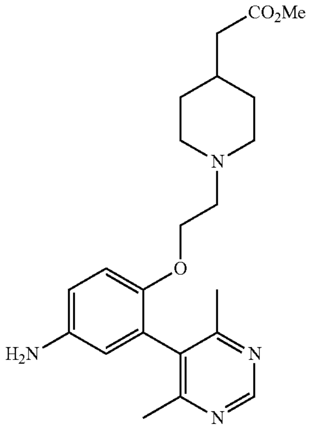

48

To a mixture of methyl 2-[1-[2-[2-(4,6-dimethylpyrimidin-5-yl)-4-nitro-phenoxy]ethyl]-4-piperidyl]acetate ((47), 180 mg, 331.80 μmol, 1 eq., TFA) in EtOH (2 mL) and $H_2O$ (2 mL) was added $NH_4Cl$ (141.99 mg, 2.65 mmol, 8 eq.). The mixture was stirred at 80° C. for 0.1 hr. Fe (92.65 mg, 1.66 mmol, 5 eq.) was added to the mixture. The mixture was stirred at 80° C. for 2 hrs. The mixture was filtered and the filtrate was concentrated under vacuum. Crude methyl 2-[1-[2-[4-amino-2-(4,6-dimethylpyrimidin-5-yl)phenoxy]ethyl]-4-piperidyl]acetate ((48), 92 mg, 230.87 μmol, 69.58% yield) was obtained as an off yellow solid.

LCMS (ESI): m/z [M+H] calcd for $C_{22}H_{31}N_4O_3$: 399.23; found: 399.2.

Preparation of methyl 2-[1-[2-[4-(cyclopropanecarbonylamino)-2-(4,6-dimethylpyrimidin-5-yl)phenoxy]ethyl]-4-piperidyl]acetate (49)

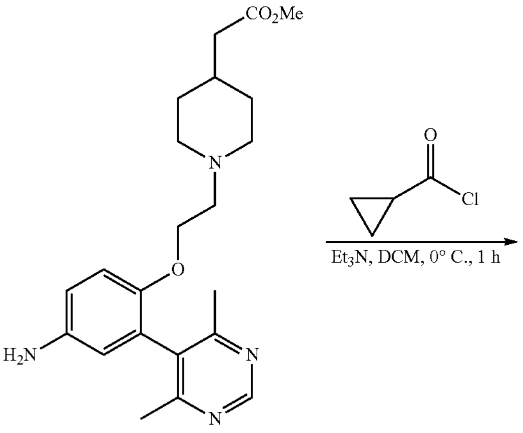

48

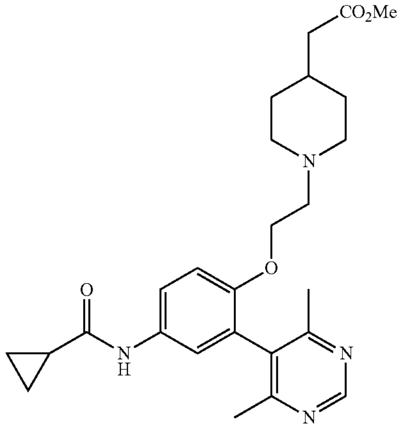

49

To a mixture of methyl 2-[1-[2-[4-amino-2-(4,6-dimethylpyrimidin-5-yl)phenoxy]ethyl]-4-piperidyl]acetate ((48), 92 mg, 230.87 μmol, 1 eq.) and $Et_3N$ (46.72 mg, 461.73 μmol, 64.27 μL, 2 eq.) in DCM (2 mL) was added cyclopropanecarbonyl chloride (24.62 mg, 235.48 μmol, 21.41 μL, 1.02 eq.) at 0° C. The mixture was stirred at 0° C. for 1 hr. The reaction mixture was concentrated under vacuum and the residue was poured into water (30 mL). The aqueous phase was extracted with ethyl acetate (50 mL×3). The combined organic phase was dried with anhydrous $Na_2SO_4$, filtered and concentrated in vacuum. Crude methyl 2-[1-[2-[4-(cyclopropanecarbonylamino)-2-(4,6-dimethylpyrimidin-5-yl)phenoxy]ethyl]-4-piperidyl]acetate ((49), 107.72 mg, 230.88 μmol, 100.00% yield) was obtained as an off yellow gum.

LCMS (ESI): m/z [M+H] calcd for $C_{26}H_{35}N_4O_4$: 467.26; found: 467.3.

Preparation of 2-[1-[2-[4-(cyclopropanecarbonylamino)-2-(4,6-dimethylpyrimidin-5-yl)phenoxy]ethyl]-4-piperidyl]acetic acid (335)

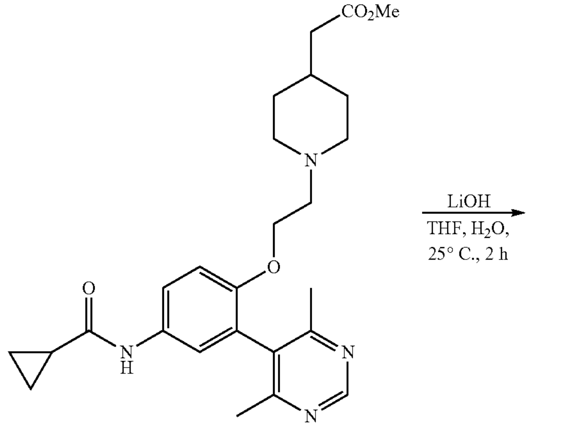

49

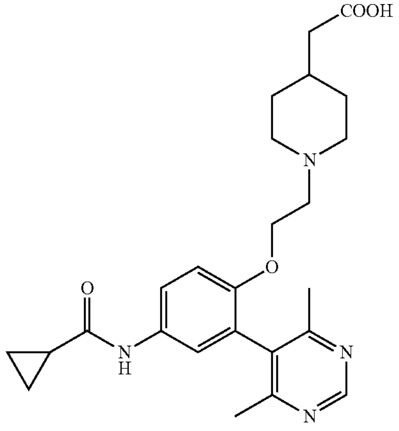

335

To a mixture of methyl 2-[1-[2-[4-(cyclopropanecarbonylamino)-2-(4,6-dimethylpyrimidin-5-yl)phenoxy]ethyl]-4-piperidyl]acetate ((49), 107 mg, 229.33 μmol, 1 eq.) in THF (1 mL) was added LiOH (32.95 mg, 1.38 mmol, 6 eq.) in $H_2O$ (1 mL). The mixture was stirred at 25° C. for 2 hrs. The mixture was filtered and the filtrate was concentrated under vacuum. The residue was purified by prep-HPLC (column: Phenomenex Luna C18 150*25 mm*10 μm; mobile phase: [water (0.1% TFA)-ACN]; B %: 1%-30%, 10 min) followed by lyophilization. 2-[1-[2-[4-(cyclopropanecarbonylamino)-2-(4,6-dimethylpyrimidin-5-yl)phenoxy]ethyl]-4-piperidyl]acetic acid (1.05 mg, 2.25 μmol, 9.81e-1% yield, 97% purity) was obtained as a yellow gum.

LCMS (ESI): m/z [M+H] calcd for $C_{25}H_{33}N_4O_4$: 453.24; found: 453.3.

$^1$H NMR (400 MHZ, methanol-$d_4$) δ=8.88 (s, 1H), 7.66 (td, J=2.4, 8.8 Hz, 1H), 7.41 (d, J=2.0 Hz, 1H), 7.17 (d, J=9.0 Hz, 1H), 4.38-4.32 (m, 2H), 3.44-3.37 (m, 2H), 3.26 (br s, 2H), 2.92-2.74 (m, 2H), 2.31-2.25 (m, 8H), 1.90 (br d, J=11.6 Hz, 3H), 1.79-1.70 (m, 1H), 1.38 (br d, J=12.8 Hz, 2H), 0.96-0.91 (m, 2H), 0.88-0.82 (m, 2H).

N-[3-(4,6-dimethylpyrimidin-5-yl)-4-[2-[(1S,4S)-2-oxa-5-azabicyclo[2.2.1]heptan-5-yl]ethoxy]phenyl]cyclopropanecarboxamide (336)

Preparation of N-[3-bromo-4-(2-bromoethoxy)phenyl]cyclopropanecarboxamide (50)

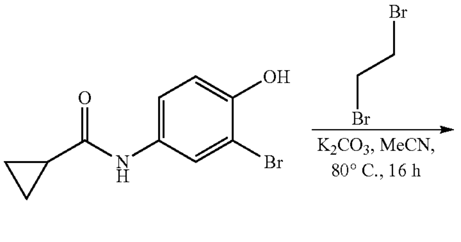

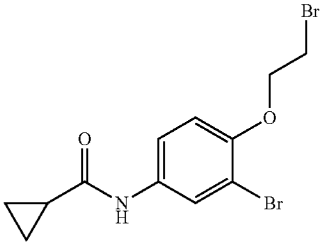

50

A mixture of N-(3-bromo-4-hydroxy-phenyl)cyclopropanecarboxamide (2 g, 7.81 mmol, 1 eq.), 1,2-dibromoethane (14.67 g, 78.10 mmol, 5.89 mL, 10 eq.), and $K_2CO_3$ (5.40 g, 39.05 mmol, 5 eq.) in MeCN (20 mL) was degassed and purged with $N_2$ three times, and then the mixture was stirred at 80° C. for 16 hrs under an $N_2$ atmosphere (monitored by LC-MS). The reaction mixture was concentrated under reduced pressure to give a residue. The residue was combined and purified by column chromatography ($SiO_2$, petroleum ether/ethyl acetate=4/0 to 1/1). N-[3-bromo-4-(2-bromoethoxy)phenyl]cyclopropanecarboxamide ((50), 2.6 g, 7.16 mmol, 91.70% yield) was obtained as a white solid.

LCMS (ESI): m/z [M+H] calcd for $C_{12}H_{14}Br^{79/80}{}_2NO_2$: 361.93, 363.93, 365.93; found: 362.0, 364.0, 366.0.

Preparation of N-[3-bromo-4-[2-[(1S,4S)-2-oxa-5-azabicyclo[2.2.1]heptan-5-yl]ethoxy]phenyl]cyclopropanecarboxamide (51)

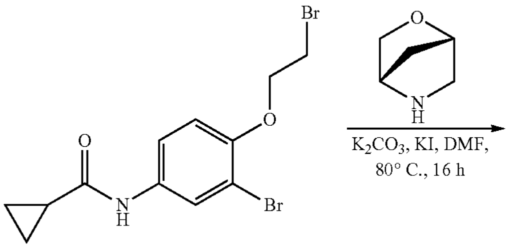

50

-continued

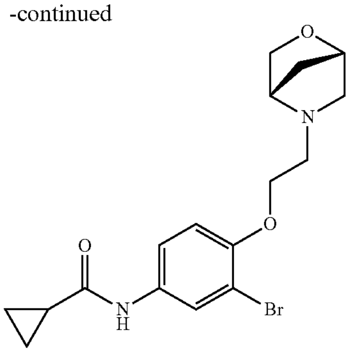

51

A mixture of N-[3-bromo-4-(2-bromoethoxy)phenyl]cyclopropanecarboxamide ((50), 300 mg, 826.34 μmol, 1 eq.), (1S,4S)-2-oxa-5-azabicyclo[2.2.1]heptane (112.04 mg, 826.34 μmol, 1 eq., HCl), $K_2CO_3$ (228.41 mg, 1.65 mmol, 2 eq.), and KI (13.72 mg, 82.63 μmol, 0.1 eq.) in DMF (1 mL) was degassed and purged with $N_2$ three times, and then the mixture was stirred at 80° C. for 16 hrs under an $N_2$ atmosphere (monitored by LC-MS). The reaction mixture was concentrated under reduced pressure to give a residue. The crude product was purified by reversed-phase HPLC (0.1% $NH_3 \cdot H_2O$). N-[3-bromo-4-[2-[(1S,4S)-2-oxa-5-azabicyclo[2.2.1]heptan-5-yl]ethoxy]phenyl]cyclopropanecarboxamide ((51), 310 mg, 813.09 μmol, 98.40% yield) was obtained as a white solid.

LCMS (ESI): m/z [M+H] calcd for $C_{17}H_{22}Br^{79/80}N_2O_3$: 381.07, 383.07; found: 381.1, 383.1.

Preparation of N-[3-(4,6-dimethylpyrimidin-5-yl)-4-[2-[(1S,4S)-2-oxa-5-azabicyclo[2.2.1]heptan-5-yl]ethoxy]phenyl]cyclopropanecarboxamide (336)

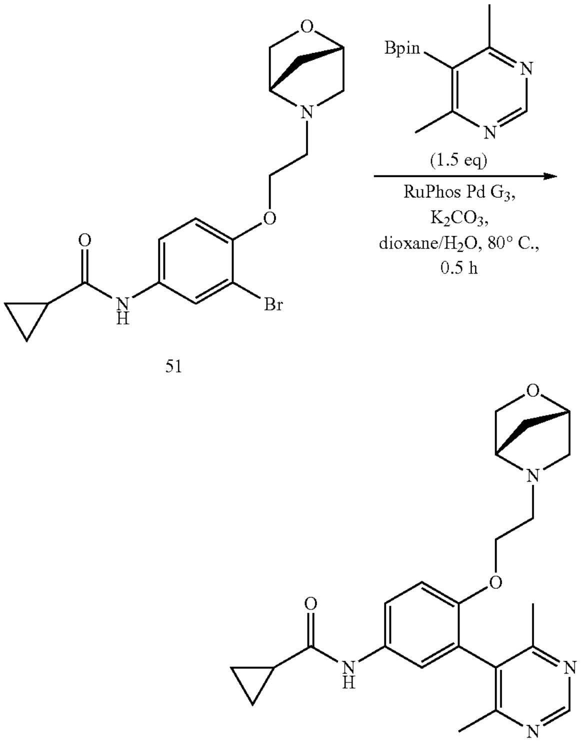

51

336

A mixture of N-[3-bromo-4-[2-[(1S,4S)-2-oxa-5-azabicyclo[2.2.1]heptan-5-yl]ethoxy]phenyl]cyclopropanecarboxamide ((51), 100 mg, 262.29 μmol, 1 eq.), 4,6-dimethyl-5-(4,4,5,5-tetramethyl-1,3,2-dioxaborolan-2-yl)pyrimidine (92.10 mg, 393.43 μmol, 1.5 eq.), $K_2CO_3$ (72.50 mg, 524.57 μmol, 2 eq.), and RuPhos Pd G3 (21.94 mg, 26.23 μmol, 0.1 eq.) in dioxane (1 mL) and $H_2O$ (0.1 mL) was degassed and purged with $N_2$ three times, and then the mixture was stirred at 80° C. for 0.5 hrs under an $N_2$ atmosphere (monitored by LC-MS). The reaction mixture was filtered and concentrated under reduced pressure to give a residue. The residue was dissolved in MeOH and to the mixture was added 5 g LS-20000B and stirred for 16 hrs. Then the mixture was filtered and concentrated to give a residue. The residue was purified by prep-HPLC (column: Waters Xbridge 150*25 mm*5 μm; mobile phase: [water (0.05% ammonia hydroxide v/v)-ACN]; B %: 12%-37%, 10 min). N-[3-(4,6-dimethylpyrimidin-5-yl)-4-[2-[(1S,4S)-2-oxa-5-azabicyclo[2.2.1]heptan-5-yl]ethoxy]phenyl]cyclopropanecarboxamide (31.63 mg, 76.66 μmol, 29.23% yield, 99% purity) was obtained as a white solid.

LCMS (ESI): m/z [M+H] calcd for $C_{23}H_{29}N_4O_3$: 409.22; found: 409.3.

$^1H$ NMR (400 MHZ, methanol-$d_4$) δ=8.85 (s, 1H), 7.59 (dd, J=2.6, 8.9 Hz, 1H), 7.38 (d, J=2.6 Hz, 1H), 7.11 (d, J=8.9 Hz, 1H), 4.25 (s, 1H), 4.15-4.03 (m, 2H), 3.78 (d, J=7.9 Hz, 1H), 3.37-3.32 (m, 2H), 2.93-2.75 (m, 2H), 2.69-2.58 (m, 1H), 2.32 (dd, J=0.8, 10.6 Hz, 1H), 2.27 (d, J=6.2 Hz, 6H), 1.78-1.69 (m, 2H), 1.61 (br d, J=10.0 Hz, 1H), 0.98-0.90 (m, 2H), 0.87-0.80 (m, 2H).

N-[3-(4,6-dimethylpyrimidin-5-yl)-4-[2-[(1S,5R)-3-oxa-6-azabicyclo[3.1.1]heptan-6-yl]ethoxy]phenyl]cyclopropanecarboxamide (337)

Preparation of N-[3-bromo-4-[2-[(1S,5R)-3-oxa-6-azabicyclo[3.1.1]heptan-6-yl]ethoxy]phenyl]cyclopropanecarboxamide (52)

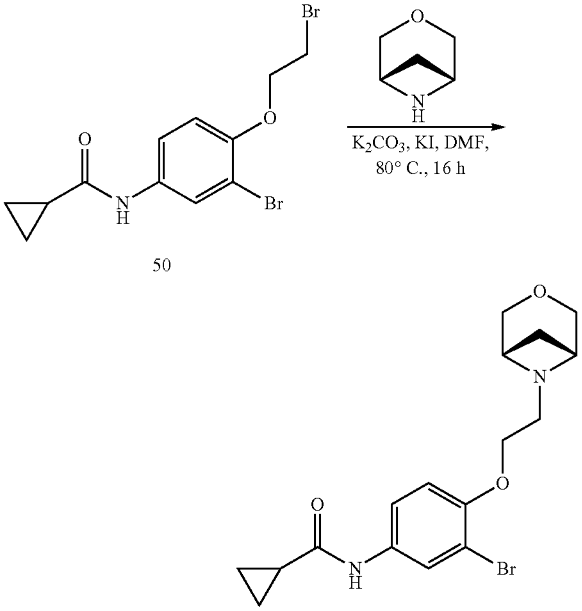

50

52

A mixture of N-[3-bromo-4-(2-bromoethoxy)phenyl]cyclopropanecarboxamide ((50), 150 mg, 413.17 μmol, 1 eq.), (1S,5R)-3-oxa-6-azabicyclo[3.1.1]heptane (45.05 mg, 454.49 μmol, 1.1 eq., HCl), $K_2CO_3$ (114.21 mg, 826.34 μmol, 2 eq.), and KI (6.86 mg, 41.32 μmol, 0.1 eq.) in DMF (1 mL) was degassed and purged with $N_2$ three times, and then the mixture was stirred at 80° C. for 16 hrs under an $N_2$ atmosphere (monitored by LC-MS). The reaction mixture was concentrated under reduced pressure to give a residue. The crude product was purified by reversed-phase HPLC (0.1% $NH_3 \cdot H_2O$). N-[3-bromo-4-[2-[(1S,5R)-3-oxa-6-azabicyclo[3.1.1]heptan-6-yl]ethoxy]phenyl]cyclopropanecarboxamide ((52), 90 mg, 236.06 μmol, 57.13% yield) was obtained as a white solid.

LCMS (ESI): m/z [M+H] calcd for $C_{17}H_{22}Br^{79/80}N_2O_3$: 381.07; 383.07; found: 381.1; 383.1.

Preparation of N-[3-(4,6-dimethylpyrimidin-5-yl)-4-[2-[(1S,5R)-3-oxa-6-azabicyclo[3.1.1]heptan-6-yl]ethoxy]phenyl]cyclopropanecarboxamide (337)

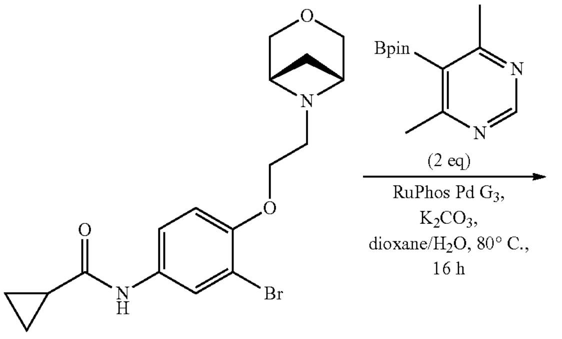

52

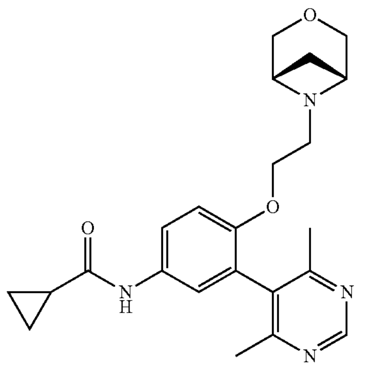

337

A mixture of N-[3-bromo-4-[2-[(1S,5R)-3-oxa-6-azabicyclo[3.1.1]heptan-6-yl]ethoxy]phenyl]cyclopropanecarboxamide ((52), 90 mg, 236.06 μmol, 1 eq.), 4,6-dimethyl-5-(4,4,5,5-tetramethyl-1,3,2-dioxaborolan-2-yl)pyrimidine (110.52 mg, 472.12 μmol, 2 eq.), RuPhos Pd G3 (19.74 mg, 23.61 μmol, 0.1 eq.), and $K_2CO_3$ (65.25 mg, 472.12 μmol, 2 eq.) in dioxane (1 mL) and $H_2O$ (0.1 mL) was degassed and purged with $N_2$ three times, and then the mixture was stirred at 80° C. for 16 hrs under an $N_2$ atmosphere (monitored by LC-MS). The reaction mixture was concentrated under reduced pressure to give a residue. The residue was purified by prep-HPLC (column: Waters Xbridge 150*25 mm*5 μm; mobile phase: [water (0.05% ammonia hydroxide v/v)-ACN]; B %: 10%-36%, 10 min). N-[3-(4,6-dimethylpyrimidin-5-yl)-4-[2-[(1S,5R)-3-oxa-6-azabicyclo[3.1.1]heptan-6-yl]ethoxy]phenyl]cyclopropanecarboxamide (13.41 mg, 32.83 μmol, 13.91% yield, 100% purity) was obtained as a yellow solid.

LCMS (ESI): m/z [M+H] calcd for $C_{23}H_{29}N_4O_3$: 409.22; found: 409.3.

$^1$H NMR (400 MHz, methanol-$d_4$) δ=8.84 (s, 1H), 7.59 (dd, J=2.7, 8.9 Hz, 1H), 7.36 (d, J=2.7 Hz, 1H), 7.11 (d, J=8.9 Hz, 1H), 4.13 (t, J=4.9 Hz, 2H), 3.86 (d, J=10.9 Hz, 2H), 3.40 (d, J=10.9 Hz, 2H), 3.12 (d, J=6.2 Hz, 2H), 2.92 (t, J=4.8 Hz, 2H), 2.58-2.46 (m, 1H), 2.24 (s, 6H), 1.78-1.65 (m, 2H), 0.96-0.90 (m, 2H), 0.87-0.81 (m, 2H).

2-[1-[2-[4-(cyclopropanecarbonylamino)-2-(4,6-dimethylpyrimidin-5-yl)phenoxy]ethyl]pyrrolidin-3-yl]acetic acid (338)

Preparation of ethyl 2-[1-(2-hydroxyethyl)pyrrolidin-3-yl]acetate (53)

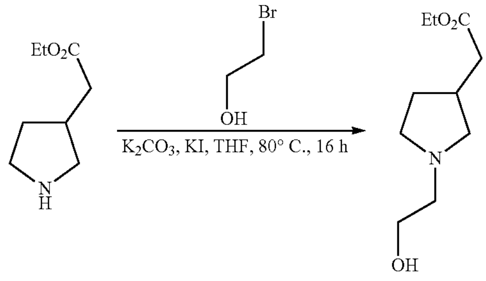

53

To the mixture of ethyl 2-pyrrolidin-3-ylacetate (200 mg, 1.03 mmol, 1 eq., HCl) and 2-bromoethanol (129.05 mg, 1.03 mmol, 73.32 μL, 1 eq.) in THF (4 mL) was added $K_2CO_3$ (570.89 mg, 4.13 mmol, 4 eq.) and KI (17.14 mg, 103.27 μmol, 0.1 eq.). The mixture was stirred at 80° C. for 16 hrs. The residue was poured into water (50 mL). The aqueous phase was extracted with ethyl acetate (50 mL×3). The combined organic phase was washed with brine (50 mL), dried with anhydrous $Na_2SO_4$, filtered and concentrated under vacuum. Crude ethyl 2-[1-(2-hydroxyethyl)pyrrolidin-3-yl]acetate ((53), 120 mg, 596.24 μmol, 57.74% yield) as a yellow gum was obtained.

LCMS (ESI): m/z [M+H] calcd for $C_{10}H_{20}NO_3$: 202.14; found: 202.1.

Preparation of ethyl 2-[1-[2-[2-(4,6-dimethylpyrimidin-5-yl)-4-nitro-phenoxy]ethyl]pyrrolidin-3-yl]acetate (54)

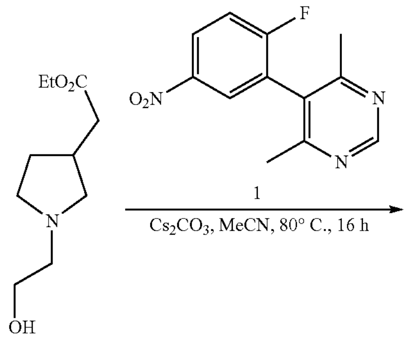

53

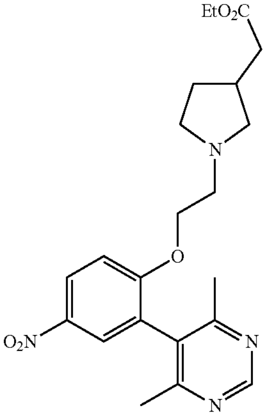

54

To a mixture of ethyl 2-[1-(2-hydroxyethyl)pyrrolidin-3-yl]acetate ((53), 120 mg, 596.24 μmol, 9.83e-1 eq.) and 5-(2-fluoro-5-nitro-phenyl)-4,6-dimethyl-pyrimidine ((1), 150 mg, 606.74 μmol, 1 eq.) in MeCN (3 mL) was added $Cs_2CO_3$ (395.37 mg, 1.21 mmol, 2 eq.). The mixture was stirred at 80° C. for 16 hrs. The residue was poured into water (50 mL). The aqueous phase was extracted with ethyl acetate (50 mL×3). The combined organic phase was washed with brine (50 mL), dried with anhydrous $Na_2SO_4$, filtered and concentrated in vacuum. The residue was purified by flash silica gel chromatography (petroleum ether: ethyl acetate=0~30%). Ethyl 2-[1-[2-[2-(4,6-dimethylpyrimidin-5-yl)-4-nitro-phenoxy]ethyl]pyrrolidin-3-yl]acetate ((54), 103 mg, 240.38 μmol, 39.62% yield) was obtained as a green gum.

LCMS (ESI): m/z [M+H] calcd for $C_{22}H_{29}N_4O_5$: 429.21; found: 429.2.

Preparation of ethyl 2-[1-[2-[4-amino-2-(4,6-dimethylpyrimidin-5-yl)phenoxy]ethyl]pyrrolidin-3-yl] acetate (55)

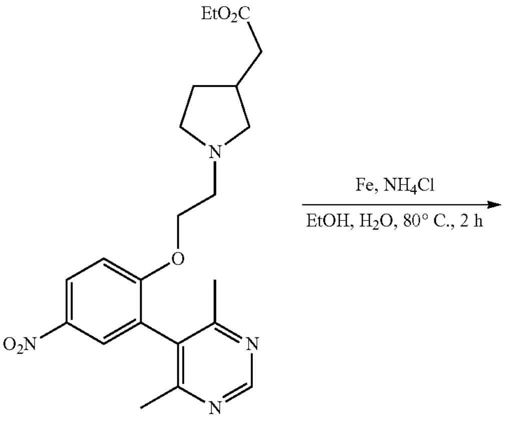

54

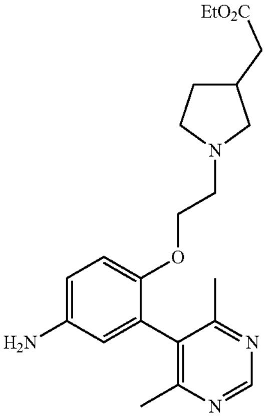

55

To a mixture of ethyl 2-[1-[2-[2-(4,6-dimethylpyrimidin-5-yl)-4-nitro-phenoxy]ethyl]pyrrolidin-3-yl]acetate (100 mg, 233.38 μmol, 1 eq.) in EtOH (1 mL) and $H_2O$ (1 mL) was added $NH_4Cl$ (99.87 mg, 1.87 mmol, 8 eq.). The mixture was stirred at 80° C. for 0.1 hr. Fe (65.17 mg, 1.17 mmol, 5 eq.) was added to the mixture. The mixture was stirred at 80° C. for 3 hrs. The mixture was filtered and the filtrate was concentrated under vacuum. The residue was purified by prep-TLC (petroleum ether:ethyl acetate=1:1). Ethyl 2-[1-[2-[4-amino-2-(4,6-dimethylpyrimidin-5-yl)phenoxy]ethyl]pyrrolidin-3-yl]acetate ((55), 30 mg, 75.28 μmol, 32.26% yield) as a yellow gum was obtained.

LCMS (ESI): m/z [M+H] calcd for $C_{22}H_{31}N_4O_3$: 399.23; found: 399.2.

Preparation of ethyl 2-[1-[2-[4-(cyclopropanecarbonylamino)-2-(4,6-dimethylpyrimidin-5-yl)phenoxy]ethyl]pyrrolidin-3-yl]acetate (56)

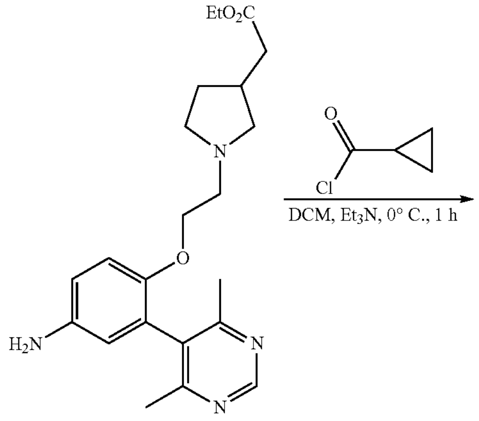

55

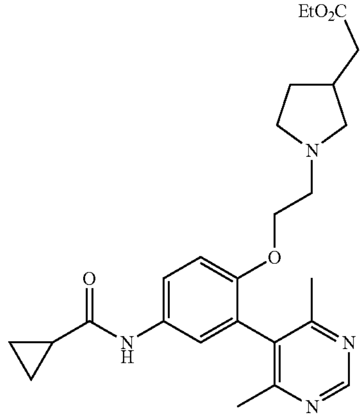

56

To a mixture of ethyl 2-[1-[2-[4-amino-2-(4,6-dimethylpyrimidin-5-yl)phenoxy]ethyl]pyrrolidin-3-yl]acetate (30 mg, 75.28 μmol, 1 eq.) and $Et_3N$ (15.24 mg, 150.57 μmol, 20.96 μL, 2 eq.) in DCM (2 mL) was added cyclopropanecarbonyl chloride (8.03 mg, 76.79 μmol, 6.98 μL, 1.02 eq.) at 0° C. The mixture was stirred at 0° C. for 1 hr. The reaction mixture was concentrated under vacuum. The residue was poured into water (20 mL). The aqueous phase was extracted with ethyl acetate (100 mL×3). The combined organic phase was dried with anhydrous $Na_2SO_4$, filtered and concentrated under vacuum. Crude ethyl 2-[1-[2-[4-(cyclopropanecarbonylamino)-2-(4,6-dimethylpyrimidin-5-yl)phenoxy]ethyl]pyrrolidin-3-yl]acetate ((56), 30 mg, 64.30 μmol, 85.41% yield) was obtained as a yellow gum.

LCMS (ESI): m/z [M+H] calcd for $C_{26}H_{35}N_4O_4$: 467.26; found: 467.3.

Preparation of 2-[1-[2-[4-(cyclopropanecarbonylamino)-2-(4,6-dimethylpyrimidin-5-yl)phenoxy]ethyl]pyrrolidin-3-yl]acetic acid (338)

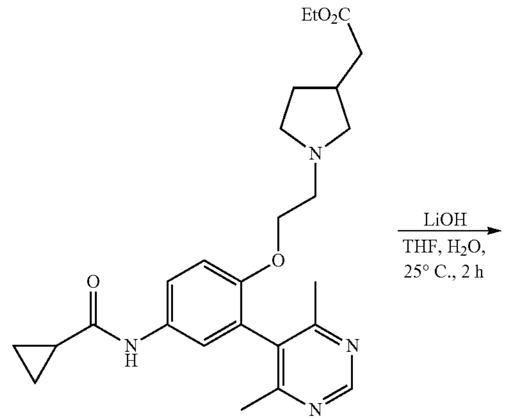

56

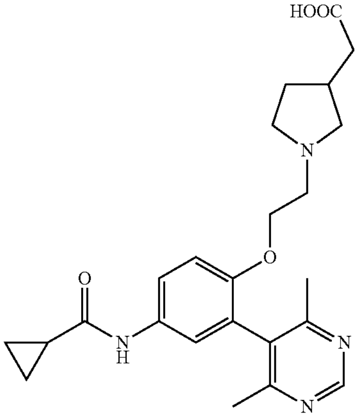

338

To a mixture of ethyl 2-[1-[2-[4-(cyclopropanecarbonylamino)-2-(4,6-dimethylpyrimidin-5-yl)phenoxy]ethyl]pyrrolidin-3-yl]acetate ((56), 30 mg, 64.30 μmol, 1 eq.) in THF (1 mL) was added the solvent of LiOH (9.24 mg, 385.79 μmol, 6 eq.) in $H_2O$ (1 mL). The mixture was stirred at 25° C. for 2 hrs. The reaction mixture was concentrated under vacuum. The residue was purified by prep-HPLC (column: Shim-pack C18 150*25*10 μm; mobile phase: [water (0.225% TFA)-ACN]; B %: 1%-30%, 10 min) followed by lyophilization. 2-[1-[2-[4-(cyclopropanecarbonylamino)-2-(4,6-dimethylpyrimidin-5-yl)phenoxy]ethyl]pyrrolidin-3-yl]acetic acid (8.11 mg, 17.75 μmol, 27.61% yield, 96% purity) as a yellow gum was obtained.

LCMS (ESI): m/z [M+H] calcd for $C_{24}H_{31}N_4O_4$: 439.23; found: 439.2.

$^1H$ NMR (400 MHZ, methanol-$d_4$) δ=8.88 (s, 1H), 8.43 (br s, 1H), 7.64 (dd, J=2.4, 8.9 Hz, 1H), 7.41 (d, J=2.4 Hz, 1H), 7.17 (d, J=8.9 Hz, 1H), 4.35-4.22 (m, 2H), 3.44-3.35 (m, 2H), 3.21-3.11 (m, 2H), 3.03-2.94 (m, 1H), 2.82 (br dd, J=7.0, 10.9 Hz, 1H), 2.57 (td, J=7.2, 14.1 Hz, 1H), 2.40-2.32 (m, 2H), 2.29 (d, J=1.6 Hz, 6H), 2.15 (td, J=4.4, 12.9 Hz, 1H), 1.78-1.70 (m, 1H), 1.68-1.57 (m, 1H), 0.97-0.82 (m, 4H).

N-[3-(4,6-dimethylpyrimidin-5-yl)-4-[2-[4-(2-hydroxyacetyl) piperazin-1-yl]ethoxy]phenyl]cyclopropanecarboxamide (339)

Preparation of tert-butyl 4-[2-[2-bromo-4-(cyclopropanecarbonylamino)phenoxy]ethyl]piperazine-1-carboxylate (57)

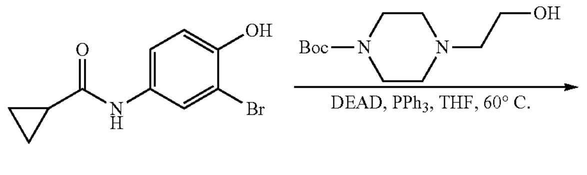

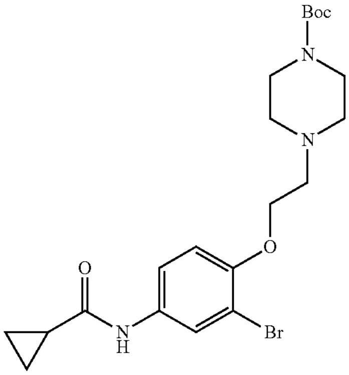

57

To a solution of tert-butyl 4-(2-hydroxyethyl) piperazine-1-carboxylate (2.00 g, 8.68 mmol, 1.11 eq.) and N-(3-bromo-4-hydroxy-phenyl)cyclopropanecarboxamide (2 g, 7.81 mmol, 1 eq.) in toluene (50 mL) was added $PPh_3$ (3.07 g, 11.71 mmol, 1.5 eq.) and DIAD (3.16 g, 15.62 mmol, 3.04 mL, 2 eq.) at 0° C., the reaction was stirred at 60° C. for 4 hrs. The mixture was filtered and concentrated under reduced pressure to give a crude product. The crude product was purified by column chromatography on silica gel, eluted with petroleum ether:ethyl acetate (10:1 to 0:1) to give tert-butyl 4-[2-[2-bromo-4-(cyclopropanecarbonylamino) phenoxy]ethyl]piperazine-1-carboxylate ((57), 1.5 g, 3.20 mmol, 41.01% yield) as a pale white solid.

LCMS (ESI): m/z [M+H] calcd for $C_{21}H_{30}Br^{79/81}N_3O_4$: 468.14, 470.14; found: 468.2, 470.2.

Preparation of tert-butyl 4-[2-[4-(cyclopropanecarbonylamino)-2-(4,4,5,5-tetramethyl-1,3,2-dioxaborolan-2-yl)phenoxy]ethyl]piperazine-1-carboxylate (58)

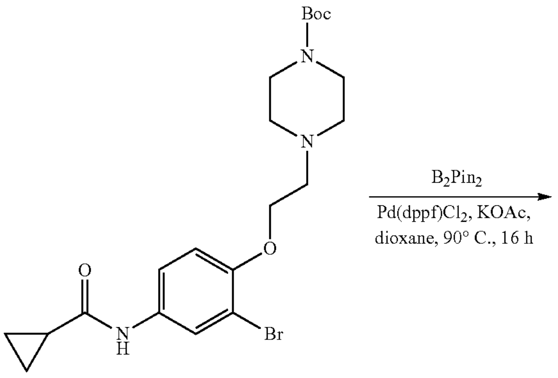

57

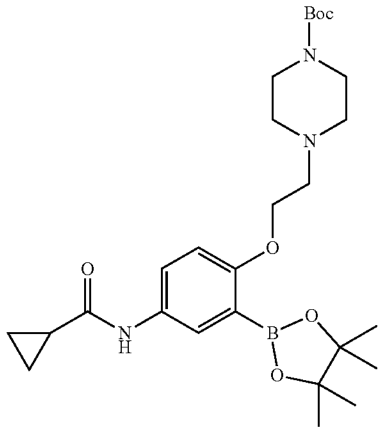

58

To a solution of tert-butyl 4-[2-[2-bromo-4-(cyclopropanecarbonylamino)phenoxy]ethyl]piperazine-1-carboxylate ((57), 3.0 g, 6.41 mmol, 1 eq.) and BPD (4.69 g, 18.46 mmol, 2.88 eq.) in 1,4-dioxane (50 mL) was added KOAc (2.81 g, 28.66 mmol, 4.47 eq.) and $Pd(dppf)Cl_2$ (468.75 mg, 640.63 μmol, 0.1 eq.). The mixture was heated at 90° C. for 2 hrs under $N_2$ atmosphere (monitored by LCMS). The mixture was filtered, the filtrate was concentrated under reduced pressure to give a crude product. The crude product was purified by column chromatography on silica gel, eluted with petroleum ether:ethyl acetate=10:1 to 0:1 to give tert-butyl 4-[2-[4-(cyclopropanecarbonylamino)-2-(4,4,5,5-tetramethyl-1,3,2-dioxaborolan-2-yl)phenoxy]ethyl]piperazine-1-carboxylate ((58), 2 g, 3.88 mmol, 60.58% yield) as brown oil.

LCMS (ESI): m/z [M+H] calcd for $C_{27}H_{42}BN_3O_6$: 516.32; found: 516.4.

Preparation of tert-butyl 4-[2-[4-(cyclopropanecarbonylamino)-2-(4,6-dimethylpyrimidin-5-yl)phenoxy]ethyl]piperazine-1-carboxylate (59)

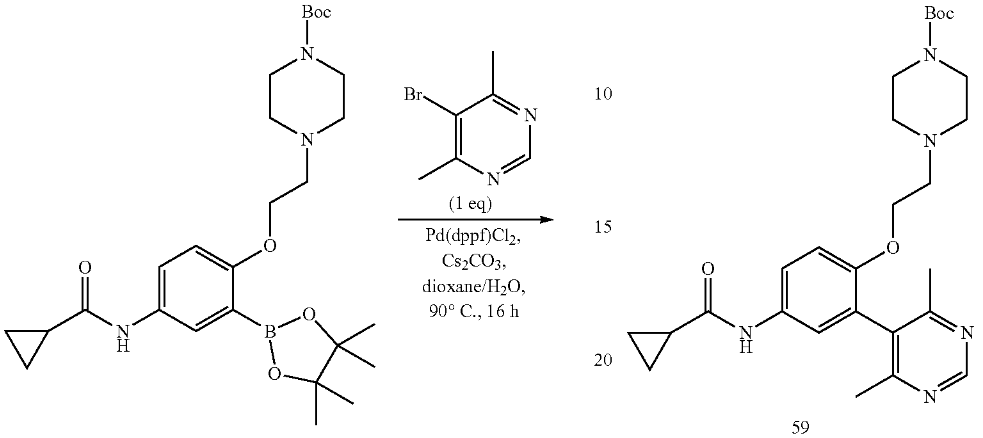

58

59

To a solution of tert-butyl 4-[2-[4-(cyclopropanecarbonylamino)-2-(4,4,5,5-tetramethyl-1,3,2-dioxaborolan-2-yl) phenoxy]ethyl]piperazine-1-carboxylate (1 g, 1.94 mmol, 1.21 eq.) and 5-bromo-4,6-dimethyl-pyrimidine (0.3 g, 1.60 mmol, 1 eq.) in 1,4-dioxane (20 mL), $H_2O$ (2 mL) was added $Cs_2CO_3$ (2 g, 6.14 mmol, 3.83 eq.) and $Pd(dppf)Cl_2$ (200 mg, 273.33 μmol, 0.17 eq). The mixture was heated at 90° C. for 12 hrs under an $N_2$ atmosphere. The mixture was filtered, the filtrate was concentrated under reduced pressure to give a crude product. The crude product was purified by column chromatography on silica gel, eluted with petroleum ether:ethyl acetate=10:1 to 0:1 to give tert-butyl 4-[2-[4-(cyclopropanecarbonylamino)-2-(4,6-dimethylpyrimidin-5-yl)phenoxy]ethyl]piperazine-1-carboxylate ((59), 0.2 g, 403.54 μmol, 25.16% yield) as a brown solid.

$^1H$ NMR (400 MHZ, $CDCl_3$) δ 0.77-0.79 (m, 2H), 0.99-1.02 (m, 2H), 1.38 (s, 10H), 2.19 (m, 10H), 2.50-2.53 (m, 2H), 3.25 (m, 4H), 3.94-3.97 (m, 2H), 6.86-6.88 (d, J=8.8 Hz, 1H), 7.25 (m, 1H), 7.44-7.45 (d, J=6.8 Hz, 1H), 8.85 (s, 1H).

Preparation of N-[3-(4,6-dimethylpyrimidin-5-yl)-4-(2-piperazin-1-ylethoxy)phenyl]cyclopropanecarboxamide (60)

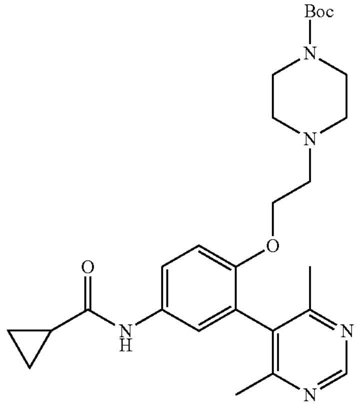

59

TFA/$CH_2Cl_2$

20° C., 1 h

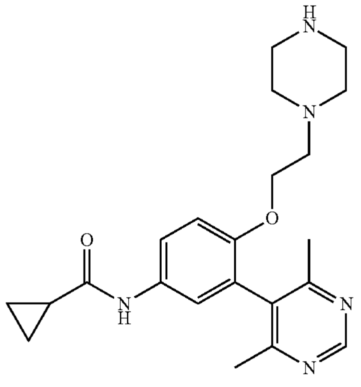

60

To a solution of tert-butyl 4-[2-[4-(cyclopropanecarbonylamino)-2-(4,6-dimethylpyrimidin-5-yl)phenoxy]ethyl] piperazine-1-carboxylate ((59), 350 mg, 706.20 μmol, 1 eq.) in EtOAc (5 mL) was added HCl/EtOAc (2 mL, 54.79 mmol, 77.59 eq.). The mixture was stirred at 20° C. for 2 hrs under an $N_2$ atmosphere. The mixture was concentrated under reduced pressure to give a crude product. N-[3-(4,6-dimethylpyrimidin-5-yl)-4-(2-piperazin-1-ylethoxy)phenyl] cyclopropanecarboxamide ((60), 0.25 g, 632.12 μmol, 89.51% yield) was obtained as a brown solid.

LCMS (ESI): m/z [M+H] calcd for $C_{22}H_{29}N_5O_2$: 396.23; found: 396.2.

Preparation of N-[3-(4,6-dimethylpyrimidin-5-yl)-4-[2-[4-(2-hydroxyacetyl) piperazin-1-yl]ethoxy]phenyl]cyclopropanecarboxamide (339)

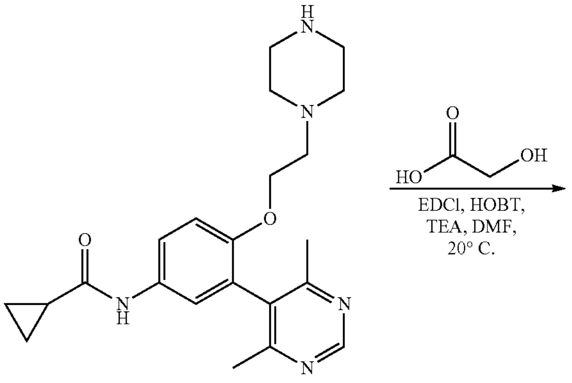

60

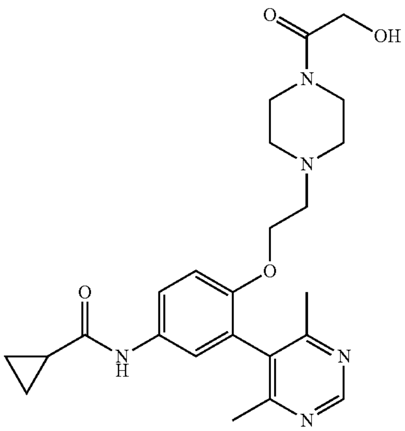

339

To a mixture of N-[3-(4,6-dimethylpyrimidin-5-yl)-4-(2-piperazin-1-ylethoxy)phenyl]cyclopropanecarboxamide ((60), 125 mg, 316.06 μmol, 1 eq.) and 2-hydroxyacetic acid (36.05 mg, 474.09 μmol, 28.84 μL, 1.5 eq.) in DMF (2 mL) was added EDCI (90.88 mg, 474.09 μmol, 1.5 eq.), HOBt (64.06 mg, 474.09 μmol, 1.5 eq.), and TEA (159.91 mg, 1.58 mmol, 219.96 μL, 5 eq.). The mixture was stirred at 20° C. for 2 hrs. The mixture was concentrated under reduced pressure to give a crude product. The crude product was purified by Prep-HPLC (column: Nano-micro Kromasil C18 80*25 mm 3 μm; mobile phase: [water (0.1% TFA)-ACN]; B %: 5%-25%, 7 min). N-[3-(4,6-dimethylpyrimidin-5-yl)-4-[2-[4-(2-hydroxyacetyl) piperazin-1-yl]ethoxy]phenyl]cyclopropanecarboxamide (20 mg, 44.10 μmol, 13.95% yield) was obtained as a white solid.

LCMS (ESI): m/z [M+H] calcd for $C_{24}H_{31}N_5O_4$: 454.34; found: 454.1.

$^1$H NMR (400 MHZ, methanol-$d_4$) δ=8.94 (s, 1H), 7.65 (dd, J=2.6, 8.9 Hz, 1H), 7.44 (d, J=2.6 Hz, 1H), 7.19 (d, J=9.0 Hz, 1H), 4.46-4.36 (m, 2H), 4.26 (s, 2H), 3.64 (br s, 4H), 3.54-3.45 (m, 2H), 3.12 (br s, 4H), 2.50-2.10 (m, 6H), 1.83-1.67 (m, 1H), 0.98-0.80 (m, 4H).

2-[4-[2-[4-(cyclopropanecarbonylamino)-2-(4,6-dimethylpyrimidin-5-yl)phenoxy]ethyl]piperazin-1-yl]-2-oxo-acetic acid (340)

Preparation of ethyl 2-[4-[2-[4-(cyclopropanecarbonylamino)-2-(4,6-dimethylpyrimidin-5-yl)phenoxy] ethyl]piperazin-1-yl]-2-oxo-acetate (61)

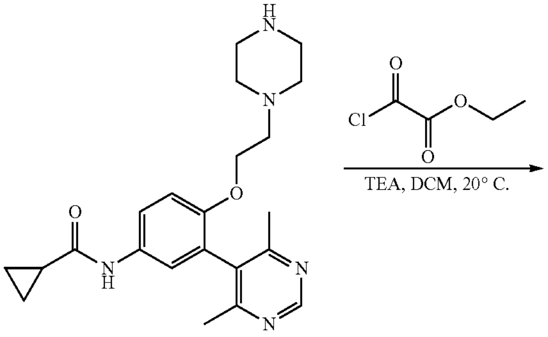

60

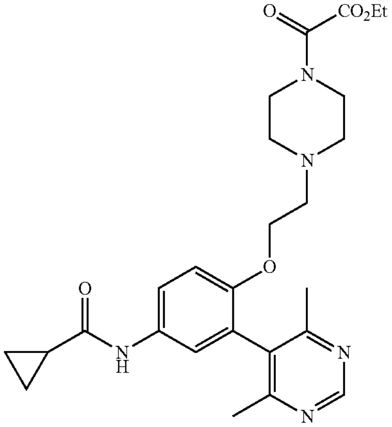

61

To a mixture of ethyl 2-chloro-2-oxo-acetate (328.97 mg, 2.41 mmol, 269.64 μL, 19.06 eq.) and N-[3-(4,6-dimethylpyrimidin-5-yl)-4-(2-piperazin-1-ylethoxy)phenyl]cyclopropanecarboxamide ((60), 50 mg, 126.42 μmol, 1 eq.) in DCM (2 mL) was added TEA (63.96 mg, 632.12 μmol, 87.98 μL, 5 eq.). The mixture was stirred at 25° C. for 1 hr. The mixture was concentrated under reduced pressure to give a crude product. Crude ethyl 2-[4-[2-[4-(cyclopropanecarbonylamino)-2-(4,6-dimethylpyrimidin-5-yl)phenoxy] ethyl]piperazin-1-yl]-2-oxo-acetate ((61), 30 mg, 60.54 μmol, 47.88% yield) was obtained as yellow oil.

LCMS (ESI): m/z [M+H] calcd for $C_{26}H_{33}N_5O_5$: 496.25; found: 496.3.

Preparation of 2-[4-[2-[4-(cyclopropanecarbonylamino)-2-(4,6-dimethylpyrimidin-5-yl)phenoxy]ethyl]piperazin-1-yl]-2-oxo-acetic acid (340)

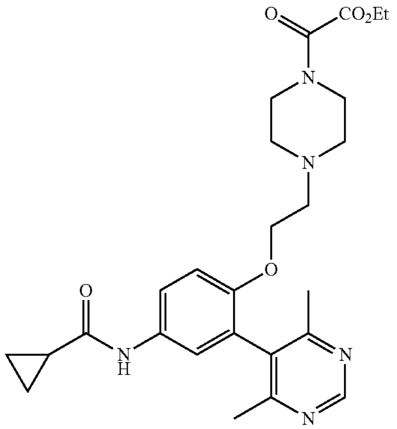

61

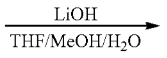

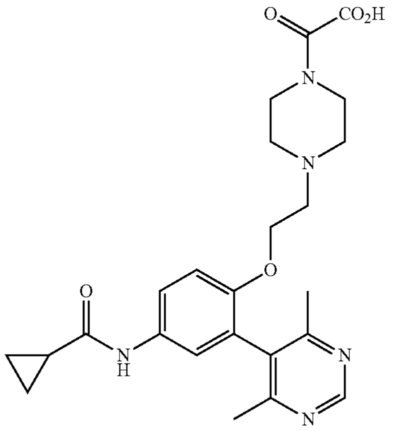

340

To a mixture of ethyl 2-[4-[2-[4-(cyclopropanecarbonylamino)-2-(4,6-dimethylpyrimidin-5-yl)phenoxy]ethyl]piperazin-1-yl]-2-oxo-acetate ((61), 30 mg, 60.54 μmol, 1 eq.) in THF (1 mL) and $H_2O$ (1 mL) was added LiOH·$H_2O$ (10 mg, 238.30 μmol, 3.94 eq.). The mixture was stirred at 25° C. for 1 hr. The mixture was lyophilized to give a crude product. The crude product was purified by Prep-HPLC column: Waters Xbridge BEH C18 100*25 mm*5 μm; mobile phase: [water (10 mM $NH_4HCO_3$)-ACN]; B %: 1%-30%, 8 min. 2-[4-[2-[4-(cyclopropanecarbonylamino)-2-(4,6-dimethylpyrimidin-5-yl)phenoxy]ethyl]piperazin-1-yl]-2-oxo-acetic acid (18 mg, 38.50 μmol, 63.60% yield) was obtained as white solid.

LCMS (ESI): m/z [M+H] calcd for $C_{24}H_{29}N_5O_5$: 468.23; found: 468.2.

$^1$H NMR (400 MHZ, methanol-$d_4$) δ=8.88 (s, 1H), 7.63 (dd, J=2.6, 8.9 Hz, 1H), 7.39 (d, J=2.7 Hz, 1H), 7.16 (d, J=9.0 Hz, 1H), 4.26 (t, J=5.0 Hz, 2H), 3.56 (br s, 4H), 3.09 (br s, 2H), 2.82 (br s, 2H), 2.73 (br s, 2H), 2.28 (s, 6H), 1.78-1.70 (m, 1H), 0.96-0.82 (m, 4H).

N-[3-(4,6-dimethylpyrimidin-5-yl)-4-[2-(4-formylpiperazin-1-yl)ethoxy]phenyl]cyclopropanecarboxamide (341)

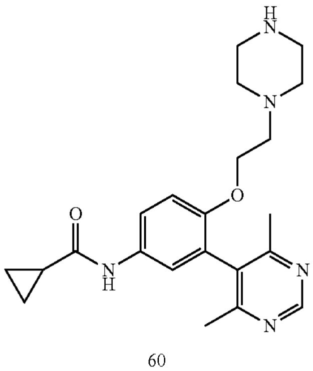

60

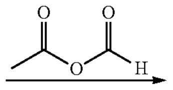

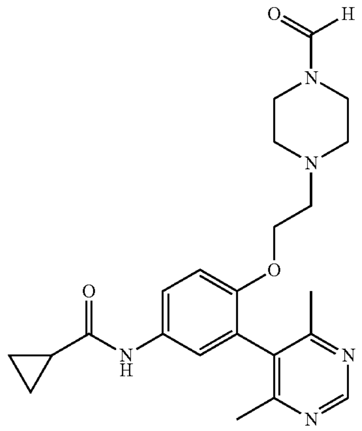

341

To a mixture of formyl acetate (212.17 mg, 2.41 mmol, 269.64 μL, 19.06 eq.) and N-[3-(4,6-dimethylpyrimidin-5-yl)-4-(2-piperazin-1-ylethoxy)phenyl]cyclopropanecarboxamide ((60), 50 mg, 126.42 μmol, 1 eq.) in DCM (2 mL) was added TEA (63.96 mg, 632.10 μmol, 87.98 μL, 5 eq.). The mixture was stirred at 25° C. for 1 hr. The mixture was concentrated under reduced pressure to give a crude product. The crude product was purified by Prep-HPLC column: Waters Xbridge BEH C18 100*30 mm*10 μm; mobile phase: [water (10 mM $NH_4HCO_3$)-ACN]; B %: 10%-33%, 10 min. N-[3-(4,6-dimethylpyrimidin-5-yl)-4-[2-(4-formylpiperazin-1-yl)ethoxy]phenyl]cyclopropanecarboxamide (20 mg, 47.22 μmol, 37.35% yield) was obtained as a white solid.

LCMS (ESI): m/z [M+H] calcd for $C_{23}H_{29}N_5O_3$: 424.23; found: 424.3.

$^1$H NMR (400 MHZ, methanol-$d_4$) δ=8.88 (s, 1H), 7.99 (s, 1H), 7.61 (dd, J=2.6, 8.9 Hz, 1H), 7.39 (d, J=2.6 Hz, 1H), 7.14 (d, J=8.9 Hz, 1H), 4.13 (t, J=5.2 Hz, 2H), 3.50-3.35 (m, 4H), 2.71-2.66 (m, 2H), 2.37-2.28 (m, 10H), 1.79-1.72 (m, 1H), 0.98-0.84 (m, 4H).

N-[3-(4,6-dimethylpyrimidin-5-yl)-4-[2-(4-methylsulfonylpiperazin-1 yl)ethoxy]phenyl]cyclopropanecarboxamide (342)

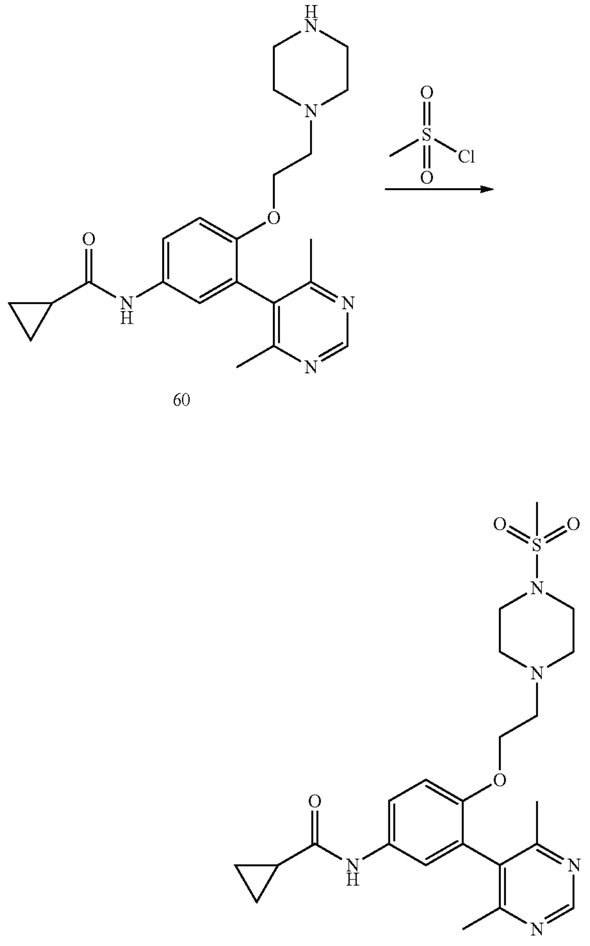

60

342

To a mixture of N-[3-(4,6-dimethylpyrimidin-5-yl)-4-(2-piperazin-1-ylethoxy)phenyl]cyclopropanecarboxamide ((60), 125 mg, 316.06 μmol, 1 eq.) and methanesulfonyl chloride (72.41 mg, 632.12 μmol, 48.93 μL, 2 eq.) in DMF (2.5 mL) was added TEA (159.91 mg, 1.58 mmol, 219.96 μL, 5 eq.). The mixture was stirred at 25° C. for 2 hrs. The mixture was concentrated under reduced pressure to give a crude product. The mixture was purified by Prep-HPLC (column: Nano-micro Kromasil C18 80*25 mm*3 μm; mobile phase: [water (0.1% TFA)-ACN]; B %: 8%-28%, 7 min). N-[3-(4,6-dimethylpyrimidin-5-yl)-4-[2-(4-methylsulfonylpiperazin-1 yl)ethoxy]phenyl]cyclopropanecarboxamide (20 mg, 42.23 μmol, 13.36% yield) was obtained as a white solid.

LCMS (ESI): m/z [M+H] calcd for $C_{23}H_{31}N_5O_4S$: 474.21; found: 474.1.

$^1$H NMR (400 MHZ, METHANOL-$d_4$) δ=8.92 (s, 1H), 7.66 (dd, J=2.6, 9.0 Hz, 1H), 7.44 (d, J=2.6 Hz, 1H), 7.19 (d, J=9.0 Hz, 1H), 4.51-4.26 (m, 2H), 3.56-3.48 (m, 2H), 3.46-3.36 (m, 4H), 3.20 (br s, 4H), 2.94 (s, 3H), 2.34 (s, 6H), 1.81-1.69 (m, 1H), 1.01-0.79 (m, 4H).

N-[3-(4,6-dimethylpyrimidin-5-yl)-4-[2-(3-oxo-5,6,8,8a-tetrahydro-1H-oxazolo[3,4-a]pyrazin-7-yl)ethoxy]phenyl]cyclopropanecarboxamide (343)

Preparation of 5-(2-fluoro-5-nitro-phenyl)-4,6-dimethyl-pyrimidine (62)

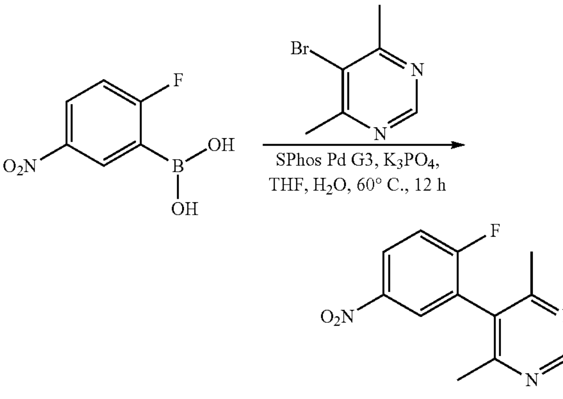

62

To a solution of (2-fluoro-5-nitro-phenyl) boronic acid (4.56 g, 24.64 mmol, 1.2 eq.) and 5-bromo-4,6-dimethyl-pyrimidine (3.84 g, 20.53 mmol, 1 eq.) in THF (200 mL) and $H_2O$ (40 mL) was added (2-dicyclohexylphosphino-2',6'-dimethoxybiphenyl) [2-(2'-amino-1,1'-biphenyl)]palladium (II) methanesulfonate (480.58 mg, 615.92 μmol, 0.03 eq.) and $K_3PO_4$ (13.07 g, 61.59 mmol, 3 eq.). The mixture was stirred at 60° C. for 12 hrs, then was diluted with water (50 mL) and extracted with ethyl acetate (20 mL×3). The combined organic layers were washed with brine (20 mL×3), dried over sodium sulfate, filtered and concentrated under reduced pressure to give a residue. The residue was dissolved in ethyl acetate (5 mL) at 40° C. to give a clear solution, then was cooled to 0° C. and stirred for 30 min. The solid was collected by filtration through a Buchner funnel. 5-(2-fluoro-5-nitro-phenyl)-4,6-dimethyl-pyrimidine ((62), 4.2 g, 16.48 mmol, 80.26% yield, 97% purity) was obtained as a light yellow solid.

$^1$H NMR (400 MHZ, methanol-$d_4$) δ 2.32 (s, 6H), 7.58 (t, J=8.88 Hz, 1H), 8.36 (dd, J=6.13, 2.75 Hz, 1H), 8.42-8.52 (m, 1H), 8.96 (s, 1H).

Preparation of 2-[2-(4,6-dimethylpyrimidin-5-yl)-4-nitro-phenoxy]ethanol (63)

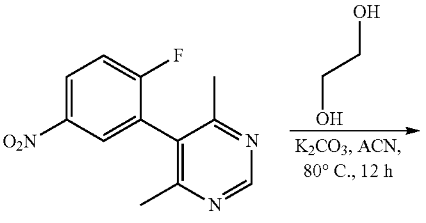

62

-continued

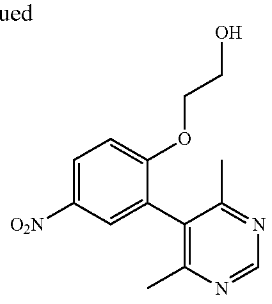

63

To a solution of ethylene glycol (5.02 g, 80.90 mmol, 4.52 mL, 10 eq.) and 5-(2-fluoro-5-nitro-phenyl)-4,6-dimethyl-pyrimidine ((62), 2 g, 8.09 mmol, 1 eq.) in ACN (100 mL) was added $K_2CO_3$ (2.24 g, 16.18 mmol, 2 eq). The mixture was stirred at 80° C. for 12 hrs. The reaction mixture was concentrated under reduced pressure to remove solvent. The residue was diluted with water (20 mL) and extracted with ethyl acetate (30 mL×3). The combined organic layers were washed with brine (20 mL×3), dried over sodium sulfate, filtered and concentrated under reduced pressure to give a residue. The residue was triturated with ethyl acetate (5 mL). The resulting solid was collected by filtration, washed with ethyl acetate (3 mL) and dried under high vacuum to give 2-[2-(4,6-dimethylpyrimidin-5-yl)-4-nitro-phenoxy]ethanol ((63), 1.5 g, 4.61 mmol, 57.04% yield, 89% purity) as a white solid.

$^1$H NMR (400 MHZ, methanol-$d_4$) δ 2.28 (s, 6H), 3.75 (t, J=4.50 Hz, 2H), 4.23 (t, J=4.57 Hz, 2H), 7.38 (d, J=9.26 Hz, 1H), 8.14 (d, J=2.75 Hz, 1H), 8.40 (dd, J=9.19, 2.81 Hz, 1H), 8.88 (s, 1H).

Preparation of 2-[4-amino-2-(4,6-dimethylpyrimidin-5-yl)phenoxy]ethanol (64)

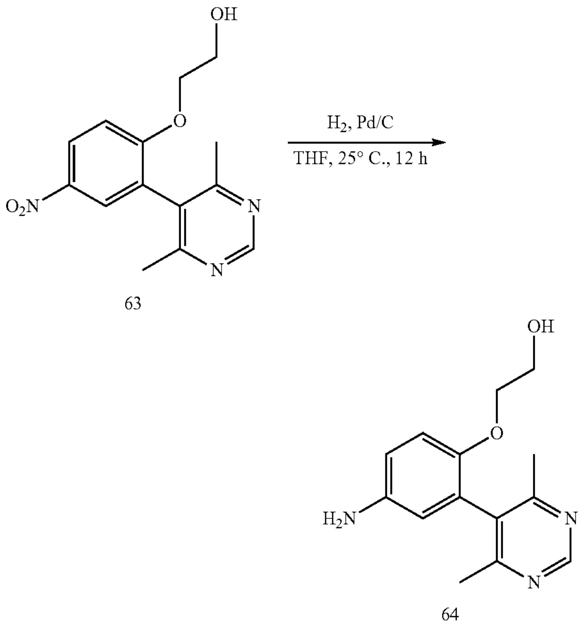

To a solution of 2-[2-(4,6-dimethylpyrimidin-5-yl)-4-nitro-phenoxy]ethanol ((63), 1.4 g, 4.84 mmol, 1 eq.) in THF (1 mL) was added Pd/C (1 g, 48.4 mmol, 10% purity, 10 eq.) under $N_2$. The suspension was degassed under vacuum and purged with $H_2$ three times. The mixture was stirred under $H_2$ (15 psi) at 25° C. for 12 hrs. The reaction mixture was concentrated under reduced pressure to give 2-[4-amino-2-(4,6-dimethylpyrimidin-5-yl)phenoxy]ethanol ((64), 1.1 g, 3.82 mmol, 78.89% yield, 90% purity) as a light gray solid. The product was used for next step without any purification.

$^1$H NMR (400 MHZ, methanol-$d_4$) δ 2.28 (s, 6H), 3.64 (t, J=4.82 Hz, 2H), 3.93 (t, J=4.88 Hz, 2H), 6.53 (d, J=2.63 Hz, 1H), 6.84 (dd, J=8.76, 2.75 Hz, 1H), 6.97 (d, J=8.75 Hz, 1H), 8.80 (s, 1H).

Preparation of N-[3-(4,6-dimethylpyrimidin-5-yl)-4-(2-hydroxyethoxy)phenyl]cyclopropanecarboxamide (65)

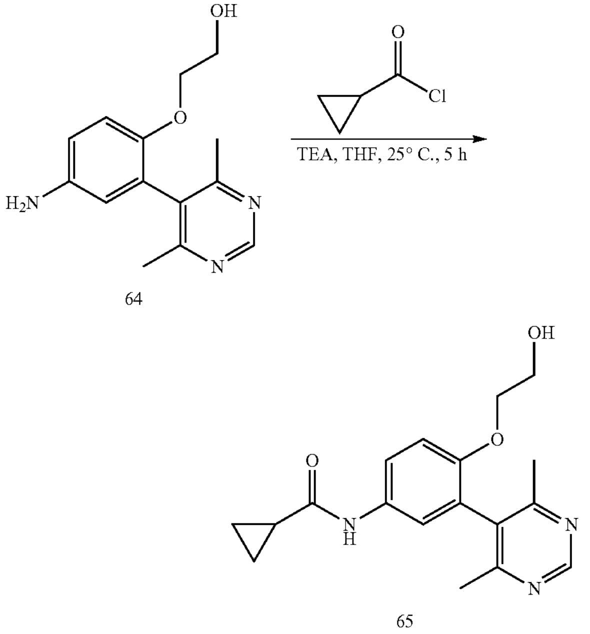 [SMILES: Cc1ncnc(C)c1-c1cc(N)ccc1OCCO ; O=C(Cl)C1CC1 ; Cc1ncnc(C)c1-c1cc(NC(=O)C2CC2)ccc1OCCO]

To a solution of cyclopropanecarbonyl chloride (483.76 mg, 4.63 mmol, 420.66 μL, 1.2 eq.) and 2-[4-amino-2-(4,6-dimethylpyrimidin-5-yl)phenoxy]ethanol ((64), 1 g, 3.86 mmol, 1 eq.) in THF (10 mL) was added TEA (780.47 mg, 7.71 mmol, 1.07 mL, 2 eq.). The mixture was stirred at 25° C. for 5 hrs. The reaction mixture was concentrated under reduced pressure to remove solvent. The residue was diluted with water (10 mL) and extracted with ethyl acetate (10 mL×5). The combined organic layers were washed with brine (10 mL×1), dried over sodium sulfate, filtered, and concentrated under reduced pressure to give N-[3-(4,6-dimethylpyrimidin-5-yl)-4-(2-hydroxyethoxy)phenyl]cyclopropanecarboxamide ((65), 1.2 g, 3.56 mmol, 92.20% yield, 97% purity) as a light gray solid.

$^1$H NMR (400 MHZ, methanol-$d_4$) δ 0.81-0.87 (m, 2H), 0.91-0.96 (m, 2H), 1.69-1.77 (m, 1H), 2.28 (s, 6H), 3.69 (t, J=4.83 Hz, 2H), 4.04 (t, J=4.83 Hz, 2H), 7.13 (d, J=8.93 Hz, 1H), 7.35 (d, J=2.57 Hz, 1H), 7.58 (dd, J=8.93, 2.57 Hz, 1H), 8.82 (s, 1H).

Preparation of 2-[4-(cyclopropanecarbonylamino)-2-(4,6-dimethylpyrimidin-5-yl)phenoxy]ethyl 4-methylbenzenesulfonate (66)

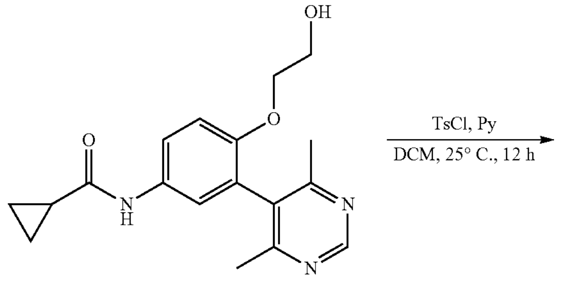

65

66

To a solution of N-[3-(4,6-dimethylpyrimidin-5-yl)-4-(2-hydroxyethoxy)phenyl]cyclopropanecarboxamide ((65), 500 mg, 1.53 mmol, 1 eq.) and pyridine (604.04 mg, 7.64 mmol, 616.37 μL, 5 eq.) in DCM (5 mL) was added TosCl (1.46 g, 7.64 mmol, 5 eq.). The mixture was stirred at 25° C. for 12 hrs. The reaction mixture was washed with 5% citric acid in water (5 mL) and filtered to give a part of product. The mixture was diluted with water (10 mL) and extracted with ethyl acetate (5 mL×5). The combined organic layers were washed with brine (5 mL×3), dried over sodium sulfate, filtered and concentrated under reduced pressure to give another part of product. The two parts of product were combined and triturated with ethyl acetate (2 mL). The resulting solid was collected by filtration, washed with ethyl acetate (1 mL) and dried under high vacuum to give 2-[4-(cyclopropanecarbonylamino)-2-(4,6-dimethylpyrimidin-5-yl)phenoxy]ethyl 4-methylbenzenesulfonate ((66), 650 mg, 1.16 mmol, 76.00% yield, 86% purity) as a white solid.

$^1$H NMR (400 MHZ, methanol-$d_4$) δ 0.82-0.87 (m, 2H), 0.91-0.96 (m, 2H), 1.69-1.78 (m, 1H), 2.27 (s, 6H), 2.45 (s, 3H), 4.12-4.19 (m, 4H), 7.07 (d, J=9.01 Hz, 1H), 7.36-7.43 (m, 3H), 7.56-7.65 (m, 3H), 8.90 (s, 1H).

Preparation of N-[3-(4,6-dimethylpyrimidin-5-yl)-4-[2-(3-oxo-5,6,8,8a-tetrahydro-1H-oxazolo[3,4-a]pyrazin-7-yl)ethoxy]phenyl]cyclopropanecarboxamide (343)

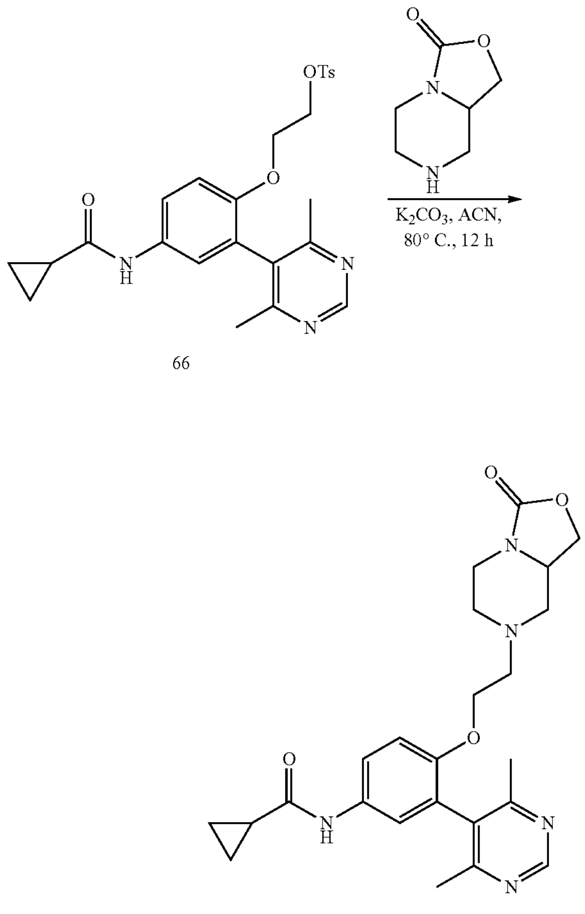

66

343

To a solution of 2-[4-(cyclopropanecarbonylamino)-2-(4,6-dimethylpyrimidin-5-yl)phenoxy]ethyl 4-methylbenzenesulfonate ((66), 80 mg, 166.13 μmol, 1 eq.) in ACN (2 mL) was added 1,5,6,7,8,8a-hexahydrooxazolo[3,4-a]pyrazin-3-one (70.85 mg, 498.38 μmol, 3 eq.) and $K_2CO_3$ (114.80 mg, 830.63 μmol, 5 eq.). The mixture was stirred at 80° C. for 12 hrs. The mixture was filtered and the filtrate was concentrated under reduced pressure to get a residue. The residue was purified by prep-HPLC (TFA conditions). N-[3-(4,6-dimethylpyrimidin-5-yl)-4-[2-(3-oxo-5,6,8,8a-tetrahydro-1H-oxazolo[3,4-a]pyrazin-7-yl)ethoxy]phenyl]cyclopropanecarboxamide (40.7 mg, 88.12 μmol, 53.05% yield, 97.76% purity) was obtained as a light yellow solid.

LCMS (ESI): m/z [M+H] calcd for $C_{24}H_{30}N_5O_4$: 452.2; found: 452.2.

$^1$H NMR (400 MHZ, methanol-$d_4$) δ=8.94 (s, 1H), 7.66 (dd, J=2.6, 8.9 Hz, 1H), 7.43 (d, J=2.4 Hz, 1H), 7.19 (d, J=8.9 Hz, 1H), 4.49 (t, J=8.7 Hz, 1H), 4.39 (t, J=4.8 Hz, 2H), 4.10 (tdd, J=4.1, 7.8, 11.8 Hz, 1H), 3.96 (dd, J=4.8, 9.3 Hz, 1H), 3.85 (dd, J=4.0, 14.2 Hz, 1H), 3.49 (br s, 2H), 3.38-3.32 (m, 1H), 3.30-3.23 (m, 2H), 2.97-2.84 (m, 2H), 2.37 (s, 6H), 1.80-1.69 (m, 1H), 0.98-0.82 (m, 4H).

N-(4-(2-(azetidin-1-yl)ethoxy)-3-(4,6-dimethylpyrimidin-5-yl)phenyl)cyclopropanecarboxamide (344)

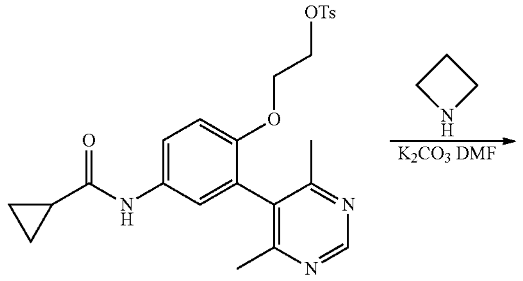

66

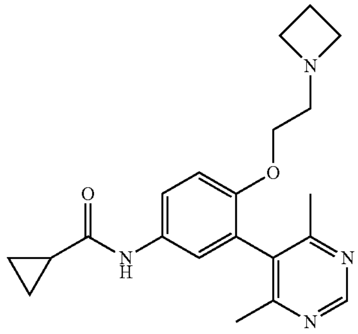

344

Compound 344 was prepared according to the synthesis described for compound 343, substituting azetidine for 1,5,6,7,8,8a-hexahydrooxazolo[3,4-a]pyrazin-3-one.

LCMS (ESI): m/z [M+H] calcd for $C_{21}H_{27}N_4O_2$: 367.2; found: 367.2.

$^1$H NMR (400 MHz, methanol-$d_4$) δ=8.87-8.71 (m, 1H), 7.58 (dd, J=2.6, 8.9 Hz, 1H), 7.38 (d, J=2.6 Hz, 1H), 7.08 (d, J=9.0 Hz, 1H), 3.99 (t, J=5.1 Hz, 2H), 3.02 (t, J=7.3 Hz, 3H), 2.74-2.64 (m, 2H), 2.29-2.16 (m, 7H), 1.97 (quin, J=7.2 Hz, 2H), 1.74 (tt, J=4.7, 7.8 Hz, 1H), 0.98-0.77 (m, 4H).

N-(4-(2-(2-oxa-6-azaspiro[3.3]heptan-6-yl)ethoxy)-3-(4,6-dimethylpyrimidin-5-yl)phenyl)cyclopropanecarboxamide (345)

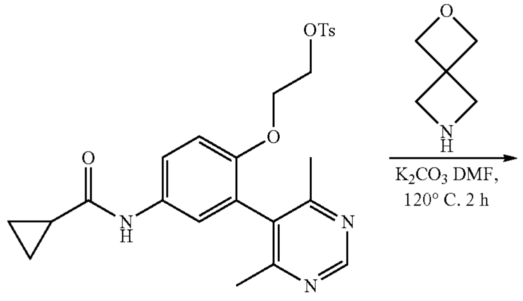

66

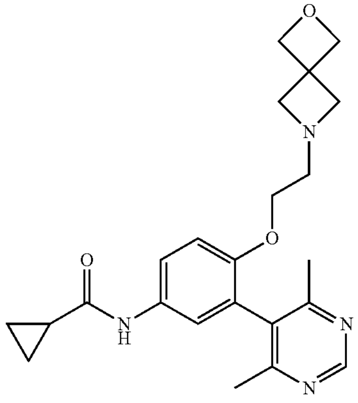

345

Compound 345 was prepared according to the synthesis described for compound 343, substituting 2-oxa-6-azaspiro[3.3]heptane for 1,5,6,7,8,8a-hexahydrooxazolo[3,4-a]pyrazin-3-one.

LCMS (ESI): m/z [M+H] calcd for $C_{23}H_{29}N_4O_2$: 409.2; found: 409.2.

$^1$H NMR (400 MHZ, methanol-$d_4$) δ=8.89 (s, 1H), 7.58 (dd, J=2.7, 8.9 Hz, 1H), 7.39 (d, J=2.6 Hz, 1H), 7.07 (d, J=9.0 Hz, 1H), 4.60 (s, 4H), 3.98 (t, J=5.1 Hz, 2H), 3.11 (s, 4H), 2.65 (t, J=5.0 Hz, 2H), 2.28 (s, 6H), 1.74 (tt, J=4.6, 7.9 Hz, 1H), 0.99-0.77 (m, 4H).

N-(3-(4,6-dimethylpyrimidin-5-yl)-4-(2-(6-oxohexahydropyrrolo[1,2-a]pyrazin-2 (1H)-yl)ethoxy)phenyl)cyclopropanecarboxamide (346)

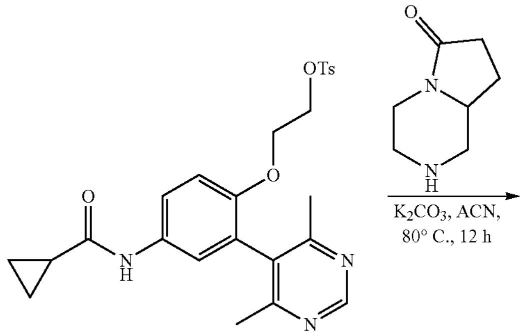

66

-continued

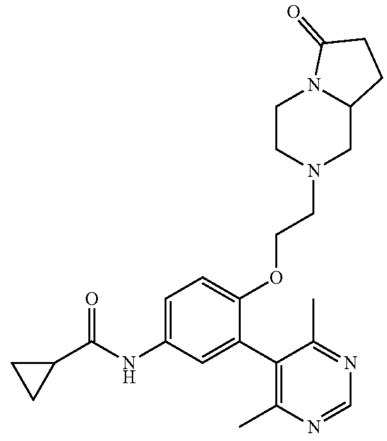

346

-continued

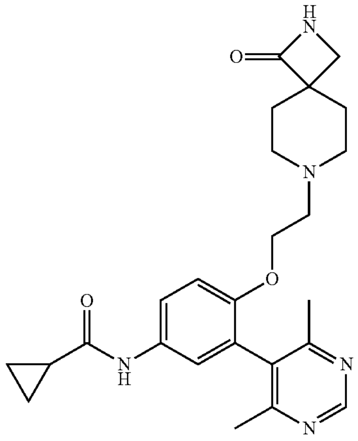

347

Compound 346 was prepared according to the synthesis described for compound substituting hexahydropyrrolo[1,2-a]pyrazin-6 (2H)-one for 1,5,6,7,8,8a-343, hexahydrooxazolo[3,4-a]pyrazin-3-one.

LCMS (ESI): m/z [M+H] calcd for $C_{25}H_{32}NO_3$: 450.2; found: 450.3.

$^1$H NMR (400 MHZ, methanol-d$_4$) δ=8.93 (s, 1H), 7.67 (dd, J=2.6, 8.9 Hz, 1H), 7.43 (d, J=2.6 Hz, 1H), 7.19 (d, J=9.0 Hz, 1H), 4.41 (t, J=4.8 Hz, 2H), 4.06 (dd, J=3.2, 14.4 Hz, 1H), 3.87-3.73 (m, 1H), 3.61-3.45 (m, 2H), 3.44-3.33 (m, 2H), 3.11-2.99 (m, 1H), 2.95-2.81 (m, 1H), 2.69 (br t, J=11.9 Hz, 1H), 2.54-2.35 (m, 2H), 2.35-2.22 (m, 7H), 1.80-1.69 (m, 1H), 1.66-1.48 (m, 1H), 0.98-0.80 (m, 4H).

N-(3-(4,6-dimethylpyrimidin-5-yl)-4-(2-(1-oxo-2,7-diazaspiro[3.5]nonan-7-yl)ethoxy)phenyl)cyclopropanecarboxamide (347)

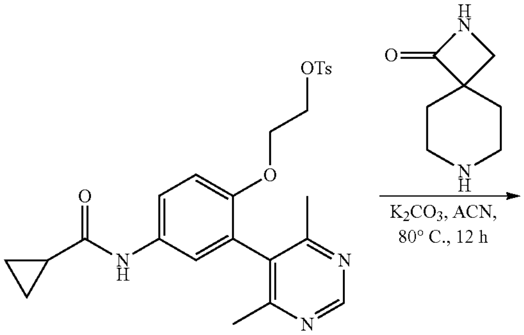

66

Compound 347 was prepared according to the synthesis described for compound 343, substituting 2,7-diazaspiro[3.5]nonan-1-one for 1,5,6,7,8,8a-hexahydrooxazolo[3,4-a]pyrazin-3-one.

LCMS (ESI): m/z [M+H] calcd for $C_{25}H_{32}N_5O_3$: 450.2; found: 450.3.

$^1$H NMR (400 MHZ, methanol-d$_4$) δ=8.92 (s, 1H), 7.66 (dd, J=2.4, 8.9 Hz, 1H), 7.44 (d, J=2.3 Hz, 1H), 7.19 (d, J=9.0 Hz, 1H), 4.38 (br s, 2H), 3.53-3.33 (m, 3H), 3.29-3.06 (m, 4H), 2.92 (br s, 1H), 2.30 (s, 6H), 2.21-1.89 (m, 4H), 1.82-1.67 (m, 1H), 1.00-0.79 (m, 4H).

N-(3-(4,6-dimethylpyrimidin-5-yl)-4-(2-(2-oxo-1,7-diazaspiro[3.5]nonan-7-yl)ethoxy)phenyl)cyclopropanecarboxamide (348)

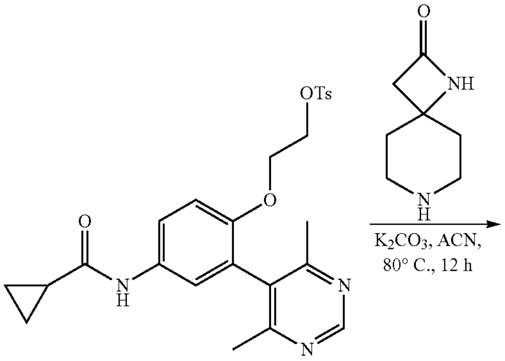

66

-continued

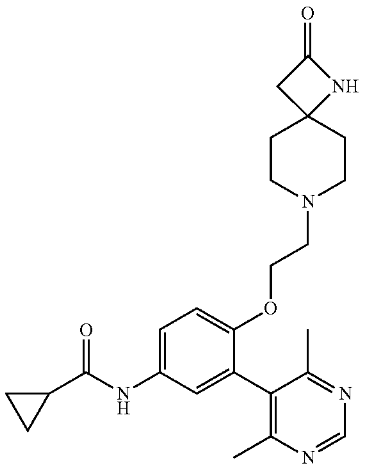

348

Compound 348 was prepared according to the synthesis described for compound 343, substituting 1,7-diazaspiro[3.5]nonan-2-one for 1,5,6,7,8,8a-hexahydrooxazolo[3,4-a]pyrazin-3-one.

LCMS (ESI): m/z [M+H] calcd for $C_{25}H_{32}N_5O_3$: 450.2; found: 450.3.

$^1$H NMR (400 MHZ, methanol-$d_4$) δ=8.92 (s, 1H), 7.67 (dd, J=2.5, 8.9 Hz, 1H), 7.43 (d, J=2.4 Hz, 1H), 7.19 (d, J=9.0 Hz, 1H), 4.38 (br s, 2H), 3.46 (br s, 2H), 3.42-3.34 (m, 2H), 3.05-2.73 (m, 4H), 2.30 (s, 6H), 2.19-1.82 (m, 4H), 1.79-1.69 (m, 1H), 1.00-0.81 (m, 4H).

N-(3-(4,6-dimethylpyrimidin-5-yl)-4-(2-(2-oxo-1-oxa-8-azaspiro[4.5]decan-8-yl)ethoxy)phenyl)cyclopropanecarboxamide (349)

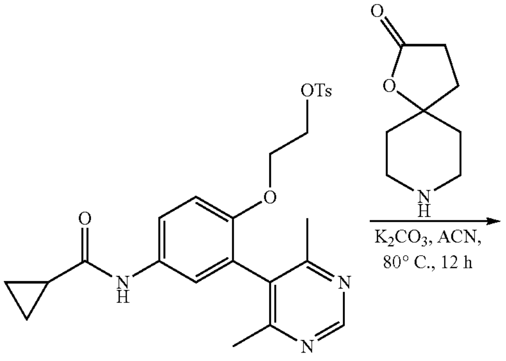

66

-continued

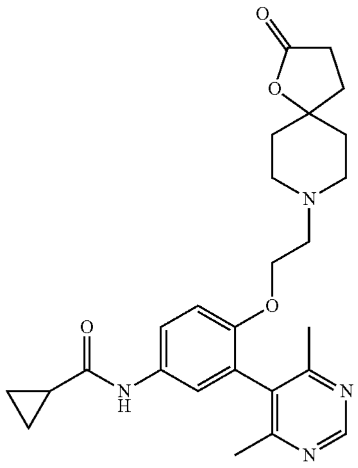

349

Compound 349 was prepared according to the synthesis described for compound substituting 1-oxa-8-azaspiro[4.5]decan-2-one for 1,5,6,7,8,8a-343, hexahydrooxazolo[3,4-a]pyrazin-3-one.

LCMS (ESI): m/z [M+H] calcd for $C_{26}H_{33}N_4O_4$: 465.2; found: 465.3.

$^1$H NMR (400 MHz, methanol-$d_4$) δ=9.33 (s, 1H), 7.69-7.57 (m, 2H), 7.29 (d, J=8.8 Hz, 1H), 4.52-4.41 (m, 2H), 3.51 (br t, J=4.5 Hz, 2H), 3.41 (br d, J=12.3 Hz, 2H), 3.20-3.06 (m, 2H), 2.69 (t, J=8.3 Hz, 2H), 2.55 (s, 6H), 2.27-2.00 (m, 6H), 1.82-1.73 (m, 1H), 0.97-0.81 (m, 4H).

N-(3-(4,6-dimethylpyrimidin-5-yl)-4-(2-(1-oxo-2-oxa-8-azaspiro[4.5]decan-8-yl)ethoxy)phenyl)cyclopropanecarboxamide (350)

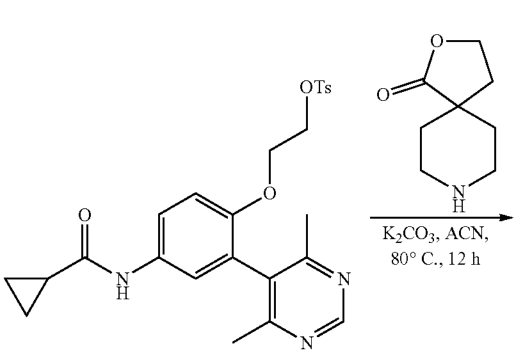

66

-continued

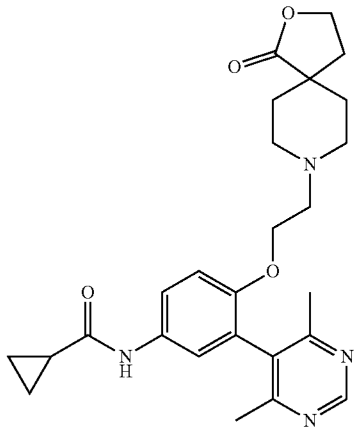

350

Compound 350 was prepared according to the synthesis described for compound 343, substituting 2-oxa-8-azaspiro[4.5]decan-1-one for 1,5,6,7,8,8a-hexahydrooxazolo[3,4-a]pyrazin-3-one.

LCMS (ESI): m/z [M+H] calcd for $C_{26}H_{33}N_4O_4$: 465.2; found: 465.3.

$^1$H NMR (400 MHz, methanol-$d_4$) δ=8.90 (s, 1H), 7.66 (dd, J=2.5, 9.0 Hz, 1H), 7.44 (d, J=2.6 Hz, 1H), 7.19 (d, J=8.9 Hz, 1H), 4.45-4.30 (m, 4H), 3.49 (br s, 2H), 3.36 (br d, J=12.2 Hz, 2H), 3.25-3.09 (m, 1H), 2.94 (br s, 1H), 2.33-2.14 (m, 8H), 2.12-1.89 (m, 2H), 1.88-1.70 (m, 3H), 1.01-0.79 (m, 4H).

N-(3-(4,6-dimethylpyrimidin-5-yl)-4-(2-(4-methoxypiperidin-1-yl)ethoxy)phenyl)cyclopropanecarboxamide (351)

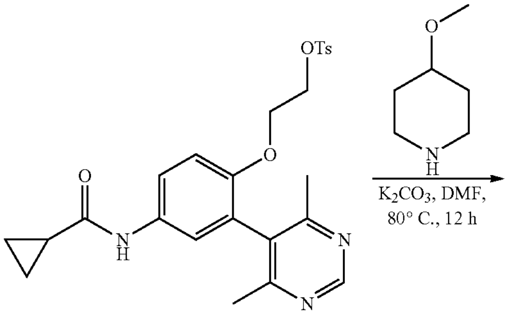

66

-continued

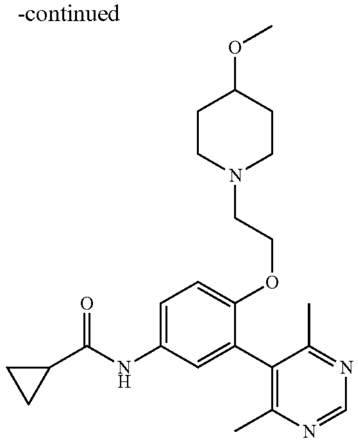

350

Compound 351 was prepared according to the synthesis described for compound 343, substituting 4-methoxypiperidine for 1,5,6,7,8,8a-hexahydrooxazolo[3,4-a]pyrazin-3-one.

LCMS (ESI): m/z [M+H] calcd for $C_{24}H_{34}N_4O_3$: 425.2; found: 425.3.

$^1$H NMR (400 MHz, DMSO-$d_6$) δ=9.94 (s, 1H), 8.87 (s, 1H), 7.65 (dd, J=2.7, 8.9 Hz, 1H), 7.40 (d, J=2.7 Hz, 1H), 7.15 (d, J=8.9 Hz, 1H), 4.29 (t, J=5.1 Hz, 2H), 3.44-3.31 (m, 3H), 3.25 (s, 3H), 3.13-2.83 (m, 4H), 2.19 (s, 6H), 1.98-1.51 (m, 5H), 0.87-0.73 (m, 4H).

(S)—N-(3-(4,6-dimethylpyrimidin-5-yl)-4-(2-(3-methoxypyrrolidin-1-yl)ethoxy)phenyl)cyclopropanecarboxamide (352)

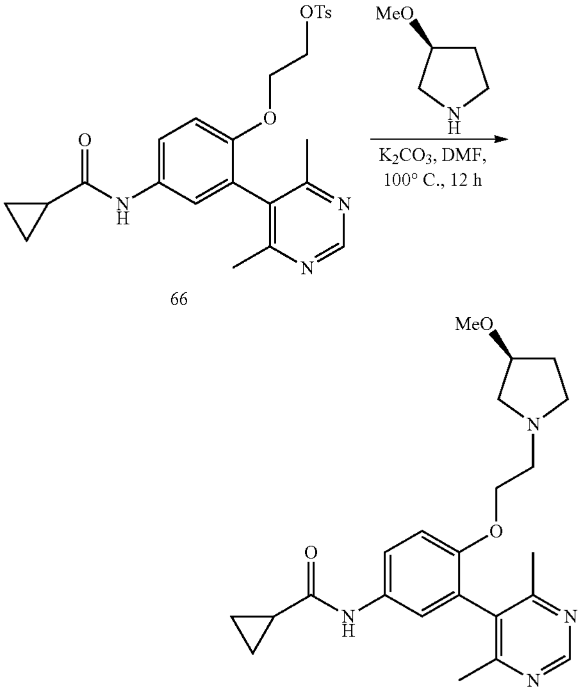

66

352

Compound 352 was prepared according to the synthesis described for compound 343, substituting(S)-3-methoxypyrrolidine for 1,5,6,7,8,8a-hexahydrooxazolo[3,4-a]pyrazin-3-one.

LCMS (ESI): m/z [M+H] calcd for $C_{23}H_{32}N_4O_3$: 411.2; found: 411.2.

$^1$H NMR (400 MHZ, methanol-$d_4$) δ=8.91 (s, 1H), 7.68 (dd, J=2.6, 8.9 Hz, 1H), 7.44 (d, J=2.5 Hz, 1H), 7.19 (d, J=9.0 Hz, 1H), 4.34 (t, J=4.9 Hz, 2H), 4.04 (br s, 1H), 3.62-3.37 (m, 4H), 3.30 (s, 3H), 2.92 (br s, 2H), 2.32 (s, 6H), 2.27-1.97 (m, 2H), 1.76 (tt, J=4.6, 7.8 Hz, 1H), 1.00-0.84 (m, 4H).

(R)—N-(3-(4,6-dimethylpyrimidin-5-yl)-4-(2-(3-methoxypyrrolidin-1-yl)ethoxy)phenyl)cyclopropanecarboxamide (353)

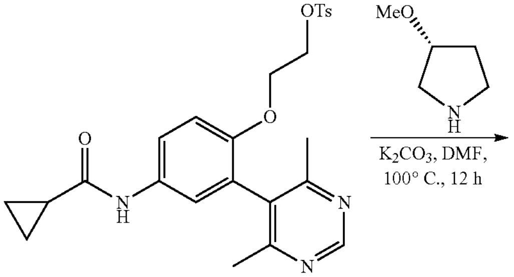

66

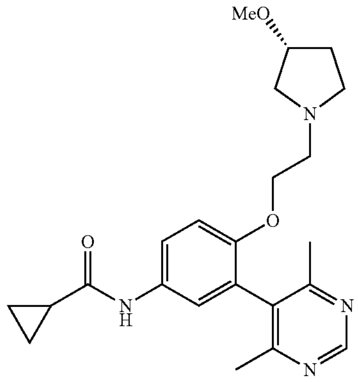

353

Compound 353 was prepared according to the synthesis described for compound 343, substituting (R)-3-methoxypyrrolidine for 1,5,6,7,8,8a-hexahydrooxazolo[3,4-a] pyrazin-3-one.

LCMS (ESI): m/z [M+H] calcd for $C_{23}H_{32}N_4O_3$: 411.2; found: 411.2.

$^1$H NMR (400 MHZ, methanol-$d_4$) δ=8.90 (s, 1H), 7.67 (dd, J=2.6, 8.9 Hz, 1H), 7.42 (d, J=2.5 Hz, 1H), 7.18 (d, J=9.0 Hz, 1H), 4.32 (t, J=4.8 Hz, 2H), 4.02 (br s, 1H), 3.60-3.36 (m, 4H), 3.28 (br s, 3H), 2.90 (br s, 2H), 2.30 (s, 6H), 2.25-1.89 (m, 2H), 1.80-1.68 (m, 1H), 0.99-0.81 (m, 4H).

N-[3-(4,6-dimethylpyrimidin-5-yl)-4-[2-[2-methoxyethyl(methyl)amino]ethoxy]phenyl]cyclopropanecarboxamide (354)

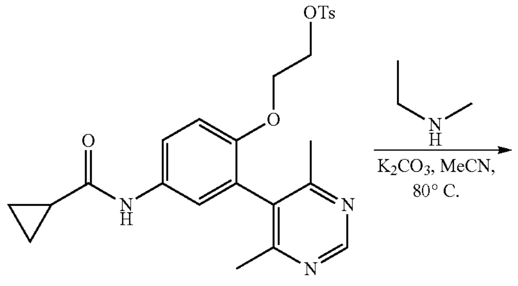

66

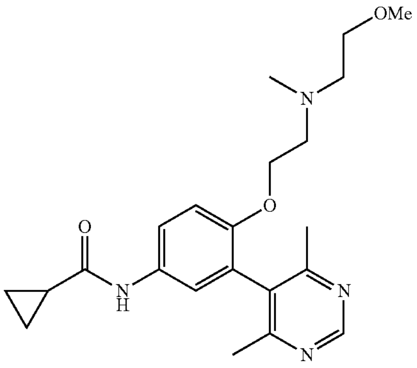

354

A mixture of 2-[4-(cyclopropanecarbonylamino)-2-(4,6-dimethylpyrimidin-5-yl)phenoxy]ethyl 4-methylbenzenesulfonate ((66), 100 mg, 207.66 μmol, 1 eq.), 2-methoxy-N-methyl-ethanamine (37.02 mg, 415.31 μmol, 44.60 μL, 2 eq.) and $K_2CO_3$ (86.10 mg, 622.97 μmol, 3 eq.) in MeCN (3 mL) was stirred at 80° C. for 12 hrs. (monitored by LCMS). Then the reaction mixture was concentrated to obtain the crude product, which was purified by prep-HPLC (TFA conditions) to obtain N-[3-(4,6-dimethylpyrimidin-5-yl)-4-[2-[2-methoxyethyl(methyl)amino]ethoxy]phenyl]cyclopropanecarboxamide (13.8 mg, 26.68 μmol, 12.85% yield, 99.1% purity, TFA) as a white solid.

LCMS (ESI): m/z [M+H] calcd for $C_{22}H_{31}N_4O_3$: 399.2; found: 399.2.

$^1$H NMR (400 MHZ, methanol-$d_4$) δ=8.90 (s, 1H), 7.66 (dd, J=2.6, 8.9 Hz, 1H), 7.42 (d, J=2.7 Hz, 1H), 7.19 (d, J=8.9 Hz, 1H), 4.38 (t, J=4.8 Hz, 2H), 3.57-3.42 (m, 4H), 3.35 (s, 3H), 3.16 (br d, J=10.5 Hz, 2H), 2.74 (s, 3H), 2.34-2.24 s, 6H), 1.81-1.69 (m, 1H), 0.98-0.91 (m, 2H), 0.90-0.82 (m, 2H).

N-(3-(4,6-dimethylpyrimidin-5-yl)-4-(2-(ethyl (2-methoxyethyl)amino)ethoxy)phenyl)cyclopropanecarboxamide (355)

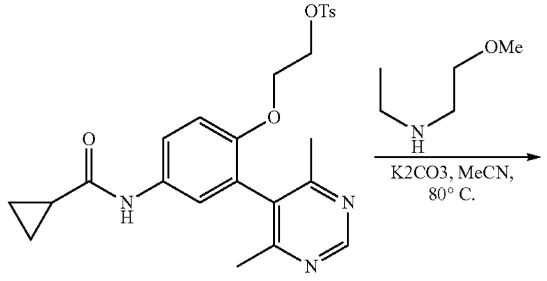

66

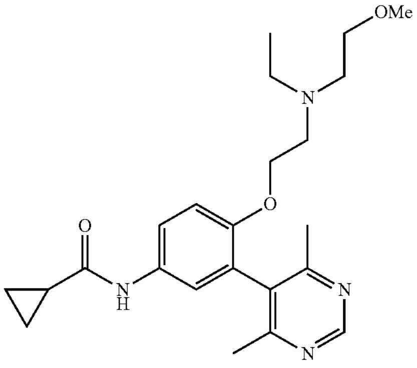

355

Compound 355 was prepared according to the synthesis described for compound 354, substituting N-ethyl-2-methoxyethan-1-amine for 2-methoxy-N-methyl-ethanamine.

LCMS (ESI): m/z [M+H] calcd for $C_{23}H_{33}N_4O_3$: 413.2; found: 413.2.

$^1$H NMR (400 MHZ, methanol-d$_4$) δ=8.90 (s, 1H), 7.66 (dd, J=2.6, 9.0 Hz, 1H), 7.42 (d, J=2.6 Hz, 1H), 7.18 (d, J=9.0 Hz, 1H), 4.38 (t, J=4.7 Hz, 2H), 3.60-3.44 (m, 4H), 3.35 (s, 3H), 3.27-3.01 (m, 4H), 2.29 (s, 6H), 1.81-1.69 (m, 1H), 1.07 (t, J=7.2 Hz, 3H), 0.98-0.81 (m, 4H).

N-(3-(4,6-dimethylpyrimidin-5-yl)-4-(2-((2-methoxyethyl)(propyl)amino)ethoxy)phenyl)cyclopropanecarboxamide (356)

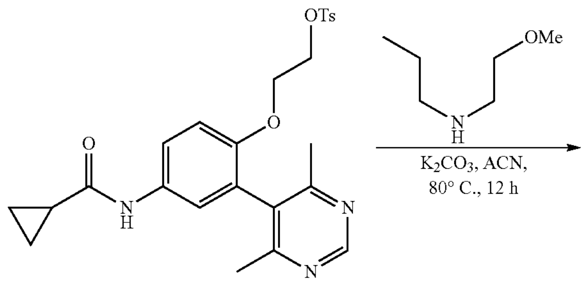

66

-continued

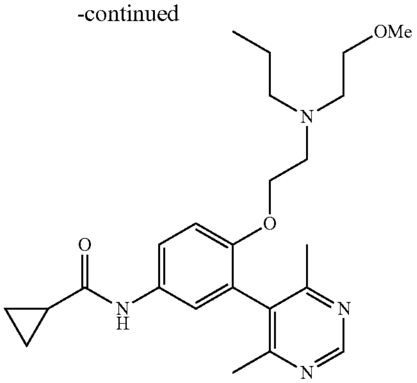

356

Compound 356 was prepared according to the synthesis described for compound 354, substituting N-(2-methoxyethyl)propan-1-amine for 2-methoxy-N-methyl-ethanamine.

LCMS (ESI): m/z [M+H] calcd for $C_{24}H_{35}N_4O_3$: 427.2; found: 427.3.

$^1$H NMR (400 MHZ, methanol-d$_4$) δ=8.91 (s, 1H), 7.67 (dd, J=2.7, 8.9 Hz, 1H), 7.40 (d, J=2.6 Hz, 1H), 7.18 (d, J=9.0 Hz, 1H), 4.38 (br d, J=3.1 Hz, 2H), 3.54 (br d, J=4.2 Hz, 2H), 3.47 (br dd, J=3.4, 4.9 Hz, 2H), 3.35 (s, 3H), 3.21 (br d, J=19.2 Hz, 2H), 3.08-2.90 (m, 2H), 2.30 (s, 6H), 1.79-1.69 (m, 1H), 1.62-1.49 (m, 2H), 0.98-0.91 (m, 2H), 0.90-0.82 (m, 5H).

N-(3-(4,6-dimethylpyrimidin-5-yl)-4-(2-((2-hydroxyethyl)(methyl)amino)ethoxy)phenyl)cyclopropanecarboxamide (357)

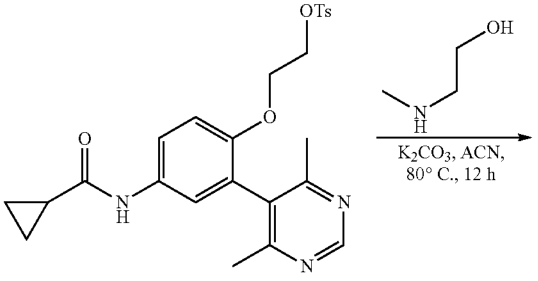

66

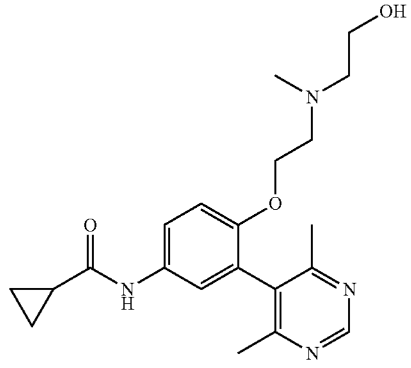

357

Compound 357 was prepared according to the synthesis described for compound 354, substituting 2-(methylamino) ethan-1-ol for 2-methoxy-N-methyl-ethanamine.

LCMS (ESI): m/z [M+H] calcd for $C_{21}H_{29}N_4O_3$: 385.2; found: 385.2.

$^1$H NMR (400 MHZ, methanol-d$_4$) δ=8.88 (s, 1H), 7.67 (dd, J=2.6, 8.9 Hz, 1H), 7.41 (d, J=2.6 Hz, 1H), 7.19 (d, J=9.0 Hz, 1H), 4.39 (t, J=4.6 Hz, 2H), 3.74-3.39 (m, 4H), 3.21-2.95 (m, 2H), 2.74 (s, 3H), 2.29 (s, 6H), 1.80-1.70 (m, 1H), 1.01-0.81 (m, 4H).

N-(3-(4,6-dimethylpyrimidin-5-yl)-4-(2-(ethyl(2-hydroxyethyl)amino)ethoxy)phenyl)cyclopropanecarboxamide (358)

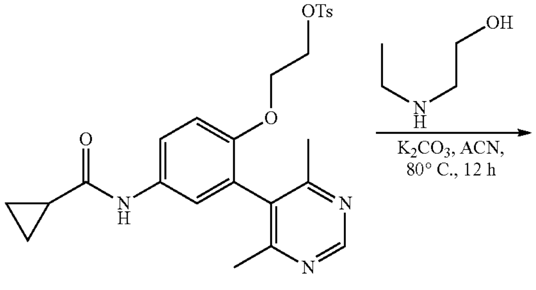

66

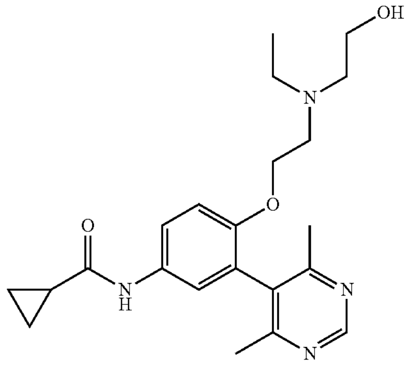

358

Compound 358 was prepared according to the synthesis described for compound 354, substituting 2-(ethylamino) ethan-1-ol for 2-methoxy-N-methyl-ethanamine.

LCMS (ESI): m/z [M+H] calcd for $C_{22}H_{31}N_4O_3$: 399.2; found: 399.2.

$^1$H NMR (400 MHZ, methanol-d$_4$) δ=8.91 (s, 1H), 7.65 (dd, J=2.6, 8.9 Hz, 1H), 7.43 (d, J=2.6 Hz, 1H), 7.18 (d, J=8.9 Hz, 1H), 4.39 (t, J=4.8 Hz, 2H), 3.66 (br s, 2H), 3.55 (br s, 2H), 3.13 (br s, 4H), 2.30 (s, 6H), 1.80-1.69 (m, 1H), 1.07 (t, J=7.3 Hz, 3H), 0.99-0.80 (m, 4H).

N-(3-(4,6-dimethylpyrimidin-5-yl)-4-(2-((2-hydroxyethyl)(propyl)amino)ethoxy)phenyl)cyclopropanecarboxamide (359)

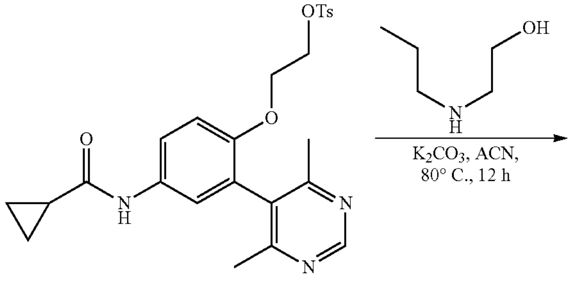

66

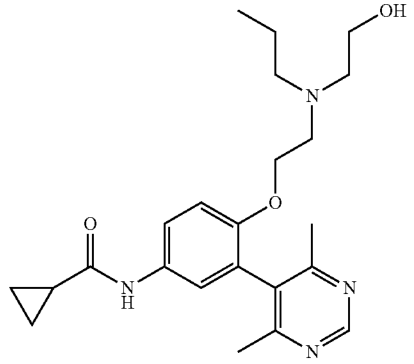

359

Compound 359 was prepared according to the synthesis described for compound 354, substituting 2-(propylamino) ethan-1-ol for 2-methoxy-N-methyl-ethanamine.

LCMS (ESI): m/z [M+H] calcd for $C_{23}H_{33}N_4O_3$: 413.2; found: 413.2.

$^1$H NMR (400 MHZ, methanol-d$_4$) δ=8.89 (s, 1H), 7.66 (dd, J=2.6, 9.0 Hz, 1H), 7.40 (d, J=2.6 Hz, 1H), 7.19 (d, J=8.9 Hz, 1H), 4.40 (br s, 2H), 3.65 (br d, J=3.3 Hz, 2H), 3.56 (br d, J=4.6 Hz, 2H), 3.23-2.90 (m, 4H), 2.29 (s, 6H), 1.80-1.69 (m, 1H), 1.61-1.46 (m, 2H), 0.97-0.91 (m, 2H), 0.91-0.82 (m, 5H).

N-(3-(4,6-dimethylpyrimidin-5-yl)-4-(2-((2-fluoroethyl)(methyl)amino)ethoxy)phenyl)cyclopropanecarboxamide (360)

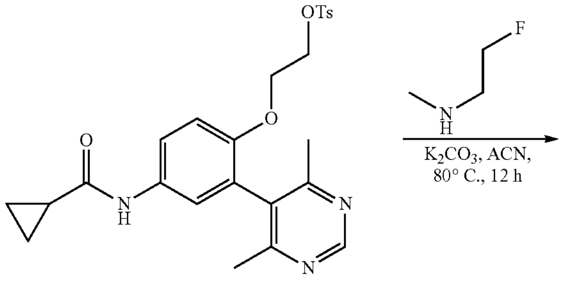

66

-continued

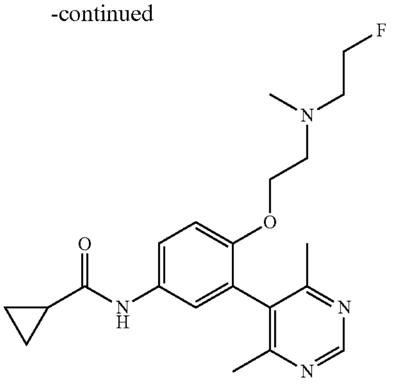

360

Compound 360 was prepared according to the synthesis described for compound 354, substituting 2-fluoro-N-methylethan-1-amine for 2-methoxy-N-methyl-ethanamine.

LCMS (ESI): m/z [M+H] calcd for $C_{21}H_{28}FN_4O_2$: 387.2; found: 387.2.

$^1$H NMR (400 MHZ, methanol-$d_4$) δ=8.90 (s, 1H), 7.67 (dd, J=2.6, 8.9 Hz, 1H), 7.42 (d, J=2.6 Hz, 1H), 7.19 (d, J=8.9 Hz, 1H), 4.73-4.67 (m, 1H), 4.61-4.55 (m, 1H), 4.44-4.34 (m, 2H), 3.56 (br s, 2H), 3.46-3.33 (m, 2H), 2.80 (s, 3H), missing proton 2.33-2.26 (m, 6H), 1.79-1.70 (m, 1H), 0.97-0.81 (m, 4H).

N-(3-(4,6-dimethylpyrimidin-5-yl)-4-(2-((2-methoxyethyl)amino)ethoxy)phenyl)cyclopropanecarboxamide (361)

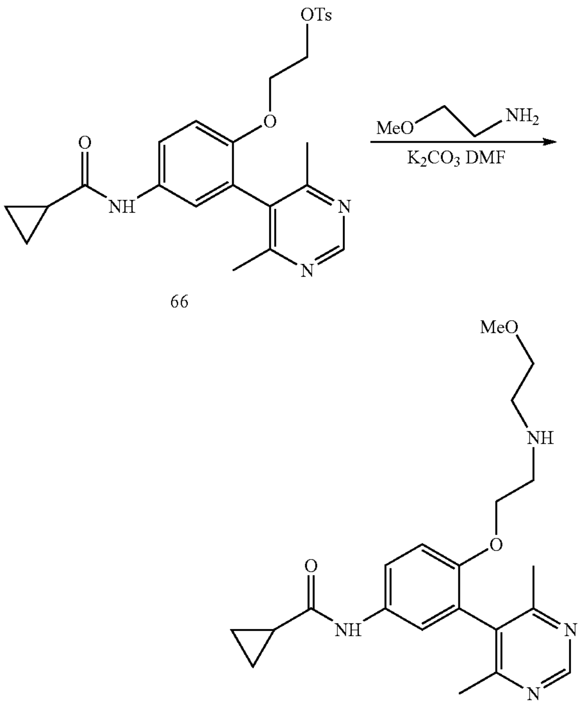

66

361

Compound 361 was prepared according to the synthesis described for compound 354, substituting 2-methoxyethan-1-amine for 2-methoxy-N-methyl-ethanamine.

LCMS (ESI): m/z [M+H] calcd for $C_{21}H_{29}N_4O_3$: 385.2; found: 385.3.

$^1$H NMR (400 MHZ, methanol-$d_4$) δ=9.25 (s, 1H), 7.64 (dd, J=2.6, 8.9 Hz, 1H), 7.55 (d, J=2.6 Hz, 1H), 7.25 (d, J=9.0 Hz, 1H), 4.33 (t, J=5.1 Hz, 2H), 3.61-3.53 (m, 2H), 3.42-3.34 (m, 5H), 3.10 (t, J=5.0 Hz, 2H), 2.48 (s, 6H), 1.83-1.72 (m, 1H), 0.98-0.82 (m, 4H).

N-[3-(4,6-dimethylpyrimidin-5-yl)-4-[2-[ethyl(2-fluoroethyl)amino]ethoxy]phenyl]cyclopropanecarboxamide (362)

Preparation of N-[3-(4,6-dimethylpyrimidin-5-yl)-4-[2-(2-fluoroethylamino)ethoxy]phenyl]cyclopropanecarboxamide (67)

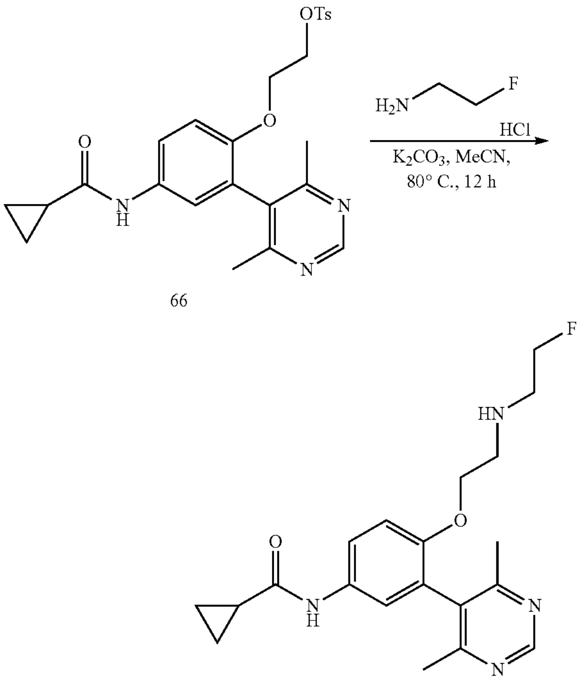

66

67

A mixture of 2-[4-(cyclopropanecarbonylamino)-2-(4,6-dimethylpyrimidin-5-yl)phenoxy]ethyl 4-methylbenzenesulfonate ((66), 500 mg, 1.04 mmol, 1 eq.), 2-fluoroethanamine (206.69 mg, 2.08 mmol, 3.34 μL, 2 eq., HCl) and $K_2CO_3$ (430.50 mg, 3.11 mmol, 3 eq.) in ACN (10 mL) was stirred at 80° C. for 12 hrs. TLC indicated partial 2-[4-(cyclopropanecarbonylamino)-2-(4,6-dimethylpyrimidin-5-yl)phenoxy]ethyl 4-methylbenzenesulfonate remaining and a new spot was found. Then the reaction mixture was concentrated to obtain the crude product, which was purified by prep-TLC to obtain N-[3-(4,6-dimethylpyrimidin-5-yl)-4-[2-(2-fluoroethylamino)ethoxy]phenyl]cyclopropanecarboxamide ((67), 110 mg, 295.35 μmol, 28.45% yield) as a yellow oil.

LCMS (ESI): Rt: 0.705 min, m/z [M+H] calcd for $C_{20}H_{26}FN_4O_2$: 373.2; found: 373.3.

Preparation of N-[3-(4,6-dimethylpyrimidin-5-yl)-4-[2-[ethyl (2-fluoroethyl)amino]ethoxy]phenyl]cyclopropanecarboxamide (362)

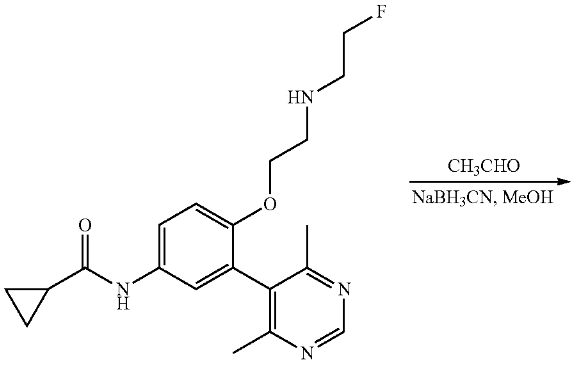

67

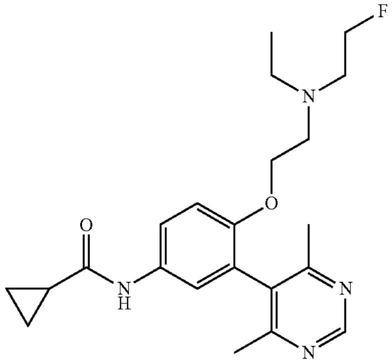

362

A mixture of N-[3-(4,6-dimethylpyrimidin-5-yl)-4-[2-(2-fluoroethylamino)ethoxy]phenyl]cyclopropanecarboxamide ((67), 55 mg, 147.68 μmol, 1 eq.), acetaldehyde (13.01 mg, 295.35 μmol, 16.57 μL, 2 eq.) and HOAc (26.60 mg, 443.03 μmol, 25.34 μL, 3 eq.) in MeOH (2 mL) was stirred at 20° C. for 1 hr. Then $NaBH_3CN$ (13.92 mg, 221.51 μmol, 1.5 eq.) was added to the reaction mixture, and the reaction mixture was stirred at 20° C. for 1 hr. (monitored by LCMS). The reaction mixture was concentrated to obtain a residue, which was purified by prep-HPLC (TFA conditions) to obtain N-[3-(4,6-dimethylpyrimidin-5-yl)-4-[2-[ethyl (2-fluoroethyl)amino]ethoxy]phenyl]cyclopropanecarboxamide (26.5 mg, 51.51 μmol, 34.88% yield, TFA) as a white solid.

LCMS (ESI): m/z [M+H] calcd for $C_{22}H_{30}FN_4O_2$: 401.3; found: 401.3.

$^1H$ NMR (400 MHZ, methanol-$d_4$) δ=8.91 (s, 1H), 7.66 (br d, J=8.8 Hz, 1H), 7.43 (br s, 1H), 7.18 (d, J=8.9 Hz, 1H), 4.69 (br s, 1H), 4.57 (br s, 1H), 4.40 (br s, 2H), 3.64-3.54 (m, 2H), 3.49-3.42 (m, 1H), 3.42-3.35 (m, 1H), 3.16 (q, J=7.1 Hz, 2H), 2.30 (s, 6H), 1.79-1.71 (m, 1H), 1.09 (t, J=7.2 Hz, 3H), 0.97-0.83 (m, 4H).

N-[3-(4,6-dimethylpyrimidin-5-yl)-4-[2-[2-fluoroethyl(propyl)amino]ethoxy]phenyl]cyclopropanecarboxamide (363)

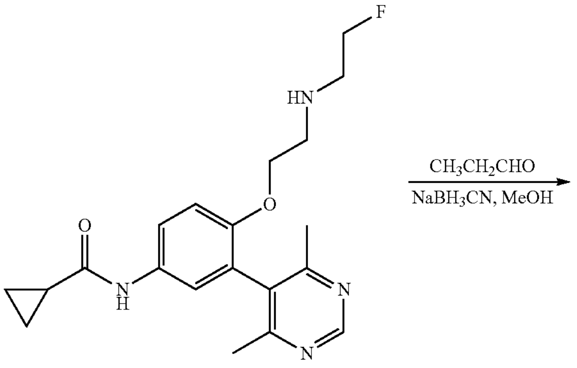

67

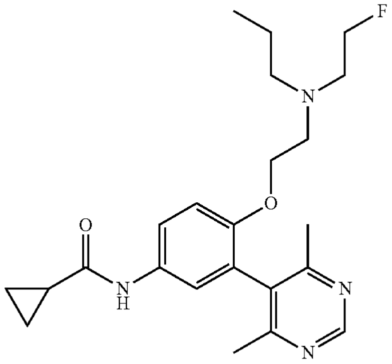

363

A mixture of N-[3-(4,6-dimethylpyrimidin-5-yl)-4-[2-(2-fluoroethylamino)ethoxy]phenyl]cyclopropanecarboxamide ((67), 55 mg, 147.68 μmol, 1 eq.), propanal (17.15 mg, 295.35 μmol, 21.50 μL, 2 eq.) and HOAc (26.60 mg, 443.03 μmol, 25.34 μL, 3 eq.) in MeOH (2 mL) was stirred at 20° C. for 1 hr. Then $NaBH_3CN$ (13.92 mg, 221.51 μmol, 1.5 eq.) was added to the reaction mixture, and the reaction mixture was stirred at 20° C. for 1 hr. (monitored by LCMS). Then the reaction mixture was concentrated to give a residue, which was purified by Prep-HPLC (TFA conditions) to obtain N-[3-(4,6-dimethylpyrimidin-5-yl)-4-[2-[2-fluoroethyl(propyl)amino]ethoxy]phenyl]cyclopropanecarboxamide (29.8 mg, 56.38 μmol, 38.18% yield, TFA) as a white solid.

LCMS (ESI): m/z [M+H] calcd for $C_{23}H_{32}FN_4O_2$: 415.2; found: 415.3.

$^1H$ NMR (400 MHZ, methanol-$d_4$) δ=8.91 (s, 1H), 7.66 (br d, J=8.9 Hz, 1H), 7.42 (br s, 1H), 7.19 (d, J=8.9 Hz, 1H), 4.72-4.65 (m, 1H), 4.57 (br s, 1H), 4.40 (br s, 2H), 3.66-3.54 (m, 2H), 3.46 (br s, 1H), 3.43-3.36 (m, 1H), 3.10-3.01 (m, 2H), 2.30 (s, 6H), 1.80-1.70 (m, 1H), 1.62-1.52 (m, 2H), 0.97-0.82 (m, 7H).

N-(3-(4,6-dimethylpyrimidin-5-yl)-4-(2-(methyl(2-(methylsulfonyl)ethyl)amino)ethoxy)phenyl)cyclopropanecarboxamide (364)

Preparation of N-(3-(4,6-dimethylpyrimidin-5-yl)-4-(2-((2-(methylsulfonyl)ethyl)amino)ethoxy)phenyl) cyclopropanecarboxamide (68)

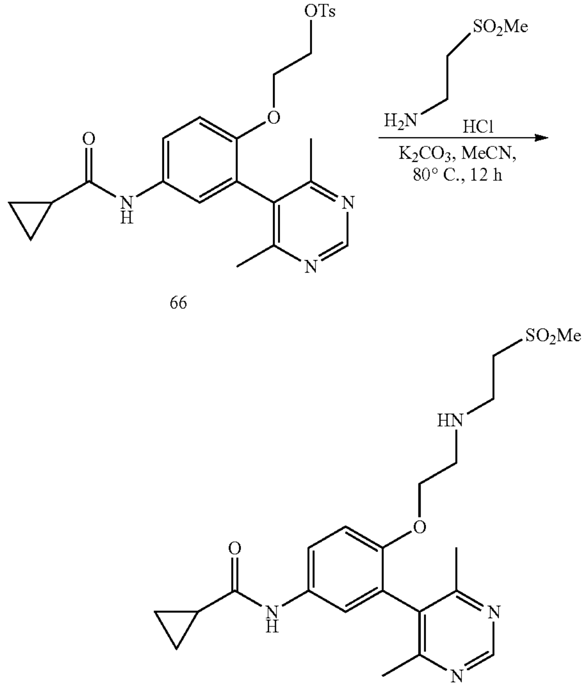

66

68

Compound (68) was prepared according to the synthesis described for compound (67), substituting 2-(methylsulfonyl)ethan-1-amine hydrochloride for 2-fluoroethanamine.

Preparation of N-(3-(4,6-dimethylpyrimidin-5-yl)-4-(2-(methyl (2-(methylsulfonyl)ethyl)amino)ethoxy) phenyl)cyclopropanecarboxamide (364)

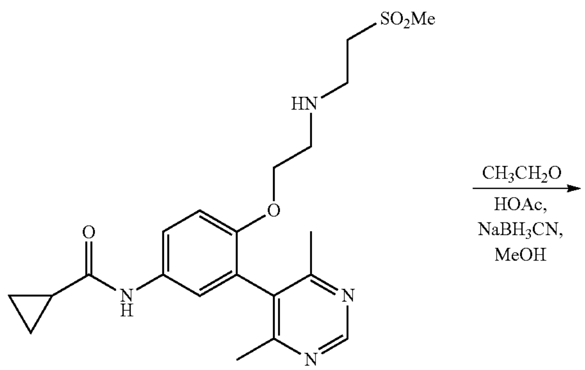

68

-continued

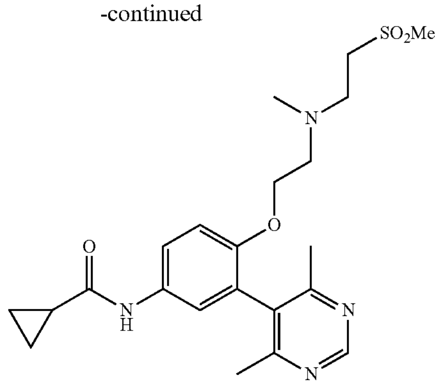

364

Compound 364 was prepared according to the synthesis described for compound 363, substituting acetaldehyde for propanal.

LCMS (ESI): m/z [M+H] calcd for $C_{22}H_{30}N_4O_4S$: 447.20; found: 447.2.

$^1H$ NMR (400 MHZ, methanol-$d_4$) δ 0.80-0.98 (m, 4H), 1.67-1.80 (m, 1H), 2.16 (s, 3H), 2.27 (s, 6H), 2.64-2.82 (m, 4H), 2.91 (s, 3H), 3.03-3.18 (m, 2H), 4.09 (t, J=5.13 Hz, 2H), 7.13 (d, J=8.88 Hz, 1H), 7.37 (d, J=2.38 Hz, 1H), 7.59 (dd, J=8.88, 2.50 Hz, 1H), 8.84 (s, 1H).

N-[3-(4,6-dimethylpyrimidin-5-yl)-4-[2-[methyl(2-methylsulfinylethyl)amino]ethoxy]phenyl]cyclopropanecarboxamide (365)

Preparation of tert-butyl N-methyl-N-(2-methylsulfanylethyl)carbamate (69)

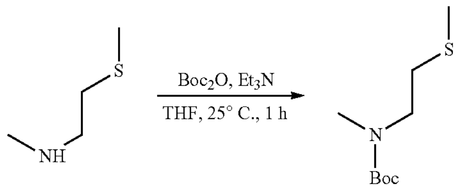

69

To a solution of N-methyl-2-methylsulfanyl-ethanamine (100 mg, 705.90 μmol, 1 eq., HCl) and $Et_3N$ (142.86 mg, 1.41 mmol, 196.51 μL, 2 eq.) in THF (2 mL) was added $Boc_2O$ (184.87 mg, 847.08 μmol, 194.60 μL, 1.2 eq.). The reaction mixture was stirred at 25° C. for 2 hrs. TLC (petroleum ether:ethyl acetate=5:1) showed one new spot. The residue was poured into water (10 mL). The aqueous phase was extracted with ethyl acetate (20 mL×3). The combined organic phase was washed with brine (20 mL), dried with anhydrous $Na_2SO_4$, filtered and concentrated in vacuum. The residue was purified by flash silica gel chromatography (4 g SepaFlash® Silica Flash Column, eluent of 0~12% ethyl acetate/petroleum ether gradient). Tert-butyl N-methyl-N-(2-methylsulfanylethyl)carbamate ((69), 125 mg, 608.81 μmol, 86.25% yield) was obtained as a colorless oil.

$^1H$ NMR (400 MHz, chloroform-d) δ=3.40 (br s, 2H), 2.89 (s, 3H), 2.62 (br s, 2H), 2.14 (s, 3H), 1.49-1.42 (m, 9H).

Preparation of tert-butyl N-methyl-N-(2-methylsulfinylethyl)carbamate (70)

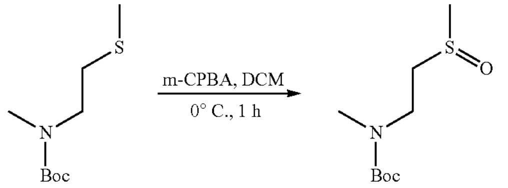

69 70

To a solution of tert-butyl N-methyl-N-(2-methylsulfanylethyl)carbamate ((69), 95 mg, 462.70 μmol, 1 eq.) in DCM (1 mL) was added m-CPBA (89.83 mg, 416.43 μmol, 80% purity, 0.9 eq.) in DCM (1 mL) at 0° C. The reaction mixture was stirred at 0° C. for 0.5 hrs. TLC (petroleum ether:ethyl acetate=2:1) showed three new spots. The residue was poured into saturated $NaHCO_3$ aq. (10 mL). The aqueous phase was extracted with DCM (20 mL×3). The combined organic phase was washed with brine (20 mL), dried with anhydrous $Na_2SO_4$, filtered and concentrated in vacuum. The residue was purified by prep-TLC (petroleum ether: ethyl acetate=2:1). Tert-butyl N-methyl-N-(2-methylsulfinylethyl)carbamate ((70), 60 mg, 271.11 μmol, 58.59% yield) was obtained as a colorless oil.

$^1$H NMR (400 MHZ, chloroform-d) δ=3.83-3.45 (m, 2H), 3.13-2.80 (m, 5H), 2.63 (s, 3H), 1.46 (s, 9H).

Preparation of N-methyl-2-methylsulfinyl-ethanamine (71)

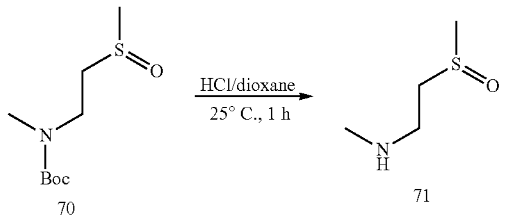

70 71

To a solution of tert-butyl N-methyl-N-(2-methylsulfinylethyl)carbamate ((70), 60 mg, 271.11 μmol, 1 eq.) in DCM (2 mL) was added HCl/dioxane (4 M, 1 mL). The reaction mixture was stirred at 25° C. for 0.5 hrs. LCMS showed desired mass was detected. The reaction mixture was concentrated in vacuum. N-methyl-2-methylsulfinyl-ethanamine ((71), 40 mg, 253.71 μmol, 93.58% yield, HCl) was obtained as a yellow oil.

Preparation of N-[3-(4,6-dimethylpyrimidin-5-yl)-4-[2-[methyl (2-methylsulfinylethyl)amino]ethoxy] phenyl]cyclopropanecarboxamide (365)

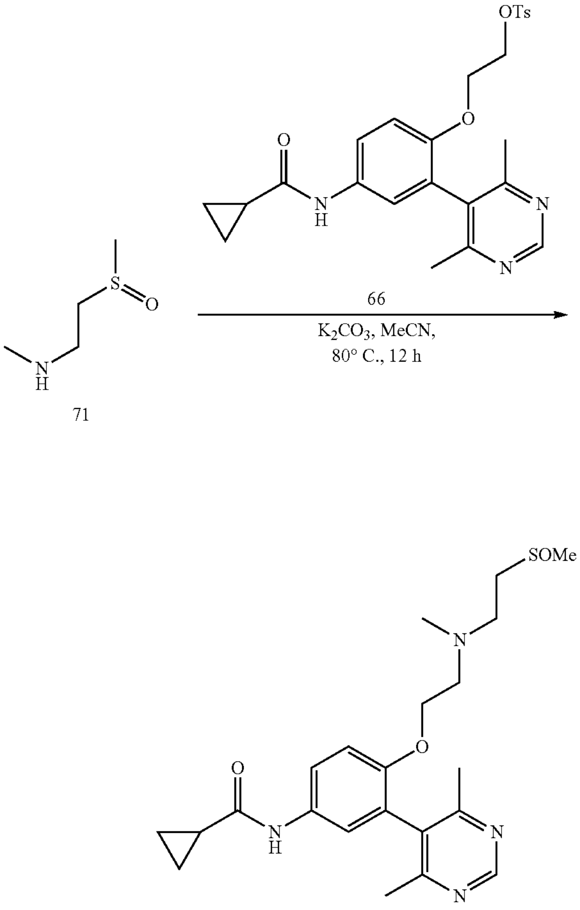

71 66 365

To a solution of 2-[4-(cyclopropanecarbonylamino)-2-(4,6-dimethylpyrimidin-5-yl)phenoxy]ethyl 4-methylbenzenesulfonate ((66), 100 mg, 207.66 μmol, 1 eq.) and N-methyl-2-methylsulfinyl-ethanamine ((71), 39.29 mg, 249.19 μmol, 1.2 eq., HCl) in ACN (2 mL) was added $K_2CO_3$ (86.10 mg, 622.97 μmol, 3 eq.). The reaction mixture was stirred at 80° C. for 16 hrs. LCMS detected one peak (19%) with desired mass. The reaction mixture was concentrated in vacuum, then was purified by prep-HPLC (column: Phenomenex Synergi C18 150*25 mm*10 μm; mobile phase: [water (0.1% TFA)-ACN]; B %: 2%-32%, 10 min) followed by lyophilization. N-[3-(4,6-dimethylpyrimidin-5-yl)-4-[2-[methyl (2-methylsulfinylethyl)amino]ethoxy]phenyl]cyclopropanecarboxamide (17.28 mg, 38.93 μmol, 18.75% yield, 97% purity) was obtained as a yellow solid.

LCMS (ESI): m/z [M+H] calcd for $C_{22}H_{31}N_4O_3S$: 431.2; found: 431.2.

$^1$H NMR (400 MHZ, methanol-d$_4$) δ=8.91 (s, 1H), 7.66 (dd, J=2.6, 9.0 Hz, 1H), 7.42 (d, J=2.6 Hz, 1H), 7.21 (d, J=9.0 Hz, 1H), 4.40 (t, J=4.8 Hz, 2H), 3.71-3.50 (m, 4H), 3.23 (td, J=7.0, 14.0 Hz, 1H), 3.05 (td, J=7.0, 14.0 Hz, 1H), 2.79 (s, 3H), 2.74-2.63 (m, 3H), 2.35 (s, 6H), 1.82-1.67 (m, 1H), 1.00-0.80 (m, 4H).

N-[3-(4,6-dimethylpyrimidin-5-yl)-4-[2-[ethyl (methyl)amino]ethoxy]phenyl]cyclopropanecarboxamide (366)

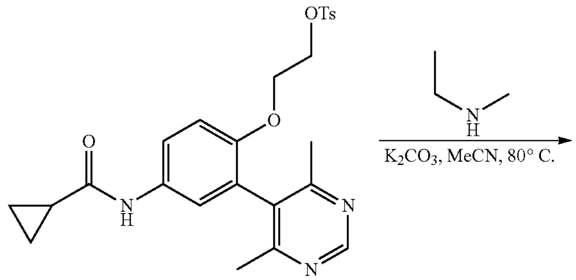

66

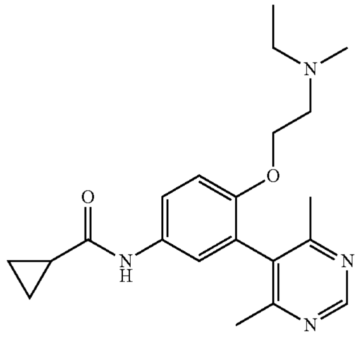

366

A mixture of 2-[4-(cyclopropanecarbonylamino)-2-(4,6-dimethylpyrimidin-5-yl)phenoxy]ethyl 4-methylbenzenesulfonate ((66), 90 mg, 186.89 μmol, 1 eq.), N-methylethanamine (33.14 mg, 560.67 μmol, 48.17 μL, 3 eq.) and $K_2CO_3$ (77.49 mg, 560.67 μmol, 3 eq.) in MeCN (3 mL) was stirred at 80° C. for 12 hrs. (monitored by LCMS). Then the reaction mixture was concentrated to remove solvent to give a residue, which was purified by Prep-HPLC (TFA conditions) to obtain N-[3-(4,6-dimethylpyrimidin-5-yl)-4-[2-[ethyl(methyl)amino]ethoxy]phenyl]cyclopropanecarboxamide (11.4 mg, 23.32 μmol, 12.48% yield, 98.7% purity, TFA) as a white solid.

LCMS (ESI): m/z [M+H] calcd for $C_{21}H_{29}N_4O_2$: 369.2; found: 369.2.

$^1$H NMR (400 MHZ, methanol-$d_4$) δ=8.88 (s, 1H), 7.67 (dd, J=2.6, 8.9 Hz, 1H), 7.41 (d, J=2.6 Hz, 1H), 7.19 (d, J=9.0 Hz, 1H), 4.35 (br d, J=2.9 Hz, 2H), 3.57-3.36 (m, 2H), 3.15-2.93 (m, 2H), 2.70 (s, 3H), 2.29 (s, 6H), 1.82-1.68 (m, 1H), 1.10 (t, J=7.3 Hz, 3H), 1.00-0.82 (m, 4H).

N-(3-(4,6-dimethylpyrimidin-5-yl)-4-(2-(methyl (propyl)amino)ethoxy)phenyl)cyclopropanecarboxamide (367)

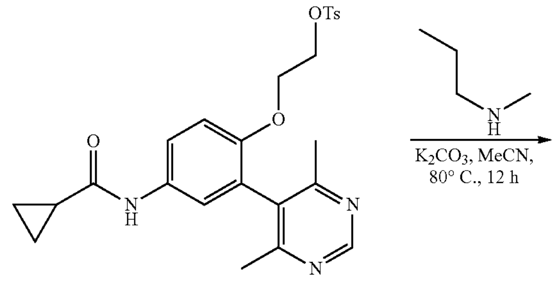

66

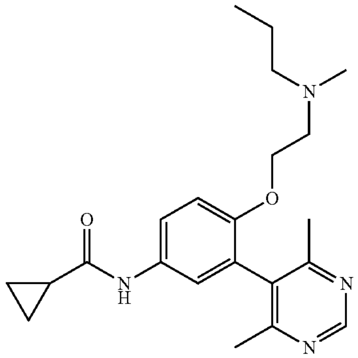

367

Compound 367 was prepared according to the synthesis described for compound 366, substituting N-methylpropan-1-amine for N-methylethanamine.

LCMS (ESI): m/z [M+H] calcd for $C_{22}H_{31}N_4O_2$: 383.2; found: 383.2.

$^1$H NMR (400 MHZ, methanol-$d_4$) δ=8.88 (s, 1H), 7.66 (dd, J=2.4, 8.9 Hz, 1H), 7.42 (d, J=2.4 Hz, 1H), 7.19 (d, J=9.0 Hz, 1H), 4.37 (br s, 2H), 3.59-3.37 (m, 2H), 3.07-2.80 (m, 2H), 2.71 (s, 3H), 2.30 (s, 6H), 1.81-1.69 (m, 1H), 1.63-1.47 (m, 2H), 1.00-0.80 (m, 7H).

N-(4-(2-((cyclopropylmethyl)(methyl)amino) ethoxy)-3-(4,6-dimethylpyrimidin-5-yl)phenyl)cyclopropanecarboxamide (368)

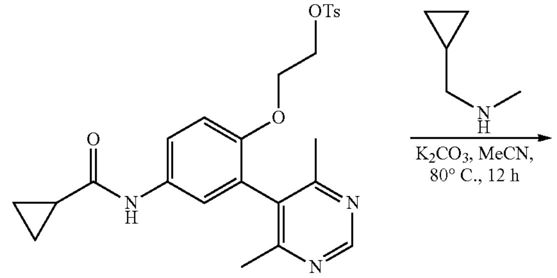

66

-continued

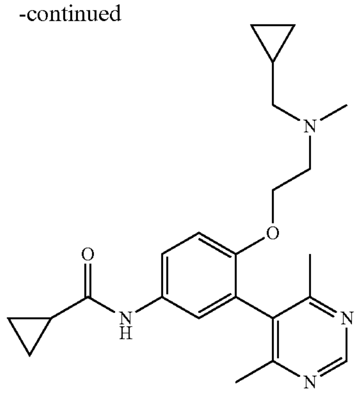

368

Compound 368 was prepared according to the synthesis described for compound 366, substituting 1-cyclopropyl-N-methylmethanamine for N-methylethanamine.

LCMS (ESI): m/z [M+H] calcd for $C_{23}H_{31}N_4O_2$: 395.2; found: 395.2.

$^1$H NMR (400 MHZ, methanol-d$_4$) δ=8.89 (s, 1H), 7.67 (dd, J=2.7, 8.9 Hz, 1H), 7.41 (d, J=2.7 Hz, 1H), 7.19 (d, J=9.0 Hz, 1H), 4.38 (br d, J=2.6 Hz, 2H), 3.66-3.40 (m, 2H), 3.03-2.79 (m, 2H), 2.77 (s, 3H), 2.30 (s, 6H), 1.79-1.70 (m, 1H), 0.98-0.82 (m, 5H), 0.69 (br d, J=6.7 Hz, 2H), 0.29 (q, J=4.9 Hz, 2H).

N-(4-(2-(cyclobutyl(methyl)amino)ethoxy)-3-(4,6-dimethylpyrimidin-5-yl)phenyl)cyclopropanecarboxamide (369)

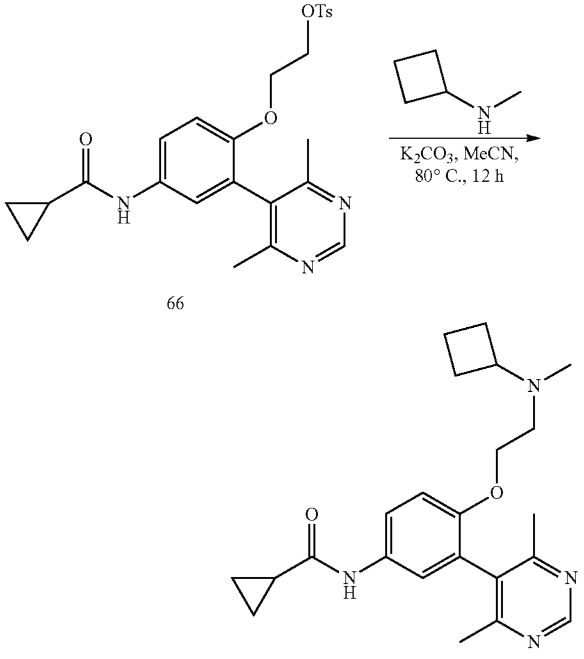

66

369

Compound 369 was prepared according to the synthesis described for compound 366, substituting N-methylcyclobutanamine for N-methylethanamine.

LCMS (ESI): m/z [M+H] calcd for $C_{23}H_{31}N_4O_2$: 395.2; found: 395.3.

$^1$H NMR (400 MHZ, DMSO-d$_6$) δ=10.24 (s, 1H), 9.96 (br s, 1H), 8.89 (s, 1H), 7.64 (dd, J=2.6, 8.9 Hz, 1H), 7.42 (d, J=2.6 Hz, 1H), 7.16 (d, J=8.9 Hz, 1H), 4.27 (t, J=4.8 Hz, 2H), 3.43 (sxt, J=8.1 Hz, 1H), 3.30-3.17 (m, 2H), 2.44 (d, J=3.9 Hz, 3H), 2.18 (s, 6H), 2.07-1.97 (m, 2H), 1.97-1.86 (m, 1H), 1.79-1.68 (m, 2H), 1.66-1.55 (m, 1H), 1.55-1.41 (m, 1H), 0.81-0.74 (m, 4H).

N-(4-(2-(diethylamino)ethoxy)-3-(4,6-dimethylpyrimidin-5-yl)phenyl)cyclopropanecarboxamide (370)

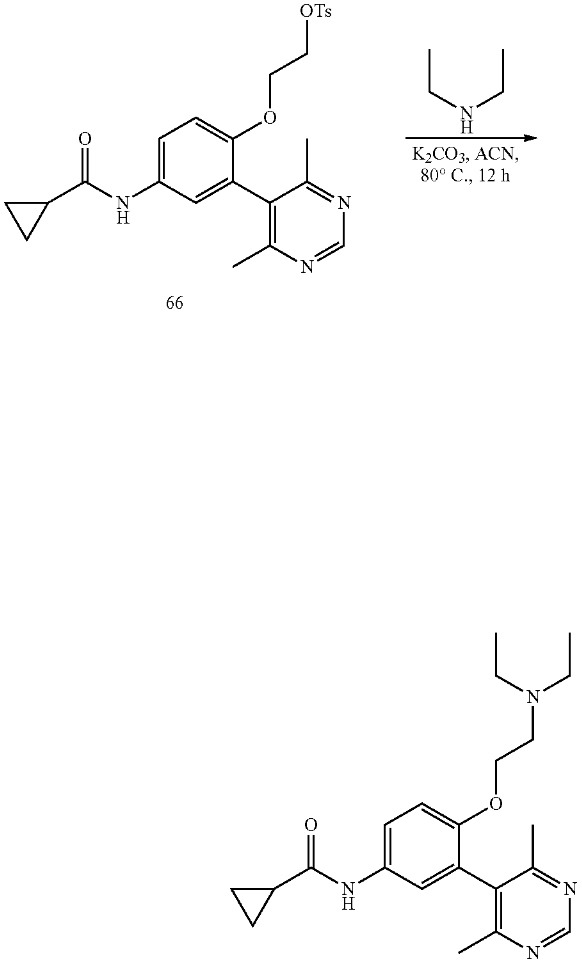

66

370

Compound 370 was prepared according to the synthesis described for compound 366, substituting diethylamine for N-methylethanamine.

LCMS (ESI): m/z [M+H] calcd for $C_{22}H_{31}N_4O_2$: 383.2; found: 383.2.

$^1$H NMR (400 MHZ, methanol-d$_4$) δ=8.90 (s, 1H), 7.67 (dd, J=2.6, 8.9 Hz, 1H), 7.41 (d, J=2.6 Hz, 1H), 7.18 (d, J=8.9 Hz, 1H), 4.42-4.30 (m, 2H), 3.53-3.43 (m, 2H), 3.17-2.94 (m, 4H), 2.30 (s, 6H), 1.80-1.69 (m, 1H), 1.08 (t, J=7.3 Hz, 6H), 1.00-0.80 (m, 4H).

N-(3-(4,6-dimethylpyrimidin-5-yl)-4-(2-((2-methoxyethyl)amino)ethoxy)phenyl) benzamide (371)

Preparation of 2-(2-(4,6-dimethylpyrimidin-5-yl)-4-nitrophenoxy)-N-(2-methoxyethyl)ethan-1-amine (72)

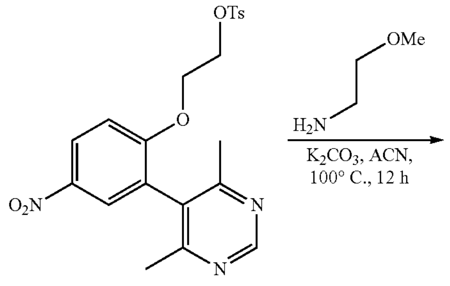

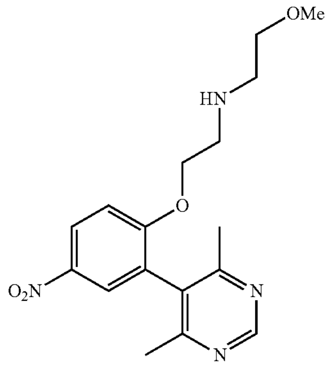

72

To a solution of 2-(2-(4,6-dimethylpyrimidin-5-yl)-4-nitrophenoxy)ethyl 4-methylbenzenesulfonate (3 g, 6.76 mmol, 1 eq.) in ACN (2 mL) was added $K_2CO_3$ (2.80 g, 20.29 mmol, 3 eq.) and 2-methoxyethanamine (609.72 mg, 8.12 mmol, 705.69 μL, 1.2 eq.). The mixture was stirred at 80° C. for 12 hrs. The organic phase was concentrated to afford the crude product. The resulting mixture was partitioned between EtOAc (300 mL) and water (100 mL), and then the aqueous phase was further extracted with EtOAc (3×100 mL), then the organic phase was washed with brine (100 mL) and dried over $Na_2SO_4$ (2 g) to afford 2-(2-(4,6-dimethylpyrimidin-5-yl)-4-nitrophenoxy)-N-(2-methoxyethyl)ethan-1-amine ((72), 2.3 g, crude) as a colorless oil.

Preparation of tert-butyl (2-(2-(4,6-dimethylpyrimidin-5-yl)-4-nitrophenoxy)ethyl)(2-methoxyethyl) carbamate (73)

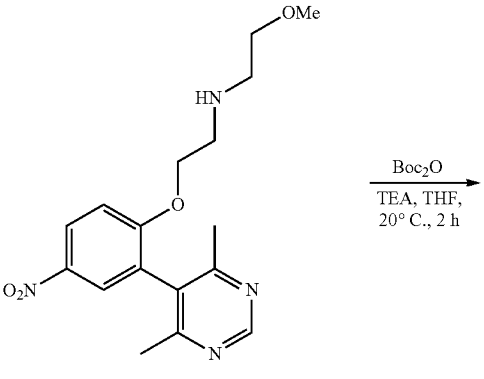

72

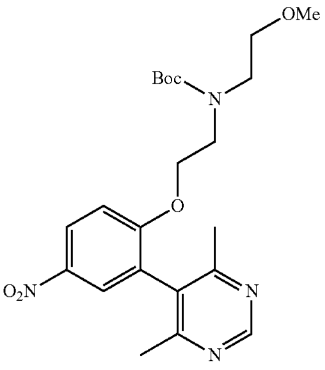

73

To a solution of 2-(2-(4,6-dimethylpyrimidin-5-yl)-4-nitrophenoxy)-N-(2-methoxyethyl)ethan-1-amine ((72), 2.2 g, 6.35 mmol, 1 eq.) in THF (20 mL) was added $Boc_2O$ (1.52 g, 6.99 mmol, 1.61 mL, 1.1 eq.) and TEA (1.29 g, 12.70 mmol, 1.77 mL, 2 eq.). The mixture was stirred at 20° C. for 2 hrs. TLC indicated 2-(2-(4,6-dimethylpyrimidin-5-yl)-4-nitrophenoxy)-N-(2-methoxyethyl)ethan-1-amine was consumed completely and one new spot formed. The reaction was clean according to TLC. The organic phase was concentrated to afford the crude product. The resulting mixture was partitioned between EtOAc (30 mL) and water (50 mL), and then the aqueous phase was further extracted with EtOAc (3×10 mL), then the organic phase was washed with brine (30 mL) and dried over $Na_2SO_4$ (2 g). The crude product was triturated with PE at 25° C. for 30 min to afford tert-butyl (2-(2-(4,6-dimethylpyrimidin-5-yl)-4-nitrophenoxy)ethyl)(2-methoxyethyl)carbamate ((73), 2 g, 4.48 mmol, 70.52% yield) as a colorless oil.

Preparation of tert-butyl (2-(4-amino-2-(4,6-dimethylpyrimidin-5-yl)phenoxy)ethyl)(2-methoxyethyl) carbamate (74)

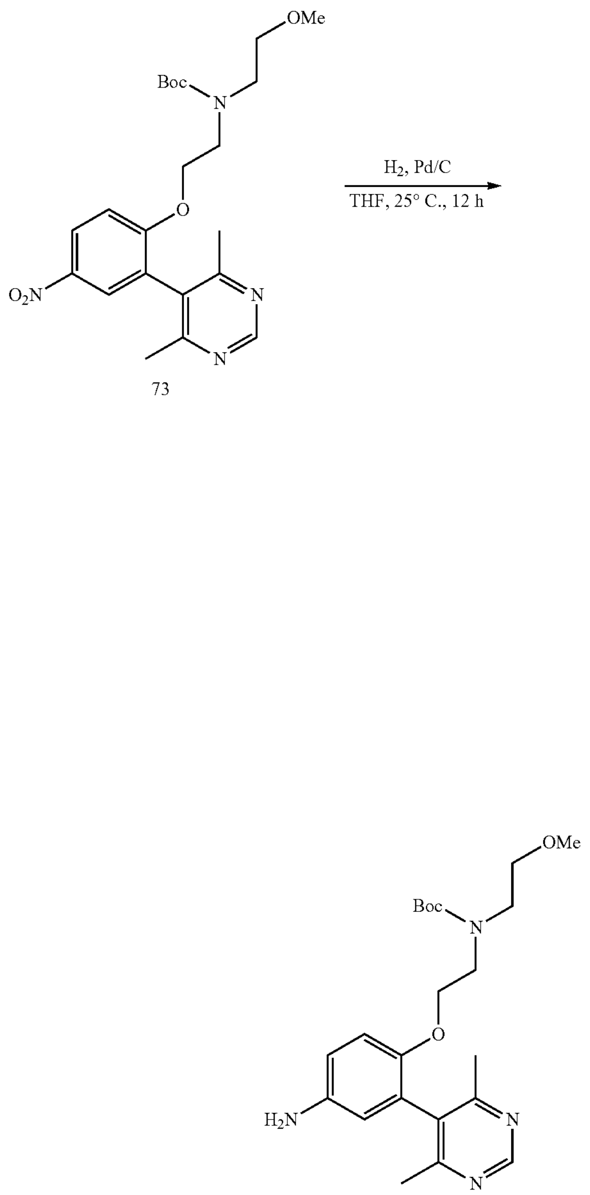

73

74

To a solution of tert-butyl (2-(2-(4,6-dimethylpyrimidin-5-yl)-4-nitrophenoxy)ethyl)(2-methoxyethyl)carbamate ((73), 1.9 g, 4.26 mmol, 1 eq.) in THF (1 mL) was added Pd/C (100 mg, 60% purity). The suspension was degassed under vacuum and purged with $H_2$ several times. The mixture was stirred under $H_2$ (15 psi) at 25° C. for 12 hrs (monitored by LC-MS), then filtered and the liquid was collected. The organic phase was concentrated to afford tert-butyl (2-(4-amino-2-(4,6-dimethylpyrimidin-5-yl)phenoxy)ethyl)(2-methoxyethyl)carbamate ((74), 1.7 g, 4.08 mmol, 95.91% yield) as a colorless oil, which was used to the next step without further purification.

Preparation of tert-butyl (2-(4-benzamido-2-(4,6-dimethylpyrimidin-5-yl)phenoxy)ethyl)(2-methoxyethyl)carbamate (75)

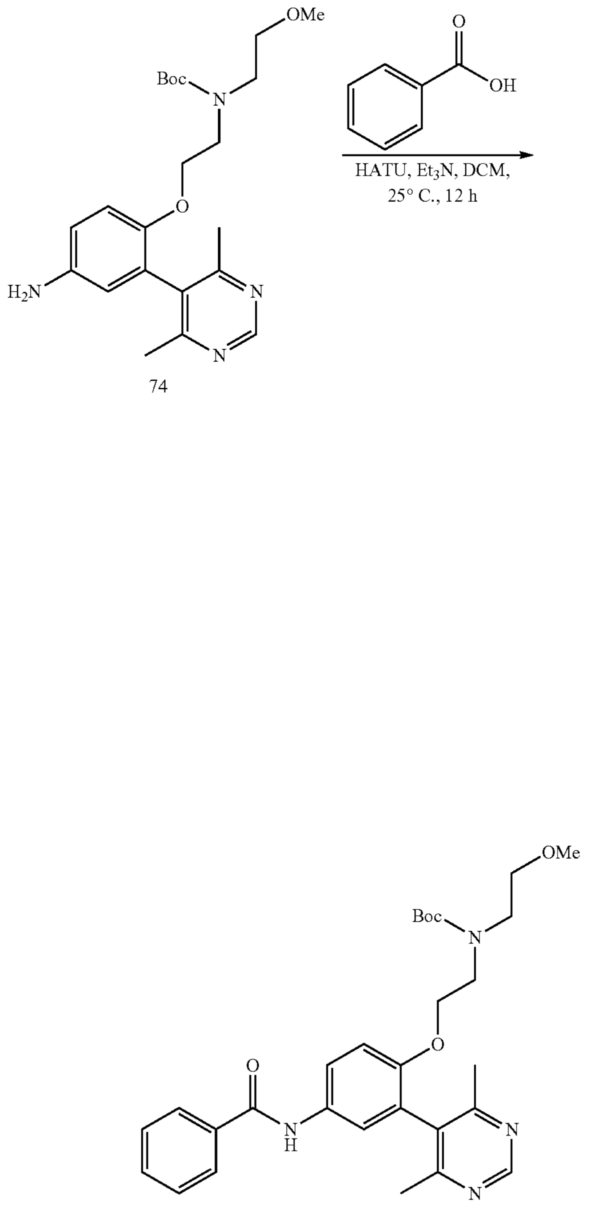

74

75

To a solution of tert-butyl (2-(4-amino-2-(4,6-dimethylpyrimidin-5-yl)phenoxy)ethyl)(2-methoxyethyl)carbamate ((74), 200 mg, 480.18 μmol, 1 eq.) in DCM (1 mL) was added HATU (273.87 mg, 720.27 μmol, 1.5 eq.) and TEA (145.77 mg, 1.44 mmol, 200.50 μL, 3 eq.) and benzoic acid (70.37 mg, 576.21 μmol, 87.96 μL, 1.2 eq.). The mixture was stirred at 25° C. for 12 hrs (monitored by LC-MS). The organic phase was concentrated to afford the crude product. The residue was purified by prep-HPLC (TFA conditions) to afford tert-butyl (2-(4-benzamido-2-(4,6-dimethylpyrimidin-5-yl)phenoxy)ethyl)(2-methoxyethyl)carbamate ((75), 150 mg, 288.12 μmol, 60.00% yield) as a white solid.

Preparation of N-(3-(4,6-dimethylpyrimidin-5-yl)-4-(2-((2-methoxyethyl)amino)ethoxy)phenyl)benzamide (371)

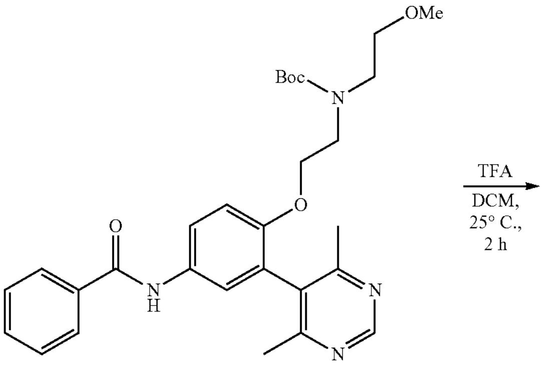

75

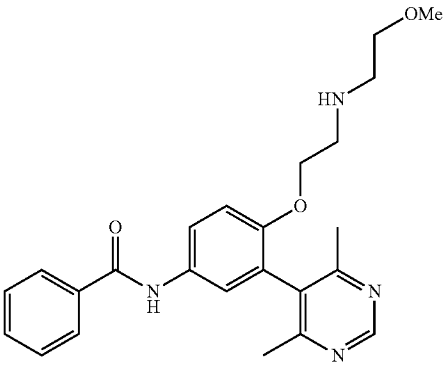

371

To a solution of tert-butyl (2-(4-benzamido-2-(4,6-dimethylpyrimidin-5-yl)phenoxy)ethyl)(2-methoxyethyl)carbamate ((75), 30 mg, 57.62 μmol, 1 eq.) in DCM (0.5 mL) was added TFA (1.85 g, 16.21 mmol, 1.20 mL, 281.26 eq.). The mixture was stirred at 25° C. for 2 hrs (monitored by LC-MS). The resulting mixture was partitioned between DCM (30 mL) and water (50 mL), and then the aqueous phase was further extracted with DCM (3×10 mL), then the organic phase was washed with brine (30 mL) and dried over $Na_2SO_4$ (2 g). The residue was purified by prep-HPLC (TFA condition) to afford N-(3-(4,6-dimethylpyrimidin-5-yl)-4-(2-((2-methoxyethyl)amino)ethoxy)phenyl)benzamide (15 mg, 35.67 μmol, 61.90% yield) as a colorless oil.

LCMS (ESI): m/z [M+H] calcd for $C_{24}H_{28}N_4O_3$: 421.3; found: 421.2.

$^1$H NMR (400 MHZ, methanol-d$_4$) δ=8.96 (s, 1H), 7.94 (d, J=7.3 Hz, 2H), 7.84 (dd, J=2.6, 8.8 Hz, 1H), 7.61-7.54 (m, 2H), 7.54-7.48 (m, 2H), 7.25 (d, J=9.0 Hz, 1H), 4.34 (t, J=5.1 Hz, 2H), 3.51-3.45 (m, 2H), 3.40-3.33 (m, 5H), 3.04-2.98 (m, 2H), 2.36 (s, 6H).

N-(3-(4,6-dimethylpyrimidin-5-yl)-4-(2-((2-methoxyethyl)amino)ethoxy)phenyl)-3-methoxybenzamide (372)

372

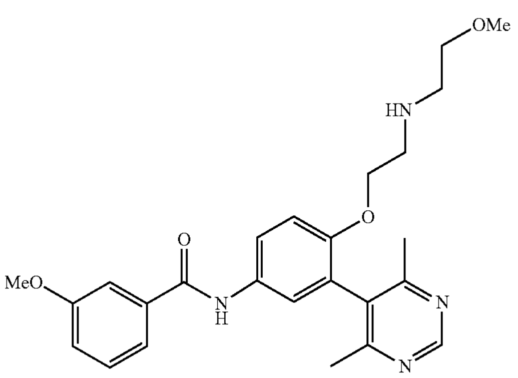

Compound 372 was prepared according to the synthesis described for compound 371, substituting 3-methoxybenzoic acid for benzoic acid.

LCMS (ESI): m/z [M+H] calcd for $C_{30}H_{38}N_4O_6$: 451.3; found: 451.2.

$^1$H NMR (400 MHZ, methanol-d$_4$) δ=8.97 (s, 1H), 7.83 (dd, J=2.6, 9.0 Hz, 1H), 7.56 (d, J=2.4 Hz, 1H), 7.53-7.46 (m, 2H), 7.41 (t, J=7.9 Hz, 1H), 7.25 (d, J=9.0 Hz, 1H), 7.13 (td, J=1.2, 8.2 Hz, 1H), 4.34 (t, J=5.2 Hz, 2H), 3.86 (s, 3H), 3.51-3.46 (m, 2H), 3.40-3.33 (m, 5H), 3.04-2.98 (m, 2H), 2.36 (s, 6H).

N-(3-(4,6-dimethylpyrimidin-5-yl)-4-(2-((2-methoxyethyl)amino)ethoxy)phenyl)-3-fluorobenzamide (373)

373

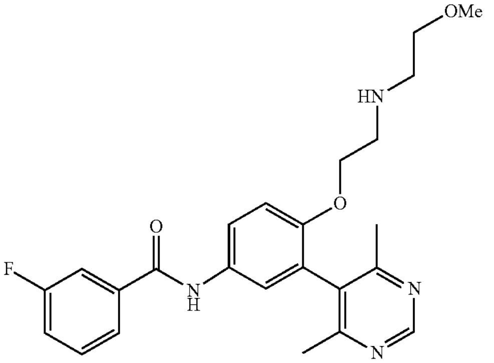

Compound 373 was prepared according to the synthesis described for compound 371, substituting 3-fluorobenzoic acid for benzoic acid.

LCMS (ESI): m/z [M+H] calcd for $C_{24}H_{27}N_4O_3F$: 439.2; found: 439.2.

$^1$H NMR (400 MHZ, methanol-d$_4$) δ=8.92 (s, 1H), 7.84 (dd, J=2.5, 8.9 Hz, 1H), 7.77 (d, J=7.7 Hz, 1H), 7.68 (dd, J=2.1, 9.6 Hz, 1H), 7.58-7.50 (m, 2H), 7.34 (dt, J=2.0, 8.4 Hz, 1H), 7.25 (d, J=9.0 Hz, 1H), 4.33 (t, J=5.2 Hz, 2H), 3.49-3.44 (m, 2H), 3.39-3.34 (m, 5H), 3.02-2.97 (m, 2H), 2.33 (s, 6H).

N-(3-(4,6-dimethylpyrimidin-5-yl)-4-(2-((2-methoxyethyl)amino)ethoxy)phenyl)-4-fluorobenzamide (374)

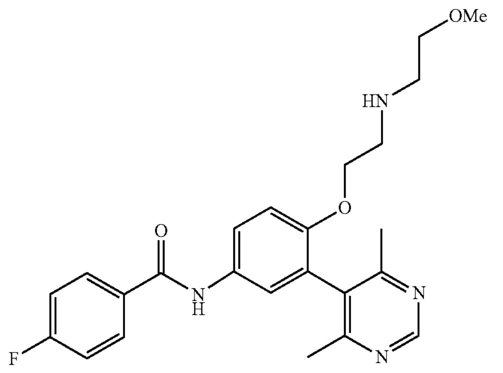

374

Compound 374 was prepared according to the synthesis described for compound 371, substituting 4-fluorobenzoic acid for benzoic acid.

LCMS (ESI): m/z [M+H] calcd for $C_{24}H_{28}FN_4O_3$: 439.2; found: 439.3.

$^1$H NMR (400 MHZ, methanol-$d_4$) δ=8.95 (s, 1H), 8.00 (dd, J=5.4, 8.7 Hz, 2H), 7.82 (dd, J=2.6, 8.9 Hz, 1H), 7.55 (d, J=2.6 Hz, 1H), 7.28-7.21 (m, 3H), 4.34 (t, J=5.1 Hz, 2H), 3.50-3.45 (m, 2H), 3.40-3.34 (m, 5H), 3.03-2.98 (m, 2H), 2.35 (s, 6H).

N-(3-(4,6-dimethylpyrimidin-5-yl)-4-(2-((2-methoxyethyl)amino)ethoxy)phenyl)-4-fluoro-1-methyl-1H-pyrazole-5-carboxamide (375)

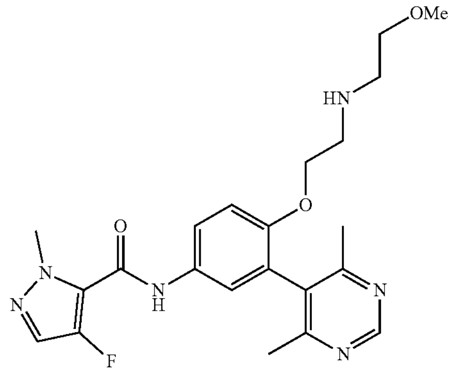

375

Compound 375 was prepared according to the synthesis described for compound 371, substituting 4-fluoro-1-methyl-1H-pyrazole-5-carboxylic acid for benzoic acid.

LCMS (ESI): m/z [M+H] calcd for $C_{22}H_{27}N_6O_3F$: 443.2; found: 443.3.

$^1$H NMR (400 MHZ, methanol-$d_4$) δ=8.93 (s, 1H), 7.79 (br dd, J=1.8, 8.8 Hz, 1H), 7.54 (br s, 1H), 7.46 (br d, J=4.2 Hz, 1H), 7.25 (br d, J=9.0 Hz, 1H), 4.33 (br t, J=5.0 Hz, 2H), 4.04 (s, 3H), 3.50-3.43 (m, 2H), 3.36 (s, 5H), 3.02-2.96 (m, 2H), 2.33 (s, 6H).

N-(3-(4,6-dimethylpyrimidin-5-yl)-4-(2-((2-methoxyethyl)(methyl)amino)ethoxy)phenyl)benzamide (376)

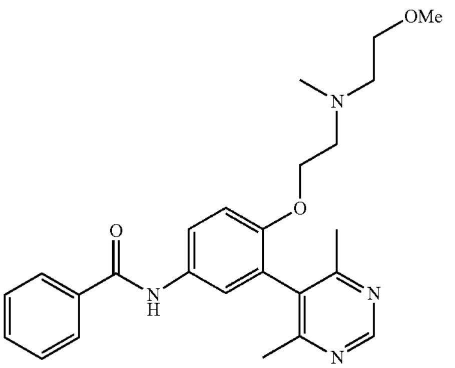

376

Compound 376 was prepared according to the synthesis described for compound 371, substituting 2-methoxy-N-methylethanamine for 2-methoxyethanamine.

LCMS (ESI): m/z [M+H] calcd for $C_{25}H_{31}N_4O_3$: 435.23; found: 435.3.

$^1$H NMR (400 MHZ, methanol-$d_4$) δ=8.91 (s, 1H), 7.96-7.91 (m, 2H), 7.86 (dd, J=2.6, 9.0 Hz, 1H), 7.62-7.48 (m, 4H), 7.25 (d, J=9.2 Hz, 1H), 4.41 (t, J=4.7 Hz, 2H), 3.58-3.43 (m, 4H), 3.36 (s, 3H), 3.24-3.10 (m, 2H), 2.76 (s, 3H), 2.33 (s, 6H).

N-(3-(4,6-dimethylpyrimidin-5-yl)-4-(2-((2-methoxyethyl)(methyl)amino)ethoxy)phenyl)-3-methoxybenzamide (377)

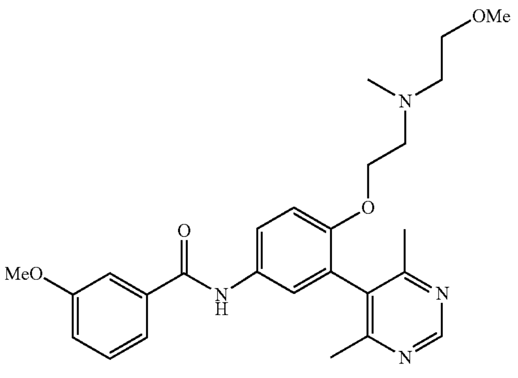

377

Compound 377 was prepared according to the synthesis described for compound 372, substituting 2-methoxy-N-methylethanamine for 2-methoxyethanamine.

$^1$H NMR (400 MHZ, methanol-$d_4$) δ=8.92 (s, 1H), 7.86 (dd, J=2.6, 9.0 Hz, 1H), 7.55-7.46 (m, 3H), 7.45-7.40 (m, 1H), 7.25 (d, J=9.0 Hz, 1H), 7.15 (ddd, J=1.0, 2.6, 8.2 Hz, 1H), 4.41 (t, J=4.9 Hz, 2H), 3.87 (s, 3H), 3.63-3.40 (m, 4H), 3.36 (s, 3H), 3.25-3.17 (m, 1H), 3.17-3.05 (m, 1H), 2.76 (s, 3H), 2.33 (s, 6H).

LCMS (ESI): m/z [M+H] calcd for $C_{26}H_{33}N_4O_4$: 465.24; found: 465.2.

N-(3-(4,6-dimethylpyrimidin-5-yl)-4-(2-((2-methoxyethyl)(methyl)amino)ethoxy)phenyl)-3-fluorobenzamide (378)

378

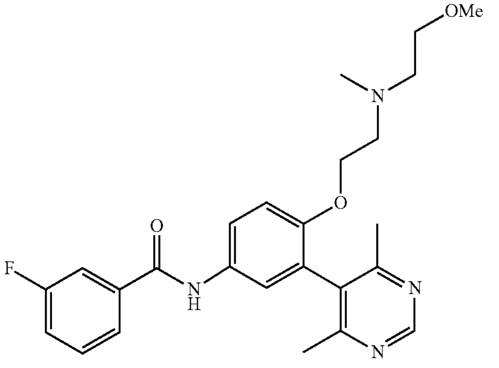

Compound 378 was prepared according to the synthesis described for compound 373, substituting 2-methoxy-N-methylethanamine for 2-methoxyethanamine.

LCMS (ESI): m/z [M+H] calcd for $C_{25}H_{30}FN_4O_3$: 453.22; found: 453.2.

$^1$H NMR (400 MHZ, DMSO-$d_6$) δ=10.35 (s, 1H), 9.51-9.38 (m, 1H), 8.92-8.89 (m, 1H), 7.87-7.73 (m, 3H), 7.63-7.54 (m, 2H), 7.48-7.41 (m, 1H), 7.25 (d, J=9.0 Hz, 1H), 4.33 (br t, J=4.9 Hz, 2H), 3.50-3.32 (m, 4H), 3.25 (s, 3H), 3.19-3.01 (m, 2H), 2.60 (d, J=4.6 Hz, 3H), 2.26-2.16 (m, 6H).

N-(3-(4,6-dimethylpyrimidin-5-yl)-4-(2-((2-methoxyethyl)(methyl)amino)ethoxy)phenyl)-4-fluorobenzamide (379)

379

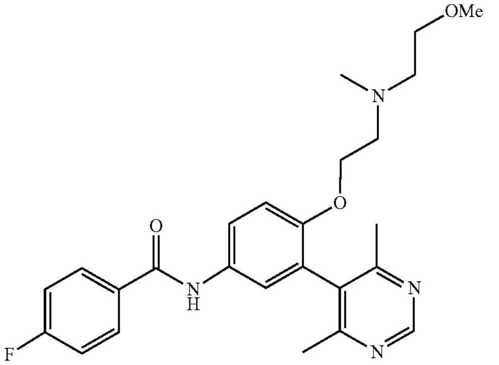

Compound 379 was prepared according to the synthesis described for compound 374, substituting 2-methoxy-N-methylethanamine for 2-methoxyethanamine.

LCMS (ESI): m/z [M+H] calcd for $C_{25}H_{30}FN_4O_3$: 453.22; found: 453.1.

$^1$H NMR (400 MHZ, DMSO-$d_6$) δ=10.28 (s, 1H), 9.55-9.41 (m, 1H), 8.91 (s, 1H), 8.07-7.99 (m, 2H), 7.84 (dd, J=2.6, 9.0 Hz, 1H), 7.57 (d, J=2.6 Hz, 1H), 7.40-7.34 (m, 2H), 7.24 (d, J=9.0 Hz, 1H), 4.33 (br t, J=4.9 Hz, 2H), 3.51-3.31 (m, 4H), 3.25 (s, 3H), 3.20-3.01 (m, 2H), 2.60 (d, J=4.2 Hz, 3H), 2.21 (s, 6H).

N-(3-(4,6-dimethylpyrimidin-5-yl)-4-(2-((2-methoxyethyl)(methyl)amino)ethoxy)phenyl)-4-fluoro-1-methyl-1H-pyrazole-5-carboxamide (380)

380

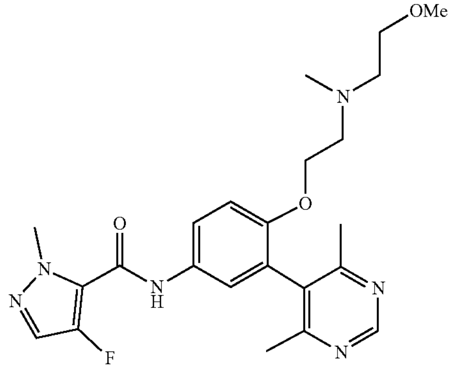

Compound 380 was prepared according to the synthesis described for compound 375, substituting 2-methoxy-N-methylethanamine for 2-methoxyethanamine.

LCMS (ESI): m/z [M+H] calcd for $C_{23}H_{30}FN_6O_3$: 457.23; found: 457.3.

$^1$H NMR (400 MHZ, methanol-$d_4$) δ=8.91 (s, 1H), 7.80 (dd, J=2.6, 9.0 Hz, 1H), 7.53 (d, J=2.6 Hz, 1H), 7.47 (d, J=4.4 Hz, 1H), 7.25 (d, J=9.0 Hz, 1H), 4.42 (t, J=4.8 Hz, 2H), 4.05 (d, J=0.9 Hz, 3H), 3.58-3.43 (m, 4H), 3.36 (s, 3H), 3.25-3.09 (m, 2H), 2.75 (s, 3H), 2.33-2.28 (m, 6H).

N-(4-(2-((1S,4S)-2-oxa-5-azabicyclo[2.2.1]heptan-5-yl)ethoxy)-3-(4,6-dimethylpyrimidin-5-yl)phenyl)benzamide (381)

Preparation of (1S,4S)-5-(2-(2-(4,6-dimethylpyrimidin-5-yl)-4-nitrophenoxy)ethyl)-2-oxa-5-azabicyclo[2.2.1]heptane (76)

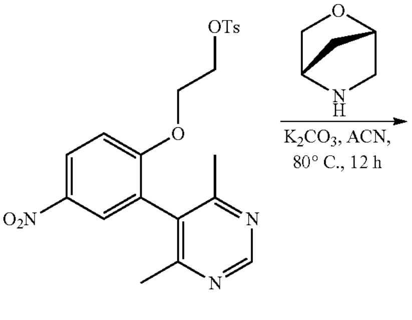

-continued

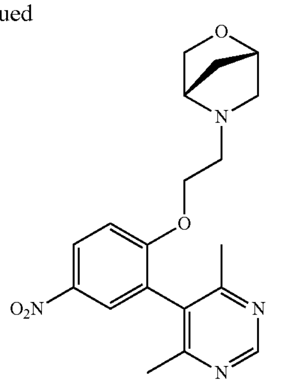

76

To a solution of 2-(2-(4,6-dimethylpyrimidin-5-yl)-4-nitrophenoxy)ethyl 4-methylbenzenesulfonate (1 g, 2.25 mmol, 1 eq.) in ACN (20 mL) was added $K_2CO_3$ (934.94 mg, 6.76 mmol, 3 eq.) and (1S,4S)-2-oxa-5-azabicyclo[2.2.1]heptane (366.90 mg, 2.71 mmol, 1.2 eq., HCl). The mixture was stirred at 80° C. for 12 hrs. The reaction was complete detected by LCMS. The solution was added water (1 mL). The residue was purified by prep-HPLC (neutral condition). (1S,4S)-5-(2-(2-(4,6-dimethylpyrimidin-5-yl)-4-nitrophenoxy)ethyl)-2-oxa-5-azabicyclo[2.2.1]heptane ((76), 640 mg, 1.73 mmol, 76.63% yield) as a yellow oil.

Preparation of 4-(2-((1S,4S)-2-oxa-5-azabicyclo[2.2.1]heptan-5-yl)ethoxy)-3-(4,6-dimethylpyrimidin-5-yl)aniline (77)

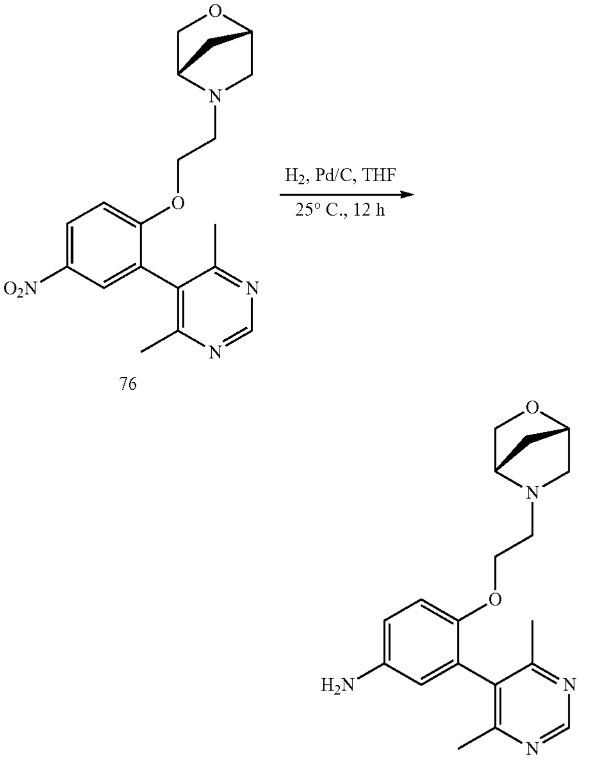

76

77

A mixture of (1S,4S)-5-(2-(2-(4,6-dimethylpyrimidin-5-yl)-4-nitrophenoxy)ethyl)-2-oxa-5-azabicyclo[2.2.1]heptane ((76), 640 mg, 1.73 mmol, 1 eq.) and Pd/C (600 mg, 1.73 mmol, 60% purity, 1 eq.) in THF (5 mL) was degassed and purged with $H_2$ three times, and then the mixture was stirred at 25° C. for 12 hrs under an $H_2$ atmosphere until the reaction was complete (detected by LCMS). The reaction mixture was filtered and the liquid was collected. 4-(2-((1S,4S)-2-oxa-5-azabicyclo[2.2.1]heptan-5-yl)ethoxy)-3-(4,6-dimethylpyrimidin-5-yl) aniline ((77), 560 mg, 1.65 mmol, 95.21% yield) was obtained as a colorless oil. The crude product was used in the next step without further purification.

Preparation of N-(4-(2-((1S,4S)-2-oxa-5-azabicyclo[2.2.1]heptan-5-yl)ethoxy)-3-(4,6-dimethylpyrimidin-5-yl)phenyl)benzamide (381)

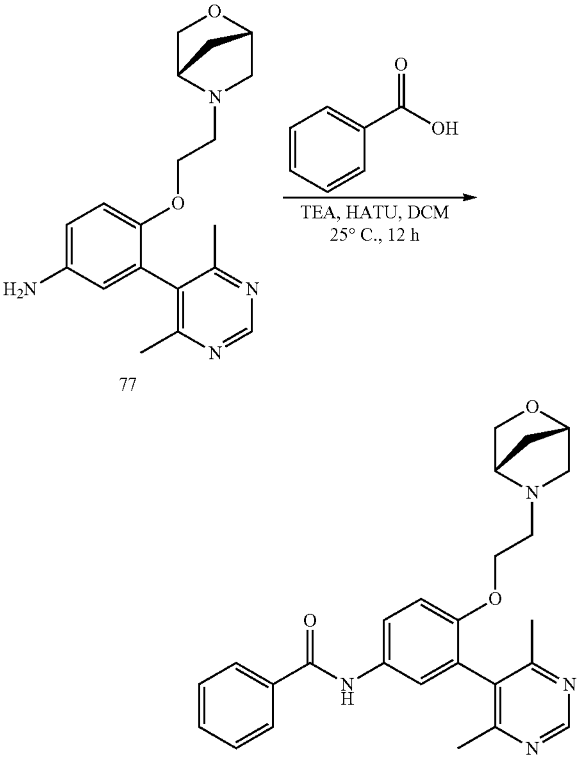

77

381

To a solution of 4-(2-((1S,4S)-2-oxa-5-azabicyclo[2.2.1]heptan-5-yl)ethoxy)-3-(4,6-dimethylpyrimidin-5-yl) aniline ((77), 80 mg, 235.00 μmol, 1 eq.) in DCM (1 mL) was added TEA (71.34 mg, 705.01 μmol, 98.13 μL, 3 eq.), HATU (134.03 mg, 352.51 μmol, 1.5 eq.), and benzoic acid (34.44 mg, 282.01 μmol, 43.05 L, 1.2 eq.). The mixture was stirred at 25° C. for 12 hrs until the reaction was complete (detected by LCMS). The organic phase was concentrated to afford the crude product. The residue was purified by prep-HPLC (TFA conditions) to afford N-(4-(2-((1S,4S)-2-oxa-5-azabicyclo[2.2.1]heptan-5-yl)ethoxy)-3-(4,6-dimethylpyrimidin-5-yl)phenyl)benzamide (57.7 mg, 129.80 μmol, 55.23% yield) as a white solid.

LCMS (ESI): m/z [M+H] calcd for $C_{26}H_{28}N_4O_3$: 445.2; found: 445.3.

$^1$H NMR (400 MHZ, methanol-$d_4$) δ=8.93 (s, 1H), 7.94 (d, J=7.5 Hz, 2H), 7.86 (dd, J=2.4, 8.9 Hz, 1H), 7.62-7.49 (m, 4H), 7.25 (d, J=9.1 Hz, 1H), 4.56 (br s, 1H), 4.40 (br s, 2H), 4.30-4.06 (m, 1H), 3.85 (br s, 1H), 3.77-3.39 (m, 4H), 3.03-2.70 (m, 1H), 2.33 (d, J=6.9 Hz, 6H), 2.22-1.94 (m, 2H).

N-(4-(2-((1S,4S)-2-oxa-5-azabicyclo[2.2.1]heptan-5-yl)ethoxy)-3-(4,6-dimethylpyrimidin-5-yl)phenyl)-1-fluorocyclopropane-1-carboxamide (382)

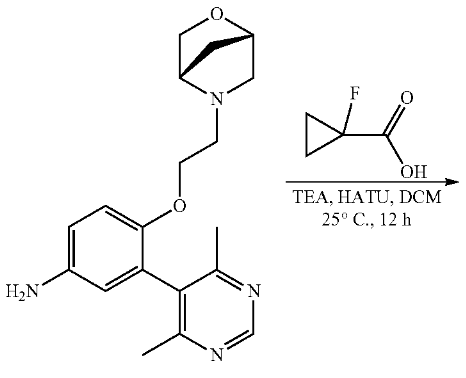

77

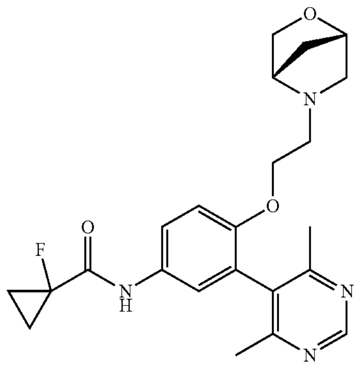

382

Compound 382 was prepared according to the synthesis described for compound 381, substituting 1-fluorocyclopropane-1-carboxylic acid for benzoic acid.

LCMS (ESI): m/z [M+H] calcd for $C_{23}H_{27}N_4O_3F$: 427.2; found: 427.2.

$^1$H NMR (400 MHZ, methanol-$d_4$) δ=8.92 (s, 1H), 7.77 (dd, J=2.6, 8.8 Hz, 1H), 7.47 (d, J=2.0 Hz, 1H), 7.22 (d, J=9.0 Hz, 1H), 4.56 (br s, 1H), 4.38 (br s, 2H), 4.26-4.05 (m, 1H), 3.84 (br s, 1H), 3.70 (br s, 2H), 3.57-3.36 (m, 2H), 2.99-2.73 (m, 1H), 2.30 (d, J=6.9 Hz, 6H), 2.22-1.89 (m, 2H), 1.47-1.31 (m, 4H).

N-(4-(2-((1S,4S)-2-oxa-5-azabicyclo[2.2.1]heptan-5-yl)ethoxy)-3-(4,6-dimethylpyrimidin-5-yl)phenyl)-1-methyl-1H-pyrazole-5-carboxamide (383)

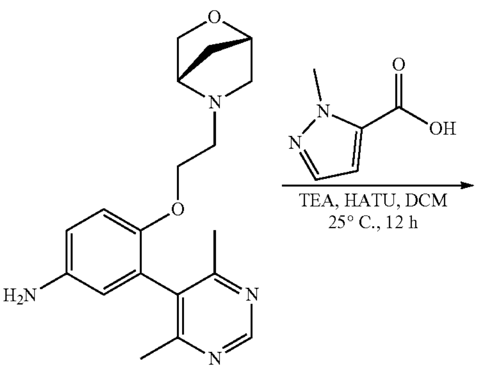

77

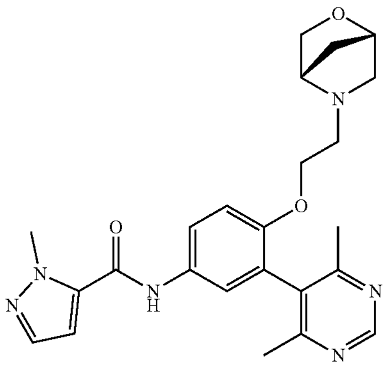

383

Compound 383 was prepared according to the synthesis described for compound 381, substituting 1-methyl-1H-pyrazole-5-carboxylic acid for benzoic acid.

LCMS (ESI): m/z [M+H] calcd for $C_{24}H_{28}N_6O_3$: 449.3; found: 449.2.

$^1$H NMR (400 MHZ, methanol-$d_4$) δ=8.93 (s, 1H), 7.83 (dd, J=2.3, 8.9 Hz, 1H), 7.53 (dd, J=1.9, 9.7 Hz, 2H), 7.25 (d, J=9.0 Hz, 1H), 6.96 (d, J=1.5 Hz, 1H), 4.56 (br s, 1H), 4.39 (br s, 2H), 4.15 (s, 4H), 3.99-3.80 (m, 1H), 3.69 (br s, 2H), 3.51 (br d, J=19.1 Hz, 2H), 3.02-2.74 (m, 1H), 2.33 (d, J=6.8 Hz, 6H), 2.22-1.90 (m, 2H).

N-[4-[2-[(1R,5S)-3-azabicyclo[3.1.0]hexan-3-yl]ethoxy]-3-(4,6-dimethylpyrimidin-5-yl)phenyl]benzamide (384)

Preparation of N-[3-(4,6-dimethylpyrimidin-5-yl)-4-(2-hydroxyethoxy)phenyl]benzamide (78)

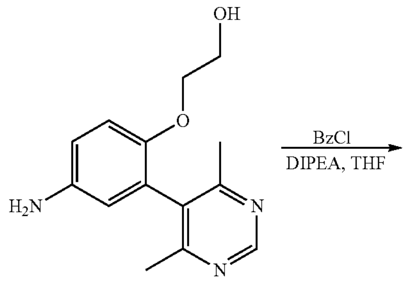

64

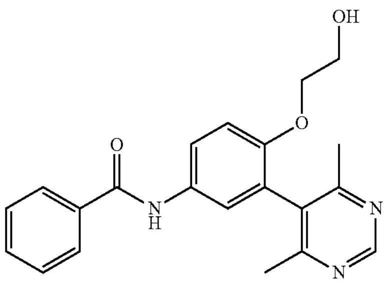

78

To a solution of 2-[4-amino-2-(4,6-dimethylpyrimidin-5-yl)phenoxy]ethanol ((64), 700 mg, 2.43 mmol, 90% purity, 1.00 eq.) in THF (20 mL) was added DIPEA (942.00 mg, 7.29 mmol, 1.27 mL, 3.00 eq.) and benzoyl chloride (409.82 mg, 2.92 mmol, 338.70 μL, 1.20 eq.) under $N_2$. The mixture was stirred under $N_2$ at 20° C. for 16 hrs. The reaction mixture was diluted with water (10 mL) and extracted with ethyl acetate (10 mL×3). The extract was washed with brine (10 mL), dried over $Na_2SO_4$ and concentrated in vacuo. Crude N-[3-(4,6-dimethylpyrimidin-5-yl)-4-(2-hydroxyethoxy)phenyl]benzamide ((78), 700 mg, 1.71 mmol, 70.56% yield, 89% purity) was obtained as a white solid and used in the next step without further purification.

Preparation of 2-[4-benzamido-2-(4,6-dimethylpyrimidin-5-yl)phenoxy]ethyl 4-methylbenzenesulfonate (79)

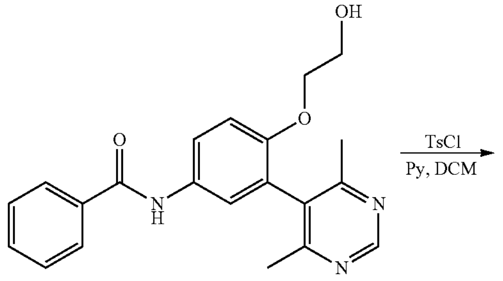

78

-continued

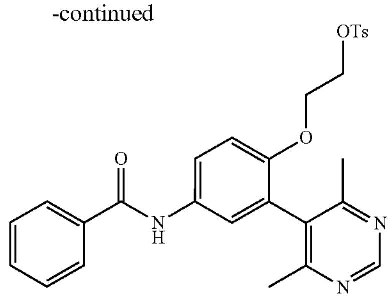

79

To a solution of N-[3-(4,6-dimethylpyrimidin-5-yl)-4-(2-hydroxyethoxy)phenyl]benzamide ((78), 700 mg, 1.93 mmol, 1 eq.) in DCM (20.0 mL) was added Py (609.45 mg, 7.70 mmol, 621.89 μL, 4.0 eq.) and 4-methylbenzenesulfonyl chloride (734.45 mg, 3.85 mmol, 2.0 eq.) under $N_2$. The mixture was stirred under $N_2$ at 20° C. for 16 hrs. Additional Py (609.45 mg, 7.70 mmol, 621.89 μL, 4.0 eq.) and 4-methylbenzenesulfonyl chloride (367.23 mg, 1.93 mmol, 1.0 eq.) were added. The mixture was stirred at 20° C. for another 16 hrs. The residue was purified by flash silica gel chromatography (ISCO®; 12 g SepaFlash® Silica Flash Column, eluent of 0~10% DCM/MeOH at 30 mL/min). 2-[4-Benzamido-2-(4,6-dimethylpyrimidin-5-yl)phenoxy]ethyl 4-methylbenzenesulfonate (450 mg, 851.15 μmol, 44.19% yield, 97.9% purity) was obtained as a white solid.

Preparation of N-[4-[2-[(1R,5S)-3-azabicyclo[3.1.0]hexan-3-yl]ethoxy]-3-(4,6-dimethylpyrimidin-5-yl)phenyl]benzamide (384)

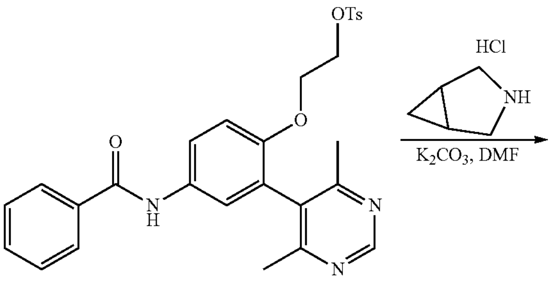

79

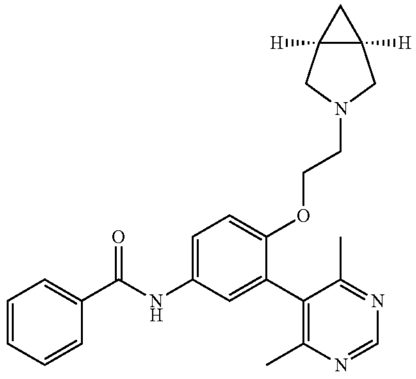

384

To a solution of 2-[4-benzamido-2-(4,6-dimethylpyrimidin-5-yl)phenoxy]ethyl 4-methylbenzenesulfonate ((79), 150 mg, 289.80 μmol, 1 eq.) in DMF (3.00 mL) was added $K_2CO_3$ (160.21 mg, 1.16 mmol, 4.00 eq.) and 3-azabicyclo [3.1.0]hexane hydrochloride (69.32 mg, 579.60 μmol, 2.0 eq.) under $N_2$. The mixture was stirred in a sealed tube at 80° C. for 16 hrs. and then the mixture was filtered. The filtrate was purified by prep-HPLC (column: YMC Triart C18 250*50 mm*7 μm; mobile phase: [water (0.225% TFA)-ACN]; B %: 0%-39%, 12 min). N-[4-[2-[(1R,5S)-3-azabicyclo[3.1.0]hexan-3-yl]ethoxy]-3-(4,6-dimethylpyrimidin-5-yl)phenyl]benzamide (55 mg, 127.45 μmol, 43.98% yield, 99.3% purity) was obtained as a white solid.

LCMS (ESI): m/z [M+H] calcd for $C_{26}H_{28}N_4O_2$: 429.22; found: 429.3.

$^1$H NMR (400 MHZ, methanol-$d_4$) δ=8.92 (s, 1H), 8.45 (br s, 1H), 8.00-7.91 (m, 2H), 7.87-7.77 (m, 1H), 7.63-7.50 (m, 4H), 7.27-7.19 (m, 1H), 4.23 (t, J=5.1 Hz, 2H), 3.20-3.06 (m, 4H), 2.76 (br d, J=9.7 Hz, 2H), 2.34 (s, 6H), 1.62-1.51 (m, 2H), 0.69-0.59 (m, 1H), 0.59-0.53 (m, 1H).

N-(4-(2-((1R,5S)-3-azabicyclo[3.1.0]hexan-3-yl)ethoxy)-3-(4,6-dimethylpyrimidin-5-yl)phenyl)cyclopropanecarboxamide (385)

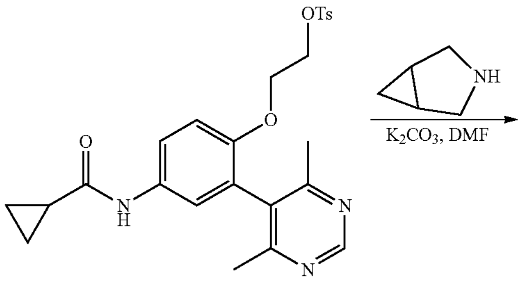

66

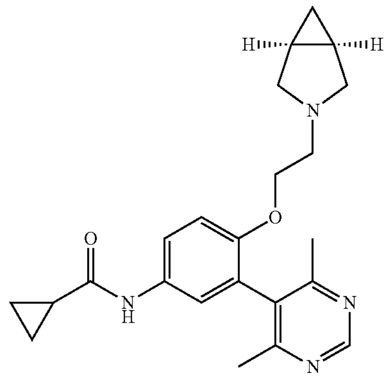

385

To a solution of 2-[4-(cyclopropanecarbonylamino)-2-(4,6-dimethylpyrimidin-5-yl)phenoxy]ethyl 4-methylbenzenesulfonate ((66), 200 mg, 415.31 μmol, 1 eq.) in DMF (3.00 mL) was added $K_2CO_3$ (229.60 mg, 1.66 mmol, 4.00 eq.) and 3-azabicyclo[3.1.0]hexane; hydrochloride (99.34 mg, 830.63 μmol, 2.0 eq.) under $N_2$. The mixture was stirred in a sealed tube at 80° C. for 16 hrs and then the mixture was filtered. The filtrate was purified by prep-HPLC (column: YMC Triart C18 250*50 mm*7 μm; mobile phase: [water (0.05% ammonia hydroxide v/v)-ACN]; B %: 21%-61%, 12 min). N-[4-[2-[(1R,5S)-3-azabicyclo[3.1.0]hexan-3-yl]ethoxy]-3-(4,6-dimethylpyrimidin-5-yl)phenyl]cyclopropanecarboxamide (90 mg, 222.42 μmol, 53.56% yield, 97% purity) was obtained as a white solid.

LCMS (ESI): m/z [M+H] calcd for $C_{23}H_{29}N_4O_2$: 393.23; found: 393.3.

$^1$H NMR (400 MHZ, methanol-$d_4$) δ=8.85 (s, 1H), 7.57 (dd, J=2.4, 9.0 Hz, 1H), 7.38 (d, J=2.3 Hz, 1H), 7.09 (d, J=8.9 Hz, 1H), 4.03 (t, J=5.3 Hz, 2H), 2.77 (d, J=9.0 Hz, 2H), 2.66 (t, J=5.3 Hz, 2H), 2.27 (s, 6H), 2.19 (br d, J=8.7 Hz, 2H), 1.77-1.70 (m, 1H), 1.31-1.24 (m, 2H), 0.96-0.88 (m, 2H), 0.88-0.81 (m, 2H), 0.53 (q, J=3.9 Hz, 1H), 0.32 (dt, J=4.5, 7.6 Hz, 1H).

N-[3-(4,6-dimethylpyrimidin-5-yl)-4-[2-(3-fluoroazetidin-1-yl)ethoxy]phenyl]cyclopropanecarboxamide (386)

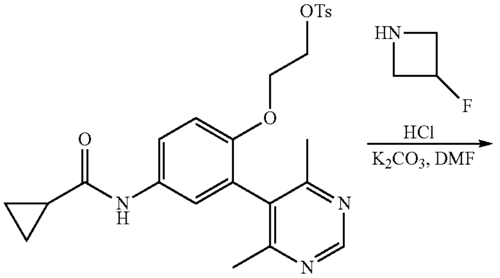

66

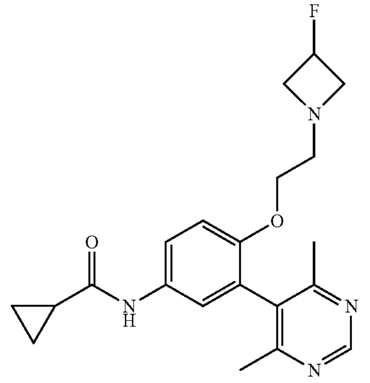

386

To a solution of 2-[4-(cyclopropanecarbonylamino)-2-(4,6-dimethylpyrimidin-5-yl)phenoxy]ethyl 4-methylbenzenesulfonate ((66), 200 mg, 415.31 μmol, 1 eq.) in DMF (2.00 mL) was added $K_2CO_3$ (229.60 mg, 1.66 mmol, 4.00 eq.) and 3-fluoroazetidine; hydrochloride (92.65 mg, 830.63 μmol, 2.0 eq.) under $N_2$. The mixture was stirred in a sealed tube at 80° C. for 16 hrs then the mixture was filtered. The filtrate was purified by prep-HPLC (column: YMC Triart C18 250*50 mm*7 μm; mobile phase: [water (0.05% ammonia hydroxide v/v)-ACN]; B %: 11%-51%, 12 min). N-[3-(4,6-Dimethylpyrimidin-5-yl)-4-[2-(3-fluoroazetidin-1-yl)ethoxy]phenyl]cyclopropanecarboxamide (30 mg, 78.03 μmol, 18.79% yield, 100% purity) was obtained as a white solid.

LCMS (ESI): m/z [M+H] calcd for $C_{21}H_{25}FN_4O_2$: 385.20; found: 385.3.

$^1$H NMR (400 MHZ, methanol-$d_4$) δ=8.75 (s, 1H), 7.48 (dd, J=2.7, 8.9 Hz, 1H), 7.28 (d, J=2.6 Hz, 1H), 6.99 (d, J=9.0 Hz, 1H), 4.96-4.81 (m, 1H), 3.91 (t, J=4.9 Hz, 2H), 3.29-3.22 (m, 2H), 2.94-2.83 (m, 2H), 2.66 (t, J=5.0 Hz, 2H), 2.18 (s, 6H), 1.67-1.60 (m, 1H), 0.86-0.81 (m, 2H), 0.77-0.72 (m, 2H).

N-[3-(4,6-dimethylpyrimidin-5-yl)-4-[2-(3-fluoroazetidin-1-yl)ethoxy]phenyl]benzamide (387)

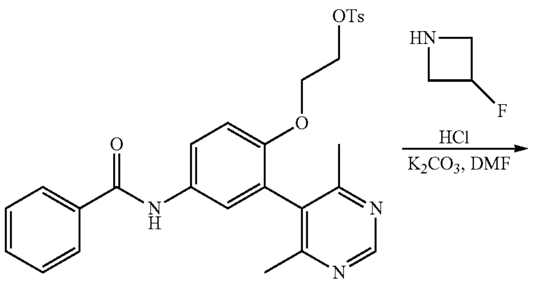

79

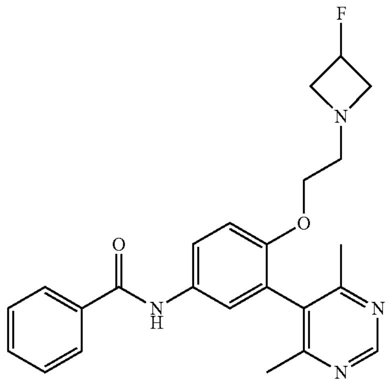

387

To a solution of 2-[4-benzamido-2-(4,6-dimethylpyrimidin-5-yl)phenoxy]ethyl 4-methylbenzenesulfonate ((79), 150 mg, 289.80 μmol, 1 eq.) in DMF (3.00 mL) was added $K_2CO_3$ (160.21 mg, 1.16 mmol, 4.00 eq.) and 3-fluoroazetidine hydrochloride (64.65 mg, 579.60 μmol, 2.0 eq.) under $N_2$. The mixture was stirred in a sealed tube at 80° C. for 16 hrs. The reaction mixture was filtered. The filtrate was purified by prep-HPLC (column: YMC Triart C18 250*50 mm*7 μm; mobile phase: [water (0.05% ammonia hydroxide v/v)-ACN]; B %: 18%-58%, 12 min). N-[3-(4,6-dimethylpyrimidin-5-yl)-4-[2-(3-fluoroazetidin-1-yl)ethoxy] phenyl]benzamide (25 mg, 47.39 μmol, 16.35% yield, 79.7% purity) was obtained as a white solid.

LCMS (ESI): m/z [M+H] calcd for $C_{24}H_{26}FN_4O_2$: 421.2; found: 421.3.

$^1$H NMR (400 MHZ, methanol-$d_4$) δ=8.87 (s, 1H), 7.93 (d, J=7.5 Hz, 2H), 7.79 (dd, J=2.5, 9.0 Hz, 1H), 7.60-7.55 (m, 1H), 7.55-7.49 (m, 3H), 7.17 (d, J=8.9 Hz, 1H), 5.14-4.93 (m, 1H), 4.10 (t, J=4.8 Hz, 2H), 3.50 (br d, J=10.3 Hz, 2H), 3.24-3.12 (m, 2H), 2.93 (br s, 2H), 2.32 (s, 6H).

N-[3-(4,6-dimethylpyrimidin-5-yl)-4-[2-(3-hydroxyazetidin-1-yl)ethoxy]phenyl]cyclopropanecarboxamide (388)

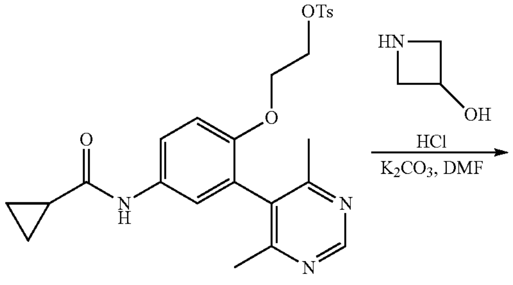

66

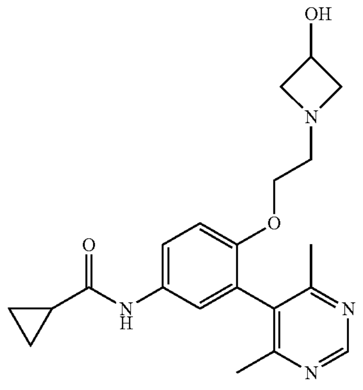

388

To a solution of 2-[4-(cyclopropanecarbonylamino)-2-(4,6-dimethylpyrimidin-5-yl)phenoxy]ethyl 4-methylbenzenesulfonate ((66), 100 mg, 207.66 μmol, 1 eq.) in $CH_3CN$ (2.0 mL) was added $K_2CO_3$ (114.80 mg, 830.63 μmol, 4.00 eq.) and azetidin-3-ol hydrochloride (45.50 mg, 415.31 μmol, 2.0 eq.) under $N_2$. The mixture was stirred in a sealed tube at 80° C. for 16 hrs. Additional DIPEA (53.68 mg, 415.31 μmol, 72.34 μL, 2.00 eq.) and azetidin-3-ol hydrochloride (34.12 mg, 311.49 μmol, 1.5 eq.) were added. The mixture was stirred at 80° C. for another 16 hrs. The reaction mixture was diluted with DMF (2 mL) and concentrated in vacuo to remove ACN. The residue was purified by prep-HPLC (column: YMC Triart C18 250*50 mm*7 μm; mobile phase: [water (0.05% ammonia hydroxide v/v)-ACN]; B %: 6%-46%, 12 min). N-[3-(4,6-dimethylpyrimidin-5-yl)-4-[2-(3-hydroxyazetidin-1-yl)ethoxy]phenyl]cyclopropanecarboxamide (45 mg, 109.42 μmol, 52.69% yield, 93% purity) was obtained as a white solid.

LCMS (ESI): m/z [M+H] calcd for $C_{21}H_{27}N_4O_3$: 383.2; found: 383.3.

$^1$H NMR (400 MHZ, methanol-$d_4$) δ=8.86 (s, 1H), 8.40 (s, 1H), 7.62 (dd, J=2.7, 8.9 Hz, 1H), 7.39 (d, J=2.6 Hz, 1H), 7.12 (d, J=9.0 Hz, 1H), 4.36 (quin, J=6.2 Hz, 1H), 4.14 (t, J=5.0 Hz, 2H), 3.80-3.74 (m, 2H), 3.28-3.19 (m, 4H), 2.29 (s, 6H), 1.77-1.71 (m, 1H), 0.96-0.83 (m, 4H).

N-[3-(4,6-dimethylpyrimidin-5-yl)-4-[2-(3-hydroxyazetidin-1-yl)ethoxy]phenyl]benzamide (389)

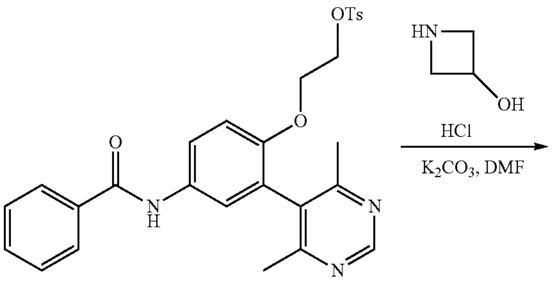

79

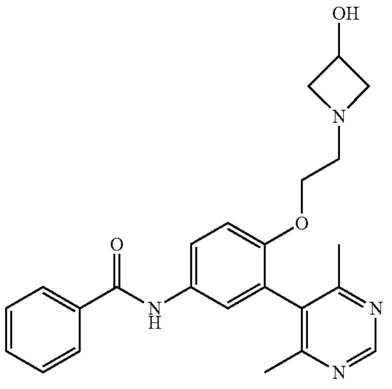

389

To a solution of 2-[4-benzamido-2-(4,6-dimethylpyrimidin-5-yl)phenoxy]ethyl 4-methylbenzenesulfonate ((79), 150 mg, 289.80 μmol, 1 eq.) in DMF (3.00 mL) was added $K_2CO_3$ (160.21 mg, 1.16 mmol, 4.00 eq.) and azetidin-3-ol hydrochloride (63.50 mg, 579.60 μmol, 2.0 eq.) under $N_2$. The mixture was stirred in a sealed tube at 80° C. for 16 hrs. The reaction mixture was filtered. The filtrate was purified by prep-HPLC (column: YMC Triart C18 250*50 mm*7 μm; mobile phase: [water (0.05% ammonia hydroxide v/v)-ACN]; B %: 13%-53%, 12 min). N-[3-(4,6-dimethylpyrimidin-5-yl)-4-[2-(3-hydroxyazetidin-1-yl)ethoxy]phenyl]benzamide (45 mg, 104.81 μmol, 36.17% yield, 97.47% purity) was obtained as a white solid.

LCMS (ESI): m/z [M+H] calcd for $C_{24}H_{26}N_4O_3$: 419.20; found: 419.3.

$^1$H NMR (400 MHZ, chloroform-d) δ=8.94 (s, 1H), 7.95-7.84 (m, 3H), 7.66 (dd, J=2.6, 8.8 Hz, 1H), 7.60-7.54 (m, 1H), 7.54-7.47 (m, 2H), 7.44 (d, J=2.3 Hz, 1H), 6.99 (d, J=8.8 Hz, 1H), 4.30 (quin, J=5.8 Hz, 1H), 3.99 (t, J=5.2 Hz, 2H), 3.43-3.34 (m, 2H), 2.80-2.63 (m, 4H), 2.31 (s, 6H).

N-[3-(4,6-dimethylpyrimidin-5-yl)-4-(2-morpholinoethoxy)phenyl]cyclopropanecarboxamide (390)

Preparation of N-(3-bromo-4-methoxy-phenyl)cyclopropanecarboxamide (80)

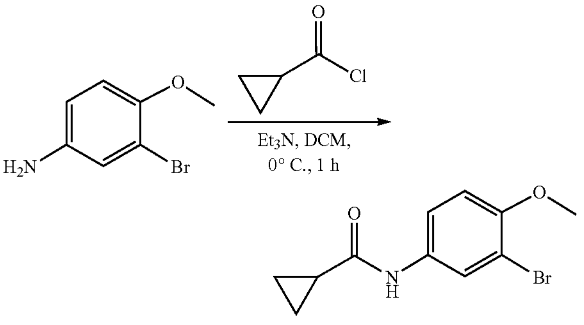

80

To the mixture of 3-bromo-4-methoxy-aniline (10 g, 49.49 mmol, 1 eq.) and $Et_3N$ (10.02 g, 98.99 mmol, 13.78 mL, 2 eq.) in the DCM (100 mL) was added cyclopropanecarbonyl chloride (5.28 g, 50.48 mmol, 4.59 mL, 1.02 eq.) under $N_2$. The mixture was stirred at 0° C. for 1 hr. The reaction mixture was concentrated under vacuum. The residue was poured into water (20 mL). The aqueous phase was extracted with ethyl acetate (100 mL×3). The combined organic phase was dried with anhydrous $Na_2SO_4$, filtered and concentrated in vacuum. The residue was triturated with petroleum ether (100 mL). N-(3-bromo-4-methoxy-phenyl)cyclopropanecarboxamide ((80), 11.43 g, 41.89 mmol, 84.64% yield, 99% purity) was obtained as a purple solid.

$^1$H NMR (400 MHZ, methanol-$d_4$) δ=7.82 (d, J=2.4 Hz, 1H), 7.43 (dd, J=2.6, 8.9 Hz, 1H), 6.98 (d, J=9.0 Hz, 1H), 3.84 (s, 3H), 1.75-1.68 (m, 1H), 0.96-0.89 (m, 2H), 0.89-0.81 (m, 2H).

Preparation of N-(3-bromo-4-hydroxy-phenyl)cyclopropanecarboxamide (81)

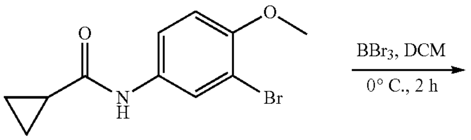

80

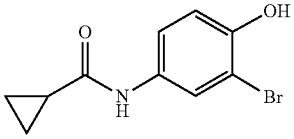

81

To a solution of N-(3-bromo-4-methoxy-phenyl)cyclopropanecarboxamide ((80), 5 g, 18.51 mmol, 1 eq.) in DCM (100 mL) was added $BBr_3$ (6.96 g, 27.77 mmol, 2.68 mL, 1.5 eq.) at 0° C. under $N_2$. The reaction mixture was stirred at 0° C. for 2 hrs. The reaction mixture was quenched with saturated $NaHCO_3$ aq. (300 mL) and stirred at 15° C. for 10 min. The mixture was filtered and the filter cake was concentrated in vacuum. N-(3-bromo-4-hydroxy-phenyl)cyclopropanecarboxamide ((81), 4 g, 15.62 mmol, 84.38% yield) was obtained as a purple solid.

Preparation of N-[3-bromo-4-(2-morpholinoethoxy)phenyl]cyclopropanecarboxamide (82)

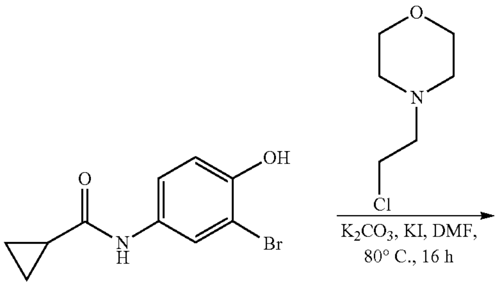

81

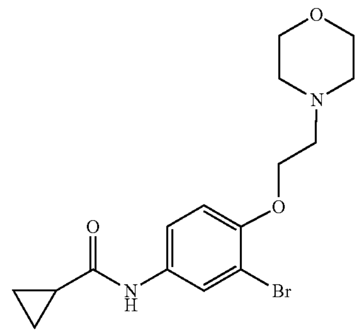

82

To a mixture of N-(3-bromo-4-hydroxy-phenyl)cyclopropanecarboxamide ((81), 3 g, 11.71 mmol, 1 eq.) and 4-(2-chloroethyl) morpholine; hydrochloride (2.61 g, 14.05 mmol, 1.2 eq.) in DMF (20 mL) was added KI (194.46 mg, 1.17 mmol, 0.1 eq.) and $K_2CO_3$ (3.24 g, 23.42 mmol, 2 eq.). The reaction mixture was stirred at 80° C. for 16 hrs. The residue was poured into water (50 mL). The aqueous phase was extracted with ethyl acetate (50 mL×3). The combined organic phase was washed with brine (100 mL), dried with anhydrous $Na_2SO_4$, filtered and concentrated in vacuum. The residue was purified by reversed-phase HPLC (0.1% $NH_3{\cdot}H_2O$). N-[3-bromo-4-(2-morpholinoethoxy)phenyl]cyclopropanecarboxamide ((82), 2.3 g, 6.23 mmol, 53.19% yield, 100% purity) was obtained as a white solid.

Preparation of [5-(cyclopropanecarbonylamino)-2-(2-morpholinoethoxy)phenyl]boronic acid (83)

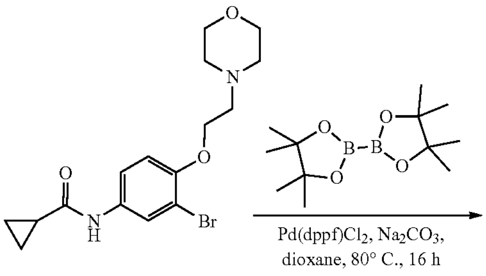

82

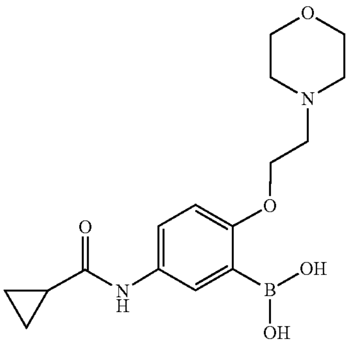

83

To a mixture of N-[3-bromo-4-(2-morpholinoethoxy)phenyl]cyclopropanecarboxamide ((82), 1.9 g, 5.15 mmol, 1 eq.), 4,4,5,5-tetramethyl-2-(4,4,5,5-tetramethyl-1,3,2-dioxaborolan-2-yl)-1,3,2-dioxaborolane (1.44 g, 5.66 mmol, 1.1 eq.) and KOAc (1.01 g, 10.29 mmol, 2 eq.) in dioxane (15 mL) was added $Pd(dppf)Cl_2$ (376.50 mg, 514.55 μmol, 0.1 eq.) under $N_2$. The mixture was stirred at 80° C. for 16 hrs under $N_2$ (monitored by LCMS). The reaction mixture was diluted with MeOH (2 mL), then thiourea resin was added to the mixture. The mixture was stirred at 15° C. for 2 hrs. The mixture was filtered and the filtrate was concentrated under vacuum. The crude product was purified by reversed-phase HPLC (0.1% $NH_3{\cdot}H_2O$). [5-(cyclopropanecarbonylamino)-2-(2-morpholinoethoxy)phenyl]boronic acid ((83), 900 mg, 2.18 mmol, 42.40% yield, 81% purity) as a white solid was obtained.

LCMS (ESI): m/z [M+H] calcd for $C_{16}H_{24}BN_2O_5$: 335.17; found: 335.1.

Preparation of N-[3-(4,6-dimethylpyrimidin-5-yl)-4-(2-morpholinoethoxy)phenyl]cyclopropanecarboxamide (390)

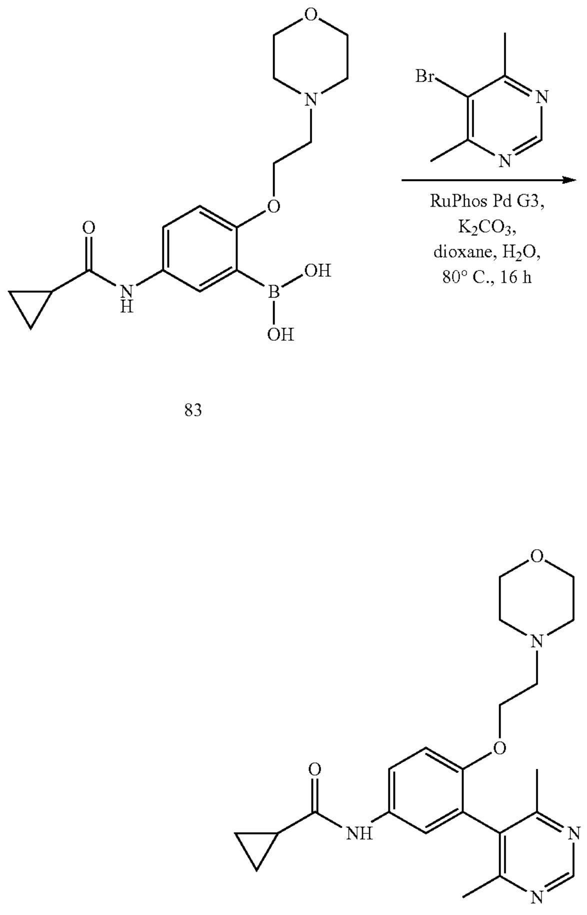

83

390

To a mixture of [5-(cyclopropanecarbonylamino)-2-(2-morpholinoethoxy)phenyl]boronic acid ((83), 50 mg, 149.62 μmol, 1 eq.), 5-bromo-4,6-dimethyl-pyrimidine (33.58 mg, 179.55 μmol, 1.2 eq.) and $K_2CO_3$ (62.04 mg, 448.87 μmol, 3 eq.) in dioxane (2 mL) and $H_2O$ (0.5 mL) was added RuPhos Pd G3 (12.51 mg, 14.96 μmol, 0.1 eq.) under $N_2$. The mixture was stirred at 80° C. for 16 hrs under $N_2$ (monitored by LCMS). The mixture was filtered and the filtrate was concentrated under vacuum. The residue was purified by prep-HPLC (column: Xtimate C18 10μ 250 mm*80 mm; mobile phase: [water (0.05% ammonia hydroxide v/v)-ACN]; B %: 18%-38%, 10 min) followed by lyophilization. N-[3-(4,6-dimethylpyrimidin-5-yl)-4-(2-morpholinoethoxy)phenyl]cyclopropanecarboxamide (18.76 mg, 47.32 μmol, 31.62% yield, 100% purity) as a white solid was obtained.

LCMS (ESI): m/z [M+H] calcd for $C_{22}H_{29}N_4O_3$: 397.22; found: 397.3.

$^1$H NMR (400 MHZ, methanol-$d_4$) δ=8.85 (s, 1H), 7.60 (dd, J=2.6, 8.9 Hz, 1H), 7.52-7.34 (m, 1H), 7.13 (d, J=9.0 Hz, 1H), 4.24-4.13 (m, 2H), 3.64-3.56 (m, 4H), 2.50-2.38 (m, 4H), 2.27 (s, 6H), 1.78-1.70 (m, 1H), 0.97-0.81 (m, 4H).

N-(3-(4-methylpyrimidin-5-yl)-4-(2-morpholinoethoxy)phenyl)cyclopropanecarboxamide (391)

391

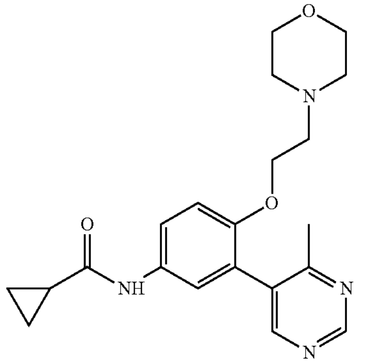

Compound 391 was prepared according to the synthesis described for compound 390, substituting 5-bromo-4-methylpyrimidine for 5-bromo-4,6-dimethylpyrimidine.

LCMS (ESI): m/z [M+H] calcd for $C_{21}H_{27}N_4O_3$: 383.20; found: 383.2.

$^1$H NMR (400 MHZ, methanol-$d_4$) δ=8.98 (s, 1H), 8.52 (s, 1H), 7.59 (dd, J=2.6, 8.9 Hz, 1H), 7.45 (d, J=2.4 Hz, 1H), 7.10 (d, J=8.9 Hz, 1H), 4.13 (t, J=5.3 Hz, 2H), 3.66-3.50 (m, 4H), 2.63 (t, J=5.3 Hz, 2H), 2.42 (s, 3H), 2.39-2.24 (m, 4H), 1.86-1.44 (m, 1H), 1.05-0.89 (m, 2H), 0.88-0.78 (m, 2H).

(1S,2S)—N-[3-(4,6-dimethylpyrimidin-5-yl)-4-(2-morpholinoethoxy)phenyl]-2-fluoro-cyclopropanecarboxamide (392)

Preparation of 4-[2-[2-(4,6-dimethylpyrimidin-5-yl)-4-nitro-phenoxy]ethyl]morpholine (84)

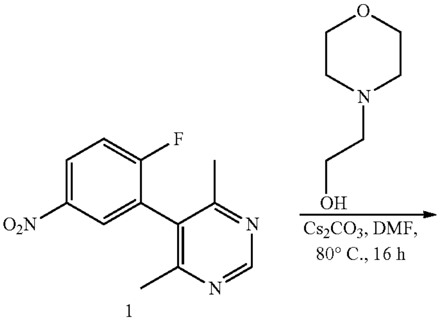

1

-continued

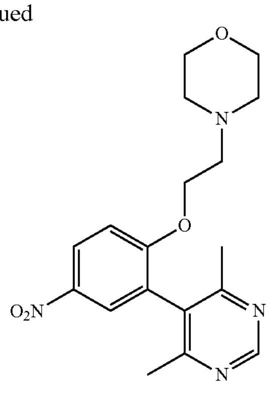

84

To a solution of 5-(2-fluoro-5-nitro-phenyl)-4,6-dimethyl-pyrimidine ((1), 2 g, 8.09 mmol, 1 eq.) in DMF (10 mL) was added $Cs_2CO_3$ (5.27 g, 16.18 mmol, 2 eq.) and 2-morpholinoethanol (1.27 g, 9.71 mmol, 1.19 mL, 1.2 eq.). The reaction mixture was stirred at 80° C. for 16 hrs. The reaction mixture was filtered and the filtrate was concentrated under vacuum to give a residue. 4-[2-[2-(4,6-dimethylpyrimidin-5-yl)-4-nitro-phenoxy]ethyl]morpholine ((84), 2.7 g, crude) was obtained as a black brown oil.

LCMS (ESI): m/z [M+H] calcd for $C_{18}H_{23}N_4O_4$: 359.16; found: 359.3.

Preparation of 3-(4,6-dimethylpyrimidin-5-yl)-4-(2-morpholinoethoxy)aniline (85)

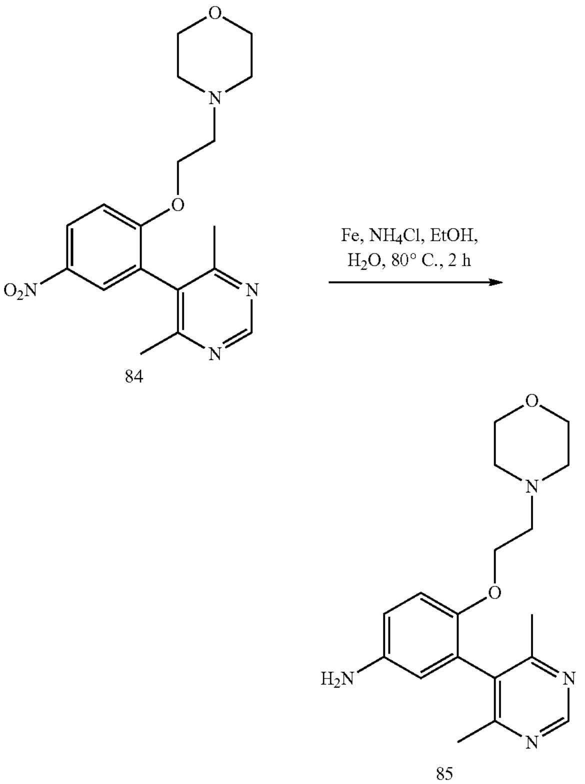

84

85

To a solution of 4-[2-[2-(4,6-dimethylpyrimidin-5-yl)-4-nitro-phenoxy]ethyl]morpholine ((84), 2.7 g, 7.53 mmol, 1 eq.) in EtOH (15 mL) and $H_2O$ (15 mL) was added Fe (1.68 g, 30.13 mmol, 4 eq.) and $NH_4Cl$ (3.22 g, 60.27 mmol, 8 eq.). The reaction mixture was stirred at 80° C. for 2 hrs. The reaction mixture was filtered and the filtrate was concentrated under vacuum to give a residue. The residue was purified by reversed-phase HPLC (0.05% $NH_3{\cdot}H_2O$ conditions). 3-(4,6-dimethylpyrimidin-5-yl)-4-(2-morpholinoethoxy)aniline ((85), 1.64 g, 4.43 mmol, 58.81% yield, 89% purity) was obtained as a black brown oil.

LCMS (ESI): m/z [M+H] calcd for $C_{18}H_{25}N_4O_2$: 329.19; found: 329.3.

Preparation of (1S,2S)—N-[3-(4,6-dimethylpyrimidin-5-yl)-4-(2-morpholinoethoxy)phenyl]-2-fluoro-cyclopropanecarboxamide (392)

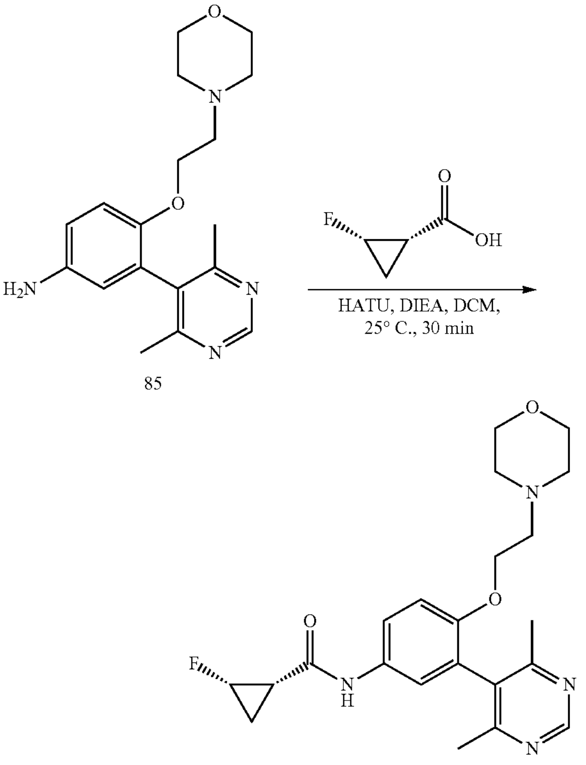

85

392

To a solution of (1S,2S)-2-fluorocyclopropanecarboxylic acid (28.49 mg, 273.71 μmol, 1.01 eq.) in DCM (2 mL) was added HATU (123.65 mg, 325.21 μmol, 1.2 eq.) and DIEA (105.08 mg, 813.01 μmol, 141.61 μL, 3 eq.). Then to the mixture was added 3-(4,6-dimethylpyrimidin-5-yl)-4-(2-morpholinoethoxy)aniline ((85), 100 mg, 271.00 μmol, 1 eq.) after 10 min. The reaction mixture was stirred at 25° C. for 20 min. The reaction mixture was concentrated under vacuum to give a residue. The residue was purified by prep-HPLC (column: Phenomenex Gemini NX-C18 (75*30 mm*3 μm); mobile phase: [water (0.05% ammonia hydroxide v/v)-ACN]; B %: 7%-35%, 7 min) followed by lyophilization. (1S,2S)—N-[3-(4,6-dimethylpyrimidin-5-yl)-4-(2-morpholinoethoxy)phenyl]-2-fluoro-cyclopropanecarboxamide (77.07 mg, 178.51 μmol, 65.87% yield, 96% purity) was obtained as an off-white solid.

LCMS (ESI): m/z [M+H] calcd for $C_{22}H_{27}FN_4O_3$: 415.21; found: 415.3.

$^1$H NMR (400 MHZ, methanol-$d_4$) δ=8.84 (s, 1H), 7.62 (dd, J=2.6, 8.9 Hz, 1H), 7.40 (d, J=2.6 Hz, 1H), 7.12 (d, J=9.0 Hz, 1H), 4.90-4.74 (m, 1H), 4.12 (t, J=5.3 Hz, 2H), 3.64-3.51 (m, 4H), 2.61 (t, J=5.2 Hz, 2H), 2.39-2.29 (m, 4H), 2.27 (s, 6H), 1.95 (tt, J=2.1, 7.0 Hz, 1H), 1.80-1.67 (m, 1H), 1.15 (tdd, J=6.4, 9.2, 12.4 Hz, 1H).

N-(3-(4,6-dimethylpyrimidin-5-yl)-4-(2-morpholinoethoxy)phenyl)-4-methyloxazole-5-carboxamide (393)

393

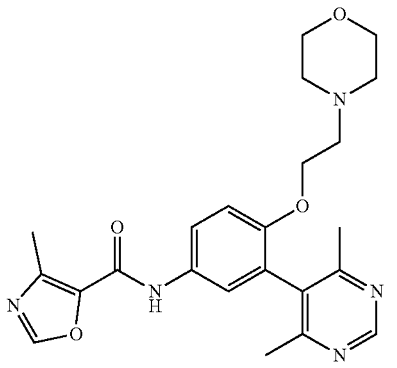

Compound 393 was prepared according to the synthesis described for compound 392, substituting 4-methyloxazole-5-carboxylic acid for (1S,2S)-2-fluorocyclopropanecarboxylic acid.

LCMS (ESI): m/z [M+H] calcd for $C_{23}H_{27}N_5O_4$: 438.21; found: 438.3.

$^1$H NMR (400 MHZ, methanol-$d_4$) δ=8.85 (s, 1H), 8.24 (s, 1H), 7.75 (dd, J=2.7, 8.9 Hz, 1H), 7.49 (d, J=2.6 Hz, 1H), 7.17 (d, J=8.9 Hz, 1H), 4.15 (t, J=5.2 Hz, 2H), 3.63-3.52 (m, 4H), 2.62 (t, J=5.2 Hz, 2H), 2.49 (s, 3H), 2.35-2.30 (m, 4H), 2.29 (s, 6H).

N-(3-(4,6-dimethylpyrimidin-5-yl)-4-(2-morpholinoethoxy)phenyl)-1-methyl-1H-pyrazole-5-carboxamide (394)

394

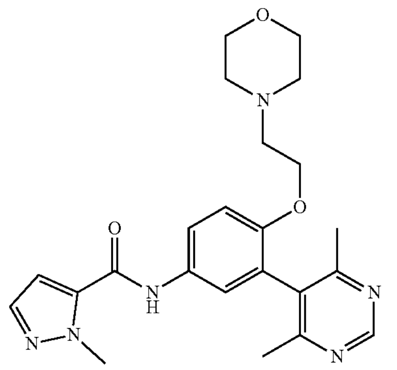

Compound 394 was prepared according to the synthesis described for compound 392, substituting 1-methyl-1H-pyrazole-5-carboxylic acid for (1S,2S)-2-fluorocyclopropanecarboxylic acid.

LCMS (ESI): m/z [M+H] calcd for $C_{23}H_{28}N_6O_3$: 437.22; found: 437.3.

$^1$H NMR (400 MHZ, methanol-$d_4$) δ=8.85 (s, 1H), 7.75 (dd, J=2.6, 8.9 Hz, 1H), 7.50 (dd, J=2.3, 7.9 Hz, 2H), 7.17 (d, J=9.0 Hz, 1H), 6.95 (d, J=2.1 Hz, 1H), 4.24-4.06 (m, 5H), 3.63-3.51 (m, 4H), 2.62 (t, J=5.2 Hz, 2H), 2.40-2.24 (m, 10H).

N-[3-(4,6-dimethylpyrimidin-5-yl)-4-(2-morpholinoethoxy)phenyl]-4-fluoro-2-methyl-pyrazole-3-carboxamide (395)

Preparation of methyl 4-fluoro-2-methyl-pyrazole-3-carboxylate (86)

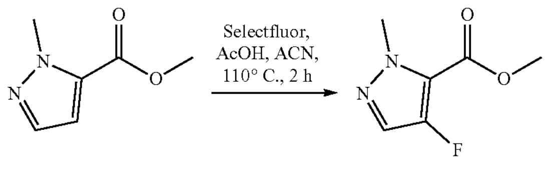

86

To a solution of methyl 2-methylpyrazole-3-carboxylate (5 g, 35.68 mmol, 1 eq.) in $CH_3CN$ (50 mL) was added Select F (25.28 g, 71.36 mmol, 2 eq.) and HOAc (10 mL). The mixture was stirred at 100° C. for 16 hrs (monitored by LCMS). The mixture was diluted with water (200 mL) and then extracted with ethyl acetate (200 mL×2). The combined organic phase was washed with brine (100 mL), dried over anhydrous $Na_2SO_4$, filtered and concentrated in vacuo (water bath was kept at room temperature to avoid loss of product under vacuum as product is very volatile). The residue was purified by flash silica gel chromatography (ISCOR; 20 g SepaFlash® Silica Flash Column, eluent of 0~10% ethyl acetate/petroleum ether gradient at 35 mL/min). Methyl 4-fluoro-2-methyl-pyrazole-3-carboxylate ((86), 1.4 g, 8.85 mmol, 24.81% yield) was obtained as a white solid.

LCMS (ESI): m/z [M+H] calcd for $C_6H_8FN_2O_2$: 159.03, found: 159.1.

$^1$H NMR (400 MHZ, chloroform-d) δ=7.34 (d, J=4.4 Hz, 1H), 4.12 (d, J=0.8 Hz, 3H), 3.94 (s, 3H).

Preparation of 4-fluoro-2-methyl-pyrazole-3-carboxylic acid (87)

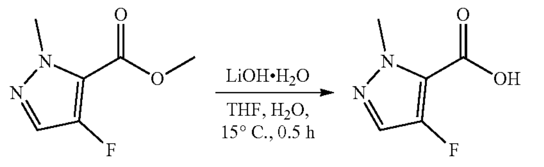

86 87

To a mixture of methyl 4-fluoro-2-methyl-pyrazole-3-carboxylate ((86), 180 mg, 1.14 mmol, 1 eq.) in MeOH (3 mL) and $H_2O$ (1 mL) was added $LiOH \cdot H_2O$ (95.53 mg, 2.28 mmol, 2 eq.). The mixture was stirred at 15° C. for 30 min (monitored by LCMS). The mixture was concentrated to remove excess EtOH. The residue was acidified with 1M HCl aq., and the pH was adjusted to 6-7. The mixture was concentrated and 4-fluoro-2-methyl-pyrazole-3-carboxylic acid ((87), 140 mg, crude) was obtained as a white solid.

Preparation of N-[3-(4,6-dimethylpyrimidin-5-yl)-4-(2-morpholinoethoxy)phenyl]-4-fluoro-2-methyl-pyrazole-3-carboxamide (395)

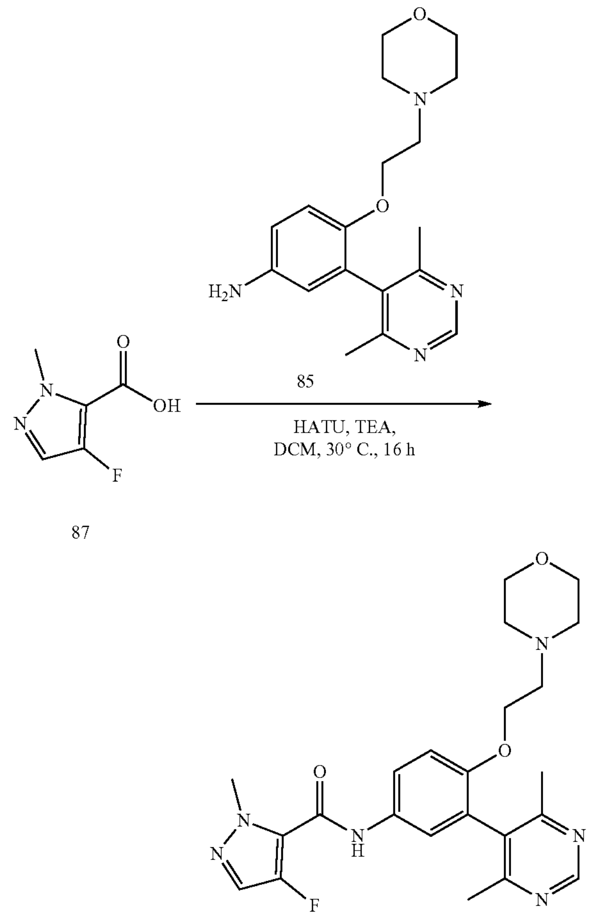

85

87

395

To a solution of 3-(4,6-dimethylpyrimidin-5-yl)-4-(2-morpholinoethoxy)aniline ((85), 50 mg, 152.25 μmol, 1 eq.) in DCM (1 mL) was added HATU (86.83 mg, 228.37 μmol, 1.5 eq.), TEA (46.22 mg, 456.75 μmol, 63.57 μL, 3 eq.) and 4-fluoro-2-methyl-pyrazole-3-carboxylic acid ((87), 26.33 mg, 182.70 μmol, 1.2 eq.). The mixture was stirred at 30° C. for 16 hrs. The mixture was concentrated in vacuo. The residue was purified by prep-HPLC (TFA condition, column: Phenomenex Gemini-NX C18 75*30 mm*3 μm; mobile phase: [water (0.1% TFA)-ACN]; B %: 15%-25%, 7 min). N-[3-(4,6-dimethylpyrimidin-5-yl)-4-(2-morpholinoethoxy)phenyl]-4-fluoro-2-methyl-pyrazole-3-carboxamide (64.25 mg, 139.95 μmol, 91.92% yield, 99% purity) was obtained as a white solid.

LCMS (ESI): m/z [M+H] calcd for $C_{23}H_{28}FN_6O_3$: 455.0, found: 455.3.

$^1$H NMR (400 MHZ, methanol-d$_4$) δ=8.92 (s, 1H), 7.80 (dd, J=2.3, 8.9 Hz, 1H), 7.55 (d, J=2.1 Hz, 1H), 7.47 (d, J=4.3 Hz, 1H), 7.26 (d, J=9.0 Hz, 1H), 4.46-4.41 (m, 2H), 4.05 (s, 3H), 3.96-3.60 (m, 4H), 3.52-3.48 (m, 2H), 3.25-2.96 (m, 4H), 2.40-2.22 (m, 6H).

N-[4-(azetidin-3-yloxy)-3-(4,6-dimethylpyrimidin-5-yl)phenyl]cyclopropanecarboxamide (396)

Preparation of tert-butyl 3-[2-(4,6-dimethylpyrimidin-5-yl)-4-nitro-phenoxy]azetidine-1-carboxylate (88)

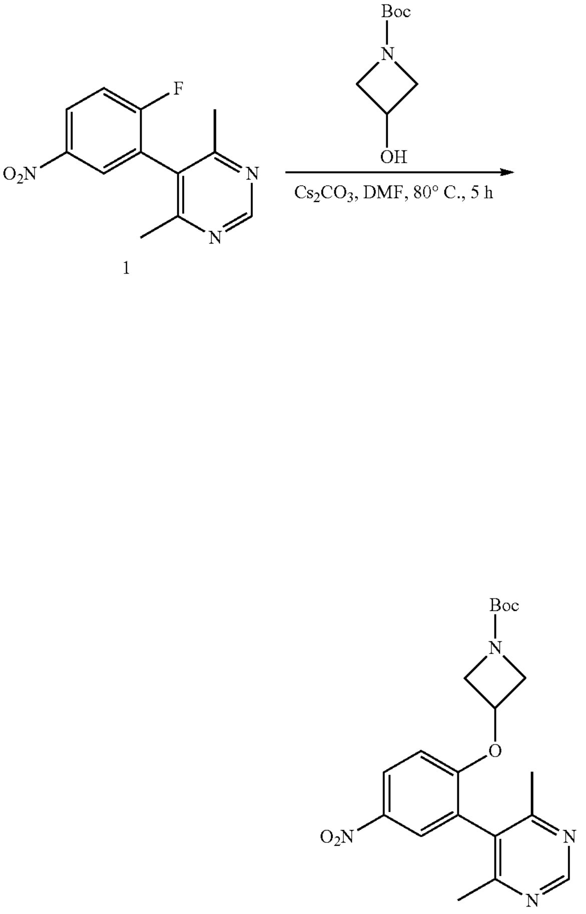

1

88

To a solution of 5-(2-fluoro-5-nitro-phenyl)-4,6-dimethyl-pyrimidine ((1), 1.5 g, 6.07 mmol, 1 eq.) and tert-butyl 3-hydroxyazetidine-1-carboxylate (1.26 g, 7.28 mmol, 1.2 eq.) in DMF (15 mL) was added $Cs_2CO_3$ (3.95 g, 12.13 mmol, 2 eq.). The reaction mixture was stirred at 80° C. for 5 hrs (monitored by LC-MS). The reaction mixture was poured into water (30 mL). The aqueous phase was extracted with EtOAc (20 mL×3). The combined organic phase was washed with brine (30 mL), dried with anhydrous $Na_2SO_4$, filtered and the filtrate was concentrated under vacuum to give a residue. Tert-butyl 3-[2-(4,6-dimethylpyrimidin-5-yl)-4-nitro-phenoxy]azetidine-1-carboxylate ((88), 2.4 g, crude) was obtained as a brown oil.

LCMS (ESI): m/z [M+H] calcd for $C_{20}H_{25}N_4O_5$: 401.17; found: 401.2.

Preparation of tert-butyl 3-[4-amino-2-(4,6-dimethylpyrimidin-5-yl)phenoxy]azetidine-1-carboxylate (89)

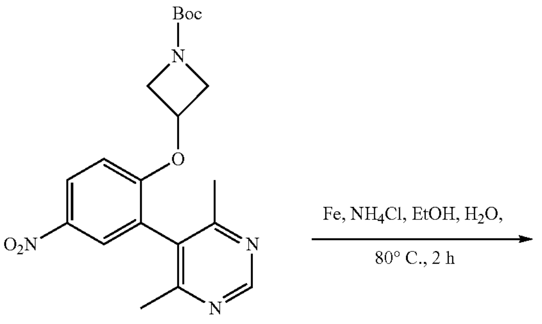

88

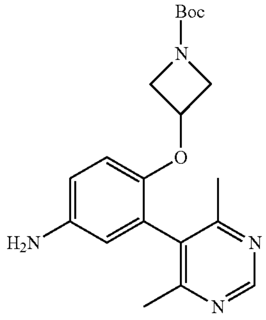

89

The mixture of tert-butyl 3-[2-(4,6-dimethylpyrimidin-5-yl)-4-nitro-phenoxy]azetidine-1-carboxylate ((88), 2.4 g, 5.99 mmol, 1 eq.), Fe (1.34 g, 23.97 mmol, 4 eq.) and $NH_4Cl$ (2.56 g, 47.95 mmol, 8 eq.) in EtOH (10 mL) and $H_2O$ (10 mL) was stirred at 80° C. for 2 hrs (monitored by LC-MS). The reaction mixture was filtered and the filtrate was concentrated under vacuum to give a residue. The residue was dissolved in MeOH (30 mL). The mixture was filtered and the filtrate was concentrated under vacuum to give a residue. The residue was purified by flash silica gel chromatography (ISCO®; 40 g SepaFlash® Silica Flash Column, eluent of 100~40% ethyl acetate/methanol). Tert-butyl 3-[4-amino-2-(4,6-dimethylpyrimidin-5-yl)phenoxy]azetidine-1-carboxylate ((89), 2 g, 5.40 mmol, 90.08% yield) was obtained as a yellow solid.

LCMS (ESI): m/z [M+H] calcd for $C_{20}H_{27}N_4O_3$: 371.20; found: 371.2.

Preparation of N-[4-(azetidin-3-yloxy)-3-(4,6-dimethylpyrimidin-5-yl)phenyl]cyclopropanecarboxamide (396)

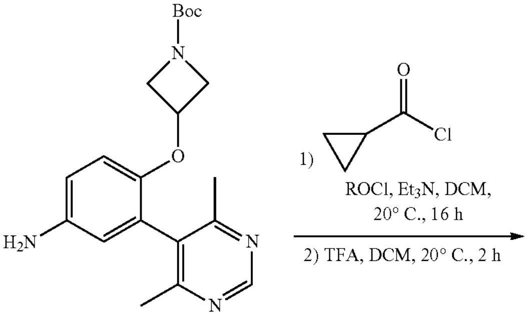

89

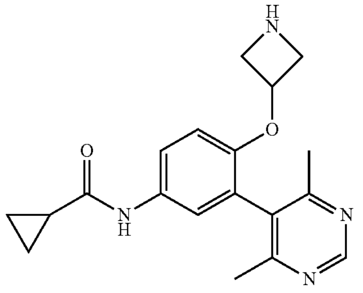

396

To a solution of tert-butyl 3-[4-amino-2-(4,6-dimethylpyrimidin-5-yl)phenoxy]azetidine-1-carboxylate ((89), 100 mg, 269.95 μmol, 1 eq.) and TEA (54.63 mg, 539.89 μmol, 75.15 μL, 2 eq.) in DCM (1.5 ml) was added cyclopropanecarbonyl chloride (33.86 mg, 323.94 μmol, 29.45 μL, 1.2 eq.) in DCM (0.5 mL) dropwise at 0° C. The reaction mixture was stirred at 20° C. for 16 hrs. To the mixture was added TFA (2.31 g, 20.26 mmol, 1.5 mL, 75.05 eq.). The reaction mixture was stirred at 20° C. for 2 hrs (monitored by LC-MS). The reaction mixture was concentrated under vacuum to give a residue. The residue was purified by prep-HPLC (column: Phenomenex Gemini-NX C18 75*30 mm*3 μm; mobile phase: [water (0.1% TFA)-ACN]; B %: 10%-20%, 7 min) followed by lyophilization. N-[4-(azetidin-3-yloxy)-3-(4,6-dimethylpyrimidin-5-yl)phenyl]cyclopropanecarboxamide (42.60 mg, 93.22 μmol, 34.53% yield, 99% purity, TFA) was obtained as a yellow solid.

LCMS (ESI): m/z [M+H] calcd for $C_{19}H_{22}N_4O_2$: 339.17; found: 339.2.

$^1H$ NMR (400 MHz, methanol-$d_4$) δ=8.93 (s, 1H), 7.63 (dd, J=2.7, 8.9 Hz, 1H), 7.45 (d, J=2.7 Hz, 1H), 6.86 (d, J=8.9 Hz, 1H), 5.22-5.12 (m, 1H), 4.50 (dd, J=6.7, 12.7 Hz, 2H), 3.97 (dd, J=4.9, 12.6 Hz, 2H), 2.32 (s, 6H), 1.74 (tt, J=4.6, 7.8 Hz, 1H), 0.97-0.81 (m, 4H).

N-(4-(azetidin-3-yloxy)-3-(4,6-dimethylpyrimidin-5-yl)phenyl) butyramide (397)

397

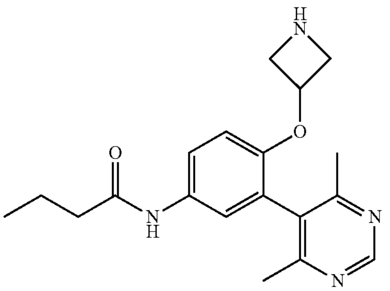

Compound 397 was prepared according to the synthesis described for compound 396, substituting butyryl chloride for cyclopropanecarbonyl chloride.

LCMS (ESI): m/z [M+H] calcd for $C_{19}H_{24}N_4O_2$: 341.19; found: 341.2.

$^1$H NMR (400 MHZ, methanol-$d_4$) δ=8.93 (s, 1H), 7.66 (dd, J=2.6, 8.9 Hz, 1H), 7.45 (d, J=2.6 Hz, 1H), 6.87 (d, J=8.9 Hz, 1H), 5.22-5.12 (m, 1H), 4.51 (dd, J=6.7, 12.7 Hz, 2H), 3.97 (dd, J=4.8, 12.7 Hz, 2H), 2.42-2.25 (m, 8H), 1.80-1.63 (m, 2H), 0.99 (t, J=7.4 Hz, 3H).

N-(4-(azetidin-3-yloxy)-3-(4,6-dimethylpyrimidin-5-yl)phenyl)-1-fluorocyclopropane-1-carboxamide (398)

398

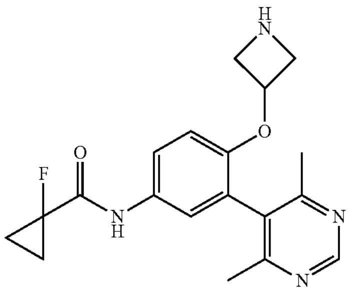

Compound 398 was prepared according to the synthesis described for compound 396, substituting 1-fluorocyclopropane-1-carbonyl chloride for cyclopropanecarbonyl chloride.

LCMS (ESI): m/z [M+H] calcd for $C_{19}H_{21}FN_4O_2$: 357.16; found: 357.2.

$^1$H NMR (400 MHZ, methanol-$d_4$) δ=8.92 (s, 1H), 7.74 (dd, J=2.7, 8.9 Hz, 1H), 7.49 (d, J=2.6 Hz, 1H), 6.89 (d, J=9.0 Hz, 1H), 5.23-5.15 (m, 1H), 4.52 (dd, J=6.6, 12.7 Hz, 2H), 3.98 (dd, J=4.8, 12.6 Hz, 2H), 2.32 (s, 6H), 1.44-1.34 (m, 4H).

N-(4-(azetidin-3-yloxy)-3-(4,6-dimethylpyrimidin-5-yl)phenyl)-1-methyl-1H-pyrazole-5-carboxamide (399)

399

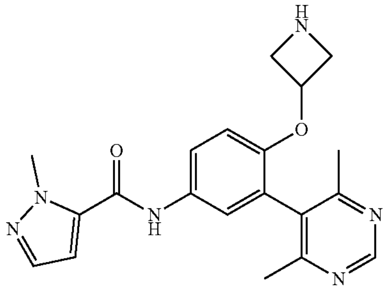

Compound 399 was prepared according to the synthesis described for compound 396, substituting 1-methyl-1H-pyrazole-5-carbonyl chloride for cyclopropanecarbonyl chloride.

LCMS (ESI): m/z [M+H] calcd for $C_{20}H_{22}N_6O_2$: 379.18; found: 379.2.

$^1$H NMR (400 MHZ, methanol-$d_4$) δ=9.01 (s, 1H), 7.79 (dd, J=2.6, 8.9 Hz, 1H), 7.60 (d, J=2.6 Hz, 1H), 7.50 (d, J=2.1 Hz, 1H), 7.03-6.88 (m, 2H), 5.28-5.18 (m, 1H), 4.54 (dd, J=6.7, 12.5 Hz, 2H), 4.14 (s, 3H), 4.01 (dd, J=4.9, 12.5 Hz, 2H), 2.38 (s, 6H).

N-(4-(azetidin-3-yloxy)-3-(4,6-dimethylpyrimidin-5-yl)phenyl)benzamide (400)

400

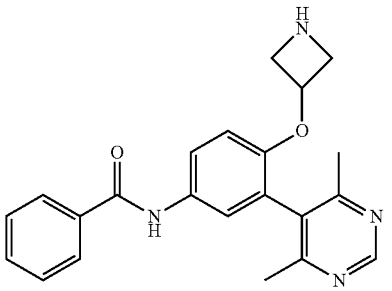

Compound 400 was prepared according to the synthesis described for compound 396, substituting benzoyl chloride for cyclopropanecarbonyl chloride.

LCMS (ESI): m/z [M+H] calcd for $C_{22}H_{22}N_4O_2$: 375.17; found: 375.2.

$^1$H NMR (400 MHZ, methanol-$d_4$) δ=8.91 (s, 1H), 7.99-7.88 (m, 2H), 7.83 (dd, J=2.6, 8.9 Hz, 1H), 7.64-7.44 (m, 4H), 6.92 (d, J=8.9 Hz, 1H), 5.26-5.15 (m, 1H), 4.53 (dd, J=6.7, 12.7 Hz, 2H), 3.99 (dd, J=4.9, 12.6 Hz, 2H), 2.34 (s, 6H).

N-(3-(4,6-dimethylpyrimidin-5-yl)-4-(2-morpholinoethoxy)phenyl)-2-ethoxycyclopropane-1-carboxamide (401)

401

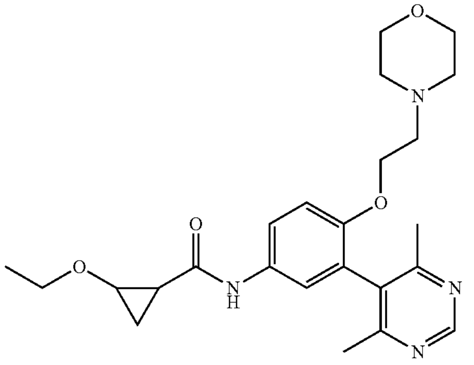

Compound 401 was prepared according to the synthesis described for compound 396, substituting 2-ethoxycyclopropane-1-carbonyl chloride for cyclopropanecarbonyl chloride.

LCMS (ESI): m/z [M+H] calcd for $C_{24}H_{33}N_4O_4$: 441.0, found: 441.3.

$^1$H NMR (400 MHZ, methanol-$d_4$) δ 8.85 (s, 1H), 7.59 (dd, J=8.9, 2.6 Hz, 1H), 7.38 (d, J=2.6 Hz, 1H), 7.13 (d, J=8.9 Hz, 1H), 4.16 (t, J=5.1 Hz, 2H), 3.65-3.56 (m, 7H), 2.75 (br s, 2H), 2.43 (br s, 4H), 2.27 (s, 6H), 1.88 (ddd, J=9.4, 6.0, 1.9 Hz, 1H), 1.28-1.16 (m, 5H).

N-(4-(azetidin-3-yloxy)-3-(4,6-dimethylpyrimidin-5-yl)phenyl)-4-fluoro-1-methyl-1H-pyrazole-5-carboxamide (402)

402

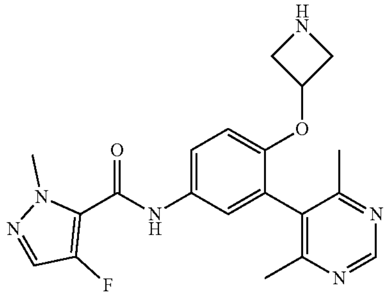

Compound 402 was prepared according to the synthesis described for compound 396, substituting 4-fluoro-1-methyl-1H-pyrazole-5-carbonyl chloride for cyclopropanecarbonyl chloride.

LCMS (ESI): m/z [M+H] calcd for $C_{20}H_{21}FN_6O_2$: 397.17; found: 397.2.

$^1$H NMR (400 MHZ, methanol-$d_4$) δ=8.95 (s, 1H), 7.77 (dd, J=2.6, 8.9 Hz, 1H), 7.57 (d, J=2.6 Hz, 1H), 7.46 (d, J=4.4 Hz, 1H), 6.93 (d, J=8.9 Hz, 1H), 5.26-5.16 (m, 1H), 4.53 (dd, J=6.6, 12.8 Hz, 2H), 4.04 (d, J=0.6 Hz, 3H), 3.99 (dd, J=4.9, 12.6 Hz, 2H), 2.35 (s, 6H).

N-[3-(4,6-dimethylpyrimidin-5-yl)-4-[(3R)-pyrrolidin-3-yl]oxy-phenyl]cyclopropanecarboxamide (403)

Preparation of tert-butyl (3R)-3-[2-bromo-4-(cyclopropanecarbonylamino)phenoxy]pyrrolidine-1-carboxylate (90)

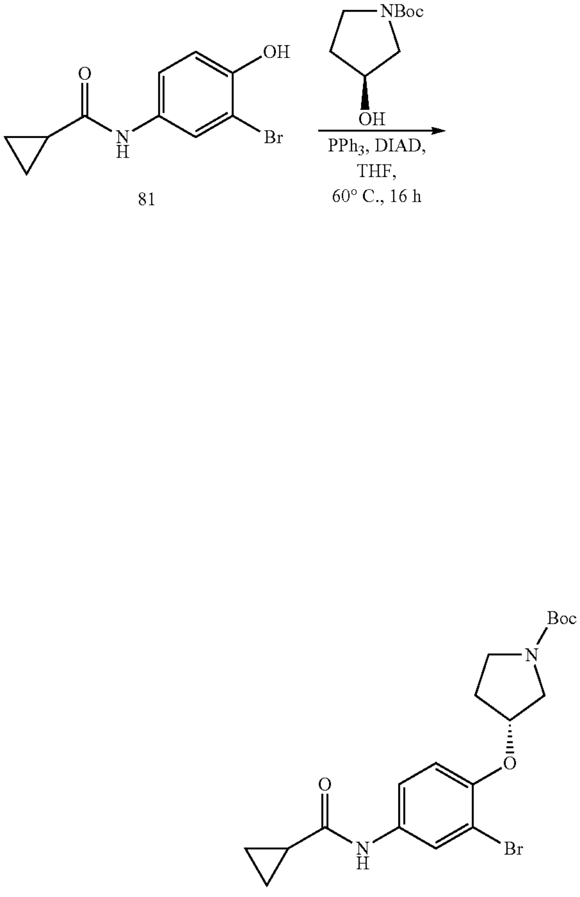

DIAD (1.78 g, 8.81 mmol, 1.71 mL, 1.5 eq.) in THF (5 mL) was added dropwise to a solution of tert-butyl (3S)-3-hydroxypyrrolidine-1-carboxylate (1.1 g, 5.87 mmol, 1 eq.), N-(3-bromo-4-hydroxy-phenyl)cyclopropanecarboxamide ((81), 1.50 g, 5.87 mmol, 1 eq.) and $PPh_3$ (3.08 g, 11.75 mmol, 2.0 eq.) in THF (20 mL) at 0° C. The resultant solution was stirred at 60° C. for 16 hrs (monitored by LC-MS). The reaction solution was quenched with water (0.2 mL). The resultant solution was concentrated in vacuo to give a residue. The residue was purified by flash silica gel chromatography (80 g SepaFlash® Silica Flash Column, eluent of 0~50% ethyl acetate/petroleum ether gradient at 60 mL/min). tert-Butyl (3R)-3-[2-bromo-4-(cyclopropanecarbonylamino)phenoxy]pyrrolidine-1-carboxylate ((90), 200 mg, 470.24 μmol, 8.00% yield, 100% purity) was obtained as a light yellow oil.

LCMS (ESI): m/z [M−56+H] calcd for $C_{15}H_{18}Br^{79/81}N_2O_4$: 369.04 and 371.04; found: 368.9 and 370.9.

Preparation of tert-butyl (3R)-3-[4-(cyclopropanecarbonylamino)-2-(4,6-dimethylpyrimidin-5-yl) phenoxy]pyrrolidine-1-carboxylate (91)

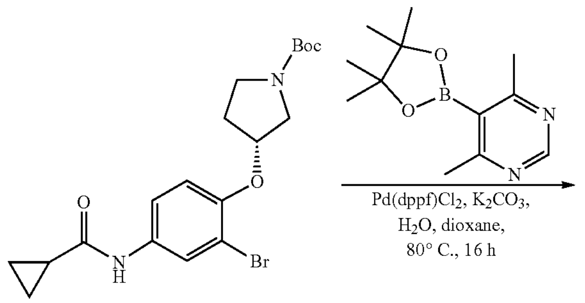

90

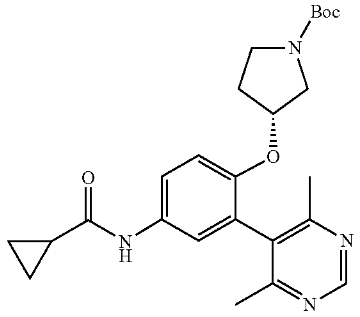

91

A mixture of tert-butyl (3R)-3-[2-bromo-4-(cyclopropanecarbonylamino)phenoxy]pyrrolidine-1-carboxylate ((90), 200 mg, 470.24 μmol, 1 eq.), 4,6-dimethyl-5-(4,4,5,5-tetramethyl-1,3,2-dioxaborolan-2-yl)pyrimidine (440.34 mg, 1.88 mmol, 106.64 μL, 4 eq.), $Pd(dppf)Cl_2$ (34.41 mg, 47.02 μmol, 0.1 eq.) and $K_2CO_3$ (97.48 mg, 705.36 μmol, 1.5 eq.) in a mixed solvent of dioxane (1 mL) and $H_2O$ (0.1 mL) was stirred under $N_2$ at 80° C. for 16 hrs (monitored by LC-MS). The reaction solution was concentrated in vacuo to give a residue. The residue was purified by flash silica gel chromatography (12 g SepaFlash® Silica Flash Column, eluent of 0~100% ethyl acetate/petroleum ether gradient at 35 mL/min). Tert-butyl (3R)-3-[4-(cyclopropanecarbonylamino)-2-(4,6-dimethylpyrimidin-5-yl)phenoxy]pyrrolidine-1-carboxylate ((91), 55 mg, 121.53 μmol, 25.85% yield, 100% purity) was obtained as a colorless oil.

LCMS (ESI): m/z [M−56+H] calcd for $C_{25}H_{33}N_4O_4$: 453.24; found: 453.2.

Preparation of N-[3-(4,6-dimethylpyrimidin-5-yl)-4-[(3R)-pyrrolidin-3-yl]oxy-phenyl]cyclopropanecarboxamide (403)

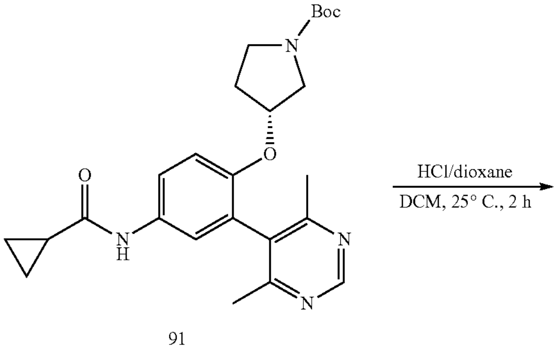

91

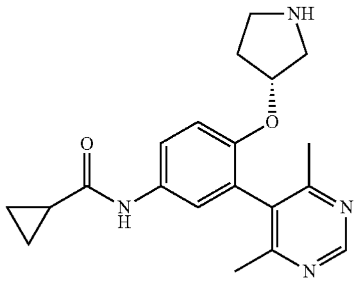

403

To the solution of tert-butyl (3R)-3-[4-(cyclopropanecarbonylamino)-2-(4,6-dimethylpyrimidin-5-yl)phenoxy]pyrrolidine-1-carboxylate ((91), 55 mg, 121.53 μmol, 1 eq.) in MeOH (1.5 mL) was added HCl/dioxane (4 M, 640.66 mL, 21085.78 eq.). The mixture was stirred at 25° C. for 2 hrs (monitored by LC-MS). The reaction mixture was concentrated in vacuo to give a residue. The residue was purified by prep-HPLC (column: Phenomenex Luna C18 150*25 mm*10 μm; mobile phase: [water (0.1% TFA)-ACN]; B %: 1%-30%, 10 min). N-[3-(4,6-dimethylpyrimidin-5-yl)-4-[(3R)-pyrrolidin-3-yl]oxy-phenyl]cyclopropanecarboxamide (38.07 mg, 108.02 μmol, 88.88% yield, 100% purity) was obtained as a yellow solid.

LCMS (ESI): m/z [M+H] calcd for $C_{20}H_{25}N_4O_2$: 353.19; found: 353.3.

$^1H$ NMR (400 MHZ, methanol-$d_4$) δ=8.89 (s, 1H), 7.65 (dd, J=2.7, 8.9 Hz, 1H), 7.41 (d, J=2.7 Hz, 1H), 7.16 (d, J=9.0 Hz, 1H), 5.17-5.12 (m, 1H), 3.63-3.54 (m, 1H), 3.42-3.34 (m, 1H), 3.30-3.27 (m, 1H), 3.09 (dt, J=7.1, 10.9 Hz, 1H), 2.32-2.22 (m, 7H), 2.18-2.10 (m, 1H), 1.78-1.71 (m, 1H), 0.96-0.83 (m, 4H).

(S)—N-(3-(4,6-dimethylpyrimidin-5-yl)-4-(pyrrolidin-3-yloxy)phenyl)cyclopropanecarboxamide (404)

404

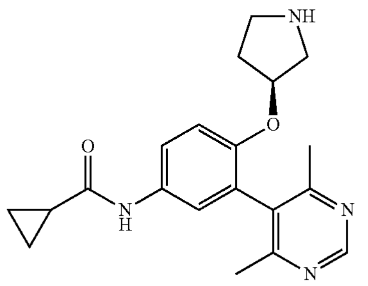

Compound 404 was prepared according to the synthesis described for compound 403, substituting tert-butyl (R)-3-hydroxypyrrolidine-1-carboxylate for tert-butyl (3S)-3-hydroxypyrrolidine-1-carboxylate.

LCMS (ESI): m/z [M+H] calcd for $C_{20}H_{25}N_4O_2$: 353.19; found: 353.2.

$^1$H NMR (400 MHZ, methanol-$d_4$) δ=8.92 (s, 1H), 7.56 (dd, J=2.6, 8.9 Hz, 1H), 7.38 (d, J=2.6 Hz, 1H), 7.10 (d, J=9.0 Hz, 1H), 5.09 (br t, J=4.7 Hz, 1H), 3.50 (dd, J=5.0, 13.1 Hz, 1H), 3.30-3.19 (m, 2H), 3.07-2.98 (m, 1H), 2.27 (s, 6H), 2.24-2.16 (m, 1H), 2.12-2.02 (m, 1H), 1.73-1.64 (m, 1H), 0.85-0.82 (m, 2H), 0.77 (td, J=3.0, 7.9 Hz, 2H).

N-[4-[[(2R)-azetidin-2-yl]methoxy]-3-(4,6-dimethylpyrimidin-5-yl)phenyl]cyclopropanecarboxamide (405)

Preparation of tert-butyl (2R)-2-[[2-bromo-4-(cyclopropanecarbonylamino) phenoxy]methyl]azetidine-1-carboxylate (92)

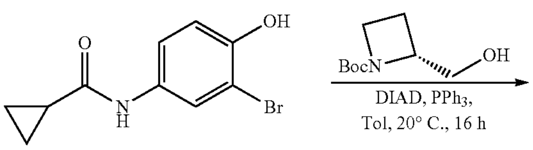

81

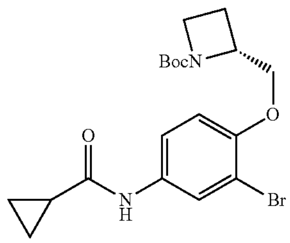

92

To a solution of N-(3-bromo-4-hydroxy-phenyl)cyclopropanecarboxamide ((81), 2.05 g, 8.01 mmol, 1.5 eq.) and tert-butyl (2R)-2-(hydroxymethyl) azetidine-1-carboxylate (1 g, 5.34 mmol, 1 eq) in toluene (10 mL) was added $PPh_3$ (4.20 g, 16.02 mmol, 3 eq.) and DIAD (3.24 g, 16.02 mmol, 3.12 mL, 3 eq.). The mixture was stirred at 20° C. for 16 hrs (monitored by LC-MS). The reaction mixture was partitioned between water (10 mL) and ethyl acetate (5 mL). The organic phase was separated, washed with water (10 mL×3), dried over sodium sulfate, filtered and concentrated under reduced pressure to give a residue. The residue was purified by column chromatography with petroleum ether: ethyl acetate=3:1. The organic phase was concentrated under reduced pressure to give tert-butyl (2R)-2-[[2-bromo-4-(cyclopropanecarbonylamino)phenoxy]methyl]azetidine-1-carboxylate ((92), 2.5 g, 2.94 mmol, 55.03% yield, 50% purity) was obtained as a white solid.

$^1$H NMR (400 MHZ, chloroform-$d_4$) δ 0.74-0.80 (m, 2H), 1.02-1.08 (m, 2H), 1.41 (s, 9H), 1.50-1.58 (m, 1H), 2.30-2.45 (m, 2H), 3.83-3.91 (m, 1H), 3.98-4.08 (m, 2H), 4.37 (br s, 1H), 4.46-4.54 (m, 1H), 6.84 (d, J=8.88 Hz, 1H), 7.45 (br s, 1H), 8.15 (br s, 1H).

Preparation of tert-butyl (2R)-2-[[4-(cyclopropanecarbonylamino)-2-(4,4,5,5-tetramethyl-1,3,2-dioxaborolan-2-yl)phenoxy]methyl]azetidine-1-carboxylate (93)

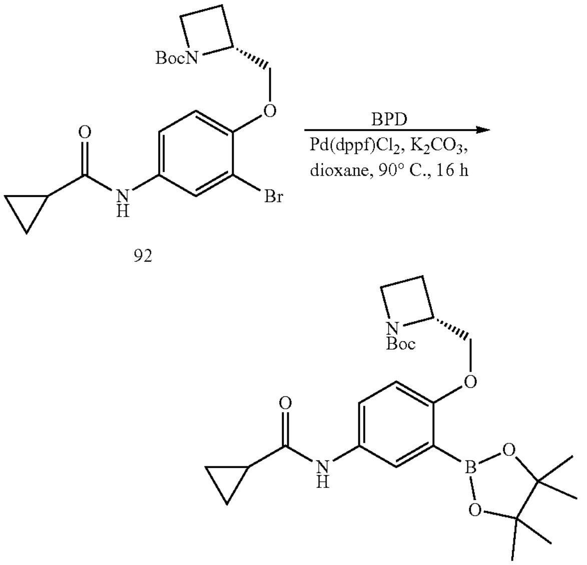

92

93

To a solution of BPD (895.58 mg, 3.53 mmol, 3 eq.) and tert-butyl (2R)-2-[[2-bromo-4-(cyclopropanecarbonylamino)phenoxy]methyl]azetidine-1-carboxylate (1 g, 1.18 mmol, 1 eq.) in dioxane (10 mL) was added Pd(dppf)$Cl_2$ (86.02 mg, 117.56 μmol, 0.1 eq.) and $K_2CO_3$ (324.95 mg, 2.35 mmol, 2 eq.). The mixture was stirred at 90° C. for 16 hrs under $N_2$ atmosphere (monitored by LC-MS). The residue was diluted with water (10 mL) and extracted with ethyl acetate (5 mL×3). The combined organic layers were washed with brine (5 mL×3), dried over sodium sulfate, filtered and concentrated under reduced pressure to give a residue. The residue was purified by column chromatography with petroleum ether:ethyl acetate=5:1 to 3:1. The organic phase was concentrated under reduced pressure to give tert-butyl (2R)-2-[[4-(cyclopropanecarbonylamino)-2-(4,4,5,5-tetramethyl-1,3,2-dioxaborolan-2-yl)phenoxy] methyl]azetidine-1-carboxylate ((93), 500 mg, 529.23 μmol, 45.02% yield, 50% purity) as a brown solid.

$^1$H NMR (400 MHZ, methanol-$d_4$) δ 0.79-0.86 (m, 2H), 0.91-0.95 (m, 2H), 1.15-1.46 (m, 21H), 1.68-1.78 (m, 1H), 2.22-2.61 (m, 2H), 3.79-3.96 (m, 2H), 4.02-4.34 (m, 2H), 4.47-4.54 (m, 1H), 6.90-6.93 (m, 1H), 7.44 (d, J=9.01 Hz, 1H), 7.67 (s, 1H).

Preparation of tert-butyl (2R)-2-[[4-(cyclopropanecarbonylamino)-2-(4,6-dimethylpyrimidin-5-yl) phenoxy]methyl]azetidine-1-carboxylate (94)

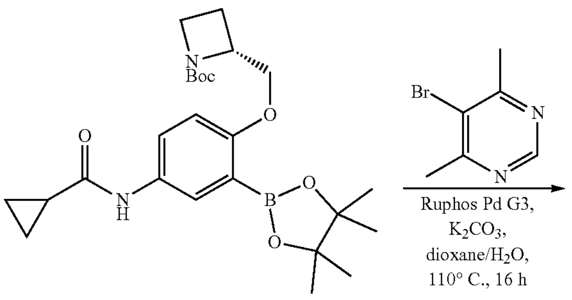

93

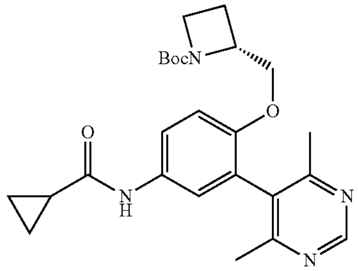

94

To a solution of tert-butyl (2R)-2-[[4-(cyclopropanecarbonylamino)-2-(4,4,5,5-tetramethyl-1,3,2-dioxaborolan-2-yl)phenoxy]methyl]azetidine-1-carboxylate ((93), 300 mg, 317.54 μmol, 1 eq.) and 5-bromo-4,6-dimethyl-pyrimidine (89.09 mg, 476.31 μmol, 1.5 eq.) in dioxane (2 mL) and water (0.2 mL) was added $K_2CO_3$ (87.77 mg, 635.08 μmol, 2 eq.) and RuPhos Pd $G_3$ (26.56 mg, 31.75 μmol, 0.1 eq.). The mixture was stirred at 110° C. for 12 hrs under an $N_2$ atmosphere (monitored by LC-MS). The reaction mixture was partitioned between water (5 mL) and ethyl acetate (5 mL). The organic phase was separated, washed with brine (5 mL×3), dried over sodium sulfate, filtered and concentrated under reduced pressure to give a residue. The residue was purified by prep-HPLC (TFA conditions). Tert-butyl (2R)-2-[[4-(cyclopropanecarbonylamino)-2-(4,6-dimethylpyrimidin-5-yl)phenoxy]methyl]azetidine-1-carboxylate ((94), 46 mg, 97.58 μmol, 30.73% yield, 96% purity) was obtained as a white solid.

$^1$H NMR (400 MHZ, methanol-$d_4$) δ 0.82-0.88 (m, 2H), 0.91-0.98 (m, 2H), 1.38 (s, 9H), 1.70-1.87 (m, 2H), 2.13-2.23 (m, 1H), 2.28 (d, J=8.38 Hz, 6H), 3.05 (br s, 1H), 3.34-3.36 (m, 1H), 3.60 (br s, 1H), 3.96 (br d, J=8.63 Hz, 1H), 4.38 (br d, J=8.13 Hz, 2H), 7.13 (d, J=8.88 Hz, 1H), 7.36-7.45 (m, 1H), 7.60 (br d, J=6.38 Hz, 1H), 8.85 (s, 1H).

Preparation of N-[3-(4,6-dimethylpyrimidin-5-yl)-4-[(3R)-pyrrolidin-3-yl]oxy-phenyl]cyclopropanecarboxamide (405)

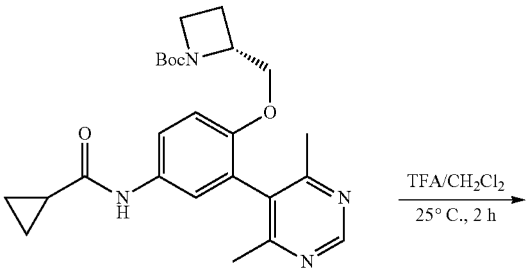

94

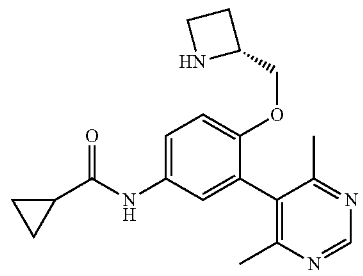

405

To a solution of tert-butyl (2R)-2-[[4-(cyclopropanecarbonylamino)-2-(4,6-dimethylpyrimidin-5-yl)phenoxy] methyl]azetidine-1-carboxylate ((94), 46 mg, 101.65 μmol, 1 eq.) in DCM (1 mL) was added TFA (11.59 mg, 101.65 μmol, 7.53 μL, 1 eq.). The mixture was stirred at 25° C. for 2 hrs (monitored by LC-MS). The reaction mixture was concentrated under reduced pressure to remove solvent. Then water was added and the aqueous solution was lyophilized to give N-[4-[[(2R)-azetidin-2-yl]methoxy]-3-(4,6-dimethylpyrimidin-5-yl)phenyl]cyclopropanecarboxamide (29 mg, 79.82 μmol, 78.52% yield, 97% purity) as a white solid.

LCMS (ESI): m/z [M+H] calcd for $C_{20}H_{25}N_4O_2$: 353.19; found: 353.1.

$^1$H NMR (400 MHZ, methanol-$d_4$) δ 0.83-0.89 (m, 2H), 0.92-0.97 (m, 2H), 1.70-1.80 (m, 1H), 2.24-2.31 (m, 7H), 2.52-2.62 (m, 1H), 3.50-3.59 (m, 1H), 3.88-3.96 (m, 1H), 4.28-4.36 (m, 2H), 4.65 (br s, 1H), 7.20 (d, J=9.04 Hz, 1H), 7.43 (d, J=2.65 Hz, 1H), 7.66 (dd, J=8.93, 2.54 Hz, 1H), 8.89 (s, 1H).

(S)—N-(4-(azetidin-2-ylmethoxy)-3-(4,6-dimethylpyrimidin-5-yl)phenyl)cyclopropanecarboxamide (406)

406

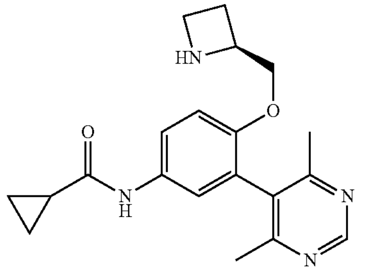

Compound 406 was prepared according to the synthesis described for compound 405, substituting tert-butyl(S)-2-(hydroxymethyl) azetidine-1-carboxylate for tert-butyl (2R)-2-(hydroxymethyl) azetidine-1-carboxylate.

LCMS (ESI): m/z [M+H] calcd for $C_{20}H_{25}N_4O_2$: 353.19; found: 353.1.

$^1$H NMR (400 MHZ, methanol-$d_4$) δ 0.83-0.89 (m, 2H), 0.91-0.98 (m, 2H), 1.71-1.78 (m, 1H), 2.24-2.31 (m, 7H), 2.58 (dtd, J=12.20, 9.31, 6.60 Hz, 1H), 3.55 (td, J=10.09, 6.72 Hz, 1H), 3.88-3.96 (m, 1H), 4.28-4.37 (m, 2H), 4.61-4.69 (m, 1H), 7.20 (d, J=9.05 Hz, 1H), 7.42 (d, J=2.57 Hz, 1H), 7.67 (dd, J=8.93, 2.69 Hz, 1H), 8.89 (s, 1H).

N-[3-(4,6-dimethylpyrimidin-5-yl)-4-[[(2S)-pyrrolidin-2-yl]methoxy]phenyl]cyclopropanecarboxamide (407)

Preparation of tert-butyl (2S)-2-[[2-(4,6-dimethylpyrimidin-5-yl)-4-nitro-phenoxy]methyl]pyrrolidine-1-carboxylate (95)

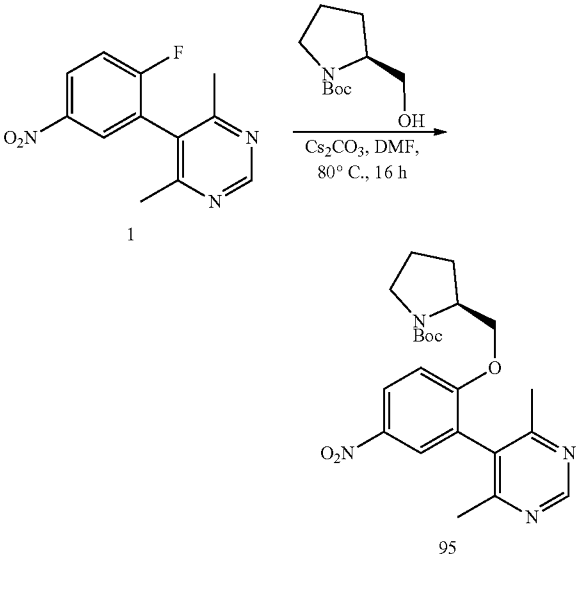

1

95

A mixture of 5-(2-fluoro-5-nitro-phenyl)-4,6-dimethylpyrimidine ((1), 200 mg, 808.98 μmol, 1 eq.), tert-butyl (2S)-2-(hydroxymethyl) pyrrolidine-1-carboxylate (162.82 mg, 808.98 μmol, 1 eq.) and $Cs_2CO_3$ (527.16 mg, 1.62 mmol, 2 eq.) in DMF (1 mL) was stirred at 80° C. for 1 hr under an $N_2$ atmosphere (monitored by LCMS). The reaction mixture was filtered and concentrated under reduced pressure to give a residue. Tert-butyl (2S)-2-[[2-(4,6-dimethylpyrimidin-5-yl)-4-nitro-phenoxy]methyl]pyrrolidine-1-carboxylate ((95), 300 mg, crude) was obtained as a black oil.

LCMS (ESI): m/z [M+H] calcd for $C_{22}H_{29}N_4O_5$: 429.21; found: 429.3.

Preparation of tert-butyl (2S)-2-[[4-amino-2-(4,6-dimethylpyrimidin-5-yl)phenoxy]methyl]pyrrolidine-1-carboxylate (96)

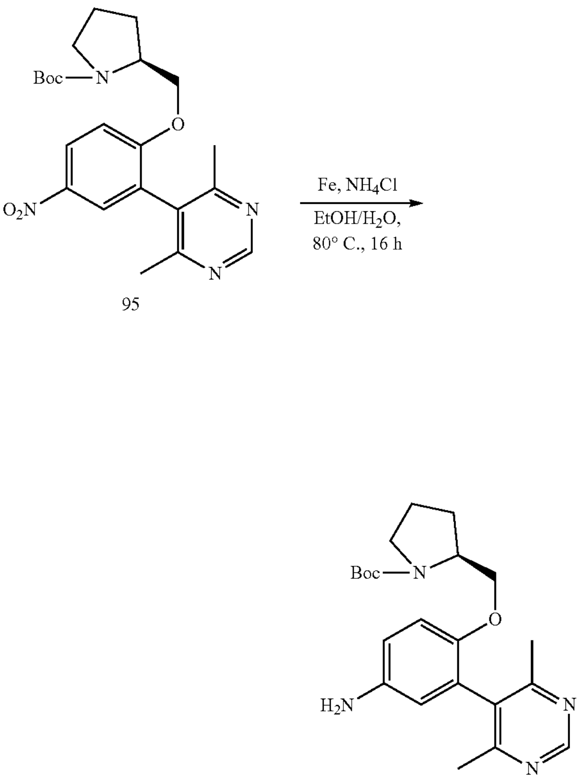

95

96

A mixture of tert-butyl (2S)-2-[[2-(4,6-dimethylpyrimidin-5-yl)-4-nitro-phenoxy]methyl]pyrrolidine-1-carboxylate ((95), 300 mg, 700.15 μmol, 1 eq.), Fe (156.40 mg, 2.80 mmol, 4 eq.), and $NH_4Cl$ (299.61 mg, 5.60 mmol, 8 eq.) in EtOH (10 mL) and $H_2O$ (10 mL) was stirred at 80° C. for 2 hrs under an $N_2$ atmosphere (monitored by LC-MS). The reaction mixture was concentrated under reduced pressure to give a residue. The residue was purified by column chromatography ($SiO_2$, petroleum ether/ethyl acetate=1/1 to 0/1). TLC ($SiO_2$, petroleum ether/ethyl acetate=0:1). Tert-butyl (2S)-2-[[4-amino-2-(4,6-dimethylpyrimidin-5-yl)phenoxy]methyl]pyrrolidine-1-carboxylate ((96), 110 mg, 168.38 μmol, 24.05% yield, 61% purity) was obtained as a white solid.

LCMS (ESI): m/z [M+H] calcd for $C_{22}H_{31}N_4O_3$: 399.23; found: 399.2.

Preparation of tert-butyl (2S)-2-[[4-(cyclopropanecarbonylamino)-2-(4,6-dimethylpyrimidin-5-yl)phenoxy]methyl]pyrrolidine-1-carboxylate (97)

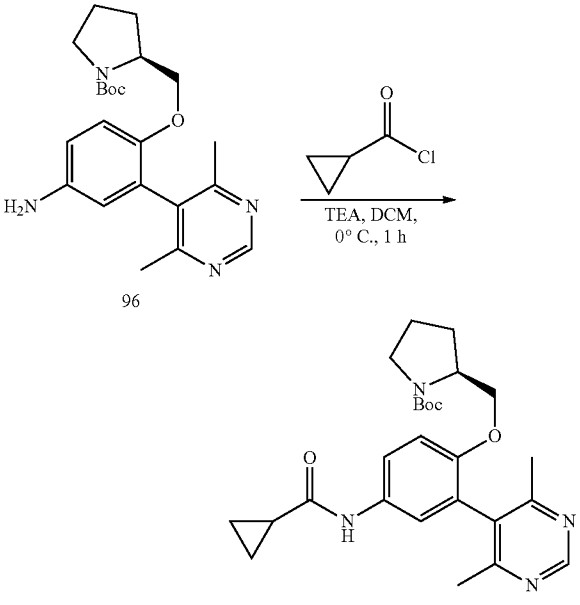

96

97

To a solution of tert-butyl (2S)-2-[[4-amino-2-(4,6-dimethylpyrimidin-5-yl)phenoxy]methyl]pyrrolidine-1-carboxylate ((96), 110 mg, 168.38 μmol, 1 eq.) and TEA (34.08 mg, 336.77 μmol, 46.87 μL, 2 eq.) in DCM (1 mL) was added cyclopropanecarbonyl chloride (17.60 mg, 168.38 μmol, 15.31 μL, 1 eq.). The mixture was stirred at 25° C. for 10 min (monitored by LC-MS). The reaction mixture was concentrated under reduced pressure to give a residue. Tert-butyl (2S)-2-[[4-(cyclopropanecarbonylamino)-2-(4,6-dimethylpyrimidin-5-yl)phenoxy]methyl]pyrrolidine-1-carboxylate ((97), 110 mg, crude) was obtained as a yellow solid.

LCMS (ESI): m/z [M+H] calcd for $C_{26}H_{35}N_4O_4$: 467.26; found: 467.3.

Preparation of N-[3-(4,6-dimethylpyrimidin-5-yl)-4-[[(2S)-pyrrolidin-2-yl]methoxy]phenyl]cyclopropanecarboxamide (407)

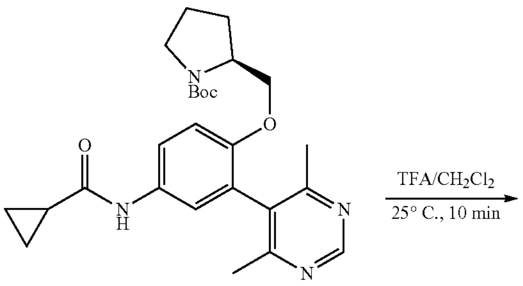

97

-continued

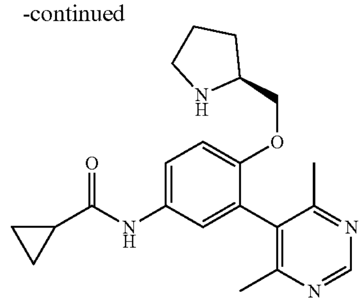

407

A mixture of tert-butyl (2S)-2-[[4-(cyclopropanecarbonylamino)-2-(4,6-dimethylpyrimidin-5-yl)phenoxy]methyl]pyrrolidine-1-carboxylate ((97), 110 mg, 235.76 μmol, 1 eq.) in TFA (1 mL) and DCM (1 mL) was stirred at 25° C. for 10 min under an $N_2$ atmosphere (monitored by LC-MS). The mixture was then stirred at 25° C. for 30 min under an $N_2$ atmosphere. The reaction mixture was concentrated under reduced pressure to give a residue. The residue was purified by prep-HPLC (column: Phenomenex Gemini-NX C18 75*30 mm*3 μm; mobile phase: [water (0.1% TFA)-ACN]; B %: 15%-25%, 7 min). N-[3-(4,6-dimethylpyrimidin-5-yl)-4-[[(2S)-pyrrolidin-2-yl]methoxy]phenyl]cyclopropanecarboxamide (56.46 mg, 116.33 μmol, 49.34% yield, 99% purity, TFA) was obtained as a yellow gum.

LCMS (ESI): m/z [M+H] calcd for $C_{21}H_{27}N_4O_2$: 367.21; found: 367.3.

$^1H$ NMR (400 MHZ, methanol-$d_4$) δ=8.98 (s, 1H), 7.64 (dd, J=2.6, 8.9 Hz, 1H), 7.45 (d, J=2.6 Hz, 1H), 7.19 (d, J=9.0 Hz, 1H), 4.32 (dd, J=3.6, 10.6 Hz, 1H), 4.16 (dd, J=7.5, 10.6 Hz, 1H), 3.88 (dq, J=3.4, 7.7 Hz, 1H), 3.21 (ddd, J=5.8, 7.4, 11.5 Hz, 1H), 3.02 (td, J=7.6, 11.4 Hz, 1H), 2.35 (s, 6H), 2.16 (dtd, J=5.1, 7.7, 12.9 Hz, 1H), 1.99-1.82 (m, 2H), 1.80-1.67 (m, 2H), 0.96-0.90 (m, 2H), 0.88-0.81 (m, 2H).

(R)—N-(3-(4,6-dimethylpyrimidin-5-yl)-4-(pyrrolidin-2-ylmethoxy)phenyl)cyclopropanecarboxamide (408)

408

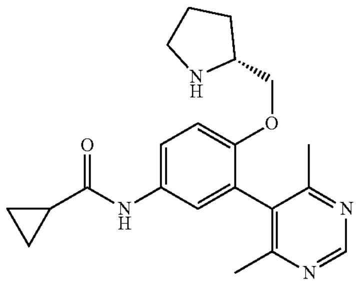

Compound 408 was prepared according to the synthesis described for compound 407, substituting tert-butyl (2R)-2-(hydroxymethyl)pyrrolidine-1-carboxylate for tert-butyl (2S)-2-(hydroxymethyl)pyrrolidine-1-carboxylate.

LCMS (ESI): m/z [M+H] calcd for $C_{21}H_{27}N_4O_2$: 367.21; found: 367.3.

$^1H$ NMR (400 MHZ, methanol-$d_4$) δ=8.85 (s, 1H), 7.61 (dd, J=2.4, 8.9 Hz, 1H), 7.36 (d, J=2.4 Hz, 1H), 7.14 (d, J=8.8 Hz, 1H), 4.02-3.96 (m, 1H), 3.93 (br s, 1H), 2.96-2.37 (m, 2H), 2.27 (s, 6H), 1/75-1.72 (m, 5H), 0.94-0.84 (m, 4H).

(1S,2R)—N-(3-(4,6-dimethylpyrimidin-5-yl)-4-(((R)-piperidin-3-yl)oxy)phenyl)-2-fluorocyclopropane-1-carboxamide (409)

Preparation of tert-butyl (3R)-3-[2-(4,6-dimethylpyrimidin-5-yl)-4-nitro-phenoxy]piperidine-1-carboxylate (98)

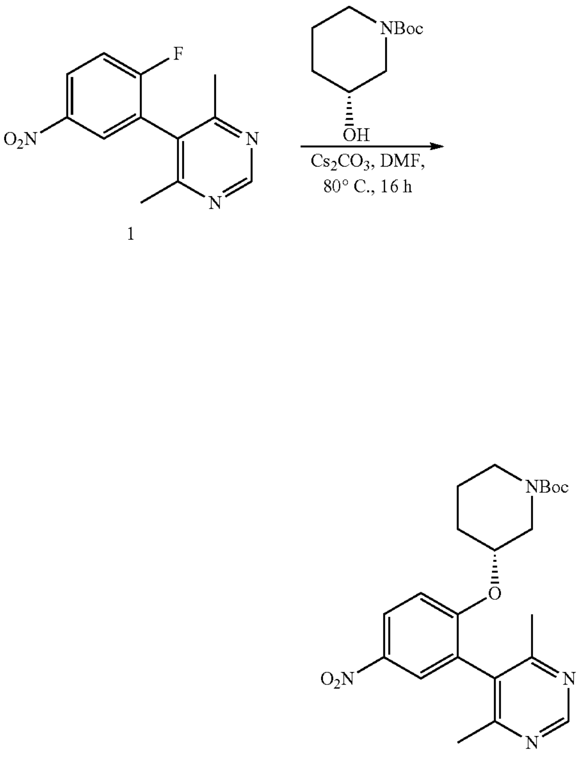

1

98

To a solution of tert-butyl (3R)-3-hydroxypiperidine-1-carboxylate (3.26 g, 16.18 mmol, 1 eq.) and 5-(2-fluoro-5-nitro-phenyl)-4,6-dimethyl-pyrimidine ((1), 4 g, 16.18 mmol, 1 eq.) in DMF (100 mL) was added $Cs_2CO_3$ (6.85 g, 21.03 mmol, 1.3 eq.). The mixture was stirred at 80° C. for 16 hrs (monitored by TLC). The residue was diluted with water (100 mL) and extracted with ethyl acetate (100 mL×3). The combined organic layers were washed with brine (50 mL×3), dried over sodium sulfate, filtered and concentrated under reduced pressure to give a residue. The residue was purified by column chromatography with petroleum ether:ethyl acetate=9:1 to 1:1. Tert-butyl (3R)-3-[2-(4,6-dimethylpyrimidin-5-yl)-4-nitro-phenoxy]piperidine-1-carboxylate ((98), 5.5 g, 12.07 mmol, 74.57% yield, 94% purity) was obtained as a brown oil.

$^1H$ NMR (400 MHZ, methanol-$d_4$) δ 1.37-1.48 (m, 11H), 1.67-1.77 (m, 1H), 1.85-1.96 (m, 1H), 2.25 (d, J=6.24 Hz, 6H), 3.16-3.26 (m, 1H), 3.40-3.54 (m, 2H), 3.62-3.75 (m, 1H), 4.63-4.72 (m, 1H), 7.41 (d, J=9.17 Hz, 1H), 8.15 (d, J=2.69 Hz, 1H), 8.40 (dd, J=9.17, 2.81 Hz, 1H), 8.88 (s, 1H).

Preparation of tert-butyl (3R)-3-[4-amino-2-(4,6-dimethylpyrimidin-5-yl)phenoxy]piperidine-1-carboxylate (99)

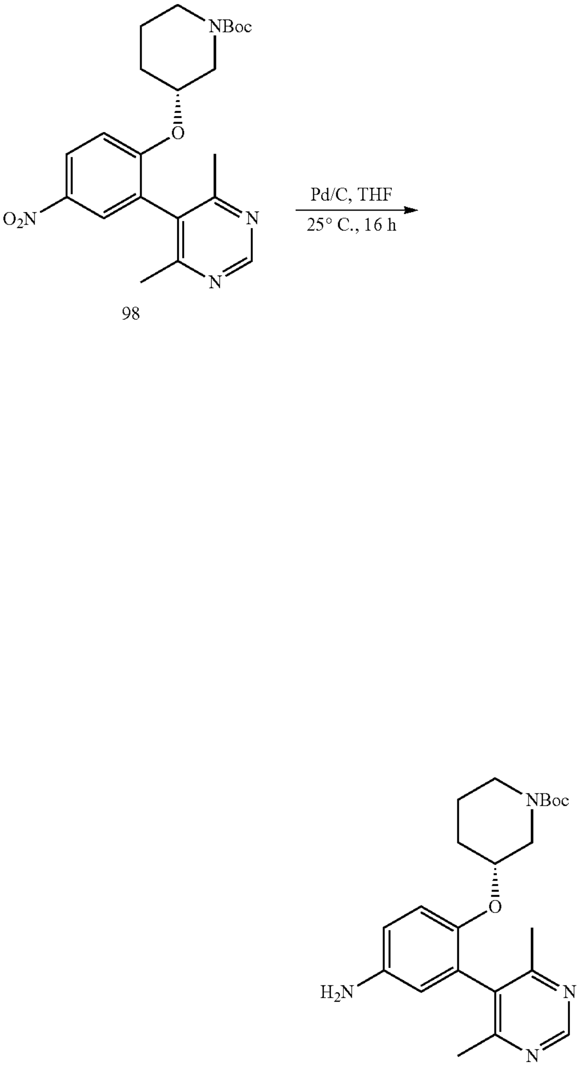

98

99

To a solution of tert-butyl (3R)-3-[2-(4,6-dimethylpyrimidin-5-yl)-4-nitro-phenoxy]piperidine-1-carboxylate ((98), 3 g, 7.00 mmol, 1 eq.) in THF (100 mL) was added Pd/C (3 g, 7.00 mmol, 10% purity, 1 eq.). The mixture was stirred at 25° C. for 16 hrs under an $H_2$ atmosphere (monitored by TLC). The reaction mixture was filtered and concentrated under reduced pressure to give a residue. Tert-butyl (3R)-3-[4-amino-2-(4,6-dimethylpyrimidin-5-yl)phenoxy]piperidine-1-carboxylate ((99), 2.4 g, 5.48 mmol, 78.28% yield, 91% purity) was obtained as a white solid. The product was used in the next step without any purification.

$^1H$ NMR (400 MHZ, methanol-$d_4$) δ 1.35-1.51 (m, 13H), 1.77 (td, J=8.57, 4.25 Hz, 1H), 2.28 (d, J=3.75 Hz, 6H), 3.16-3.29 (m, 2H), 3.56 (br d, J=12.88 Hz, 1H), 4.06 (br d, J=14.01 Hz, 1H), 6.54 (d, J=2.75 Hz, 1H), 6.83 (dd, J=8.75, 2.88 Hz, 1H), 7.00 (d, J=8.75 Hz, 1H), 8.81 (s, 1H).

Preparation of tert-butyl (3R)-3-[2-(4,6-dimethylpyrimidin-5-yl)-4-[[(1S,2R)-2-fluorocyclopropanecarbonyl]amino]phenoxy]piperidine-1-carboxylate (100)

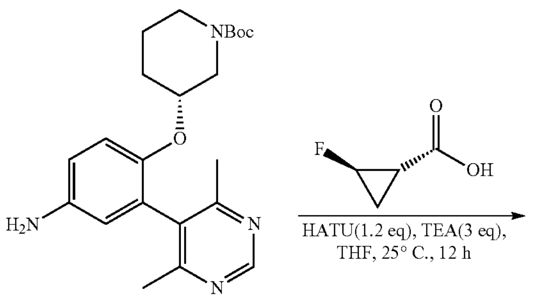

99

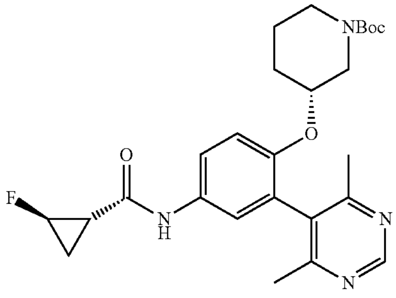

100

To a solution of tert-butyl (3R)-3-[4-amino-2-(4,6-dimethylpyrimidin-5-yl)phenoxy]piperidine-1-carboxylate ((99), 100 mg, 250.94 μmol, 1 eq.) and (1S,2R)-2-fluorocyclopropanecarboxylic acid (31.34 mg, 301.13 μmol, 1.2 eq.) in THF (2 mL) was added HATU (114.50 mg, 301.13 μmol, 1.2 eq.) and TEA (76.18 mg, 752.82 μmol, 104.79 μL, 3 eq.). The mixture was stirred at 25° C. for 12 hrs (monitored by TLC). The reaction mixture were washed with 5% citric acid in water (5 mL×3) and saturated sodium bicarbonate solution (5 mL×3), dried over sodium sulfate, filtered and concentrated under reduced pressure to give tert-butyl (3R)-3-[2-(4,6-dimethylpyrimidin-5-yl)-4-[[(1S,2R)-2-fluorocyclopropanecarbonyl]amino]phenoxy]piperidine-1-carboxylate ((100), 120 mg, 198.12 μmol, 78.95% yield, 80% purity) as a brown solid.

$^1$H NMR (400 MHz, methanol-$d_4$) δ 1.35-1.50 (m, 11H), 1.53-1.60 (m, 1H), 1.79-1.87 (m, 1H), 2.15-2.30 (m, 8H), 3.39-3.46 (m, 1H), 3.54 (br s, 1H), 4.32 (br s, 1H), 4.74 (br d, J=15.63 Hz, 3H), 4.88 (br d, J=1.75 Hz, 1H), 7.17 (br d, J=8.88 Hz, 1H), 7.37 (d, J=2.50 Hz, 1H), 7.57 (br d, J=8.88 Hz, 1H), 8.83 (s, 1H).

Preparation of (1S,2R)—N-(3-(4,6-dimethylpyrimidin-5-yl)-4-(((R)-piperidin-3-yl)oxy)phenyl)-2-fluorocyclopropane-1-carboxamide (409)

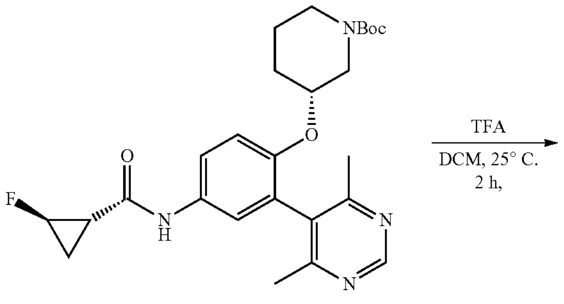

100

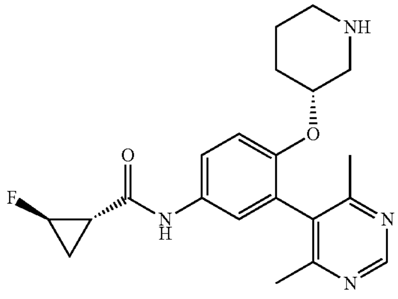

409

To a solution of tert-butyl (3R)-3-[2-(4,6-dimethylpyrimidin-5-yl)-4-[[(1S,2R)-2-fluorocyclopropanecarbonyl]amino]phenoxy]piperidine-1-carboxylate ((100), 110 mg, 227.01 μmol, 1 eq.) in DCM (2 mL) was added TFA (282.33 mg, 2.48 mmol, 183.33 μL, 10.91 eq.). The mixture was stirred at 25° C. for 2 hrs (monitored by LC-MS). The reaction mixture was concentrated under reduced pressure to remove the solvent. The residue was purified by prep-HPLC (TFA conditions). (1S,2R)—N-[3-(4,6-dimethylpyrimidin-5-yl)-4-[[(3R)-3-piperidyl]oxy]phenyl]-2-fluoro-cyclopropanecarboxamide (57.5 mg, 148.07 μmol, 65.23% yield, 99% purity) was obtained as a white solid.

LCMS (ESI): m/z [M+H] calcd for $C_{21}H_{26}FN_4O_2$: 385.2; found: 385.2.

$^1$H NMR (400 MHZ, methanol-$d_4$) δ=8.91 (s, 1H), 7.63 (dd, J=2.6, 8.9 Hz, 1H), 7.41 (d, J=2.6 Hz, 1H), 7.23 (d, J=9.0 Hz, 1H), 4.90-4.72 (m, 1H), 4.49 (tt, J=3.3, 6.7 Hz, 1H), 3.35 (dd, J=2.9, 12.8 Hz, 1H), 3.19-2.99 (m, 3H), 2.31 (s, 6H), 2.26-2.13 (m, 1H), 2.02-1.90 (m, 1H), 1.88-1.56 (m, 3H), 1.54-1.40 (m, 1H), 1.32 (qd, J=6.4, 12.8 Hz, 1H).

(1R,2R)—N-(3-(4,6-dimethylpyrimidin-5-yl)-4-(((R)-piperidin-3-yl)oxy)phenyl)-2-fluorocyclopropane-1-carboxamide (410)

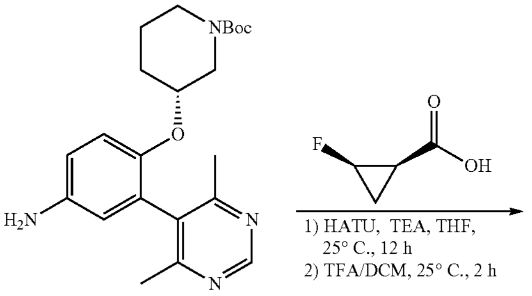

99

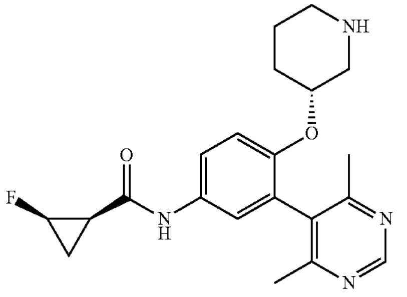

410

Compound 410 was prepared according to the synthesis described for compound 409, substituting (1R,2R)-2-fluorocyclopropane-1-carboxylic acid for (1S,2R)-2-fluorocyclopropanecarboxylic acid.

LCMS (ESI): m/z [M+H] calcd for $C_{21}H_{26}FN_4O_2$: 385.2; found: 385.2.

$^1$H NMR (400 MHZ, methanol-d$_4$) δ=8.91 (s, 1H), 7.67 (dd, J=2.6, 8.9 Hz, 1H), 7.43 (d, J=2.8 Hz, 1H), 7.24 (d, J=9.1 Hz, 1H 4.95-4.75 (m, 1H) 4.49 (tt, J=3.4, 6.7 Hz, 1H), 3.35 (dd, J=2.8, 12.8 Hz, 1H), 3.19-2.99 (m, 3H), 2.32 (s, 6H), 2.02-1.89 (m, 2H), 1.88-1.56 (m, 4H), 1.16 (tdd, J=6.4, 9.2, 12.4 Hz, 1H).

(1S,2S)—N-(3-(4,6-dimethylpyrimidin-5-yl)-4-(((R)-piperidin-3-yl)oxy)phenyl)-2-fluorocyclopropane-1-carboxamide (411)

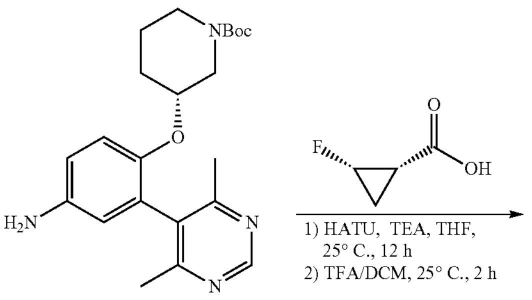

99

-continued

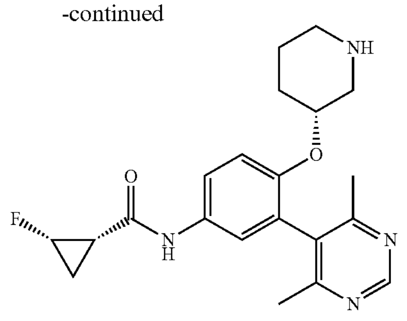

411

Compound 411 was prepared according to the synthesis described for compound 409, substituting (1S,2S)-2-fluorocyclopropane-1-carboxylic acid for (1S,2R)-2-fluorocyclopropanecarboxylic acid.

LCMS (ESI): m/z [M+H] calcd for $C_{21}H_{26}FN_4O_2$: 385.2; found: 385.2.

$^1$H NMR (400 MHZ, methanol-d$_4$) δ=8.85 (s, 1H), 7.60 (dd, J=2.6, 8.9 Hz, 1H), 7.39 (d, J=2.5 Hz, 1H), 7.16 (d, J=9.0 Hz, 1H), 4.93-4.74 (m, 1H), 4.24 (tt, J=3.9, 8.1 Hz, 1H), 3.05 (dd, J=2.4, 12.4 Hz, 1H), 2.80 (td, J=4.2, 12.8 Hz, 1H), 2.58-2.38 (m, 2H), 2.28 (s, 6H), 2.08-1.87 (m, 2H), 1.84-1.58 (m, 2H), 1.55-1.31 (m, 2H), 1.15 (tdd, J=6.4, 9.1, 12.4 Hz, 1H).

(R)—N-(3-(4,6-dimethylpyrimidin-5-yl)-4-(piperidin-3-yloxy)phenyl)-4-methylthiazole-5-carboxamide (412)

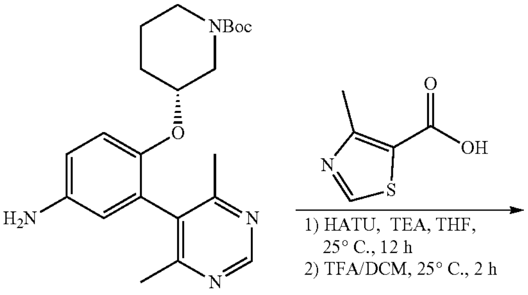

99

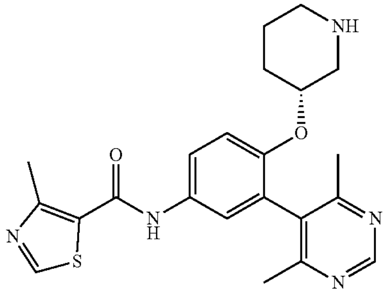

412

Compound 412 was prepared according to the synthesis described for compound 409, substituting 4-methylthiazole-5-carboxylic acid for (1S,2R)-2-fluorocyclopropanecarboxylic acid.

LCMS (ESI): m/z [M+H] calcd for $C_{22}H_{26}N_5O_2S$: 424.2; found: 424.2.

$^1$H NMR (400 MHZ, methanol-$d_4$) δ=9.02 (s, 1H), 8.92 (s, 1H), 7.76 (dd, J=2.6, 8.9 Hz, 1H), 7.49 (d, J=2.6 Hz, 1H), 7.29 (d, J=9.0 Hz, 1H), 4.55 (td, J=3.3, 6.6 Hz, 1H), 3.38 (dd, J=2.7, 12.8 Hz, 1H), 3.21-3.01 (m, 3H), 2.69 (s, 3H), 2.34 (d, J=1.4 Hz, 6H), 2.05-1.94 (m, 1H), 1.90-1.60 (m, 3H).

(R)—N-(3-(4,6-dimethylpyrimidin-5-yl)-4-(piperidin-3-yloxy)phenyl)-2,4-dimethylthiazole-5-carboxamide (413)

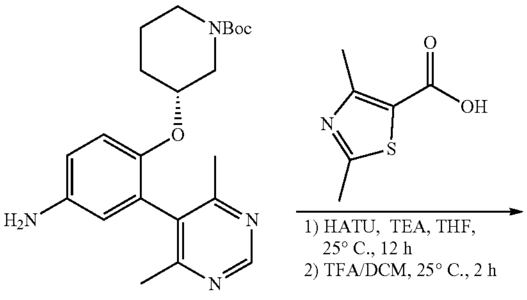

99

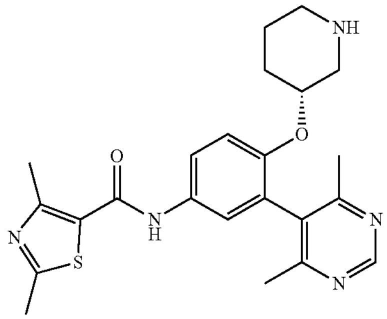

413

Compound 413 was prepared according to the synthesis described for compound 409, substituting 2,4-dimethylthiazole-5-carboxylic acid for (1S,2R)-2-fluorocyclopropanecarboxylic acid.

LCMS (ESI): m/z [M+H] calcd for $C_{23}H_{28}N_5O_2S$: 438.2; found: 438.2.

$^1$H NMR (400 MHZ, methanol-$d_4$) δ=8.93 (s, 1H), 7.73 (dd, J=2.6, 8.9 Hz, 1H), 7.47 (d, J=2.6 Hz, 1H), 7.28 (d, J=9.0 Hz, 1H), 4.55 (td, J=3.3, 6.6 Hz, 1H), 3.38 (dd, J=2.9, 12.7 Hz, 1H), 3.20-3.00 (m, 3H), 2.70 (s, 3H), 2.61 (s, 3H), 2.34 (d, J=1.3 Hz, 6H), 2.06-1.94 (m, 1H), 1.90-1.59 (m, 3H).

(R)—N-(3-(4,6-dimethylpyrimidin-5-yl)-4-(piperidin-3-yloxy)phenyl)-4-methylisoxazole-5-carboxamide (414)

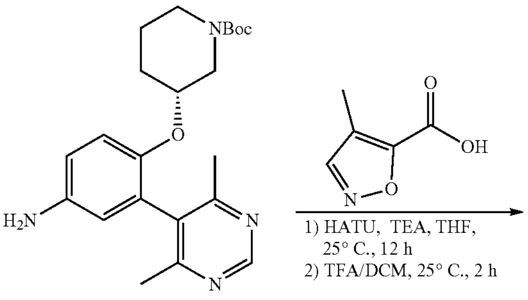

99

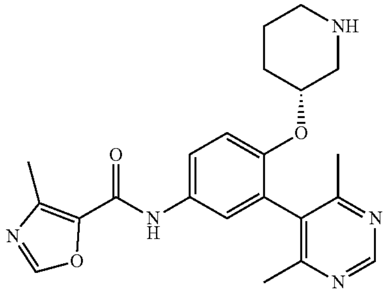

414

Compound 414 was prepared according to the synthesis described for compound 409, substituting 4-methylisoxazole-5-carboxylic acid for (1S,2R)-2-fluorocyclopropanecarboxylic acid.

LCMS (ESI): m/z [M+H] calcd for $C_{22}H_{26}N_5O_3$: 408.2; found: 408.2.

$^1$H NMR (400 MHz, methanol-$d_4$) δ=8.91 (s, 1H), 8.43 (s, 1H), 7.85 (dd, J=2.7, 8.9 Hz, 1H), 7.56 (d, J=2.6 Hz, 1H), 7.29 (d, J=9.0 Hz, 1H), 4.55 (td, J=3.4, 6.8 Hz, 1H), 3.38 (dd, J=3.0, 12.8 Hz, 1H), 3.21-3.01 (m, 3H), 2.40-2.29 (m, 9H), 2.04-1.94 (m, 1H), 1.90-1.59 (m, 3H).

(R)—N-(3-(4,6-dimethylpyrimidin-5-yl)-4-(piperidin-3-yloxy)phenyl)-4-methyloxazole-5-carboxamide (415)

415

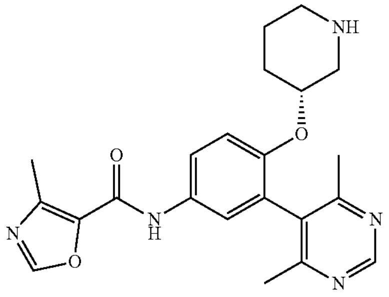

Compound 415 was prepared according to the synthesis described for compound 409, substituting 4-methyloxazole-5-carboxylic acid for (1S,2R)-2-fluorocyclopropanecarboxylic acid.

LCMS (ESI): m/z [M+H] calcd for $C_{22}H_{26}N_5O_3$: 408.2; found: 408.3.

$^1$H NMR (400 MHZ, methanol-$d_4$) δ=8.91 (d, J=2.2 Hz, 1H), 8.25 (s, 1H), 7.82 (br d, J=9.0 Hz, 1H), 7.52 (br s, 1H), 7.28 (d, J=9.0 Hz, 1H), 4.53 (br s, 1H), 3.37 (br d, J=13.0 Hz, 1H), 3.20-3.01 (m, 3H), 2.50 (s, 3H), 2.33 (s, 6H), 2.03-1.93 (m, 1H), 1.89-1.59 (m, 3H).

(R)—N-(3-(4,6-dimethylpyrimidin-5-yl)-4-(piperidin-3-yloxy)phenyl)-1-methyl-1H-pyrrole-2-carboxamide (416)

416

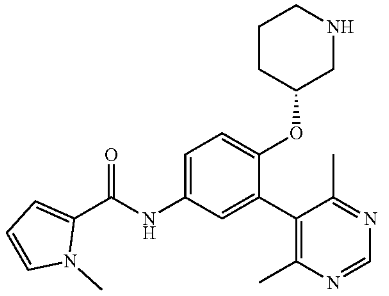

Compound 416 was prepared according to the synthesis described for compound 409, substituting 1-methyl-1H-pyrrole-2-carboxylic acid for (1S,2R)-2-fluorocyclopropanecarboxylic acid.

LCMS (ESI): m/z [M+H] calcd for $C_{23}H_{28}N_5O_2$: 406.2; found: 406.3.

$^1$H NMR (400 MHZ, methanol-$d_4$) δ=8.92 (s, 1H), 7.75 (dd, J=2.6, 9.0 Hz, 1H), 7.47 (s, 1H), 7.25 (d, J=8.9 Hz, 1H), 6.96 (dd, J=1.7, 4.0 Hz, 1H), 6.89 (t, J=2.0 Hz, 1H), 6.11 (dd, J=2.6, 4.0 Hz, 1H), 4.50 (br s, 1H), 3.92 (s, 3H), 3.36 (dd, J=2.8, 12.8 Hz, 1H), 3.20-3.00 (m, 3H), 2.35 (s, 6H), 1.97 (dt, J=4.1, 8.8 Hz, 1H), 1.90-1.57 (m, 3H).

(R)—N-(3-(4,6-dimethylpyrimidin-5-yl)-4-(piperidin-3-yloxy)phenyl)-1-methyl-1H-pyrazole-5-carboxamide (417)

417

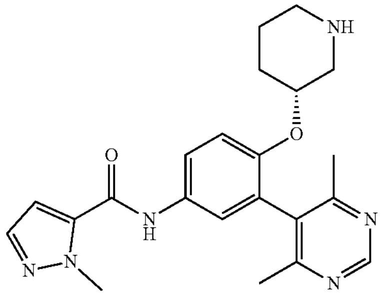

Compound 417 was prepared according to the synthesis described for compound 409, substituting 1-methyl-1H-pyrazole-5-carboxylic acid for (1S,2R)-2-fluorocyclopropanecarboxylic acid.

LCMS (ESI): m/z [M+H] calcd for $C_{22}H_{27}N_6O_2$: 407.2; found: 407.3.

$^1$H NMR (400 MHZ, methanol-$d_4$) δ=8.92 (d, J=2.6 Hz, 1H), 7.81 (br d, J=9.0 Hz, 1H), 7.55-7.49 (m, 2H), 7.29 (d, J=9.0 Hz, 1H), 6.96 (d, J=2.0 Hz, 1H), 4.54 (br d, J=3.1 Hz, 1H), 4.15 (s, 3H), 3.38 (br d, J=12.7 Hz, 1H), 3.21-3.02 (m, 3H), 2.34 (s, 6H), 1.99 (dt, J=4.2, 8.7 Hz, 1H), 1.90-1.58 (m, 3H).

(R)—N-(3-(4,6-dimethylpyrimidin-5-yl)-4-(piperidin-3-yloxy)phenyl)cyclopropanecarboxamide (418)

418

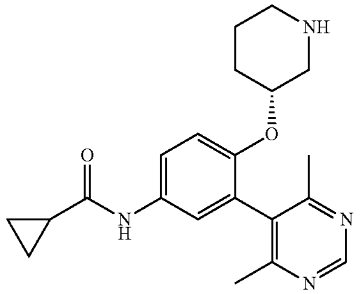

Compound 418 was prepared according to the synthesis described for compound 409, substituting cyclopropanecarboxylic acid for (1S,2R)-2-fluorocyclopropanecarboxylic acid.

LCMS (ESI): m/z [M+H] calcd for $C_{21}H_{27}N_4O_2$: 367.2; found: 367.1.

$^1$H NMR (400 MHz, methanol-$d_4$) δ=0.81-0.98 (m, 4H), 1.56-1.67 (m, 1H), 1.67-1.89 (m, 3H), 1.91-2.02 (m, 1H), 2.32 (d, J=0.98 Hz, 6H), 2.99-3.20 (m, 3H), 3.35 (dd, J=12.90, 2.87 Hz, 1H), 4.49 (tt, J=6.68, 3.22 Hz, 1H), 7.23 (d, J=8.93 Hz, 1H), 7.42 (d, J=2.69 Hz, 1H), 7.64 (dd, J=8.93, 2.57 Hz, 1H), 8.92 (s, 1H).

F NMR (400 MHz, methanol-$d_4$) δ=−77.28 (s, 1F).

SFC: 5_95CD_2 min-220-254-ELSD: LC/MS. The gradient was 5-95% B in 0.30 min and 30-95% B at 0.30-0.80 min, hold on 95% B for 0.4 min, and then 95-5% B in 0.01 min, the flow rate was 1.5 mL/min. Mobile phase A was $H_2O$+10 mM $NH_4HCO_3$, mobile phase B was Acetonitrile. The column used for chromatography was a Xbridge Shield $RP^{18}$ 2.1×50 mm column (5 μm particles). Detection methods were diode array (DAD) and evaporative light scattering (ELSD) detection as well as positive electrospray ionization. MS range was 100-1000.

(S)—N-(3-(4,6-dimethylpyrimidin-5-yl)-4-(piperidin-3-yloxy)phenyl)cyclopropanecarboxamide (419)

419

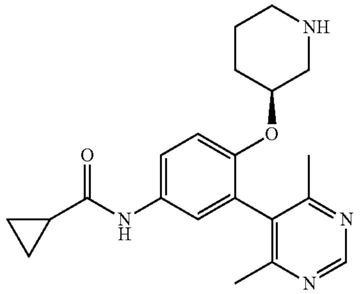

Compound 419 was prepared according to the synthesis described for compound 409, substituting cyclopropanecarboxylic acid for (1S,2R)-2-fluorocyclopropanecarboxylic acid and (3S)-3-hydroxypiperidine-1-carboxylate for (3R)-3-hydroxypiperidine-1-carboxylate.

$^1H$ NMR (400 MHZ, methanol-$d_4$) δ=0.81-0.97 (m, 4H), 1.54-1.67 (m, 1H), 1.67-1.88 (m, 3H), 1.89-2.04 (m, 1H), 2.32 (d, J=0.73 Hz, 6H), 2.98-3.20 (m, 3H), 3.36 (dd, J=12.78, 2.87 Hz, 1H), 4.50 (dt, J=6.72, 3.36 Hz, 1H), 7.23 (d, J=9.05 Hz, 1H), 7.43 (d, J=2.57 Hz, 1H), 7.64 (dd, J=8.99, 2.63 Hz, 1H), 8.92 (s, 1H).

F NMR (400 MHZ, methanol-$d_4$) δ=−77.18 (s, 1F).

LCMS (ESI): m/z [M+H] calcd for $C_{21}H_{27}N_4O_2$: 367.4; found: 367.1.

SFC: 5_95CD_6 min-220-254-ELSD: LC/MS. The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was $H_2O$+10 mM $NH_4HCO_3$, mobile phase B was acetonitrile. The column used for chromatography was a Xbridge Shield $RP^{18}$ 2.1×50 mm column (5 μm particles). Detection methods were diode array (DAD) and evaporative light scattering (ELSD) detection as well as positive electrospray ionization. MS range was 100-1000.

N-[3-(4,6-dimethylpyrimidin-5-yl)-4-[[(2S)-2-piperidyl]methoxy]phenyl]cyclopropanecarboxamide (420)

Preparation of tert-butyl (2S)-2-[[(2-bromo-4-nitro-phenoxy)methyl]piperidine-1-carboxylate (101)

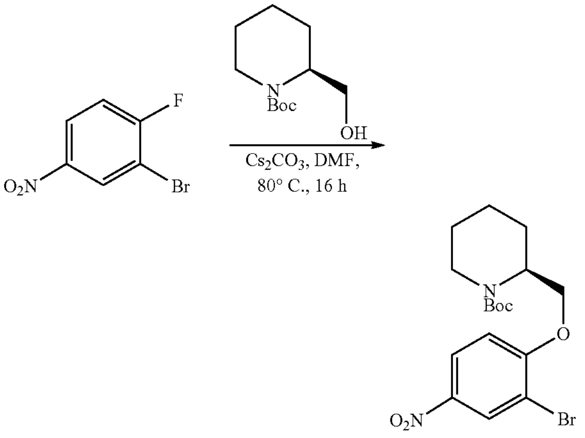

101

To a solution of 2-bromo-1-fluoro-4-nitro-benzene (1 g, 4.55 mmol, 1 eq.) and tert-butyl (2S)-2-(hydroxymethyl) piperidine-1-carboxylate (1.08 g, 5.00 mmol, 1.1 eq.) in DMF (15 mL) was added $Cs_2CO_3$ (1.93 g, 5.91 mmol, 1.3 eq.). The mixture was stirred at 80° C. for 16 hrs (monitored by LC-MS). The reaction mixture was filtered and the filtrate was concentrated under vacuum to give a residue. The residue was purified by column chromatography ($SiO_2$, petroleum ether/ethyl acetate=1:0 to 5:1). Tert-butyl (2S)-2-[(2-bromo-4-nitro-phenoxy)methyl]piperidine-1-carboxylate ((101), 1.8 g, 4.33 mmol, 95.36% yield) was obtained as a yellow oil.

LCMS (ESI): m/z [M+H] calcd for $C_{13}H_{24}Br^{79/81}N_2O_5$: 415.08 and 417.08; found: [M+H-Boc] 315.0 and 317.0.

Preparation of tert-butyl (2S)-2-[(4-amino-2-bromo-phenoxy)methyl]piperidine-1-carboxylate (102)

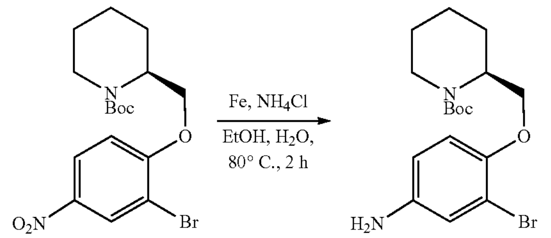

101 102

To a solution of tert-butyl (2S)-2-[(2-bromo-4-nitro-phenoxy)methyl]piperidine-1-carboxylate ((101), 1.8 g, 4.33 mmol, 1 eq.) in EtOH (15 mL) and $H_2O$ (5 mL) was added Fe (1.21 g, 21.67 mmol, 5 eq.) and $NH_4Cl$ (1.85 g, 34.68 mmol, 8 eq.). The mixture was stirred at 80° C. for 2 hrs. TLC (PE:EA=3:1) indicated the starting material was consumed completely and one new spot formed. The reaction mixture was filtered and the filtrate was concentrated under vacuum to give a residue. The residue was purified by column chromatography ($SiO_2$, petroleum ether/ethyl acetate=1:0 to 5:1). Tert-butyl (2S)-2-[(4-amino-2-bromo-phenoxy)methyl]piperidine-1-carboxylate ((102), 1.3 g, 3.37 mmol, 77.84% yield) was obtained as a yellow oil.

Preparation of tert-butyl (2S)-2-[[2-bromo-4-(cyclopropanecarbonylamino)phenoxy]methyl]piperidine-1-carboxylate (103)

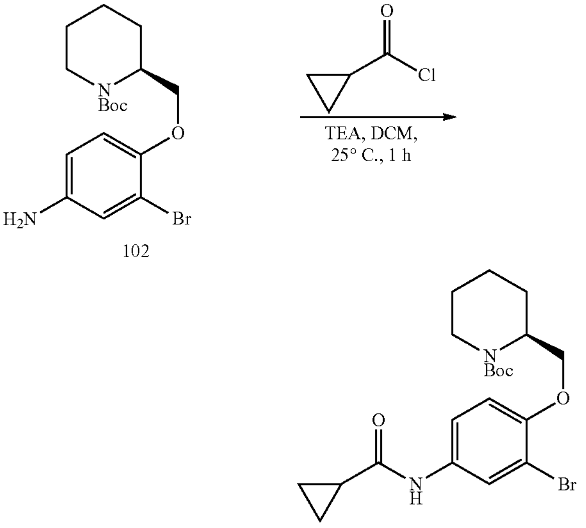

102

103

To a solution of tert-butyl (2S)-2-[(4-amino-2-bromo-phenoxy)methyl]piperidine-1-carboxylate ((102), 300 mg, 778.62 μmol, 1 eq.) and $Et_3N$ (157.58 mg, 1.56 mmol, 216.75 μL, 2 eq.) in DCM (2 mL) was added cyclopropanecarbonyl chloride (97.67 mg, 934.35 μmol, 84.93 μL, 1.2 eq.) at 0° C. The mixture was stirred at 25° C. for 1 hr (monitored by LC-MS). To the mixture was added cyclopropanecarbonyl chloride (30 mg), and the mixture was stirred at 25° C. for 0.5 hrs. TLC (PE:EA=5:1) indicated the starting material was consumed completely and one new spot formed. The reaction mixture was diluted with $H_2O$ (2 mL) and extracted with DCM (2 mL×2). The combined organic layers were washed with sat. NaCl (2 mL), dried over anhydrous $Na_2SO_4$, filtered and concentrated under reduced pressure to give a residue. The crude product tert-butyl (2S)-2-[[2-bromo-4-(cyclopropanecarbonylamino)phenoxy]methyl]piperidine-1-carboxylate ((103), 350 mg, crude) as a yellow oil was used into the next step without further purification.

LCMS (ESI): m/z [M+H] calcd for $C_{17}H_{22}Br^{79/81}N_2O_4$: 397.07 and 399.07; found: 397.0 and 399.0.

Preparation of tert-butyl (2S)-2-[[4-(cyclopropanecarbonylamino)-2-(4,4,5,5-tetramethyl-1,3,2-dioxaborolan-2-yl)phenoxy]methyl]piperidine-1-carboxylate (104)

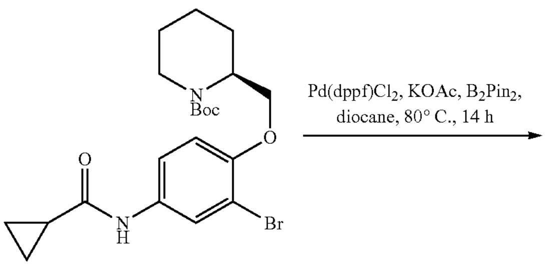

103

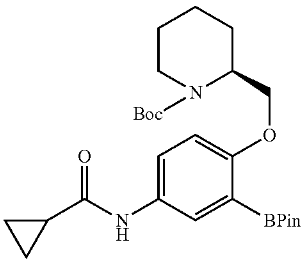

104

A mixture of tert-butyl (2S)-2-[[2-bromo-4-(cyclopropanecarbonylamino)phenoxy]methyl]piperidine-1-carboxylate ((103), 520 mg, 1.15 mmol, 1 eq.), 4,4,5,5-tetramethyl-2-(4,4,5,5-tetramethyl-1,3,2-dioxaborolan-2-yl)-1,3,2-dioxaborolane (873.78 mg, 3.44 mmol, 3 eq.), $Pd(dppf)Cl_2$ (83.92 mg, 114.70 μmol, 0.1 eq.), $K_2CO_3$ (317.04 mg, 2.29 mmol, 2 eq.) in dioxane (15 mL) was degassed and purged with $N_2$ three times, and then the mixture was stirred at 80° C. for 14 hrs under an $N_2$ atmosphere (monitored by LC-MS). The reaction mixture was concentrated under vacuum to give a residue. The residue was purified by column chromatography ($SiO_2$, petroleum ether/ethyl acetate=1:0 to 1:1). Tert-butyl (2S)-2-[[4-(cyclopropanecarbonylamino)-2-(4,4,5,5-tetramethyl-1,3,2-dioxaborolan-2-yl)phenoxy]methyl]piperidine-1-carboxylate ((104), 550 mg, 1.10 mmol, 95.82% yield) was obtained as a yellow oil.

LCMS (ESI): m/z [M+H] calcd for $C_{16}H_{24}BN_2O_4$: 319.18; found: 319.4.

Preparation of tert-butyl (2S)-2-[[4-(cyclopropanecarbonylamino)-2-(4,6-dimethylpyrimidin-5-yl)phenoxy]methyl]piperidine-1-carboxylate (105)

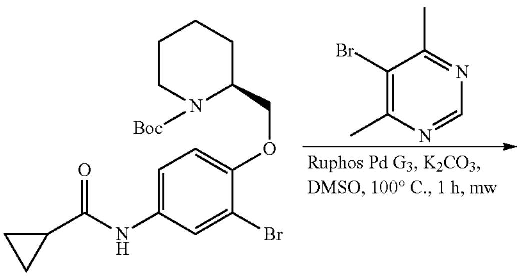

104

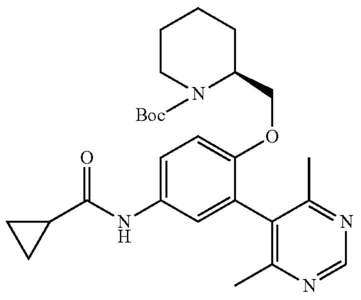

105 tert-Butyl (2S)-2-[[4-(cyclopropanecarbonylamino)-2-(4,4,5,5-tetramethyl-1,3,2-dioxaborolan-2-yl)phenoxy]methyl]piperidine-1-carboxylate ((104), 220 mg, 439.62 μmol, 1 eq.), 5-bromo-4,6-dimethyl-pyrimidine (82.22 mg, 439.62 μmol, 1 eq.), RuPhos Pd G3 (36.77 mg, 43.96 μmol, 0.1 eq.) and $K_2CO_3$ (91.14 mg, 659.43 μmol, 1.5 eq.) were taken up into a microwave tube in DMSO (2 mL). The sealed tube was heated at 100° C. for 1 hr under microwave. The residue was purified by column chromatography ($SiO_2$, petroleum ether/ethyl acetate=1:0 to 0:1). Tert-butyl (2S)-2-[[4-(cyclopropanecarbonylamino)-2-(4,6-dimethylpyrimidin-5-yl)phenoxy]methyl]piperidine-1-carboxylate ((105), 57 mg, 103.18 μmol, 23.47% yield, 87% purity) was obtained as a yellow oil.

LCMS (ESI): m/z [M+H] calcd for $C_{27}H_{37}N_4O_4$: 481.28; found: 481.3.

Preparation of N-[3-(4,6-dimethylpyrimidin-5-yl)-4-[[(2S)-2-piperidyl]methoxy]phenyl]cyclopropanecarboxamide (420)

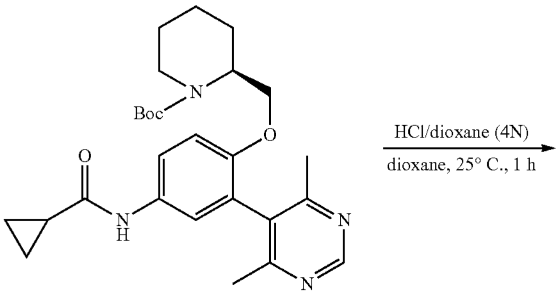

105

-continued

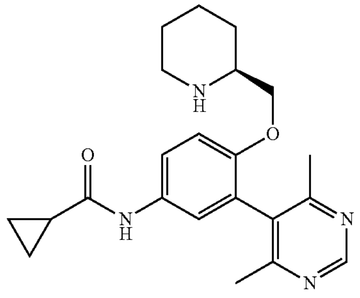

420

To a solution of tert-butyl (2S)-2-[[4-(cyclopropanecarbonylamino)-2-(4,6-dimethylpyrimidin-5-yl)phenoxy]methyl]piperidine-1-carboxylate ((105), 57 mg, 103.18 μmol, 1 eq.) in dioxane (1 mL) was added HCl/dioxane (4 M, 25.80 μL). The mixture was stirred at 25° C. for 1 hr (monitored by LC-MS). To the reaction mixture was added sat. $NaHCO_3$ (2 mL) to adjust the pH to 7, then the reaction mixture was concentrated under reduced pressure to give a residue. The residue was purified by prep-HPLC (TFA conditions). Column: Phenomenex Gemini-NX C18 75*30 mm*3 μm; mobile phase: [water (0.1% TFA)-ACN]; B %: 15%-25%, 7 min. N-[3-(4,6-dimethylpyrimidin-5-yl)-4-[[(2S)-2-piperidyl]methoxy]phenyl]cyclopropanecarboxamide (30.65 mg, 61.98 μmol, 60.07% yield, 100% purity, TFA) was obtained as an off-white gum.

LCMS (ESI): m/z [M+H] calcd for $C_{22}H_{29}N_4O_2$: 381.22; found: 381.3.

$^1$H NMR (400 MHZ, methanol-$d_4$) δ=8.97 (s, 1H), 7.64 (dd, J=2.7, 8.9 Hz, 1H), 7.45 (d, J=2.6 Hz, 1H), 7.22 (d, J=9.0 Hz, 1H), 4.23-4.01 (m, 2H), 3.43-3.31 (m, 2H), 3.01-2.90 (m, 1H), 2.35 (d, J=3.7 Hz, 6H), 1.91-1.71 (m, 4H), 1.68-1.36 (m, 3H), 0.98-0.81 (m, 4H).

N-[3-(4,6-dimethylpyrimidin-5-yl)-4-[[(2R)-2-piperidyl]methoxy]phenyl]cyclopropanecarboxamide (421)

Preparation of tert-butyl (2R)-2-[[2-bromo-4-(cyclopropanecarbonylamino)phenoxy]methyl]piperidine-1-carboxylate (106)

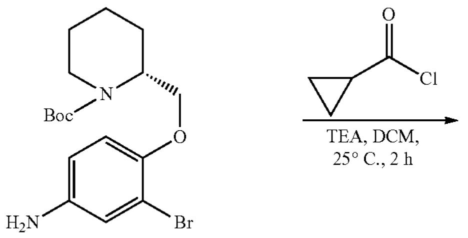

-continued

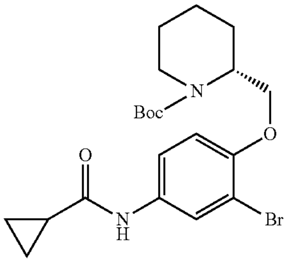

106

To a mixture of tert-butyl (2R)-2-[(4-amino-2-bromophenoxy)methyl]piperidine-1-carboxylate (1.5 g, 3.70 mmol, 1 eq.) and cyclopropanecarbonyl chloride (425.28 mg, 4.07 mmol, 369.81 μL, 1.1 eq.) in DCM (20 mL) was added TEA (1.12 g, 11.10 mmol, 1.54 mL, 3 eq.). The mixture was stirred at 25° C. for 2 hrs (monitored by LC-MS). The reaction mixture was partitioned between $H_2O$ (30 mL) and EtOAc (30 mL). The organic phase was separated and concentrated under vacuum. The residue was purified by column chromatography ($SiO_2$, petroleum ether/ethyl acetate=3/2 to 1/1). TLC (petroleum ether/ethyl acetate 1:1). Tert-butyl (2R)-2-[[2-bromo-4-(cyclopropanecarbonylamino)phenoxy]methyl]piperidine-1-carboxylate ((106), 1.42 g, 3.11 mmol, 83.96% yield, 99% purity) was obtained as a white solid and used in the next step.

LCMS (ESI): m/z [M+H] calcd for $C_{21}H_{30}Br^{79/80}N_2O_4$: 453.13 and 455.13; found: 453.2 and 455.2.

Preparation of tert-butyl (2R)-2-[[4-(cyclopropanecarbonylamino)-2-(4,4,5,5-tetramethyl-1,3,2-dioxaborolan-2-yl)phenoxy]methyl]piperidine-1-carboxylate (107)

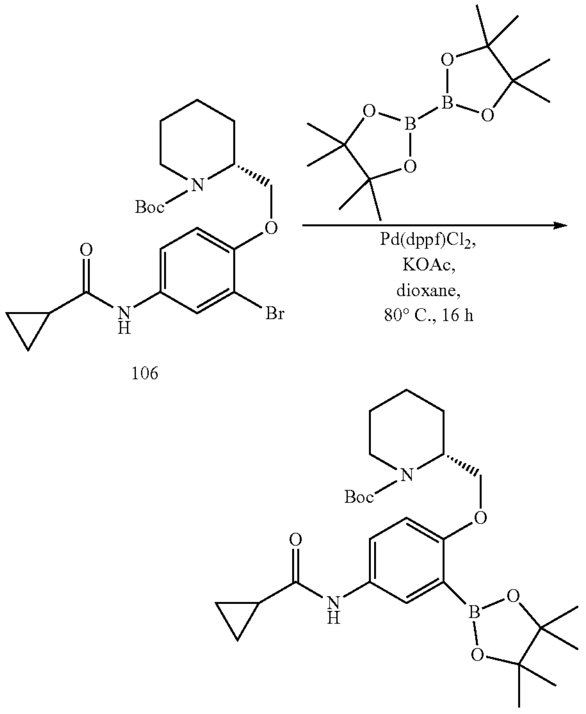

106

107

A mixture of tert-butyl (2R)-2-[[2-bromo-4-(cyclopropanecarbonylamino)phenoxy]methyl]piperidine-1-carboxylate ((106), 500 mg, 1.09 mmol, 1 eq.), 4,4,5,5-tetramethyl-2-(4,4,5,5-tetramethyl-1,3,2-dioxaborolan-2-yl)-1,3,2-dioxaborolane (831.77 mg, 3.28 mmol, 3 eq.), KOAc (160.73 mg, 1.64 mmol, 1.5 eq.) and RuPhos Pd G3 (91.32 mg, 109.18 μmol, 0.1 eq.) in dioxane (5 mL) was degassed and purged with $N_2$ three times, and then the mixture was stirred at 80° C. for 16 hrs under an $N_2$ atmosphere (monitored by LC-MS). The reaction mixture was filtered and concentrated under reduced pressure to give a residue. The residue was purified by prep-HPLC (column: Phenomenex Luna C18 150*40 mm*15 μm; mobile phase: [water (0.1% TFA)-ACN]; B %: 58%-88%, 10 min). Tert-butyl (2R)-2-[[4-(cyclopropanecarbonylamino)-2-(4,4,5,5-tetramethyl-1,3,2-dioxaborolan-2-yl)phenoxy]methyl]piperidine-1-carboxylate ((107), 100 mg, 81.93 μmol, 7.50% yield, 41% purity) was obtained as a white solid and used in the next step.

LCMS (ESI): m/z [M+H] calcd for $C_{27}H_{42}BN_2O_6$: 501.31; found: 501.4.

Preparation of tert-butyl (2R)-2-[[4-(cyclopropanecarbonylamino)-2-(4,6-dimethylpyrimidin-5-yl)phenoxy]methyl]piperidine-1-carboxylate (108)

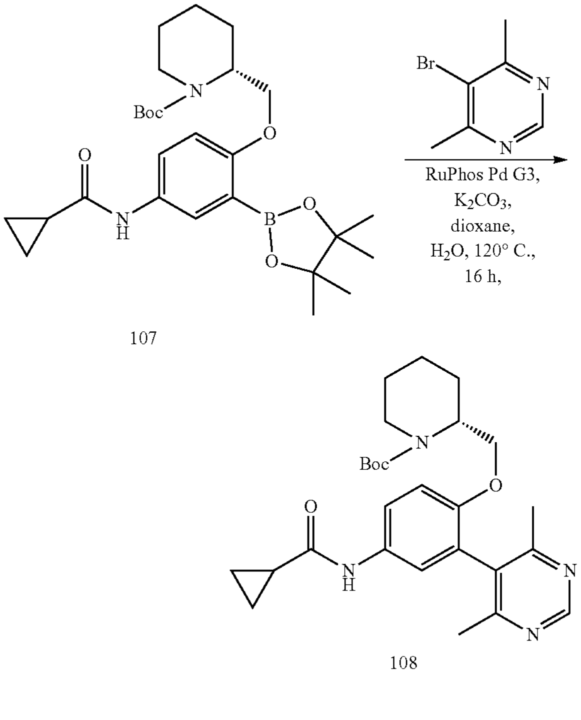

107

108

A mixture of tert-butyl (2R)-2-[[4-(cyclopropanecarbonylamino)-2-(4,4,5,5-tetramethyl-1,3,2-dioxaborolan-2-yl)phenoxy]methyl]piperidine-1-carboxylate ((107), 200 mg, 311.73 μmol, 1 eq.), 5-bromo-4,6-dimethyl-pyrimidine (87.46 mg, 467.59 μmol, 1.5 eq.), $K_2CO_3$ (86.17 mg, 623.46 μmol, 2 eq.) and RuPhos Pd G3 (26.07 mg, 31.17 μmol, 0.1 eq.) in dioxane (2 mL) and $H_2O$ (0.2 mL) was degassed and purged with $N_2$ three times, and then the mixture was stirred at 120° C. for 16 hrs under an $N_2$ atmosphere (monitored by LC-MS). The reaction mixture was filtered and concentrated under reduced pressure to give a residue. The residue was purified by prep-HPLC (column: Waters Xbridge 150*25 mm*5 μm; mobile phase: [water (10 mM $NH_4HCO_3$)-ACN]; B %: 26%-56%, 10 min). Tert-butyl (2R)-2-[[4-(cyclopropanecarbonylamino)-2-(4,6-dimethylpyrimidin-5-yl)phenoxy]methyl]piperidine-1-carboxylate ((108), 70 mg, 145.65 μmol, 46.72% yield, 100% purity) was obtained as a white solid and used in the next step.

LCMS (ESI): m/z [M+H] calcd for $C_{22}H_{29}N_4O_2$: 481.27; found: 481.3.

Preparation of N-[3-(4,6-dimethylpyrimidin-5-yl)-4-[[(2R)-2-piperidyl]methoxy]phenyl]cyclopropanecarboxamide (421)

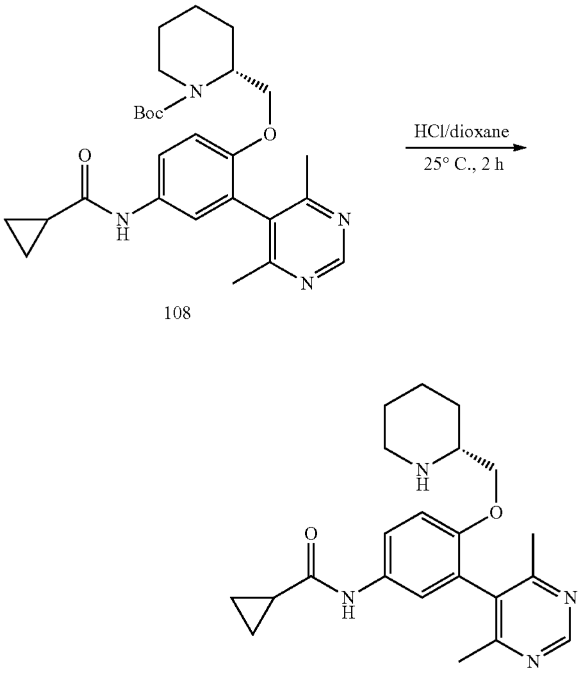

108

421

To a mixture of tert-butyl (2R)-2-[[4-(cyclopropanecarbonylamino)-2-(4,6-dimethylpyrimidin-5-yl)phenoxy]methyl]piperidine-1-carboxylate ((108), 70 mg, 145.65 μmol, 1 eq.) in dioxane (1 mL) was added HCl/dioxane (4 M, 2.00 L, 54925.45 eq.). The mixture was stirred at 25° C. for 1 hr (monitored by LC-MS). The reaction mixture was adjusted to pH=7.0 with NaOH (1 mol), then the mixture was filtered and concentrated under reduced pressure to give a residue. The residue was purified by prep-HPLC (column: Waters Xbridge 150*25 mm*5 μm; mobile phase: [water (10 mM $NH_4HCO_3$)-ACN]; B %: 5%-35%, 10 min). N-[3-(4,6-dimethylpyrimidin-5-yl)-4-[[(2R)-2-piperidyl]methoxy]phenyl]cyclopropanecarboxamide (30.28 mg, 77.20 μmol, 53.00% yield, 97% purity) was obtained as a white solid.

LCMS (ESI): m/z [M+H] calcd for $C_{22}H_{28}N_4O_2$: 381.22; found: 381.3.

$^1H$ NMR (400 MHz, methanol-$d_4$) δ=8.87 (s, 1H), 7.65 (dd, J=2.6, 8.9 Hz, 1H), 7.42 (d, J=2.6 Hz, 1H), 7.23 (d, J=8.9 Hz, 1H), 4.15-4.04 (m, 2H), 3.40-3.32 (m, 2H), 2.96 (dt, J=2.9, 12.5 Hz, 1H), 2.29 (d, J=3.8 Hz, 6H), 1.89-1.73 (m, 4H), 1.65-1.36 (m, 3H), 0.96-0.82 (m, 4H).

(1S,2R)—N-[3-(4,6-dimethylpyrimidin-5-yl)-4-[[(2R)-2-piperidyl]methoxy]phenyl]-2-fluoro-cyclopropanecarboxamide (422)

Preparation of tert-butyl (2R)-2-[[2-(4,6-dimethylpyrimidin-5-yl)-4-nitro-phenoxy]methyl]piperidine-1-carboxylate (109)

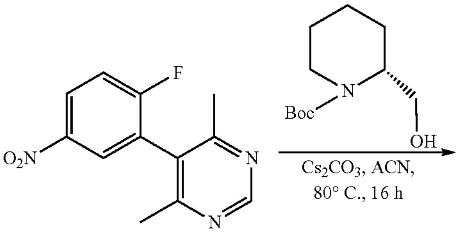

1

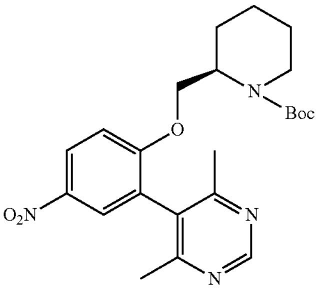

109

To a solution of 5-(2-fluoro-5-nitro-phenyl)-4,6-dimethyl-pyrimidine ((1), 890.00 mg, 3.60 mmol, 1 eq.) in $CH_3CN$ (20 mL) was added tert-butyl (2R)-2-(hydroxymethyl) piperidine-1-carboxylate (852.53 mg, 3.96 mmol, 1.1 eq.) and $Cs_2CO_3$ (2.35 g, 7.20 mmol, 2 eq.). The mixture was stirred at 80° C. for 16 hrs (monitored by LC-MS). The mixture was diluted with water (50 mL) and then extracted with ethyl acetate (100 mL×2). The combined organic phase was washed with brine (50 mL), dried over anhydrous $Na_2SO_4$, filtered and concentrated in vacuo. The residue was purified by flash silica gel chromatography (ISCO®; 20 g SepaFlash® Silica Flash Column, eluent of 0~50% ethyl acetate/petroleum ether gradient at 35 mL/min). TLC: (PE: EA=2:1). Tert-butyl (2R)-2-[[2-(4,6-dimethylpyrimidin-5-yl)-4-nitro-phenoxy]methyl]piperidine-1-carboxylate ((109), 1.1 g, 1.86 mmol, 51.67% yield, 75% purity) was obtained as a yellow oil.

LCMS (ESI): m/z [M+H] calcd for $C_{23}H_{31}N_4O_5$: 443.22; found: 443.3.

Preparation of tert-butyl (2R)-2-[[4-amino-2-(4,6-dimethylpyrimidin-5-yl)phenoxy]methyl]piperidine-1-carboxylate (110)

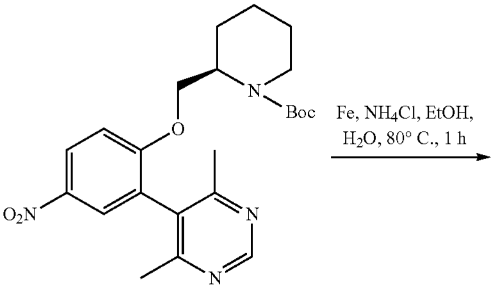

109

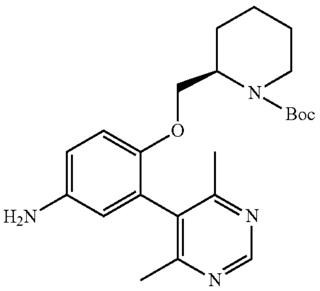

110

To a solution of tert-butyl (2R)-2-[[2-(4,6-dimethylpyrimidin-5-yl)-4-nitro-phenoxy]methyl]piperidine-1-carboxylate ((109), 1.1 g, 1.86 mmol, 1 eq.) in EtOH (15 mL) and $H_2O$ (15 mL) was added $NH_4Cl$ (797.82 mg, 14.92 mmol, 8 eq.). The mixture was stirred at 80° C. for 0.1 hr. To the mixture was added Fe (520.58 mg, 9.32 mmol, 5 eq.). The mixture was stirred at 80° C. for 2 hrs (monitored by LC-MS). The mixture was diluted with water (50 mL) and then extracted with ethyl acetate (100 mL×2). The combined organic phase was washed with brine (50 mL), dried over anhydrous $Na_2SO_4$, filtered and concentrated in vacuo. The residue was purified by flash silica gel chromatography (ISCO®; 20 g SepaFlash® Silica Flash Column, eluent of 0~100% ethyl acetate/petroleum ether gradient at 40 mL/min). Tert-butyl (2R)-2-[[4-amino-2-(4,6-dimethylpyrimidin-5-yl)phenoxy]methyl]piperidine-1-carboxylate ((110), 720 mg, 1.68 mmol, 89.87% yield, 96% purity) was obtained as a yellow oil.

LCMS (ESI): m/z [M+H] calcd for $C_{23}H_{33}N_4O_3$: 413.25; found: 413.3.

Preparation of tert-butyl (2R)-2-[[2-(4,6-dimethylpyrimidin-5-yl)-4-[[(1S,2R)-2-fluorocyclopropanecarbonyl]amino]phenoxy]methyl]piperidine-1-carboxylate (111)

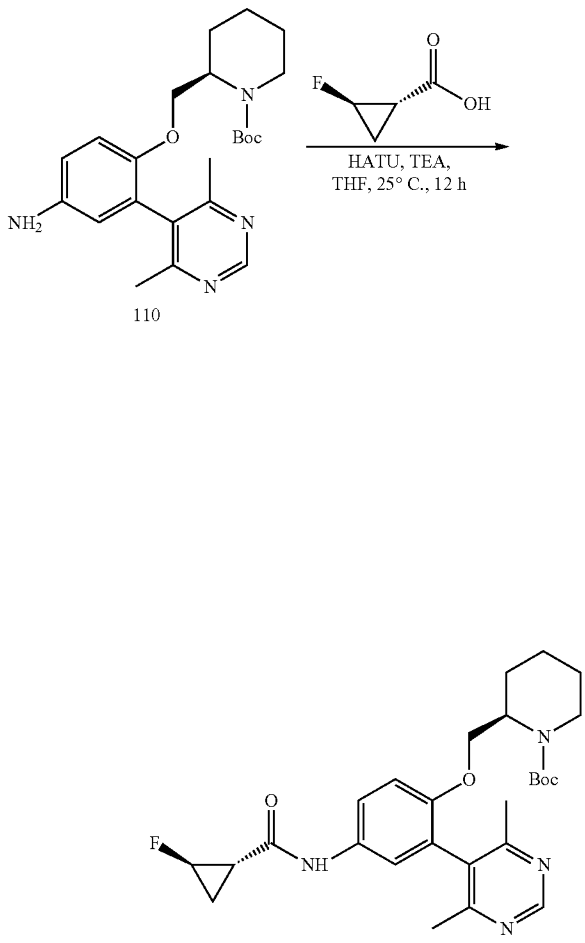

110

111

To a solution of (1S,2R)-2-fluorocyclopropanecarboxylic acid (37.84 mg, 363.62 μmol, 1.5 eq.) and tert-butyl (2R)-2-[[4-amino-2-(4,6-dimethylpyrimidin-5-yl)phenoxy]methyl]piperidine-1-carboxylate ((110), 100 mg, 242.41 μmol, 1 eq.) in THF (1 mL) was added HATU (110.61 mg, 290.89 μmol, 1.2 eq.) and TEA (73.59 mg, 727.23 μmol, 101.22 μL, 3 eq.). The mixture was stirred at 25° C. for 2 hrs (monitored by LC-MS). The reaction mixture were washed with 5% citric acid in water (5 mL×3) and saturated sodium bicarbonate solution (5 mL×3), dried over sodium sulfate, filtered and concentrated under reduced pressure to give tert-butyl (2R)-2-[[2-(4,6-dimethylpyrimidin-5-yl)-4-[[(1S,2R)-2-fluorocyclopropanecarbonyl]amino]phenoxy]methyl]piperidine-1-carboxylate ((111), 190 mg, 198.16 μmol, 81.75% yield, 52% purity) as a brown solid.

$^1$H NMR (400 MHZ, chloroform-d) δ 1.37-1.54 (m, 17H), 2.00 (br dd, J=17.26, 8.63 Hz, 1H), 2.24 (d, J=5.63 Hz, 6H), 2.53-2.65 (m, 1H), 3.94 (br d, J=4.13 Hz, 2H), 3.99-4.05 (m, 1H), 4.32 (br s, 1H), 4.69-5.01 (m, 1H), 7.00 (d, J=8.88 Hz, 1H), 7.49 (br d, J=8.63 Hz, 1H), 7.71 (s, 1H), 8.93 (s, 1H).

Preparation of (1S,2R)—N-[3-(4,6-dimethylpyrimidin-5-yl)-4-[[(2R)-2-piperidyl]methoxy]phenyl]-2-fluoro-cyclopropanecarboxamide (422)

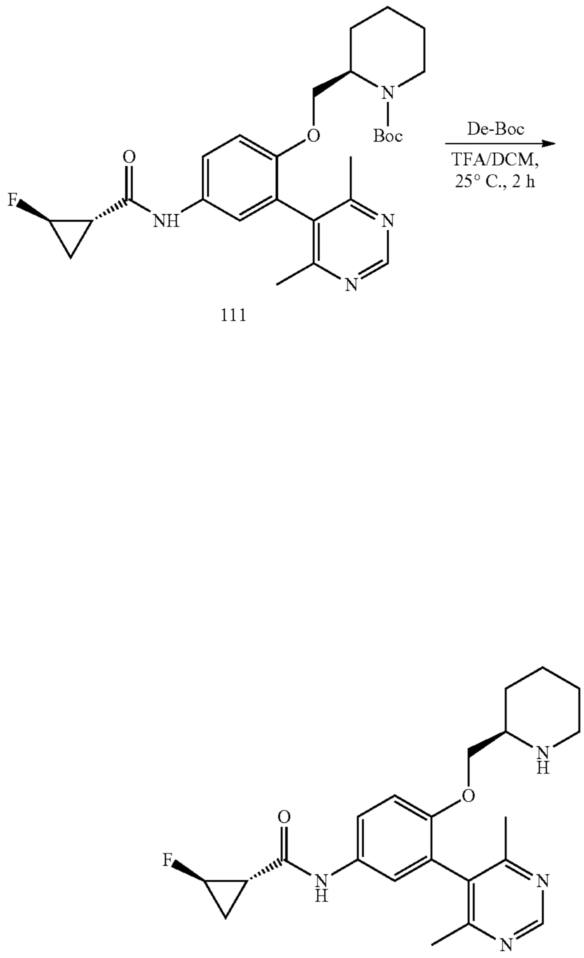

111

422

To a solution of tert-butyl (2R)-2-[[2-(4,6-dimethylpyrimidin-5-yl)-4-[[(1S,2R)-2-fluorocyclopropanecarbonyl]amino]phenoxy]methyl]piperidine-1-carboxylate ((111), 190 mg, 381.08 μmol, 1 eq.) in DCM (2 mL) was added TFA (308.00 mg, 2.70 mmol, 0.2 mL, 7.09 eq.). The mixture was stirred at 25° C. for 2 hrs. The reaction mixture was concentrated under reduced pressure to remove the solvent. The residue was purified by prep-HPLC (TFA conditions). (1S,2R)—N-[3-(4,6-dimethylpyrimidin-5-yl)-4-[[(2R)-2-piperidyl]methoxy]phenyl]-2-fluoro-cyclopropanecarboxamide (99.5 mg, 247.21 μmol, 64.87% yield, 99% purity) was obtained as an orange solid.

LCMS (ESI): m/z [M+H] calcd for $C_{22}H_{28}FN_4O_2$: 399.2; found: 399.1.

$^1$H NMR (400 MHZ, methanol-$d_4$) δ=8.90 (s, 1H), 7.65 (dd, J=2.6, 9.0 Hz, 1H), 7.39 (d, J=2.6 Hz, 1H), 7.21 (d, J=8.9 Hz, 1H), 4.91-4.72 (m, 1H), 4.15-4.09 (m, 1H), 4.08-4.01 (m, 1H), 3.34 (br s, 2H), 3.03-2.92 (m, 1H), 2.30 (d, J=4.4 Hz, 6H), 2.26-2.16 (m, 1H), 1.93-1.76 (m, 3H), 1.65-1.37 (m, 4H), 1.36-1.27 (m, 1H).

(1R,2R)—N-(3-(4,6-dimethylpyrimidin-5-yl)-4-(((R)-piperidin-2-yl)methoxy)phenyl)-2-fluorocyclopropane-1-carboxamide (423)

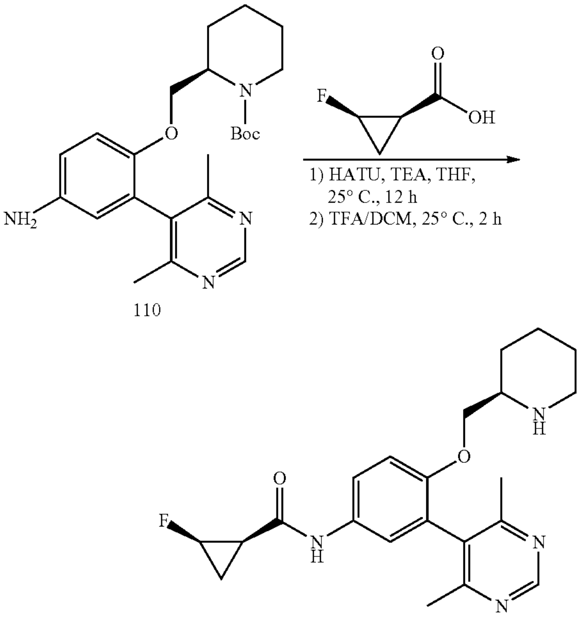

110

423

Compound 423 was prepared according to the synthesis described for compound 422, substituting (1R,2R)-2-fluorocyclopropane-1-carboxylic acid for (1S,2R)-2-fluorocyclopropanecarboxylic acid.

LCMS (ESI): m/z [M+H] calcd for $C_{22}H_{28}FN_4O_2$: 399.1; found: 399.1.

$^1H$ NMR (400 MHZ, methanol-$d_4$) δ=8.90 (s, 1H), 7.69 (dd, J=2.6, 8.9 Hz, 1H), 7.41 (d, J=2.6 Hz, 1H), 7.22 (d, J=9.0 Hz, 1H), 4.92-4.75 (m, 1H), 4.15-4.09 (m, 1H), 4.07-4.01 (m, 1H), 3.43-3.32 (m, 2H), 3.03-2.93 (m, 1H), 2.31 (d, J=4.1 Hz, 6H), 1.96 (dtd, J=4.8, 6.9, 9.2 Hz, 1H), 1.91-1.68 (m, 4H), 1.65-1.48 (m, 2H), 1.47-1.34 (m, 1H), 1.16 (tdd, J=6.5, 9.2, 12.4 Hz, 1H).

(1S,2S)—N-(3-(4,6-dimethylpyrimidin-5-yl)-4-(((R)-piperidin-2-yl) methoxy)phenyl)-2-fluorocyclopropane-1-carboxamide (424)

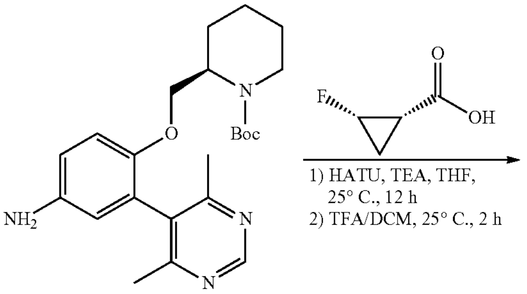

110

-continued

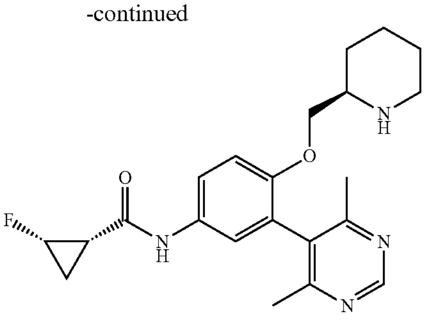

424

Compound 424 was prepared according to the synthesis described for compound 422, substituting (1S,2S)-2-fluorocyclopropane-1-carboxylic acid for (1S,2R)-2-fluorocyclopropanecarboxylic acid.

LCMS (ESI): m/z [M+H] calcd for $C_{22}H_{28}FN_4O_2$: 399.1; found: 399.1.

$^1H$ NMR (400 MHZ, methanol-$d_4$) δ=8.90 (s, 1H), 7.69 (dd, J=2.8, 8.8 Hz, 1H), 7.41 (d, J=2.4 Hz, 1H), 7.22 (d, J=8.8 Hz, 1H), 4.92-4.75 (m, 1H), 4.13-4.10 (m, 1H), 4.07-4.04 (m, 1H), 3.37-3.34 (m, 2H), 2.96-2.94 (m, 1H), 2.31 (s, 6H), 1.96-1.95 (m, 1H), 1.85-1.83 (m, 4H), 1.79-1.16 (m, 4H).

(R)—N-(3-(4,6-dimethylpyrimidin-5-yl)-4-(piperidin-2-ylmethoxy)phenyl)-4-methylthiazole-5-carboxamide (425)

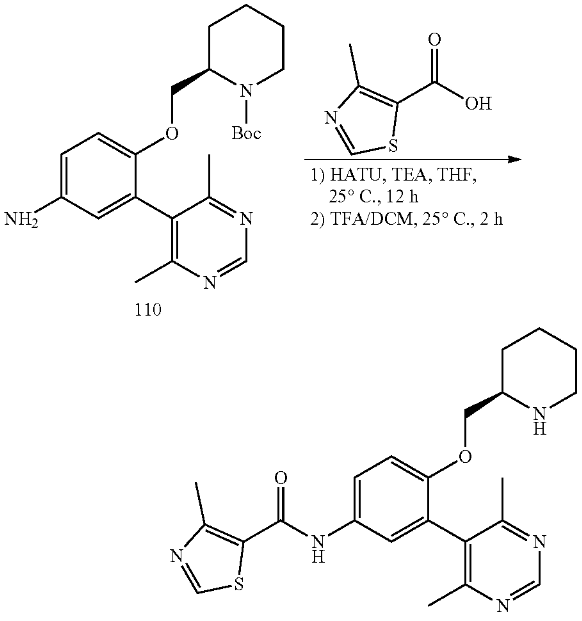

110

425

Compound 425 was prepared according to the synthesis described for compound substituting 4-methylthiazole-5-carboxylic acid for (1S,2R)-2-422, fluorocyclopropanecarboxylic acid.

LCMS (ESI): m/z [M+H] calcd for $C_{23}H_{28}N_5O_2S$: 438.1; found: 438.1.

$^1H$ NMR (400 MHZ, methanol-$d_4$) δ=9.02 (s, 1H), 8.91 (s, 1H), 7.78 (dd, J=2.6, 8.9 Hz, 1H), 7.47 (d, J=2.5 Hz, 1H), 7.27 (d, J=9.0 Hz, 1H), 4.19-4.13 (m, 1H), 4.11-4.05 (m, 1H), 3.45-3.32 (m, 2H), 3.04-2.93 (m, 1H), 2.69 (s, 3H), 2.33 (d, J=3.9 Hz, 6H), 1.92-1.79 (m, 3H), 1.67-1.49 (m, 2H), 1.48-1.34 (m, 1H).

(R)—N-(3-(4,6-dimethylpyrimidin-5-yl)-4-(piperidin-2-ylmethoxy)phenyl)-2,4-dimethylthiazole-5-carboxamide (426)

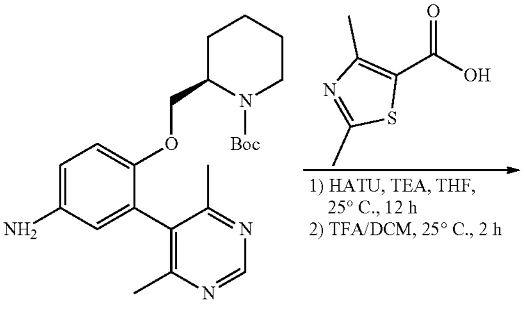

110

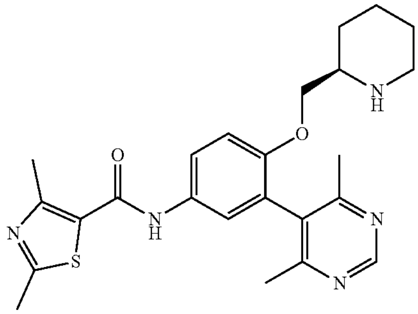

426

Compound 426 was prepared according to the synthesis described for compound 422, substituting 2,4-dimethylthiazole-5-carboxylic acid for (1S,2R)-2-fluorocyclopropanecarboxylic acid.

LCMS (ESI): m/z [M+H] calcd for $C_{24}H_{30}N_5O_2S$: 452.20; found: 452.1.

$^1$H NMR (400 MHZ, methanol-$d_4$) δ=8.92 (s, 1H), 7.76 (dd, J=2.6, 9.0 Hz, 1H), 7.44 (d, J=2.6 Hz, 1H), 7.26 (d, J=9.0 Hz, 1H), 4.18-4.12 (m, 1H), 4.10-4.04 (m, 1H), 3.37 (br d, J=12.9 Hz, 2H), 3.03-2.94 (m, 1H), 2.70 (s, 3H), 2.61 (s, 3H), 2.33 (d, J=3.9 Hz, 6H), 1.92-1.79 (m, 3H), 1.57 (br d, J=3.9 Hz, 2H), 1.48-1.34 (m, 1H).

(R)—N-(3-(4,6-dimethylpyrimidin-5-yl)-4-(piperidin-2-ylmethoxy)phenyl)-4-methylisoxazole-5-carboxamide (427)

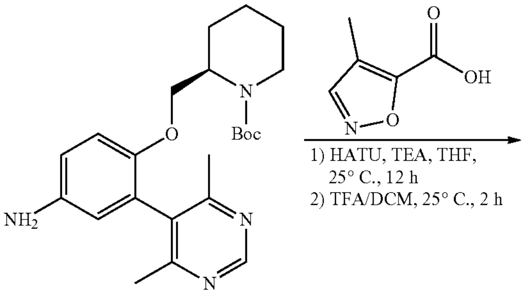

110

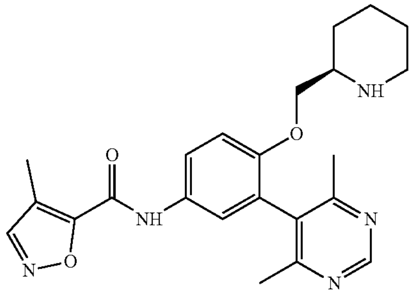

427

Compound 427 was prepared according to the synthesis described for compound 422, substituting 4-methylisoxazole-5-carboxylic acid for (1S,2R)-2-fluorocyclopropanecarboxylic acid.

LCMS (ESI): m/z [M+H] calcd for $C_{23}H_{28}N_5O_3$: 422.20; found: 422.1.

$^1$H NMR (400 MHz, DMSO-$d_6$) δ=10.71 (s, 1H), 8.91 (s, 1H), 8.71 (s, 1H), 8.52 (br d, J=9.5 Hz, 1H), 8.27 (br d, J=9.6 Hz, 1H), 7.84 (dd, J=2.6, 9.0 Hz, 1H), 7.59 (d, J=2.6 Hz, 1H), 7.26 (d, J=9.0 Hz, 1H), 4.08-3.99 (m, 2H), 3.33 (br s, 1H), 3.21 (br d, J=12.5 Hz, 1H), 2.89 (br d, J=10.4 Hz, 1H), 2.27 (s, 3H), 2.20 (d, J=5.8 Hz, 6H), 1.75-1.62 (m, 3H), 1.42 (br d, J=8.0 Hz, 2H), 1.32-1.20 (m, 1H).

(R)—N-(3-(4,6-dimethylpyrimidin-5-yl)-4-(piperidin-2-ylmethoxy)phenyl)-4-methyloxazole-5-carboxamide (428)

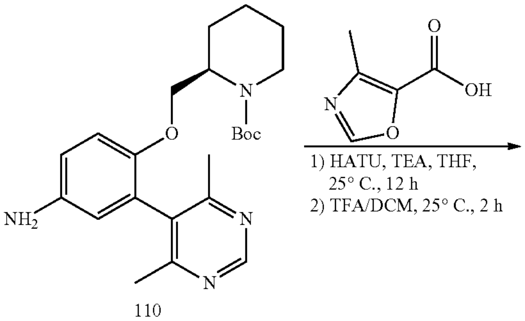

110

-continued

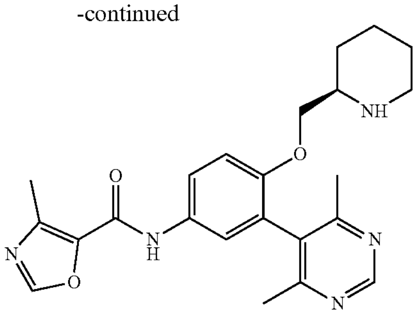

428

Compound 428 was prepared according to the synthesis described for compound substituting 422, 4-methyloxazole-5-carboxylic acid for (1S,2R)-2-fluorocyclopropanecarboxylic acid.

LCMS (ESI): m/z [M+H] calcd for $C_{23}H_{28}N_5O_3$: 422.20; found: 422.1.

$^1$H NMR (400 MHZ, methanol-$d_4$) δ=8.92 (s, 1H), 8.25 (s, 1H), 7.83 (dd, J=2.6, 9.0 Hz, 1H), 7.51 (d, J=2.6 Hz, 1H), 7.27 (d, J=9.0 Hz, 1H), 4.18-4.13 (m, 1H), 4.11-4.05 (m, 1H), 3.37 (br d, J=12.0 Hz, 2H), 3.03-2.94 (m, 1H), 2.50 (s, 3H), 2.33 (d, J=3.9 Hz, 6H), 1.91-1.80 (m, 3H), 1.63-1.52 (m, 2H), 1.47-1.35 (m, 1H).

(R)—N-(3-(4,6-dimethylpyrimidin-5-yl)-4-(piperidin-2-ylmethoxy)phenyl)isoxazole-4-carboxamide (429)

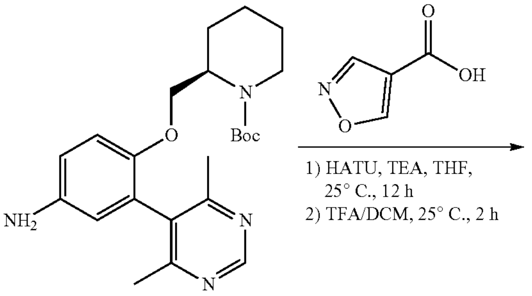

110

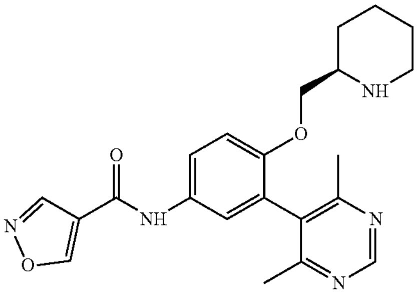

429

Compound 429 was prepared according to the synthesis described for compound 422, substituting isoxazole-4-carboxylic acid for (1S,2R)-2-fluorocyclopropanecarboxylic acid.

LCMS (ESI): m/z [M+H] calcd for $C_{22}H_{26}N_5O_3$: 408.2; found: 408.1.

$^1$H NMR (400 MHZ, methanol-$d_4$) δ=9.30 (s, 1H), 8.92 (s, 1H), 8.85 (s, 1H), 7.81 (dd, J=2.6, 8.9 Hz, 1H), 7.50 (d, J=2.6 Hz, 1H), 7.27 (d, J=9.0 Hz, 1H), 4.19-4.12 (m, 1H), 4.12-4.05 (m, 1H), 3.46-3.34 (m, 2H), 3.07-2.91 (m, 1H), 2.32 (d, J=3.9 Hz, 6H), 1.95-1.77 (m, 3H), 1.68-1.33 (m, 3H).

(R)—N-(3-(4,6-dimethylpyrimidin-5-yl)-4-(piperidin-2-ylmethoxy)phenyl)-3-methylisoxazole-4-carboxamide (430)

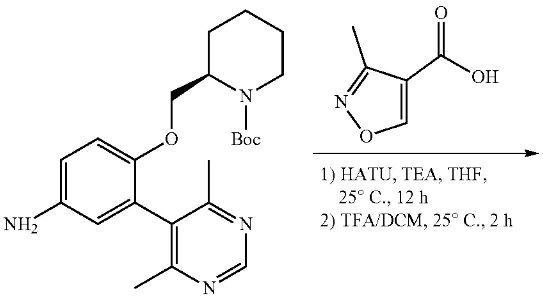

110

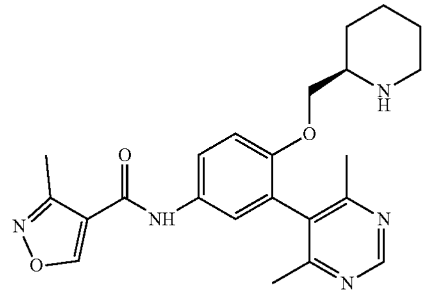

430

Compound 430 was prepared according to the synthesis described for compound 422, substituting 3-methylisoxazole-4-carboxylic acid for (1S,2R)-2-fluorocyclopropanecarboxylic acid.

LCMS (ESI): m/z [M+H] calcd for $C_{23}H_{28}N_5O_3$: 422.20; found: 422.1.

$^1$H NMR (400 MHZ, methanol-$d_4$) δ=9.17 (s, 1H), 8.95 (s, 1H), 7.76 (dd, J=2.7, 8.9 Hz, 1H), 7.51 (d, J=2.6 Hz, 1H), 7.27 (d, J=9.0 Hz, 1H), 4.22-4.06 (m, 2H), 3.45-3.32 (m, 2H), 3.04-2.92 (m, 1H), 2.52-2.45 (m, 3H), 2.35 (d, J=3.8 Hz, 6H), 1.95-1.79 (m, 3H), 1.69-1.35 (m, 3H).

(R)—N-(3-(4,6-dimethylpyrimidin-5-yl)-4-(piperidin-2-ylmethoxy)phenyl)-5-methylisoxazole-4-carboxamide (431)

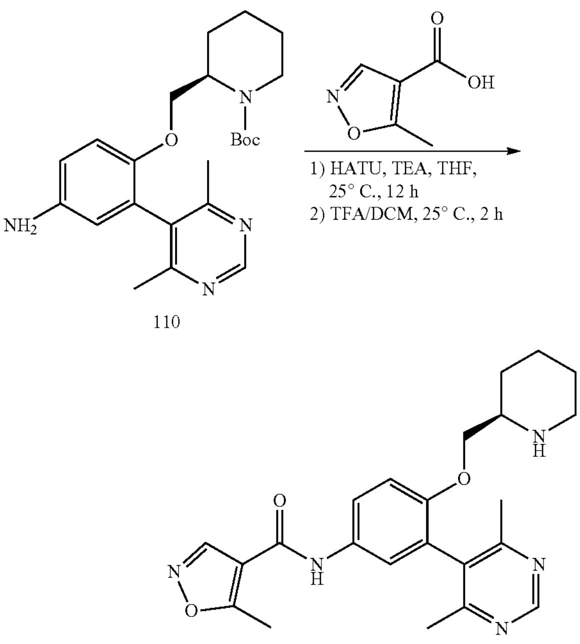

110

431

Compound 431 was prepared according to the synthesis described for compound 422, substituting 5-methylisoxazole-4-carboxylic acid for (1S,2R)-2-fluorocyclopropanecarboxylic acid.

LCMS (ESI): m/z [M+H] calcd for $C_{23}H_{28}N_5O_3$: 422.2; found: 422.1.

$^1$H NMR (400 MHZ, methanol-$d_4$) δ=8.92 (s, 1H), 8.81 (s, 1H), 7.78 (dd, J=2.6, 8.9 Hz, 1H), 7.49 (d, J=2.6 Hz, 1H), 7.27 (d, J=9.0 Hz, 1H), 4.19-4.04 (m, 2H), 3.46-3.34 (m, 2H), 3.07-2.92 (m, 1H), 2.71 (s, 3H), 2.33 (d, J=3.8 Hz, 6H), 1.97-1.79 (m, 3H), 1.70-1.33 (m, 3H).

(R)—N-(3-(4,6-dimethylpyrimidin-5-yl)-4-(piperidin-2-ylmethoxy)phenyl)-5-methyloxazole-4-carboxamide (432)

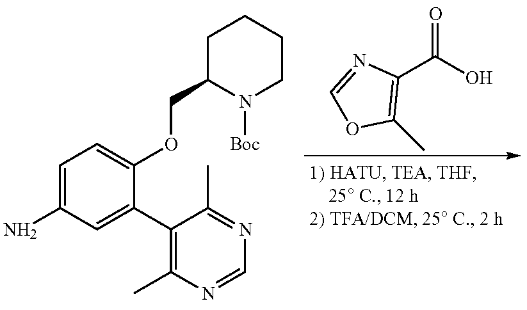

110

-continued

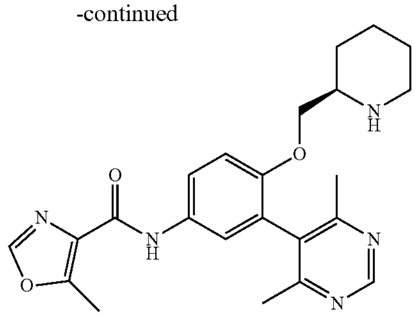

432

Compound 432 was prepared according to the synthesis described for compound 422, substituting 5-methyloxazole-4-carboxylic acid for (1S,2R)-2-fluorocyclopropanecarboxylic acid.

LCMS (ESI): m/z [M+H] calcd for $C_{23}H_{28}N_5O_3$: 422.2; found: 422.1.

$^1$H NMR (400 MHZ, methanol-$d_4$) δ=8.94 (s, 1H), 8.06 (s, 1H), 7.83 (dd, J=2.6, 9.0 Hz, 1H), 7.57 (d, J=2.6 Hz, 1H), 7.27 (d, J=9.0 Hz, 1H), 4.22-4.04 (m, 2H), 3.45-3.32 (m, 2H), 3.04-2.91 (m, 1H), 2.66 (s, 3H), 2.34 (d, J=3.8 Hz, 6H), 1.94-1.77 (m, 3H), 1.70-1.33 (m, 3H).

(R)—N-(3-(4,6-dimethylpyrimidin-5-yl)-4-(piperidin-2-ylmethoxy)phenyl) isothiazole-4-carboxamide (433)

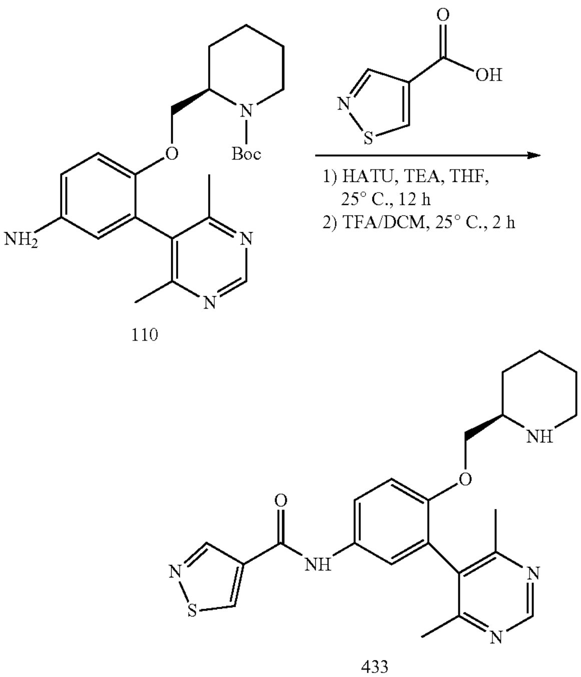

110

433

Compound 433 was prepared according to the synthesis described for compound 422, substituting isothiazole-4-carboxylic acid for (1S,2R)-2-fluorocyclopropanecarboxylic acid.

LCMS (ESI): m/z [M+H] calcd for $C_{22}H_{26}N_5O_2S$: 424.20; found: 424.1.

$^1$H NMR (400 MHZ, methanol-$d_4$) δ=9.58 (s, 1H), 8.98 (br s, 2H), 7.83 (dd, J=2.6, 9.0 Hz, 1H), 7.56 (d, J=2.6 Hz, 1H), 7.29 (d, J=9.0 Hz, 1H), 4.32-4.01 (m, 2H), 3.54-3.32 (m, 2H), 3.10-2.87 (m, 1H), 2.34 (br d, J=3.5 Hz, 6H), 2.00-1.76 (m, 3H), 1.70-1.35 (m, 3H).

(R)—N-(3-(4,6-dimethylpyrimidin-5-yl)-4-(piperidin-2-ylmethoxy)phenyl)-3-methylisothiazole-4-carboxamide (434)

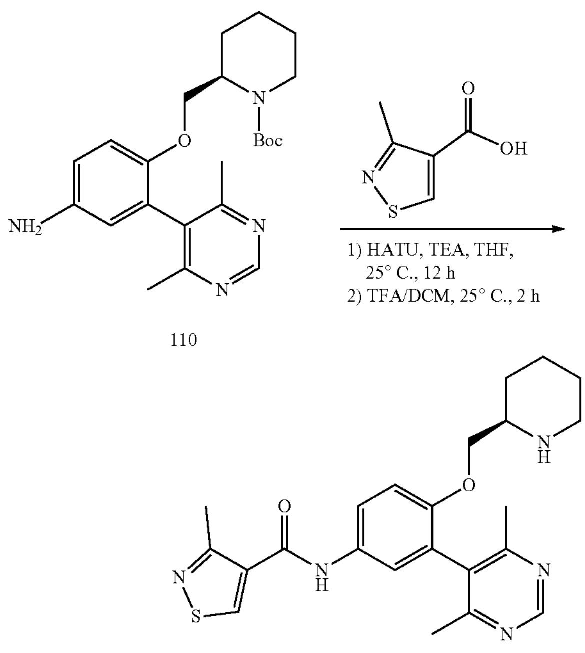

110

434

Compound 434 was prepared according to the synthesis described for compound 422, substituting 3-methylisothiazole-4-carboxylic acid for (1S,2R)-2-fluorocyclopropanecarboxylic acid.

LCMS (ESI): m/z [M+H] calcd for $C_{23}H_{28}N_5O_2S$: 438.20; found: 438.2.

$^1H$ NMR (400 MHZ, methanol-$d_4$) δ=9.37 (s, 1H), 8.95 (s, 1H), 7.80 (dd, J=2.6, 8.9 Hz, 1H), 7.53 (d, J=2.5 Hz, 1H), 7.28 (d, J=9.0 Hz, 1H), 4.23-4.05 (m, 2H), 3.34 (br d, J=12.9 Hz, 2H), 2.98 (br d, J=2.5 Hz, 1H), 2.69-2.62 (m, 3H), 2.35 (d, J=3.6 Hz, 6H), 1.96-1.77 (m, 3H), 1.68-1.36 (m, 3H).

(R)—N-(3-(4,6-dimethylpyrimidin-5-yl)-4-(piperidin-2-ylmethoxy)phenyl)-5-methylthiazole-4-carboxamide (435)

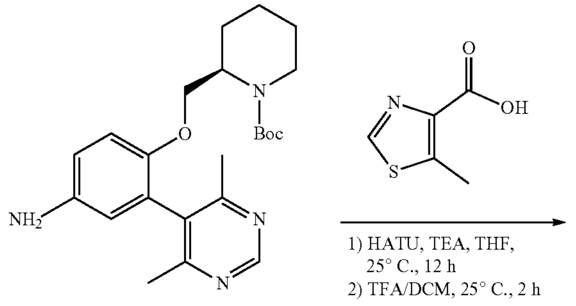

110

-continued

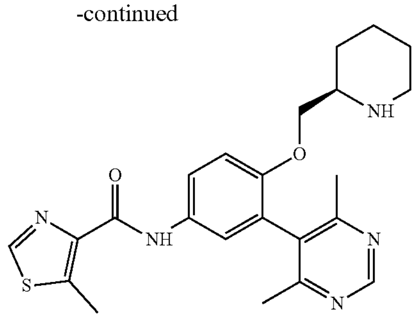

435

Compound 435 was prepared according to the synthesis described for compound 422, substituting 5-methylthiazole-4-carboxylic acid for (1S,2R)-2-fluorocyclopropanecarboxylic acid.

LCMS (ESI): m/z [M+H] calcd for $C_{23}H_{28}N_5O_2S$: 438.20; found: 438.2.

$^1H$ NMR (400 MHZ, methanol-$d_4$) δ=8.94 (s, 1H), 8.78 (s, 1H), 7.86 (dd, J=2.7, 8.9 Hz, 1H), 7.59 (d, J=2.6 Hz, 1H), 7.27 (d, J=9.0 Hz, 1H), 4.21-4.04 (m, 2H), 3.34 (br d, J=13.0 Hz, 2H), 3.06-2.92 (m, 1H), 2.84 (s, 3H), 2.35 (d, J=3.6 Hz, 6H), 1.94-1.75 (m, 3H), 1.68-1.36 (m, 3H).

(R)—N-(3-(4,6-dimethylpyrimidin-5-yl)-4-(piperidin-2-ylmethoxy)phenyl)-1-methyl-1H-pyrrole-2-carboxamide (436)

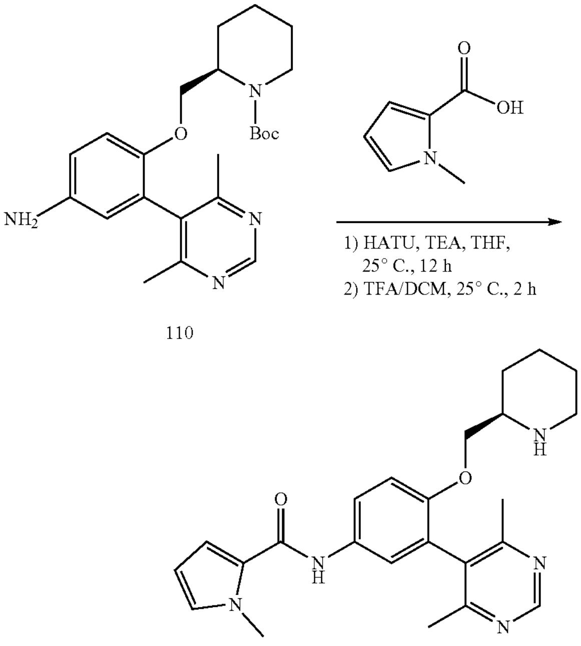

110

436

Compound 436 was prepared according to the synthesis described for compound 422, substituting 1-methyl-1H-pyrrole-2-carboxylic acid for (1S,2R)-2-fluorocyclopropanecarboxylic acid.

LCMS (ESI): m/z [M+H] calcd for $C_{24}H_{30}N_5O_2$: 420.20; found: 420.2.

$^1H$ NMR (400 MHZ, methanol-$d_4$) δ=8.95 (s, 1H), 7.74 (dd, J=2.6, 9.0 Hz, 1H), 7.48 (d, J=2.6 Hz, 1H), 7.24 (d, J=9.0 Hz, 1H), 6.96 (dd, J=1.6, 4.0 Hz, 1H), 6.89 (t, J=2.1 Hz, 1H), 6.11 (dd, J=2.5, 4.0 Hz, 1H), 4.19-4.04 (m, 2H), 3.92 (s, 3H), 3.45-3.32 (m, 2H), 3.02-2.92 (m, 1H), 2.36 (d, J=3.5 Hz, 6H), 1.91-1.78 (m, 3H), 1.67-1.37 (m, 3H).

N-[3-(4,6-dimethylpyrimidin-5-yl)-4-[[(2R)-2-piperidyl]methoxy]phenyl]-2-methyl-pyrazole-3-carboxamide (437)

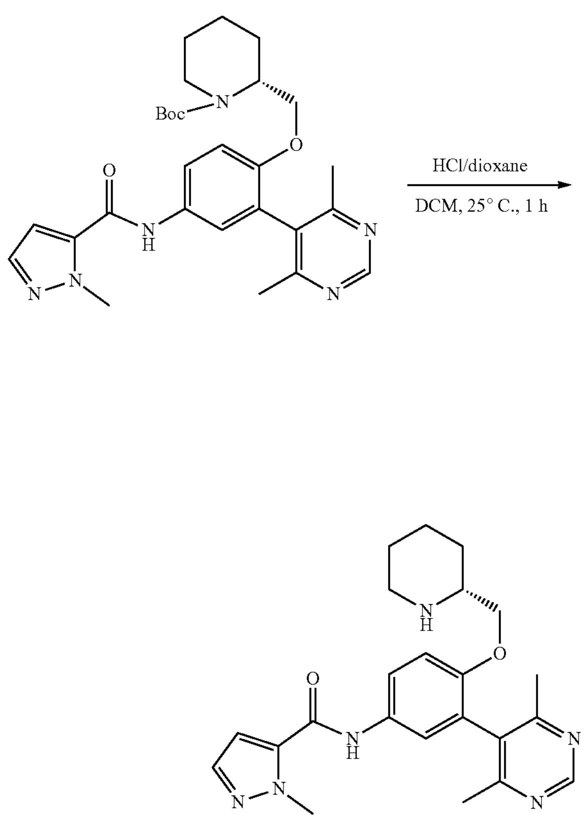

437

To a mixture of tert-butyl (2R)-2-[[2-(4,6-dimethylpyrimidin-5-yl)-4-[(2-methylpyrazole-3-carbonyl)amino]phenoxy]methyl]piperidine-1-carboxylate (84 mg, 161.35 µmol, 1 eq.) in DCM (1 mL) was added HCl/dioxane (4 M, 1 mL, 24.79 eq.). The mixture was stirred at 25° C. for 1 hr. The reaction mixture was concentrated under vacuum. N-[3-(4,6-dimethylpyrimidin-5-yl)-4-[[(2R)-2-piperidyl]methoxy]phenyl]-2-methyl-pyrazole-3-carboxamide (25.94 mg, 58.60 µmol, 36.32% yield, 95% purity) as a brown gum was obtained.

LCMS (ESI): m/z [M+H] calcd for $C_{23}H_{29}N_6O_2$: 421.23; found: 421.3.

$^1H$ NMR (400 MHZ, methanol-$d_4$) δ ppm 1.38-1.50 (m, 1H) 1.52-1.69 (m, 2H) 1.85 (br t, J=9.78 Hz, 3H) 2.36 (d, J=3.67 Hz, 6H) 2.92-3.04 (m, 1H) 3.35 (br d, J=12.96 Hz, 1H) 3.38-3.46 (m, 1H) 4.07-4.24 (m, 5H) 6.97 (d, J=1.96 Hz, 1H) 7.28 (d, J=9.05 Hz, 1H) 7.53 (dd, J=15.77, 2.32 Hz, 2H) 7.81 (dd, J=8.93, 2.57 Hz, 1H) 8.97 (s, 1H).

N-[3-(4,6-dimethylpyrimidin-5-yl)-4-[[(2R)-2-piperidyl]methoxy]phenyl]-1-fluoro-cyclopropanecarboxamide (438)

Preparation of tert-butyl (2R)-2-[[2-(4,6-dimethylpyrimidin-5-yl)-4-[(1-fluorocyclopropanecarbonyl)amino]phenoxy]methyl]piperidine-1-carboxylate (112)

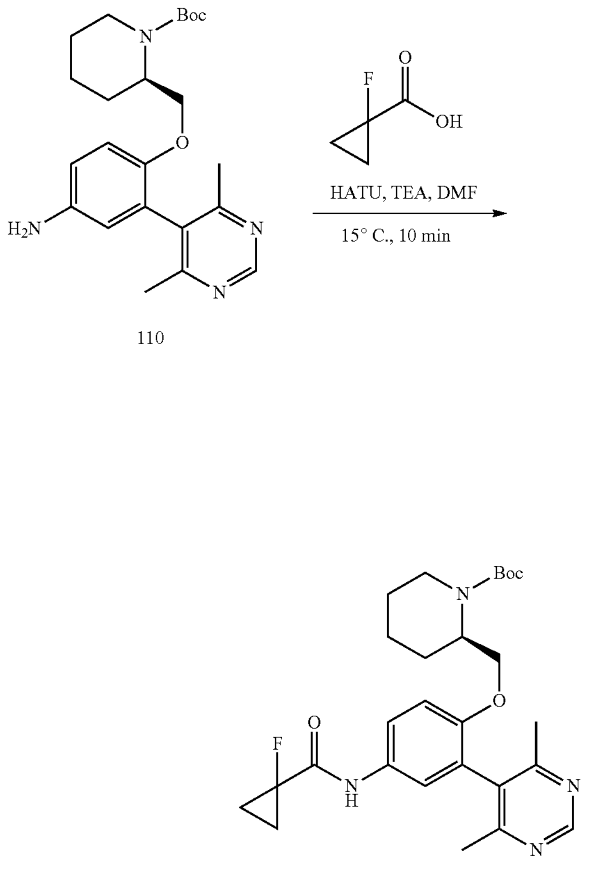

112

To a mixture of 1-fluorocyclopropanecarboxylic acid (30.28 mg, 290.89 µmol, 1.2 eq.), HATU (110.61 mg, 290.89 µmol, 1.2 eq.) and TEA (49.06 mg, 484.82 µmol, 67.48 µL, 2 eq.) in DCM (1 mL) was added tert-butyl (2R)-2-[[4-amino-2-(4,6-dimethylpyrimidin-5-yl)phenoxy]methyl]piperidine-1-carboxylate ((110), 100 mg, 242.41 µmol, 1 eq.). The mixture was stirred at 15° C. for 10 min (monitored by LC-MS). The reaction mixture was concentrated under reduced pressure to give a residue. The residue was diluted with $H_2O$ (2 mL) and extracted with EtOAc (5 mL×3). The combined organic layers were dried over $Na_2SO_4$, filtered and concentrated under reduced pressure to give a residue. Tert-butyl (2R)-2-[[2-(4,6-dimethylpyrimidin-5-yl)-4-[(1-fluorocyclopropanecarbonyl)amino]phenoxy]methyl]piperidine-1-carboxylate ((112), 100 mg, crude) was obtained as a yellow oil.

LCMS (ESI): m/z [M+H] calcd for $C_{26}H_{37}FN_4O_4$: 499.26; found: 499.4.

Preparation of N-[3-(4,6-dimethylpyrimidin-5-yl)-4-[[(2R)-2-piperidyl]methoxy]phenyl]-1-fluoro-cyclopropanecarboxamide (438)

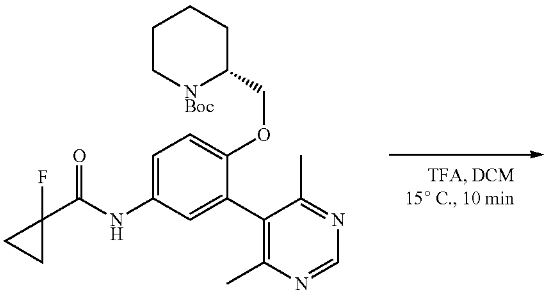

112

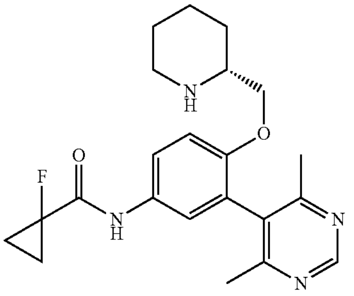

438

A mixture of tert-butyl (2R)-2-[[2-(4,6-dimethylpyrimidin-5-yl)-4-[(1-fluorocyclopropanecarbonyl)amino]phenoxy]methyl]piperidine-1-carboxylate ((112), 100 mg, 200.57 μmol, 1 eq.) in TFA (0.5 mL) and DCM (0.5 mL) was stirred at 15° C. for 10 min. The reaction mixture was concentrated under reduced pressure to give a residue (monitored by LC-MS). The residue was purified by prep-HPLC (column: Phenomenex Luna C18 150*25 mm*10 μm; mobile phase: [water (0.1% TFA)-ACN]; B %: 5%-35%, 10 min). N-[3-(4,6-dimethylpyrimidin-5-yl)-4-[[(2R)-2-piperidyl]methoxy]phenyl]-1-fluoro-cyclopropanecarboxamide (96.63 mg, 186.66 μmol, 93.07% yield, 99% purity, TFA) was obtained as a yellow solid.

LCMS (ESI): m/z [M+H] calcd for $C_{22}H_{28}FN_4O_2$: 399.21; found: 399.2.

$^1$H NMR (400 MHz, methanol-$d_4$) δ=10.11 (br d, J=2.4 Hz, 1H), 8.98-8.88 (m, 1H), 7.81-7.71 (m, 1H), 7.46 (d, J=2.5 Hz, 1H), 7.25 (d, J=9.0 Hz, 1H), 4.18-4.03 (m, 2H), 3.46-3.33 (m, 2H), 3.02-2.90 (m, 1H), 2.32 (d, J=3.5 Hz, 6H), 1.92-1.76 (m, 3H), 1.66-1.51 (m, 2H), 1.47-1.34 (m, 5H).

(R)—N-(3-(4,6-dimethylpyrimidin-5-yl)-4-(piperidin-2-ylmethoxy)phenyl)-1-methoxycyclopropane-1-carboxamide (439)

439

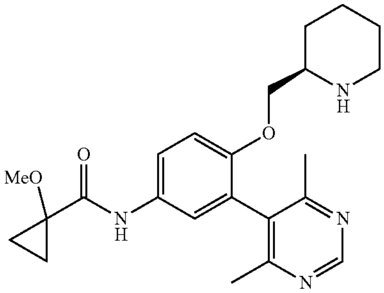

Compound 439 was prepared according to the synthesis described for compound 438, substituting 1-methoxycyclopropane-1-carboxylic acid for 1-fluorocyclopropanecarboxylic acid.

LCMS (ESI): m/z [M+H] calcd for $C_{23}H_{31}N_4O_3$: 411.23; found: 411.3.

$^1$H NMR (400 MHZ, methanol-$d_4$) δ=8.87 (s, 1H), 7.73 (dd, J=2.6, 9.0 Hz, 1H), 7.43 (d, J=2.7 Hz, 1H), 7.21 (d, J=8.9 Hz, 1H), 4.11-3.96 (m, 2H), 3.42 (s, 3H), 3.24 (br d, J=11.2 Hz, 2H), 2.92-2.82 (m, 1H), 2.30 (d, J=2.9 Hz, 6H), 1.88-1.71 (m, 3H), 1.59-1.46 (m, 2H), 1.39-1.29 (m, 1H), 1.29-1.24 (m, 2H), 1.23-1.14 (m, 2H).

(R)—N-(3-(4,6-dimethylpyrimidin-5-yl)-4-(piperidin-2-ylmethoxy)phenyl)-1-hydroxycyclopropane-1-carboxamide (440)

440

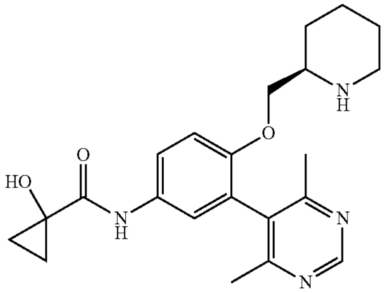

Compound 440 was prepared according to the synthesis described for compound 438, substituting 1-hydroxycyclopropane-1-carboxylic acid for 1-fluorocyclopropanecarboxylic acid.

LCMS (ESI): m/z [M+H] calcd for $C_{22}H_{29}N_4O_3$: 397.22; found: 397.2.

$^1$H NMR (400 MHZ, methanol-$d_4$) δ=8.86 (s, 1H), 7.67 (dd, J=2.6, 8.9 Hz, 1H), 7.43 (d, J=2.6 Hz, 1H), 7.15 (d, J=9.0 Hz, 1H), 3.96-3.81 (m, 2H), 2.98 (br d, J=12.0 Hz, 1H), 2.78 (br s, 1H), 2.56 (br t, J=11.8 Hz, 1H), 2.28 (s, 6H), 1.75 (br s, 1H), 1.66-1.50 (m, 2H), 1.42-1.31 (m, 2H), 1.30-1.24 (m, 2H), 1.17-1.00 (m, 3H).

(R)—N-[3-(4,6-dimethylpyrimidin-5-yl)-4-[[(2R)-2-piperidyl]methoxy]phenyl]-2-fluoro-pentanamide (441)

Preparation of ethyl 2-fluoropentanoate (113)

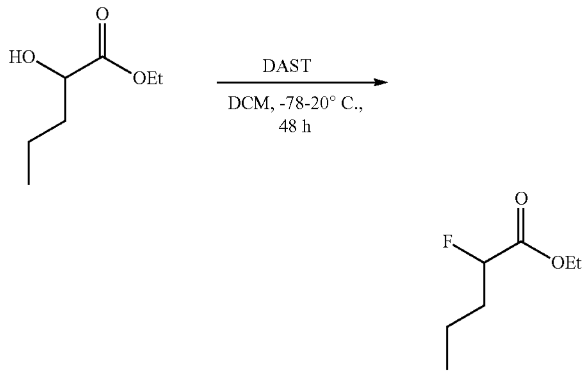

113

To a mixture of ethyl 2-hydroxypentanoate (3 g, 20.52 mmol, 3.05 mL, 1 eq.) in DCM (40 mL) was added DAST (4.96 g, 30.78 mmol, 4.07 mL, 1.5 eq.) at −78° C. under $N_2$. The mixture was stirred at −78° C. for 2 hrs, then warmed to 20° C. and stirred for 48 hrs. The mixture was poured into water (50 mL). The aqueous phase was extracted with ethyl acetate (50 mL×3). The combined organic phase was washed with brine (60 mL), dried with anhydrous $Na_2SO_4$, filtered and concentrated under vacuum. The residue was purified by silica gel chromatography (petroleum ether/ethyl acetate=10/1, 8/1). Ethyl 2-fluoropentanoate ((113), 1.04 g, 7.02 mmol, 34.20% yield) was obtained as a colorless oil.

$^1$H NMR (400 MHZ, chloroform-d) δ=4.79-4.89 (m, 1H), 4.19 (q, J=7.2 Hz, 2H), 1.86-1.73 (m, 2H), 1.48-1.37 (m, 2H), 1.29-1.22 (m, 3H), 0.90 (t, J=7.4 Hz, 3H).

Preparation of 2-fluoropentanoic acid (114)

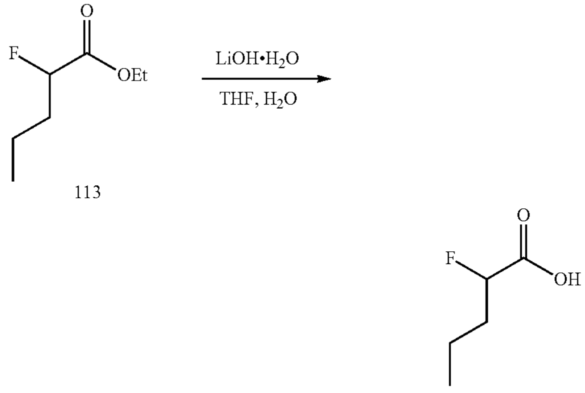

113

114

To a mixture of ethyl 2-fluoropentanoate ((113), 0.3 g, 2.02 mmol, 1 eq.) in THF (3 mL) and $H_2O$ (1 mL) was added LiOH·$H_2O$ (169.92 mg, 4.05 mmol, 2 eq.). The mixture was stirred at 30° C. for 1 hr. TLC (petroleum ether:ethyl acetate=5:1) showed the ethyl 2-fluoropentanoate was consumed. The mixture was concentrated to remove excess THF. The residue was acidified with 1M HCl aq, the pH was adjusted to 4-5, and then the mixture was extracted with ethyl acetate (10 mL×3). The combined organic phase was washed with brine (10 mL), dried with anhydrous $Na_2SO_4$, filtered and concentrated under vacuum. 2-fluoropentanoic acid ((114), 30 mg, crude) was obtained as a yellow oil.

$^1$H NMR (400 MHZ, chloroform-d) δ=5.07-4.87 (m, 1H), 1.99-1.83 (m, 2H), 1.54 (qd, J=7.5, 15.1 Hz, 2H), 1.04-0.95 (m, 3H).

Preparation of tert-butyl (2R)-2-[[2-(4,6-dimethylpyrimidin-5-yl)-4-(2-fluoropentanoylamino)phenoxy]methyl]piperidine-1-carboxylate (115)

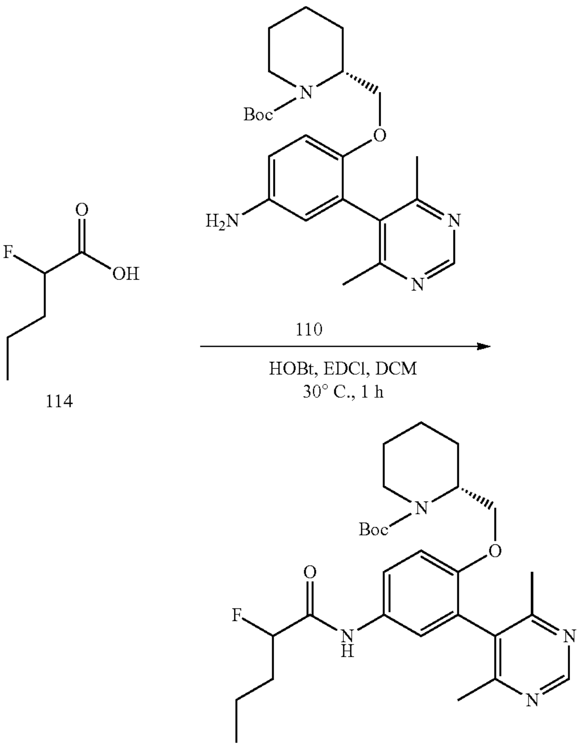

114

115

To a mixture of tert-butyl (2R)-2-[[4-amino-2-(4,6-dimethylpyrimidin-5-yl)phenoxy]methyl]piperidine-1-carboxylate ((110), 50 mg, 121.21 μmol, 1 eq.) and 2-fluoropentanoic acid ((114), 17.47 mg, 145.45 μmol, 1.2 eq.) in DCM (1 mL) was added HOBt (19.65 mg, 145.45 μmol, 1.2 eq.), and EDCI (27.88 mg, 145.45 μmol, 1.2 eq.). The mixture was stirred at 30° C. for 1 hr (monitored by LC-MS). The mixture was concentrated under vacuum. The residue was purified by column chromatography ($SiO_2$, petroleum ether/ethyl acetate=3/1 to 1/1). Tert-butyl (2R)-2-[[2-(4,6-dimethylpyrimidin-5-yl)-4-(2-fluoropentanoylamino)phenoxy]methyl]piperidine-1-carboxylate ((115), 40 mg, 77.73 μmol, 64.13% yield, 100% purity) was obtained as a yellow oil.

LCMS (ESI): m/z [M+H] calcd for $C_{28}H_{40}FN_4O_4$: 515.30; found: 515.3.

Preparation of (R)—N-[3-(4,6-dimethylpyrimidin-5-yl)-4-[[(2R)-2-piperidyl]methoxy]phenyl]-2-fluoro-pentanamide (441)

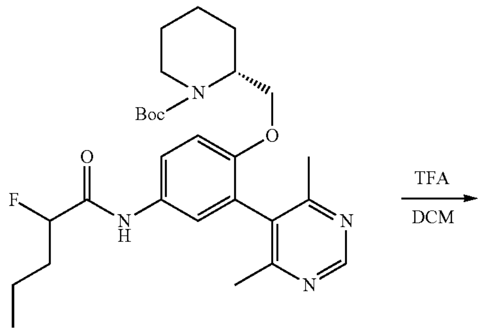

115

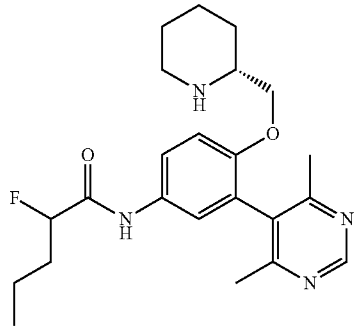

441

To a mixture of tert-butyl (2R)-2-[[2-(4,6-dimethylpyrimidin-5-yl)-4-(2-fluoropentanoylamino)phenoxy]methyl] piperidine-1-carboxylate ((115), 40 mg, 77.73 μmol, 1 eq.) in DCM (1 mL) was added TFA (0.2 mL). The mixture was stirred at 20° C. for 30 min (monitored by LC-MS). The mixture was concentrated under reduced pressure. The residue was purified by prep-HPLC (column: Waters Xbridge C18 150*50 mm*10 μm; mobile phase: [water (10 mM $NH_4HCO_3$)-ACN]; B %: 18%-48%, 8 min). (R)—N-[3-(4,6-dimethylpyrimidin-5-yl)-4-[[(2R)-2-piperidyl]methoxy] phenyl]-2-fluoro-pentanamide (20 mg, 48.25 μmol, 62.08% yield, 100% purity) was obtained as a white solid.

LCMS (ESI): m/z [M+H] calcd for $C_{23}H_{32}FN_4O_2$: 415.30; found: 415.3.

$^1$H NMR (400 MHZ, methanol-$d_4$) δ=8.86 (s, 1H), 7.69 (dd, J=2.7, 8.9 Hz, 1H), 7.42 (d, J=2.6 Hz, 1H), 7.16 (d, J=8.9 Hz, 1H), 5.10-4.91 (m, 1H), 3.96-3.81 (m, 2H), 2.97 (br d, J=10.8 Hz, 1H), 2.82-2.72 (m, 1H), 2.55 (dt, J=2.8, 11.8 Hz, 1H), 2.27 (s, 6H), 2.04-1.84 (m, 2H), 1.75 (br s, 1H), 1.62-1.49 (m, 4H), 1.42-1.27 (m, 2H), 1.17-1.04 (m, 1H), 1.00 (t, J=7.4 Hz, 3H).

(R)—N-(3-(4,6-dimethylpyrimidin-5-yl)-4-(((R)-piperidin-2-yl) methoxy)phenyl)-2-fluoro-3-methylbutanamide (442)

442

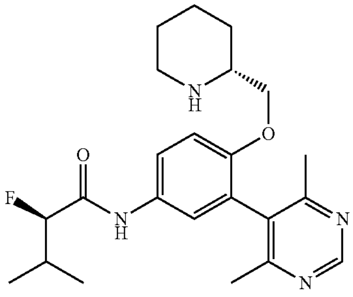

Compound 442 was prepared according to the synthesis described for compound 441, substituting (R)-2-fluoro-3-methylbutanoic acid for 2-fluoropentanoic acid.

LCMS (ESI): m/z [M+H] calcd for $C_{28}H_{40}FN_4O_4$: 415.25; found: 415.3.

$^1$H NMR (400 MHZ, methanol-$d_4$) δ=8.89 (s, 1H), 7.77 (dd, J=2.6, 9.0 Hz, 1H), 7.43 (d, J=2.6 Hz, 1H), 7.24 (d, J=9.0 Hz, 1H), 4.88-4.75 (m, 1H), 4.16-4.04 (m, 2H), 3.43-3.32 (m, 2H), 3.02-2.94 (m, 1H), 2.30 (d, J=3.9 Hz, 7H), 1.91-1.79 (m, 3H), 1.64-1.49 (m, 2H), 1.40 (br d, J=11.4 Hz, 1H), 1.11 (d, J=7.1 Hz, 3H), 1.02 (d, J=7.0 Hz, 3H).

(S)—N-(3-(4,6-dimethylpyrimidin-5-yl)-4-(((R)-piperidin-2-yl) methoxy)phenyl)-2-fluoro-3-methylbutanamide (443)

443

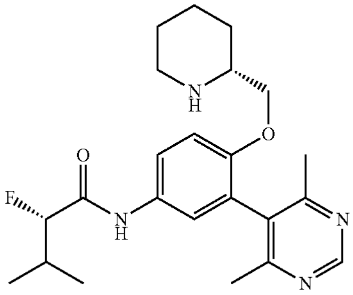

Compound 443 was prepared according to the synthesis described for compound 441, substituting(S)-2-fluoro-3-methylbutanoic acid for 2-fluoropentanoic acid.

LCMS (ESI): m/z [M+H] calcd for $C_{28}H_{40}FN_4O_4$: 415.25; found: 415.3.

$^1$H NMR (400 MHZ, methanol-$d_4$) δ=8.89 (s, 1H), 7.76 (dd, J=2.6, 9.0 Hz, 1H), 7.43 (d, J=2.6 Hz, 1H), 7.24 (d, J=9.0 Hz, 1H), 4.88-4.76 (m, 1H), 4.19-4.01 (m, 2H), 3.45-3.32 (m, 2H), 3.04-2.90 (m, 1H), 2.33-2.26 (m, 7H), 1.93-1.77 (m, 3H), 1.67-1.50 (m, 2H), 1.48-1.33 (m, 1H), 1.11 (d, J=7.0 Hz, 3H), 1.02 (d, J=6.8 Hz, 3H).

(R)—N-(3-(4,6-dimethylpyrimidin-5-yl)-4-(piperidin-2-ylmethoxy)phenyl)-1-fluorocyclobutane-1-carboxamide (444)

444

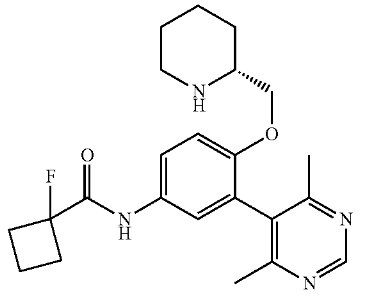

Compound 444 was prepared according to the synthesis described for compound 441, substituting 1-fluorocyclobutane-1-carboxylic acid for 2-fluoropentanoic acid.

LCMS (ESI): m/z [M+H] calcd for $C_{23}H_{30}FN_4O_2$: 413.23; found: 413.4.

$^1$H NMR (400 MHZ, methanol-$d_4$) δ=8.87 (s, 1H), 7.71 (dd, J=2.7, 8.9 Hz, 1H), 7.43 (d, J=2.7 Hz, 1H), 7.17 (d, J=8.9 Hz, 1H), 3.98-3.87 (m, 2H), 3.04 (br d, J=10.9 Hz, 1H), 2.95-2.82 (m, 1H), 2.75-2.58 (m, 3H), 2.56-2.39 (m, 2H), 2.28 (s, 6H), 2.08-1.86 (m, 2H), 1.84-1.71 (m, 1H), 1.70-1.54 (m, 2H), 1.47-1.30 (m, 2H), 1.22-1.07 (m, 1H).

(R)—N-(3-(4,6-dimethylpyrimidin-5-yl)-4-(piperidin-2-ylmethoxy)phenyl)-4-fluorotetrahydro-2H-pyran-4-carboxamide (445)

445

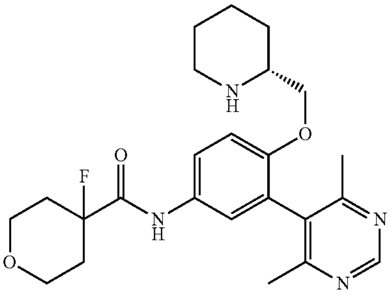

Compound 445 was prepared according to the synthesis described for compound 441, substituting 4-fluorotetrahydro-2H-pyran-4-carboxylic acid for 2-fluoropentanoic acid.

LCMS (ESI): m/z [M+H] calcd for $C_{24}H_{32}FN_4O_3$: 443.24; found: 443.3.

$^1$H NMR (400 MHZ, methanol-$d_4$) δ=8.93-8.89 (m, 1H), 7.80-7.74 (m, 1H), 7.48-7.43 (m, 1H), 7.24 (d, J=8.9 Hz, 1H), 4.16-4.04 (m, 2H), 3.93 (dd, J=5.1, 11.5 Hz, 2H), 3.75 (dt, J=1.9, 12.0 Hz, 2H), 3.43-3.32 (m, 2H), 2.97 (br t, J=12.3 Hz, 1H), 2.37-2.19 (m, 8H), 1.84 (br t, J=12.8 Hz, 5H), 1.64-1.49 (m, 2H), 1.47-1.35 (m, 1H).

(R)—N-(3-(4,6-dimethylpyrimidin-5-yl)-4-(piperidin-2-ylmethoxy)phenyl)-4-fluoro-1-methyl-1H-pyrazole-5-carboxamide (446)

446

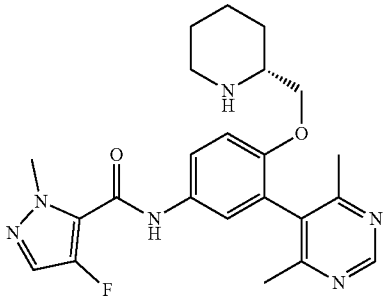

Compound 446 was prepared according to the synthesis described for compound 441, substituting 4-fluoro-1-methyl-1H-pyrazole-5-carboxylic acid for 2-fluoropentanoic acid.

LCMS (ESI): m/z [M+H] calcd for $C_{23}H_{28}FN_6O_2$: 439.0, found: 439.3.

$^1$H NMR (400 MHZ, methanol-$d_4$) δ=8.91 (s, 1H), 7.80 (br d, J=8.8 Hz, 1H), 7.52 (s, 1H), 7.47 (d, J=4.4 Hz, 1H), 7.28 (d, J=9.0 Hz, 1H), 4.19-4.07 (m, 2H), 4.05 (s, 3H), 3.45-3.32 (m, 2H), 3.04-2.94 (m, 1H), 2.33 (d, J=3.8 Hz, 6H), 1.91-1.80 (m, 3H), 1.65-1.49 (m, 2H), 1.48-1.33 (m, 1H).

N-(3-(4,6-dimethylpyrimidin-5-yl)-4-(((R)-piperidin-2-yl) methoxy)phenyl)-2-ethoxycyclopropane-1-carboxamide (447)

447

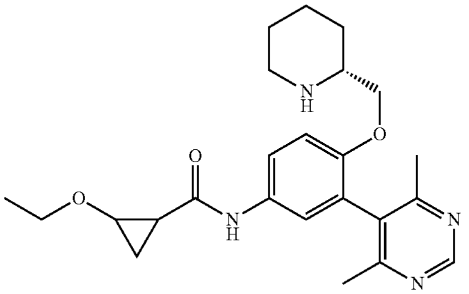

Compound 447 was prepared according to the synthesis described for compound 441, substituting 2-ethoxycyclopropane-1-carboxylic acid for 2-fluoropentanoic acid.

LCMS (ESI): m/z [M+H] calcd for $C_{24}H_{33}N_4O_3$: 425.25; found: 425.3.

$^1$H NMR (400 MHZ, methanol-$d_4$) δ=8.86 (s, 1H), 7.58 (dd, J=2.6, 8.9 Hz, 1H), 7.39 (d, J=2.6 Hz, 1H), 7.13 (d, J=9.0 Hz, 1H), 3.93-3.80 (m, 2H), 3.66-3.59 (m, 2H), 3.59-3.52 (m, 1H), 2.97 (br d, J=11.3 Hz, 1H), 2.77 (br dd, J=3.0, 5.8 Hz, 1H), 2.62-2.48 (m, 1H), 2.27 (s, 6H), 1.88 (ddd, J=1.9, 5.9, 9.3 Hz, 1H), 1.82-1.71 (m, 1H), 1.64-1.52 (m, 2H), 1.35 (br t, J=9.3 Hz, 2H), 1.24 (q, J=5.9 Hz, 1H), 1.22-1.14 (m, 4H), 1.14-1.03 (m, 1H).

(R)—N-(3-(4,6-dimethylpyrimidin-5-yl)-4-(piperidin-2-ylmethoxy)phenyl)benzamide (448)

448

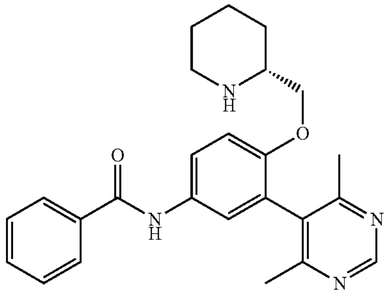

Compound 448 was prepared according to the synthesis described for compound 441, substituting benzoic acid for 2-fluoropentanoic acid.

LCMS (ESI): m/z [M+H] calcd for $C_{25}H_{29}N_4O_2$: 417.5; found: 417.2.

$^1$H NMR (400 MHZ, DMSO-$d_6$) δ ppm 1.22-1.35 (m, 1H), 1.36-1.54 (m, 2H), 1.61-1.79 (m, 3H), 2.23 (d, J=5.13 Hz, 6H), 2.84-2.99 (m, 1H), 3.23 (br d, J=12.13 Hz, 1H), 3.35 (br s, 1H), 4.01-4.12 (m, 2H), 7.29 (d, J=9.01 Hz, 1H), 7.46 (td, J=8.50, 2.38 Hz, 1H), 7.54-7.65 (m, 2H), 7.74-7.92 (m, 3H), 8.44 (br d, J=9.88 Hz, 1H), 8.71 (br d, J=9.63 Hz, 1H), 8.93 (s, 1H), 10.39 (s, 1H).

(R)—N-(3-(4,6-dimethylpyrimidin-5-yl)-4-(piperidin-2-ylmethoxy)phenyl)-3-fluorobenzamide (449)

449

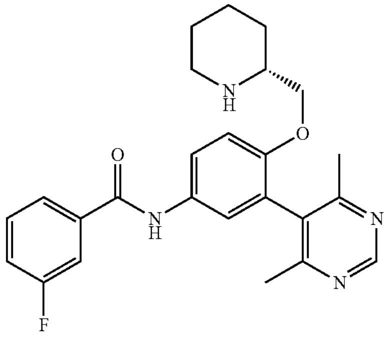

Compound 449 was prepared according to the synthesis described for compound 441, substituting 3-fluorobenzoic acid for 2-fluoropentanoic acid.

LCMS (ESI): m/z [M+H] calcd for $C_{25}H_{28}FN_4O_2$: 435.5; found: 435.2.

$^1$H NMR (400 MHZ, DMSO-$d_6$) δ ppm 1.21-1.32 (m, 1H), 1.21-1.32 (m, 1H), 1.35-1.55 (m, 2H), 1.59-1.76 (m, 3H), 2.22 (d, J=4.75 Hz, 6H), 2.82-2.94 (m, 1H), 3.21 (br d, J=12.13 Hz, 1H), 3.32 (br s, 1H), 4.00-4.10 (m, 2H), 7.26 (d, J=9.01 Hz, 1H), 7.49-7.55 (m, 2H), 7.55-7.62 (m, 2H), 7.85 (dd, J=8.94, 2.44 Hz, 1H), 7.95 (d, J=7.25 Hz, 2H), 8.50 (br d, J=9.76 Hz, 1H), 8.77 (br d, J=10.01 Hz, 1H), 8.91 (s, 1H), 10.32 (s, 1H).

(R)—N-(3-(4,6-dimethylpyrimidin-5-yl)-4-(piperidin-2-ylmethoxy)phenyl)-3-methoxybenzamide (450)

450

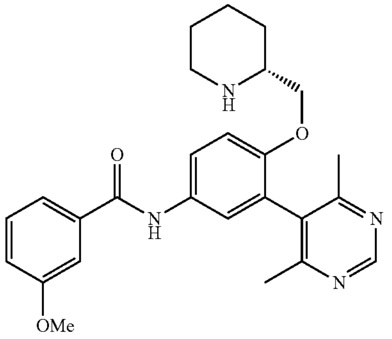

Compound 450 was prepared according to the synthesis described for compound 441, substituting 3-methoxybenzoic acid for 2-fluoropentanoic acid.

LCMS (ESI): m/z [M+H] calcd for $C_{26}H_{31}N_4O_3$: 447.5; found: 447.3.

$^1$H NMR (400 MHZ, DMSO-$d_6$) δ ppm 1.19-1.31 (m, 1H), 1.33-1.52 (m, 2H), 1.60-1.76 (m, 3H), 2.21 (d, J=5.13 Hz, 6H), 2.89 (br d, J=10.26 Hz, 1H), 3.21 (br d, J=12.51 Hz, 1H), 3.33 (br s, 1H), 3.83 (s, 3H), 3.99-4.09 (m, 2H), 7.16 (dd, J=8.13, 1.88 Hz, 1H), 7.26 (d, J=9.01 Hz, 1H), 7.41-7.49 (m, 2H), 7.50-7.59 (m, 2H), 7.85 (dd, J=8.94, 2.44 Hz, 1H), 8.35 (br d, J=9.76 Hz, 1H), 8.61 (br d, J=11.01 Hz, 1H), 8.91 (s, 1H), 10.26 (s, 1H).

N-(4-(2-acetimidamidoethoxy)-3-(4,6-dimethylpyrimidin-5-yl)phenyl)cyclopropanecarboxamide (451)

451

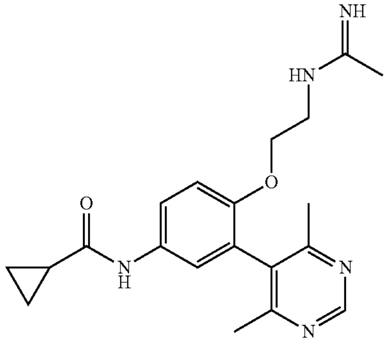

Compound 451 was prepared according to the synthesis described for compound 371, substituting cyclopropanecarboxylic acid for benzoic acid.

LCMS (ESI): m/z [M+H] calcd for $C_{20}H_{26}N_5O_2$: 368.2; found: 368.2.

$^1$H NMR (400 MHZ, methanol-$d_4$) δ=8.89 (s, 1H), 7.63 (dd, J=2.6, 8.9 Hz, 1H), 7.38 (d, J=2.7 Hz, 1H), 7.15 (d, J=9.0 Hz, 1H), 4.15 (t, J=5.1 Hz, 2H), 3.55 (t, J=5.0 Hz, 2H), 2.26 (s, 6H), 2.10 (s, 3H), 1.77-1.70 (m, 1H), 0.96-0.83 (m, 4H).

(R)—N-(3-(4,6-dimethylpyrimidin-5-yl)-4-(piperidin-3-yloxy)phenyl)-1-fluorocyclopropane-1-carboxamide (452)

Preparation of tert-butyl (3R)-3-[2-(4,6-dimethylpyrimidin-5-yl)-4-[(1-fluorocyclopropanecarbonyl) amino]phenoxy]piperidine-1-carboxylate (116)

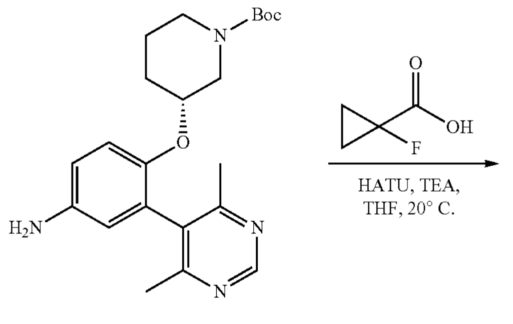

99

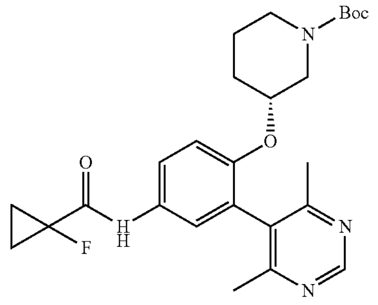

116

To a solution of 1-fluorocyclopropanecarboxylic acid (28.7 mg, 276.04 μmol, 1.1 eq.) in THF (2 mL) was added tert-butyl (3R)-3-[4-amino-2-(4,6-dimethylpyrimidin-5-yl) phenoxy]piperidine-1-carboxylate ((99), 100.0 mg, 250.94 μmol, 1 eq.), TEA (76.1 mg, 752.83 μmol, 104.78 μL, 3 eq.) and HATU (143.12 mg, 376.41 μmol, 1.5 eq.) at 0° C. The mixture was stirred at 20° C. for 2 hrs. TLC (ethyl acetate) indicated tert-butyl (3R)-3-[4-amino-2-(4,6-dimethylpyrimidin-5-yl)phenoxy]piperidine-1-carboxylate (99) was consumed, and one major new spot with lower polarity was detected. The reaction mixture was quenched by addition of water (5 mL) at 0° C., and then diluted with water (5 mL) and extracted with ethyl acetate 4 mL (4 mL×3). The combined organic layers were dried over sodium sulfate, filtered and concentrated under reduced pressure to give a residue. The crude product tert-butyl (3R)-3-[2-(4,6-dimethylpyrimidin-5-yl)-4-[(1-fluorocyclopropanecarbonyl) amino]phenoxy]piperidine-1-carboxylate ((116), 100.0 mg, 206.37 μmol, 82.24% yield) was obtained as a light yellow oil and was used in the next step without further purification.

LCMS (ESI): m/z [M+H] calcd for $C_{26}H_{34}FN_4O_4$: 485.2; found: 485.3.

Preparation of (R)—N-(3-(4,6-dimethylpyrimidin-5-yl)-4-(piperidin-3-yloxy)phenyl)-1-fluorocyclopropane-1-carboxamide (452)

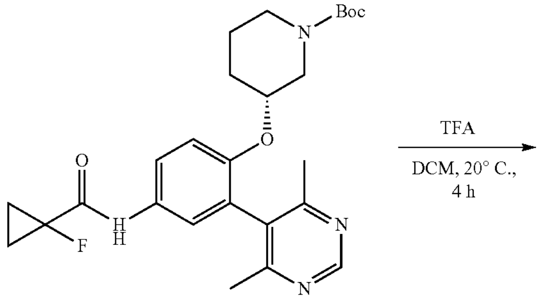

116

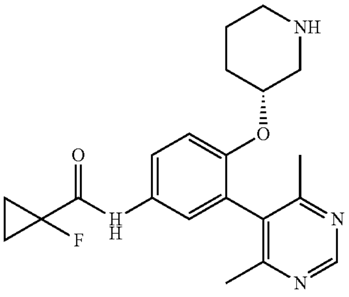

452

To a solution of tert-butyl (3R)-3-[2-(4,6-dimethylpyrimidin-5-yl)-4-[(1-fluorocyclopropanecarbonyl)amino]phenoxy]piperidine-1-carboxylate ((116), 100.0 mg, 206.37 μmol, 1 eq.) in DCM (3 mL) was added TFA (924.0 mg, 8.10 mmol, 0.6 mL, 39.27 eq.). The mixture was stirred at 20° C. for 2 hrs. LC-MS showed tert-butyl (3R)-3-[2-(4,6-dimethylpyrimidin-5-yl)-4-[(1-fluorocyclopropanecarbonyl) amino]phenoxy]piperidine-1-carboxylate (116) was consumed completely and one main peak with desired mass was detected. The reaction mixture was concentrated under reduced pressure to remove the solvent. The residue was purified by prep-HPLC (TFA conditions; column: Nano-micro Kromasil C18 100*40 mm*10 μm; mobile phase: [water (0.1% TFA)-ACN]; B %: 1%-30%, 8 min). N-[3-(4,6-dimethylpyrimidin-5-yl)-4-[[(3R)-3-piperidyl]oxy]phenyl]-1-fluoro-cyclopropanecarboxamide (44.0 mg, 114.45 μmol, 55.46% yield) was obtained as a white solid.

LCMS (ESI): m/z [M+H] calcd for $C_{21}H_{26}FN_4O_2$: 385.20; found: 385.2.

$^1H$ NMR (400 MHZ, methanol-$d_4$) δ=8.92 (s, 1H), 7.75 (dd, J=2.6, 9.0 Hz, 1H), 7.47 (d, J=2.7 Hz, 1H), 7.26 (d, J=9.0 Hz, 1H), 4.54 (tt, J=3.3, 6.7 Hz, 1H), 3.37 (dd, J=2.9, 12.7 Hz, 1H), 3.21-2.99 (m, 3H), 2.33 (d, J=1.3 Hz, 6H), 1.98 (dt, J=4.2, 8.7 Hz, 1H), 1.90-1.58 (m, 3H), 1.48-1.34 (m, 4H).

N-(3-(4,6-dimethylpyrimidin-5-yl)-4-(2-((2-methoxyethyl)amino)ethoxy)phenyl)-1-fluorocyclopropane-1-carboxamide (453)

Preparation of N-[3-(4,6-dimethylpyrimidin-5-yl)-4-(2-hydroxyethoxy)phenyl]-1-fluoro-cyclopropanecarboxamide (117)

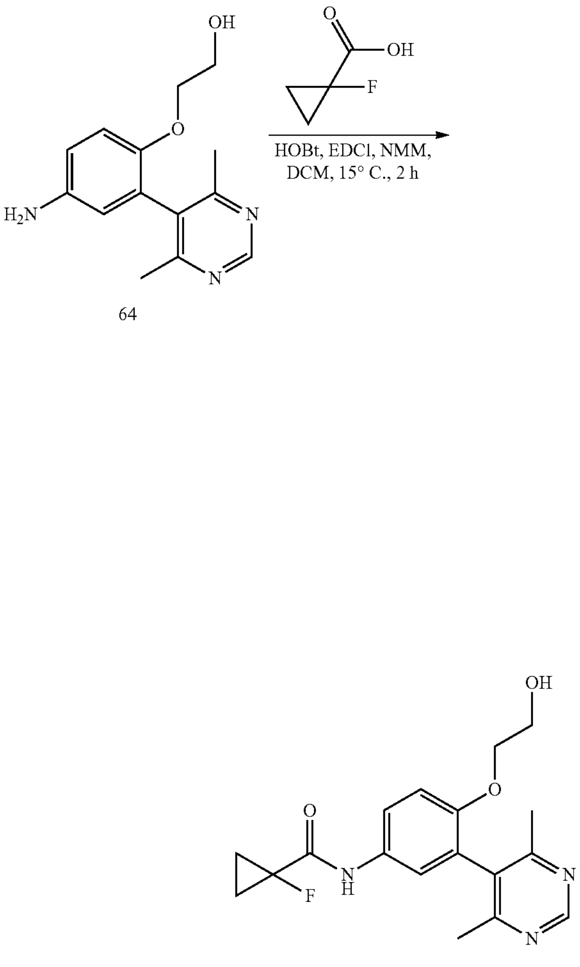

64

117

To a solution of 2-[4-amino-2-(4,6-dimethylpyrimidin-5-yl)phenoxy]ethanol ((64), 320 mg, 1.09 mmol, 1 eq.), 1-fluorocyclopropanecarboxylic acid (136.14 mg, 1.31 mmol, 1.2 eq.), EDCI (250.74 mg, 1.31 mmol, 1.2 eq.) and HOBt (176.74 mg, 1.31 mmol, 1.2 eq.) in DCM (5 mL) was added NMM (165.38 mg, 1.64 mmol, 179.76 μL, 1.5 eq.). The reaction mixture was stirred at 15° C. for 1 hr. The residue was poured into water (50 mL). The aqueous phase was extracted with ethyl acetate (30 mL×3). The combined organic phase was washed with brine (30 mL), dried with anhydrous $Na_2SO_4$, filtered and concentrated under vacuum. The residue was purified by prep-TLC (ethyl acetate:methanol=20:1). N-[3-(4,6-dimethylpyrimidin-5-yl)-4-(2-hydroxyethoxy)phenyl]-1-fluoro-cyclopropanecarboxamide ((117), 200 mg, 579.09 μmol, 53.13% yield) was obtained as a yellow solid.

Preparation of 2-[2-(4,6-dimethylpyrimidin-5-yl)-4-[(1-fluorocyclopropanecarbonyl)amino]phenoxy]ethyl 4-methylbenzenesulfonate (118)

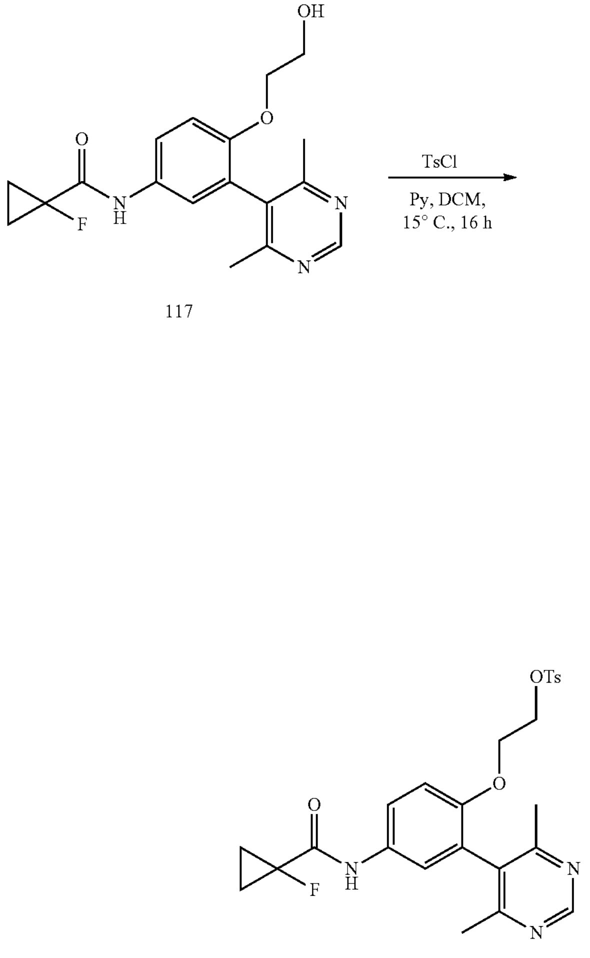

117

118

To a solution of N-[3-(4,6-dimethylpyrimidin-5-yl)-4-(2-hydroxyethoxy)phenyl]-1-fluoro-cyclopropanecarboxamide ((117), 200 mg, 579.09 μmol, 1 eq.) and Py (91.61 mg, 1.16 mmol, 93.48 μL, 2 eq.) in DCM (5 mL) was added TosCl (121.44 mg, 637.00 μmol, 1.1 eq.). The reaction mixture was stirred at 15° C. for 1 hr. TosCl (110.40 mg, 579.09 μmol, 1 eq.) was added to the reaction mixture. The reaction mixture was stirred at 30° C. for 1 hr. Py (137.42 mg, 1.74 mmol, 140.22 μL, 3 eq.) was added to the reaction mixture. The reaction mixture was stirred at 30° C. for 16 hrs. The residue was poured into water (30 mL) and citric acid (500 mg) in water (20 mL). The aqueous phase was extracted with ethyl acetate (50 mL×3). The combined organic phase was washed with brine (40 mL), dried with anhydrous $Na_2SO_4$, filtered and concentrated in vacuum. The residue was purified by flash silica gel chromatography (12 g SepaFlash® Silica Flash Column, eluent of 0~100% ethyl acetate/petroleum ether gradient). 2-[2-(4,6-dimethylpyrimidin-5-yl)-4-[(1-fluorocyclopropanecarbonyl)amino]phenoxy]ethyl 4-methylbenzenesulfonate ((118), 120 mg, 240.21 μmol, 41.48% yield) was obtained as a colorless gum.

Preparation of N-(3-(4,6-dimethylpyrimidin-5-yl)-4-(2-((2-methoxyethyl)amino)ethoxy)phenyl)-1-fluorocyclopropane-1-carboxamide (453)

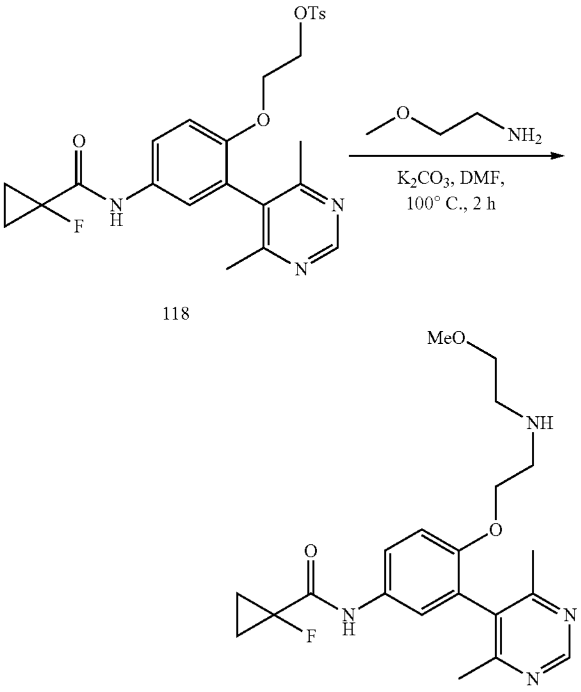

118

453

To a solution of 2-[2-(4,6-dimethylpyrimidin-5-yl)-4-[(1-fluorocyclopropanecarbonyl)amino]phenoxy]ethyl 4-methylbenzenesulfonate ((118), 120 mg, 240.21 μmol, 1 eq.) and 2-methoxyethanamine (21.65 mg, 288.26 μmol, 25.06 μL, 1.2 eq.) in DMF (1 mL) was added $K_2CO_3$ (33.20 mg, 240.21 μmol, 1 eq.). The reaction mixture was stirred at 100° C. for 2 hrs. The reaction mixture was filtered. The mixture was purified by prep-HPLC (column: Phenomenex Luna C18 150*25 mm*10 μm; mobile phase: [water (0.1% TFA)-ACN]; B %: 4%-34%, 10 min) followed by lyophilization. N-[3-(4,6-dimethylpyrimidin-5-yl)-4-[2-(2-methoxyethylamino)ethoxy]phenyl]-1-fluoro-cyclopropanecarboxamide (35.08 mg, 67.92 μmol, 28.28% yield, 100% purity, TFA) was obtained as a brown gum.

LCMS (ESI): m/z [M+H] calcd for $C_{21}H_{28}FN_4O_3$: 403.21; found: 403.2.

$^1$H NMR (400 MHZ, methanol-$d_4$) δ=8.96 (s, 1H), 7.75 (dd, J=2.7, 8.9 Hz, 1H), 7.48 (d, J=2.6 Hz, 1H), 7.23 (d, J=9.0 Hz, 1H), 4.33 (t, J=5.2 Hz, 2H), 3.51-3.44 (m, 2H), 3.41-3.33 (m, 5H), 3.03-2.96 (m, 2H), 2.34 (s, 6H), 1.44-1.35 (m, 4H).

Example 2—In Vitro Binding Assays

Radioligand Binding Assay Protocol

Radioligand binding assays were performed using [$^3$H]5-HT as the radioligand using cell membranes prepared from HEK293 cells expressing recombinant 5-$HT_{2A}$, 5-$HT_{2B}$ and 5-$HT_{2C}$ (INI) receptors. Competition binding experiments consisted of addition of 5 μL of serially diluted test compound, 50 μL of radioligand stock diluted in Assay Buffer (20 mM HEPES, pH 7.4, 10 mM $MgCl_2$), and 145 μL of diluted membrane expressing the receptor of interest to 96-well microtiter plates, which were then incubated for one hour at room temperature. Assay incubations were terminated by rapid filtration through Perkin Elmer GF/C filtration plates under vacuum pressure using a 96-well Packard filtration apparatus, followed by washing the filter plates several times with ice cold Assay Buffer. Plates were then dried at 45° C. for a minimum of four hours. Finally, 25 μL of BetaScint scintillation cocktail was added to each well and the plates were counted in a Packard TopCount scintillation counter. In each competition study, test compounds were assayed at 10 concentrations with three replicates at each test concentration. Dose-response curves were constructed to determine $IC_{50}$ values and these were converted to corresponding Ki values using the Cheng-Prusoff equation.

TABLE 2

Assay Conditions for 5-$HT_2$ Receptor Binding Assays

| Receptor | Final [$^3$H]5-HT Assay Concentration (nM) | Membrane Protein Amount (μg) | Measured Radioligand $K_d$ (nM) |
|---|---|---|---|
| 5-$HT_{2A}$ | 2.7 | 12 | 4.79 |
| 5-$HT_{2B}$ | 5.4 | 40 | 12.1 |
| 5-$HT_{2C(INI)}$ | 2.7 | 12 | 0.53 |

TABLE 3

5-$HT_{2A}$ serotonin binding

| Compound | $K_i$ value (nM) | Compound | $K_i$ value (nM) |
|---|---|---|---|
| 200 | 3.72 | 225 | 712 |
| 201 | 33.4 | 226 | 714 |
| 202 | 5.25 | 227 | 83.1 |
| 203 | 783 | 228 | 13 |
| 204 | 13.2 | 229 | 113 |
| 205 | 10.4 | 230 | 252 |
| 206 | 6.51 | 231 | 45.7 |
| 207 | 44.2 | 232 | 24.5 |
| 208 | 22.5 | 233 | 3.81 |
| 209 | 4.8 | 233 | 4.66 |
| 210 | 134 | 234 | 121 |
| 211 | 2.08 | 235 | 211 |
| 212 | 5.56 | 236 | 21.4 |
| 213 | 4.6 | 237 | 12.7 |
| 214 | 3.25 | 238 | |
| 215 | 15.7 | 239 | 92.3 |
| 216 | 16.6 | 240 | 60900 |
| 217 | 7.23 | 241 | 27.8 |
| 218 | 1510 | 242 | 37.6 |
| 219 | 6.51 | 243 | 8.59 |
| 220 | 22 | 244 | 6.51 |
| 221 | 11.4 | 245 | 4.3 |
| 222 | 8.14 | 246 | 16.3 |
| 223 | 10.5 | 247 | 4.47 |
| 224 | 2.48 | 248 | 0.845 |
| 249 | 78.3 | 279 | 65800 |
| 250 | 9.04 | 280 | 65800 |
| 251 | 2.05 | 281 | 30.6 |
| 252 | 9.53 | 282 | 8.84 |
| 253 | 6.34 | 283 | 24 |
| 254 | 1.3 | 284 | 87.5 |
| 255 | 1.72 | 285 | 33.4 |
| 256 | 9.89 | 286 | 10.1 |
| 257 | 14.8 | 287 | 3250 |
| 258 | 10.8 | 288 | 81.2 |
| 259 | 19.6 | 289 | 123 |
| 260 | 63.3 | 290 | 3.86 |
| 261 | 91.7 | 291 | 5.04 |
| 262 | 35.7 | 291 | 15.5 |
| 263 | 10.1 | 292 | 17.6 |

TABLE 3-continued

| 5-$HT_{2A}$ serotonin binding | | | |
|---|---|---|---|
| Compound | $K_i$ value (nM) | Compound | $K_i$ value (nM) |
| 264 | 9.18 | 293 | 8.56 |
| 265 | 18.2 | 294 | 17.9 |
| 266 | 4.11 | 295 | 2.01 |
| 267 | 692 | 296 | 4.49 |
| 268 | 7.78 | 297 | 2.71 |
| 269 | 559 | 298 | 16.9 |
| 270 | 51.6 | 299 | 20.6 |
| 271 | 3.26 | 300 | 1.48 |
| 272 | 2.43 | 301 | 3.4 |
| 273 | 1.11 | 302 | 3.18 |
| 274 | 3.92 | 303 | 9.36 |
| 275 | 1.7 | 304 | 7.25 |
| 276 | 0.843 | 305 | 2.61 |
| 277 | 33.4 | 306 | 2.65 |
| 278 | 32.6 | 307 | 5.89 |
| 308 | 3.28 | 338 | 485 |
| 309 | 1.71 | 339 | 18.4 |
| 310 | 1.58 | 340 | 374 |
| 311 | 3.01 | 341 | 9.84 |
| 312 | 0.813 | 342 | 6.95 |
| 313 | 1.7 | 343 | 48.4 |
| 314 | 5.42 | 344 | 6.53 |
| 315 | 12.6 | 345 | 19.5 |
| 316 | 4.98 | 346 | 31 |
| 317 | 96.3 | 347 | 42.3 |
| 318 | 4.09 | 348 | 66.6 |
| 319 | 3.62 | 349 | 12.6 |
| 320 | 1.77 | 350 | 43.1 |
| 321 | | 351 | 4.56 |
| 322 | 3.39 | 352 | 15.5 |
| 323 | 3.77 | 353 | 4.06 |
| 324 | 59700 | 354 | 32.1 |
| 325 | 1.7 | 355 | 177 |
| 326 | 13.7 | 356 | 533 |
| 327 | 15.9 | 357 | 47.3 |
| 328 | 13.6 | 358 | 66.7 |
| 329 | 11.5 | 359 | 102 |
| 330 | 334 | 360 | 11 |
| 331 | 23.7 | 361 | 4.33 |
| 332 | 18.6 | 362 | 96.5 |
| 333 | 224 | 363 | 107 |
| 334 | 17.6 | 364 | 368 |
| 335 | 196 | 365 | 232 |
| 336 | 6.42 | 366 | 11.2 |
| 337 | 7.29 | 367 | 37.6 |
| 368 | 19.6 | 399 | 12.8 |
| 369 | 51.8 | 400 | 4.2 |
| 370 | 78.6 | 401 | 30.9 |
| 371 | 4.77 | 402 | 2.87 |
| 372 | 1.99 | 403 | 24.9 |
| 373 | 1.73 | 404 | 69.2 |
| 374 | 3.44 | 405 | 52.4 |
| 375 | 13.3 | 406 | 57 |
| 376 | 63.3 | 407 | 168 |
| 377 | 2.64 | 408 | 29.9 |
| 378 | 12.5 | 409 | 6.67 |
| 379 | 8.38 | 410 | 37.4 |
| 380 | 9.47 | 411 | 12.8 |
| 381 | 5.54 | 412 | 20 |
| 382 | 8.81 | 413 | 255 |
| 383 | 8.89 | 414 | 91 |
| 384 | 3.63 | 415 | 101 |
| 385 | | 416 | 45.3 |
| 386 | 1.48 | 417 | 40.3 |
| 387 | 13.3 | 418 | 7.29 |
| 388 | 13.7 | 419 | 443 |
| 389 | 11.2 | 420 | 92.7 |
| 390 | 5.25 | 421 | 9.41 |
| 391 | 25.3 | 422 | 4.58 |
| 392 | 15.2 | 423 | 16.2 |
| 393 | 11.2 | 424 | 12.5 |
| 394 | 13 | 425 | 43.8 |
| 396 | 5.93 | 426 | 87.2 |
| 397 | 8.59 | 427 | 27.2 |
| 398 | 6.26 | 428 | 35.3 |
| 429 | 131 | 442 | 17.1 |

TABLE 3-continued

| 5-$HT_{2A}$ serotonin binding | | | |
|---|---|---|---|
| Compound | $K_i$ value (nM) | Compound | $K_i$ value (nM) |
| 430 | 21.6 | 443 | 18.8 |
| 431 | 54.9 | 444 | 4.93 |
| 432 | 19.1 | 445 | 63.3 |
| 433 | 9.98 | 447 | 7.08 |
| 434 | 19.3 | 447 | 19.6 |
| 435 | 10.7 | 448 | 1.7 |
| 436 | 6.05 | 449 | 6.49 |
| 437 | 10.7 | 450 | 1.03 |
| 438 | 9.18 | 451 | 52.6 |
| 439 | 14.6 | 452 | 15 |
| 440 | 65.1 | 453 | 4.76 |
| 441 | 5.67 | | |

HTRF IP-One Antagonist Assays

HEK293 cells stably expressing 5-$HT_2$ receptors were generated using standard procedures. Cells were dilution cloned and clonal cell lines stably expressing the receptors at low levels were selected for pharmacology studies. In radioligand binding studies using a variety of radiolabeled probes, receptor densities in the 2A, 2B and 2C cell lines were estimated to be 50-70, 150-200, and 10-20 fmol/mg, respectively.

Inositol phosphate accumulation assays were performed using the HTRF IP-One assay system developed by Cisbio and generally followed the manufacturer's instructions. Briefly, HEK293 cells stably expressing recombinant human receptors were harvested and resuspended in phenol-red free OptiMEM (ThermoFisher), plated into 384-well assay plates (Perkin Elmer, ProxiPlate-Plus® Cat #6008280) at 10,000 cells/well in a volume of 10 µL/well, and incubated overnight at 37° C., 5% $CO_2$. Test compounds were solubilized and serially diluted in DMSO, and then diluted into Assay Buffer (Tris HCl 20 mM, NaCl 150 mM, LiCl 40 mM, pargyline 25 µM, pH 8) containing 80 nM 5-HT. Test compounds were added to the cells (4 µL/well addition, maximal final assay concentration typically 10 µM) and plates, incubated for 2 hrs at 37° C./5% $CO_2$ and then removed from the incubator and allowed to cool to room temperature for 30 minutes prior to addition of IP-One detection reagents. IP-One detection reagents (6 µL/well) were added and plates incubated for 1 hr at room temperature before reading on an HTRF compatible reader such as a Perkin Elmer EnVision® or BMG PheraStar®. Dose-response experiments utilized 10-point curves, typically starting at 10 µM, with 5-fold serial dilutions. Experiments were performed with triplicate data points and independent replicate experiments were performed to ensure data consistency.

TABLE 4

| 5-$HT_2$ $IC_{50}$ values | | | |
|---|---|---|---|
| Compound | 5-$HT_{2A}$ | 5-$HT_{2B}$ | 5-$HT_{2C}$ |
| 200 | 11.7 nM | 100 uM | 100 uM |
| 202 | 6.35 nM | 100 uM | 100 uM |
| 209 | 26.2 nM | 100 uM | 100 uM |
| 214 | 5.16 nM | 100 uM | 100 uM |
| 217 | 18.5 nM | 100 uM | 100 uM |
| 224 | 16.1 nM | | 100 uM |
| 232 | 140 nM | 100 uM | 100 uM |
| 233 | 8.55 nM | 100 uM | 100 uM |
| 243 | 14.8 nM | 100 uM | 100 uM |
| 244 | 13.5 nM | 100 uM | 100 uM |
| 245 | 9.66 nM | 100 uM | 100 uM |

TABLE 4-continued

| 5-HT$_2$ IC$_{50}$ values | | | |
|---|---|---|---|
| Compound | 5-HT$_{2A}$ | 5-HT$_{2B}$ | 5-HT$_{2C}$ |
| 247 | 10.6 nM | 100 uM | 100 uM |
| 250 | 13.9 nM | 100 uM | 100 uM |
| 256 | 56 nM | 100 uM | 100 uM |
| 257 | 33.5 nM | 100 uM | 100 uM |
| 263 | 35.9 nM | 100 uM | 100 uM |
| 266 | 5.23 nM | 100 uM | 100 uM |
| 268 | 62.4 nM | 100 uM | 100 uM |
| 271 | 6.1 nM | 100 uM | 100 uM |
| 272 | 7.8 nM | 2.68 uM | 100 uM |
| 273 | 1.68 nM | | 100 uM |
| 275 | 6.32 nM | 100 uM | 100 uM |
| 276 | 3.07 nM | 100 uM | 100 uM |
| 290 | 7.36 nM | 100 uM | 100 uM |
| 291 | 9.75 nM | 100 uM | 100 uM |
| 293 | 15.9 nM | 9.37 uM | 100 uM |
| 304 | 8.86 nM | 100 uM | 100 uM |
| 305 | 4.44 nM | 100 uM | 100 uM |
| 306 | 6.14 nM | | 100 uM |
| 307 | 9.84 nM | 100 uM | 100 uM |
| 308 | 14.7 nM | 100 uM | 100 uM |
| 309 | 6.32 nM | 806 nM | 100 uM |
| 310 | 3.31 nM | 1.91 uM | 100 uM |
| 312 | 2.38 nM | | 100 uM |
| 314 | 15.3 nM | 100 uM | 100 uM |
| 316 | 6.99 nM | 3.19 uM | 100 uM |
| 318 | 16.8 nM | 4.5 uM | 100 uM |
| 319 | 14.3 nM | 2.36 uM | 100 uM |
| 321 | 25.7 nM | 5.4 uM | 100 uM |
| 325 | 8.54 nM | 2.89 uM | 100 uM |
| 344 | 10.2 nM | 1.21 uM | 100 uM |
| 351 | 7.03 nM | 100 uM | 100 uM |
| 353 | 24.8 nM | 100 uM | 100 uM |
| 361 | 9.27 nM | 100 uM | 100 uM |
| 396 | 50.5 nM | 100 uM | 100 uM |
| 398 | 33.8 nM | 100 uM | 100 uM |
| 400 | 38.6 nM | 100 uM | 100 uM |
| 409 | 18.9 nM | 2.92 uM | 100 uM |
| 435 | 43.2 nM | | 100 uM |
| 436 | 27.2 nM | | 100 uM |
| 438 | 16.4 nM | 100 uM | 100 uM |
| 441 | 12.1 nM | | 100 uM |
| 444 | 11.8 nM | 100 uM | 100 uM |
| 447 | 9.05 nM | 100 uM | 100 uM |
| 453 | 4.84 nM | 100 uM | 100 uM |

OTHER EMBODIMENTS

It is to be understood that the foregoing description is intended to illustrate and not limit the scope of the disclosure, which is defined by the scope of the appended claims. Other aspects, advantages, and modifications are within the scope of the following claims.

What is claimed is:

1. A compound of Formula (I)

(I)

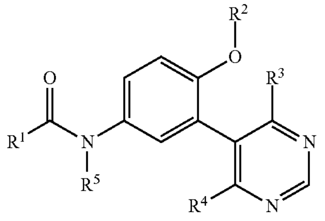

or a pharmaceutically acceptable salt thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, —$C_1$-$C_3$ haloalkyl, $C_3$-$C_6$ cycloalkyl-, —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, —$C_1$-$C_3$ alkyl-, —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, —$C_1$-$C_3$ haloalkyl-, —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S;

$R^3$ and $R^4$ are each independently selected from H, $C_1$-$C_6$ alkyl, and $C_1$-$C_6$ haloalkyl; and $R^5$ is selected from H and $C_1$-$C_6$ alkyl.

2. The compound of claim 1, or a pharmaceutically acceptable salt thereof, wherein $R^1$ is $C_1$-$C_6$ alkyl optionally substituted with one or more substituents independently selected from halogen and —O—($C_1$-$C_3$ alkyl).

3. The compound of claim 1, or a pharmaceutically acceptable salt thereof, wherein $R^1$ is $C_3$-$C_6$ cycloalkyl optionally substituted with one or more substituents independently selected from halogen, —OH, $C_1$-$C_3$ haloalkyl, —$C_3$-$C_6$ cycloalkyl-, —O—($C_1$-$C_3$ alkyl), ($C_1$-$C_3$ alkylene)-O—($C_1$-$C_3$ alkyl), and phenyl.

4. The compound of claim 1, or a pharmaceutically acceptable salt thereof, wherein $R^1$ is phenyl optionally substituted with one or more substituents independently selected from halogen, —CN, —$NH_2$, $C_1$-$C_3$ alkyl, —$C_1$-$C_3$ haloalkyl-, and —O—($C_1$-$C_3$ alkyl).

5. The compound of claim 1, or a pharmaceutically acceptable salt thereof, wherein $R^1$ is 5-10 membered heteroaryl optionally substituted with one or more substituents independently selected from halogen, $C_1$-$C_3$ alkyl, and —O—($C_1$-$C_3$ alkyl).

6. The compound of claim 1, or a pharmaceutically acceptable salt thereof, wherein $R^1$ is 5-9 membered heterocycloalkyl optionally substituted with one or more substituents independently selected from halogen and $C_1$-$C_3$ alkyl.

7. The compound of claim 1, or a pharmaceutically acceptable salt thereof, wherein $R^2$ is 4-6 membered heterocycloalkyl optionally substituted with one or more substituents independently selected from halogen, oxo, —OH, —$C_1$-$C_3$ alkyl-, —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl).

8. The compound of claim 1, or a pharmaceutically acceptable salt thereof, wherein $R^2$ is ($C_1$-$C_3$ alkylene)-(4-10 membered heterocycloalkyl), wherein the heterocycloalkyl is optionally substituted with one or more substituents independently selected from halogen, oxo, —OH, —$C_1$-$C_3$ alkyl-, —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl).

9. The compound of claim 1, or a pharmaceutically acceptable salt thereof, wherein $R^2$ is ($C_1$-$C_3$ alkylene)-$NR^{2A}R^{2B}$.

10. The compound of claim 9, or a pharmaceutically acceptable salt thereof, where $R^{2A}$ is selected from H and $C_1$-$C_3$ alkyl.

11. The compound of claim 9, or a pharmaceutically acceptable salt thereof, wherein $R^{2B}$ is selected from $C_1$-$C_3$ alkyl, $C_3$-$C_6$ cycloalkyl, $C_1$-$C_3$ haloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl).

12. The compound of claim 1, or a pharmaceutically acceptable salt thereof, wherein $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, —$C_1$-$C_3$ haloalkyl-, —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S.

13. The compound of claim 1, or a pharmaceutically acceptable salt thereof, wherein one of $R^3$ and $R^4$ is H and the other is $C_1$-$C_6$ alkyl.

14. The compound of claim 1, or a pharmaceutically acceptable salt thereof, wherein one of $R^3$ and $R^4$ is H and the other is methyl.

15. The compound of claim 1, or a pharmaceutically acceptable salt thereof, wherein $R^3$ and $R^4$ are each $C_1$-$C_3$ alkyl.

16. The compound of claim 1, having the structure of Formula (Ia)

(Ia)

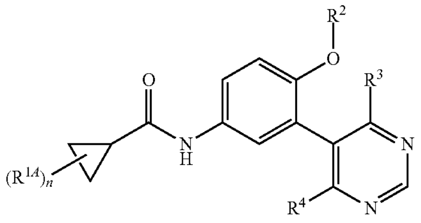

wherein:

each $R^{1A}$ is independently selected from halogen, —OH, —$NH_2$, $C_1$-$C_3$ alkyl, —$C_1$-$C_3$ haloalkyl, $C_3$-$C_6$ cycloalkyl-, —O—($C_1$-$C_3$ alkyl), ($C_1$-$C_3$ alkylene)-O—($C_1$-$C_3$ alkyl), and phenyl;

$R^2$ is selected from 4-6 membered heterocycloalkyl, ($C_1$-$C_3$ alkylene)-(4-10 membered heterocycloalkyl), and ($C_1$-$C_3$ alkylene)-$NR^{2A}R^{2B}$, wherein the alkylene and heterocycloalkyl are each optionally substituted with one or more substituents independently selected from halogen, oxo, —OH, —$C_1$-$C_3$ alkyl-, —O—($C_1$-$C_3$ alkyl), ($C_1$-$C_3$ alkylene)-C(O)OH, —C(O)H, —C(O)OH, —C(O)($C_1$-$C_3$ alkyl), —C(O)($C_1$-$C_3$ alkylene)-OH, —C(O)C(O)OH, and —$SO_2$($C_1$-$C_3$ alkyl);

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-$SO_2$—($C_1$-$C_3$ alkyl), and C(═NH)($C_1$-$C_3$ alkyl);

or $R^{2A}$ and $R^{2B}$, taken together with the nitrogen to which they are attached, form a 3-9 membered heterocycloalkyl ring optionally substituted with one or more substituents independently selected from halogen, oxo, —OH, $C_1$-$C_3$ alkyl, ($C_1$-$C_3$ haloalkyl), —O—($C_1$-$C_3$ alkyl), ($C_1$-$C_3$ alkylene)-C(O)OH, —C(O)H, —C(O)($C_1$-$C_3$ alkyl), —C(O)($C_1$-$C_3$ alkylene)-OH, —C(O)C(O)OH, and —$SO_2$($C_1$-$C_3$ alkyl), and optionally containing one additional heteroatom selected from the group of N, O, and S;

$R^3$ and $R^4$ are each independently selected from H, $C_1$-$C_6$ alkyl, and $C_1$-$C_6$ haloalkyl; and n is 0, 1, 2, 3, 4, or 5;

or a pharmaceutically acceptable salt thereof.

17. The compound of claim 1, having the structure of Formula (If):

(If)

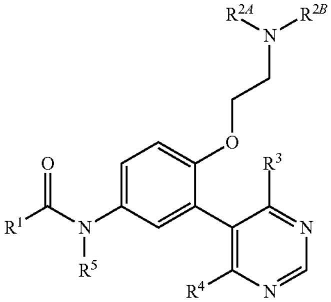

or a pharmaceutically acceptable salt thereof, wherein:

$R^1$ is selected from $C_1$-$C_6$ alkyl, $C_3$-$C_6$ cycloalkyl, phenyl, 5-10 membered heteroaryl, 5-9 membered heterocycloalkyl, ($C_1$-$C_3$ alkylene)-($C_3$-$C_6$ cycloalkyl), ($C_1$-$C_3$ alkylene)-phenyl, ($C_1$-$C_3$ haloalkylene)-phenyl, ($C_1$-$C_3$ alkylene)-(5-10 membered heteroaryl), ($C_1$-$C_3$ alkylene)-(5-9 membered heterocycloalkyl), ($C_1$-$C_3$ alkylene)-O—($C_3$-$C_6$ cycloalkyl), and ($C_1$-$C_3$ alkylene)-NH—($C_3$-$C_6$ cycloalkyl), wherein the alkyl, alkylene, cycloalkyl, phenyl, heteroaryl, and heterocycloalkyl are each optionally substituted with one or more substituents independently selected from halogen, —CN, —OH, —$NH_2$, $C_1$-$C_3$ alkyl, —$C_1$-$C_3$ haloalkyl, $C_3$-$C_6$ cycloalkyl-, —O—($C_1$-$C_3$ alkyl), ($C_1$-$C_3$ alkylene)-O—($C_1$-$C_3$ alkyl), and phenyl;

$R^{2A}$ and $R^{2B}$ are each independently selected from H, $C_1$-$C_3$ alkyl, $C_1$-$C_3$ haloalkyl, $C_3$-$C_6$ cycloalkyl, ($C_1$-$C_3$ alkylene)-O—($C_1$-$C_3$ alkyl), ($C_1$-$C_3$ alkylene)-OH, ($C_1$-$C_3$ alkylene)-($C_3$-$C_6$ cycloalkyl), ($C_1$-$C_3$ alkylene)-S(═O)—($C_1$-$C_3$ alkyl), ($C_1$-$C_3$ alkylene)-$SO_2$—($C_1$-$C_3$ alkyl), and C(═NH)($C_1$-$C_3$ alkyl);

$R^3$ and $R^4$ are each independently selected from H, $C_1$-$C_6$ alkyl, and $C_1$-$C_6$ haloalkyl; and $R^5$ is selected from H and $C_1$-$C_6$ alkyl;
or a pharmaceutically acceptable salt thereof.

* * * * *